US012807710B2

(12) United States Patent
Lightwood et al.

(10) Patent No.: US 12,807,710 B2
(45) Date of Patent: Nov. 24, 2026

(54) ANTIBODIES

(71) Applicant: UCB BIOPHARMA SRL, Brussels (BE)

(72) Inventors: Daniel John Lightwood, Slough (GB); Irena Kadiu, Brussels (BE); Pallavi Bhatta, Slough (GB); Anastasios Spiliotopoulos, Slough (GB); Peter Charles Elliott, Slough (GB); James Martin Keaney, Brussels (BE); Silvia L. Delker, Brussels (BE); Jan Abendroth, Brussels (BE)

(73) Assignee: UCB BIOPHARMA SRL, Brussels (BE)

( * ) Notice: Subject to any disclaimer, the term of this patent is extended or adjusted under 35 U.S.C. 154(b) by 482 days.

(21) Appl. No.: 18/558,686

(22) PCT Filed: May 2, 2022

(86) PCT No.: PCT/EP2022/061661
§ 371 (c)(1),
(2) Date: Nov. 2, 2023

(87) PCT Pub. No.: WO2022/233764
PCT Pub. Date: Nov. 10, 2022

(65) Prior Publication Data

US 2024/0254224 A1 Aug. 1, 2024

Related U.S. Application Data

(60) Provisional application No. 63/183,280, filed on May 3, 2021.

(51) Int. Cl.

| | |
|---|---|
| ***C07K 16/28*** | (2006.01) |
| ***A61P 25/28*** | (2006.01) |
| *A61K 39/00* | (2006.01) |

(52) U.S. Cl.
CPC .......... *C07K 16/2803* (2013.01); *A61P 25/28* (2018.01); *A61K 2039/505* (2013.01); *C07K 2317/24* (2013.01); *C07K 2317/33* (2013.01); *C07K 2317/34* (2013.01); *C07K 2317/55* (2013.01); *C07K 2317/565* (2013.01); *C07K 2317/76* (2013.01); *C07K 2317/92* (2013.01)

(58) Field of Classification Search
CPC .................................................. C07K 16/2803
See application file for complete search history.

(56) References Cited

U.S. PATENT DOCUMENTS

| | | | |
|---|---|---|---|
| 9,000,127 | B2 | 4/2015 | Stennicke et al. |
| 2013/0211050 | A1 | 8/2013 | Stennicke et al. |
| 2019/0300608 | A1 | 10/2019 | Pashine et al. |
| 2020/0255529 | A1 | 8/2020 | Chan et al. |

FOREIGN PATENT DOCUMENTS

| | | | |
|---|---|---|---|
| WO | 2017/152102 | A2 | 9/2017 |
| WO | 2021/011681 | A1 | 1/2021 |

OTHER PUBLICATIONS

International Search Report, International Application No. PCT/EP2022/061661, Mailing Date: Aug. 9, 2022.
Bardelli et al., "Epitope mapping by solution NMR spectroscopy: Epitope Mapping by Solution NMR Spectroscopy," Journal of Molecular Recognition 28(6):393-400 (2015).
Simonyan et al., "Conformational Epitope Mapping by Cross-link Mass Spectrometry: Analysis of Ipilimumab, Nivolumab and Pembrolizumab," Retrieved from the Internet: URL:https://covalx.com/pdf/171113-CovalX-X LMS%20Xray%20Comparions-PEGSEU17.pdf [retrieved on Jun. 3, 2019] (Nov. 15, 2017).

*Primary Examiner* — Prema M Mertz
(74) *Attorney, Agent, or Firm* — MEDLER FERRO WOODHOUSE & MILLS PLLC

(57) ABSTRACT

The present invention relates to antibodies binding to TREM1 and inhibiting its interaction with one or more of its natural ligands. Specific examples of such antibodies are provided. The therapeutic uses of the antibodies and methods of generating such are also provided.

17 Claims, 18 Drawing Sheets

Specification includes a Sequence Listing.

LIGHT CHAIN Graft 12172

```
              1   5    10   15   20   25   30   35   40   45   50   55   60   65   70   75   80   85   90   95   100  105  110
Light 12172   AVVLTQTASPVSAFVGGTVTIKCQASQNIGSDLAWYQQEPGQPPKLLIYKAATLASGVPSRFKGSGSGTEFTLTISGVQCEDGATYYCQQYYYGSAGADTDTFGGGTEVVVK
              |||   || ||  |  ||   | |   | | |      | ||      | |  |       |             || |  |       |||||||||||      | ||
IGKV1-9       DIQLTQSPSFLSASVGDRVTITCRASQGISSYLAWYQQKPGKAPKLLIYAASTLQSGVPSRFSGSGSGTEFTLTISSLQPEDFATYYCQQLNSYP------LTFGGGTKVEIK
              |||
12172gL1      AVVLTQSPSFLSASVGDRVTITCQASQNIGSDLAWYQQKPGKAPKLLIYKAATLASGVPSRFSGSGSGTEFTLTISSLQPEDFATYYCQQYYYGSAGADTDTFGGGTKVEIK
12172gL2      DIQLTQSPSFLSASVGDRVTITCQASQNIGSDLAWYQQKPGKAPKLLIYKAATLASGVPSRFSGSGSGTEFTLTISSLQPEDFATYYCQQYYYGSAGADTDTFGGGTKVEIK
12172gL6      DIVLTQSPSFLSASVGDRVTITCQASQNIGSDLAWYQQKPGKAPKLLIYKAATLASGVPSRFSGSGSGTEFTLTISSLQPEDFATYYCQQYYYGSAGADTDTFGGGTKVEIK
12172gL9      DIQLTQSPSFLSASVGDSVTITCQASQNIGSDLAWYQQKPGKAPKLLIYKAATLASGVPSRFSGSGSGTEFTLTISSLQPEDFATYYCQQYYYGSAGADTDTFGGGTKVEIK
12172gL11     DIQLTQSPSFLSASVGDRVTITCQASQNIGSDLAWYQQKPGKAPKLLIYSAATLASGVPSRFSGSGSGTEFTLTISSLQPEDFATYYCQQYYYGSAGADTDTFGGGTKVEIK
```

Legend

12172 = Rabbit variable light chain sequence.
12172gL1, gL2, gL6, gL9 and gL11 = Humanized grafts of 12172 variable light chain using IGKV1-9 human germline as the acceptor framework.

CDRs are shown in bold/underlined.
Donor residues are shown in bold/italic and are highlighted: A1, V2 and V3.
Mutations to decrease the number of positively charged amino acids (R18S and K50S) are shown in bold/underlined and are highlighted: R18S and K50S

FIG. 1

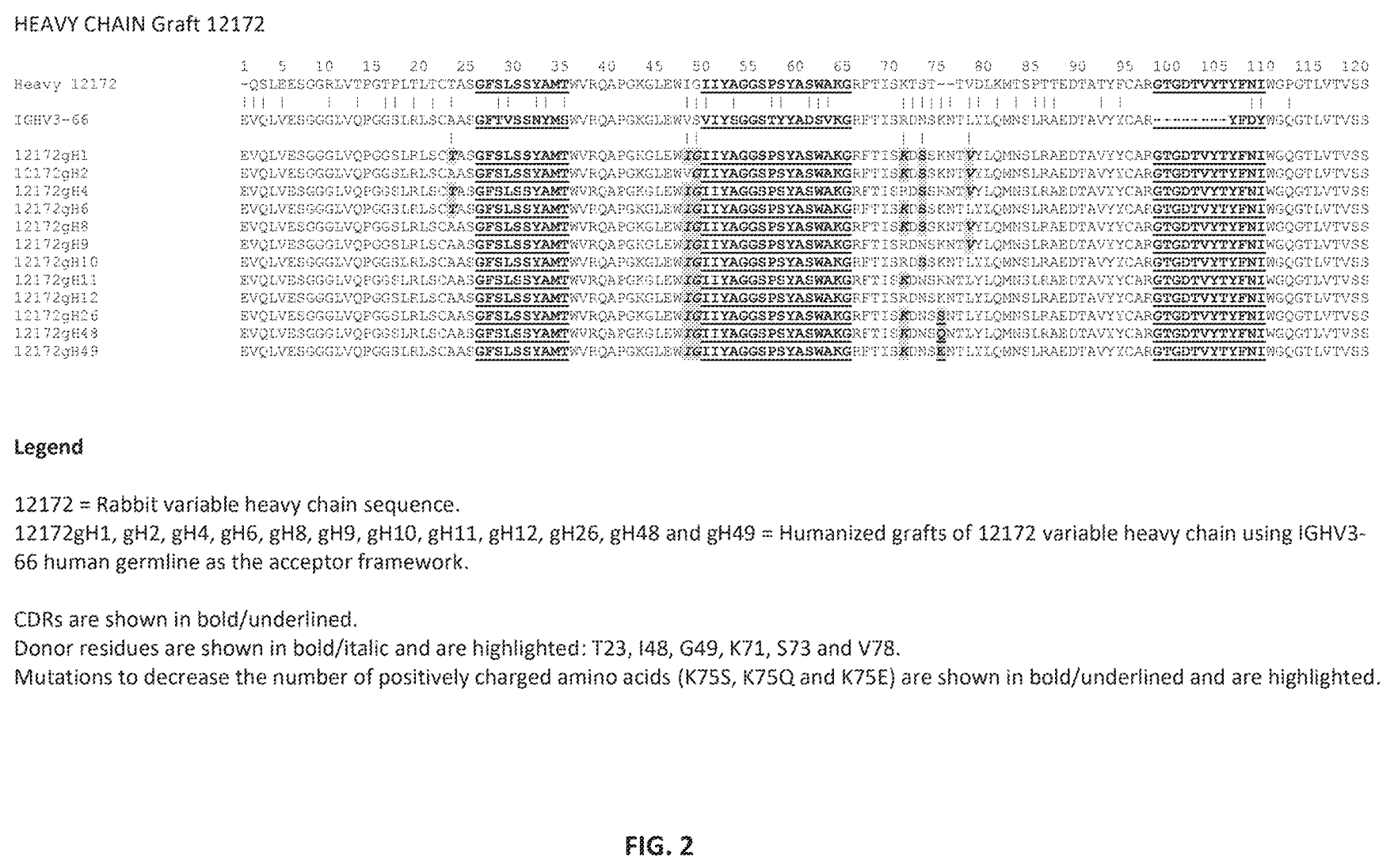

HEAVY CHAIN Graft 12172

```
             1   5    10   15   20   25   30   35   40   45   50   55   60   65   70   75   80   85   90   95   100  105  110  115  120
Heavy 12172  -QSLEESGGRLVTPGTPLTLTCTASGFSLSSYAMTWVRQAPGKGLEWIGIIYAGGSPSYASWAKGRFTISKTST--TVDLKMTSPTTEDTATYFCARGTGDTVYTYFNIWGPGTLVTVSS
IGHV3-66     EVQLVESGGGLVQPGGSLRLSCAASGFTVSSNYMSWVRQAPGKGLEWVSVIYSGGSTYYADSVKGRFTISRDNSKNTLYLQMNSLRAEDTAVYYCAR--------YFDYWGQGTLVTVSS

12172gH1     EVQLVESGGGLVQPGGSLRLSCTASGFSLSSYAMTWVRQAPGKGLEWIGIIYAGGSPSYASWAKGRFTISKDSSKNTVYLQMNSLRAEDTAVYYCARGTGDTVYTYFNIWGQGTLVTVSS
12172gH2     EVQLVESGGGLVQPGGSLRLSCAASGFSLSSYAMTWVRQAPGKGLEWVGIIYAGGSPSYASWAKGRFTISKDSSKNTVYLQMNSLRAEDTAVYYCARGTGDTVYTYFNIWGQGTLVTVSS
12172gH4     EVQLVESGGGLVQPGGSLRLSCTASGFSLSSYAMTWVRQAPGKGLEWIGIIYAGGSPSYASWAKGRFTISRDSSKNTVYLQMNSLRAEDTAVYYCARGTGDTVYTYFNIWGQGTLVTVSS
12172gH6     EVQLVESGGGLVQPGGSLRLSCTASGFSLSSYAMTWVRQAPGKGLEWIGIIYAGGSPSYASWAKGRFTISKDSSKNTLYLQMNSLRAEDTAVYYCARGTGDTVYTYFNIWGQGTLVTVSS
12172gH8     EVQLVESGGGLVQPGGSLRLSCAASGFSLSSYAMTWVRQAPGKGLEWIGIIYAGGSPSYASWAKGRFTISKDSSKNTVYLQMNSLRAEDTAVYYCARGTGDTVYTYFNIWGQGTLVTVSS
12172gH9     EVQLVESGGGLVQPGGSLRLSCAASGFSLSSYAMTWVRQAPGKGLEWIGIIYAGGSPSYASWAKGRFTISRDNSKNTVYLQMNSLRAEDTAVYYCARGTGDTVYTYFNIWGQGTLVTVSS
12172gH10    EVQLVESGGGLVQPGGSLRLSCAASGFSLSSYAMTWVRQAPGKGLEWIGIIYAGGSPSYASWAKGRFTISRDSSKNTLYLQMNSLRAEDTAVYYCARGTGDTVYTYFNIWGQGTLVTVSS
12172gH11    EVQLVESGGGLVQPGGSLRLSCAASGFSLSSYAMTWVRQAPGKGLEWIGIIYAGGSPSYASWAKGRFTISKDNSKNTLYLQMNSLRAEDTAVYYCARGTGDTVYTYFNIWGQGTLVTVSS
12172gH12    EVQLVESGGGLVQPGGSLRLSCAASGFSLSSYAMTWVRQAPGKGLEWIGIIYAGGSPSYASWAKGRFTISRDNSKNTLYLQMNSLRAEDTAVYYCARGTGDTVYTYFNIWGQGTLVTVSS
12172gH26    EVQLVESGGGLVQPGGSLRLSCAASGFSLSSYAMTWVRQAPGKGLEWIGIIYAGGSPSYASWAKGRFTISKDNSSNTLYLQMNSLRAEDTAVYYCARGTGDTVYTYFNIWGQGTLVTVSS
12172gH48    EVQLVESGGGLVQPGGSLRLSCAASGFSLSSYAMTWVRQAPGKGLEWIGIIYAGGSPSYASWAKGRFTISKDNSQNTLYLQMNSLRAEDTAVYYCARGTGDTVYTYFNIWGQGTLVTVSS
12172gH49    EVQLVESGGGLVQPGGSLRLSCAASGFSLSSYAMTWVRQAPGKGLEWIGIIYAGGSPSYASWAKGRFTISKDNSENTLYLQMNSLRAEDTAVYYCARGTGDTVYTYFNIWGQGTLVTVSS
```

Legend

12172 = Rabbit variable heavy chain sequence.
12172gH1, gH2, gH4, gH6, gH8, gH9, gH10, gH11, gH12, gH26, gH48 and gH49 = Humanized grafts of 12172 variable heavy chain using IGHV3-66 human germline as the acceptor framework.

CDRs are shown in bold/underlined.
Donor residues are shown in bold/italic and are highlighted: T23, I48, G49, K71, S73 and V78.
Mutations to decrease the number of positively charged amino acids (K75S, K75Q and K75E) are shown in bold/underlined and are highlighted.

FIG. 2

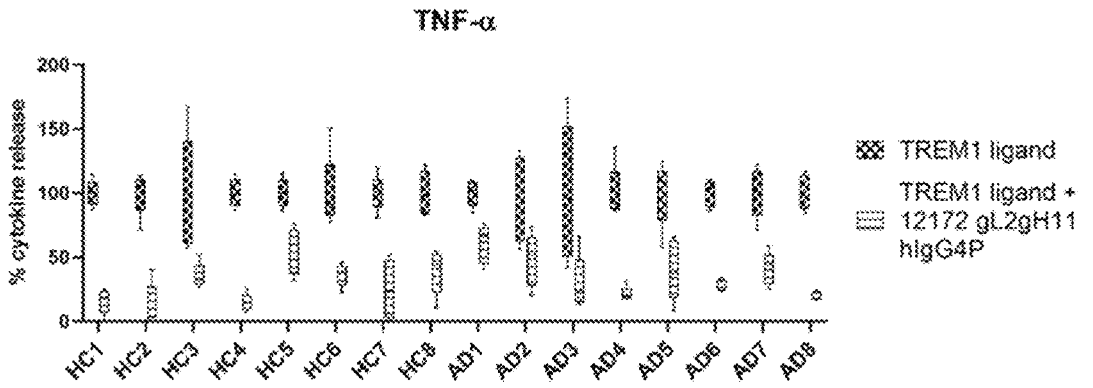
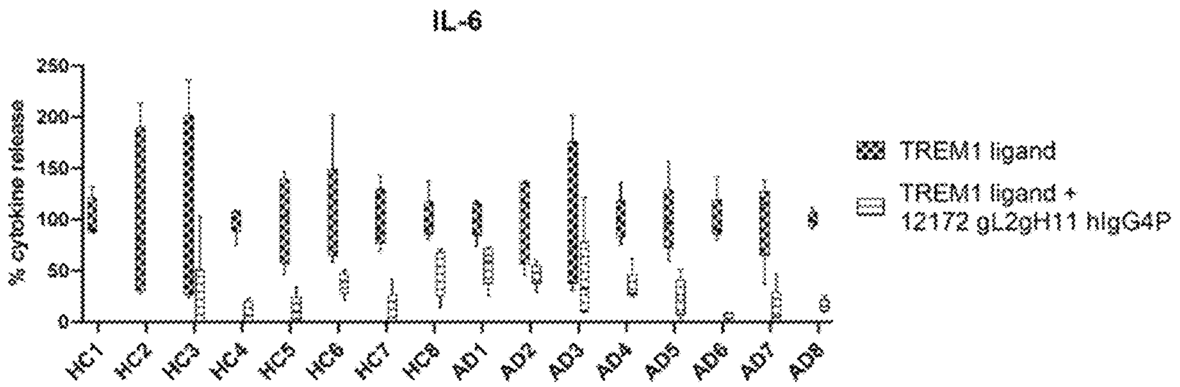
FIG. 8

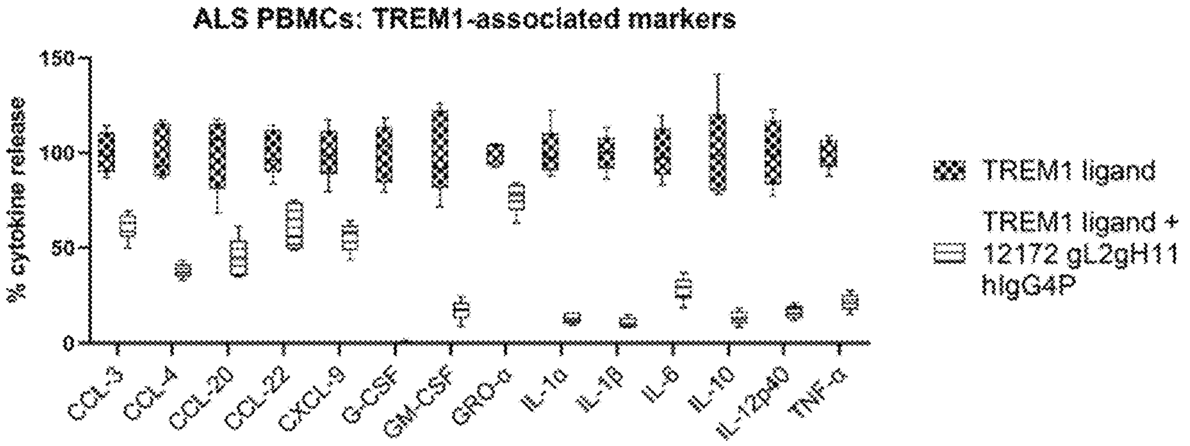
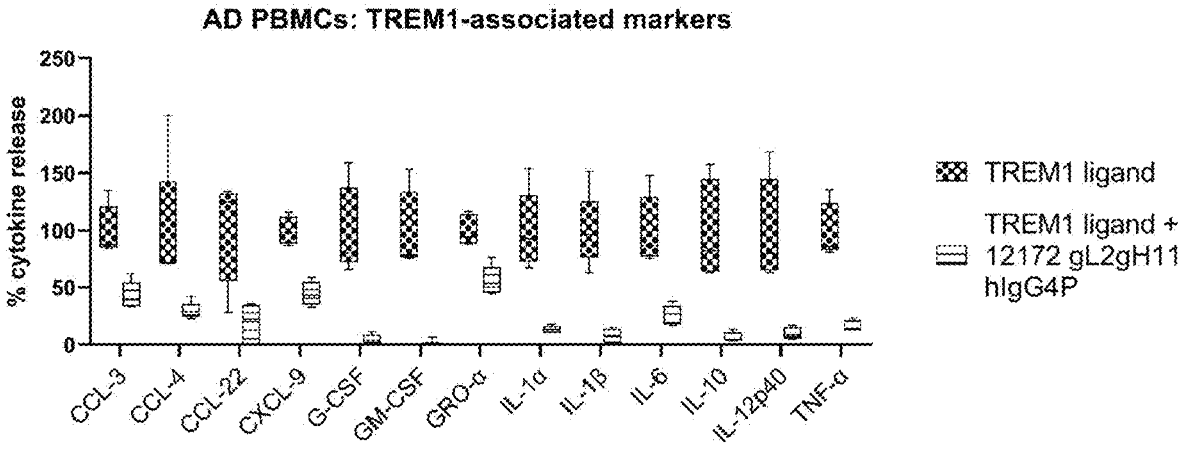
FIG. 10

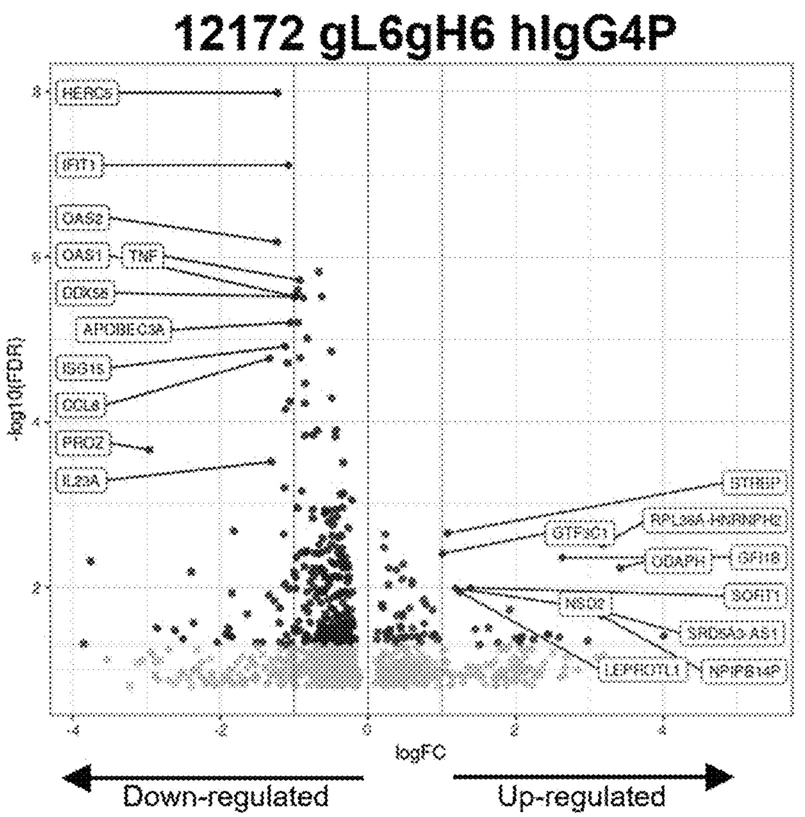
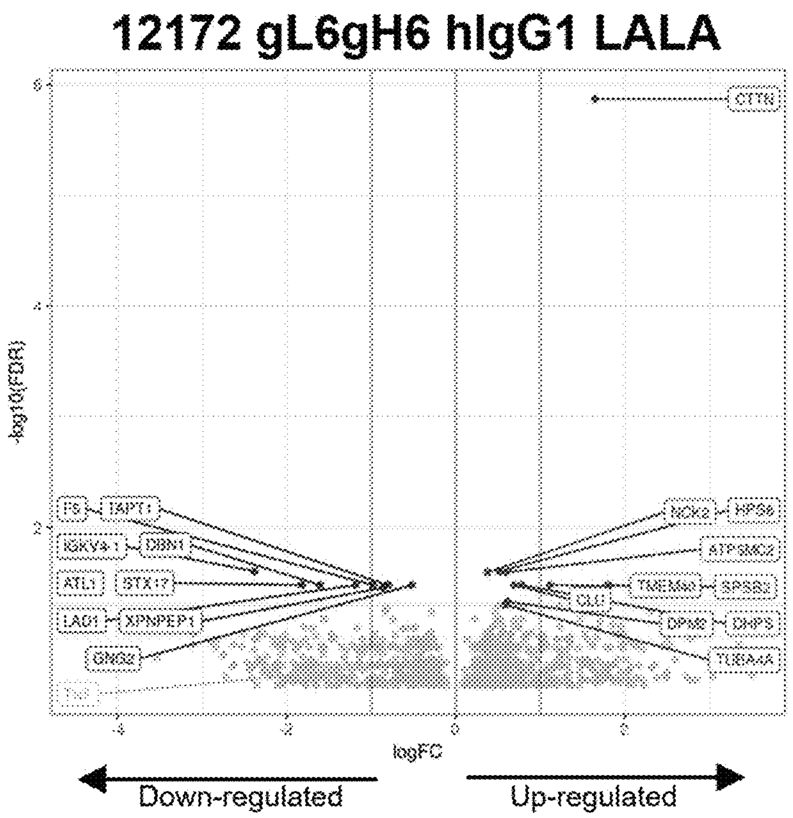
FIG. 11B

12172 gL2gH11 hIgG4P
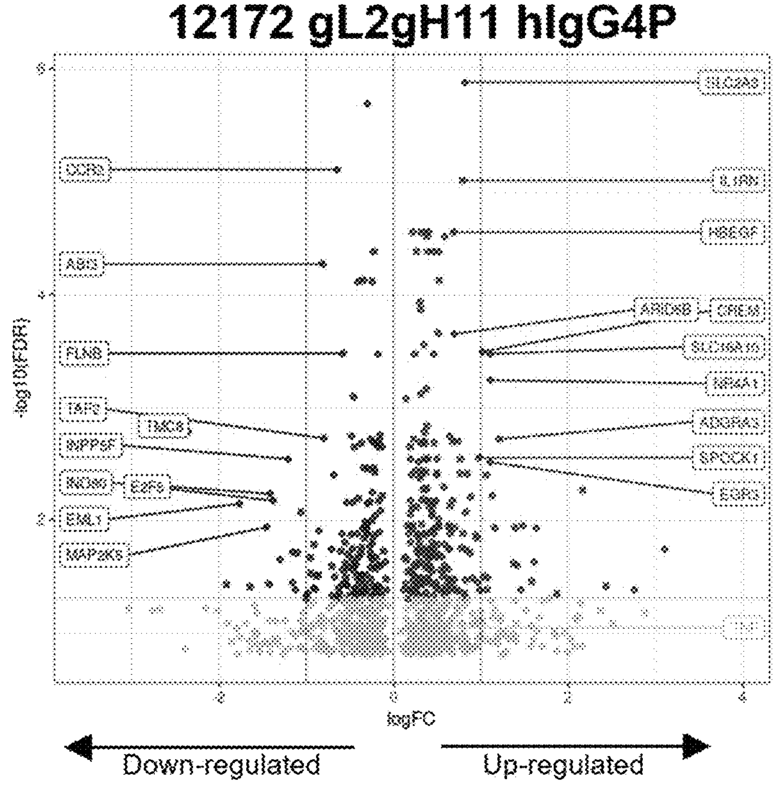
12172 gL2gH11 hIgG1 LALA
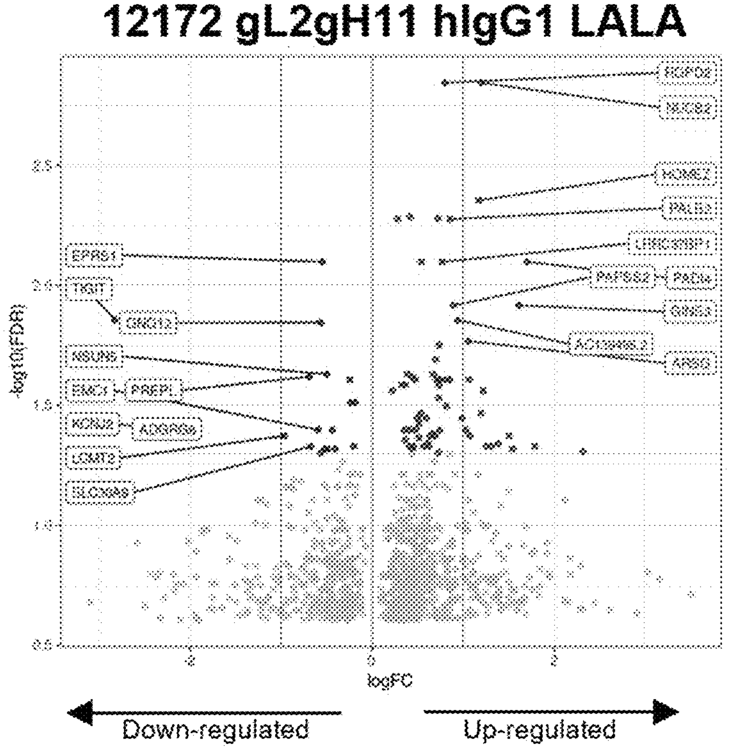
FIG. 12A

SEQUENCE LISTING

```
<160> NUMBER OF SEQ ID NOS: 294

<210> SEQ ID NO 1
<211> LENGTH: 234
<212> TYPE: PRT
<213> ORGANISM: Homo sapiens

<400> SEQUENCE: 1

Met Arg Lys Thr Arg Leu Trp Gly Leu Leu Trp Met Leu Phe Val Ser
```

```
1               5                   10                  15

Glu Leu Arg Ala Ala Thr Lys Leu Thr Glu Glu Lys Tyr Glu Leu Lys
            20                  25                  30

Glu Gly Gln Thr Leu Asp Val Lys Cys Asp Tyr Thr Leu Glu Lys Phe
        35                  40                  45

Ala Ser Ser Gln Lys Ala Trp Gln Ile Ile Arg Asp Gly Glu Met Pro
    50                  55                  60

Lys Thr Leu Ala Cys Thr Glu Arg Pro Ser Lys Asn Ser His Pro Val
65                  70                  75                  80

Gln Val Gly Arg Ile Ile Leu Glu Asp Tyr His Asp His Gly Leu Leu
                85                  90                  95

Arg Val Arg Met Val Asn Leu Gln Val Glu Asp Ser Gly Leu Tyr Gln
            100                 105                 110

Cys Val Ile Tyr Gln Pro Pro Lys Glu Pro His Met Leu Phe Asp Arg
        115                 120                 125

Ile Arg Leu Val Val Thr Lys Gly Phe Ser Gly Thr Pro Gly Ser Asn
    130                 135                 140

Glu Asn Ser Thr Gln Asn Val Tyr Lys Ile Pro Pro Thr Thr Thr Lys
145                 150                 155                 160

Ala Leu Cys Pro Leu Tyr Thr Ser Pro Arg Thr Val Thr Gln Ala Pro
                165                 170                 175

Pro Lys Ser Thr Ala Asp Val Ser Thr Pro Asp Ser Glu Ile Asn Leu
            180                 185                 190

Thr Asn Val Thr Asp Ile Ile Arg Val Pro Val Phe Asn Ile Val Ile
        195                 200                 205

Leu Leu Ala Gly Gly Phe Leu Ser Lys Ser Leu Val Phe Ser Val Leu
    210                 215                 220

Phe Ala Val Thr Leu Arg Ser Phe Val Pro
225                 230


<210> SEQ ID NO 2
<211> LENGTH: 214
<212> TYPE: PRT
<213> ORGANISM: Homo sapiens

<400> SEQUENCE: 2

Ala Thr Lys Leu Thr Glu Glu Lys Tyr Glu Leu Lys Glu Gly Gln Thr
1               5                   10                  15

Leu Asp Val Lys Cys Asp Tyr Thr Leu Glu Lys Phe Ala Ser Ser Gln
            20                  25                  30

Lys Ala Trp Gln Ile Ile Arg Asp Gly Glu Met Pro Lys Thr Leu Ala
        35                  40                  45

Cys Thr Glu Arg Pro Ser Lys Asn Ser His Pro Val Gln Val Gly Arg
    50                  55                  60

Ile Ile Leu Glu Asp Tyr His Asp His Gly Leu Leu Arg Val Arg Met
65                  70                  75                  80

Val Asn Leu Gln Val Glu Asp Ser Gly Leu Tyr Gln Cys Val Ile Tyr
                85                  90                  95

Gln Pro Pro Lys Glu Pro His Met Leu Phe Asp Arg Ile Arg Leu Val
            100                 105                 110

Val Thr Lys Gly Phe Ser Gly Thr Pro Gly Ser Asn Glu Asn Ser Thr
        115                 120                 125

Gln Asn Val Tyr Lys Ile Pro Pro Thr Thr Thr Lys Ala Leu Cys Pro
    130                 135                 140
```

Leu Tyr Thr Ser Pro Arg Thr Val Thr Gln Ala Pro Pro Lys Ser Thr
145 150 155 160

Ala Asp Val Ser Thr Pro Asp Ser Glu Ile Asn Leu Thr Asn Val Thr
165 170 175

Asp Ile Ile Arg Val Pro Val Phe Asn Ile Val Ile Leu Leu Ala Gly
180 185 190

Gly Phe Leu Ser Lys Ser Leu Val Phe Ser Val Leu Phe Ala Val Thr
195 200 205

Leu Arg Ser Phe Val Pro
210

<210> SEQ ID NO 3
<211> LENGTH: 225
<212> TYPE: PRT
<213> ORGANISM: Homo sapiens

<400> SEQUENCE: 3

Met Arg Lys Thr Arg Leu Trp Gly Leu Leu Trp Met Leu Phe Val Ser
1 5 10 15

Glu Leu Arg Ala Ala Thr Lys Leu Thr Glu Glu Lys Tyr Glu Leu Lys
20 25 30

Glu Gly Gln Thr Leu Asp Val Lys Cys Asp Tyr Thr Leu Glu Lys Phe
35 40 45

Ala Ser Ser Gln Lys Ala Trp Gln Ile Ile Arg Asp Gly Glu Met Pro
50 55 60

Lys Thr Leu Ala Cys Thr Glu Arg Pro Ser Lys Asn Ser His Pro Val
65 70 75 80

Gln Val Gly Arg Ile Ile Leu Glu Asp Tyr His Asp His Gly Leu Leu
85 90 95

Arg Val Arg Met Val Asn Leu Gln Val Glu Asp Ser Gly Leu Tyr Gln
100 105 110

Cys Val Ile Tyr Gln Pro Pro Lys Glu Pro His Met Leu Phe Asp Arg
115 120 125

Ile Arg Leu Val Val Thr Lys Gly Phe Ser Gly Thr Pro Gly Ser Asn
130 135 140

Glu Asn Ser Thr Gln Asn Val Tyr Lys Ile Pro Pro Thr Thr Thr Lys
145 150 155 160

Ala Leu Cys Pro Leu Tyr Thr Ser Pro Arg Thr Val Thr Gln Ala Pro
165 170 175

Pro Lys Ser Thr Ala Asp Val Ser Thr Pro Asp Ser Glu Ile Asn Leu
180 185 190

Thr Asn Val Thr Asp Ile Ile Arg Tyr Ser Phe Gln Val Pro Gly Pro
195 200 205

Leu Val Trp Thr Leu Ser Pro Leu Phe Pro Ser Leu Cys Ala Glu Arg
210 215 220

Met
225

<210> SEQ ID NO 4
<211> LENGTH: 150
<212> TYPE: PRT
<213> ORGANISM: Homo sapiens

<400> SEQUENCE: 4

Met Arg Lys Thr Arg Leu Trp Gly Leu Leu Trp Met Leu Phe Val Ser
1 5 10 15

```
Glu Leu Arg Ala Ala Thr Lys Leu Thr Glu Glu Lys Tyr Glu Leu Lys
            20                  25                  30

Glu Gly Gln Thr Leu Asp Val Lys Cys Asp Tyr Thr Leu Glu Lys Phe
        35                  40                  45

Ala Ser Ser Gln Lys Ala Trp Gln Ile Ile Arg Asp Gly Glu Met Pro
    50                  55                  60

Lys Thr Leu Ala Cys Thr Glu Arg Pro Ser Lys Asn Ser His Pro Val
65                  70                  75                  80

Gln Val Gly Arg Ile Ile Leu Glu Asp Tyr His Asp His Gly Leu Leu
                85                  90                  95

Arg Val Arg Met Val Asn Leu Gln Val Glu Asp Ser Gly Leu Tyr Gln
            100                 105                 110

Cys Val Ile Tyr Gln Pro Pro Lys Glu Pro His Met Leu Phe Asp Arg
        115                 120                 125

Ile Arg Leu Val Val Thr Lys Gly Phe Arg Cys Ser Thr Leu Ser Phe
    130                 135                 140

Ser Trp Leu Val Asp Ser
145                 150


<210> SEQ ID NO 5
<211> LENGTH: 233
<212> TYPE: PRT
<213> ORGANISM: Macaca mulatta

<400> SEQUENCE: 5

Met Arg Lys Thr Arg Leu Trp Gly Leu Leu Trp Met Leu Phe Val Ser
1               5                   10                  15

Glu Leu Arg Ala Thr Thr Glu Leu Thr Glu Glu Lys Tyr Glu Tyr Lys
            20                  25                  30

Glu Gly Gln Thr Leu Glu Val Lys Cys Asp Tyr Ala Leu Glu Lys Tyr
        35                  40                  45

Ala Asn Ser Arg Lys Ala Trp Gln Lys Met Glu Gly Lys Met Pro Lys
    50                  55                  60

Ile Leu Ala Lys Thr Glu Arg Pro Ser Glu Asn Ser His Pro Val Gln
65                  70                  75                  80

Val Gly Arg Ile Thr Leu Glu Asp Tyr Pro Asp His Gly Leu Leu Gln
                85                  90                  95

Val Gln Met Thr Asn Leu Gln Val Glu Asp Ser Gly Leu Tyr Gln Cys
            100                 105                 110

Val Ile Tyr Gln His Pro Lys Glu Ser His Val Leu Phe Asn Pro Ile
        115                 120                 125

Cys Leu Val Val Thr Lys Gly Ser Ser Gly Thr Pro Gly Ser Ser Glu
    130                 135                 140

Asn Ser Thr Gln Asn Val Tyr Arg Thr Pro Ser Thr Thr Ala Lys Ala
145                 150                 155                 160

Leu Gly Pro Arg Tyr Thr Ser Pro Arg Thr Val Thr Gln Ala Pro Pro
                165                 170                 175

Glu Ser Thr Val Val Val Ser Thr Pro Gly Ser Glu Ile Asn Leu Thr
            180                 185                 190

Asn Val Thr Asp Ile Ile Arg Val Pro Val Phe Asn Ile Val Ile Ile
        195                 200                 205

Val Ala Gly Gly Phe Leu Ser Lys Ser Leu Val Phe Ser Val Leu Phe
    210                 215                 220

Ala Val Thr Leu Arg Ser Phe Gly Pro
225                 230
```

<210> SEQ ID NO 6
<211> LENGTH: 196
<212> TYPE: PRT
<213> ORGANISM: Homo sapiens

<400> SEQUENCE: 6

```
Met Ser Arg Arg Ser Met Leu Leu Ala Trp Ala Leu Pro Ser Leu Leu
1               5                   10                  15

Arg Leu Gly Ala Ala Gln Glu Thr Glu Asp Pro Ala Cys Cys Ser Pro
            20                  25                  30

Ile Val Pro Arg Asn Glu Trp Lys Ala Leu Ala Ser Glu Cys Ala Gln
        35                  40                  45

His Leu Ser Leu Pro Leu Arg Tyr Val Val Val Ser His Thr Ala Gly
    50                  55                  60

Ser Ser Cys Asn Thr Pro Ala Ser Cys Gln Gln Gln Ala Arg Asn Val
65                  70                  75                  80

Gln His Tyr His Met Lys Thr Leu Gly Trp Cys Asp Val Gly Tyr Asn
                85                  90                  95

Phe Leu Ile Gly Glu Asp Gly Leu Val Tyr Glu Gly Arg Gly Trp Asn
            100                 105                 110

Phe Thr Gly Ala His Ser Gly His Leu Trp Asn Pro Met Ser Ile Gly
        115                 120                 125

Ile Ser Phe Met Gly Asn Tyr Met Asp Arg Val Pro Thr Pro Gln Ala
    130                 135                 140

Ile Arg Ala Ala Gln Gly Leu Leu Ala Cys Gly Val Ala Gln Gly Ala
145                 150                 155                 160

Leu Arg Ser Asn Tyr Val Leu Lys Gly His Arg Asp Val Gln Arg Thr
                165                 170                 175

Leu Ser Pro Gly Asn Gln Leu Tyr His Leu Ile Gln Asn Trp Pro His
            180                 185                 190

Tyr Arg Ser Pro
        195
```

<210> SEQ ID NO 7
<211> LENGTH: 263
<212> TYPE: PRT
<213> ORGANISM: Artificial Sequence
<220> FEATURE:
<223> OTHER INFORMATION: CID101904 hTREM1_1-200-Avi-Tev-HKH

<400> SEQUENCE: 7

```
Met Arg Lys Thr Arg Leu Trp Gly Leu Leu Trp Met Leu Phe Val Ser
1               5                   10                  15

Glu Leu Arg Ala Ala Thr Lys Leu Thr Glu Glu Lys Tyr Glu Leu Lys
            20                  25                  30

Glu Gly Gln Thr Leu Asp Val Lys Cys Asp Tyr Thr Leu Glu Lys Phe
        35                  40                  45

Ala Ser Ser Gln Lys Ala Trp Gln Ile Ile Arg Asp Gly Glu Met Pro
    50                  55                  60

Lys Thr Leu Ala Cys Thr Glu Arg Pro Ser Lys Asn Ser His Pro Val
65                  70                  75                  80

Gln Val Gly Arg Ile Ile Leu Glu Asp Tyr His Asp His Gly Leu Leu
                85                  90                  95

Arg Val Arg Met Val Asn Leu Gln Val Glu Asp Ser Gly Leu Tyr Gln
            100                 105                 110
```

```
Cys Val Ile Tyr Gln Pro Pro Lys Glu Pro His Met Leu Phe Asp Arg
        115                 120                 125

Ile Arg Leu Val Val Thr Lys Gly Phe Ser Gly Thr Pro Gly Ser Asn
    130                 135                 140

Glu Asn Ser Thr Gln Asn Val Tyr Lys Ile Pro Pro Thr Thr Thr Lys
145                 150                 155                 160

Ala Leu Cys Pro Leu Tyr Thr Ser Pro Arg Thr Val Thr Gln Ala Pro
                165                 170                 175

Pro Lys Ser Thr Ala Asp Val Ser Thr Pro Asp Ser Glu Ile Asn Leu
            180                 185                 190

Thr Asn Val Thr Asp Ile Ile Arg Leu Glu Gly Gly Gly Ser Gly Gly
        195                 200                 205

Ser Gly Gly Leu Asn Asp Ile Phe Glu Ala Gln Lys Ile Glu Trp His
    210                 215                 220

Glu Asn Leu Tyr Phe Gln Gly Gly Ser His His His His His His Lys
225                 230                 235                 240

Ala Lys Gly Ser Lys Gly Lys Gly Ser Lys Lys Ala Gly His His His
                245                 250                 255

His His His His His His His
            260
```

<210> SEQ ID NO 8
<211> LENGTH: 264
<212> TYPE: PRT
<213> ORGANISM: Artificial Sequence
<220> FEATURE:
<223> OTHER INFORMATION: CID101953 cTREM1_1-201-Avi-Tev-HKH

<400> SEQUENCE: 8

```
Met Arg Lys Thr Arg Leu Trp Gly Leu Leu Trp Met Leu Phe Val Ser
1               5                   10                  15

Glu Leu Arg Ala Thr Thr Glu Leu Thr Glu Glu Lys Tyr Glu Tyr Lys
            20                  25                  30

Glu Gly Gln Thr Leu Glu Val Lys Cys Asp Tyr Ala Leu Glu Lys Tyr
        35                  40                  45

Ala Asn Ser Arg Lys Ala Trp Gln Lys Met Glu Gly Lys Met Pro Lys
    50                  55                  60

Ile Leu Ala Lys Thr Glu Arg Pro Ser Glu Asn Ser His Pro Val Gln
65                  70                  75                  80

Val Gly Arg Ile Thr Leu Glu Asp Tyr Pro Asp His Gly Leu Leu Gln
                85                  90                  95

Val Arg Met Thr Asn Leu Gln Val Glu Asp Ser Gly Leu Tyr Gln Cys
            100                 105                 110

Val Ile Tyr Gln His Pro Lys Glu Ser His Val Leu Phe Asn Pro Ile
        115                 120                 125

Cys Leu Val Val Thr Lys Gly Ser Ser Gly Thr Pro Gly Ser Ser Glu
    130                 135                 140

Asn Ser Thr Gln Asn Val Tyr Arg Thr Pro Ser Thr Thr Ala Lys Ala
145                 150                 155                 160

Leu Gly Pro Arg Tyr Thr Ser Pro Arg Thr Val Thr Gln Ala Pro Pro
                165                 170                 175

Glu Ser Thr Val Val Val Ser Thr Pro Gly Ser Glu Ile Asn Leu Thr
            180                 185                 190

Asn Val Thr Asp Ile Ile Arg Val Pro Leu Glu Gly Gly Gly Ser Gly
        195                 200                 205
```

```
Gly Ser Gly Gly Leu Asn Asp Ile Phe Glu Ala Gln Lys Ile Glu Trp
    210                 215                 220

His Glu Asn Leu Tyr Phe Gln Gly Gly Ser His His His His His His
225                 230                 235                 240

Lys Ala Lys Gly Ser Lys Gly Lys Gly Ser Lys Lys Ala Gly His His
                245                 250                 255

His His His His His His His His
            260


<210> SEQ ID NO 9
<211> LENGTH: 215
<212> TYPE: PRT
<213> ORGANISM: Artificial Sequence
<220> FEATURE:
<223> OTHER INFORMATION: CID101907 hTREM1 IgV (His-Smt-TREM1_21-139)

<400> SEQUENCE: 9

Met Gly His His His His His His Ser Gly Glu Val Lys Pro Glu Val
1               5                   10                  15

Lys Pro Glu Thr His Ile Asn Leu Lys Val Ser Asp Gly Ser Ser Glu
            20                  25                  30

Ile Phe Phe Lys Ile Lys Lys Thr Thr Pro Leu Arg Arg Leu Met Glu
        35                  40                  45

Ala Phe Ala Lys Arg Gln Gly Lys Glu Met Asp Ser Leu Arg Phe Leu
    50                  55                  60

Tyr Asp Gly Ile Arg Ile Gln Ala Asp Gln Thr Pro Glu Asp Leu Asp
65                  70                  75                  80

Met Glu Asp Asn Asp Ile Ile Glu Ala His Arg Glu Gln Ile Gly Gly
                85                  90                  95

Ala Thr Lys Leu Thr Glu Glu Lys Tyr Glu Leu Lys Glu Gly Gln Thr
            100                 105                 110

Leu Asp Val Lys Cys Asp Tyr Thr Leu Glu Lys Phe Ala Ser Ser Gln
        115                 120                 125

Lys Ala Trp Gln Ile Ile Arg Asp Gly Glu Met Pro Lys Thr Leu Ala
    130                 135                 140

Cys Thr Glu Arg Pro Ser Lys Asn Ser His Pro Val Gln Val Gly Arg
145                 150                 155                 160

Ile Ile Leu Glu Asp Tyr His Asp His Gly Leu Leu Arg Val Arg Met
                165                 170                 175

Val Asn Leu Gln Val Glu Asp Ser Gly Leu Tyr Gln Cys Val Ile Tyr
            180                 185                 190

Gln Pro Pro Lys Glu Pro His Met Leu Phe Asp Arg Ile Arg Leu Val
        195                 200                 205

Val Thr Lys Gly Phe Ser Gly
    210                 215


<210> SEQ ID NO 10
<211> LENGTH: 202
<212> TYPE: PRT
<213> ORGANISM: Artificial Sequence
<220> FEATURE:
<223> OTHER INFORMATION: CID101951 hPGLYRP1_1-196-His

<400> SEQUENCE: 10

Met Ser Arg Arg Ser Met Leu Leu Ala Trp Ala Leu Pro Ser Leu Leu
1               5                   10                  15

Arg Leu Gly Ala Ala Gln Glu Thr Glu Asp Pro Ala Cys Cys Ser Pro
            20                  25                  30
```

-continued

Ile Val Pro Arg Asn Glu Trp Lys Ala Leu Ala Ser Glu Cys Ala Gln
35 40 45

His Leu Ser Leu Pro Leu Arg Tyr Val Val Val Ser His Thr Ala Gly
50 55 60

Ser Ser Cys Asn Thr Pro Ala Ser Cys Gln Gln Gln Ala Arg Asn Val
65 70 75 80

Gln His Tyr His Met Lys Thr Leu Gly Trp Cys Asp Val Gly Tyr Asn
85 90 95

Phe Leu Ile Gly Glu Asp Gly Leu Val Tyr Glu Gly Arg Gly Trp Asn
100 105 110

Phe Thr Gly Ala His Ser Gly His Leu Trp Asn Pro Met Ser Ile Gly
115 120 125

Ile Ser Phe Met Gly Asn Tyr Met Asp Arg Val Pro Thr Pro Gln Ala
130 135 140

Ile Arg Ala Ala Gln Gly Leu Leu Ala Cys Gly Val Ala Gln Gly Ala
145 150 155 160

Leu Arg Ser Asn Tyr Val Leu Lys Gly His Arg Asp Val Gln Arg Thr
165 170 175

Leu Ser Pro Gly Asn Gln Leu Tyr His Leu Ile Gln Asn Trp Pro His
180 185 190

Tyr Arg Ser Pro His His His His His His
195 200

<210> SEQ ID NO 11
<211> LENGTH: 11
<212> TYPE: PRT
<213> ORGANISM: Artificial Sequence
<220> FEATURE:
<223> OTHER INFORMATION: CDRL1

<400> SEQUENCE: 11

Gln Ala Ser Gln Asn Ile Gly Ser Asp Leu Ala
1 5 10

<210> SEQ ID NO 12
<211> LENGTH: 7
<212> TYPE: PRT
<213> ORGANISM: Artificial Sequence
<220> FEATURE:
<223> OTHER INFORMATION: CDRL2

<400> SEQUENCE: 12

Lys Ala Ala Thr Leu Ala Ser
1 5

<210> SEQ ID NO 13
<211> LENGTH: 14
<212> TYPE: PRT
<213> ORGANISM: Artificial Sequence
<220> FEATURE:
<223> OTHER INFORMATION: CDRL3

<400> SEQUENCE: 13

Gln Gln Tyr Tyr Tyr Gly Ser Ala Gly Ala Asp Thr Asp Thr
1 5 10

<210> SEQ ID NO 14
<211> LENGTH: 10
<212> TYPE: PRT
<213> ORGANISM: Artificial Sequence
<220> FEATURE:

<223> OTHER INFORMATION: CDRH1

<400> SEQUENCE: 14

Gly Phe Ser Leu Ser Ser Tyr Ala Met Thr
1 5 10

<210> SEQ ID NO 15
<211> LENGTH: 16
<212> TYPE: PRT
<213> ORGANISM: Artificial Sequence
<220> FEATURE:
<223> OTHER INFORMATION: CDRH2

<400> SEQUENCE: 15

Ile Ile Tyr Ala Gly Gly Ser Pro Ser Tyr Ala Ser Trp Ala Lys Gly
1 5 10 15

<210> SEQ ID NO 16
<211> LENGTH: 12
<212> TYPE: PRT
<213> ORGANISM: Artificial Sequence
<220> FEATURE:
<223> OTHER INFORMATION: CDRH3

<400> SEQUENCE: 16

Gly Thr Gly Asp Thr Val Tyr Thr Tyr Phe Asn Ile
1 5 10

<210> SEQ ID NO 17
<211> LENGTH: 112
<212> TYPE: PRT
<213> ORGANISM: Artificial Sequence
<220> FEATURE:
<223> OTHER INFORMATION: Rabbit Ab 12172 VL region

<400> SEQUENCE: 17

Ala Val Val Leu Thr Gln Thr Ala Ser Pro Val Ser Ala Pro Val Gly
1 5 10 15

Gly Thr Val Thr Ile Lys Cys Gln Ala Ser Gln Asn Ile Gly Ser Asp
20 25 30

Leu Ala Trp Tyr Gln Gln Glu Pro Gly Gln Pro Pro Lys Leu Leu Ile
35 40 45

Tyr Lys Ala Ala Thr Leu Ala Ser Gly Val Pro Ser Arg Phe Lys Gly
50 55 60

Ser Gly Ser Gly Thr Glu Phe Thr Leu Thr Ile Ser Gly Val Gln Cys
65 70 75 80

Glu Asp Gly Ala Thr Tyr Tyr Cys Gln Gln Tyr Tyr Tyr Gly Ser Ala
85 90 95

Gly Ala Asp Thr Asp Thr Phe Gly Gly Gly Thr Glu Val Val Val Lys
100 105 110

<210> SEQ ID NO 18
<211> LENGTH: 336
<212> TYPE: DNA
<213> ORGANISM: Artificial Sequence
<220> FEATURE:
<223> OTHER INFORMATION: Rabbit Ab 12172 VL region

<400> SEQUENCE: 18
gccgtcgtgc tgacccagac tgcatccccc gtgtctgcac ctgtgggagg cacagtcacc 60
atcaagtgcc aggccagtca gaacattggt agcgacttag cctggtatca gcaggaacca 120
gggcagccac ccaagctcct gatctacaag gcagccactc tggcatctgg ggtcccatcg 180

```
cggttcaaag gcagtggatc tgggacagag ttcactctca ccatcagtgg cgtgcagtgt    240

gaagatggtg ccacttacta ctgtcaacag tattattatg gtagtgctgg tgctgatacg    300

gatactttcg gcggagggac cgaggtggtg gtcaaa                              336


<210> SEQ ID NO 19
<211> LENGTH: 216
<212> TYPE: PRT
<213> ORGANISM: Artificial Sequence
<220> FEATURE:
<223> OTHER INFORMATION: CID102770: Rabbit Ab 12172 light chain (Fab)

<400> SEQUENCE: 19

Ala Val Val Leu Thr Gln Thr Ala Ser Pro Val Ser Ala Pro Val Gly
1               5                   10                  15

Gly Thr Val Thr Ile Lys Cys Gln Ala Ser Gln Asn Ile Gly Ser Asp
            20                  25                  30

Leu Ala Trp Tyr Gln Gln Glu Pro Gly Gln Pro Pro Lys Leu Leu Ile
        35                  40                  45

Tyr Lys Ala Ala Thr Leu Ala Ser Gly Val Pro Ser Arg Phe Lys Gly
    50                  55                  60

Ser Gly Ser Gly Thr Glu Phe Thr Leu Thr Ile Ser Gly Val Gln Cys
65                  70                  75                  80

Glu Asp Gly Ala Thr Tyr Tyr Cys Gln Gln Tyr Tyr Tyr Gly Ser Ala
                85                  90                  95

Gly Ala Asp Thr Asp Thr Phe Gly Gly Gly Thr Glu Val Val Val Lys
            100                 105                 110

Arg Thr Pro Val Ala Pro Thr Val Leu Ile Phe Pro Pro Ala Ala Asp
        115                 120                 125

Gln Val Ala Thr Gly Thr Val Thr Ile Val Cys Val Ala Asn Lys Tyr
    130                 135                 140

Phe Pro Asp Val Thr Val Thr Trp Glu Val Asp Gly Thr Thr Gln Thr
145                 150                 155                 160

Thr Gly Ile Glu Asn Ser Lys Thr Pro Gln Asn Ser Ala Asp Cys Thr
                165                 170                 175

Tyr Asn Leu Ser Ser Thr Leu Thr Leu Thr Ser Thr Gln Tyr Asn Ser
            180                 185                 190

His Lys Glu Tyr Thr Cys Lys Val Thr Gln Gly Thr Thr Ser Val Val
        195                 200                 205

Gln Ser Phe Asn Arg Gly Asp Cys
    210                 215


<210> SEQ ID NO 20
<211> LENGTH: 648
<212> TYPE: DNA
<213> ORGANISM: Artificial Sequence
<220> FEATURE:
<223> OTHER INFORMATION: Rabbit Ab 12172 light chain

<400> SEQUENCE: 20

gccgtcgtgc tgacccagac tgcatccccc gtgtctgcac ctgtgggagg cacagtcacc     60

atcaagtgcc aggccagtca gaacattggt agcgacttag cctggtatca gcaggaacca    120

gggcagccac ccaagctcct gatctacaag gcagccactc tggcatctgg ggtcccatcg    180

cggttcaaag gcagtggatc tgggacagag ttcactctca ccatcagtgg cgtgcagtgt    240

gaagatggtg ccacttacta ctgtcaacag tattattatg gtagtgctgg tgctgatacg    300
```

gatactttcg gcggagggac cgaggtggtg gtcaaacgta cgccagttgc acctactgtc 360
ctcatcttcc caccagctgc tgatcaggtg gcaactggaa cagtcaccat cgtgtgtgtg 420
gcgaataaat actttcccga tgtcaccgtc acctgggagg tggatggcac cacccaaaca 480
actggcatcg agaacagtaa aacaccgcag aattctgcag attgtaccta caacctcagc 540
agcactctga cactgaccag cacacagtac aacagccaca aagagtacac ctgcaaggtg 600
acccagggca cgacctcagt cgtccagagc ttcaataggg gtgactgt 648

<210> SEQ ID NO 21
<211> LENGTH: 117
<212> TYPE: PRT
<213> ORGANISM: Artificial Sequence
<220> FEATURE:
<223> OTHER INFORMATION: Rabbit Ab 12172 VH region

<400> SEQUENCE: 21

Gln Ser Leu Glu Glu Ser Gly Gly Arg Leu Val Thr Pro Gly Thr Pro
1 5 10 15

Leu Thr Leu Thr Cys Thr Ala Ser Gly Phe Ser Leu Ser Ser Tyr Ala
20 25 30

Met Thr Trp Val Arg Gln Ala Pro Gly Lys Gly Leu Glu Trp Ile Gly
35 40 45

Ile Ile Tyr Ala Gly Gly Ser Pro Ser Tyr Ala Ser Trp Ala Lys Gly
50 55 60

Arg Phe Thr Ile Ser Lys Thr Ser Thr Thr Val Asp Leu Lys Met Thr
65 70 75 80

Ser Pro Thr Thr Glu Asp Thr Ala Thr Tyr Phe Cys Ala Arg Gly Thr
85 90 95

Gly Asp Thr Val Tyr Thr Tyr Phe Asn Ile Trp Gly Pro Gly Thr Leu
100 105 110

Val Thr Val Ser Ser
115

<210> SEQ ID NO 22
<211> LENGTH: 351
<212> TYPE: DNA
<213> ORGANISM: Artificial Sequence
<220> FEATURE:
<223> OTHER INFORMATION: Rabbit Ab 12172 VH region

<400> SEQUENCE: 22
cagtcgctgg aggagtccgg gggtcgcctg gtcacgcctg ggacacccct gacactcacc 60
tgcacagcct ctggattctc cctcagtagc tatgcaatga cctgggtccg ccaggctcca 120
gggaaggggc tggaatggat cggaatcatt tatgctggtg gtagcccatc ctacgcgagc 180
tgggcgaaag gccgattcac catctccaaa acctcgacca cggtggatct gaaaatgacc 240
agtccgacaa ccgaggacac ggccacctat ttctgtgcca gagggactgg tgatactgtt 300
tatacctact ttaatatttg gggcccaggc accctggtca ccgtctcgag t 351

<210> SEQ ID NO 23
<211> LENGTH: 220
<212> TYPE: PRT
<213> ORGANISM: Artificial Sequence
<220> FEATURE:
<223> OTHER INFORMATION: CID120769: Rabbit Ab 12172 heavy chain (Fab)

<400> SEQUENCE: 23

Gln Ser Leu Glu Glu Ser Gly Gly Arg Leu Val Thr Pro Gly Thr Pro

```
1               5                   10                  15

Leu Thr Leu Thr Cys Thr Ala Ser Gly Phe Ser Leu Ser Ser Tyr Ala
            20                  25                  30

Met Thr Trp Val Arg Gln Ala Pro Gly Lys Gly Leu Glu Trp Ile Gly
        35                  40                  45

Ile Ile Tyr Ala Gly Gly Ser Pro Ser Tyr Ala Ser Trp Ala Lys Gly
    50                  55                  60

Arg Phe Thr Ile Ser Lys Thr Ser Thr Thr Val Asp Leu Lys Met Thr
65                  70                  75                  80

Ser Pro Thr Thr Glu Asp Thr Ala Thr Tyr Phe Cys Ala Arg Gly Thr
                85                  90                  95

Gly Asp Thr Val Tyr Thr Tyr Phe Asn Ile Trp Gly Pro Gly Thr Leu
            100                 105                 110

Val Thr Val Ser Ser Gly Gln Pro Lys Ala Pro Ser Val Phe Pro Leu
        115                 120                 125

Ala Pro Cys Cys Gly Asp Thr Pro Ser Ser Thr Val Thr Leu Gly Cys
    130                 135                 140

Leu Val Lys Gly Tyr Leu Pro Glu Pro Val Thr Val Thr Trp Asn Ser
145                 150                 155                 160

Gly Thr Leu Thr Asn Gly Val Arg Thr Phe Pro Ser Val Arg Gln Ser
                165                 170                 175

Ser Gly Leu Tyr Ser Leu Ser Ser Val Val Ser Val Thr Ser Ser Ser
            180                 185                 190

Gln Pro Val Thr Cys Asn Val Ala His Pro Ala Thr Asn Thr Lys Val
        195                 200                 205

Asp Lys Thr Val Ala Pro Ser Thr Cys Ser Lys Pro
    210                 215                 220
```

<210> SEQ ID NO 24
<211> LENGTH: 660
<212> TYPE: DNA
<213> ORGANISM: Artificial Sequence
<220> FEATURE:
<223> OTHER INFORMATION: Rabbit Ab 12172 heavy chain (Fab)

<400> SEQUENCE: 24

```
cagtcgctgg aggagtccgg gggtcgcctg gtcacgcctg ggacacccct gacactcacc     60

tgcacagcct ctggattctc cctcagtagc tatgcaatga cctgggtccg ccaggctcca    120

gggaaggggc tggaatggat cggaatcatt tatgctggtg gtagcccatc ctacgcgagc    180

tgggcgaaag gccgattcac catctccaaa acctcgacca cggtggatct gaaaatgacc    240

agtccgacaa ccgaggacac ggccacctat ttctgtgcca gagggactgg tgatactgtt    300

tatacctact ttaatatttg gggcccaggc accctggtca ccgtctcgag tgggcaacct    360

aaggctccat cagtcttccc actggccccc tgctgcgggg acacacccag ctccacggtg    420

accctgggct gcctggtcaa aggctacctc ccggagccag tgaccgtgac ctggaactcg    480

ggcaccctca ccaatggggt acgcaccttc ccgtccgtcc ggcagtcctc aggcctctac    540

tcgctgagca gcgtggtgag cgtgacctca agcagccagc ccgtcacctg caacgtggcc    600

cacccagcca ccaacaccaa agtggacaag accgttgcgc cctcgacatg cagcaagccc    660
```

<210> SEQ ID NO 25
<211> LENGTH: 112
<212> TYPE: PRT
<213> ORGANISM: Artificial Sequence
<220> FEATURE:

<223> OTHER INFORMATION: 12172gL1 V-region

<400> SEQUENCE: 25

Ala Val Val Leu Thr Gln Ser Pro Ser Phe Leu Ser Ala Ser Val Gly
1 5 10 15

Asp Arg Val Thr Ile Thr Cys Gln Ala Ser Gln Asn Ile Gly Ser Asp
20 25 30

Leu Ala Trp Tyr Gln Gln Lys Pro Gly Lys Ala Pro Lys Leu Leu Ile
35 40 45

Tyr Lys Ala Ala Thr Leu Ala Ser Gly Val Pro Ser Arg Phe Ser Gly
50 55 60

Ser Gly Ser Gly Thr Glu Phe Thr Leu Thr Ile Ser Ser Leu Gln Pro
65 70 75 80

Glu Asp Phe Ala Thr Tyr Tyr Cys Gln Gln Tyr Tyr Tyr Gly Ser Ala
85 90 95

Gly Ala Asp Thr Asp Thr Phe Gly Gly Gly Thr Lys Val Glu Ile Lys
100 105 110

<210> SEQ ID NO 26
<211> LENGTH: 336
<212> TYPE: DNA
<213> ORGANISM: Artificial Sequence
<220> FEATURE:
<223> OTHER INFORMATION: 12172gL1 V-region

<400> SEQUENCE: 26
gccgtggtgc tgactcagtc cccctccttc ctgagcgcct cagtgggaga tcgcgtgacc 60
atcacctgtc aagccagcca gaacattggg tccgacttgg cctggtatca gcagaagcct 120
ggcaaagcgc cgaagctgct gatctacaag gccgctactc tcgcgtcggg agtgccatcc 180
cggttttccg gttcgggaag cgggaccgag ttcaccctta ccatttcctc gctccaaccg 240
gaggacttcg ccacgtacta ctgccagcag tactactacg gttcagccgg agcagacact 300
gataccttcg gcggaggcac caaggtcgaa atcaag 336

<210> SEQ ID NO 27
<211> LENGTH: 219
<212> TYPE: PRT
<213> ORGANISM: Artificial Sequence
<220> FEATURE:
<223> OTHER INFORMATION: 12172gL1 light chain

<400> SEQUENCE: 27

Ala Val Val Leu Thr Gln Ser Pro Ser Phe Leu Ser Ala Ser Val Gly
1 5 10 15

Asp Arg Val Thr Ile Thr Cys Gln Ala Ser Gln Asn Ile Gly Ser Asp
20 25 30

Leu Ala Trp Tyr Gln Gln Lys Pro Gly Lys Ala Pro Lys Leu Leu Ile
35 40 45

Tyr Lys Ala Ala Thr Leu Ala Ser Gly Val Pro Ser Arg Phe Ser Gly
50 55 60

Ser Gly Ser Gly Thr Glu Phe Thr Leu Thr Ile Ser Ser Leu Gln Pro
65 70 75 80

Glu Asp Phe Ala Thr Tyr Tyr Cys Gln Gln Tyr Tyr Tyr Gly Ser Ala
85 90 95

Gly Ala Asp Thr Asp Thr Phe Gly Gly Gly Thr Lys Val Glu Ile Lys
100 105 110

Arg Thr Val Ala Ala Pro Ser Val Phe Ile Phe Pro Pro Ser Asp Glu

```
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215


<210> SEQ ID NO 28
<211> LENGTH: 657
<212> TYPE: DNA
<213> ORGANISM: Artificial Sequence
<220> FEATURE:
<223> OTHER INFORMATION: 12172gL1 light chain

<400> SEQUENCE: 28

gccgtggtgc tgactcagtc cccctccttc ctgagcgcct cagtgggaga tcgcgtgacc     60

atcacctgtc aagccagcca gaacattggg tccgacttgg cctggtatca gcagaagcct    120

ggcaaagcgc cgaagctgct gatctacaag gccgctactc tcgcgtcggg agtgccatcc    180

cggttttccg gttcgggaag cgggaccgag ttcaccctta ccatttcctc gctccaaccg    240

gaggacttcg ccacgtacta ctgccagcag tactactacg gttcagccgg agcagacact    300

gataccttcg gcggaggcac caaggtcgaa atcaagcgta cggtagcggc cccatctgtc    360

ttcatcttcc cgccatctga tgagcagttg aaatctggaa ctgcctctgt tgtgtgcctg    420

ctgaataact tctatcccag agaggccaaa gtacagtgga aggtggataa cgccctccaa    480

tcgggtaact cccaggagag tgtcacagag caggacagca aggacagcac ctacagcctc    540

agcagcaccc tgacgctgag caaagcagac tacgagaaac acaaagtcta cgcctgcgaa    600

gtcacccatc agggcctgag ctcgcccgtc acaaagagct tcaacagggg agagtgt       657


<210> SEQ ID NO 29
<211> LENGTH: 112
<212> TYPE: PRT
<213> ORGANISM: Artificial Sequence
<220> FEATURE:
<223> OTHER INFORMATION: 12172gL2 V-region

<400> SEQUENCE: 29

Asp Ile Gln Leu Thr Gln Ser Pro Ser Phe Leu Ser Ala Ser Val Gly
1               5                   10                  15

Asp Arg Val Thr Ile Thr Cys Gln Ala Ser Gln Asn Ile Gly Ser Asp
            20                  25                  30

Leu Ala Trp Tyr Gln Gln Lys Pro Gly Lys Ala Pro Lys Leu Leu Ile
        35                  40                  45

Tyr Lys Ala Ala Thr Leu Ala Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Tyr Tyr Tyr Gly Ser Ala
                85                  90                  95
```

```
Gly Ala Asp Thr Asp Thr Phe Gly Gly Gly Thr Lys Val Glu Ile Lys
            100                 105                 110


<210> SEQ ID NO 30
<211> LENGTH: 336
<212> TYPE: DNA
<213> ORGANISM: Artificial Sequence
<220> FEATURE:
<223> OTHER INFORMATION: 12172gL2 V-region

<400> SEQUENCE: 30

gacatccagc tgactcagtc cccctccttc ctgagcgcct cagtgggaga tcgcgtgacc      60

atcacctgtc aagccagcca gaacattggg tccgacttgg cctggtatca gcagaagcct     120

ggcaaagcgc cgaagctgct gatctacaag gccgctactc tcgcgtcggg agtgccatcc     180

cggttttccg gttcgggaag cgggaccgag ttcaccctta ccatttcctc gctccaaccg     240

gaggacttcg ccacgtacta ctgccagcag tactactacg gttcagccgg agcagacact     300

gataccttcg gcggaggcac caaggtcgaa atcaag                               336


<210> SEQ ID NO 31
<211> LENGTH: 219
<212> TYPE: PRT
<213> ORGANISM: Artificial Sequence
<220> FEATURE:
<223> OTHER INFORMATION: 12172gL2 light chain

<400> SEQUENCE: 31

Asp Ile Gln Leu Thr Gln Ser Pro Ser Phe Leu Ser Ala Ser Val Gly
1               5                   10                  15

Asp Arg Val Thr Ile Thr Cys Gln Ala Ser Gln Asn Ile Gly Ser Asp
            20                  25                  30

Leu Ala Trp Tyr Gln Gln Lys Pro Gly Lys Ala Pro Lys Leu Leu Ile
        35                  40                  45

Tyr Lys Ala Ala Thr Leu Ala Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Tyr Tyr Tyr Gly Ser Ala
                85                  90                  95

Gly Ala Asp Thr Asp Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 32
<211> LENGTH: 657
<212> TYPE: DNA
<213> ORGANISM: Artificial Sequence
<220> FEATURE:
<223> OTHER INFORMATION: 12172gL2 light chain

<400> SEQUENCE: 32
gacatccagc tgactcagtc cccctccttc ctgagcgcct cagtgggaga tcgcgtgacc 60
atcacctgtc aagccagcca gaacattggg tccgacttgg cctggtatca gcagaagcct 120
ggcaaagcgc cgaagctgct gatctacaag gccgctactc tcgcgtcggg agtgccatcc 180
cggttttccg gttcgggaag cgggaccgag ttcaccctta ccatttcctc gctccaaccg 240
gaggacttcg ccacgtacta ctgccagcag tactactacg gttcagccgg agcagacact 300
gataccttcg gcggaggcac caaggtcgaa atcaagcgta cggtggccgc tccctccgtg 360
ttcatcttcc caccctccga cgagcagctg aagtccggca ccgcctccgt cgtgtgcctg 420
ctgaacaact tctacccccg cgaggccaag gtgcagtgga aggtggacaa cgccctgcag 480
tccggcaact cccaggaatc cgtcaccgag caggactcca aggacagcac ctactccctg 540
tcctccaccc tgaccctgtc caaggccgac tacgagaagc acaaggtgta cgcctgcgaa 600
gtgacccacc agggcctgtc cagccccgtg accaagtcct tcaaccgggg cgagtgc 657

<210> SEQ ID NO 33
<211> LENGTH: 112
<212> TYPE: PRT
<213> ORGANISM: Artificial Sequence
<220> FEATURE:
<223> OTHER INFORMATION: 12172gL6 V-region

<400> SEQUENCE: 33

Asp Ile Val Leu Thr Gln Ser Pro Ser Phe Leu Ser Ala Ser Val Gly
1               5                   10                  15

Asp Arg Val Thr Ile Thr Cys Gln Ala Ser Gln Asn Ile Gly Ser Asp
            20                  25                  30

Leu Ala Trp Tyr Gln Gln Lys Pro Gly Lys Ala Pro Lys Leu Leu Ile
        35                  40                  45

Tyr Lys Ala Ala Thr Leu Ala Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Tyr Tyr Tyr Gly Ser Ala
                85                  90                  95

Gly Ala Asp Thr Asp Thr Phe Gly Gly Gly Thr Lys Val Glu Ile Lys
            100                 105                 110

<210> SEQ ID NO 34
<211> LENGTH: 336
<212> TYPE: DNA
<213> ORGANISM: Artificial Sequence
<220> FEATURE:
<223> OTHER INFORMATION: 12172gL6 V-region

<400> SEQUENCE: 34
gacatcgtgc tgactcagtc cccctccttc ctgagcgcct cagtgggaga tcgcgtgacc 60
atcacctgtc aagccagcca gaacattggg tccgacttgg cctggtatca gcagaagcct 120
ggcaaagcgc cgaagctgct gatctacaag gccgctactc tcgcgtcggg agtgccatcc 180
cggttttccg gttcgggaag cgggaccgag ttcaccctta ccatttcctc gctccaaccg 240
gaggacttcg ccacgtacta ctgccagcag tactactacg gttcagccgg agcagacact 300
gataccttcg gcggaggcac caaggtcgaa atcaag 336

<210> SEQ ID NO 35
<211> LENGTH: 219
<212> TYPE: PRT
<213> ORGANISM: Artificial Sequence
<220> FEATURE:
<223> OTHER INFORMATION: 12172gL6 light chain

<400> SEQUENCE: 35

Asp Ile Val Leu Thr Gln Ser Pro Ser Phe Leu Ser Ala Ser Val Gly
1 5 10 15

Asp Arg Val Thr Ile Thr Cys Gln Ala Ser Gln Asn Ile Gly Ser Asp
20 25 30

Leu Ala Trp Tyr Gln Gln Lys Pro Gly Lys Ala Pro Lys Leu Leu Ile
35 40 45

Tyr Lys Ala Ala Thr Leu Ala Ser Gly Val Pro Ser Arg Phe Ser Gly
50 55 60

Ser Gly Ser Gly Thr Glu Phe Thr Leu Thr Ile Ser Ser Leu Gln Pro
65 70 75 80

Glu Asp Phe Ala Thr Tyr Tyr Cys Gln Gln Tyr Tyr Tyr Gly Ser Ala
85 90 95

Gly Ala Asp Thr Asp Thr Phe Gly Gly Gly Thr Lys Val Glu Ile Lys
100 105 110

Arg Thr Val Ala Ala Pro Ser Val Phe Ile Phe Pro Pro Ser Asp Glu
115 120 125

Gln Leu Lys Ser Gly Thr Ala Ser Val Val Cys Leu Leu Asn Asn Phe
130 135 140

Tyr Pro Arg Glu Ala Lys Val Gln Trp Lys Val Asp Asn Ala Leu Gln
145 150 155 160

Ser Gly Asn Ser Gln Glu Ser Val Thr Glu Gln Asp Ser Lys Asp Ser
165 170 175

Thr Tyr Ser Leu Ser Ser Thr Leu Thr Leu Ser Lys Ala Asp Tyr Glu
180 185 190

Lys His Lys Val Tyr Ala Cys Glu Val Thr His Gln Gly Leu Ser Ser
195 200 205

Pro Val Thr Lys Ser Phe Asn Arg Gly Glu Cys
210 215

<210> SEQ ID NO 36
<211> LENGTH: 657
<212> TYPE: DNA
<213> ORGANISM: Artificial Sequence
<220> FEATURE:
<223> OTHER INFORMATION: 12172gL6 light chain

<400> SEQUENCE: 36
gacatcgtgc tgactcagtc cccctccttc ctgagcgcct cagtgggaga tcgcgtgacc 60
atcacctgtc aagccagcca gaacattggg tccgacttgg cctggtatca gcagaagcct 120
ggcaaagcgc cgaagctgct gatctacaag gccgctactc tcgcgtcggg agtgccatcc 180
cggttttccg gttcgggaag cgggaccgag ttcaccctta ccatttcctc gctccaaccg 240
gaggacttcg ccacgtacta ctgccagcag tactactacg gttcagccgg agcagacact 300
gataccttcg gcggaggcac caaggtcgaa atcaagcgta cggtggccgc tccctccgtg 360
ttcatcttcc caccctccga cgagcagctg aagtccggca ccgcctccgt cgtgtgcctg 420
ctgaacaact tctacccccg cgaggccaag gtgcagtgga aggtggacaa cgccctgcag 480
tccggcaact cccaggaatc cgtcaccgag caggactcca aggacagcac ctactccctg 540
tcctccaccc tgaccctgtc caaggccgac tacgagaagc acaaggtgta cgcctgcgaa 600
gtgacccacc agggcctgtc cagccccgtg accaagtcct tcaaccgggg cgagtgc 657

<210> SEQ ID NO 37
<211> LENGTH: 112
<212> TYPE: PRT
<213> ORGANISM: Artificial Sequence
<220> FEATURE:
<223> OTHER INFORMATION: 12172gL9 V-region

<400> SEQUENCE: 37

Asp Ile Gln Leu Thr Gln Ser Pro Ser Phe Leu Ser Ala Ser Val Gly
1 5 10 15

Asp Ser Val Thr Ile Thr Cys Gln Ala Ser Gln Asn Ile Gly Ser Asp
20 25 30

Leu Ala Trp Tyr Gln Gln Lys Pro Gly Lys Ala Pro Lys Leu Leu Ile
35 40 45

Tyr Lys Ala Ala Thr Leu Ala Ser Gly Val Pro Ser Arg Phe Ser Gly
50 55 60

Ser Gly Ser Gly Thr Glu Phe Thr Leu Thr Ile Ser Ser Leu Gln Pro
65 70 75 80

Glu Asp Phe Ala Thr Tyr Tyr Cys Gln Gln Tyr Tyr Tyr Gly Ser Ala
85 90 95

Gly Ala Asp Thr Asp Thr Phe Gly Gly Gly Thr Lys Val Glu Ile Lys
100 105 110

<210> SEQ ID NO 38
<211> LENGTH: 336
<212> TYPE: DNA
<213> ORGANISM: Artificial Sequence
<220> FEATURE:
<223> OTHER INFORMATION: 12172gL9 V-region

<400> SEQUENCE: 38
gacatccagc tgactcagtc cccctccttc ctgagcgcct cagtgggaga tagcgtgacc 60
atcacctgtc aagccagcca gaacattggg tccgacttgg cctggtatca gcagaagcct 120
ggcaaagcgc cgaagctgct gatctacaag gccgctactc tcgcgtcggg agtgccatcc 180
cggttttccg gttcgggaag cgggaccgag ttcaccctta ccatttcctc gctccaaccg 240
gaggacttcg ccacgtacta ctgccagcag tactactacg gttcagccgg agcagacact 300
gataccttcg gcggaggcac caaggtcgaa atcaag 336

<210> SEQ ID NO 39
<211> LENGTH: 219
<212> TYPE: PRT
<213> ORGANISM: Artificial Sequence
<220> FEATURE:
<223> OTHER INFORMATION: 12172gL9 light chain

<400> SEQUENCE: 39

Asp Ile Gln Leu Thr Gln Ser Pro Ser Phe Leu Ser Ala Ser Val Gly
1 5 10 15

Asp Ser Val Thr Ile Thr Cys Gln Ala Ser Gln Asn Ile Gly Ser Asp
20 25 30

```
Leu Ala Trp Tyr Gln Gln Lys Pro Gly Lys Ala Pro Lys Leu Leu Ile
        35                  40                  45

Tyr Lys Ala Ala Thr Leu Ala Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Tyr Tyr Tyr Gly Ser Ala
                85                  90                  95

Gly Ala Asp Thr Asp Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 40
<211> LENGTH: 657
<212> TYPE: DNA
<213> ORGANISM: Artificial Sequence
<220> FEATURE:
<223> OTHER INFORMATION: 12172gL9 light chain

<400> SEQUENCE: 40

```
gacatccagc tgactcagtc cccctccttc ctgagcgcct cagtgggaga tagcgtgacc      60

atcacctgtc aagccagcca gaacattggg tccgacttgg cctggtatca gcagaagcct     120

ggcaaagcgc cgaagctgct gatctacaag gccgctactc tcgcgtcggg agtgccatcc     180

cggttttccg gttcgggaag cgggaccgag ttcaccctta ccatttcctc gctccaaccg     240

gaggacttcg ccacgtacta ctgccagcag tactactacg gttcagccgg agcagacact     300

gataccttcg gcggaggcac caaggtcgaa atcaagcgta cggtagcggc cccatctgtc     360

ttcatcttcc cgccatctga tgagcagttg aaatctggaa ctgcctctgt tgtgtgcctg     420

ctgaataact tctatcccag agaggccaaa gtacagtgga aggtggataa cgccctccaa     480

tcgggtaact cccaggagag tgtcacagag caggacagca aggacagcac ctacagcctc     540

agcagcaccc tgacgctgag caaagcagac tacgagaaac acaaagtcta cgcctgcgaa     600

gtcacccatc agggcctgag ctcgcccgtc acaaagagct tcaacagggg agagtgt        657
```

<210> SEQ ID NO 41
<211> LENGTH: 112
<212> TYPE: PRT
<213> ORGANISM: Artificial Sequence
<220> FEATURE:
<223> OTHER INFORMATION: 12172gL11 V-region

<400> SEQUENCE: 41

```
Asp Ile Gln Leu Thr Gln Ser Pro Ser Phe Leu Ser Ala Ser Val Gly
```

```
1               5                   10                  15

Asp Arg Val Thr Ile Thr Cys Gln Ala Ser Gln Asn Ile Gly Ser Asp
            20                  25                  30

Leu Ala Trp Tyr Gln Gln Lys Pro Gly Lys Ala Pro Lys Leu Leu Ile
        35                  40                  45

Tyr Ser Ala Ala Thr Leu Ala Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Tyr Tyr Tyr Gly Ser Ala
                85                  90                  95

Gly Ala Asp Thr Asp Thr Phe Gly Gly Gly Thr Lys Val Glu Ile Lys
            100                 105                 110


<210> SEQ ID NO 42
<211> LENGTH: 336
<212> TYPE: DNA
<213> ORGANISM: Artificial Sequence
<220> FEATURE:
<223> OTHER INFORMATION: 12172gL11 V-region

<400> SEQUENCE: 42

gacatccagc tgactcagtc cccctccttc ctgagcgcct cagtgggaga tcgcgtgacc      60

atcacctgtc aagccagcca gaacattggg tccgacttgg cctggtatca gcagaagcct     120

ggcaaagcgc cgaagctgct gatctacagc gccgctactc tcgcgtcggg agtgccatcc     180

cggttttccg gttcgggaag cgggaccgag ttcaccctta ccatttcctc gctccaaccg     240

gaggacttcg ccacgtacta ctgccagcag tactactacg gttcagccgg agcagacact     300

gataccttcg gcggaggcac caaggtcgaa atcaag                               336


<210> SEQ ID NO 43
<211> LENGTH: 219
<212> TYPE: PRT
<213> ORGANISM: Artificial Sequence
<220> FEATURE:
<223> OTHER INFORMATION: 12172gL11 light chain

<400> SEQUENCE: 43

Asp Ile Gln Leu Thr Gln Ser Pro Ser Phe Leu Ser Ala Ser Val Gly
1               5                   10                  15

Asp Arg Val Thr Ile Thr Cys Gln Ala Ser Gln Asn Ile Gly Ser Asp
            20                  25                  30

Leu Ala Trp Tyr Gln Gln Lys Pro Gly Lys Ala Pro Lys Leu Leu Ile
        35                  40                  45

Tyr Ser Ala Ala Thr Leu Ala Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Tyr Tyr Tyr Gly Ser Ala
                85                  90                  95

Gly Ala Asp Thr Asp Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140
```

```
Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 44
<211> LENGTH: 657
<212> TYPE: DNA
<213> ORGANISM: Artificial Sequence
<220> FEATURE:
<223> OTHER INFORMATION: 12172gL11 light chain

<400> SEQUENCE: 44

```
gacatccagc tgactcagtc cccctccttc ctgagcgcct cagtgggaga tcgcgtgacc     60

atcacctgtc aagccagcca gaacattggg tccgacttgg cctggtatca gcagaagcct    120

ggcaaagcgc cgaagctgct gatctacagc gccgctactc tcgcgtcggg agtgccatcc    180

cggttttccg gttcgggaag cgggaccgag ttcaccctta ccatttcctc gctccaaccg    240

gaggacttcg ccacgtacta ctgccagcag tactactacg gttcagccgg agcagacact    300

gataccttcg gcggaggcac caaggtcgaa atcaagcgta cggtagcggc cccatctgtc    360

ttcatcttcc cgccatctga tgagcagttg aaatctggaa ctgcctctgt tgtgtgcctg    420

ctgaataact tctatcccag agaggccaaa gtacagtgga aggtggataa cgccctccaa    480

tcgggtaact cccaggagag tgtcacagag caggacagca aggacagcac ctacagcctc    540

agcagcaccc tgacgctgag caaagcagac tacgagaaac acaaagtcta cgcctgcgaa    600

gtcacccatc agggcctgag ctcgcccgtc acaaagagct tcaacagggg agagtgt       657
```

<210> SEQ ID NO 45
<211> LENGTH: 120
<212> TYPE: PRT
<213> ORGANISM: Artificial Sequence
<220> FEATURE:
<223> OTHER INFORMATION: 12172gH1 V-region

<400> SEQUENCE: 45

```
Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Ser Leu Ser Ser Tyr
            20                  25                  30

Ala Met Thr Trp Val Arg Gln Ala Pro Gly Lys Gly Leu Glu Trp Ile
        35                  40                  45

Gly Ile Ile Tyr Ala Gly Gly Ser Pro Ser Tyr Ala Ser Trp Ala Lys
    50                  55                  60

Gly Arg Phe Thr Ile Ser Lys Asp Ser Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Gly Thr Gly Asp Thr Val Tyr Thr Tyr Phe Asn Ile Trp Gly Gln
            100                 105                 110

Gly Thr Leu Val Thr Val Ser Ser
```

115 120

<210> SEQ ID NO 46
<211> LENGTH: 360
<212> TYPE: DNA
<213> ORGANISM: Artificial Sequence
<220> FEATURE:
<223> OTHER INFORMATION: 12172gH1 V-region

<400> SEQUENCE: 46
gaagtgcagc tcgtggagtc gggcggaggt ctggtgcagc ccggaggaag cctgcgcctg 60
tcatgcaccg ccagcgggtt ctcgctttcc tcctacgcca tgacctgggt cagacaggca 120
ccgggaaagg gcctcgaatg gattggcatt atctatgcgg gtggcagccc ttcctacgcc 180
tcctgggcta aagggcggtt caccatctcg aaggactcct ccaagaacac ggtgtacttg 240
caaatgaact cactgagggc cgaggacact gcggtgtact actgtgcccg gggaactgga 300
gataccgtgt acacctactt taacatctgg ggccagggaa ccctggtcac tgtctcgagc 360

<210> SEQ ID NO 47
<211> LENGTH: 447
<212> TYPE: PRT
<213> ORGANISM: Artificial Sequence
<220> FEATURE:
<223> OTHER INFORMATION: 12172gH1 heavy chain (IgG4P)

<400> SEQUENCE: 47

Glu Val Gln Leu Val Glu Ser Gly Gly Gly Leu Val Gln Pro Gly Gly
1 5 10 15

Ser Leu Arg Leu Ser Cys Thr Ala Ser Gly Phe Ser Leu Ser Ser Tyr
20 25 30

Ala Met Thr Trp Val Arg Gln Ala Pro Gly Lys Gly Leu Glu Trp Ile
35 40 45

Gly Ile Ile Tyr Ala Gly Gly Ser Pro Ser Tyr Ala Ser Trp Ala Lys
50 55 60

Gly Arg Phe Thr Ile Ser Lys Asp Ser Ser Lys Asn Thr Val Tyr Leu
65 70 75 80

Gln Met Asn Ser Leu Arg Ala Glu Asp Thr Ala Val Tyr Tyr Cys Ala
85 90 95

Arg Gly Thr Gly Asp Thr Val Tyr Thr Tyr Phe Asn Ile Trp Gly Gln
100 105 110

Gly Thr Leu Val Thr Val Ser Ser Ala Ser Thr Lys Gly Pro Ser Val
115 120 125

Phe Pro Leu Ala Pro Cys Ser Arg Ser Thr Ser Glu Ser Thr Ala Ala
130 135 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Ser Leu Gly Thr Lys Thr Tyr Thr Cys Asn Val Asp His Lys
195 200 205

Pro Ser Asn Thr Lys Val Asp Lys Arg Val Glu Ser Lys Tyr Gly Pro
210 215 220

Pro Cys Pro Pro Cys Pro Ala Pro Glu Phe Leu Gly Gly Pro Ser Val
225 230 235 240

```
Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445
```

<210> SEQ ID NO 48
<211> LENGTH: 1341
<212> TYPE: DNA
<213> ORGANISM: Artificial Sequence
<220> FEATURE:
<223> OTHER INFORMATION: 12172gH1 heavy chain (IgG4P)

<400> SEQUENCE: 48

```
gaagtgcagc tcgtggagtc gggcggaggt ctggtgcagc ccggaggaag cctgcgcctg      60

tcatgcaccg ccagcgggtt ctcgctttcc tcctacgcca tgacctgggt cagacaggca     120

ccgggaaagg gcctcgaatg gattggcatt atctatgcgg gtggcagccc ttcctacgcc     180

tcctgggcta aagggcggtt caccatctcg aaggactcct ccaagaacac ggtgtacttg     240

caaatgaact cactgagggc cgaggacact gcggtgtact actgtgcccg gggaactgga     300

gataccgtgt acacctactt taacatctgg ggccagggaa ccctggtcac tgtctcgagc     360

gcttctacaa agggcccatc cgtcttcccc ctggcgccct gctccaggag cacctccgag     420

agcacagccg ccctgggctg cctggtcaag gactacttcc ccgaaccggt gacggtgtcg     480

tggaactcag gcgccctgac cagcggcgtg cacaccttcc cggctgtcct acagtcctca     540

ggactctact ccctcagcag cgtggtgacc gtgccctcca gcagcttggg cacgaagacc     600

tacacctgca acgtagatca caagcccagc aacaccaagg tggacaagag agttgagtcc     660

aaatatggtc ccccatgccc accatgccca gcacctgagt tcctgggggg accatcagtc     720

ttcctgttcc ccccaaaacc caaggacact ctcatgatct cccggacccc tgaggtcacg     780

tgcgtggtgg tggacgtgag ccaggaagac cccgaggtcc agttcaactg gtacgtggat     840

ggcgtggagg tgcataatgc caagacaaag ccgcgggagg agcagttcaa cagcacgtac     900
```

cgtgtggtca gcgtcctcac cgtcctgcac caggactggc tgaacggcaa ggagtacaag 960
tgcaaggtct ccaacaaagg cctcccgtcc tccatcgaga aaaccatctc caaagccaaa 1020
gggcagcccc gagagccaca ggtgtacacc ctgcccccat cccaggagga gatgaccaag 1080
aaccaggtca gcctgacctg cctggtcaaa ggcttctacc ccagcgacat cgccgtggag 1140
tgggagagca atgggcagcc ggagaacaac tacaagacca cgcctcccgt gctggactcc 1200
gacggctcct tcttcctcta cagcaggcta accgtggaca agagcaggtg gcaggagggg 1260
aatgtcttct catgctccgt gatgcatgag gctctgcaca accactacac acagaagagc 1320
ctctccctgt ctctgggtaa a 1341

<210> SEQ ID NO 49
<211> LENGTH: 120
<212> TYPE: PRT
<213> ORGANISM: Artificial Sequence
<220> FEATURE:
<223> OTHER INFORMATION: 12172gH2 V-region

<400> SEQUENCE: 49

Glu Val Gln Leu Val Glu Ser Gly Gly Gly Leu Val Gln Pro Gly Gly
1 5 10 15

Ser Leu Arg Leu Ser Cys Ala Ala Ser Gly Phe Ser Leu Ser Ser Tyr
20 25 30

Ala Met Thr Trp Val Arg Gln Ala Pro Gly Lys Gly Leu Glu Trp Val
35 40 45

Gly Ile Ile Tyr Ala Gly Gly Ser Pro Ser Tyr Ala Ser Trp Ala Lys
50 55 60

Gly Arg Phe Thr Ile Ser Lys Asp Ser Ser Lys Asn Thr Val Tyr Leu
65 70 75 80

Gln Met Asn Ser Leu Arg Ala Glu Asp Thr Ala Val Tyr Tyr Cys Ala
85 90 95

Arg Gly Thr Gly Asp Thr Val Tyr Thr Tyr Phe Asn Ile Trp Gly Gln
100 105 110

Gly Thr Leu Val Thr Val Ser Ser
115 120

<210> SEQ ID NO 50
<211> LENGTH: 360
<212> TYPE: DNA
<213> ORGANISM: Artificial Sequence
<220> FEATURE:
<223> OTHER INFORMATION: 12172gH2 V-region

<400> SEQUENCE: 50
gaagtgcagc tcgtggagtc gggcggaggt ctggtgcagc ccggaggaag cctgcgcctg 60
tcatgcgctg ccagcgggtt ctcgctttcc tcctacgcca tgacctgggt cagacaggca 120
ccgggaaagg gcctcgaatg ggtcggcatt atctatgcgg gtggcagccc ttcctacgcc 180
tcctgggcta aagggcggtt caccatctcg aaggactcct ccaagaacac ggtgtacttg 240
caaatgaact cactgagggc cgaggacact gcggtgtact actgtgcccg gggaactgga 300
gataccgtgt acacctactt taacatctgg ggccagggaa ccctggtcac tgtctcgagc 360

<210> SEQ ID NO 51
<211> LENGTH: 447
<212> TYPE: PRT
<213> ORGANISM: Artificial Sequence
<220> FEATURE:
<223> OTHER INFORMATION: 12172gH2 heavy chain (IgG4P)

<400> SEQUENCE: 51

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Ser Tyr
            20                  25                  30

Ala Met Thr Trp Val Arg Gln Ala Pro Gly Lys Gly Leu Glu Trp Val
        35                  40                  45

Gly Ile Ile Tyr Ala Gly Gly Ser Pro Ser Tyr Ala Ser Trp Ala Lys
    50                  55                  60

Gly Arg Phe Thr Ile Ser Lys Asp Ser Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Gly Thr Gly Asp Thr Val Tyr Thr Tyr Phe Asn Ile Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg 405 410 415

Trp Gln Glu Gly Asn Val Phe Ser Cys Ser Val Met His Glu Ala Leu
420 425 430

His Asn His Tyr Thr Gln Lys Ser Leu Ser Leu Ser Leu Gly Lys
435 440 445

<210> SEQ ID NO 52
<211> LENGTH: 1341
<212> TYPE: DNA
<213> ORGANISM: Artificial Sequence
<220> FEATURE:
<223> OTHER INFORMATION: 12172gH2 heavy chain (IgG4P)

<400> SEQUENCE: 52
gaagtgcagc tcgtggagtc gggcggaggt ctggtgcagc ccggaggaag cctgcgcctg 60
tcatgcgctg ccagcgggtt ctcgctttcc tcctacgcca tgacctgggt cagacaggca 120
ccgggaaagg gcctcgaatg ggtcggcatt atctatgcgg gtggcagccc ttcctacgcc 180
tcctgggcta aagggcggtt caccatctcg aaggactcct ccaagaacac ggtgtacttg 240
caaatgaact cactgagggc cgaggacact gcggtgtact actgtgcccg gggaactgga 300
gataccgtgt acacctactt taacatctgg ggccagggaa ccctggtcac tgtctcgagc 360
gcttctacaa agggcccatc cgtcttcccc ctggcgccct gctccaggag cacctccgag 420
agcacagccg ccctgggctg cctggtcaag gactacttcc ccgaaccggt gacggtgtcg 480
tggaactcag gcgccctgac cagcggcgtg cacaccttcc cggctgtcct acagtcctca 540
ggactctact ccctcagcag cgtggtgacc gtgccctcca gcagcttggg cacgaagacc 600
tacacctgca acgtagatca caagcccagc aacaccaagg tggacaagag agttgagtcc 660
aaatatggtc ccccatgccc accatgccca gcacctgagt tcctgggggg accatcagtc 720
ttcctgttcc ccccaaaacc caaggacact ctcatgatct cccggacccc tgaggtcacg 780
tgcgtggtgg tggacgtgag ccaggaagac cccgaggtcc agttcaactg gtacgtggat 840
ggcgtggagg tgcataatgc caagacaaag ccgcgggagg agcagttcaa cagcacgtac 900
cgtgtggtca gcgtcctcac cgtcctgcac caggactggc tgaacggcaa ggagtacaag 960
tgcaaggtct ccaacaaagg cctcccgtcc tccatcgaga aaaccatctc caaagccaaa 1020
gggcagcccc gagagccaca ggtgtacacc ctgcccccat cccaggagga gatgaccaag 1080
aaccaggtca gcctgacctg cctggtcaaa ggcttctacc ccagcgacat cgccgtggag 1140
tgggagagca atgggcagcc ggagaacaac tacaagacca cgcctcccgt gctggactcc 1200
gacggctcct tcttcctcta cagcaggcta accgtggaca agagcaggtg gcaggagggg 1260
aatgtcttct catgctccgt gatgcatgag gctctgcaca accactacac acagaagagc 1320
ctctccctgt ctctgggtaa a 1341

<210> SEQ ID NO 53
<211> LENGTH: 120
<212> TYPE: PRT
<213> ORGANISM: Artificial Sequence
<220> FEATURE:
<223> OTHER INFORMATION: 12172gH4 V-region

<400> SEQUENCE: 53

Glu Val Gln Leu Val Glu Ser Gly Gly Gly Leu Val Gln Pro Gly Gly
1 5 10 15

Ser Leu Arg Leu Ser Cys Thr Ala Ser Gly Phe Ser Leu Ser Ser Tyr
20 25 30

```
Ala Met Thr Trp Val Arg Gln Ala Pro Gly Lys Gly Leu Glu Trp Ile
        35                  40                  45

Gly Ile Ile Tyr Ala Gly Gly Ser Pro Ser Tyr Ala Ser Trp Ala Lys
    50                  55                  60

Gly Arg Phe Thr Ile Ser Arg Asp Ser Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Gly Thr Gly Asp Thr Val Tyr Thr Tyr Phe Asn Ile Trp Gly Gln
            100                 105                 110

Gly Thr Leu Val Thr Val Ser Ser
        115                 120


<210> SEQ ID NO 54
<211> LENGTH: 360
<212> TYPE: DNA
<213> ORGANISM: Artificial Sequence
<220> FEATURE:
<223> OTHER INFORMATION: 12172gH4 V-region

<400> SEQUENCE: 54

gaagtgcagc tcgtggagtc gggcggaggt ctggtgcagc ccggaggaag cctgcgcctg      60

tcatgcaccg ccagcgggtt ctcgctttcc tcctacgcca tgacctgggt cagacaggca     120

ccgggaaagg gcctcgaatg gattggcatt atctatgcgg gtggcagccc ttcctacgcc     180

tcctgggcta aagggcggtt caccatctcg cgcgactcct ccaagaacac ggtgtacttg     240

caaatgaact cactgagggc cgaggacact gcggtgtact actgtgcccg gggaactgga     300

gataccgtgt acacctactt taacatctgg ggccagggaa ccctggtcac tgtctcgagc     360


<210> SEQ ID NO 55
<211> LENGTH: 447
<212> TYPE: PRT
<213> ORGANISM: Artificial Sequence
<220> FEATURE:
<223> OTHER INFORMATION: 12172gH4 heavy chain (IgG4P)

<400> SEQUENCE: 55

Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Ser Leu Ser Ser Tyr
            20                  25                  30

Ala Met Thr Trp Val Arg Gln Ala Pro Gly Lys Gly Leu Glu Trp Ile
        35                  40                  45

Gly Ile Ile Tyr Ala Gly Gly Ser Pro Ser Tyr Ala Ser Trp Ala Lys
    50                  55                  60

Gly Arg Phe Thr Ile Ser Arg Asp Ser Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Gly Thr Gly Asp Thr Val Tyr Thr Tyr Phe Asn Ile Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
```

```
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445
```

<210> SEQ ID NO 56
<211> LENGTH: 1341
<212> TYPE: DNA
<213> ORGANISM: Artificial Sequence
<220> FEATURE:
<223> OTHER INFORMATION: 12172gH4 heavy chain (IgG4P)

<400> SEQUENCE: 56

```
gaagtgcagc tcgtggagtc gggcggaggt ctggtgcagc ccggaggaag cctgcgcctg      60

tcatgcaccg ccagcgggtt ctcgctttcc tcctacgcca tgacctgggt cagacaggca     120

ccgggaaagg gcctcgaatg gattggcatt atctatgcgg gtggcagccc ttcctacgcc     180

tcctgggcta aagggcggtt caccatctcg cgcgactcct ccaagaacac ggtgtacttg     240

caaatgaact cactgagggc cgaggacact gcggtgtact actgtgcccg gggaactgga     300

gataccgtgt acacctactt taacatctgg ggccagggaa ccctggtcac tgtctcgagc     360

gcttctacaa agggcccatc cgtcttcccc ctggcgccct gctccaggag cacctccgag     420
```

```
agcacagccg ccctgggctg cctggtcaag gactacttcc ccgaaccggt gacggtgtcg    480

tggaactcag gcgccctgac cagcggcgtg cacaccttcc cggctgtcct acagtcctca    540

ggactctact ccctcagcag cgtggtgacc gtgccctcca gcagcttggg cacgaagacc    600

tacacctgca acgtagatca caagcccagc aacaccaagg tggacaagag agttgagtcc    660

aaatatggtc ccccatgccc accatgccca gcacctgagt tcctgggggg accatcagtc    720

ttcctgttcc ccccaaaacc caaggacact ctcatgatct cccggacccc tgaggtcacg    780

tgcgtggtgg tggacgtgag ccaggaagac cccgaggtcc agttcaactg gtacgtggat    840

ggcgtggagg tgcataatgc caagacaaag ccgcgggagg agcagttcaa cagcacgtac    900

cgtgtggtca gcgtcctcac cgtcctgcac caggactggc tgaacggcaa ggagtacaag    960

tgcaaggtct ccaacaaagg cctcccgtcc tccatcgaga aaaccatctc caaagccaaa   1020

gggcagcccc gagagccaca ggtgtacacc ctgcccccat cccaggagga gatgaccaag   1080

aaccaggtca gcctgacctg cctggtcaaa ggcttctacc ccagcgacat cgccgtggag   1140

tgggagagca atgggcagcc ggagaacaac tacaagacca cgcctcccgt gctggactcc   1200

gacggctcct tcttcctcta cagcaggcta accgtggaca agagcaggtg gcaggagggg   1260

aatgtcttct catgctccgt gatgcatgag gctctgcaca accactacac acagaagagc   1320

ctctccctgt ctctgggtaa a                                             1341
```

<210> SEQ ID NO 57
<211> LENGTH: 120
<212> TYPE: PRT
<213> ORGANISM: Artificial Sequence
<220> FEATURE:
<223> OTHER INFORMATION: 12172gH6 V-region

<400> SEQUENCE: 57

```
Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Ser Leu Ser Ser Tyr
            20                  25                  30

Ala Met Thr Trp Val Arg Gln Ala Pro Gly Lys Gly Leu Glu Trp Ile
        35                  40                  45

Gly Ile Ile Tyr Ala Gly Gly Ser Pro Ser Tyr Ala Ser Trp Ala Lys
    50                  55                  60

Gly Arg Phe Thr Ile Ser Lys Asp Ser Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Thr Gly Asp Thr Val Tyr Thr Tyr Phe Asn Ile Trp Gly Gln
            100                 105                 110

Gly Thr Leu Val Thr Val Ser Ser
        115                 120
```

<210> SEQ ID NO 58
<211> LENGTH: 360
<212> TYPE: DNA
<213> ORGANISM: Artificial Sequence
<220> FEATURE:
<223> OTHER INFORMATION: 12172gH6 V-region

<400> SEQUENCE: 58

```
gaagtgcagc tcgtggagtc gggcggaggt ctggtgcagc ccggaggaag cctgcgcctg     60
```

```
tcatgcaccg ccagcgggtt ctcgctttcc tcctacgcca tgacctgggt cagacaggca    120

ccgggaaagg gcctcgaatg gattggcatt atctatgcgg gtggcagccc ttcctacgcc    180

tcctgggcta aagggcggtt caccatctcg aaggactcct ccaagaacac gctgtacttg    240

caaatgaact cactgagggc cgaggacact gcggtgtact actgtgcccg gggaactgga    300

gataccgtgt acacctactt taacatctgg ggccagggaa ccctggtcac tgtctcgagc    360


<210> SEQ ID NO 59
<211> LENGTH: 447
<212> TYPE: PRT
<213> ORGANISM: Artificial Sequence
<220> FEATURE:
<223> OTHER INFORMATION: 12172gH6 heavy chain (IgG4P)

<400> SEQUENCE: 59

Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Ser Leu Ser Ser Tyr
            20                  25                  30

Ala Met Thr Trp Val Arg Gln Ala Pro Gly Lys Gly Leu Glu Trp Ile
        35                  40                  45

Gly Ile Ile Tyr Ala Gly Gly Ser Pro Ser Tyr Ala Ser Trp Ala Lys
    50                  55                  60

Gly Arg Phe Thr Ile Ser Lys Asp Ser Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Thr Gly Asp Thr Val Tyr Thr Tyr Phe Asn Ile Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320
```

```
Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445


<210> SEQ ID NO 60
<211> LENGTH: 1341
<212> TYPE: DNA
<213> ORGANISM: Artificial Sequence
<220> FEATURE:
<223> OTHER INFORMATION: 12172gH6 heavy chain (IgG4P)

<400> SEQUENCE: 60

gaagtgcagc tcgtggagtc gggcggaggt ctggtgcagc ccggaggaag cctgcgcctg     60

tcatgcaccg ccagcgggtt ctcgctttcc tcctacgcca tgacctgggt cagacaggca    120

ccgggaaagg gcctcgaatg gattggcatt atctatgcgg gtggcagccc ttcctacgcc    180

tcctgggcta aagggcggtt caccatctcg aaggactcct ccaagaacac gctgtacttg    240

caaatgaact cactgagggc cgaggacact gcggtgtact actgtgcccg gggaactgga    300

gataccgtgt acacctactt taacatctgg ggccagggaa ccctggtcac tgtctcgagc    360

gcttctacaa agggcccatc cgtcttcccc ctggcgccct gctccaggag cacctccgag    420

agcacagccg ccctgggctg cctggtcaag gactacttcc ccgaaccggt gacggtgtcg    480

tggaactcag gcgccctgac cagcggcgtg cacaccttcc cggctgtcct acagtcctca    540

ggactctact ccctcagcag cgtggtgacc gtgccctcca gcagcttggg cacgaagacc    600

tacacctgca acgtagatca caagcccagc aacaccaagg tggacaagag agttgagtcc    660

aaatatggtc ccccatgccc accatgccca gcacctgagt tcctgggggg accatcagtc    720

ttcctgttcc ccccaaaacc caaggacact ctcatgatct cccggacccc tgaggtcacg    780

tgcgtggtgg tggacgtgag ccaggaagac cccgaggtcc agttcaactg gtacgtggat    840

ggcgtggagg tgcataatgc caagacaaag ccgcgggagg agcagttcaa cagcacgtac    900

cgtgtggtca gcgtcctcac cgtcctgcac caggactggc tgaacggcaa ggagtacaag    960

tgcaaggtct ccaacaaagg cctcccgtcc tccatcgaga aaaccatctc caaagccaaa   1020

gggcagcccc gagagccaca ggtgtacacc ctgcccccat cccaggagga gatgaccaag   1080

aaccaggtca gcctgacctg cctggtcaaa ggcttctacc ccagcgacat cgccgtggag   1140

tgggagagca atgggcagcc ggagaacaac tacaagacca cgcctcccgt gctggactcc   1200

gacggctcct tcttcctcta cagcaggcta accgtggaca agagcaggtg gcaggagggg   1260

aatgtcttct catgctccgt gatgcatgag gctctgcaca accactacac acagaagagc   1320
```

ctctccctgt ctctgggtaa a 1341

<210> SEQ ID NO 61
<211> LENGTH: 447
<212> TYPE: PRT
<213> ORGANISM: Artificial Sequence
<220> FEATURE:
<223> OTHER INFORMATION: 12172gH6 heavy chain (IgG4P F234A L235A)

<400> SEQUENCE: 61

```
Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Ser Leu Ser Ser Tyr
            20                  25                  30

Ala Met Thr Trp Val Arg Gln Ala Pro Gly Lys Gly Leu Glu Trp Ile
        35                  40                  45

Gly Ile Ile Tyr Ala Gly Gly Ser Pro Ser Tyr Ala Ser Trp Ala Lys
    50                  55                  60

Gly Arg Phe Thr Ile Ser Lys Asp Ser Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Thr Gly Asp Thr Val Tyr Thr Tyr Phe Asn Ile Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
```

```
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445
```

<210> SEQ ID NO 62
<211> LENGTH: 1341
<212> TYPE: DNA
<213> ORGANISM: Artificial Sequence
<220> FEATURE:
<223> OTHER INFORMATION: 12172gH6 heavy chain (IgG4P F234A L235A)

<400> SEQUENCE: 62

```
gaagtgcagc tcgtggagtc gggcggaggt ctggtgcagc ccggaggaag cctgcgcctg     60

tcatgcaccg ccagcgggtt ctcgctttcc tcctacgcca tgacctgggt cagacaggca    120

ccgggaaagg gcctcgaatg gattggcatt atctatgcgg gtggcagccc ttcctacgcc    180

tcctgggcta aagggcggtt caccatctcg aaggactcct ccaagaacac gctgtacttg    240

caaatgaact cactgagggc cgaggacact gcggtgtact actgtgcccg gggaactgga    300

gataccgtgt acacctactt taacatctgg ggccagggaa ccctggtcac tgtctcgagc    360

gcttctacaa agggcccatc cgtcttcccc ctggcgccct gctccaggag cacctccgag    420

agcacagccg ccctgggctg cctggtcaag gactacttcc ccgaaccggt gacggtgtcg    480

tggaactcag gcgccctgac cagcggcgtg cacaccttcc cggctgtcct acagtcctca    540

ggactctact ccctcagcag cgtggtgacc gtgccctcca gcagcttggg cacgaagacc    600

tacacctgca acgtagatca caagcccagc aacaccaagg tggacaagag agttgagtcc    660

aaatatggtc ccccatgccc accatgccca gcacctgaag ccgcgggggg accgtcagtc    720

ttcctgttcc ccccaaaacc caaggacact ctcatgatct cccggacccc tgaggtcacg    780

tgcgtggtgg tggacgtgag ccaggaagac cccgaggtcc agttcaactg gtacgtggat    840

ggcgtggagg tgcataatgc caagacaaag ccgcgggagg agcagttcaa cagcacgtac    900

cgtgtggtca gcgtcctcac cgtcctgcac caggactggc tgaacggcaa ggagtacaag    960

tgcaaggtct ccaacaaagg cctcccgtcc tccatcgaga aaaccatctc caaagccaaa   1020

gggcagcccc gagagccaca ggtgtacacc ctgcccccat cccaggagga gatgaccaag   1080

aaccaggtca gcctgacctg cctggtcaaa ggcttctacc ccagcgacat cgccgtggag   1140

tgggagagca atgggcagcc ggagaacaac tacaagacca cgcctcccgt gctggactcc   1200

gacggctcct tcttcctcta cagcaggcta accgtggaca agagcaggtg gcaggagggg   1260

aatgtcttct catgctccgt gatgcatgag gctctgcaca accactacac acagaagagc   1320

ctctccctgt ctctgggtaa a                                               1341
```

<210> SEQ ID NO 63
<211> LENGTH: 450
<212> TYPE: PRT
<213> ORGANISM: Artificial Sequence
<220> FEATURE:

<223> OTHER INFORMATION: 12172gH6 heavy chain (IgG1)

<400> SEQUENCE: 63

```
Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Ser Leu Ser Ser Tyr
            20                  25                  30

Ala Met Thr Trp Val Arg Gln Ala Pro Gly Lys Gly Leu Glu Trp Ile
        35                  40                  45

Gly Ile Ile Tyr Ala Gly Gly Ser Pro Ser Tyr Ala Ser Trp Ala Lys
    50                  55                  60

Gly Arg Phe Thr Ile Ser Lys Asp Ser Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Thr Gly Asp Thr Val Tyr Thr Tyr Phe Asn Ile Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400
```

```
Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 64
<211> LENGTH: 1350
<212> TYPE: DNA
<213> ORGANISM: Artificial Sequence
<220> FEATURE:
<223> OTHER INFORMATION: 12172gH6 heavy chain (IgG1)

<400> SEQUENCE: 64

gaagtgcagc tcgtggagtc gggcggaggt ctggtgcagc ccggaggaag cctgcgcctg     60

tcatgcaccg ccagcgggtt ctcgctttcc tcctacgcca tgacctgggt cagacaggca    120

ccgggaaagg gcctcgaatg gattggcatt atctatgcgg gtggcagccc ttcctacgcc    180

tcctgggcta aagggcggtt caccatctcg aaggactcct ccaagaacac gctgtacttg    240

caaatgaact cactgagggc cgaggacact gcggtgtact actgtgcccg gggaactgga    300

gataccgtgt acacctactt taacatctgg ggccagggaa ccctggtcac tgtctcgagc    360

gcttctacaa agggcccatc ggtcttcccc ctggcaccct cctccaagag cacctctggg    420

ggcacagcgg ccctgggctg cctggtcaag gactacttcc ccgaaccggt gacggtgtcg    480

tggaactcag gcgccctgac cagcggcgtg cacaccttcc cggctgtcct acagtcctca    540

ggactctact ccctcagcag cgtggtgacc gtgccctcca gcagcttggg cacccagacc    600

tacatctgca acgtgaatca caagcccagc aacaccaagg tggacaagaa agttgagccc    660

aaatcttgtg acaaaactca cacatgccca ccgtgcccag cacctgaact cctgggggga    720

ccgtcagtct tcctcttccc cccaaaaccc aaggacaccc tcatgatctc ccggacccct    780

gaggtcacat gcgtggtggt ggacgtgagc cacgaagacc ctgaggtcaa gttcaactgg    840

tacgtggacg gcgtggaggt gcataatgcc aagacaaagc cgcgggagga gcagtacaac    900

agcacgtacc gtgtggtcag cgtcctcacc gtcctgcacc aggactggct gaatggcaag    960

gagtacaagt gcaaggtctc caacaaagcc ctcccagccc ccatcgagaa aaccatctcc   1020

aaagccaaag ggcagccccg agaaccacag gtgtacaccc tgcccccatc ccgggatgag   1080

ctgaccaaga accaggtcag cctgacctgc ctggtcaaag gcttctatcc cagcgacatc   1140

gccgtggagt gggagagcaa tgggcagccg gagaacaact acaagaccac gcctcccgtg   1200

ctggactccg acggctcctt cttcctctac agcaagctca ccgtggacaa gagcaggtgg   1260

cagcagggga acgtcttctc atgctccgtg atgcatgagg ctctgcacaa ccactacacg   1320

cagaagagcc tctccctgtc tccgggtaaa                                    1350


<210> SEQ ID NO 65
<211> LENGTH: 450
<212> TYPE: PRT
<213> ORGANISM: Artificial Sequence
<220> FEATURE:
<223> OTHER INFORMATION: 12172gH6 heavy chain (IgG1 L234A L235A)

<400> SEQUENCE: 65

Glu Val Gln Leu Val Glu Ser Gly Gly Gly Leu Val Gln Pro Gly Gly
```

-continued

```
1               5                   10                  15

Ser Leu Arg Leu Ser Cys Thr Ala Ser Gly Phe Ser Leu Ser Ser Tyr
            20                  25                  30

Ala Met Thr Trp Val Arg Gln Ala Pro Gly Lys Gly Leu Glu Trp Ile
        35                  40                  45

Gly Ile Ile Tyr Ala Gly Gly Ser Pro Ser Tyr Ala Ser Trp Ala Lys
    50                  55                  60

Gly Arg Phe Thr Ile Ser Lys Asp Ser Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Thr Gly Asp Thr Val Tyr Thr Tyr Phe Asn Ile Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430
```

Glu Ala Leu His Asn His Tyr Thr Gln Lys Ser Leu Ser Leu Ser Pro
        435                 440                 445

Gly Lys
    450

<210> SEQ ID NO 66
<211> LENGTH: 1350
<212> TYPE: DNA
<213> ORGANISM: Artificial Sequence
<220> FEATURE:
<223> OTHER INFORMATION: 12172gH6 heavy chain (IgG1 L234A L235A)

<400> SEQUENCE: 66
gaagtgcagc tcgtggagtc gggcggaggt ctggtgcagc ccggaggaag cctgcgcctg 60
tcatgcaccg ccagcgggtt ctcgctttcc tcctacgcca tgacctgggt cagacaggca 120
ccgggaaagg gcctcgaatg gattggcatt atctatgcgg gtggcagccc ttcctacgcc 180
tcctgggcta aagggcggtt caccatctcg aaggactcct ccaagaacac gctgtacttg 240
caaatgaact cactgagggc cgaggacact gcggtgtact actgtgcccg gggaactgga 300
gataccgtgt acacctactt taacatctgg ggccagggaa ccctggtcac tgtctcgagc 360
gcttctacaa agggcccctc cgtgttcccg ctcgctccat catcgaagtc taccagcgga 420
ggcactgcgg ctctcggttg cctcgtgaag gactacttcc cggagccggt gaccgtgtcg 480
tggaacagcg gagccctgac cagcggggtg cacacctttc cggccgtctt gcagtcaagc 540
ggcctttact ccctgtcatc agtggtgact gtcccgtcca gctcattggg aacccaaacc 600
tacatctgca atgtgaatca caaacctagc aacaccaagg ttgacaagaa agtcgagccc 660
aaatcgtgtg acaagactca cacttgtccg ccgtgcccgg cacccgaagc cgcaggaggt 720
cccagcgtct ttctgttccc tccaaagccg aaagacacgc tgatgatctc ccgcaccccg 780
gaggtcactt gcgtggtcgt ggacgtgtca catgaggacc cagaggtgaa gttcaattgg 840
tacgtggatg gcgtcgaagt ccacaatgcc aaaactaagc ccagagaaga acagtacaat 900
tcgacctacc gcgtcgtgtc cgtgctcacg gtgttgcatc aggattggct gaacgggaag 960
gaatacaagt gcaaagtgtc caacaaggcg ctgccggcac cgatcgagaa aactatctcc 1020
aaagcgaagg gacagcctag ggaacctcaa gtctacacgc tgccaccatc acgggatgaa 1080
ctgactaaga atcaagtctc actgacttgt ctggtgaagg ggttttaccc tagcgacatt 1140
gccgtggagt gggaatccaa cggccagcca gagaacaact acaagactac ccctccagtg 1200
ctcgactcgg atggatcgtt cttcctttac tcgaagctca ccgtggataa gtcccggtgg 1260
cagcagggaa acgtgttctc ctgctcggtg atgcatgaag ccctccataa ccactatacc 1320
caaaagtcgc tgtccctgtc gccgggaaag 1350

<210> SEQ ID NO 67
<211> LENGTH: 120
<212> TYPE: PRT
<213> ORGANISM: Artificial Sequence
<220> FEATURE:
<223> OTHER INFORMATION: 12172gH8 V-region

<400> SEQUENCE: 67

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Ser Tyr
            20                  25                  30

```
Ala Met Thr Trp Val Arg Gln Ala Pro Gly Lys Gly Leu Glu Trp Ile
        35                  40                  45

Gly Ile Ile Tyr Ala Gly Gly Ser Pro Ser Tyr Ala Ser Trp Ala Lys
    50                  55                  60

Gly Arg Phe Thr Ile Ser Lys Asp Ser Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Gly Thr Gly Asp Thr Val Tyr Thr Tyr Phe Asn Ile Trp Gly Gln
            100                 105                 110

Gly Thr Leu Val Thr Val Ser Ser
        115                 120
```

<210> SEQ ID NO 68
<211> LENGTH: 360
<212> TYPE: DNA
<213> ORGANISM: Artificial Sequence
<220> FEATURE:
<223> OTHER INFORMATION: 12172gH8 V-region

<400> SEQUENCE: 68

```
gaagtgcagc tcgtggagtc gggcggaggt ctggtgcagc ccggaggaag cctgcgcctg      60

tcatgcgctg ccagcgggtt ctcgctttcc tcctacgcca tgacctgggt cagacaggca     120

ccgggaaagg gcctcgaatg gattggcatt atctatgcgg gtggcagccc ttcctacgcc     180

tcctgggcta aagggcggtt caccatctcg aaggactcct ccaagaacac ggtgtacttg     240

caaatgaact cactgagggc cgaggacact gcggtgtact actgtgcccg gggaactgga     300

gataccgtgt acacctactt taacatctgg ggccagggaa ccctggtcac tgtctcgagc     360
```

<210> SEQ ID NO 69
<211> LENGTH: 447
<212> TYPE: PRT
<213> ORGANISM: Artificial Sequence
<220> FEATURE:
<223> OTHER INFORMATION: 12172gH8 heavy chain (IgG4P)

<400> SEQUENCE: 69

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Ser Tyr
            20                  25                  30

Ala Met Thr Trp Val Arg Gln Ala Pro Gly Lys Gly Leu Glu Trp Ile
        35                  40                  45

Gly Ile Ile Tyr Ala Gly Gly Ser Pro Ser Tyr Ala Ser Trp Ala Lys
    50                  55                  60

Gly Arg Phe Thr Ile Ser Lys Asp Ser Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Gly Thr Gly Asp Thr Val Tyr Thr Tyr Phe Asn Ile Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160
```

```
Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445
```

<210> SEQ ID NO 70
<211> LENGTH: 1341
<212> TYPE: DNA
<213> ORGANISM: Artificial Sequence
<220> FEATURE:
<223> OTHER INFORMATION: 12172gH8 heavy chain (IgG4P)

<400> SEQUENCE: 70

```
gaagtgcagc tcgtggagtc gggcggaggt ctggtgcagc ccggaggaag cctgcgcctg      60

tcatgcgctg ccagcgggtt ctcgctttcc tcctacgcca tgacctgggt cagacaggca     120

ccgggaaagg gcctcgaatg gattggcatt atctatgcgg gtggcagccc ttcctacgcc     180

tcctgggcta aagggcggtt caccatctcg aaggactcct ccaagaacac ggtgtacttg     240

caaatgaact cactgagggc cgaggacact gcggtgtact actgtgcccg gggaactgga     300

gataccgtgt acacctactt taacatctgg ggccagggaa ccctggtcac tgtctcgagc     360

gcttctacaa agggcccatc cgtcttcccc ctggcgccct gctccaggag cacctccgag     420
```

```
agcacagccg ccctgggctg cctggtcaag gactacttcc ccgaaccggt gacggtgtcg    480

tggaactcag gcgccctgac cagcggcgtg cacaccttcc cggctgtcct acagtcctca    540

ggactctact ccctcagcag cgtggtgacc gtgccctcca gcagcttggg cacgaagacc    600

tacacctgca acgtagatca caagcccagc aacaccaagg tggacaagag agttgagtcc    660

aaatatggtc ccccatgccc accatgccca gcacctgagt tcctgggggg accatcagtc    720

ttcctgttcc ccccaaaacc caaggacact ctcatgatct cccggacccc tgaggtcacg    780

tgcgtggtgg tggacgtgag ccaggaagac cccgaggtcc agttcaactg gtacgtggat    840

ggcgtggagg tgcataatgc caagacaaag ccgcgggagg agcagttcaa cagcacgtac    900

cgtgtggtca gcgtcctcac cgtcctgcac caggactggc tgaacggcaa ggagtacaag    960

tgcaaggtct ccaacaaagg cctcccgtcc tccatcgaga aaaccatctc caaagccaaa   1020

gggcagcccc gagagccaca ggtgtacacc ctgcccccat cccaggagga gatgaccaag   1080

aaccaggtca gcctgacctg cctggtcaaa ggcttctacc ccagcgacat cgccgtggag   1140

tgggagagca atgggcagcc ggagaacaac tacaagacca cgcctcccgt gctggactcc   1200

gacggctcct tcttcctcta cagcaggcta accgtggaca agagcaggtg gcaggagggg   1260

aatgtcttct catgctccgt gatgcatgag gctctgcaca accactacac acagaagagc   1320

ctctccctgt ctctgggtaa a                                              1341
```

<210> SEQ ID NO 71
<211> LENGTH: 120
<212> TYPE: PRT
<213> ORGANISM: Artificial Sequence
<220> FEATURE:
<223> OTHER INFORMATION: 12172gH9 V-region

<400> SEQUENCE: 71

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Ser Tyr
            20                  25                  30

Ala Met Thr Trp Val Arg Gln Ala Pro Gly Lys Gly Leu Glu Trp Ile
        35                  40                  45

Gly Ile Ile Tyr Ala Gly Gly Ser Pro Ser Tyr Ala Ser Trp Ala Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Gly Thr Gly Asp Thr Val Tyr Thr Tyr Phe Asn Ile Trp Gly Gln
            100                 105                 110

Gly Thr Leu Val Thr Val Ser Ser
        115                 120
```

<210> SEQ ID NO 72
<211> LENGTH: 360
<212> TYPE: DNA
<213> ORGANISM: Artificial Sequence
<220> FEATURE:
<223> OTHER INFORMATION: 12172gH9 V-region

<400> SEQUENCE: 72

```
gaagtgcagc tcgtggagtc gggcggaggt ctggtgcagc ccggaggaag cctgcgcctg     60

tcatgcgctg ccagcgggtt ctcgctttcc tcctacgcca tgacctgggt cagacaggca    120
```

ccgggaaagg gcctcgaatg gattggcatt atctatgcgg gtggcagccc ttcctacgcc 180
tcctgggcta aagggcggtt caccatctcg cgcgacaatt ccaagaacac ggtgtacttg 240
caaatgaact cactgagggc cgaggacact gcggtgtact actgtgcccg gggaactgga 300
gataccgtgt acacctactt taacatctgg ggccagggaa ccctggtcac tgtctcgagc 360

<210> SEQ ID NO 73
<211> LENGTH: 447
<212> TYPE: PRT
<213> ORGANISM: Artificial Sequence
<220> FEATURE:
<223> OTHER INFORMATION: 12172gH9 heavy chain (IgG4P)

<400> SEQUENCE: 73

Glu Val Gln Leu Val Glu Ser Gly Gly Gly Leu Val Gln Pro Gly Gly
1 5 10 15

Ser Leu Arg Leu Ser Cys Ala Ala Ser Gly Phe Ser Leu Ser Ser Tyr
20 25 30

Ala Met Thr Trp Val Arg Gln Ala Pro Gly Lys Gly Leu Glu Trp Ile
35 40 45

Gly Ile Ile Tyr Ala Gly Gly Ser Pro Ser Tyr Ala Ser Trp Ala Lys
50 55 60

Gly Arg Phe Thr Ile Ser Arg Asp Asn Ser Lys Asn Thr Val Tyr Leu
65 70 75 80

Gln Met Asn Ser Leu Arg Ala Glu Asp Thr Ala Val Tyr Tyr Cys Ala
85 90 95

Arg Gly Thr Gly Asp Thr Val Tyr Thr Tyr Phe Asn Ile Trp Gly Gln
100 105 110

Gly Thr Leu Val Thr Val Ser Ser Ala Ser Thr Lys Gly Pro Ser Val
115 120 125

Phe Pro Leu Ala Pro Cys Ser Arg Ser Thr Ser Glu Ser Thr Ala Ala
130 135 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Ser Leu Gly Thr Lys Thr Tyr Thr Cys Asn Val Asp His Lys
195 200 205

Pro Ser Asn Thr Lys Val Asp Lys Arg Val Glu Ser Lys Tyr Gly Pro
210 215 220

Pro Cys Pro Pro Cys Pro Ala Pro Glu Phe Leu Gly Gly Pro Ser Val
225 230 235 240

Phe Leu Phe Pro Pro Lys Pro Lys Asp Thr Leu Met Ile Ser Arg Thr
245 250 255

Pro Glu Val Thr Cys Val Val Val Asp Val Ser Gln Glu Asp Pro Glu
260 265 270

Val Gln Phe Asn Trp Tyr Val Asp Gly Val Glu Val His Asn Ala Lys
275 280 285

Thr Lys Pro Arg Glu Glu Gln Phe Asn Ser Thr Tyr Arg Val Val Ser
290 295 300

Val Leu Thr Val Leu His Gln Asp Trp Leu Asn Gly Lys Glu Tyr Lys
305 310 315 320

```
Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445
```

<210> SEQ ID NO 74
<211> LENGTH: 1341
<212> TYPE: DNA
<213> ORGANISM: Artificial Sequence
<220> FEATURE:
<223> OTHER INFORMATION: 12172gH9 heavy chain (IgG4P)

<400> SEQUENCE: 74

```
gaagtgcagc tcgtggagtc gggcggaggt ctggtgcagc ccggaggaag cctgcgcctg     60

tcatgcgctg ccagcgggtt ctcgctttcc tcctacgcca tgacctgggt cagacaggca    120

ccgggaaagg gcctcgaatg gattggcatt atctatgcgg gtggcagccc ttcctacgcc    180

tcctgggcta aagggcggtt caccatctcg cgcgacaatt ccaagaacac ggtgtacttg    240

caaatgaact cactgagggc cgaggacact gcggtgtact actgtgcccg gggaactgga    300

gataccgtgt acacctactt taacatctgg ggccagggaa ccctggtcac tgtctcgagc    360

gcttctacaa agggcccatc cgtcttcccc ctggcgccct gctccaggag cacctccgag    420

agcacagccg ccctgggctg cctggtcaag gactacttcc ccgaaccggt gacggtgtcg    480

tggaactcag gcgccctgac cagcggcgtg cacaccttcc cggctgtcct acagtcctca    540

ggactctact ccctcagcag cgtggtgacc gtgccctcca gcagcttggg cacgaagacc    600

tacacctgca acgtagatca caagcccagc aacaccaagg tggacaagag agttgagtcc    660

aaatatggtc ccccatgccc accatgccca gcacctgagt tcctgggggg accatcagtc    720

ttcctgttcc ccccaaaacc caaggacact ctcatgatct cccggacccc tgaggtcacg    780

tgcgtggtgg tggacgtgag ccaggaagac cccgaggtcc agttcaactg gtacgtggat    840

ggcgtggagg tgcataatgc caagacaaag ccgcgggagg agcagttcaa cagcacgtac    900

cgtgtggtca gcgtcctcac cgtcctgcac caggactggc tgaacggcaa ggagtacaag    960

tgcaaggtct ccaacaaagg cctcccgtcc tccatcgaga aaaccatctc caaagccaaa   1020

gggcagcccc gagagccaca ggtgtacacc ctgcccccat cccaggagga gatgaccaag   1080

aaccaggtca gcctgacctg cctggtcaaa ggcttctacc ccagcgacat cgccgtggag   1140

tgggagagca atgggcagcc ggagaacaac tacaagacca cgcctcccgt gctggactcc   1200

gacggctcct tcttcctcta cagcaggcta accgtggaca agagcaggtg gcaggagggg   1260

aatgtcttct catgctccgt gatgcatgag gctctgcaca accactacac acagaagagc   1320

ctctccctgt ctctgggtaa a                                              1341
```

<210> SEQ ID NO 75
<211> LENGTH: 120
<212> TYPE: PRT
<213> ORGANISM: Artificial Sequence
<220> FEATURE:
<223> OTHER INFORMATION: 12172gH10 V-region

<400> SEQUENCE: 75

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Ser Tyr
            20                  25                  30

Ala Met Thr Trp Val Arg Gln Ala Pro Gly Lys Gly Leu Glu Trp Ile
        35                  40                  45

Gly Ile Ile Tyr Ala Gly Gly Ser Pro Ser Tyr Ala Ser Trp Ala Lys
    50                  55                  60

Gly Arg Phe Thr Ile Ser Arg Asp Ser Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Thr Gly Asp Thr Val Tyr Thr Tyr Phe Asn Ile Trp Gly Gln
            100                 105                 110

Gly Thr Leu Val Thr Val Ser Ser
        115                 120

<210> SEQ ID NO 76
<211> LENGTH: 360
<212> TYPE: DNA
<213> ORGANISM: Artificial Sequence
<220> FEATURE:
<223> OTHER INFORMATION: 12172gH10 V-region

<400> SEQUENCE: 76
gaagtgcagc tcgtggagtc gggcggaggt ctggtgcagc ccggaggaag cctgcgcctg 60
tcatgcgctg ccagcgggtt ctcgctttcc tcctacgcca tgacctgggt cagacaggca 120
ccgggaaagg gcctcgaatg gattggcatt atctatgcgg gtggcagccc ttcctacgcc 180
tcctgggcta aagggcggtt caccatctcg cgcgactcct ccaagaacac gctgtacttg 240
caaatgaact cactgagggc cgaggacact gcggtgtact actgtgcccg gggaactgga 300
gataccgtgt acacctactt taacatctgg ggccagggaa ccctggtcac tgtctcgagc 360

<210> SEQ ID NO 77
<211> LENGTH: 447
<212> TYPE: PRT
<213> ORGANISM: Artificial Sequence
<220> FEATURE:
<223> OTHER INFORMATION: 12172gH10 heavy chain (IgG4P)

<400> SEQUENCE: 77

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Ser Tyr
            20                  25                  30

Ala Met Thr Trp Val Arg Gln Ala Pro Gly Lys Gly Leu Glu Trp Ile
        35                  40                  45

Gly Ile Ile Tyr Ala Gly Gly Ser Pro Ser Tyr Ala Ser Trp Ala Lys
    50                  55                  60

```
Gly Arg Phe Thr Ile Ser Arg Asp Ser Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Thr Gly Asp Thr Val Tyr Thr Tyr Phe Asn Ile Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445
```

<210> SEQ ID NO 78
<211> LENGTH: 1341
<212> TYPE: DNA
<213> ORGANISM: Artificial Sequence
<220> FEATURE:
<223> OTHER INFORMATION: 12172gH10 heavy chain (IgG4P)

<400> SEQUENCE: 78
gaagtgcagc tcgtggagtc gggcggaggt ctggtgcagc ccggaggaag cctgcgcctg 60
tcatgcgctg ccagcgggtt ctcgctttcc tcctacgcca tgacctgggt cagacaggca 120
ccgggaaagg gcctcgaatg gattggcatt atctatgcgg gtggcagccc ttcctacgcc 180
tcctgggcta aagggcggtt caccatctcg cgcgactcct ccaagaacac gctgtacttg 240
caaatgaact cactgagggc cgaggacact gcggtgtact actgtgcccg gggaactgga 300
gataccgtgt acacctactt taacatctgg ggccagggaa ccctggtcac tgtctcgagc 360
gcttctacaa agggcccatc cgtcttcccc ctggcgccct gctccaggag cacctccgag 420
agcacagccg ccctgggctg cctggtcaag gactacttcc ccgaaccggt gacggtgtcg 480
tggaactcag gcgccctgac cagcggcgtg cacaccttcc cggctgtcct acagtcctca 540
ggactctact ccctcagcag cgtggtgacc gtgccctcca gcagcttggg cacgaagacc 600
tacacctgca acgtagatca caagcccagc aacaccaagg tggacaagag agttgagtcc 660
aaatatggtc ccccatgccc accatgccca gcacctgagt tcctgggggg accatcagtc 720
ttcctgttcc ccccaaaacc caaggacact ctcatgatct cccggacccc tgaggtcacg 780
tgcgtggtgg tggacgtgag ccaggaagac cccgaggtcc agttcaactg gtacgtggat 840
ggcgtggagg tgcataatgc caagacaaag ccgcgggagg agcagttcaa cagcacgtac 900
cgtgtggtca gcgtcctcac cgtcctgcac caggactggc tgaacggcaa ggagtacaag 960
tgcaaggtct ccaacaaagg cctcccgtcc tccatcgaga aaaccatctc caaagccaaa 1020
gggcagcccc gagagccaca ggtgtacacc ctgcccccat cccaggagga gatgaccaag 1080
aaccaggtca gcctgacctg cctggtcaaa ggcttctacc ccagcgacat cgccgtggag 1140
tgggagagca atgggcagcc ggagaacaac tacaagacca cgcctcccgt gctggactcc 1200
gacggctcct tcttcctcta cagcaggcta accgtggaca agagcaggtg gcaggagggg 1260
aatgtcttct catgctccgt gatgcatgag gctctgcaca accactacac acagaagagc 1320
ctctccctgt ctctgggtaa a 1341

<210> SEQ ID NO 79
<211> LENGTH: 120
<212> TYPE: PRT
<213> ORGANISM: Artificial Sequence
<220> FEATURE:
<223> OTHER INFORMATION: 12172gH11 V-region

<400> SEQUENCE: 79

Glu Val Gln Leu Val Glu Ser Gly Gly Gly Leu Val Gln Pro Gly Gly
1 5 10 15

Ser Leu Arg Leu Ser Cys Ala Ala Ser Gly Phe Ser Leu Ser Ser Tyr
20 25 30

Ala Met Thr Trp Val Arg Gln Ala Pro Gly Lys Gly Leu Glu Trp Ile
35 40 45

Gly Ile Ile Tyr Ala Gly Gly Ser Pro Ser Tyr Ala Ser Trp Ala Lys
50 55 60

Gly Arg Phe Thr Ile Ser Lys Asp Asn Ser Lys Asn Thr Leu Tyr Leu
65 70 75 80

Gln Met Asn Ser Leu Arg Ala Glu Asp Thr Ala Val Tyr Tyr Cys Ala
85 90 95

Arg Gly Thr Gly Asp Thr Val Tyr Thr Tyr Phe Asn Ile Trp Gly Gln
100 105 110

Gly Thr Leu Val Thr Val Ser Ser
115 120

<210> SEQ ID NO 80
<211> LENGTH: 360
<212> TYPE: DNA
<213> ORGANISM: Artificial Sequence
<220> FEATURE:
<223> OTHER INFORMATION: 12172gH11 V-region

<400> SEQUENCE: 80
gaagtgcagc tcgtggagtc gggcggaggt ctggtgcagc ccggaggaag cctgcgcctg 60
tcatgcgctg ccagcgggtt ctcgctttcc tcctacgcca tgacctgggt cagacaggca 120
ccgggaaagg gcctcgaatg gattggcatt atctatgcgg gtggcagccc ttcctacgcc 180
tcctgggcta aagggcggtt caccatctcg aaggacaatt ccaagaacac gctgtacttg 240
caaatgaact cactgagggc cgaggacact gcggtgtact actgtgcccg gggaactgga 300
gataccgtgt acacctactt taacatctgg ggccagggaa ccctggtcac tgtctcgagc 360

<210> SEQ ID NO 81
<211> LENGTH: 447
<212> TYPE: PRT
<213> ORGANISM: Artificial Sequence
<220> FEATURE:
<223> OTHER INFORMATION: 12172gH11 heavy chain (IgG4P)

<400> SEQUENCE: 81

Glu Val Gln Leu Val Glu Ser Gly Gly Gly Leu Val Gln Pro Gly Gly
1 5 10 15

Ser Leu Arg Leu Ser Cys Ala Ala Ser Gly Phe Ser Leu Ser Ser Tyr
20 25 30

Ala Met Thr Trp Val Arg Gln Ala Pro Gly Lys Gly Leu Glu Trp Ile
35 40 45

Gly Ile Ile Tyr Ala Gly Gly Ser Pro Ser Tyr Ala Ser Trp Ala Lys
50 55 60

Gly Arg Phe Thr Ile Ser Lys Asp Asn Ser Lys Asn Thr Leu Tyr Leu
65 70 75 80

Gln Met Asn Ser Leu Arg Ala Glu Asp Thr Ala Val Tyr Tyr Cys Ala
85 90 95

Arg Gly Thr Gly Asp Thr Val Tyr Thr Tyr Phe Asn Ile Trp Gly Gln
100 105 110

Gly Thr Leu Val Thr Val Ser Ser Ala Ser Thr Lys Gly Pro Ser Val
115 120 125

Phe Pro Leu Ala Pro Cys Ser Arg Ser Thr Ser Glu Ser Thr Ala Ala
130 135 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Ser Leu Gly Thr Lys Thr Tyr Thr Cys Asn Val Asp His Lys
195 200 205

Pro Ser Asn Thr Lys Val Asp Lys Arg Val Glu Ser Lys Tyr Gly Pro
210 215 220

Pro Cys Pro Pro Cys Pro Ala Pro Glu Phe Leu Gly Gly Pro Ser Val

```
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445
```

<210> SEQ ID NO 82
<211> LENGTH: 1341
<212> TYPE: DNA
<213> ORGANISM: Artificial Sequence
<220> FEATURE:
<223> OTHER INFORMATION: 12172gH11 heavy chain (IgG4P)

<400> SEQUENCE: 82

```
gaagtgcagc tcgtggagtc gggcggaggt ctggtgcagc ccggaggaag cctgcgcctg     60

tcatgcgctg ccagcgggtt ctcgctttcc tcctacgcca tgacctgggt cagacaggca    120

ccgggaaagg gcctcgaatg gattggcatt atctatgcgg gtggcagccc ttcctacgcc    180

tcctgggcta aagggcggtt caccatctcg aaggacaatt ccaagaacac gctgtacttg    240

caaatgaact cactgagggc cgaggacact gcggtgtact actgtgcccg gggaactgga    300

gataccgtgt acacctactt taacatctgg ggccagggaa ccctggtcac tgtctcgagc    360

gcttctacaa agggcccctc cgtgttccct ctggcccctt gctcccggtc cacctccgag    420

tctaccgccg ctctgggctg cctggtcaag gactacttcc ccgagcccgt gacagtgtcc    480

tggaactctg gcgccctgac ctccggcgtg cacaccttcc ctgccgtgct gcagtcctcc    540

ggcctgtact ccctgtcctc cgtcgtgacc gtgccctcct ccagcctggg caccaagacc    600

tacacctgta acgtggacca caagccctcc aacaccaagg tggacaagcg ggtggaatct    660

aagtacggcc ctccctgccc cccctgccct gcccctgaat ttctgggcgg accttccgtg    720

ttcctgttcc ccccaaagcc caaggacacc ctgatgatct cccggacccc cgaagtgacc    780

tgcgtggtgg tggacgtgtc ccaggaagat cccgaggtcc agttcaattg gtacgtggac    840
```

```
ggcgtggaag tgcacaatgc caagaccaag cccagagagg aacagttcaa ctccacctac    900

cgggtggtgt ccgtgctgac cgtgctgcac caggactggc tgaacggcaa agagtacaag    960

tgcaaggtgt ccaacaaggg cctgccctcc agcatcgaaa agaccatctc caaggccaag   1020

ggccagcccc gcgagcccca ggtgtacacc ctgcccccta gccaggaaga gatgaccaag   1080

aaccaggtgt ccctgacctg tctggtcaag ggcttctacc cctccgacat tgccgtggaa   1140

tgggagtcca acggccagcc cgagaacaac tacaagacca ccccccctgt gctggacagc   1200

gacggctcct tcttcctgta ctctcggctg accgtggaca agtcccggtg gcaggaaggc   1260

aacgtcttct cctgctccgt gatgcacgag gccctgcaca accactacac ccagaagtcc   1320

ctgtccctga gcctgggcaa g                                              1341
```

```
<210> SEQ ID NO 83
<211> LENGTH: 447
<212> TYPE: PRT
<213> ORGANISM: Artificial Sequence
<220> FEATURE:
<223> OTHER INFORMATION: 12172gH11 heavy chain (IgG4P F234A L235A)

<400> SEQUENCE: 83

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Ser Tyr
            20                  25                  30

Ala Met Thr Trp Val Arg Gln Ala Pro Gly Lys Gly Leu Glu Trp Ile
        35                  40                  45

Gly Ile Ile Tyr Ala Gly Gly Ser Pro Ser Tyr Ala Ser Trp Ala Lys
    50                  55                  60

Gly Arg Phe Thr Ile Ser Lys Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Thr Gly Asp Thr Val Tyr Thr Tyr Phe Asn Ile Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270
```

```
Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445


<210> SEQ ID NO 84
<211> LENGTH: 1341
<212> TYPE: DNA
<213> ORGANISM: Artificial Sequence
<220> FEATURE:
<223> OTHER INFORMATION: 12172gH11 heavy chain (IgG4P F234A L235A)

<400> SEQUENCE: 84

gaagtgcagc tcgtggagtc gggcggaggt ctggtgcagc ccggaggaag cctgcgcctg      60

tcatgcgctg ccagcgggtt ctcgctttcc tcctacgcca tgacctgggt cagacaggca     120

ccgggaaagg gcctcgaatg gattggcatt atctatgcgg gtggcagccc ttcctacgcc     180

tcctgggcta aagggcggtt caccatctcg aaggacaatt ccaagaacac gctgtacttg     240

caaatgaact cactgagggc cgaggacact gcggtgtact actgtgcccg gggaactgga     300

gataccgtgt acacctactt taacatctgg ggccagggaa ccctggtcac tgtctcgagc     360

gcttctacaa agggcccatc cgtcttcccc ctggcgccct gctccaggag cacctccgag     420

agcacagccg ccctgggctg cctggtcaag gactacttcc ccgaaccggt gacggtgtcg     480

tggaactcag gcgccctgac cagcggcgtg cacaccttcc cggctgtcct acagtcctca     540

ggactctact ccctcagcag cgtggtgacc gtgccctcca gcagcttggg cacgaagacc     600

tacacctgca acgtagatca caagcccagc aacaccaagg tggacaagag agttgagtcc     660

aaatatggtc ccccatgccc accatgccca gcacctgaag ccgcgggggg accgtcagtc     720

ttcctgttcc ccccaaaacc caaggacact ctcatgatct cccggacccc tgaggtcacg     780

tgcgtggtgg tggacgtgag ccaggaagac cccgaggtcc agttcaactg gtacgtggat     840

ggcgtggagg tgcataatgc caagacaaag ccgcgggagg agcagttcaa cagcacgtac     900

cgtgtggtca gcgtcctcac cgtcctgcac caggactggc tgaacggcaa ggagtacaag     960

tgcaaggtct ccaacaaagg cctcccgtcc tccatcgaga aaaccatctc caaagccaaa    1020

gggcagcccc gagagccaca ggtgtacacc ctgcccccat cccaggagga gatgaccaag    1080
```

```
aaccaggtca gcctgacctg cctggtcaaa ggcttctacc ccagcgacat cgccgtggag   1140

tgggagagca atgggcagcc ggagaacaac tacaagacca cgcctcccgt gctggactcc   1200

gacggctcct tcttcctcta cagcaggcta accgtggaca agagcaggtg gcaggagggg   1260

aatgtcttct catgctccgt gatgcatgag gctctgcaca accactacac acagaagagc   1320

ctctccctgt ctctgggtaa a                                              1341


<210> SEQ ID NO 85
<211> LENGTH: 450
<212> TYPE: PRT
<213> ORGANISM: Artificial Sequence
<220> FEATURE:
<223> OTHER INFORMATION: 12172gH11 heavy chain (IgG1)

<400> SEQUENCE: 85

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Ser Tyr
            20                  25                  30

Ala Met Thr Trp Val Arg Gln Ala Pro Gly Lys Gly Leu Glu Trp Ile
        35                  40                  45

Gly Ile Ile Tyr Ala Gly Gly Ser Pro Ser Tyr Ala Ser Trp Ala Lys
    50                  55                  60

Gly Arg Phe Thr Ile Ser Lys Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Thr Gly Asp Thr Val Tyr Thr Tyr Phe Asn Ile Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320
```

```
Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450
```

<210> SEQ ID NO 86
<211> LENGTH: 1350
<212> TYPE: DNA
<213> ORGANISM: Artificial Sequence
<220> FEATURE:
<223> OTHER INFORMATION: 12172gH11 heavy chain (IgG1)

<400> SEQUENCE: 86

```
gaagtgcagc tcgtggagtc gggcggaggt ctggtgcagc ccggaggaag cctgcgcctg     60

tcatgcgctg ccagcgggtt ctcgctttcc tcctacgcca tgacctgggt cagacaggca    120

ccgggaaagg gcctcgaatg gattggcatt atctatgcgg gtggcagccc ttcctacgcc    180

tcctgggcta aagggcggtt caccatctcg aaggacaatt ccaagaacac gctgtacttg    240

caaatgaact cactgagggc cgaggacact gcggtgtact actgtgcccg gggaactgga    300

gataccgtgt acacctactt taacatctgg ggccagggaa ccctggtcac tgtctcgagc    360

gcttctacaa agggcccatc ggtcttcccc ctggcaccct cctccaagag cacctctggg    420

ggcacagcgg ccctgggctg cctggtcaag gactacttcc ccgaaccggt gacggtgtcg    480

tggaactcag gcgccctgac cagcggcgtg cacaccttcc cggctgtcct acagtcctca    540

ggactctact ccctcagcag cgtggtgacc gtgccctcca gcagcttggg cacccagacc    600

tacatctgca acgtgaatca caagcccagc aacaccaagg tggacaagaa agttgagccc    660

aaatcttgtg acaaaactca cacatgccca ccgtgcccag cacctgaact cctgggggga    720

ccgtcagtct tcctcttccc cccaaaaccc aaggacaccc tcatgatctc ccggacccct    780

gaggtcacat gcgtggtggt ggacgtgagc cacgaagacc ctgaggtcaa gttcaactgg    840

tacgtggacg gcgtggaggt gcataatgcc aagacaaagc cgcgggagga gcagtacaac    900

agcacgtacc gtgtggtcag cgtcctcacc gtcctgcacc aggactggct gaatggcaag    960

gagtacaagt gcaaggtctc caacaaagcc ctcccagccc ccatcgagaa aaccatctcc   1020

aaagccaaag ggcagccccg agaaccacag gtgtacaccc tgcccccatc ccgggatgag   1080

ctgaccaaga accaggtcag cctgacctgc ctggtcaaag gcttctatcc cagcgacatc   1140

gccgtggagt gggagagcaa tgggcagccg gagaacaact acaagaccac gcctcccgtg   1200

ctggactccg acggctcctt cttcctctac agcaagctca ccgtggacaa gagcaggtgg   1260
```

cagcagggga acgtcttctc atgctccgtg atgcatgagg ctctgcacaa ccactacacg 1320
cagaagagcc tctccctgtc tccgggtaaa 1350

<210> SEQ ID NO 87
<211> LENGTH: 450
<212> TYPE: PRT
<213> ORGANISM: Artificial Sequence
<220> FEATURE:
<223> OTHER INFORMATION: 12172gH11 heavy chain (IgG1 L234A L235A)

<400> SEQUENCE: 87

Glu Val Gln Leu Val Glu Ser Gly Gly Gly Leu Val Gln Pro Gly Gly
1 5 10 15

Ser Leu Arg Leu Ser Cys Ala Ala Ser Gly Phe Ser Leu Ser Ser Tyr
20 25 30

Ala Met Thr Trp Val Arg Gln Ala Pro Gly Lys Gly Leu Glu Trp Ile
35 40 45

Gly Ile Ile Tyr Ala Gly Gly Ser Pro Ser Tyr Ala Ser Trp Ala Lys
50 55 60

Gly Arg Phe Thr Ile Ser Lys Asp Asn Ser Lys Asn Thr Leu Tyr Leu
65 70 75 80

Gln Met Asn Ser Leu Arg Ala Glu Asp Thr Ala Val Tyr Tyr Cys Ala
85 90 95

Arg Gly Thr Gly Asp Thr Val Tyr Thr Tyr Phe Asn Ile Trp Gly Gln
100 105 110

Gly Thr Leu Val Thr Val Ser Ser Ala Ser Thr Lys Gly Pro Ser Val
115 120 125

Phe Pro Leu Ala Pro Ser Ser Lys Ser Thr Ser Gly Gly Thr Ala Ala
130 135 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Ser Leu Gly Thr Gln Thr Tyr Ile Cys Asn Val Asn His Lys
195 200 205

Pro Ser Asn Thr Lys Val Asp Lys Lys Val Glu Pro Lys Ser Cys Asp
210 215 220

Lys Thr His Thr Cys Pro Pro Cys Pro Ala Pro Glu Ala Ala Gly Gly
225 230 235 240

Pro Ser Val Phe Leu Phe Pro Pro Lys Pro Lys Asp Thr Leu Met Ile
245 250 255

Ser Arg Thr Pro Glu Val Thr Cys Val Val Val Asp Val Ser His Glu
260 265 270

Asp Pro Glu Val Lys Phe Asn Trp Tyr Val Asp Gly Val Glu Val His
275 280 285

Asn Ala Lys Thr Lys Pro Arg Glu Glu Gln Tyr Asn Ser Thr Tyr Arg
290 295 300

Val Val Ser Val Leu Thr Val Leu His Gln Asp Trp Leu Asn Gly Lys
305 310 315 320

Glu Tyr Lys Cys Lys Val Ser Asn Lys Ala Leu Pro Ala Pro Ile Glu
325 330 335

Lys Thr Ile Ser Lys Ala Lys Gly Gln Pro Arg Glu Pro Gln Val Tyr

```
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 88
<211> LENGTH: 1350
<212> TYPE: DNA
<213> ORGANISM: Artificial Sequence
<220> FEATURE:
<223> OTHER INFORMATION: 12172gH11 heavy chain (IgG1 L234A L235A)

<400> SEQUENCE: 88

gaagtgcagc tcgtggagtc gggcggaggt ctggtgcagc ccggaggaag cctgcgcctg      60

tcatgcgctg ccagcgggtt ctcgctttcc tcctacgcca tgacctgggt cagacaggca     120

ccgggaaagg gcctcgaatg gattggcatt atctatgcgg gtggcagccc ttcctacgcc     180

tcctgggcta aagggcggtt caccatctcg aaggacaatt ccaagaacac gctgtacttg     240

caaatgaact cactgagggc cgaggacact gcggtgtact actgtgcccg gggaactgga     300

gataccgtgt acacctactt taacatctgg ggccagggaa ccctggtcac tgtctcgagc     360

gcttctacaa agggcccctc cgtgttcccg ctcgctccat catcgaagtc taccagcgga     420

ggcactgcgg ctctcggttg cctcgtgaag gactacttcc cggagccggt gaccgtgtcg     480

tggaacagcg gagccctgac cagcggggtg cacacctttc cggccgtctt gcagtcaagc     540

ggcctttact ccctgtcatc agtggtgact gtcccgtcca gctcattggg aacccaaacc     600

tacatctgca atgtgaatca caaacctagc aacaccaagg ttgacaagaa agtcgagccc     660

aaatcgtgtg acaagactca cacttgtccg ccgtgcccgg cacccgaagc cgcaggaggt     720

cccagcgtct ttctgttccc tccaaagccg aaagacacgc tgatgatctc ccgcaccccg     780

gaggtcactt gcgtggtcgt ggacgtgtca catgaggacc cagaggtgaa gttcaattgg     840

tacgtggatg gcgtcgaagt ccacaatgcc aaaactaagc ccagagaaga acagtacaat     900

tcgacctacc gcgtcgtgtc cgtgctcacg gtgttgcatc aggattggct gaacgggaag     960

gaatacaagt gcaaagtgtc caacaaggcg ctgccggcac cgatcgagaa aactatctcc    1020

aaagcgaagg gacagcctag ggaacctcaa gtctacacgc tgccaccatc acgggatgaa    1080

ctgactaaga atcaagtctc actgacttgt ctggtgaagg ggttttaccc tagcgacatt    1140

gccgtggagt gggaatccaa cggccagcca gagaacaact acaagactac ccctccagtg    1200

ctcgactcgg atggatcgtt cttcctttac tcgaagctca ccgtggataa gtcccggtgg    1260

cagcagggaa acgtgttctc ctgctcggtg atgcatgaag ccctccataa ccactatacc    1320

caaaagtcgc tgtccctgtc gccgggaaag                                     1350
```

<210> SEQ ID NO 89
<211> LENGTH: 120
<212> TYPE: PRT
<213> ORGANISM: Artificial Sequence
<220> FEATURE:
<223> OTHER INFORMATION: 12172gH12 V-region

<400> SEQUENCE: 89

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Ser Tyr
            20                  25                  30

Ala Met Thr Trp Val Arg Gln Ala Pro Gly Lys Gly Leu Glu Trp Ile
        35                  40                  45

Gly Ile Ile Tyr Ala Gly Gly Ser Pro Ser Tyr Ala Ser Trp Ala Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Thr Gly Asp Thr Val Tyr Thr Tyr Phe Asn Ile Trp Gly Gln
            100                 105                 110

Gly Thr Leu Val Thr Val Ser Ser
        115                 120
```

<210> SEQ ID NO 90
<211> LENGTH: 360
<212> TYPE: DNA
<213> ORGANISM: Artificial Sequence
<220> FEATURE:
<223> OTHER INFORMATION: 12172gH12 V-region

<400> SEQUENCE: 90

```
gaagtgcagc tcgtggagtc gggcggaggt ctggtgcagc ccggaggaag cctgcgcctg     60

tcatgcgctg ccagcgggtt ctcgctttcc tcctacgcca tgacctgggt cagacaggca    120

ccgggaaagg gcctcgaatg gattggcatt atctatgcgg gtggcagccc ttcctacgcc    180

tcctgggcta aagggcggtt caccatctcg cgcgacaatt ccaagaacac gctgtacttg    240

caaatgaact cactgagggc cgaggacact gcggtgtact actgtgcccg gggaactgga    300

gataccgtgt acacctactt taacatctgg ggccagggaa ccctggtcac tgtctcgagc    360
```

<210> SEQ ID NO 91
<211> LENGTH: 447
<212> TYPE: PRT
<213> ORGANISM: Artificial Sequence
<220> FEATURE:
<223> OTHER INFORMATION: 12172gH12 heavy chain (IgG4P)

<400> SEQUENCE: 91

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Ser Tyr
            20                  25                  30

Ala Met Thr Trp Val Arg Gln Ala Pro Gly Lys Gly Leu Glu Trp Ile
        35                  40                  45

Gly Ile Ile Tyr Ala Gly Gly Ser Pro Ser Tyr Ala Ser Trp Ala Lys
    50                  55                  60

Gly Arg Phe Thr Ile Ser Arg Asp Asn Ser Lys Asn Thr Leu Tyr Leu
```

```
65                  70                  75                  80

Gln Met Asn Ser Leu Arg Ala Glu Asp Thr Ala Val Tyr Tyr Cys Ala
                85                  90                  95

Arg Gly Thr Gly Asp Thr Val Tyr Thr Tyr Phe Asn Ile Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445
```

<210> SEQ ID NO 92
<211> LENGTH: 1341
<212> TYPE: DNA
<213> ORGANISM: Artificial Sequence
<220> FEATURE:
<223> OTHER INFORMATION: 12172gH12 heavy chain (IgG4P)

<400> SEQUENCE: 92
gaagtgcagc tcgtggagtc gggcggaggt ctggtgcagc ccggaggaag cctgcgcctg 60
tcatgcgctg ccagcgggtt ctcgctttcc tcctacgcca tgacctgggt cagacaggca 120
ccgggaaagg gcctcgaatg gattggcatt atctatgcgg gtggcagccc ttcctacgcc 180
tcctgggcta aagggcggtt caccatctcg cgcgacaatt ccaagaacac gctgtacttg 240
caaatgaact cactgagggc cgaggacact gcggtgtact actgtgcccg gggaactgga 300
gataccgtgt acacctactt taacatctgg ggccagggaa ccctggtcac tgtctcgagc 360
gcttctacaa agggcccatc cgtcttcccc ctggcgccct gctccaggag cacctccgag 420
agcacagccg ccctgggctg cctggtcaag gactacttcc ccgaaccggt gacggtgtcg 480
tggaactcag gcgccctgac cagcggcgtg cacaccttcc cggctgtcct acagtcctca 540
ggactctact ccctcagcag cgtggtgacc gtgccctcca gcagcttggg cacgaagacc 600
tacacctgca acgtagatca caagcccagc aacaccaagg tggacaagag agttgagtcc 660
aaatatggtc ccccatgccc accatgccca gcacctgagt tcctgggggg accatcagtc 720
ttcctgttcc ccccaaaacc caaggacact ctcatgatct cccggacccc tgaggtcacg 780
tgcgtggtgg tggacgtgag ccaggaagac cccgaggtcc agttcaactg gtacgtggat 840
ggcgtggagg tgcataatgc caagacaaag ccgcgggagg agcagttcaa cagcacgtac 900
cgtgtggtca gcgtcctcac cgtcctgcac caggactggc tgaacggcaa ggagtacaag 960
tgcaaggtct ccaacaaagg cctcccgtcc tccatcgaga aaaccatctc caaagccaaa 1020
gggcagcccc gagagccaca ggtgtacacc ctgcccccat cccaggagga gatgaccaag 1080
aaccaggtca gcctgacctg cctggtcaaa ggcttctacc ccagcgacat cgccgtggag 1140
tgggagagca atgggcagcc ggagaacaac tacaagacca cgcctcccgt gctggactcc 1200
gacggctcct tcttcctcta cagcaggcta accgtggaca agagcaggtg gcaggagggg 1260
aatgtcttct catgctccgt gatgcatgag gctctgcaca accactacac acagaagagc 1320
ctctccctgt ctctgggtaa a 1341

<210> SEQ ID NO 93
<211> LENGTH: 120
<212> TYPE: PRT
<213> ORGANISM: Artificial Sequence
<220> FEATURE:
<223> OTHER INFORMATION: 12172gH26 V-region

<400> SEQUENCE: 93

Glu Val Gln Leu Val Glu Ser Gly Gly Gly Leu Val Gln Pro Gly Gly
1 5 10 15

Ser Leu Arg Leu Ser Cys Ala Ala Ser Gly Phe Ser Leu Ser Ser Tyr
20 25 30

Ala Met Thr Trp Val Arg Gln Ala Pro Gly Lys Gly Leu Glu Trp Ile
35 40 45

Gly Ile Ile Tyr Ala Gly Gly Ser Pro Ser Tyr Ala Ser Trp Ala Lys
50 55 60

Gly Arg Phe Thr Ile Ser Lys Asp Asn Ser Ser Asn Thr Leu Tyr Leu
65 70 75 80

Gln Met Asn Ser Leu Arg Ala Glu Asp Thr Ala Val Tyr Tyr Cys Ala
85 90 95

Arg Gly Thr Gly Asp Thr Val Tyr Thr Tyr Phe Asn Ile Trp Gly Gln
100 105 110

Gly Thr Leu Val Thr Val Ser Ser
115 120

<210> SEQ ID NO 94
<211> LENGTH: 360
<212> TYPE: DNA
<213> ORGANISM: Artificial Sequence
<220> FEATURE:
<223> OTHER INFORMATION: 12172gH26 V-region

<400> SEQUENCE: 94
gaagtgcagc tcgtggagtc gggcggaggt ctggtgcagc ccggaggaag cctgcgcctg 60
tcatgcgctg ccagcgggtt ctcgctttcc tcctacgcca tgacctgggt cagacaggca 120
ccgggaaagg gcctcgaatg gattggcatt atctatgcgg gtggcagccc ttcctacgcc 180
tcctgggcta aagggcggtt caccatctcg aaggacaatt ccagcaacac gctgtacttg 240
caaatgaact cactgagggc cgaggacact gcggtgtact actgtgcccg gggaactgga 300
gataccgtgt acacctactt taacatctgg ggccagggaa ccctggtcac tgtctcgagc 360

<210> SEQ ID NO 95
<211> LENGTH: 447
<212> TYPE: PRT
<213> ORGANISM: Artificial Sequence
<220> FEATURE:
<223> OTHER INFORMATION: 12172gH26 heavy chain (hIgG4P)

<400> SEQUENCE: 95

Glu Val Gln Leu Val Glu Ser Gly Gly Gly Leu Val Gln Pro Gly Gly
1 5 10 15

Ser Leu Arg Leu Ser Cys Ala Ala Ser Gly Phe Ser Leu Ser Ser Tyr
20 25 30

Ala Met Thr Trp Val Arg Gln Ala Pro Gly Lys Gly Leu Glu Trp Ile
35 40 45

Gly Ile Ile Tyr Ala Gly Gly Ser Pro Ser Tyr Ala Ser Trp Ala Lys
50 55 60

Gly Arg Phe Thr Ile Ser Lys Asp Asn Ser Ser Asn Thr Leu Tyr Leu
65 70 75 80

Gln Met Asn Ser Leu Arg Ala Glu Asp Thr Ala Val Tyr Tyr Cys Ala
85 90 95

Arg Gly Thr Gly Asp Thr Val Tyr Thr Tyr Phe Asn Ile Trp Gly Gln
100 105 110

Gly Thr Leu Val Thr Val Ser Ser Ala Ser Thr Lys Gly Pro Ser Val
115 120 125

Phe Pro Leu Ala Pro Cys Ser Arg Ser Thr Ser Glu Ser Thr Ala Ala
130 135 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Ser Leu Gly Thr Lys Thr Tyr Thr Cys Asn Val Asp His Lys
195 200 205

Pro Ser Asn Thr Lys Val Asp Lys Arg Val Glu Ser Lys Tyr Gly Pro
210 215 220

Pro Cys Pro Pro Cys Pro Ala Pro Glu Phe Leu Gly Gly Pro Ser Val
225 230 235 240

Phe Leu Phe Pro Pro Lys Pro Lys Asp Thr Leu Met Ile Ser Arg Thr
245 250 255

Pro Glu Val Thr Cys Val Val Val Asp Val Ser Gln Glu Asp Pro Glu
260 265 270

Val Gln Phe Asn Trp Tyr Val Asp Gly Val Glu Val His Asn Ala Lys
275 280 285

Thr Lys Pro Arg Glu Glu Gln Phe Asn Ser Thr Tyr Arg Val Val Ser
290 295 300

Val Leu Thr Val Leu His Gln Asp Trp Leu Asn Gly Lys Glu Tyr Lys
305 310 315 320

Cys Lys Val Ser Asn Lys Gly Leu Pro Ser Ser Ile Glu Lys Thr Ile
325 330 335

Ser Lys Ala Lys Gly Gln Pro Arg Glu Pro Gln Val Tyr Thr Leu Pro
340 345 350

Pro Ser Gln Glu Glu Met Thr Lys Asn Gln Val Ser Leu Thr Cys Leu
355 360 365

Val Lys Gly Phe Tyr Pro Ser Asp Ile Ala Val Glu Trp Glu Ser Asn
370 375 380

Gly Gln Pro Glu Asn Asn Tyr Lys Thr Thr Pro Pro Val Leu Asp Ser
385 390 395 400

Asp Gly Ser Phe Phe Leu Tyr Ser Arg Leu Thr Val Asp Lys Ser Arg
405 410 415

Trp Gln Glu Gly Asn Val Phe Ser Cys Ser Val Met His Glu Ala Leu
420 425 430

His Asn His Tyr Thr Gln Lys Ser Leu Ser Leu Ser Leu Gly Lys
435 440 445

<210> SEQ ID NO 96
<211> LENGTH: 1341
<212> TYPE: DNA
<213> ORGANISM: Artificial Sequence
<220> FEATURE:
<223> OTHER INFORMATION: 12172gH26 heavy chain (hIgG4P)

<400> SEQUENCE: 96
gaagtgcagc tcgtggagtc gggcggaggt ctggtgcagc ccggaggaag cctgcgcctg 60
tcatgcgctg ccagcgggtt ctcgctttcc tcctacgcca tgacctgggt cagacaggca 120
ccgggaaagg gcctcgaatg gattggcatt atctatgcgg gtggcagccc ttcctacgcc 180
tcctgggcta aagggcggtt caccatctcg aaggacaatt ccagcaacac gctgtacttg 240
caaatgaact cactgagggc cgaggacact gcggtgtact actgtgcccg gggaactgga 300
gataccgtgt acacctactt taacatctgg ggccagggaa ccctggtcac tgtctcgagc 360
gcttctacaa agggcccatc cgtcttcccc ctggcgccct gctccaggag cacctccgag 420
agcacagccg ccctgggctg cctggtcaag gactacttcc ccgaaccggt gacggtgtcg 480
tggaactcag gcgccctgac cagcggcgtg cacaccttcc cggctgtcct acagtcctca 540
ggactctact ccctcagcag cgtggtgacc gtgccctcca gcagcttggg cacgaagacc 600
tacacctgca acgtagatca caagcccagc aacaccaagg tggacaagag agttgagtcc 660
aaatatggtc ccccatgccc accatgccca gcacctgagt tcctgggggg accatcagtc 720
ttcctgttcc ccccaaaacc caaggacact ctcatgatct cccggacccc tgaggtcacg 780
tgcgtggtgg tggacgtgag ccaggaagac cccgaggtcc agttcaactg gtacgtggat 840
ggcgtggagg tgcataatgc caagacaaag ccgcgggagg agcagttcaa cagcacgtac 900

```
cgtgtggtca gcgtcctcac cgtcctgcac caggactggc tgaacggcaa ggagtacaag    960

tgcaaggtct ccaacaaagg cctcccgtcc tccatcgaga aaaccatctc caaagccaaa   1020

gggcagcccc gagagccaca ggtgtacacc ctgcccccat cccaggagga gatgaccaag   1080

aaccaggtca gcctgacctg cctggtcaaa ggcttctacc ccagcgacat cgccgtggag   1140

tgggagagca atgggcagcc ggagaacaac tacaagacca cgcctcccgt gctggactcc   1200

gacggctcct tcttcctcta cagcaggcta accgtggaca agagcaggtg gcaggagggg   1260

aatgtcttct catgctccgt gatgcatgag gctctgcaca accactacac acagaagagc   1320

ctctccctgt ctctgggtaa a                                             1341
```

<210> SEQ ID NO 97
<211> LENGTH: 120
<212> TYPE: PRT
<213> ORGANISM: Artificial Sequence
<220> FEATURE:
<223> OTHER INFORMATION: 12172gH48 V-region

<400> SEQUENCE: 97

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Ser Tyr
            20                  25                  30

Ala Met Thr Trp Val Arg Gln Ala Pro Gly Lys Gly Leu Glu Trp Ile
        35                  40                  45

Gly Ile Ile Tyr Ala Gly Gly Ser Pro Ser Tyr Ala Ser Trp Ala Lys
    50                  55                  60

Gly Arg Phe Thr Ile Ser Lys Asp Asn Ser Gln Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Thr Gly Asp Thr Val Tyr Thr Tyr Phe Asn Ile Trp Gly Gln
            100                 105                 110

Gly Thr Leu Val Thr Val Ser Ser
        115                 120
```

<210> SEQ ID NO 98
<211> LENGTH: 360
<212> TYPE: DNA
<213> ORGANISM: Artificial Sequence
<220> FEATURE:
<223> OTHER INFORMATION: 12172gH48 V-region

<400> SEQUENCE: 98

```
gaagtgcagc tcgtggagtc gggcggaggt ctggtgcagc ccggaggaag cctgcgcctg     60

tcatgcgctg ccagcgggtt ctcgctttcc tcctacgcca tgacctgggt cagacaggca    120

ccgggaaagg gcctcgaatg gattggcatt atctatgcgg gtggcagccc ttcctacgcc    180

tcctgggcta aagggcggtt caccatctcg aaggacaatt cccagaacac gctgtacttg    240

caaatgaact cactgagggc cgaggacact gcggtgtact actgtgcccg gggaactgga    300

gataccgtgt acacctactt taacatctgg ggccagggaa ccctggtcac tgtctcgagc    360
```

<210> SEQ ID NO 99
<211> LENGTH: 447
<212> TYPE: PRT
<213> ORGANISM: Artificial Sequence
<220> FEATURE:

<223> OTHER INFORMATION: 12172gH48 heavy chain (hIgG4P)

<400> SEQUENCE: 99

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Ser Tyr
            20                  25                  30

Ala Met Thr Trp Val Arg Gln Ala Pro Gly Lys Gly Leu Glu Trp Ile
        35                  40                  45

Gly Ile Ile Tyr Ala Gly Gly Ser Pro Ser Tyr Ala Ser Trp Ala Lys
    50                  55                  60

Gly Arg Phe Thr Ile Ser Lys Asp Asn Ser Gln Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Thr Gly Asp Thr Val Tyr Thr Tyr Phe Asn Ile Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400
```

Asp Gly Ser Phe Phe Leu Tyr Ser Arg Leu Thr Val Asp Lys Ser Arg
405 410 415

Trp Gln Glu Gly Asn Val Phe Ser Cys Ser Val Met His Glu Ala Leu
420 425 430

His Asn His Tyr Thr Gln Lys Ser Leu Ser Leu Ser Leu Gly Lys
435 440 445

<210> SEQ ID NO 100
<211> LENGTH: 1341
<212> TYPE: DNA
<213> ORGANISM: Artificial Sequence
<220> FEATURE:
<223> OTHER INFORMATION: 12172gH48 heavy chain (hIgG4P)

<400> SEQUENCE: 100
gaagtgcagc tcgtggagtc gggcggaggt ctggtgcagc ccggaggaag cctgcgcctg 60
tcatgcgctg ccagcgggtt ctcgctttcc tcctacgcca tgacctgggt cagacaggca 120
ccgggaaagg gcctcgaatg gattggcatt atctatgcgg gtggcagccc ttcctacgcc 180
tcctgggcta aagggcggtt caccatctcg aaggacaatt cccagaacac gctgtacttg 240
caaatgaact cactgagggc cgaggacact gcggtgtact actgtgcccg gggaactgga 300
gataccgtgt acacctactt taacatctgg ggccagggaa ccctggtcac tgtctcgagc 360
gcttctacaa agggcccatc cgtcttcccc ctggcgccct gctccaggag cacctccgag 420
agcacagccg ccctgggctg cctggtcaag gactacttcc ccgaaccggt gacggtgtcg 480
tggaactcag gcgccctgac cagcggcgtg cacaccttcc cggctgtcct acagtcctca 540
ggactctact ccctcagcag cgtggtgacc gtgccctcca gcagcttggg cacgaagacc 600
tacacctgca acgtagatca caagcccagc aacaccaagg tggacaagag agttgagtcc 660
aaatatggtc ccccatgccc accatgccca gcacctgagt tcctgggggg accatcagtc 720
ttcctgttcc ccccaaaacc caaggacact ctcatgatct cccggacccc tgaggtcacg 780
tgcgtggtgg tggacgtgag ccaggaagac cccgaggtcc agttcaactg gtacgtggat 840
ggcgtggagg tgcataatgc caagacaaag ccgcgggagg agcagttcaa cagcacgtac 900
cgtgtggtca gcgtcctcac cgtcctgcac caggactggc tgaacggcaa ggagtacaag 960
tgcaaggtct ccaacaaagg cctcccgtcc tccatcgaga aaaccatctc caaagccaaa 1020
gggcagcccc gagagccaca ggtgtacacc ctgcccccat cccaggagga gatgaccaag 1080
aaccaggtca gcctgacctg cctggtcaaa ggcttctacc ccagcgacat cgccgtggag 1140
tgggagagca atgggcagcc ggagaacaac tacaagacca cgcctcccgt gctggactcc 1200
gacggctcct tcttcctcta cagcaggcta accgtggaca agagcaggtg gcaggagggg 1260
aatgtcttct catgctccgt gatgcatgag gctctgcaca accactacac acagaagagc 1320
ctctccctgt ctctgggtaa a 1341

<210> SEQ ID NO 101
<211> LENGTH: 120
<212> TYPE: PRT
<213> ORGANISM: Artificial Sequence
<220> FEATURE:
<223> OTHER INFORMATION: 12172gH49 V-region

<400> SEQUENCE: 101

Glu Val Gln Leu Val Glu Ser Gly Gly Gly Leu Val Gln Pro Gly Gly
1 5 10 15

Ser Leu Arg Leu Ser Cys Ala Ala Ser Gly Phe Ser Leu Ser Ser Tyr

```
            20                  25                  30

Ala Met Thr Trp Val Arg Gln Ala Pro Gly Lys Gly Leu Glu Trp Ile
        35                  40                  45

Gly Ile Ile Tyr Ala Gly Gly Ser Pro Ser Tyr Ala Ser Trp Ala Lys
    50                  55                  60

Gly Arg Phe Thr Ile Ser Lys Asp Asn Ser Glu Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Thr Gly Asp Thr Val Tyr Thr Tyr Phe Asn Ile Trp Gly Gln
            100                 105                 110

Gly Thr Leu Val Thr Val Ser Ser
        115                 120


<210> SEQ ID NO 102
<211> LENGTH: 360
<212> TYPE: DNA
<213> ORGANISM: Artificial Sequence
<220> FEATURE:
<223> OTHER INFORMATION: 12172gH49 V-region

<400> SEQUENCE: 102

gaagtgcagc tcgtggagtc gggcggaggt ctggtgcagc ccggaggaag cctgcgcctg      60

tcatgcgctg ccagcgggtt ctcgctttcc tcctacgcca tgacctgggt cagacaggca     120

ccgggaaagg gcctcgaatg gattggcatt atctatgcgg gtggcagccc ttcctacgcc     180

tcctgggcta aagggcggtt caccatctcg aaggacaatt ccgagaacac gctgtacttg     240

caaatgaact cactgagggc cgaggacact gcggtgtact actgtgcccg gggaactgga     300

gataccgtgt acacctactt taacatctgg ggccagggaa ccctggtcac tgtctcgagc     360


<210> SEQ ID NO 103
<211> LENGTH: 447
<212> TYPE: PRT
<213> ORGANISM: Artificial Sequence
<220> FEATURE:
<223> OTHER INFORMATION: 12172gH49 heavy chain (hIgG4P)

<400> SEQUENCE: 103

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Ser Tyr
            20                  25                  30

Ala Met Thr Trp Val Arg Gln Ala Pro Gly Lys Gly Leu Glu Trp Ile
        35                  40                  45

Gly Ile Ile Tyr Ala Gly Gly Ser Pro Ser Tyr Ala Ser Trp Ala Lys
    50                  55                  60

Gly Arg Phe Thr Ile Ser Lys Asp Asn Ser Glu Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Thr Gly Asp Thr Val Tyr Thr Tyr Phe Asn Ile Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140
```

```
Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445
```

```
<210> SEQ ID NO 104
<211> LENGTH: 1341
<212> TYPE: DNA
<213> ORGANISM: Artificial Sequence
<220> FEATURE:
<223> OTHER INFORMATION: 12172gH49 heavy chain (hIgG4P)

<400> SEQUENCE: 104

gaagtgcagc tcgtggagtc gggcggaggt ctggtgcagc ccggaggaag cctgcgcctg      60

tcatgcgctg ccagcgggtt ctcgctttcc tcctacgcca tgacctgggt cagacaggca     120

ccgggaaagg gcctcgaatg gattggcatt atctatgcgg gtggcagccc ttcctacgcc     180

tcctgggcta aagggcggtt caccatctcg aaggacaatt ccgagaacac gctgtacttg     240

caaatgaact cactgagggc cgaggacact gcggtgtact actgtgcccg gggaactgga     300

gataccgtgt acacctactt taacatctgg ggccagggaa ccctggtcac tgtctcgagc     360
```

```
gcttctacaa agggcccatc cgtcttcccc ctggcgccct gctccaggag cacctccgag    420

agcacagccg ccctgggctg cctggtcaag gactacttcc ccgaaccggt gacggtgtcg    480

tggaactcag gcgccctgac cagcggcgtg cacaccttcc cggctgtcct acagtcctca    540

ggactctact ccctcagcag cgtggtgacc gtgccctcca gcagcttggg cacgaagacc    600

tacacctgca acgtagatca caagcccagc aacaccaagg tggacaagag agttgagtcc    660

aaatatggtc ccccatgccc accatgccca gcacctgagt tcctgggggg accatcagtc    720

ttcctgttcc ccccaaaacc caaggacact ctcatgatct cccggacccc tgaggtcacg    780

tgcgtggtgg tggacgtgag ccaggaagac cccgaggtcc agttcaactg gtacgtggat    840

ggcgtggagg tgcataatgc caagacaaag ccgcgggagg agcagttcaa cagcacgtac    900

cgtgtggtca gcgtcctcac cgtcctgcac caggactggc tgaacggcaa ggagtacaag    960

tgcaaggtct ccaacaaagg cctcccgtcc tccatcgaga aaaccatctc caaagccaaa   1020

gggcagcccc gagagccaca ggtgtacacc ctgcccccat cccaggagga gatgaccaag   1080

aaccaggtca gcctgacctg cctggtcaaa ggcttctacc ccagcgacat cgccgtggag   1140

tgggagagca atgggcagcc ggagaacaac tacaagacca cgcctcccgt gctggactcc   1200

gacggctcct tcttcctcta cagcaggcta accgtggaca agagcaggtg gcaggagggg   1260

aatgtcttct catgctccgt gatgcatgag gctctgcaca accactacac acagaagagc   1320

ctctccctgt ctctgggtaa a                                             1341
```

<210> SEQ ID NO 105
<211> LENGTH: 107
<212> TYPE: PRT
<213> ORGANISM: Artificial Sequence
<220> FEATURE:
<223> OTHER INFORMATION: Human IGKV1-9 IGKJ4 acceptor framework

<400> SEQUENCE: 105

```
Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro Leu
                85                  90                  95

Thr Phe Gly Gly Gly Thr Lys Val Glu Ile Lys
            100                 105
```

<210> SEQ ID NO 106
<211> LENGTH: 321
<212> TYPE: DNA
<213> ORGANISM: Artificial Sequence
<220> FEATURE:
<223> OTHER INFORMATION: Human IGKV1-9 IGKJ4 acceptor framework

<400> SEQUENCE: 106

```
gacatccagt tgacccagtc tccatccttc ctgtctgcat ctgtaggaga cagagtcacc     60

atcacttgcc gggccagtca gggcattagc agttatttag cctggtatca gcaaaaacca    120
```

```
gggaaagccc ctaagctcct gatctatgct gcatccactt tgcaaagtgg ggtcccatca    180

aggttcagcg gcagtggatc tgggacagaa ttcactctca caatcagcag cctgcagcct    240

gaagattttg caacttatta ctgtcaacag cttaatagtt accctctcac tttcggcgga    300

gggaccaagg tggagatcaa a                                              321


<210> SEQ ID NO 107
<211> LENGTH: 112
<212> TYPE: PRT
<213> ORGANISM: Artificial Sequence
<220> FEATURE:
<223> OTHER INFORMATION: Human IGHV3-66 IGHJ4 acceptor framework

<400> SEQUENCE: 107

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Tyr Phe Asp Tyr Trp Gly Gln Gly Thr Leu Val Thr Val Ser Ser
            100                 105                 110


<210> SEQ ID NO 108
<211> LENGTH: 336
<212> TYPE: DNA
<213> ORGANISM: Artificial Sequence
<220> FEATURE:
<223> OTHER INFORMATION: Human IGHV3-66 IGHJ4 acceptor framework

<400> SEQUENCE: 108

gaggtgcagc tggtggagtc tgggggaggc ttggtccagc ctggggggtc cctgagactc     60

tcctgtgcag cctctggatt caccgtcagt agcaactaca tgagctgggt ccgccaggct    120

ccagggaagg ggctggagtg ggtctcagtt atttatagcg gtggtagcac atactacgca    180

gactccgtga agggcagatt caccatctcc agagacaatt ccaagaacac gctgtatctt    240

caaatgaaca gcctgagagc cgaggacacg gctgtgtatt actgtgcgag atactttgac    300

tactggggcc aaggaaccct ggtcaccgtc tcctca                              336


<210> SEQ ID NO 109
<211> LENGTH: 121
<212> TYPE: PRT
<213> ORGANISM: Artificial Sequence
<220> FEATURE:
<223> OTHER INFORMATION: Human TREM1  WT 01_WT_3A

<400> SEQUENCE: 109

Met Glu Leu Arg Ala Ala Thr Lys Leu Thr Glu Glu Lys Tyr Glu Leu
1               5                   10                  15

Lys Glu Gly Gln Thr Leu Asp Val Lys Cys Asp Tyr Thr Leu Glu Lys
            20                  25                  30

Phe Ala Ser Ser Gln Lys Ala Trp Gln Ile Ile Arg Asp Gly Glu Met
        35                  40                  45
```

```
Pro Lys Thr Leu Ala Cys Thr Glu Arg Pro Ser Lys Asn Ser His Pro
    50                  55                  60

Val Gln Val Gly Arg Ile Ile Leu Glu Asp Tyr His Asp His Gly Leu
65                  70                  75                  80

Leu Arg Val Arg Met Val Asn Leu Gln Val Glu Asp Ser Gly Leu Tyr
                85                  90                  95

Gln Cys Val Ile Tyr Gln Pro Pro Lys Glu Pro His Met Leu Phe Asp
            100                 105                 110

Arg Ile Arg Leu Val Val Thr Leu Glu
        115                 120


<210> SEQ ID NO 110
<211> LENGTH: 121
<212> TYPE: PRT
<213> ORGANISM: Artificial Sequence
<220> FEATURE:
<223> OTHER INFORMATION: Human TREM1 mutant  02_6

<400> SEQUENCE: 110

Met Glu Leu Arg Ala Ala Ala Lys Leu Thr Glu Glu Lys Tyr Glu Leu
1               5                   10                  15

Lys Glu Gly Gln Thr Leu Asp Val Lys Cys Asp Tyr Thr Leu Glu Lys
            20                  25                  30

Phe Ala Ser Ser Gln Lys Ala Trp Gln Ile Ile Arg Asp Gly Glu Met
        35                  40                  45

Pro Lys Thr Leu Ala Cys Thr Glu Arg Pro Ser Lys Asn Ser His Pro
    50                  55                  60

Val Gln Val Gly Arg Ile Ile Leu Glu Asp Tyr His Asp His Gly Leu
65                  70                  75                  80

Leu Arg Val Arg Met Val Asn Leu Gln Val Glu Asp Ser Gly Leu Tyr
                85                  90                  95

Gln Cys Val Ile Tyr Gln Pro Pro Lys Glu Pro His Met Leu Phe Asp
            100                 105                 110

Arg Ile Arg Leu Val Val Thr Leu Glu
        115                 120


<210> SEQ ID NO 111
<211> LENGTH: 121
<212> TYPE: PRT
<213> ORGANISM: Artificial Sequence
<220> FEATURE:
<223> OTHER INFORMATION: Human TREM1 mutant  03_6_7

<400> SEQUENCE: 111

Met Glu Leu Arg Ala Ala Ala Ala Leu Thr Glu Glu Lys Tyr Glu Leu
1               5                   10                  15

Lys Glu Gly Gln Thr Leu Asp Val Lys Cys Asp Tyr Thr Leu Glu Lys
            20                  25                  30

Phe Ala Ser Ser Gln Lys Ala Trp Gln Ile Ile Arg Asp Gly Glu Met
        35                  40                  45

Pro Lys Thr Leu Ala Cys Thr Glu Arg Pro Ser Lys Asn Ser His Pro
    50                  55                  60

Val Gln Val Gly Arg Ile Ile Leu Glu Asp Tyr His Asp His Gly Leu
65                  70                  75                  80

Leu Arg Val Arg Met Val Asn Leu Gln Val Glu Asp Ser Gly Leu Tyr
                85                  90                  95

Gln Cys Val Ile Tyr Gln Pro Pro Lys Glu Pro His Met Leu Phe Asp
```

```
            100                 105                 110

Arg Ile Arg Leu Val Val Thr Leu Glu
        115                 120


<210> SEQ ID NO 112
<211> LENGTH: 121
<212> TYPE: PRT
<213> ORGANISM: Artificial Sequence
<220> FEATURE:
<223> OTHER INFORMATION: Human TREM1 mutant  04_6_7_9

<400> SEQUENCE: 112

Met Glu Leu Arg Ala Ala Ala Ala Leu Ala Glu Glu Lys Tyr Glu Leu
1               5                   10                  15

Lys Glu Gly Gln Thr Leu Asp Val Lys Cys Asp Tyr Thr Leu Glu Lys
            20                  25                  30

Phe Ala Ser Ser Gln Lys Ala Trp Gln Ile Ile Arg Asp Gly Glu Met
        35                  40                  45

Pro Lys Thr Leu Ala Cys Thr Glu Arg Pro Ser Lys Asn Ser His Pro
    50                  55                  60

Val Gln Val Gly Arg Ile Ile Leu Glu Asp Tyr His Asp His Gly Leu
65                  70                  75                  80

Leu Arg Val Arg Met Val Asn Leu Gln Val Glu Asp Ser Gly Leu Tyr
                85                  90                  95

Gln Cys Val Ile Tyr Gln Pro Pro Lys Glu Pro His Met Leu Phe Asp
            100                 105                 110

Arg Ile Arg Leu Val Val Thr Leu Glu
        115                 120


<210> SEQ ID NO 113
<211> LENGTH: 121
<212> TYPE: PRT
<213> ORGANISM: Artificial Sequence
<220> FEATURE:
<223> OTHER INFORMATION: Human TREM1 mutant  05_7_8_9

<400> SEQUENCE: 113

Met Glu Leu Arg Ala Ala Thr Ala Ala Ala Glu Glu Lys Tyr Glu Leu
1               5                   10                  15

Lys Glu Gly Gln Thr Leu Asp Val Lys Cys Asp Tyr Thr Leu Glu Lys
            20                  25                  30

Phe Ala Ser Ser Gln Lys Ala Trp Gln Ile Ile Arg Asp Gly Glu Met
        35                  40                  45

Pro Lys Thr Leu Ala Cys Thr Glu Arg Pro Ser Lys Asn Ser His Pro
    50                  55                  60

Val Gln Val Gly Arg Ile Ile Leu Glu Asp Tyr His Asp His Gly Leu
65                  70                  75                  80

Leu Arg Val Arg Met Val Asn Leu Gln Val Glu Asp Ser Gly Leu Tyr
                85                  90                  95

Gln Cys Val Ile Tyr Gln Pro Pro Lys Glu Pro His Met Leu Phe Asp
            100                 105                 110

Arg Ile Arg Leu Val Val Thr Leu Glu
        115                 120


<210> SEQ ID NO 114
<211> LENGTH: 121
<212> TYPE: PRT
<213> ORGANISM: Artificial Sequence
<220> FEATURE:
```

<223> OTHER INFORMATION: Human TREM1 mutant 06_9_10_111

<400> SEQUENCE: 114

```
Met Glu Leu Arg Ala Ala Thr Lys Leu Ala Ala Glu Lys Tyr Glu Leu
1               5                   10                  15

Lys Glu Gly Gln Thr Leu Asp Val Lys Cys Asp Tyr Thr Leu Glu Lys
            20                  25                  30

Phe Ala Ser Ser Gln Lys Ala Trp Gln Ile Ile Arg Asp Gly Glu Met
        35                  40                  45

Pro Lys Thr Leu Ala Cys Thr Glu Arg Pro Ser Lys Asn Ser His Pro
    50                  55                  60

Val Gln Val Gly Arg Ile Ile Leu Glu Asp Tyr His Asp His Gly Leu
65                  70                  75                  80

Leu Arg Val Arg Met Val Asn Leu Gln Val Glu Asp Ser Gly Leu Tyr
                85                  90                  95

Gln Cys Val Ile Tyr Gln Pro Pro Lys Glu Pro His Met Leu Phe Ala
            100                 105                 110

Arg Ile Arg Leu Val Val Thr Leu Glu
        115                 120
```

<210> SEQ ID NO 115
<211> LENGTH: 121
<212> TYPE: PRT
<213> ORGANISM: Artificial Sequence
<220> FEATURE:
<223> OTHER INFORMATION: Human TREM1 mutant 07_9_10_11

<400> SEQUENCE: 115

```
Met Glu Leu Arg Ala Ala Thr Lys Leu Ala Ala Ala Lys Tyr Glu Leu
1               5                   10                  15

Lys Glu Gly Gln Thr Leu Asp Val Lys Cys Asp Tyr Thr Leu Glu Lys
            20                  25                  30

Phe Ala Ser Ser Gln Lys Ala Trp Gln Ile Ile Arg Asp Gly Glu Met
        35                  40                  45

Pro Lys Thr Leu Ala Cys Thr Glu Arg Pro Ser Lys Asn Ser His Pro
    50                  55                  60

Val Gln Val Gly Arg Ile Ile Leu Glu Asp Tyr His Asp His Gly Leu
65                  70                  75                  80

Leu Arg Val Arg Met Val Asn Leu Gln Val Glu Asp Ser Gly Leu Tyr
                85                  90                  95

Gln Cys Val Ile Tyr Gln Pro Pro Lys Glu Pro His Met Leu Phe Asp
            100                 105                 110

Arg Ile Arg Leu Val Val Thr Leu Glu
        115                 120
```

<210> SEQ ID NO 116
<211> LENGTH: 121
<212> TYPE: PRT
<213> ORGANISM: Artificial Sequence
<220> FEATURE:
<223> OTHER INFORMATION: Human TREM1 mutant 08_10_11_12

<400> SEQUENCE: 116

```
Met Glu Leu Arg Ala Ala Thr Lys Leu Thr Ala Ala Ala Tyr Glu Leu
1               5                   10                  15

Lys Glu Gly Gln Thr Leu Asp Val Lys Cys Asp Tyr Thr Leu Glu Lys
            20                  25                  30

Phe Ala Ser Ser Gln Lys Ala Trp Gln Ile Ile Arg Asp Gly Glu Met
```

```
        35                  40                  45

Pro Lys Thr Leu Ala Cys Thr Glu Arg Pro Ser Lys Asn Ser His Pro
    50                  55                  60

Val Gln Val Gly Arg Ile Ile Leu Glu Asp Tyr His Asp His Gly Leu
65                  70                  75                  80

Leu Arg Val Arg Met Val Asn Leu Gln Val Glu Asp Ser Gly Leu Tyr
                85                  90                  95

Gln Cys Val Ile Tyr Gln Pro Pro Lys Glu Pro His Met Leu Phe Asp
            100                 105                 110

Arg Ile Arg Leu Val Val Thr Leu Glu
        115                 120


<210> SEQ ID NO 117
<211> LENGTH: 121
<212> TYPE: PRT
<213> ORGANISM: Artificial Sequence
<220> FEATURE:
<223> OTHER INFORMATION: Human TREM1 mutant  09_11_12_13

<400> SEQUENCE: 117

Met Glu Leu Arg Ala Ala Thr Lys Leu Thr Glu Ala Ala Ala Glu Leu
1               5                   10                  15

Lys Glu Gly Gln Thr Leu Asp Val Lys Cys Asp Tyr Thr Leu Glu Lys
            20                  25                  30

Phe Ala Ser Ser Gln Lys Ala Trp Gln Ile Ile Arg Asp Gly Glu Met
        35                  40                  45

Pro Lys Thr Leu Ala Cys Thr Glu Arg Pro Ser Lys Asn Ser His Pro
    50                  55                  60

Val Gln Val Gly Arg Ile Ile Leu Glu Asp Tyr His Asp His Gly Leu
65                  70                  75                  80

Leu Arg Val Arg Met Val Asn Leu Gln Val Glu Asp Ser Gly Leu Tyr
                85                  90                  95

Gln Cys Val Ile Tyr Gln Pro Pro Lys Glu Pro His Met Leu Phe Asp
            100                 105                 110

Arg Ile Arg Leu Val Val Thr Leu Glu
        115                 120


<210> SEQ ID NO 118
<211> LENGTH: 121
<212> TYPE: PRT
<213> ORGANISM: Artificial Sequence
<220> FEATURE:
<223> OTHER INFORMATION: Human TREM1 mutant  10_16_118_119

<400> SEQUENCE: 118

Met Glu Leu Arg Ala Ala Thr Lys Leu Thr Glu Glu Lys Tyr Glu Leu
1               5                   10                  15

Ala Glu Gly Gln Thr Leu Asp Val Lys Cys Asp Tyr Thr Leu Glu Lys
            20                  25                  30

Phe Ala Ser Ser Gln Lys Ala Trp Gln Ile Ile Arg Asp Gly Glu Met
        35                  40                  45

Pro Lys Thr Leu Ala Cys Thr Glu Arg Pro Ser Lys Asn Ser His Pro
    50                  55                  60

Val Gln Val Gly Arg Ile Ile Leu Glu Asp Tyr His Asp His Gly Leu
65                  70                  75                  80

Leu Arg Val Arg Met Val Asn Leu Gln Val Glu Asp Ser Gly Leu Tyr
                85                  90                  95
```

```
Gln Cys Val Ile Tyr Gln Pro Pro Lys Glu Pro His Met Leu Phe Asp
            100                 105                 110

Arg Ile Arg Leu Val Val Ala Ala Glu
        115                 120


<210> SEQ ID NO 119
<211> LENGTH: 121
<212> TYPE: PRT
<213> ORGANISM: Artificial Sequence
<220> FEATURE:
<223> OTHER INFORMATION: Human TREM1 mutant  11_19_20_85

<400> SEQUENCE: 119

Met Glu Leu Arg Ala Ala Thr Lys Leu Thr Glu Glu Lys Tyr Glu Leu
1               5                   10                  15

Lys Glu Gly Ala Ala Leu Asp Val Lys Cys Asp Tyr Thr Leu Glu Lys
            20                  25                  30

Phe Ala Ser Ser Gln Lys Ala Trp Gln Ile Ile Arg Asp Gly Glu Met
        35                  40                  45

Pro Lys Thr Leu Ala Cys Thr Glu Arg Pro Ser Lys Asn Ser His Pro
    50                  55                  60

Val Gln Val Gly Arg Ile Ile Leu Glu Asp Tyr His Asp His Gly Leu
65                  70                  75                  80

Leu Arg Val Arg Met Ala Asn Leu Gln Val Glu Asp Ser Gly Leu Tyr
                85                  90                  95

Gln Cys Val Ile Tyr Gln Pro Pro Lys Glu Pro His Met Leu Phe Asp
            100                 105                 110

Arg Ile Arg Leu Val Val Thr Leu Glu
        115                 120


<210> SEQ ID NO 120
<211> LENGTH: 121
<212> TYPE: PRT
<213> ORGANISM: Artificial Sequence
<220> FEATURE:
<223> OTHER INFORMATION: Human TREM1 mutant  12_22_24_26

<400> SEQUENCE: 120

Met Glu Leu Arg Ala Ala Thr Lys Leu Thr Glu Glu Lys Tyr Glu Leu
1               5                   10                  15

Lys Glu Gly Gln Thr Leu Ala Val Ala Cys Ala Tyr Thr Leu Glu Lys
            20                  25                  30

Phe Ala Ser Ser Gln Lys Ala Trp Gln Ile Ile Arg Asp Gly Glu Met
        35                  40                  45

Pro Lys Thr Leu Ala Cys Thr Glu Arg Pro Ser Lys Asn Ser His Pro
    50                  55                  60

Val Gln Val Gly Arg Ile Ile Leu Glu Asp Tyr His Asp His Gly Leu
65                  70                  75                  80

Leu Arg Val Arg Met Val Asn Leu Gln Val Glu Asp Ser Gly Leu Tyr
                85                  90                  95

Gln Cys Val Ile Tyr Gln Pro Pro Lys Glu Pro His Met Leu Phe Asp
            100                 105                 110

Arg Ile Arg Leu Val Val Thr Leu Glu
        115                 120


<210> SEQ ID NO 121
<211> LENGTH: 121
<212> TYPE: PRT
<213> ORGANISM: Artificial Sequence
```

```
<220> FEATURE:
<223> OTHER INFORMATION: Human TREM1 mutant  13_24_26_28

<400> SEQUENCE: 121

Met Glu Leu Arg Ala Ala Thr Lys Leu Thr Glu Glu Lys Tyr Glu Leu
1               5                   10                  15

Lys Glu Gly Gln Thr Leu Asp Val Ala Cys Ala Tyr Ala Leu Glu Lys
            20                  25                  30

Phe Ala Ser Ser Gln Lys Ala Trp Gln Ile Ile Arg Asp Gly Glu Met
        35                  40                  45

Pro Lys Thr Leu Ala Cys Thr Glu Arg Pro Ser Lys Asn Ser His Pro
    50                  55                  60

Val Gln Val Gly Arg Ile Ile Leu Glu Asp Tyr His Asp His Gly Leu
65                  70                  75                  80

Leu Arg Val Arg Met Val Asn Leu Gln Val Glu Asp Ser Gly Leu Tyr
                85                  90                  95

Gln Cys Val Ile Tyr Gln Pro Pro Lys Glu Pro His Met Leu Phe Asp
            100                 105                 110

Arg Ile Arg Leu Val Val Thr Leu Glu
        115                 120


<210> SEQ ID NO 122
<211> LENGTH: 121
<212> TYPE: PRT
<213> ORGANISM: Artificial Sequence
<220> FEATURE:
<223> OTHER INFORMATION: Human TREM1 mutant  14_26_28_29

<400> SEQUENCE: 122

Met Glu Leu Arg Ala Ala Thr Lys Leu Thr Glu Glu Lys Tyr Glu Leu
1               5                   10                  15

Lys Glu Gly Gln Thr Leu Asp Val Lys Cys Ala Tyr Ala Ala Glu Lys
            20                  25                  30

Phe Ala Ser Ser Gln Lys Ala Trp Gln Ile Ile Arg Asp Gly Glu Met
        35                  40                  45

Pro Lys Thr Leu Ala Cys Thr Glu Arg Pro Ser Lys Asn Ser His Pro
    50                  55                  60

Val Gln Val Gly Arg Ile Ile Leu Glu Asp Tyr His Asp His Gly Leu
65                  70                  75                  80

Leu Arg Val Arg Met Val Asn Leu Gln Val Glu Asp Ser Gly Leu Tyr
                85                  90                  95

Gln Cys Val Ile Tyr Gln Pro Pro Lys Glu Pro His Met Leu Phe Asp
            100                 105                 110

Arg Ile Arg Leu Val Val Thr Leu Glu
        115                 120


<210> SEQ ID NO 123
<211> LENGTH: 121
<212> TYPE: PRT
<213> ORGANISM: Artificial Sequence
<220> FEATURE:
<223> OTHER INFORMATION: Human TREM1 mutant  15_28_29_30

<400> SEQUENCE: 123

Met Glu Leu Arg Ala Ala Thr Lys Leu Thr Glu Glu Lys Tyr Glu Leu
1               5                   10                  15

Lys Glu Gly Gln Thr Leu Asp Val Lys Cys Asp Tyr Ala Ala Ala Lys
            20                  25                  30
```

```
Phe Ala Ser Ser Gln Lys Ala Trp Gln Ile Ile Arg Asp Gly Glu Met
        35                  40                  45

Pro Lys Thr Leu Ala Cys Thr Glu Arg Pro Ser Lys Asn Ser His Pro
    50                  55                  60

Val Gln Val Gly Arg Ile Ile Leu Glu Asp Tyr His Asp His Gly Leu
65                  70                  75                  80

Leu Arg Val Arg Met Val Asn Leu Gln Val Glu Asp Ser Gly Leu Tyr
                85                  90                  95

Gln Cys Val Ile Tyr Gln Pro Pro Lys Glu Pro His Met Leu Phe Asp
            100                 105                 110

Arg Ile Arg Leu Val Val Thr Leu Glu
        115                 120


<210> SEQ ID NO 124
<211> LENGTH: 121
<212> TYPE: PRT
<213> ORGANISM: Artificial Sequence
<220> FEATURE:
<223> OTHER INFORMATION: Human TREM1 mutant  16_29_30_31

<400> SEQUENCE: 124

Met Glu Leu Arg Ala Ala Thr Lys Leu Thr Glu Glu Lys Tyr Glu Leu
1               5                   10                  15

Lys Glu Gly Gln Thr Leu Asp Val Lys Cys Asp Tyr Thr Ala Ala Ala
            20                  25                  30

Phe Ala Ser Ser Gln Lys Ala Trp Gln Ile Ile Arg Asp Gly Glu Met
        35                  40                  45

Pro Lys Thr Leu Ala Cys Thr Glu Arg Pro Ser Lys Asn Ser His Pro
    50                  55                  60

Val Gln Val Gly Arg Ile Ile Leu Glu Asp Tyr His Asp His Gly Leu
65                  70                  75                  80

Leu Arg Val Arg Met Val Asn Leu Gln Val Glu Asp Ser Gly Leu Tyr
                85                  90                  95

Gln Cys Val Ile Tyr Gln Pro Pro Lys Glu Pro His Met Leu Phe Asp
            100                 105                 110

Arg Ile Arg Leu Val Val Thr Leu Glu
        115                 120


<210> SEQ ID NO 125
<211> LENGTH: 121
<212> TYPE: PRT
<213> ORGANISM: Artificial Sequence
<220> FEATURE:
<223> OTHER INFORMATION: Human TREM1 mutant  17_31_32_35

<400> SEQUENCE: 125

Met Glu Leu Arg Ala Ala Thr Lys Leu Thr Glu Glu Lys Tyr Glu Leu
1               5                   10                  15

Lys Glu Gly Gln Thr Leu Asp Val Lys Cys Asp Tyr Thr Leu Glu Ala
            20                  25                  30

Ala Ala Ser Ala Gln Lys Ala Trp Gln Ile Ile Arg Asp Gly Glu Met
        35                  40                  45

Pro Lys Thr Leu Ala Cys Thr Glu Arg Pro Ser Lys Asn Ser His Pro
    50                  55                  60

Val Gln Val Gly Arg Ile Ile Leu Glu Asp Tyr His Asp His Gly Leu
65                  70                  75                  80

Leu Arg Val Arg Met Val Asn Leu Gln Val Glu Asp Ser Gly Leu Tyr
                85                  90                  95
```

Gln Cys Val Ile Tyr Gln Pro Pro Lys Glu Pro His Met Leu Phe Asp
100 105 110

Arg Ile Arg Leu Val Val Thr Leu Glu
115 120

<210> SEQ ID NO 126
<211> LENGTH: 121
<212> TYPE: PRT
<213> ORGANISM: Artificial Sequence
<220> FEATURE:
<223> OTHER INFORMATION: Human TREM1 mutant 18_30_34

<400> SEQUENCE: 126

Met Glu Leu Arg Ala Ala Thr Lys Leu Thr Glu Glu Lys Tyr Glu Leu
1 5 10 15

Lys Glu Gly Gln Thr Leu Asp Val Lys Cys Asp Tyr Thr Leu Ala Lys
20 25 30

Phe Ala Ala Ser Gln Lys Ala Trp Gln Ile Ile Arg Asp Gly Glu Met
35 40 45

Pro Lys Thr Leu Ala Cys Thr Glu Arg Pro Ser Lys Asn Ser His Pro
50 55 60

Val Gln Val Gly Arg Ile Ile Leu Glu Asp Tyr His Asp His Gly Leu
65 70 75 80

Leu Arg Val Arg Met Val Asn Leu Gln Val Glu Asp Ser Gly Leu Tyr
85 90 95

Gln Cys Val Ile Tyr Gln Pro Pro Lys Glu Pro His Met Leu Phe Asp
100 105 110

Arg Ile Arg Leu Val Val Thr Leu Glu
115 120

<210> SEQ ID NO 127
<211> LENGTH: 121
<212> TYPE: PRT
<213> ORGANISM: Artificial Sequence
<220> FEATURE:
<223> OTHER INFORMATION: Human TREM1 mutant 19_34_35_57

<400> SEQUENCE: 127

Met Glu Leu Arg Ala Ala Thr Lys Leu Thr Glu Glu Lys Tyr Glu Leu
1 5 10 15

Lys Glu Gly Gln Thr Leu Asp Val Lys Cys Asp Tyr Thr Leu Glu Lys
20 25 30

Phe Ala Ala Ala Gln Lys Ala Trp Gln Ile Ile Arg Asp Gly Glu Met
35 40 45

Pro Lys Thr Leu Ala Cys Thr Glu Arg Ala Ser Lys Asn Ser His Pro
50 55 60

Val Gln Val Gly Arg Ile Ile Leu Glu Asp Tyr His Asp His Gly Leu
65 70 75 80

Leu Arg Val Arg Met Val Asn Leu Gln Val Glu Asp Ser Gly Leu Tyr
85 90 95

Gln Cys Val Ile Tyr Gln Pro Pro Lys Glu Pro His Met Leu Phe Asp
100 105 110

Arg Ile Arg Leu Val Val Thr Leu Glu
115 120

<210> SEQ ID NO 128
<211> LENGTH: 121
<212> TYPE: PRT

```
<213> ORGANISM: Artificial Sequence
<220> FEATURE:
<223> OTHER INFORMATION: Human TREM1 mutant  20_35_36_56

<400> SEQUENCE: 128

Met Glu Leu Arg Ala Ala Thr Lys Leu Thr Glu Glu Lys Tyr Glu Leu
1               5                   10                  15

Lys Glu Gly Gln Thr Leu Asp Val Lys Cys Asp Tyr Thr Leu Glu Lys
            20                  25                  30

Phe Ala Ser Ala Ala Lys Ala Trp Gln Ile Ile Arg Asp Gly Glu Met
        35                  40                  45

Pro Lys Thr Leu Ala Cys Thr Glu Ala Pro Ser Lys Asn Ser His Pro
    50                  55                  60

Val Gln Val Gly Arg Ile Ile Leu Glu Asp Tyr His Asp His Gly Leu
65                  70                  75                  80

Leu Arg Val Arg Met Val Asn Leu Gln Val Glu Asp Ser Gly Leu Tyr
                85                  90                  95

Gln Cys Val Ile Tyr Gln Pro Pro Lys Glu Pro His Met Leu Phe Asp
            100                 105                 110

Arg Ile Arg Leu Val Val Thr Leu Glu
        115                 120


<210> SEQ ID NO 129
<211> LENGTH: 121
<212> TYPE: PRT
<213> ORGANISM: Artificial Sequence
<220> FEATURE:
<223> OTHER INFORMATION: Human TREM1 mutant  21_40_49_50

<400> SEQUENCE: 129

Met Glu Leu Arg Ala Ala Thr Lys Leu Thr Glu Glu Lys Tyr Glu Leu
1               5                   10                  15

Lys Glu Gly Gln Thr Leu Asp Val Lys Cys Asp Tyr Thr Leu Glu Lys
            20                  25                  30

Phe Ala Ser Ser Gln Lys Ala Trp Ala Ile Ile Arg Asp Gly Glu Met
        35                  40                  45

Pro Ala Ala Leu Ala Cys Thr Glu Arg Pro Ser Lys Asn Ser His Pro
    50                  55                  60

Val Gln Val Gly Arg Ile Ile Leu Glu Asp Tyr His Asp His Gly Leu
65                  70                  75                  80

Leu Arg Val Arg Met Val Asn Leu Gln Val Glu Asp Ser Gly Leu Tyr
                85                  90                  95

Gln Cys Val Ile Tyr Gln Pro Pro Lys Glu Pro His Met Leu Phe Asp
            100                 105                 110

Arg Ile Arg Leu Val Val Thr Leu Glu
        115                 120


<210> SEQ ID NO 130
<211> LENGTH: 121
<212> TYPE: PRT
<213> ORGANISM: Artificial Sequence
<220> FEATURE:
<223> OTHER INFORMATION: Human TREM1 mutant  22_43_44_47

<400> SEQUENCE: 130

Met Glu Leu Arg Ala Ala Thr Lys Leu Thr Glu Glu Lys Tyr Glu Leu
1               5                   10                  15

Lys Glu Gly Gln Thr Leu Asp Val Lys Cys Asp Tyr Thr Leu Glu Lys
            20                  25                  30
```

Phe Ala Ser Ser Gln Lys Ala Trp Gln Ile Ile Ala Ala Gly Glu Ala
35 40 45

Pro Lys Thr Leu Ala Cys Thr Glu Arg Pro Ser Lys Asn Ser His Pro
50 55 60

Val Gln Val Gly Arg Ile Ile Leu Glu Asp Tyr His Asp His Gly Leu
65 70 75 80

Leu Arg Val Arg Met Val Asn Leu Gln Val Glu Asp Ser Gly Leu Tyr
85 90 95

Gln Cys Val Ile Tyr Gln Pro Pro Lys Glu Pro His Met Leu Phe Asp
100 105 110

Arg Ile Arg Leu Val Val Thr Leu Glu
115 120

<210> SEQ ID NO 131
<211> LENGTH: 121
<212> TYPE: PRT
<213> ORGANISM: Artificial Sequence
<220> FEATURE:
<223> OTHER INFORMATION: Human TREM1 mutant 23_43_44_45

<400> SEQUENCE: 131

Met Glu Leu Arg Ala Ala Thr Lys Leu Thr Glu Glu Lys Tyr Glu Leu
1 5 10 15

Lys Glu Gly Gln Thr Leu Asp Val Lys Cys Asp Tyr Thr Leu Glu Lys
20 25 30

Phe Ala Ser Ser Gln Lys Ala Trp Gln Ile Ile Ala Ala Ala Glu Met
35 40 45

Pro Lys Thr Leu Ala Cys Thr Glu Arg Pro Ser Lys Asn Ser His Pro
50 55 60

Val Gln Val Gly Arg Ile Ile Leu Glu Asp Tyr His Asp His Gly Leu
65 70 75 80

Leu Arg Val Arg Met Val Asn Leu Gln Val Glu Asp Ser Gly Leu Tyr
85 90 95

Gln Cys Val Ile Tyr Gln Pro Pro Lys Glu Pro His Met Leu Phe Asp
100 105 110

Arg Ile Arg Leu Val Val Thr Leu Glu
115 120

<210> SEQ ID NO 132
<211> LENGTH: 121
<212> TYPE: PRT
<213> ORGANISM: Artificial Sequence
<220> FEATURE:
<223> OTHER INFORMATION: Human TREM1 mutant 24_44_45_46

<400> SEQUENCE: 132

Met Glu Leu Arg Ala Ala Thr Lys Leu Thr Glu Glu Lys Tyr Glu Leu
1 5 10 15

Lys Glu Gly Gln Thr Leu Asp Val Lys Cys Asp Tyr Thr Leu Glu Lys
20 25 30

Phe Ala Ser Ser Gln Lys Ala Trp Gln Ile Ile Arg Ala Ala Ala Met
35 40 45

Pro Lys Thr Leu Ala Cys Thr Glu Arg Pro Ser Lys Asn Ser His Pro
50 55 60

Val Gln Val Gly Arg Ile Ile Leu Glu Asp Tyr His Asp His Gly Leu
65 70 75 80

Leu Arg Val Arg Met Val Asn Leu Gln Val Glu Asp Ser Gly Leu Tyr

```
                85                  90                  95

Gln Cys Val Ile Tyr Gln Pro Pro Lys Glu Pro His Met Leu Phe Asp
            100                 105                 110

Arg Ile Arg Leu Val Val Thr Leu Glu
        115                 120


<210> SEQ ID NO 133
<211> LENGTH: 121
<212> TYPE: PRT
<213> ORGANISM: Artificial Sequence
<220> FEATURE:
<223> OTHER INFORMATION: Human TREM1 mutant  25_45_46_47

<400> SEQUENCE: 133

Met Glu Leu Arg Ala Ala Thr Lys Leu Thr Glu Glu Lys Tyr Glu Leu
1               5                   10                  15

Lys Glu Gly Gln Thr Leu Asp Val Lys Cys Asp Tyr Thr Leu Glu Lys
            20                  25                  30

Phe Ala Ser Ser Gln Lys Ala Trp Gln Ile Ile Arg Asp Ala Ala Ala
        35                  40                  45

Pro Lys Thr Leu Ala Cys Thr Glu Arg Pro Ser Lys Asn Ser His Pro
    50                  55                  60

Val Gln Val Gly Arg Ile Ile Leu Glu Asp Tyr His Asp His Gly Leu
65                  70                  75                  80

Leu Arg Val Arg Met Val Asn Leu Gln Val Glu Asp Ser Gly Leu Tyr
                85                  90                  95

Gln Cys Val Ile Tyr Gln Pro Pro Lys Glu Pro His Met Leu Phe Asp
            100                 105                 110

Arg Ile Arg Leu Val Val Thr Leu Glu
        115                 120


<210> SEQ ID NO 134
<211> LENGTH: 121
<212> TYPE: PRT
<213> ORGANISM: Artificial Sequence
<220> FEATURE:
<223> OTHER INFORMATION: Human TREM1 mutant  26_43_46_47

<400> SEQUENCE: 134

Met Glu Leu Arg Ala Ala Thr Lys Leu Thr Glu Glu Lys Tyr Glu Leu
1               5                   10                  15

Lys Glu Gly Gln Thr Leu Asp Val Lys Cys Asp Tyr Thr Leu Glu Lys
            20                  25                  30

Phe Ala Ser Ser Gln Lys Ala Trp Gln Ile Ile Ala Asp Gly Ala Ala
        35                  40                  45

Pro Lys Thr Leu Ala Cys Thr Glu Arg Pro Ser Lys Asn Ser His Pro
    50                  55                  60

Val Gln Val Gly Arg Ile Ile Leu Glu Asp Tyr His Asp His Gly Leu
65                  70                  75                  80

Leu Arg Val Arg Met Val Asn Leu Gln Val Glu Asp Ser Gly Leu Tyr
                85                  90                  95

Gln Cys Val Ile Tyr Gln Pro Pro Lys Glu Pro His Met Leu Phe Asp
            100                 105                 110

Arg Ile Arg Leu Val Val Thr Leu Glu
        115                 120


<210> SEQ ID NO 135
<211> LENGTH: 121
```

<212> TYPE: PRT
<213> ORGANISM: Artificial Sequence
<220> FEATURE:
<223> OTHER INFORMATION: Human TREM1 mutant 27_47_48_49

<400> SEQUENCE: 135

```
Met Glu Leu Arg Ala Ala Thr Lys Leu Thr Glu Glu Lys Tyr Glu Leu
1               5                   10                  15

Lys Glu Gly Gln Thr Leu Asp Val Lys Cys Asp Tyr Thr Leu Glu Lys
            20                  25                  30

Phe Ala Ser Ser Gln Lys Ala Trp Gln Ile Ile Arg Asp Gly Glu Ala
        35                  40                  45

Ala Ala Thr Leu Ala Cys Thr Glu Arg Pro Ser Lys Asn Ser His Pro
    50                  55                  60

Val Gln Val Gly Arg Ile Ile Leu Glu Asp Tyr His Asp His Gly Leu
65                  70                  75                  80

Leu Arg Val Arg Met Val Asn Leu Gln Val Glu Asp Ser Gly Leu Tyr
                85                  90                  95

Gln Cys Val Ile Tyr Gln Pro Pro Lys Glu Pro His Met Leu Phe Asp
            100                 105                 110

Arg Ile Arg Leu Val Val Thr Leu Glu
        115                 120
```

<210> SEQ ID NO 136
<211> LENGTH: 121
<212> TYPE: PRT
<213> ORGANISM: Artificial Sequence
<220> FEATURE:
<223> OTHER INFORMATION: Human TREM1 mutant 28_47_49_50

<400> SEQUENCE: 136

```
Met Glu Leu Arg Ala Ala Thr Lys Leu Thr Glu Glu Lys Tyr Glu Leu
1               5                   10                  15

Lys Glu Gly Gln Thr Leu Asp Val Lys Cys Asp Tyr Thr Leu Glu Lys
            20                  25                  30

Phe Ala Ser Ser Gln Lys Ala Trp Gln Ile Ile Arg Asp Gly Glu Ala
        35                  40                  45

Pro Ala Ala Leu Ala Cys Thr Glu Arg Pro Ser Lys Asn Ser His Pro
    50                  55                  60

Val Gln Val Gly Arg Ile Ile Leu Glu Asp Tyr His Asp His Gly Leu
65                  70                  75                  80

Leu Arg Val Arg Met Val Asn Leu Gln Val Glu Asp Ser Gly Leu Tyr
                85                  90                  95

Gln Cys Val Ile Tyr Gln Pro Pro Lys Glu Pro His Met Leu Phe Asp
            100                 105                 110

Arg Ile Arg Leu Val Val Thr Leu Glu
        115                 120
```

<210> SEQ ID NO 137
<211> LENGTH: 121
<212> TYPE: PRT
<213> ORGANISM: Artificial Sequence
<220> FEATURE:
<223> OTHER INFORMATION: Human TREM1 mutant 29_49_50_53

<400> SEQUENCE: 137

```
Met Glu Leu Arg Ala Ala Thr Lys Leu Thr Glu Glu Lys Tyr Glu Leu
1               5                   10                  15

Lys Glu Gly Gln Thr Leu Asp Val Lys Cys Asp Tyr Thr Leu Glu Lys
```

```
            20                  25                  30

Phe Ala Ser Ser Gln Lys Ala Trp Gln Ile Ile Arg Asp Gly Glu Met
        35                  40                  45

Pro Ala Ala Leu Ala Ala Thr Glu Arg Pro Ser Lys Asn Ser His Pro
    50                  55                  60

Val Gln Val Gly Arg Ile Ile Leu Glu Asp Tyr His Asp His Gly Leu
65                  70                  75                  80

Leu Arg Val Arg Met Val Asn Leu Gln Val Glu Asp Ser Gly Leu Tyr
                85                  90                  95

Gln Cys Val Ile Tyr Gln Pro Pro Lys Glu Pro His Met Leu Phe Asp
            100                 105                 110

Arg Ile Arg Leu Val Val Thr Leu Glu
        115                 120


<210> SEQ ID NO 138
<211> LENGTH: 121
<212> TYPE: PRT
<213> ORGANISM: Artificial Sequence
<220> FEATURE:
<223> OTHER INFORMATION: Human TREM1 mutant  30_50_53_55

<400> SEQUENCE: 138

Met Glu Leu Arg Ala Ala Thr Lys Leu Thr Glu Glu Lys Tyr Glu Leu
1               5                   10                  15

Lys Glu Gly Gln Thr Leu Asp Val Lys Cys Asp Tyr Thr Leu Glu Lys
            20                  25                  30

Phe Ala Ser Ser Gln Lys Ala Trp Gln Ile Ile Arg Asp Gly Glu Met
        35                  40                  45

Pro Lys Ala Leu Ala Ala Thr Ala Arg Pro Ser Lys Asn Ser His Pro
    50                  55                  60

Val Gln Val Gly Arg Ile Ile Leu Glu Asp Tyr His Asp His Gly Leu
65                  70                  75                  80

Leu Arg Val Arg Met Val Asn Leu Gln Val Glu Asp Ser Gly Leu Tyr
                85                  90                  95

Gln Cys Val Ile Tyr Gln Pro Pro Lys Glu Pro His Met Leu Phe Asp
            100                 105                 110

Arg Ile Arg Leu Val Val Thr Leu Glu
        115                 120


<210> SEQ ID NO 139
<211> LENGTH: 121
<212> TYPE: PRT
<213> ORGANISM: Artificial Sequence
<220> FEATURE:
<223> OTHER INFORMATION: Human TREM1 mutant  31_55_56_57

<400> SEQUENCE: 139

Met Glu Leu Arg Ala Ala Thr Lys Leu Thr Glu Glu Lys Tyr Glu Leu
1               5                   10                  15

Lys Glu Gly Gln Thr Leu Asp Val Lys Cys Asp Tyr Thr Leu Glu Lys
            20                  25                  30

Phe Ala Ser Ser Gln Lys Ala Trp Gln Ile Ile Arg Asp Gly Glu Met
        35                  40                  45

Pro Lys Thr Leu Ala Cys Thr Ala Ala Ala Ser Lys Asn Ser His Pro
    50                  55                  60

Val Gln Val Gly Arg Ile Ile Leu Glu Asp Tyr His Asp His Gly Leu
65                  70                  75                  80
```

```
Leu Arg Val Arg Met Val Asn Leu Gln Val Glu Asp Ser Gly Leu Tyr
                85                  90                  95

Gln Cys Val Ile Tyr Gln Pro Pro Lys Glu Pro His Met Leu Phe Asp
            100                 105                 110

Arg Ile Arg Leu Val Val Thr Leu Glu
        115                 120


<210> SEQ ID NO 140
<211> LENGTH: 121
<212> TYPE: PRT
<213> ORGANISM: Artificial Sequence
<220> FEATURE:
<223> OTHER INFORMATION: Human TREM1 mutant  32_34_56_57

<400> SEQUENCE: 140

Met Glu Leu Arg Ala Ala Thr Lys Leu Thr Glu Glu Lys Tyr Glu Leu
1               5                   10                  15

Lys Glu Gly Gln Thr Leu Asp Val Lys Cys Asp Tyr Thr Leu Glu Lys
            20                  25                  30

Phe Ala Ala Ser Gln Lys Ala Trp Gln Ile Ile Arg Asp Gly Glu Met
        35                  40                  45

Pro Lys Thr Leu Ala Cys Thr Glu Ala Ala Ser Lys Asn Ser His Pro
    50                  55                  60

Val Gln Val Gly Arg Ile Ile Leu Glu Asp Tyr His Asp His Gly Leu
65                  70                  75                  80

Leu Arg Val Arg Met Val Asn Leu Gln Val Glu Asp Ser Gly Leu Tyr
                85                  90                  95

Gln Cys Val Ile Tyr Gln Pro Pro Lys Glu Pro His Met Leu Phe Asp
            100                 105                 110

Arg Ile Arg Leu Val Val Thr Leu Glu
        115                 120


<210> SEQ ID NO 141
<211> LENGTH: 121
<212> TYPE: PRT
<213> ORGANISM: Artificial Sequence
<220> FEATURE:
<223> OTHER INFORMATION: Human TREM1 mutant  33_57_59_60

<400> SEQUENCE: 141

Met Glu Leu Arg Ala Ala Thr Lys Leu Thr Glu Glu Lys Tyr Glu Leu
1               5                   10                  15

Lys Glu Gly Gln Thr Leu Asp Val Lys Cys Asp Tyr Thr Leu Glu Lys
            20                  25                  30

Phe Ala Ser Ser Gln Lys Ala Trp Gln Ile Ile Arg Asp Gly Glu Met
        35                  40                  45

Pro Lys Thr Leu Ala Cys Thr Glu Arg Ala Ser Ala Ala Ser His Pro
    50                  55                  60

Val Gln Val Gly Arg Ile Ile Leu Glu Asp Tyr His Asp His Gly Leu
65                  70                  75                  80

Leu Arg Val Arg Met Val Asn Leu Gln Val Glu Asp Ser Gly Leu Tyr
                85                  90                  95

Gln Cys Val Ile Tyr Gln Pro Pro Lys Glu Pro His Met Leu Phe Asp
            100                 105                 110

Arg Ile Arg Leu Val Val Thr Leu Glu
        115                 120


<210> SEQ ID NO 142
```

<211> LENGTH: 121
<212> TYPE: PRT
<213> ORGANISM: Artificial Sequence
<220> FEATURE:
<223> OTHER INFORMATION: Human TREM1 mutant 34_59_60_61

<400> SEQUENCE: 142

```
Met Glu Leu Arg Ala Ala Thr Lys Leu Thr Glu Glu Lys Tyr Glu Leu
1               5                   10                  15

Lys Glu Gly Gln Thr Leu Asp Val Lys Cys Asp Tyr Thr Leu Glu Lys
            20                  25                  30

Phe Ala Ser Ser Gln Lys Ala Trp Gln Ile Ile Arg Asp Gly Glu Met
        35                  40                  45

Pro Lys Thr Leu Ala Cys Thr Glu Arg Pro Ser Ala Ala Ala His Pro
    50                  55                  60

Val Gln Val Gly Arg Ile Ile Leu Glu Asp Tyr His Asp His Gly Leu
65                  70                  75                  80

Leu Arg Val Arg Met Val Asn Leu Gln Val Glu Asp Ser Gly Leu Tyr
                85                  90                  95

Gln Cys Val Ile Tyr Gln Pro Pro Lys Glu Pro His Met Leu Phe Asp
            100                 105                 110

Arg Ile Arg Leu Val Val Thr Leu Glu
        115                 120
```

<210> SEQ ID NO 143
<211> LENGTH: 121
<212> TYPE: PRT
<213> ORGANISM: Artificial Sequence
<220> FEATURE:
<223> OTHER INFORMATION: Human TREM1 mutant 35_60_61_62

<400> SEQUENCE: 143

```
Met Glu Leu Arg Ala Ala Thr Lys Leu Thr Glu Glu Lys Tyr Glu Leu
1               5                   10                  15

Lys Glu Gly Gln Thr Leu Asp Val Lys Cys Asp Tyr Thr Leu Glu Lys
            20                  25                  30

Phe Ala Ser Ser Gln Lys Ala Trp Gln Ile Ile Arg Asp Gly Glu Met
        35                  40                  45

Pro Lys Thr Leu Ala Cys Thr Glu Arg Pro Ser Lys Ala Ala Ala Pro
    50                  55                  60

Val Gln Val Gly Arg Ile Ile Leu Glu Asp Tyr His Asp His Gly Leu
65                  70                  75                  80

Leu Arg Val Arg Met Val Asn Leu Gln Val Glu Asp Ser Gly Leu Tyr
                85                  90                  95

Gln Cys Val Ile Tyr Gln Pro Pro Lys Glu Pro His Met Leu Phe Asp
            100                 105                 110

Arg Ile Arg Leu Val Val Thr Leu Glu
        115                 120
```

<210> SEQ ID NO 144
<211> LENGTH: 121
<212> TYPE: PRT
<213> ORGANISM: Artificial Sequence
<220> FEATURE:
<223> OTHER INFORMATION: Human TREM1 mutant 36_61_62_63

<400> SEQUENCE: 144

```
Met Glu Leu Arg Ala Ala Thr Lys Leu Thr Glu Glu Lys Tyr Glu Leu
1               5                   10                  15
```

```
Lys Glu Gly Gln Thr Leu Asp Val Lys Cys Asp Tyr Thr Leu Glu Lys
            20                  25                  30

Phe Ala Ser Ser Gln Lys Ala Trp Gln Ile Ile Arg Asp Gly Glu Met
        35                  40                  45

Pro Lys Thr Leu Ala Cys Thr Glu Arg Pro Ser Lys Asn Ala Ala Ala
    50                  55                  60

Val Gln Val Gly Arg Ile Ile Leu Glu Asp Tyr His Asp His Gly Leu
65                  70                  75                  80

Leu Arg Val Arg Met Val Asn Leu Gln Val Glu Asp Ser Gly Leu Tyr
                85                  90                  95

Gln Cys Val Ile Tyr Gln Pro Pro Lys Glu Pro His Met Leu Phe Asp
            100                 105                 110

Arg Ile Arg Leu Val Val Thr Leu Glu
        115                 120
```

<210> SEQ ID NO 145
<211> LENGTH: 121
<212> TYPE: PRT
<213> ORGANISM: Artificial Sequence
<220> FEATURE:
<223> OTHER INFORMATION: Human TREM1 mutant 37_62_63_64

<400> SEQUENCE: 145

```
Met Glu Leu Arg Ala Ala Thr Lys Leu Thr Glu Glu Lys Tyr Glu Leu
1               5                   10                  15

Lys Glu Gly Gln Thr Leu Asp Val Lys Cys Asp Tyr Thr Leu Glu Lys
            20                  25                  30

Phe Ala Ser Ser Gln Lys Ala Trp Gln Ile Ile Arg Asp Gly Glu Met
        35                  40                  45

Pro Lys Thr Leu Ala Cys Thr Glu Arg Pro Ser Lys Asn Ser Ala Ala
    50                  55                  60

Ala Gln Val Gly Arg Ile Ile Leu Glu Asp Tyr His Asp His Gly Leu
65                  70                  75                  80

Leu Arg Val Arg Met Val Asn Leu Gln Val Glu Asp Ser Gly Leu Tyr
                85                  90                  95

Gln Cys Val Ile Tyr Gln Pro Pro Lys Glu Pro His Met Leu Phe Asp
            100                 105                 110

Arg Ile Arg Leu Val Val Thr Leu Glu
        115                 120
```

<210> SEQ ID NO 146
<211> LENGTH: 121
<212> TYPE: PRT
<213> ORGANISM: Artificial Sequence
<220> FEATURE:
<223> OTHER INFORMATION: Human TREM1 mutant 38_63_64_65

<400> SEQUENCE: 146

```
Met Glu Leu Arg Ala Ala Thr Lys Leu Thr Glu Glu Lys Tyr Glu Leu
1               5                   10                  15

Lys Glu Gly Gln Thr Leu Asp Val Lys Cys Asp Tyr Thr Leu Glu Lys
            20                  25                  30

Phe Ala Ser Ser Gln Lys Ala Trp Gln Ile Ile Arg Asp Gly Glu Met
        35                  40                  45

Pro Lys Thr Leu Ala Cys Thr Glu Arg Pro Ser Lys Asn Ser His Ala
    50                  55                  60

Ala Ala Val Gly Arg Ile Ile Leu Glu Asp Tyr His Asp His Gly Leu
65                  70                  75                  80
```

```
Leu Arg Val Arg Met Val Asn Leu Gln Val Glu Asp Ser Gly Leu Tyr
                85                  90                  95

Gln Cys Val Ile Tyr Gln Pro Pro Lys Glu Pro His Met Leu Phe Asp
            100                 105                 110

Arg Ile Arg Leu Val Val Thr Leu Glu
        115                 120


<210> SEQ ID NO 147
<211> LENGTH: 121
<212> TYPE: PRT
<213> ORGANISM: Artificial Sequence
<220> FEATURE:
<223> OTHER INFORMATION: Human TREM1 mutant  39_64_65_66

<400> SEQUENCE: 147

Met Glu Leu Arg Ala Ala Thr Lys Leu Thr Glu Glu Lys Tyr Glu Leu
1               5                   10                  15

Lys Glu Gly Gln Thr Leu Asp Val Lys Cys Asp Tyr Thr Leu Glu Lys
            20                  25                  30

Phe Ala Ser Ser Gln Lys Ala Trp Gln Ile Ile Arg Asp Gly Glu Met
        35                  40                  45

Pro Lys Thr Leu Ala Cys Thr Glu Arg Pro Ser Lys Asn Ser His Pro
    50                  55                  60

Ala Ala Ala Gly Arg Ile Ile Leu Glu Asp Tyr His Asp His Gly Leu
65                  70                  75                  80

Leu Arg Val Arg Met Val Asn Leu Gln Val Glu Asp Ser Gly Leu Tyr
                85                  90                  95

Gln Cys Val Ile Tyr Gln Pro Pro Lys Glu Pro His Met Leu Phe Asp
            100                 105                 110

Arg Ile Arg Leu Val Val Thr Leu Glu
        115                 120


<210> SEQ ID NO 148
<211> LENGTH: 121
<212> TYPE: PRT
<213> ORGANISM: Artificial Sequence
<220> FEATURE:
<223> OTHER INFORMATION: Human TREM1 mutant  40_60_74_76

<400> SEQUENCE: 148

Met Glu Leu Arg Ala Ala Thr Lys Leu Thr Glu Glu Lys Tyr Glu Leu
1               5                   10                  15

Lys Glu Gly Gln Thr Leu Asp Val Lys Cys Asp Tyr Thr Leu Glu Lys
            20                  25                  30

Phe Ala Ser Ser Gln Lys Ala Trp Gln Ile Ile Arg Asp Gly Glu Met
        35                  40                  45

Pro Lys Thr Leu Ala Cys Thr Glu Arg Pro Ser Lys Ala Ser His Pro
    50                  55                  60

Val Gln Val Gly Arg Ile Ile Leu Glu Asp Ala His Ala His Gly Leu
65                  70                  75                  80

Leu Arg Val Arg Met Val Asn Leu Gln Val Glu Asp Ser Gly Leu Tyr
                85                  90                  95

Gln Cys Val Ile Tyr Gln Pro Pro Lys Glu Pro His Met Leu Phe Asp
            100                 105                 110

Arg Ile Arg Leu Val Val Thr Leu Glu
        115                 120
```

<210> SEQ ID NO 149
<211> LENGTH: 121
<212> TYPE: PRT
<213> ORGANISM: Artificial Sequence
<220> FEATURE:
<223> OTHER INFORMATION: Human TREM1 mutant 41_60_75_76

<400> SEQUENCE: 149

```
Met Glu Leu Arg Ala Ala Thr Lys Leu Thr Glu Glu Lys Tyr Glu Leu
1               5                   10                  15

Lys Glu Gly Gln Thr Leu Asp Val Lys Cys Asp Tyr Thr Leu Glu Lys
            20                  25                  30

Phe Ala Ser Ser Gln Lys Ala Trp Gln Ile Ile Arg Asp Gly Glu Met
        35                  40                  45

Pro Lys Thr Leu Ala Cys Thr Glu Arg Pro Ser Lys Ala Ser His Pro
    50                  55                  60

Val Gln Val Gly Arg Ile Ile Leu Glu Asp Tyr Ala Ala His Gly Leu
65                  70                  75                  80

Leu Arg Val Arg Met Val Asn Leu Gln Val Glu Asp Ser Gly Leu Tyr
                85                  90                  95

Gln Cys Val Ile Tyr Gln Pro Pro Lys Glu Pro His Met Leu Phe Asp
            100                 105                 110

Arg Ile Arg Leu Val Val Thr Leu Glu
        115                 120
```

<210> SEQ ID NO 150
<211> LENGTH: 121
<212> TYPE: PRT
<213> ORGANISM: Artificial Sequence
<220> FEATURE:
<223> OTHER INFORMATION: Human TREM1 mutant 42_60_76_77

<400> SEQUENCE: 150

```
Met Glu Leu Arg Ala Ala Thr Lys Leu Thr Glu Glu Lys Tyr Glu Leu
1               5                   10                  15

Lys Glu Gly Gln Thr Leu Asp Val Lys Cys Asp Tyr Thr Leu Glu Lys
            20                  25                  30

Phe Ala Ser Ser Gln Lys Ala Trp Gln Ile Ile Arg Asp Gly Glu Met
        35                  40                  45

Pro Lys Thr Leu Ala Cys Thr Glu Arg Pro Ser Lys Ala Ser His Pro
    50                  55                  60

Val Gln Val Gly Arg Ile Ile Leu Glu Asp Tyr His Ala Ala Gly Leu
65                  70                  75                  80

Leu Arg Val Arg Met Val Asn Leu Gln Val Glu Asp Ser Gly Leu Tyr
                85                  90                  95

Gln Cys Val Ile Tyr Gln Pro Pro Lys Glu Pro His Met Leu Phe Asp
            100                 105                 110

Arg Ile Arg Leu Val Val Thr Leu Glu
        115                 120
```

<210> SEQ ID NO 151
<211> LENGTH: 121
<212> TYPE: PRT
<213> ORGANISM: Artificial Sequence
<220> FEATURE:
<223> OTHER INFORMATION: Human TREM1 mutant 43_28_76_77

<400> SEQUENCE: 151

```
Met Glu Leu Arg Ala Ala Thr Lys Leu Thr Glu Glu Lys Tyr Glu Leu
1               5                   10                  15
```

```
Lys Glu Gly Gln Thr Leu Asp Val Lys Cys Asp Tyr Ala Leu Glu Lys
            20                  25                  30

Phe Ala Ser Ser Gln Lys Ala Trp Gln Ile Ile Arg Asp Gly Glu Met
        35                  40                  45

Pro Lys Thr Leu Ala Cys Thr Glu Arg Pro Ser Lys Asn Ser His Pro
    50                  55                  60

Val Gln Val Gly Arg Ile Ile Leu Glu Asp Tyr His Ala Ala Gly Leu
65                  70                  75                  80

Leu Arg Val Arg Met Val Asn Leu Gln Val Glu Asp Ser Gly Leu Tyr
                85                  90                  95

Gln Cys Val Ile Tyr Gln Pro Pro Lys Glu Pro His Met Leu Phe Asp
            100                 105                 110

Arg Ile Arg Leu Val Val Thr Leu Glu
        115                 120


<210> SEQ ID NO 152
<211> LENGTH: 121
<212> TYPE: PRT
<213> ORGANISM: Artificial Sequence
<220> FEATURE:
<223> OTHER INFORMATION: Human TREM1 mutant  44_28_77_78

<400> SEQUENCE: 152

Met Glu Leu Arg Ala Ala Thr Lys Leu Thr Glu Glu Lys Tyr Glu Leu
1               5                   10                  15

Lys Glu Gly Gln Thr Leu Asp Val Lys Cys Asp Tyr Ala Leu Glu Lys
            20                  25                  30

Phe Ala Ser Ser Gln Lys Ala Trp Gln Ile Ile Arg Asp Gly Glu Met
        35                  40                  45

Pro Lys Thr Leu Ala Cys Thr Glu Arg Pro Ser Lys Asn Ser His Pro
    50                  55                  60

Val Gln Val Gly Arg Ile Ile Leu Glu Asp Tyr His Asp Ala Ala Leu
65                  70                  75                  80

Leu Arg Val Arg Met Val Asn Leu Gln Val Glu Asp Ser Gly Leu Tyr
                85                  90                  95

Gln Cys Val Ile Tyr Gln Pro Pro Lys Glu Pro His Met Leu Phe Asp
            100                 105                 110

Arg Ile Arg Leu Val Val Thr Leu Glu
        115                 120


<210> SEQ ID NO 153
<211> LENGTH: 121
<212> TYPE: PRT
<213> ORGANISM: Artificial Sequence
<220> FEATURE:
<223> OTHER INFORMATION: Human TREM1 mutant  45_96_109_111

<400> SEQUENCE: 153

Met Glu Leu Arg Ala Ala Thr Lys Leu Thr Glu Glu Lys Tyr Glu Leu
1               5                   10                  15

Lys Glu Gly Gln Thr Leu Asp Val Lys Cys Asp Tyr Thr Leu Glu Lys
            20                  25                  30

Phe Ala Ser Ser Gln Lys Ala Trp Gln Ile Ile Arg Asp Gly Glu Met
        35                  40                  45

Pro Lys Thr Leu Ala Cys Thr Glu Arg Pro Ser Lys Asn Ser His Pro
    50                  55                  60

Val Gln Val Gly Arg Ile Ile Leu Glu Asp Tyr His Asp His Gly Leu
```

```
65                  70                  75                  80

Leu Arg Val Arg Met Val Asn Leu Gln Val Glu Asp Ser Gly Leu Tyr
                85                  90                  95

Ala Cys Val Ile Tyr Gln Pro Pro Lys Glu Pro His Met Ala Phe Ala
            100                 105                 110

Arg Ile Arg Leu Val Val Thr Leu Glu
        115                 120


<210> SEQ ID NO 154
<211> LENGTH: 121
<212> TYPE: PRT
<213> ORGANISM: Artificial Sequence
<220> FEATURE:
<223> OTHER INFORMATION: Human TREM1 mutant  46_98_100_109

<400> SEQUENCE: 154

Met Glu Leu Arg Ala Ala Thr Lys Leu Thr Glu Glu Lys Tyr Glu Leu
1               5                   10                  15

Lys Glu Gly Gln Thr Leu Asp Val Lys Cys Asp Tyr Thr Leu Glu Lys
            20                  25                  30

Phe Ala Ser Ser Gln Lys Ala Trp Gln Ile Ile Arg Asp Gly Glu Met
        35                  40                  45

Pro Lys Thr Leu Ala Cys Thr Glu Arg Pro Ser Lys Asn Ser His Pro
    50                  55                  60

Val Gln Val Gly Arg Ile Ile Leu Glu Asp Tyr His Asp His Gly Leu
65                  70                  75                  80

Leu Arg Val Arg Met Val Asn Leu Gln Val Glu Asp Ser Gly Leu Tyr
                85                  90                  95

Gln Cys Ala Ile Ala Gln Pro Pro Lys Glu Pro His Met Ala Phe Asp
            100                 105                 110

Arg Ile Arg Leu Val Val Thr Leu Glu
        115                 120


<210> SEQ ID NO 155
<211> LENGTH: 121
<212> TYPE: PRT
<213> ORGANISM: Artificial Sequence
<220> FEATURE:
<223> OTHER INFORMATION: Human TREM1 mutant  47_35_100_102

<400> SEQUENCE: 155

Met Glu Leu Arg Ala Ala Thr Lys Leu Thr Glu Glu Lys Tyr Glu Leu
1               5                   10                  15

Lys Glu Gly Gln Thr Leu Asp Val Lys Cys Asp Tyr Thr Leu Glu Lys
            20                  25                  30

Phe Ala Ser Ala Gln Lys Ala Trp Gln Ile Ile Arg Asp Gly Glu Met
        35                  40                  45

Pro Lys Thr Leu Ala Cys Thr Glu Arg Pro Ser Lys Asn Ser His Pro
    50                  55                  60

Val Gln Val Gly Arg Ile Ile Leu Glu Asp Tyr His Asp His Gly Leu
65                  70                  75                  80

Leu Arg Val Arg Met Val Asn Leu Gln Val Glu Asp Ser Gly Leu Tyr
                85                  90                  95

Gln Cys Val Ile Ala Gln Ala Pro Lys Glu Pro His Met Leu Phe Asp
            100                 105                 110

Arg Ile Arg Leu Val Val Thr Leu Glu
        115                 120
```

<210> SEQ ID NO 156
<211> LENGTH: 121
<212> TYPE: PRT
<213> ORGANISM: Artificial Sequence
<220> FEATURE:
<223> OTHER INFORMATION: Human TREM1 mutant 48_102_103_104

<400> SEQUENCE: 156

```
Met Glu Leu Arg Ala Ala Thr Lys Leu Thr Glu Glu Lys Tyr Glu Leu
1               5                   10                  15

Lys Glu Gly Gln Thr Leu Asp Val Lys Cys Asp Tyr Thr Leu Glu Lys
            20                  25                  30

Phe Ala Ser Ser Gln Lys Ala Trp Gln Ile Ile Arg Asp Gly Glu Met
        35                  40                  45

Pro Lys Thr Leu Ala Cys Thr Glu Arg Pro Ser Lys Asn Ser His Pro
    50                  55                  60

Val Gln Val Gly Arg Ile Ile Leu Glu Asp Tyr His Asp His Gly Leu
65                  70                  75                  80

Leu Arg Val Arg Met Val Asn Leu Gln Val Glu Asp Ser Gly Leu Tyr
                85                  90                  95

Gln Cys Val Ile Tyr Gln Ala Ala Ala Glu Pro His Met Leu Phe Asp
            100                 105                 110

Arg Ile Arg Leu Val Val Thr Leu Glu
        115                 120
```

<210> SEQ ID NO 157
<211> LENGTH: 121
<212> TYPE: PRT
<213> ORGANISM: Artificial Sequence
<220> FEATURE:
<223> OTHER INFORMATION: Human TREM1 mutant 49_103_104_105

<400> SEQUENCE: 157

```
Met Glu Leu Arg Ala Ala Thr Lys Leu Thr Glu Glu Lys Tyr Glu Leu
1               5                   10                  15

Lys Glu Gly Gln Thr Leu Asp Val Lys Cys Asp Tyr Thr Leu Glu Lys
            20                  25                  30

Phe Ala Ser Ser Gln Lys Ala Trp Gln Ile Ile Arg Asp Gly Glu Met
        35                  40                  45

Pro Lys Thr Leu Ala Cys Thr Glu Arg Pro Ser Lys Asn Ser His Pro
    50                  55                  60

Val Gln Val Gly Arg Ile Ile Leu Glu Asp Tyr His Asp His Gly Leu
65                  70                  75                  80

Leu Arg Val Arg Met Val Asn Leu Gln Val Glu Asp Ser Gly Leu Tyr
                85                  90                  95

Gln Cys Val Ile Tyr Gln Pro Ala Ala Ala Pro His Met Leu Phe Asp
            100                 105                 110

Arg Ile Arg Leu Val Val Thr Leu Glu
        115                 120
```

<210> SEQ ID NO 158
<211> LENGTH: 121
<212> TYPE: PRT
<213> ORGANISM: Artificial Sequence
<220> FEATURE:
<223> OTHER INFORMATION: Human TREM1 mutant 50_104_105_106

<400> SEQUENCE: 158

```
Met Glu Leu Arg Ala Ala Thr Lys Leu Thr Glu Glu Lys Tyr Glu Leu
```

```
1               5                   10                  15

Lys Glu Gly Gln Thr Leu Asp Val Lys Cys Asp Tyr Thr Leu Glu Lys
            20                  25                  30

Phe Ala Ser Ser Gln Lys Ala Trp Gln Ile Ile Arg Asp Gly Glu Met
        35                  40                  45

Pro Lys Thr Leu Ala Cys Thr Glu Arg Pro Ser Lys Asn Ser His Pro
    50                  55                  60

Val Gln Val Gly Arg Ile Ile Leu Glu Asp Tyr His Asp His Gly Leu
65                  70                  75                  80

Leu Arg Val Arg Met Val Asn Leu Gln Val Glu Asp Ser Gly Leu Tyr
                85                  90                  95

Gln Cys Val Ile Tyr Gln Pro Pro Ala Ala Ala His Met Leu Phe Asp
            100                 105                 110

Arg Ile Arg Leu Val Val Thr Leu Glu
        115                 120
```

<210> SEQ ID NO 159
<211> LENGTH: 121
<212> TYPE: PRT
<213> ORGANISM: Artificial Sequence
<220> FEATURE:
<223> OTHER INFORMATION: Human TREM1 mutant 51_105_106_107

<400> SEQUENCE: 159

```
Met Glu Leu Arg Ala Ala Thr Lys Leu Thr Glu Glu Lys Tyr Glu Leu
1               5                   10                  15

Lys Glu Gly Gln Thr Leu Asp Val Lys Cys Asp Tyr Thr Leu Glu Lys
            20                  25                  30

Phe Ala Ser Ser Gln Lys Ala Trp Gln Ile Ile Arg Asp Gly Glu Met
        35                  40                  45

Pro Lys Thr Leu Ala Cys Thr Glu Arg Pro Ser Lys Asn Ser His Pro
    50                  55                  60

Val Gln Val Gly Arg Ile Ile Leu Glu Asp Tyr His Asp His Gly Leu
65                  70                  75                  80

Leu Arg Val Arg Met Val Asn Leu Gln Val Glu Asp Ser Gly Leu Tyr
                85                  90                  95

Gln Cys Val Ile Tyr Gln Pro Pro Lys Ala Ala Ala Met Leu Phe Asp
            100                 105                 110

Arg Ile Arg Leu Val Val Thr Leu Glu
        115                 120
```

<210> SEQ ID NO 160
<211> LENGTH: 121
<212> TYPE: PRT
<213> ORGANISM: Artificial Sequence
<220> FEATURE:
<223> OTHER INFORMATION: Human TREM1 mutant 52_106_107_108

<400> SEQUENCE: 160

```
Met Glu Leu Arg Ala Ala Thr Lys Leu Thr Glu Glu Lys Tyr Glu Leu
1               5                   10                  15

Lys Glu Gly Gln Thr Leu Asp Val Lys Cys Asp Tyr Thr Leu Glu Lys
            20                  25                  30

Phe Ala Ser Ser Gln Lys Ala Trp Gln Ile Ile Arg Asp Gly Glu Met
        35                  40                  45

Pro Lys Thr Leu Ala Cys Thr Glu Arg Pro Ser Lys Asn Ser His Pro
    50                  55                  60
```

Val Gln Val Gly Arg Ile Ile Leu Glu Asp Tyr His Asp His Gly Leu
65 70 75 80

Leu Arg Val Arg Met Val Asn Leu Gln Val Glu Asp Ser Gly Leu Tyr
85 90 95

Gln Cys Val Ile Tyr Gln Pro Pro Lys Glu Ala Ala Ala Leu Phe Asp
100 105 110

Arg Ile Arg Leu Val Val Thr Leu Glu
115 120

<210> SEQ ID NO 161
<211> LENGTH: 121
<212> TYPE: PRT
<213> ORGANISM: Artificial Sequence
<220> FEATURE:
<223> OTHER INFORMATION: Human TREM1 mutant 53_107_108_109

<400> SEQUENCE: 161

Met Glu Leu Arg Ala Ala Thr Lys Leu Thr Glu Glu Lys Tyr Glu Leu
1 5 10 15

Lys Glu Gly Gln Thr Leu Asp Val Lys Cys Asp Tyr Thr Leu Glu Lys
20 25 30

Phe Ala Ser Ser Gln Lys Ala Trp Gln Ile Ile Arg Asp Gly Glu Met
35 40 45

Pro Lys Thr Leu Ala Cys Thr Glu Arg Pro Ser Lys Asn Ser His Pro
50 55 60

Val Gln Val Gly Arg Ile Ile Leu Glu Asp Tyr His Asp His Gly Leu
65 70 75 80

Leu Arg Val Arg Met Val Asn Leu Gln Val Glu Asp Ser Gly Leu Tyr
85 90 95

Gln Cys Val Ile Tyr Gln Pro Pro Lys Glu Pro Ala Ala Ala Phe Asp
100 105 110

Arg Ile Arg Leu Val Val Thr Leu Glu
115 120

<210> SEQ ID NO 162
<211> LENGTH: 121
<212> TYPE: PRT
<213> ORGANISM: Artificial Sequence
<220> FEATURE:
<223> OTHER INFORMATION: Human TREM1 mutant 54_109_110_111

<400> SEQUENCE: 162

Met Glu Leu Arg Ala Ala Thr Lys Leu Thr Glu Glu Lys Tyr Glu Leu
1 5 10 15

Lys Glu Gly Gln Thr Leu Asp Val Lys Cys Asp Tyr Thr Leu Glu Lys
20 25 30

Phe Ala Ser Ser Gln Lys Ala Trp Gln Ile Ile Arg Asp Gly Glu Met
35 40 45

Pro Lys Thr Leu Ala Cys Thr Glu Arg Pro Ser Lys Asn Ser His Pro
50 55 60

Val Gln Val Gly Arg Ile Ile Leu Glu Asp Tyr His Asp His Gly Leu
65 70 75 80

Leu Arg Val Arg Met Val Asn Leu Gln Val Glu Asp Ser Gly Leu Tyr
85 90 95

Gln Cys Val Ile Tyr Gln Pro Pro Lys Glu Pro His Met Ala Ala Ala
100 105 110

Arg Ile Arg Leu Val Val Thr Leu Glu
115 120

<210> SEQ ID NO 163
<211> LENGTH: 121
<212> TYPE: PRT
<213> ORGANISM: Artificial Sequence
<220> FEATURE:
<223> OTHER INFORMATION: Human TREM1 mutant 55_11_113_114

<400> SEQUENCE: 163

```
Met Glu Leu Arg Ala Ala Thr Lys Leu Thr Glu Ala Lys Tyr Glu Leu
1               5                   10                  15

Lys Glu Gly Gln Thr Leu Asp Val Lys Cys Asp Tyr Thr Leu Glu Lys
            20                  25                  30

Phe Ala Ser Ser Gln Lys Ala Trp Gln Ile Ile Arg Asp Gly Glu Met
        35                  40                  45

Pro Lys Thr Leu Ala Cys Thr Glu Arg Pro Ser Lys Asn Ser His Pro
    50                  55                  60

Val Gln Val Gly Arg Ile Ile Leu Glu Asp Tyr His Asp His Gly Leu
65                  70                  75                  80

Leu Arg Val Arg Met Val Asn Leu Gln Val Glu Asp Ser Gly Leu Tyr
                85                  90                  95

Gln Cys Val Ile Tyr Gln Pro Pro Lys Glu Pro His Met Leu Phe Asp
            100                 105                 110

Arg Ala Ala Leu Val Val Thr Leu Glu
        115                 120
```

<210> SEQ ID NO 164
<211> LENGTH: 121
<212> TYPE: PRT
<213> ORGANISM: Artificial Sequence
<220> FEATURE:
<223> OTHER INFORMATION: Human TREM1 mutant 56_10_12_114

<400> SEQUENCE: 164

```
Met Glu Leu Arg Ala Ala Thr Lys Leu Thr Ala Glu Ala Tyr Glu Leu
1               5                   10                  15

Lys Glu Gly Gln Thr Leu Asp Val Lys Cys Asp Tyr Thr Leu Glu Lys
            20                  25                  30

Phe Ala Ser Ser Gln Lys Ala Trp Gln Ile Ile Arg Asp Gly Glu Met
        35                  40                  45

Pro Lys Thr Leu Ala Cys Thr Glu Arg Pro Ser Lys Asn Ser His Pro
    50                  55                  60

Val Gln Val Gly Arg Ile Ile Leu Glu Asp Tyr His Asp His Gly Leu
65                  70                  75                  80

Leu Arg Val Arg Met Val Asn Leu Gln Val Glu Asp Ser Gly Leu Tyr
                85                  90                  95

Gln Cys Val Ile Tyr Gln Pro Pro Lys Glu Pro His Met Leu Phe Asp
            100                 105                 110

Arg Ile Ala Leu Val Val Thr Leu Glu
        115                 120
```

<210> SEQ ID NO 165
<211> LENGTH: 121
<212> TYPE: PRT
<213> ORGANISM: Artificial Sequence
<220> FEATURE:
<223> OTHER INFORMATION: Human TREM1 mutant 57_118_119_120

<400> SEQUENCE: 165

```
Met Glu Leu Arg Ala Ala Thr Lys Leu Thr Glu Glu Lys Tyr Glu Leu
1               5                   10                  15

Lys Glu Gly Gln Thr Leu Asp Val Lys Cys Asp Tyr Thr Leu Glu Lys
            20                  25                  30

Phe Ala Ser Ser Gln Lys Ala Trp Gln Ile Ile Arg Asp Gly Glu Met
        35                  40                  45

Pro Lys Thr Leu Ala Cys Thr Glu Arg Pro Ser Lys Asn Ser His Pro
    50                  55                  60

Val Gln Val Gly Arg Ile Ile Leu Glu Asp Tyr His Asp His Gly Leu
65                  70                  75                  80

Leu Arg Val Arg Met Val Asn Leu Gln Val Glu Asp Ser Gly Leu Tyr
                85                  90                  95

Gln Cys Val Ile Tyr Gln Pro Pro Lys Glu Pro His Met Leu Phe Asp
            100                 105                 110

Arg Ile Arg Leu Val Val Ala Ala Ala
        115                 120


<210> SEQ ID NO 166
<211> LENGTH: 121
<212> TYPE: PRT
<213> ORGANISM: Artificial Sequence
<220> FEATURE:
<223> OTHER INFORMATION: Human TREM1 mutant  58_16_119_120

<400> SEQUENCE: 166

Met Glu Leu Arg Ala Ala Thr Lys Leu Thr Glu Glu Lys Tyr Glu Leu
1               5                   10                  15

Ala Glu Gly Gln Thr Leu Asp Val Lys Cys Asp Tyr Thr Leu Glu Lys
            20                  25                  30

Phe Ala Ser Ser Gln Lys Ala Trp Gln Ile Ile Arg Asp Gly Glu Met
        35                  40                  45

Pro Lys Thr Leu Ala Cys Thr Glu Arg Pro Ser Lys Asn Ser His Pro
    50                  55                  60

Val Gln Val Gly Arg Ile Ile Leu Glu Asp Tyr His Asp His Gly Leu
65                  70                  75                  80

Leu Arg Val Arg Met Val Asn Leu Gln Val Glu Asp Ser Gly Leu Tyr
                85                  90                  95

Gln Cys Val Ile Tyr Gln Pro Pro Lys Glu Pro His Met Leu Phe Asp
            100                 105                 110

Arg Ile Arg Leu Val Val Thr Ala Ala
        115                 120


<210> SEQ ID NO 167
<211> LENGTH: 117
<212> TYPE: PRT
<213> ORGANISM: Artificial Sequence
<220> FEATURE:
<223> OTHER INFORMATION: Human TREM1 WT 01_WT_2A

<400> SEQUENCE: 167

Ala Ala Thr Lys Leu Thr Glu Glu Lys Tyr Glu Leu Lys Glu Gly Gln
1               5                   10                  15

Thr Leu Asp Val Lys Cys Asp Tyr Thr Leu Glu Lys Phe Ala Ser Ser
            20                  25                  30

Gln Lys Ala Trp Gln Ile Ile Arg Asp Gly Glu Met Pro Lys Thr Leu
        35                  40                  45

Ala Cys Thr Glu Arg Pro Ser Lys Asn Ser His Pro Val Gln Val Gly
    50                  55                  60
```

Arg Ile Ile Leu Glu Asp Tyr His Asp His Gly Leu Leu Arg Val Arg
65 70 75 80

Met Val Asn Leu Gln Val Glu Asp Ser Gly Leu Tyr Gln Cys Val Ile
85 90 95

Tyr Gln Pro Pro Lys Glu Pro His Met Leu Phe Asp Arg Ile Arg Leu
100 105 110

Val Val Thr Lys Gly
115

<210> SEQ ID NO 168
<211> LENGTH: 117
<212> TYPE: PRT
<213> ORGANISM: Artificial Sequence
<220> FEATURE:
<223> OTHER INFORMATION: Human TREM1 mutant 02_2_3

<400> SEQUENCE: 168

Ala Ala Ala Ala Leu Thr Glu Glu Lys Tyr Glu Leu Lys Glu Gly Gln
1 5 10 15

Thr Leu Asp Val Lys Cys Asp Tyr Thr Leu Glu Lys Phe Ala Ser Ser
20 25 30

Gln Lys Ala Trp Gln Ile Ile Arg Asp Gly Glu Met Pro Lys Thr Leu
35 40 45

Ala Cys Thr Glu Arg Pro Ser Lys Asn Ser His Pro Val Gln Val Gly
50 55 60

Arg Ile Ile Leu Glu Asp Tyr His Asp His Gly Leu Leu Arg Val Arg
65 70 75 80

Met Val Asn Leu Gln Val Glu Asp Ser Gly Leu Tyr Gln Cys Val Ile
85 90 95

Tyr Gln Pro Pro Lys Glu Pro His Met Leu Phe Asp Arg Ile Arg Leu
100 105 110

Val Val Thr Lys Gly
115

<210> SEQ ID NO 169
<211> LENGTH: 117
<212> TYPE: PRT
<213> ORGANISM: Artificial Sequence
<220> FEATURE:
<223> OTHER INFORMATION: Human TREM1 mutant 03_3_4

<400> SEQUENCE: 169

Ala Ala Thr Ala Ala Thr Glu Glu Lys Tyr Glu Leu Lys Glu Gly Gln
1 5 10 15

Thr Leu Asp Val Lys Cys Asp Tyr Thr Leu Glu Lys Phe Ala Ser Ser
20 25 30

Gln Lys Ala Trp Gln Ile Ile Arg Asp Gly Glu Met Pro Lys Thr Leu
35 40 45

Ala Cys Thr Glu Arg Pro Ser Lys Asn Ser His Pro Val Gln Val Gly
50 55 60

Arg Ile Ile Leu Glu Asp Tyr His Asp His Gly Leu Leu Arg Val Arg
65 70 75 80

Met Val Asn Leu Gln Val Glu Asp Ser Gly Leu Tyr Gln Cys Val Ile
85 90 95

Tyr Gln Pro Pro Lys Glu Pro His Met Leu Phe Asp Arg Ile Arg Leu
100 105 110

Val Val Thr Lys Gly

115

<210> SEQ ID NO 170
<211> LENGTH: 117
<212> TYPE: PRT
<213> ORGANISM: Artificial Sequence
<220> FEATURE:
<223> OTHER INFORMATION: Human TREM1 mutant 04_4_5

<400> SEQUENCE: 170

Ala Ala Thr Lys Ala Ala Glu Glu Lys Tyr Glu Leu Lys Glu Gly Gln
1 5 10 15

Thr Leu Asp Val Lys Cys Asp Tyr Thr Leu Glu Lys Phe Ala Ser Ser
20 25 30

Gln Lys Ala Trp Gln Ile Ile Arg Asp Gly Glu Met Pro Lys Thr Leu
35 40 45

Ala Cys Thr Glu Arg Pro Ser Lys Asn Ser His Pro Val Gln Val Gly
50 55 60

Arg Ile Ile Leu Glu Asp Tyr His Asp His Gly Leu Leu Arg Val Arg
65 70 75 80

Met Val Asn Leu Gln Val Glu Asp Ser Gly Leu Tyr Gln Cys Val Ile
85 90 95

Tyr Gln Pro Pro Lys Glu Pro His Met Leu Phe Asp Arg Ile Arg Leu
100 105 110

Val Val Thr Lys Gly
115

<210> SEQ ID NO 171
<211> LENGTH: 117
<212> TYPE: PRT
<213> ORGANISM: Artificial Sequence
<220> FEATURE:
<223> OTHER INFORMATION: Human TREM1 mutant 05_5_104

<400> SEQUENCE: 171

Ala Ala Thr Lys Leu Ala Glu Glu Lys Tyr Glu Leu Lys Glu Gly Gln
1 5 10 15

Thr Leu Asp Val Lys Cys Asp Tyr Thr Leu Glu Lys Phe Ala Ser Ser
20 25 30

Gln Lys Ala Trp Gln Ile Ile Arg Asp Gly Glu Met Pro Lys Thr Leu
35 40 45

Ala Cys Thr Glu Arg Pro Ser Lys Asn Ser His Pro Val Gln Val Gly
50 55 60

Arg Ile Ile Leu Glu Asp Tyr His Asp His Gly Leu Leu Arg Val Arg
65 70 75 80

Met Val Asn Leu Gln Val Glu Asp Ser Gly Leu Tyr Gln Cys Val Ile
85 90 95

Tyr Gln Pro Pro Lys Glu Pro His Ala Leu Phe Asp Arg Ile Arg Leu
100 105 110

Val Val Thr Lys Gly
115

<210> SEQ ID NO 172
<211> LENGTH: 117
<212> TYPE: PRT
<213> ORGANISM: Artificial Sequence
<220> FEATURE:
<223> OTHER INFORMATION: Human TREM1 mutant 06_5_106

<400> SEQUENCE: 172

```
Ala Ala Thr Lys Leu Ala Glu Glu Lys Tyr Glu Leu Lys Glu Gly Gln
1               5                   10                  15

Thr Leu Asp Val Lys Cys Asp Tyr Thr Leu Glu Lys Phe Ala Ser Ser
            20                  25                  30

Gln Lys Ala Trp Gln Ile Ile Arg Asp Gly Glu Met Pro Lys Thr Leu
        35                  40                  45

Ala Cys Thr Glu Arg Pro Ser Lys Asn Ser His Pro Val Gln Val Gly
    50                  55                  60

Arg Ile Ile Leu Glu Asp Tyr His Asp His Gly Leu Leu Arg Val Arg
65                  70                  75                  80

Met Val Asn Leu Gln Val Glu Asp Ser Gly Leu Tyr Gln Cys Val Ile
                85                  90                  95

Tyr Gln Pro Pro Lys Glu Pro His Met Leu Ala Asp Arg Ile Arg Leu
            100                 105                 110

Val Val Thr Lys Gly
        115
```

<210> SEQ ID NO 173
<211> LENGTH: 117
<212> TYPE: PRT
<213> ORGANISM: Artificial Sequence
<220> FEATURE:
<223> OTHER INFORMATION: Human TREM1 mutant 07_5_107

<400> SEQUENCE: 173

```
Ala Ala Thr Lys Leu Ala Glu Glu Lys Tyr Glu Leu Lys Glu Gly Gln
1               5                   10                  15

Thr Leu Asp Val Lys Cys Asp Tyr Thr Leu Glu Lys Phe Ala Ser Ser
            20                  25                  30

Gln Lys Ala Trp Gln Ile Ile Arg Asp Gly Glu Met Pro Lys Thr Leu
        35                  40                  45

Ala Cys Thr Glu Arg Pro Ser Lys Asn Ser His Pro Val Gln Val Gly
    50                  55                  60

Arg Ile Ile Leu Glu Asp Tyr His Asp His Gly Leu Leu Arg Val Arg
65                  70                  75                  80

Met Val Asn Leu Gln Val Glu Asp Ser Gly Leu Tyr Gln Cys Val Ile
                85                  90                  95

Tyr Gln Pro Pro Lys Glu Pro His Met Leu Phe Ala Arg Ile Arg Leu
            100                 105                 110

Val Val Thr Lys Gly
        115
```

<210> SEQ ID NO 174
<211> LENGTH: 117
<212> TYPE: PRT
<213> ORGANISM: Artificial Sequence
<220> FEATURE:
<223> OTHER INFORMATION: Human TREM1 mutant 08_7_9

<400> SEQUENCE: 174

```
Ala Ala Thr Lys Leu Thr Glu Ala Lys Ala Glu Leu Lys Glu Gly Gln
1               5                   10                  15

Thr Leu Asp Val Lys Cys Asp Tyr Thr Leu Glu Lys Phe Ala Ser Ser
            20                  25                  30

Gln Lys Ala Trp Gln Ile Ile Arg Asp Gly Glu Met Pro Lys Thr Leu
        35                  40                  45

Ala Cys Thr Glu Arg Pro Ser Lys Asn Ser His Pro Val Gln Val Gly
```

```
    50                  55                  60

Arg Ile Ile Leu Glu Asp Tyr His Asp His Gly Leu Leu Arg Val Arg
65                  70                  75                  80

Met Val Asn Leu Gln Val Glu Asp Ser Gly Leu Tyr Gln Cys Val Ile
                85                  90                  95

Tyr Gln Pro Pro Lys Glu Pro His Met Leu Phe Asp Arg Ile Arg Leu
            100                 105                 110

Val Val Thr Lys Gly
        115


<210> SEQ ID NO 175
<211> LENGTH: 117
<212> TYPE: PRT
<213> ORGANISM: Artificial Sequence
<220> FEATURE:
<223> OTHER INFORMATION: Human TREM1 mutant  09_7_107

<400> SEQUENCE: 175

Ala Ala Thr Lys Leu Thr Glu Ala Lys Tyr Glu Leu Lys Glu Gly Gln
1               5                   10                  15

Thr Leu Asp Val Lys Cys Asp Tyr Thr Leu Glu Lys Phe Ala Ser Ser
            20                  25                  30

Gln Lys Ala Trp Gln Ile Ile Arg Asp Gly Glu Met Pro Lys Thr Leu
        35                  40                  45

Ala Cys Thr Glu Arg Pro Ser Lys Asn Ser His Pro Val Gln Val Gly
    50                  55                  60

Arg Ile Ile Leu Glu Asp Tyr His Asp His Gly Leu Leu Arg Val Arg
65                  70                  75                  80

Met Val Asn Leu Gln Val Glu Asp Ser Gly Leu Tyr Gln Cys Val Ile
                85                  90                  95

Tyr Gln Pro Pro Lys Glu Pro His Met Leu Phe Ala Arg Ile Arg Leu
            100                 105                 110

Val Val Thr Lys Gly
        115


<210> SEQ ID NO 176
<211> LENGTH: 117
<212> TYPE: PRT
<213> ORGANISM: Artificial Sequence
<220> FEATURE:
<223> OTHER INFORMATION: Human TREM1 mutant  10_8_10

<400> SEQUENCE: 176

Ala Ala Thr Lys Leu Thr Glu Glu Ala Tyr Ala Leu Lys Glu Gly Gln
1               5                   10                  15

Thr Leu Asp Val Lys Cys Asp Tyr Thr Leu Glu Lys Phe Ala Ser Ser
            20                  25                  30

Gln Lys Ala Trp Gln Ile Ile Arg Asp Gly Glu Met Pro Lys Thr Leu
        35                  40                  45

Ala Cys Thr Glu Arg Pro Ser Lys Asn Ser His Pro Val Gln Val Gly
    50                  55                  60

Arg Ile Ile Leu Glu Asp Tyr His Asp His Gly Leu Leu Arg Val Arg
65                  70                  75                  80

Met Val Asn Leu Gln Val Glu Asp Ser Gly Leu Tyr Gln Cys Val Ile
                85                  90                  95

Tyr Gln Pro Pro Lys Glu Pro His Met Leu Phe Asp Arg Ile Arg Leu
            100                 105                 110
```

Val Val Thr Lys Gly
115

<210> SEQ ID NO 177
<211> LENGTH: 117
<212> TYPE: PRT
<213> ORGANISM: Artificial Sequence
<220> FEATURE:
<223> OTHER INFORMATION: Human TREM1 mutant 11_11_12

<400> SEQUENCE: 177

Ala Ala Thr Lys Leu Thr Glu Glu Lys Tyr Glu Ala Ala Glu Gly Gln
1 5 10 15

Thr Leu Asp Val Lys Cys Asp Tyr Thr Leu Glu Lys Phe Ala Ser Ser
20 25 30

Gln Lys Ala Trp Gln Ile Ile Arg Asp Gly Glu Met Pro Lys Thr Leu
35 40 45

Ala Cys Thr Glu Arg Pro Ser Lys Asn Ser His Pro Val Gln Val Gly
50 55 60

Arg Ile Ile Leu Glu Asp Tyr His Asp His Gly Leu Leu Arg Val Arg
65 70 75 80

Met Val Asn Leu Gln Val Glu Asp Ser Gly Leu Tyr Gln Cys Val Ile
85 90 95

Tyr Gln Pro Pro Lys Glu Pro His Met Leu Phe Asp Arg Ile Arg Leu
100 105 110

Val Val Thr Lys Gly
115

<210> SEQ ID NO 178
<211> LENGTH: 117
<212> TYPE: PRT
<213> ORGANISM: Artificial Sequence
<220> FEATURE:
<223> OTHER INFORMATION: Human TREM1 mutant 12_12_13

<400> SEQUENCE: 178

Ala Ala Thr Lys Leu Thr Glu Glu Lys Tyr Glu Leu Ala Ala Gly Gln
1 5 10 15

Thr Leu Asp Val Lys Cys Asp Tyr Thr Leu Glu Lys Phe Ala Ser Ser
20 25 30

Gln Lys Ala Trp Gln Ile Ile Arg Asp Gly Glu Met Pro Lys Thr Leu
35 40 45

Ala Cys Thr Glu Arg Pro Ser Lys Asn Ser His Pro Val Gln Val Gly
50 55 60

Arg Ile Ile Leu Glu Asp Tyr His Asp His Gly Leu Leu Arg Val Arg
65 70 75 80

Met Val Asn Leu Gln Val Glu Asp Ser Gly Leu Tyr Gln Cys Val Ile
85 90 95

Tyr Gln Pro Pro Lys Glu Pro His Met Leu Phe Asp Arg Ile Arg Leu
100 105 110

Val Val Thr Lys Gly
115

<210> SEQ ID NO 179
<211> LENGTH: 117
<212> TYPE: PRT
<213> ORGANISM: Artificial Sequence
<220> FEATURE:
<223> OTHER INFORMATION: Human TREM1 mutant 13_12_15

<400> SEQUENCE: 179

Ala Ala Thr Lys Leu Thr Glu Glu Lys Tyr Glu Leu Ala Glu Gly Ala
1               5                   10                  15

Thr Leu Asp Val Lys Cys Asp Tyr Thr Leu Glu Lys Phe Ala Ser Ser
            20                  25                  30

Gln Lys Ala Trp Gln Ile Ile Arg Asp Gly Glu Met Pro Lys Thr Leu
        35                  40                  45

Ala Cys Thr Glu Arg Pro Ser Lys Asn Ser His Pro Val Gln Val Gly
    50                  55                  60

Arg Ile Ile Leu Glu Asp Tyr His Asp His Gly Leu Leu Arg Val Arg
65                  70                  75                  80

Met Val Asn Leu Gln Val Glu Asp Ser Gly Leu Tyr Gln Cys Val Ile
                85                  90                  95

Tyr Gln Pro Pro Lys Glu Pro His Met Leu Phe Asp Arg Ile Arg Leu
            100                 105                 110

Val Val Thr Lys Gly
        115

<210> SEQ ID NO 180
<211> LENGTH: 117
<212> TYPE: PRT
<213> ORGANISM: Artificial Sequence
<220> FEATURE:
<223> OTHER INFORMATION: Human TREM1 mutant 14_13_85

<400> SEQUENCE: 180

Ala Ala Thr Lys Leu Thr Glu Glu Lys Tyr Glu Leu Lys Ala Gly Gln
1               5                   10                  15

Thr Leu Asp Val Lys Cys Asp Tyr Thr Leu Glu Lys Phe Ala Ser Ser
            20                  25                  30

Gln Lys Ala Trp Gln Ile Ile Arg Asp Gly Glu Met Pro Lys Thr Leu
        35                  40                  45

Ala Cys Thr Glu Arg Pro Ser Lys Asn Ser His Pro Val Gln Val Gly
    50                  55                  60

Arg Ile Ile Leu Glu Asp Tyr His Asp His Gly Leu Leu Arg Val Arg
65                  70                  75                  80

Met Val Asn Leu Gln Ala Glu Asp Ser Gly Leu Tyr Gln Cys Val Ile
                85                  90                  95

Tyr Gln Pro Pro Lys Glu Pro His Met Leu Phe Asp Arg Ile Arg Leu
            100                 105                 110

Val Val Thr Lys Gly
        115

<210> SEQ ID NO 181
<211> LENGTH: 117
<212> TYPE: PRT
<213> ORGANISM: Artificial Sequence
<220> FEATURE:
<223> OTHER INFORMATION: Human TREM1 mutant 15_16_81

<400> SEQUENCE: 181

Ala Ala Thr Lys Leu Thr Glu Glu Lys Tyr Glu Leu Lys Glu Gly Gln
1               5                   10                  15

Ala Leu Asp Val Lys Cys Asp Tyr Thr Leu Glu Lys Phe Ala Ser Ser
            20                  25                  30

Gln Lys Ala Trp Gln Ile Ile Arg Asp Gly Glu Met Pro Lys Thr Leu
        35                  40                  45

```
Ala Cys Thr Glu Arg Pro Ser Lys Asn Ser His Pro Val Gln Val Gly
    50                  55                  60

Arg Ile Ile Leu Glu Asp Tyr His Asp His Gly Leu Leu Arg Val Arg
65                  70                  75                  80

Met Ala Asn Leu Gln Val Glu Asp Ser Gly Leu Tyr Gln Cys Val Ile
                85                  90                  95

Tyr Gln Pro Pro Lys Glu Pro His Met Leu Phe Asp Arg Ile Arg Leu
            100                 105                 110

Val Val Thr Lys Gly
        115


<210> SEQ ID NO 182
<211> LENGTH: 117
<212> TYPE: PRT
<213> ORGANISM: Artificial Sequence
<220> FEATURE:
<223> OTHER INFORMATION: Human TREM1 mutant  16_20_75

<400> SEQUENCE: 182

Ala Ala Thr Lys Leu Thr Glu Glu Lys Tyr Glu Leu Lys Glu Gly Gln
1               5                   10                  15

Thr Leu Asp Val Ala Cys Asp Tyr Thr Leu Glu Lys Phe Ala Ser Ser
            20                  25                  30

Gln Lys Ala Trp Gln Ile Ile Arg Asp Gly Glu Met Pro Lys Thr Leu
        35                  40                  45

Ala Cys Thr Glu Arg Pro Ser Lys Asn Ser His Pro Val Gln Val Gly
    50                  55                  60

Arg Ile Ile Leu Glu Asp Tyr His Asp His Gly Ala Leu Arg Val Arg
65                  70                  75                  80

Met Val Asn Leu Gln Val Glu Asp Ser Gly Leu Tyr Gln Cys Val Ile
                85                  90                  95

Tyr Gln Pro Pro Lys Glu Pro His Met Leu Phe Asp Arg Ile Arg Leu
            100                 105                 110

Val Val Thr Lys Gly
        115


<210> SEQ ID NO 183
<211> LENGTH: 117
<212> TYPE: PRT
<213> ORGANISM: Artificial Sequence
<220> FEATURE:
<223> OTHER INFORMATION: Human TREM1 mutant  17_24_25

<400> SEQUENCE: 183

Ala Ala Thr Lys Leu Thr Glu Glu Lys Tyr Glu Leu Lys Glu Gly Gln
1               5                   10                  15

Thr Leu Asp Val Lys Cys Asp Tyr Ala Ala Glu Lys Phe Ala Ser Ser
            20                  25                  30

Gln Lys Ala Trp Gln Ile Ile Arg Asp Gly Glu Met Pro Lys Thr Leu
        35                  40                  45

Ala Cys Thr Glu Arg Pro Ser Lys Asn Ser His Pro Val Gln Val Gly
    50                  55                  60

Arg Ile Ile Leu Glu Asp Tyr His Asp His Gly Leu Leu Arg Val Arg
65                  70                  75                  80

Met Val Asn Leu Gln Val Glu Asp Ser Gly Leu Tyr Gln Cys Val Ile
                85                  90                  95

Tyr Gln Pro Pro Lys Glu Pro His Met Leu Phe Asp Arg Ile Arg Leu
            100                 105                 110
```

Val Val Thr Lys Gly
115

<210> SEQ ID NO 184
<211> LENGTH: 117
<212> TYPE: PRT
<213> ORGANISM: Artificial Sequence
<220> FEATURE:
<223> OTHER INFORMATION: Human TREM1 mutant 18_24_26

<400> SEQUENCE: 184

Ala Ala Thr Lys Leu Thr Glu Glu Lys Tyr Glu Leu Lys Glu Gly Gln
1 5 10 15

Thr Leu Asp Val Lys Cys Asp Tyr Ala Leu Ala Lys Phe Ala Ser Ser
20 25 30

Gln Lys Ala Trp Gln Ile Ile Arg Asp Gly Glu Met Pro Lys Thr Leu
35 40 45

Ala Cys Thr Glu Arg Pro Ser Lys Asn Ser His Pro Val Gln Val Gly
50 55 60

Arg Ile Ile Leu Glu Asp Tyr His Asp His Gly Leu Leu Arg Val Arg
65 70 75 80

Met Val Asn Leu Gln Val Glu Asp Ser Gly Leu Tyr Gln Cys Val Ile
85 90 95

Tyr Gln Pro Pro Lys Glu Pro His Met Leu Phe Asp Arg Ile Arg Leu
100 105 110

Val Val Thr Lys Gly
115

<210> SEQ ID NO 185
<211> LENGTH: 117
<212> TYPE: PRT
<213> ORGANISM: Artificial Sequence
<220> FEATURE:
<223> OTHER INFORMATION: Human TREM1 mutant 19_24_27

<400> SEQUENCE: 185

Ala Ala Thr Lys Leu Thr Glu Glu Lys Tyr Glu Leu Lys Glu Gly Gln
1 5 10 15

Thr Leu Asp Val Lys Cys Asp Tyr Ala Leu Glu Ala Phe Ala Ser Ser
20 25 30

Gln Lys Ala Trp Gln Ile Ile Arg Asp Gly Glu Met Pro Lys Thr Leu
35 40 45

Ala Cys Thr Glu Arg Pro Ser Lys Asn Ser His Pro Val Gln Val Gly
50 55 60

Arg Ile Ile Leu Glu Asp Tyr His Asp His Gly Leu Leu Arg Val Arg
65 70 75 80

Met Val Asn Leu Gln Val Glu Asp Ser Gly Leu Tyr Gln Cys Val Ile
85 90 95

Tyr Gln Pro Pro Lys Glu Pro His Met Leu Phe Asp Arg Ile Arg Leu
100 105 110

Val Val Thr Lys Gly
115

<210> SEQ ID NO 186
<211> LENGTH: 117
<212> TYPE: PRT
<213> ORGANISM: Artificial Sequence
<220> FEATURE:
<223> OTHER INFORMATION: Human TREM1 mutant 20_25_26

<400> SEQUENCE: 186

Ala Ala Thr Lys Leu Thr Glu Glu Lys Tyr Glu Leu Lys Glu Gly Gln
1               5                   10                  15

Thr Leu Asp Val Lys Cys Asp Tyr Thr Ala Ala Lys Phe Ala Ser Ser
            20                  25                  30

Gln Lys Ala Trp Gln Ile Ile Arg Asp Gly Glu Met Pro Lys Thr Leu
        35                  40                  45

Ala Cys Thr Glu Arg Pro Ser Lys Asn Ser His Pro Val Gln Val Gly
    50                  55                  60

Arg Ile Ile Leu Glu Asp Tyr His Asp His Gly Leu Leu Arg Val Arg
65                  70                  75                  80

Met Val Asn Leu Gln Val Glu Asp Ser Gly Leu Tyr Gln Cys Val Ile
                85                  90                  95

Tyr Gln Pro Pro Lys Glu Pro His Met Leu Phe Asp Arg Ile Arg Leu
            100                 105                 110

Val Val Thr Lys Gly
        115

<210> SEQ ID NO 187
<211> LENGTH: 117
<212> TYPE: PRT
<213> ORGANISM: Artificial Sequence
<220> FEATURE:
<223> OTHER INFORMATION: Human TREM1 mutant 21_26_27

<400> SEQUENCE: 187

Ala Ala Thr Lys Leu Thr Glu Glu Lys Tyr Glu Leu Lys Glu Gly Gln
1               5                   10                  15

Thr Leu Asp Val Lys Cys Asp Tyr Thr Leu Ala Ala Phe Ala Ser Ser
            20                  25                  30

Gln Lys Ala Trp Gln Ile Ile Arg Asp Gly Glu Met Pro Lys Thr Leu
        35                  40                  45

Ala Cys Thr Glu Arg Pro Ser Lys Asn Ser His Pro Val Gln Val Gly
    50                  55                  60

Arg Ile Ile Leu Glu Asp Tyr His Asp His Gly Leu Leu Arg Val Arg
65                  70                  75                  80

Met Val Asn Leu Gln Val Glu Asp Ser Gly Leu Tyr Gln Cys Val Ile
                85                  90                  95

Tyr Gln Pro Pro Lys Glu Pro His Met Leu Phe Asp Arg Ile Arg Leu
            100                 105                 110

Val Val Thr Lys Gly
        115

<210> SEQ ID NO 188
<211> LENGTH: 117
<212> TYPE: PRT
<213> ORGANISM: Artificial Sequence
<220> FEATURE:
<223> OTHER INFORMATION: Human TREM1 mutant 22_30_31

<400> SEQUENCE: 188

Ala Ala Thr Lys Leu Thr Glu Glu Lys Tyr Glu Leu Lys Glu Gly Gln
1               5                   10                  15

Thr Leu Asp Val Lys Cys Asp Tyr Thr Leu Glu Lys Phe Ala Ala Ala
            20                  25                  30

Gln Lys Ala Trp Gln Ile Ile Arg Asp Gly Glu Met Pro Lys Thr Leu
        35                  40                  45

```
Ala Cys Thr Glu Arg Pro Ser Lys Asn Ser His Pro Val Gln Val Gly
    50                  55                  60

Arg Ile Ile Leu Glu Asp Tyr His Asp His Gly Leu Leu Arg Val Arg
65                  70                  75                  80

Met Val Asn Leu Gln Val Glu Asp Ser Gly Leu Tyr Gln Cys Val Ile
                85                  90                  95

Tyr Gln Pro Pro Lys Glu Pro His Met Leu Phe Asp Arg Ile Arg Leu
            100                 105                 110

Val Val Thr Lys Gly
        115


<210> SEQ ID NO 189
<211> LENGTH: 117
<212> TYPE: PRT
<213> ORGANISM: Artificial Sequence
<220> FEATURE:
<223> OTHER INFORMATION: Human TREM1 mutant  23_30_53

<400> SEQUENCE: 189

Ala Ala Thr Lys Leu Thr Glu Glu Lys Tyr Glu Leu Lys Glu Gly Gln
1               5                   10                  15

Thr Leu Asp Val Lys Cys Asp Tyr Thr Leu Glu Lys Phe Ala Ala Ser
            20                  25                  30

Gln Lys Ala Trp Gln Ile Ile Arg Asp Gly Glu Met Pro Lys Thr Leu
        35                  40                  45

Ala Cys Thr Glu Arg Ala Ser Lys Asn Ser His Pro Val Gln Val Gly
    50                  55                  60

Arg Ile Ile Leu Glu Asp Tyr His Asp His Gly Leu Leu Arg Val Arg
65                  70                  75                  80

Met Val Asn Leu Gln Val Glu Asp Ser Gly Leu Tyr Gln Cys Val Ile
                85                  90                  95

Tyr Gln Pro Pro Lys Glu Pro His Met Leu Phe Asp Arg Ile Arg Leu
            100                 105                 110

Val Val Thr Lys Gly
        115


<210> SEQ ID NO 190
<211> LENGTH: 117
<212> TYPE: PRT
<213> ORGANISM: Artificial Sequence
<220> FEATURE:
<223> OTHER INFORMATION: Human TREM1 mutant  24_37_38

<400> SEQUENCE: 190

Ala Ala Thr Lys Leu Thr Glu Glu Lys Tyr Glu Leu Lys Glu Gly Gln
1               5                   10                  15

Thr Leu Asp Val Lys Cys Asp Tyr Thr Leu Glu Lys Phe Ala Ser Ser
            20                  25                  30

Gln Lys Ala Trp Gln Ala Ala Arg Asp Gly Glu Met Pro Lys Thr Leu
        35                  40                  45

Ala Cys Thr Glu Arg Pro Ser Lys Asn Ser His Pro Val Gln Val Gly
    50                  55                  60

Arg Ile Ile Leu Glu Asp Tyr His Asp His Gly Leu Leu Arg Val Arg
65                  70                  75                  80

Met Val Asn Leu Gln Val Glu Asp Ser Gly Leu Tyr Gln Cys Val Ile
                85                  90                  95

Tyr Gln Pro Pro Lys Glu Pro His Met Leu Phe Asp Arg Ile Arg Leu
```

100 105 110

Val Val Thr Lys Gly
115

<210> SEQ ID NO 191
<211> LENGTH: 117
<212> TYPE: PRT
<213> ORGANISM: Artificial Sequence
<220> FEATURE:
<223> OTHER INFORMATION: Human TREM1 mutant 25_37_39

<400> SEQUENCE: 191

Ala Ala Thr Lys Leu Thr Glu Glu Lys Tyr Glu Leu Lys Glu Gly Gln
1 5 10 15

Thr Leu Asp Val Lys Cys Asp Tyr Thr Leu Glu Lys Phe Ala Ser Ser
20 25 30

Gln Lys Ala Trp Gln Ala Ile Ala Asp Gly Glu Met Pro Lys Thr Leu
35 40 45

Ala Cys Thr Glu Arg Pro Ser Lys Asn Ser His Pro Val Gln Val Gly
50 55 60

Arg Ile Ile Leu Glu Asp Tyr His Asp His Gly Leu Leu Arg Val Arg
65 70 75 80

Met Val Asn Leu Gln Val Glu Asp Ser Gly Leu Tyr Gln Cys Val Ile
85 90 95

Tyr Gln Pro Pro Lys Glu Pro His Met Leu Phe Asp Arg Ile Arg Leu
100 105 110

Val Val Thr Lys Gly
115

<210> SEQ ID NO 192
<211> LENGTH: 117
<212> TYPE: PRT
<213> ORGANISM: Artificial Sequence
<220> FEATURE:
<223> OTHER INFORMATION: Human TREM1 mutant 26_37_45

<400> SEQUENCE: 192

Ala Ala Thr Lys Leu Thr Glu Glu Lys Tyr Glu Leu Lys Glu Gly Gln
1 5 10 15

Thr Leu Asp Val Lys Cys Asp Tyr Thr Leu Glu Lys Phe Ala Ser Ser
20 25 30

Gln Lys Ala Trp Gln Ala Ile Arg Asp Gly Glu Met Pro Ala Thr Leu
35 40 45

Ala Cys Thr Glu Arg Pro Ser Lys Asn Ser His Pro Val Gln Val Gly
50 55 60

Arg Ile Ile Leu Glu Asp Tyr His Asp His Gly Leu Leu Arg Val Arg
65 70 75 80

Met Val Asn Leu Gln Val Glu Asp Ser Gly Leu Tyr Gln Cys Val Ile
85 90 95

Tyr Gln Pro Pro Lys Glu Pro His Met Leu Phe Asp Arg Ile Arg Leu
100 105 110

Val Val Thr Lys Gly
115

<210> SEQ ID NO 193
<211> LENGTH: 117
<212> TYPE: PRT
<213> ORGANISM: Artificial Sequence
<220> FEATURE:

<223> OTHER INFORMATION: Human TREM1 mutant 27_37_47

<400> SEQUENCE: 193

```
Ala Ala Thr Lys Leu Thr Glu Glu Lys Tyr Glu Leu Lys Glu Gly Gln
1               5                   10                  15

Thr Leu Asp Val Lys Cys Asp Tyr Thr Leu Glu Lys Phe Ala Ser Ser
            20                  25                  30

Gln Lys Ala Trp Gln Ala Ile Arg Asp Gly Glu Met Pro Lys Thr Ala
        35                  40                  45

Ala Cys Thr Glu Arg Pro Ser Lys Asn Ser His Pro Val Gln Val Gly
    50                  55                  60

Arg Ile Ile Leu Glu Asp Tyr His Asp His Gly Leu Leu Arg Val Arg
65                  70                  75                  80

Met Val Asn Leu Gln Val Glu Asp Ser Gly Leu Tyr Gln Cys Val Ile
                85                  90                  95

Tyr Gln Pro Pro Lys Glu Pro His Met Leu Phe Asp Arg Ile Arg Leu
            100                 105                 110

Val Val Thr Lys Gly
        115
```

<210> SEQ ID NO 194
<211> LENGTH: 117
<212> TYPE: PRT
<213> ORGANISM: Artificial Sequence
<220> FEATURE:
<223> OTHER INFORMATION: Human TREM1 mutant 28_38_44

<400> SEQUENCE: 194

```
Ala Ala Thr Lys Leu Thr Glu Glu Lys Tyr Glu Leu Lys Glu Gly Gln
1               5                   10                  15

Thr Leu Asp Val Lys Cys Asp Tyr Thr Leu Glu Lys Phe Ala Ser Ser
            20                  25                  30

Gln Lys Ala Trp Gln Ile Ala Arg Asp Gly Glu Met Ala Lys Thr Leu
        35                  40                  45

Ala Cys Thr Glu Arg Pro Ser Lys Asn Ser His Pro Val Gln Val Gly
    50                  55                  60

Arg Ile Ile Leu Glu Asp Tyr His Asp His Gly Leu Leu Arg Val Arg
65                  70                  75                  80

Met Val Asn Leu Gln Val Glu Asp Ser Gly Leu Tyr Gln Cys Val Ile
                85                  90                  95

Tyr Gln Pro Pro Lys Glu Pro His Met Leu Phe Asp Arg Ile Arg Leu
            100                 105                 110

Val Val Thr Lys Gly
        115
```

<210> SEQ ID NO 195
<211> LENGTH: 117
<212> TYPE: PRT
<213> ORGANISM: Artificial Sequence
<220> FEATURE:
<223> OTHER INFORMATION: Human TREM1 mutant 29_38_90

<400> SEQUENCE: 195

```
Ala Ala Thr Lys Leu Thr Glu Glu Lys Tyr Glu Leu Lys Glu Gly Gln
1               5                   10                  15

Thr Leu Asp Val Lys Cys Asp Tyr Thr Leu Glu Lys Phe Ala Ser Ser
            20                  25                  30

Gln Lys Ala Trp Gln Ile Ala Arg Asp Gly Glu Met Pro Lys Thr Leu
```

```
        35                  40                  45

Ala Cys Thr Glu Arg Pro Ser Lys Asn Ser His Pro Val Gln Val Gly
    50                  55                  60

Arg Ile Ile Leu Glu Asp Tyr His Asp His Gly Leu Leu Arg Val Arg
65                  70                  75                  80

Met Val Asn Leu Gln Val Glu Asp Ser Gly Ala Tyr Gln Cys Val Ile
                85                  90                  95

Tyr Gln Pro Pro Lys Glu Pro His Met Leu Phe Asp Arg Ile Arg Leu
            100                 105                 110

Val Val Thr Lys Gly
        115


<210> SEQ ID NO 196
<211> LENGTH: 117
<212> TYPE: PRT
<213> ORGANISM: Artificial Sequence
<220> FEATURE:
<223> OTHER INFORMATION: Human TREM1 mutant  30_42_43

<400> SEQUENCE: 196

Ala Ala Thr Lys Leu Thr Glu Glu Lys Tyr Glu Leu Lys Glu Gly Gln
1               5                   10                  15

Thr Leu Asp Val Lys Cys Asp Tyr Thr Leu Glu Lys Phe Ala Ser Ser
            20                  25                  30

Gln Lys Ala Trp Gln Ile Ile Arg Asp Gly Ala Ala Pro Lys Thr Leu
        35                  40                  45

Ala Cys Thr Glu Arg Pro Ser Lys Asn Ser His Pro Val Gln Val Gly
    50                  55                  60

Arg Ile Ile Leu Glu Asp Tyr His Asp His Gly Leu Leu Arg Val Arg
65                  70                  75                  80

Met Val Asn Leu Gln Val Glu Asp Ser Gly Leu Tyr Gln Cys Val Ile
                85                  90                  95

Tyr Gln Pro Pro Lys Glu Pro His Met Leu Phe Asp Arg Ile Arg Leu
            100                 105                 110

Val Val Thr Lys Gly
        115


<210> SEQ ID NO 197
<211> LENGTH: 117
<212> TYPE: PRT
<213> ORGANISM: Artificial Sequence
<220> FEATURE:
<223> OTHER INFORMATION: Human TREM1 mutant  31_42_45

<400> SEQUENCE: 197

Ala Ala Thr Lys Leu Thr Glu Glu Lys Tyr Glu Leu Lys Glu Gly Gln
1               5                   10                  15

Thr Leu Asp Val Lys Cys Asp Tyr Thr Leu Glu Lys Phe Ala Ser Ser
            20                  25                  30

Gln Lys Ala Trp Gln Ile Ile Arg Asp Gly Ala Met Pro Ala Thr Leu
        35                  40                  45

Ala Cys Thr Glu Arg Pro Ser Lys Asn Ser His Pro Val Gln Val Gly
    50                  55                  60

Arg Ile Ile Leu Glu Asp Tyr His Asp His Gly Leu Leu Arg Val Arg
65                  70                  75                  80

Met Val Asn Leu Gln Val Glu Asp Ser Gly Leu Tyr Gln Cys Val Ile
                85                  90                  95
```

```
Tyr Gln Pro Pro Lys Glu Pro His Met Leu Phe Asp Arg Ile Arg Leu
            100                 105                 110

Val Val Thr Lys Gly
        115


<210> SEQ ID NO 198
<211> LENGTH: 117
<212> TYPE: PRT
<213> ORGANISM: Artificial Sequence
<220> FEATURE:
<223> OTHER INFORMATION: Human TREM1 mutant  32_43_44

<400> SEQUENCE: 198

Ala Ala Thr Lys Leu Thr Glu Glu Lys Tyr Glu Leu Lys Glu Gly Gln
1               5                   10                  15

Thr Leu Asp Val Lys Cys Asp Tyr Thr Leu Glu Lys Phe Ala Ser Ser
            20                  25                  30

Gln Lys Ala Trp Gln Ile Ile Arg Asp Gly Glu Ala Ala Lys Thr Leu
        35                  40                  45

Ala Cys Thr Glu Arg Pro Ser Lys Asn Ser His Pro Val Gln Val Gly
    50                  55                  60

Arg Ile Ile Leu Glu Asp Tyr His Asp His Gly Leu Leu Arg Val Arg
65                  70                  75                  80

Met Val Asn Leu Gln Val Glu Asp Ser Gly Leu Tyr Gln Cys Val Ile
                85                  90                  95

Tyr Gln Pro Pro Lys Glu Pro His Met Leu Phe Asp Arg Ile Arg Leu
            100                 105                 110

Val Val Thr Lys Gly
        115


<210> SEQ ID NO 199
<211> LENGTH: 117
<212> TYPE: PRT
<213> ORGANISM: Artificial Sequence
<220> FEATURE:
<223> OTHER INFORMATION: Human TREM1 mutant  33_43_101

<400> SEQUENCE: 199

Ala Ala Thr Lys Leu Thr Glu Glu Lys Tyr Glu Leu Lys Glu Gly Gln
1               5                   10                  15

Thr Leu Asp Val Lys Cys Asp Tyr Thr Leu Glu Lys Phe Ala Ser Ser
            20                  25                  30

Gln Lys Ala Trp Gln Ile Ile Arg Asp Gly Glu Ala Pro Lys Thr Leu
        35                  40                  45

Ala Cys Thr Glu Arg Pro Ser Lys Asn Ser His Pro Val Gln Val Gly
    50                  55                  60

Arg Ile Ile Leu Glu Asp Tyr His Asp His Gly Leu Leu Arg Val Arg
65                  70                  75                  80

Met Val Asn Leu Gln Val Glu Asp Ser Gly Leu Tyr Gln Cys Val Ile
                85                  90                  95

Tyr Gln Pro Pro Lys Ala Pro His Met Leu Phe Asp Arg Ile Arg Leu
            100                 105                 110

Val Val Thr Lys Gly
        115


<210> SEQ ID NO 200
<211> LENGTH: 117
<212> TYPE: PRT
<213> ORGANISM: Artificial Sequence
```

<220> FEATURE:
<223> OTHER INFORMATION: Human TREM1 mutant 34_44_45

<400> SEQUENCE: 200

Ala Ala Thr Lys Leu Thr Glu Glu Lys Tyr Glu Leu Lys Glu Gly Gln
1 5 10 15

Thr Leu Asp Val Lys Cys Asp Tyr Thr Leu Glu Lys Phe Ala Ser Ser
20 25 30

Gln Lys Ala Trp Gln Ile Ile Arg Asp Gly Glu Met Ala Ala Thr Leu
35 40 45

Ala Cys Thr Glu Arg Pro Ser Lys Asn Ser His Pro Val Gln Val Gly
50 55 60

Arg Ile Ile Leu Glu Asp Tyr His Asp His Gly Leu Leu Arg Val Arg
65 70 75 80

Met Val Asn Leu Gln Val Glu Asp Ser Gly Leu Tyr Gln Cys Val Ile
85 90 95

Tyr Gln Pro Pro Lys Glu Pro His Met Leu Phe Asp Arg Ile Arg Leu
100 105 110

Val Val Thr Lys Gly
115

<210> SEQ ID NO 201
<211> LENGTH: 117
<212> TYPE: PRT
<213> ORGANISM: Artificial Sequence
<220> FEATURE:
<223> OTHER INFORMATION: Human TREM1 mutant 35_45_47

<400> SEQUENCE: 201

Ala Ala Thr Lys Leu Thr Glu Glu Lys Tyr Glu Leu Lys Glu Gly Gln
1 5 10 15

Thr Leu Asp Val Lys Cys Asp Tyr Thr Leu Glu Lys Phe Ala Ser Ser
20 25 30

Gln Lys Ala Trp Gln Ile Ile Arg Asp Gly Glu Met Pro Ala Thr Ala
35 40 45

Ala Cys Thr Glu Arg Pro Ser Lys Asn Ser His Pro Val Gln Val Gly
50 55 60

Arg Ile Ile Leu Glu Asp Tyr His Asp His Gly Leu Leu Arg Val Arg
65 70 75 80

Met Val Asn Leu Gln Val Glu Asp Ser Gly Leu Tyr Gln Cys Val Ile
85 90 95

Tyr Gln Pro Pro Lys Glu Pro His Met Leu Phe Asp Arg Ile Arg Leu
100 105 110

Val Val Thr Lys Gly
115

<210> SEQ ID NO 202
<211> LENGTH: 117
<212> TYPE: PRT
<213> ORGANISM: Artificial Sequence
<220> FEATURE:
<223> OTHER INFORMATION: Human TREM1 mutant 36_47_65

<400> SEQUENCE: 202

Ala Ala Thr Lys Leu Thr Glu Glu Lys Tyr Glu Leu Lys Glu Gly Gln
1 5 10 15

Thr Leu Asp Val Lys Cys Asp Tyr Thr Leu Glu Lys Phe Ala Ser Ser
20 25 30

Gln Lys Ala Trp Gln Ile Ile Arg Asp Gly Glu Met Pro Lys Thr Ala
        35                  40                  45

Ala Cys Thr Glu Arg Pro Ser Lys Asn Ser His Pro Val Gln Val Gly
    50                  55                  60

Arg Ala Ile Leu Glu Asp Tyr His Asp His Gly Leu Leu Arg Val Arg
65                  70                  75                  80

Met Val Asn Leu Gln Val Glu Asp Ser Gly Leu Tyr Gln Cys Val Ile
                85                  90                  95

Tyr Gln Pro Pro Lys Glu Pro His Met Leu Phe Asp Arg Ile Arg Leu
            100                 105                 110

Val Val Thr Lys Gly
        115

<210> SEQ ID NO 203
<211> LENGTH: 117
<212> TYPE: PRT
<213> ORGANISM: Artificial Sequence
<220> FEATURE:
<223> OTHER INFORMATION: Human TREM1 mutant 37_51_55

<400> SEQUENCE: 203

Ala Ala Thr Lys Leu Thr Glu Glu Lys Tyr Glu Leu Lys Glu Gly Gln
1               5                   10                  15

Thr Leu Asp Val Lys Cys Asp Tyr Thr Leu Glu Lys Phe Ala Ser Ser
            20                  25                  30

Gln Lys Ala Trp Gln Ile Ile Arg Asp Gly Glu Met Pro Lys Thr Leu
        35                  40                  45

Ala Cys Thr Ala Arg Pro Ser Ala Asn Ser His Pro Val Gln Val Gly
    50                  55                  60

Arg Ile Ile Leu Glu Asp Tyr His Asp His Gly Leu Leu Arg Val Arg
65                  70                  75                  80

Met Val Asn Leu Gln Val Glu Asp Ser Gly Leu Tyr Gln Cys Val Ile
                85                  90                  95

Tyr Gln Pro Pro Lys Glu Pro His Met Leu Phe Asp Arg Ile Arg Leu
            100                 105                 110

Val Val Thr Lys Gly
        115

<210> SEQ ID NO 204
<211> LENGTH: 117
<212> TYPE: PRT
<213> ORGANISM: Artificial Sequence
<220> FEATURE:
<223> OTHER INFORMATION: Human TREM1 mutant 38_56_57

<400> SEQUENCE: 204

Ala Ala Thr Lys Leu Thr Glu Glu Lys Tyr Glu Leu Lys Glu Gly Gln
1               5                   10                  15

Thr Leu Asp Val Lys Cys Asp Tyr Thr Leu Glu Lys Phe Ala Ser Ser
            20                  25                  30

Gln Lys Ala Trp Gln Ile Ile Arg Asp Gly Glu Met Pro Lys Thr Leu
        35                  40                  45

Ala Cys Thr Glu Arg Pro Ser Lys Ala Ala His Pro Val Gln Val Gly
    50                  55                  60

Arg Ile Ile Leu Glu Asp Tyr His Asp His Gly Leu Leu Arg Val Arg
65                  70                  75                  80

Met Val Asn Leu Gln Val Glu Asp Ser Gly Leu Tyr Gln Cys Val Ile
                85                  90                  95

```
Tyr Gln Pro Pro Lys Glu Pro His Met Leu Phe Asp Arg Ile Arg Leu
            100                 105                 110

Val Val Thr Lys Gly
        115


<210> SEQ ID NO 205
<211> LENGTH: 117
<212> TYPE: PRT
<213> ORGANISM: Artificial Sequence
<220> FEATURE:
<223> OTHER INFORMATION: Human TREM1 mutant  39_58_59

<400> SEQUENCE: 205

Ala Ala Thr Lys Leu Thr Glu Glu Lys Tyr Glu Leu Lys Glu Gly Gln
1               5                   10                  15

Thr Leu Asp Val Lys Cys Asp Tyr Thr Leu Glu Lys Phe Ala Ser Ser
            20                  25                  30

Gln Lys Ala Trp Gln Ile Ile Arg Asp Gly Glu Met Pro Lys Thr Leu
        35                  40                  45

Ala Cys Thr Glu Arg Pro Ser Lys Asn Ser Ala Ala Val Gln Val Gly
    50                  55                  60

Arg Ile Ile Leu Glu Asp Tyr His Asp His Gly Leu Leu Arg Val Arg
65                  70                  75                  80

Met Val Asn Leu Gln Val Glu Asp Ser Gly Leu Tyr Gln Cys Val Ile
                85                  90                  95

Tyr Gln Pro Pro Lys Glu Pro His Met Leu Phe Asp Arg Ile Arg Leu
            100                 105                 110

Val Val Thr Lys Gly
        115


<210> SEQ ID NO 206
<211> LENGTH: 117
<212> TYPE: PRT
<213> ORGANISM: Artificial Sequence
<220> FEATURE:
<223> OTHER INFORMATION: Human TREM1 mutant  40_59_60

<400> SEQUENCE: 206

Ala Ala Thr Lys Leu Thr Glu Glu Lys Tyr Glu Leu Lys Glu Gly Gln
1               5                   10                  15

Thr Leu Asp Val Lys Cys Asp Tyr Thr Leu Glu Lys Phe Ala Ser Ser
            20                  25                  30

Gln Lys Ala Trp Gln Ile Ile Arg Asp Gly Glu Met Pro Lys Thr Leu
        35                  40                  45

Ala Cys Thr Glu Arg Pro Ser Lys Asn Ser His Ala Ala Gln Val Gly
    50                  55                  60

Arg Ile Ile Leu Glu Asp Tyr His Asp His Gly Leu Leu Arg Val Arg
65                  70                  75                  80

Met Val Asn Leu Gln Val Glu Asp Ser Gly Leu Tyr Gln Cys Val Ile
                85                  90                  95

Tyr Gln Pro Pro Lys Glu Pro His Met Leu Phe Asp Arg Ile Arg Leu
            100                 105                 110

Val Val Thr Lys Gly
        115


<210> SEQ ID NO 207
<211> LENGTH: 117
<212> TYPE: PRT
```

<213> ORGANISM: Artificial Sequence
<220> FEATURE:
<223> OTHER INFORMATION: Human TREM1 mutant 41_59_61

<400> SEQUENCE: 207

Ala Ala Thr Lys Leu Thr Glu Glu Lys Tyr Glu Leu Lys Glu Gly Gln
1 5 10 15

Thr Leu Asp Val Lys Cys Asp Tyr Thr Leu Glu Lys Phe Ala Ser Ser
20 25 30

Gln Lys Ala Trp Gln Ile Ile Arg Asp Gly Glu Met Pro Lys Thr Leu
35 40 45

Ala Cys Thr Glu Arg Pro Ser Lys Asn Ser His Ala Val Ala Val Gly
50 55 60

Arg Ile Ile Leu Glu Asp Tyr His Asp His Gly Leu Leu Arg Val Arg
65 70 75 80

Met Val Asn Leu Gln Val Glu Asp Ser Gly Leu Tyr Gln Cys Val Ile
85 90 95

Tyr Gln Pro Pro Lys Glu Pro His Met Leu Phe Asp Arg Ile Arg Leu
100 105 110

Val Val Thr Lys Gly
115

<210> SEQ ID NO 208
<211> LENGTH: 117
<212> TYPE: PRT
<213> ORGANISM: Artificial Sequence
<220> FEATURE:
<223> OTHER INFORMATION: Human TREM1 mutant 42_59_66

<400> SEQUENCE: 208

Ala Ala Thr Lys Leu Thr Glu Glu Lys Tyr Glu Leu Lys Glu Gly Gln
1 5 10 15

Thr Leu Asp Val Lys Cys Asp Tyr Thr Leu Glu Lys Phe Ala Ser Ser
20 25 30

Gln Lys Ala Trp Gln Ile Ile Arg Asp Gly Glu Met Pro Lys Thr Leu
35 40 45

Ala Cys Thr Glu Arg Pro Ser Lys Asn Ser His Ala Val Gln Val Gly
50 55 60

Arg Ile Ala Leu Glu Asp Tyr His Asp His Gly Leu Leu Arg Val Arg
65 70 75 80

Met Val Asn Leu Gln Val Glu Asp Ser Gly Leu Tyr Gln Cys Val Ile
85 90 95

Tyr Gln Pro Pro Lys Glu Pro His Met Leu Phe Asp Arg Ile Arg Leu
100 105 110

Val Val Thr Lys Gly
115

<210> SEQ ID NO 209
<211> LENGTH: 117
<212> TYPE: PRT
<213> ORGANISM: Artificial Sequence
<220> FEATURE:
<223> OTHER INFORMATION: Human TREM1 mutant 43_60_61

<400> SEQUENCE: 209

Ala Ala Thr Lys Leu Thr Glu Glu Lys Tyr Glu Leu Lys Glu Gly Gln
1 5 10 15

Thr Leu Asp Val Lys Cys Asp Tyr Thr Leu Glu Lys Phe Ala Ser Ser
20 25 30

```
Gln Lys Ala Trp Gln Ile Ile Arg Asp Gly Glu Met Pro Lys Thr Leu
        35                  40                  45

Ala Cys Thr Glu Arg Pro Ser Lys Asn Ser His Pro Ala Ala Val Gly
    50                  55                  60

Arg Ile Ile Leu Glu Asp Tyr His Asp His Gly Leu Leu Arg Val Arg
65                  70                  75                  80

Met Val Asn Leu Gln Val Glu Asp Ser Gly Leu Tyr Gln Cys Val Ile
                85                  90                  95

Tyr Gln Pro Pro Lys Glu Pro His Met Leu Phe Asp Arg Ile Arg Leu
            100                 105                 110

Val Val Thr Lys Gly
        115
```

<210> SEQ ID NO 210
<211> LENGTH: 117
<212> TYPE: PRT
<213> ORGANISM: Artificial Sequence
<220> FEATURE:
<223> OTHER INFORMATION: Human TREM1 mutant 44_60_62

<400> SEQUENCE: 210

```
Ala Ala Thr Lys Leu Thr Glu Glu Lys Tyr Glu Leu Lys Glu Gly Gln
1               5                   10                  15

Thr Leu Asp Val Lys Cys Asp Tyr Thr Leu Glu Lys Phe Ala Ser Ser
            20                  25                  30

Gln Lys Ala Trp Gln Ile Ile Arg Asp Gly Glu Met Pro Lys Thr Leu
        35                  40                  45

Ala Cys Thr Glu Arg Pro Ser Lys Asn Ser His Pro Ala Gln Ala Gly
    50                  55                  60

Arg Ile Ile Leu Glu Asp Tyr His Asp His Gly Leu Leu Arg Val Arg
65                  70                  75                  80

Met Val Asn Leu Gln Val Glu Asp Ser Gly Leu Tyr Gln Cys Val Ile
                85                  90                  95

Tyr Gln Pro Pro Lys Glu Pro His Met Leu Phe Asp Arg Ile Arg Leu
            100                 105                 110

Val Val Thr Lys Gly
        115
```

<210> SEQ ID NO 211
<211> LENGTH: 117
<212> TYPE: PRT
<213> ORGANISM: Artificial Sequence
<220> FEATURE:
<223> OTHER INFORMATION: Human TREM1 mutant 45_61_62

<400> SEQUENCE: 211

```
Ala Ala Thr Lys Leu Thr Glu Glu Lys Tyr Glu Leu Lys Glu Gly Gln
1               5                   10                  15

Thr Leu Asp Val Lys Cys Asp Tyr Thr Leu Glu Lys Phe Ala Ser Ser
            20                  25                  30

Gln Lys Ala Trp Gln Ile Ile Arg Asp Gly Glu Met Pro Lys Thr Leu
        35                  40                  45

Ala Cys Thr Glu Arg Pro Ser Lys Asn Ser His Pro Val Ala Ala Gly
    50                  55                  60

Arg Ile Ile Leu Glu Asp Tyr His Asp His Gly Leu Leu Arg Val Arg
65                  70                  75                  80

Met Val Asn Leu Gln Val Glu Asp Ser Gly Leu Tyr Gln Cys Val Ile
```

```
                85                  90                  95

Tyr Gln Pro Pro Lys Glu Pro His Met Leu Phe Asp Arg Ile Arg Leu
            100                 105                 110

Val Val Thr Lys Gly
        115


<210> SEQ ID NO 212
<211> LENGTH: 117
<212> TYPE: PRT
<213> ORGANISM: Artificial Sequence
<220> FEATURE:
<223> OTHER INFORMATION: Human TREM1 mutant  46_61_66

<400> SEQUENCE: 212

Ala Ala Thr Lys Leu Thr Glu Glu Lys Tyr Glu Leu Lys Glu Gly Gln
1               5                   10                  15

Thr Leu Asp Val Lys Cys Asp Tyr Thr Leu Glu Lys Phe Ala Ser Ser
            20                  25                  30

Gln Lys Ala Trp Gln Ile Ile Arg Asp Gly Glu Met Pro Lys Thr Leu
        35                  40                  45

Ala Cys Thr Glu Arg Pro Ser Lys Asn Ser His Pro Val Ala Val Gly
    50                  55                  60

Arg Ile Ala Leu Glu Asp Tyr His Asp His Gly Leu Leu Arg Val Arg
65                  70                  75                  80

Met Val Asn Leu Gln Val Glu Asp Ser Gly Leu Tyr Gln Cys Val Ile
                85                  90                  95

Tyr Gln Pro Pro Lys Glu Pro His Met Leu Phe Asp Arg Ile Arg Leu
            100                 105                 110

Val Val Thr Lys Gly
        115


<210> SEQ ID NO 213
<211> LENGTH: 117
<212> TYPE: PRT
<213> ORGANISM: Artificial Sequence
<220> FEATURE:
<223> OTHER INFORMATION: Human TREM1 mutant  47_62_65

<400> SEQUENCE: 213

Ala Ala Thr Lys Leu Thr Glu Glu Lys Tyr Glu Leu Lys Glu Gly Gln
1               5                   10                  15

Thr Leu Asp Val Lys Cys Asp Tyr Thr Leu Glu Lys Phe Ala Ser Ser
            20                  25                  30

Gln Lys Ala Trp Gln Ile Ile Arg Asp Gly Glu Met Pro Lys Thr Leu
        35                  40                  45

Ala Cys Thr Glu Arg Pro Ser Lys Asn Ser His Pro Val Gln Ala Gly
    50                  55                  60

Arg Ala Ile Leu Glu Asp Tyr His Asp His Gly Leu Leu Arg Val Arg
65                  70                  75                  80

Met Val Asn Leu Gln Val Glu Asp Ser Gly Leu Tyr Gln Cys Val Ile
                85                  90                  95

Tyr Gln Pro Pro Lys Glu Pro His Met Leu Phe Asp Arg Ile Arg Leu
            100                 105                 110

Val Val Thr Lys Gly
        115


<210> SEQ ID NO 214
<211> LENGTH: 117
```

<212> TYPE: PRT
<213> ORGANISM: Artificial Sequence
<220> FEATURE:
<223> OTHER INFORMATION: Human TREM1 mutant 48_65_66

<400> SEQUENCE: 214

```
Ala Ala Thr Lys Leu Thr Glu Glu Lys Tyr Glu Leu Lys Glu Gly Gln
1               5                   10                  15

Thr Leu Asp Val Lys Cys Asp Tyr Thr Leu Glu Lys Phe Ala Ser Ser
            20                  25                  30

Gln Lys Ala Trp Gln Ile Ile Arg Asp Gly Glu Met Pro Lys Thr Leu
        35                  40                  45

Ala Cys Thr Glu Arg Pro Ser Lys Asn Ser His Pro Val Gln Val Gly
    50                  55                  60

Arg Ala Ala Leu Glu Asp Tyr His Asp His Gly Leu Leu Arg Val Arg
65                  70                  75                  80

Met Val Asn Leu Gln Val Glu Asp Ser Gly Leu Tyr Gln Cys Val Ile
                85                  90                  95

Tyr Gln Pro Pro Lys Glu Pro His Met Leu Phe Asp Arg Ile Arg Leu
            100                 105                 110

Val Val Thr Lys Gly
        115
```

<210> SEQ ID NO 215
<211> LENGTH: 117
<212> TYPE: PRT
<213> ORGANISM: Artificial Sequence
<220> FEATURE:
<223> OTHER INFORMATION: Human TREM1 mutant 49_66_81

<400> SEQUENCE: 215

```
Ala Ala Thr Lys Leu Thr Glu Glu Lys Tyr Glu Leu Lys Glu Gly Gln
1               5                   10                  15

Thr Leu Asp Val Lys Cys Asp Tyr Thr Leu Glu Lys Phe Ala Ser Ser
            20                  25                  30

Gln Lys Ala Trp Gln Ile Ile Arg Asp Gly Glu Met Pro Lys Thr Leu
        35                  40                  45

Ala Cys Thr Glu Arg Pro Ser Lys Asn Ser His Pro Val Gln Val Gly
    50                  55                  60

Arg Ile Ala Leu Glu Asp Tyr His Asp His Gly Leu Leu Arg Val Arg
65                  70                  75                  80

Met Ala Asn Leu Gln Val Glu Asp Ser Gly Leu Tyr Gln Cys Val Ile
                85                  90                  95

Tyr Gln Pro Pro Lys Glu Pro His Met Leu Phe Asp Arg Ile Arg Leu
            100                 105                 110

Val Val Thr Lys Gly
        115
```

<210> SEQ ID NO 216
<211> LENGTH: 117
<212> TYPE: PRT
<213> ORGANISM: Artificial Sequence
<220> FEATURE:
<223> OTHER INFORMATION: Human TREM1 mutant 50_72_73

<400> SEQUENCE: 216

```
Ala Ala Thr Lys Leu Thr Glu Glu Lys Tyr Glu Leu Lys Glu Gly Gln
1               5                   10                  15

Thr Leu Asp Val Lys Cys Asp Tyr Thr Leu Glu Lys Phe Ala Ser Ser
```

```
            20                  25                  30

Gln Lys Ala Trp Gln Ile Ile Arg Asp Gly Glu Met Pro Lys Thr Leu
        35                  40                  45

Ala Cys Thr Glu Arg Pro Ser Lys Asn Ser His Pro Val Gln Val Gly
    50                  55                  60

Arg Ile Ile Leu Glu Asp Tyr His Ala Ala Gly Leu Leu Arg Val Arg
65                  70                  75                  80

Met Val Asn Leu Gln Val Glu Asp Ser Gly Leu Tyr Gln Cys Val Ile
                85                  90                  95

Tyr Gln Pro Pro Lys Glu Pro His Met Leu Phe Asp Arg Ile Arg Leu
            100                 105                 110

Val Val Thr Lys Gly
        115


<210> SEQ ID NO 217
<211> LENGTH: 117
<212> TYPE: PRT
<213> ORGANISM: Artificial Sequence
<220> FEATURE:
<223> OTHER INFORMATION: Human TREM1 mutant  51_73_75

<400> SEQUENCE: 217

Ala Ala Thr Lys Leu Thr Glu Glu Lys Tyr Glu Leu Lys Glu Gly Gln
1               5                   10                  15

Thr Leu Asp Val Lys Cys Asp Tyr Thr Leu Glu Lys Phe Ala Ser Ser
            20                  25                  30

Gln Lys Ala Trp Gln Ile Ile Arg Asp Gly Glu Met Pro Lys Thr Leu
        35                  40                  45

Ala Cys Thr Glu Arg Pro Ser Lys Asn Ser His Pro Val Gln Val Gly
    50                  55                  60

Arg Ile Ile Leu Glu Asp Tyr His Asp Ala Gly Ala Leu Arg Val Arg
65                  70                  75                  80

Met Val Asn Leu Gln Val Glu Asp Ser Gly Leu Tyr Gln Cys Val Ile
                85                  90                  95

Tyr Gln Pro Pro Lys Glu Pro His Met Leu Phe Asp Arg Ile Arg Leu
            100                 105                 110

Val Val Thr Lys Gly
        115


<210> SEQ ID NO 218
<211> LENGTH: 117
<212> TYPE: PRT
<213> ORGANISM: Artificial Sequence
<220> FEATURE:
<223> OTHER INFORMATION: Human TREM1 mutant  52_81_82

<400> SEQUENCE: 218

Ala Ala Thr Lys Leu Thr Glu Glu Lys Tyr Glu Leu Lys Glu Gly Gln
1               5                   10                  15

Thr Leu Asp Val Lys Cys Asp Tyr Thr Leu Glu Lys Phe Ala Ser Ser
            20                  25                  30

Gln Lys Ala Trp Gln Ile Ile Arg Asp Gly Glu Met Pro Lys Thr Leu
        35                  40                  45

Ala Cys Thr Glu Arg Pro Ser Lys Asn Ser His Pro Val Gln Val Gly
    50                  55                  60

Arg Ile Ile Leu Glu Asp Tyr His Asp His Gly Leu Leu Arg Val Arg
65                  70                  75                  80
```

```
Met Ala Ala Leu Gln Val Glu Asp Ser Gly Leu Tyr Gln Cys Val Ile
                85                  90                  95

Tyr Gln Pro Pro Lys Glu Pro His Met Leu Phe Asp Arg Ile Arg Leu
            100                 105                 110

Val Val Thr Lys Gly
        115


<210> SEQ ID NO 219
<211> LENGTH: 117
<212> TYPE: PRT
<213> ORGANISM: Artificial Sequence
<220> FEATURE:
<223> OTHER INFORMATION: Human TREM1 mutant  53_85_86

<400> SEQUENCE: 219

Ala Ala Thr Lys Leu Thr Glu Glu Lys Tyr Glu Leu Lys Glu Gly Gln
1               5                   10                  15

Thr Leu Asp Val Lys Cys Asp Tyr Thr Leu Glu Lys Phe Ala Ser Ser
            20                  25                  30

Gln Lys Ala Trp Gln Ile Ile Arg Asp Gly Glu Met Pro Lys Thr Leu
        35                  40                  45

Ala Cys Thr Glu Arg Pro Ser Lys Asn Ser His Pro Val Gln Val Gly
    50                  55                  60

Arg Ile Ile Leu Glu Asp Tyr His Asp His Gly Leu Leu Arg Val Arg
65                  70                  75                  80

Met Val Asn Leu Gln Ala Ala Asp Ser Gly Leu Tyr Gln Cys Val Ile
                85                  90                  95

Tyr Gln Pro Pro Lys Glu Pro His Met Leu Phe Asp Arg Ile Arg Leu
            100                 105                 110

Val Val Thr Lys Gly
        115


<210> SEQ ID NO 220
<211> LENGTH: 117
<212> TYPE: PRT
<213> ORGANISM: Artificial Sequence
<220> FEATURE:
<223> OTHER INFORMATION: Human TREM1 mutant  54_98_99

<400> SEQUENCE: 220

Ala Ala Thr Lys Leu Thr Glu Glu Lys Tyr Glu Leu Lys Glu Gly Gln
1               5                   10                  15

Thr Leu Asp Val Lys Cys Asp Tyr Thr Leu Glu Lys Phe Ala Ser Ser
            20                  25                  30

Gln Lys Ala Trp Gln Ile Ile Arg Asp Gly Glu Met Pro Lys Thr Leu
        35                  40                  45

Ala Cys Thr Glu Arg Pro Ser Lys Asn Ser His Pro Val Gln Val Gly
    50                  55                  60

Arg Ile Ile Leu Glu Asp Tyr His Asp His Gly Leu Leu Arg Val Arg
65                  70                  75                  80

Met Val Asn Leu Gln Val Glu Asp Ser Gly Leu Tyr Gln Cys Val Ile
                85                  90                  95

Tyr Gln Ala Ala Lys Glu Pro His Met Leu Phe Asp Arg Ile Arg Leu
            100                 105                 110

Val Val Thr Lys Gly
        115


<210> SEQ ID NO 221
```

<211> LENGTH: 117
<212> TYPE: PRT
<213> ORGANISM: Artificial Sequence
<220> FEATURE:
<223> OTHER INFORMATION: Human TREM1 mutant 55_99_100

<400> SEQUENCE: 221

Ala Ala Thr Lys Leu Thr Glu Glu Lys Tyr Glu Leu Lys Glu Gly Gln
1 5 10 15

Thr Leu Asp Val Lys Cys Asp Tyr Thr Leu Glu Lys Phe Ala Ser Ser
20 25 30

Gln Lys Ala Trp Gln Ile Ile Arg Asp Gly Glu Met Pro Lys Thr Leu
35 40 45

Ala Cys Thr Glu Arg Pro Ser Lys Asn Ser His Pro Val Gln Val Gly
50 55 60

Arg Ile Ile Leu Glu Asp Tyr His Asp His Gly Leu Leu Arg Val Arg
65 70 75 80

Met Val Asn Leu Gln Val Glu Asp Ser Gly Leu Tyr Gln Cys Val Ile
85 90 95

Tyr Gln Pro Ala Ala Glu Pro His Met Leu Phe Asp Arg Ile Arg Leu
100 105 110

Val Val Thr Lys Gly
115

<210> SEQ ID NO 222
<211> LENGTH: 117
<212> TYPE: PRT
<213> ORGANISM: Artificial Sequence
<220> FEATURE:
<223> OTHER INFORMATION: Human TREM1 mutant 56_100_101

<400> SEQUENCE: 222

Ala Ala Thr Lys Leu Thr Glu Glu Lys Tyr Glu Leu Lys Glu Gly Gln
1 5 10 15

Thr Leu Asp Val Lys Cys Asp Tyr Thr Leu Glu Lys Phe Ala Ser Ser
20 25 30

Gln Lys Ala Trp Gln Ile Ile Arg Asp Gly Glu Met Pro Lys Thr Leu
35 40 45

Ala Cys Thr Glu Arg Pro Ser Lys Asn Ser His Pro Val Gln Val Gly
50 55 60

Arg Ile Ile Leu Glu Asp Tyr His Asp His Gly Leu Leu Arg Val Arg
65 70 75 80

Met Val Asn Leu Gln Val Glu Asp Ser Gly Leu Tyr Gln Cys Val Ile
85 90 95

Tyr Gln Pro Pro Ala Ala Pro His Met Leu Phe Asp Arg Ile Arg Leu
100 105 110

Val Val Thr Lys Gly
115

<210> SEQ ID NO 223
<211> LENGTH: 117
<212> TYPE: PRT
<213> ORGANISM: Artificial Sequence
<220> FEATURE:
<223> OTHER INFORMATION: Human TREM1 mutant 57_101_102

<400> SEQUENCE: 223

Ala Ala Thr Lys Leu Thr Glu Glu Lys Tyr Glu Leu Lys Glu Gly Gln
1 5 10 15

```
Thr Leu Asp Val Lys Cys Asp Tyr Thr Leu Glu Lys Phe Ala Ser Ser
            20                  25                  30

Gln Lys Ala Trp Gln Ile Ile Arg Asp Gly Glu Met Pro Lys Thr Leu
        35                  40                  45

Ala Cys Thr Glu Arg Pro Ser Lys Asn Ser His Pro Val Gln Val Gly
    50                  55                  60

Arg Ile Ile Leu Glu Asp Tyr His Asp His Gly Leu Leu Arg Val Arg
65                  70                  75                  80

Met Val Asn Leu Gln Val Glu Asp Ser Gly Leu Tyr Gln Cys Val Ile
                85                  90                  95

Tyr Gln Pro Pro Lys Ala Ala His Met Leu Phe Asp Arg Ile Arg Leu
            100                 105                 110

Val Val Thr Lys Gly
        115


<210> SEQ ID NO 224
<211> LENGTH: 117
<212> TYPE: PRT
<213> ORGANISM: Artificial Sequence
<220> FEATURE:
<223> OTHER INFORMATION: Human TREM1 mutant  58_102_103

<400> SEQUENCE: 224

Ala Ala Thr Lys Leu Thr Glu Glu Lys Tyr Glu Leu Lys Glu Gly Gln
1               5                   10                  15

Thr Leu Asp Val Lys Cys Asp Tyr Thr Leu Glu Lys Phe Ala Ser Ser
            20                  25                  30

Gln Lys Ala Trp Gln Ile Ile Arg Asp Gly Glu Met Pro Lys Thr Leu
        35                  40                  45

Ala Cys Thr Glu Arg Pro Ser Lys Asn Ser His Pro Val Gln Val Gly
    50                  55                  60

Arg Ile Ile Leu Glu Asp Tyr His Asp His Gly Leu Leu Arg Val Arg
65                  70                  75                  80

Met Val Asn Leu Gln Val Glu Asp Ser Gly Leu Tyr Gln Cys Val Ile
                85                  90                  95

Tyr Gln Pro Pro Lys Glu Ala Ala Met Leu Phe Asp Arg Ile Arg Leu
            100                 105                 110

Val Val Thr Lys Gly
        115


<210> SEQ ID NO 225
<211> LENGTH: 117
<212> TYPE: PRT
<213> ORGANISM: Artificial Sequence
<220> FEATURE:
<223> OTHER INFORMATION: Human TREM1 mutant  59_103_104

<400> SEQUENCE: 225

Ala Ala Thr Lys Leu Thr Glu Glu Lys Tyr Glu Leu Lys Glu Gly Gln
1               5                   10                  15

Thr Leu Asp Val Lys Cys Asp Tyr Thr Leu Glu Lys Phe Ala Ser Ser
            20                  25                  30

Gln Lys Ala Trp Gln Ile Ile Arg Asp Gly Glu Met Pro Lys Thr Leu
        35                  40                  45

Ala Cys Thr Glu Arg Pro Ser Lys Asn Ser His Pro Val Gln Val Gly
    50                  55                  60

Arg Ile Ile Leu Glu Asp Tyr His Asp His Gly Leu Leu Arg Val Arg
65                  70                  75                  80
```

Met Val Asn Leu Gln Val Glu Asp Ser Gly Leu Tyr Gln Cys Val Ile
85 90 95

Tyr Gln Pro Pro Lys Glu Pro Ala Ala Leu Phe Asp Arg Ile Arg Leu
100 105 110

Val Val Thr Lys Gly
115

<210> SEQ ID NO 226
<211> LENGTH: 117
<212> TYPE: PRT
<213> ORGANISM: Artificial Sequence
<220> FEATURE:
<223> OTHER INFORMATION: Human TREM1 mutant 60_104_106

<400> SEQUENCE: 226

Ala Ala Thr Lys Leu Thr Glu Glu Lys Tyr Glu Leu Lys Glu Gly Gln
1 5 10 15

Thr Leu Asp Val Lys Cys Asp Tyr Thr Leu Glu Lys Phe Ala Ser Ser
20 25 30

Gln Lys Ala Trp Gln Ile Ile Arg Asp Gly Glu Met Pro Lys Thr Leu
35 40 45

Ala Cys Thr Glu Arg Pro Ser Lys Asn Ser His Pro Val Gln Val Gly
50 55 60

Arg Ile Ile Leu Glu Asp Tyr His Asp His Gly Leu Leu Arg Val Arg
65 70 75 80

Met Val Asn Leu Gln Val Glu Asp Ser Gly Leu Tyr Gln Cys Val Ile
85 90 95

Tyr Gln Pro Pro Lys Glu Pro His Ala Leu Ala Asp Arg Ile Arg Leu
100 105 110

Val Val Thr Lys Gly
115

<210> SEQ ID NO 227
<211> LENGTH: 117
<212> TYPE: PRT
<213> ORGANISM: Artificial Sequence
<220> FEATURE:
<223> OTHER INFORMATION: Human TREM1 mutant 61_106_107

<400> SEQUENCE: 227

Ala Ala Thr Lys Leu Thr Glu Glu Lys Tyr Glu Leu Lys Glu Gly Gln
1 5 10 15

Thr Leu Asp Val Lys Cys Asp Tyr Thr Leu Glu Lys Phe Ala Ser Ser
20 25 30

Gln Lys Ala Trp Gln Ile Ile Arg Asp Gly Glu Met Pro Lys Thr Leu
35 40 45

Ala Cys Thr Glu Arg Pro Ser Lys Asn Ser His Pro Val Gln Val Gly
50 55 60

Arg Ile Ile Leu Glu Asp Tyr His Asp His Gly Leu Leu Arg Val Arg
65 70 75 80

Met Val Asn Leu Gln Val Glu Asp Ser Gly Leu Tyr Gln Cys Val Ile
85 90 95

Tyr Gln Pro Pro Lys Glu Pro His Met Leu Ala Ala Arg Ile Arg Leu
100 105 110

Val Val Thr Lys Gly
115

<210> SEQ ID NO 228
<211> LENGTH: 117
<212> TYPE: PRT
<213> ORGANISM: Artificial Sequence
<220> FEATURE:
<223> OTHER INFORMATION: Human TREM1 mutant 62_8_10_112

<400> SEQUENCE: 228

```
Ala Ala Thr Lys Leu Thr Glu Glu Ala Tyr Ala Leu Lys Glu Gly Gln
1               5                   10                  15

Thr Leu Asp Val Lys Cys Asp Tyr Thr Leu Glu Lys Phe Ala Ser Ser
            20                  25                  30

Gln Lys Ala Trp Gln Ile Ile Arg Asp Gly Glu Met Pro Lys Thr Leu
        35                  40                  45

Ala Cys Thr Glu Arg Pro Ser Lys Asn Ser His Pro Val Gln Val Gly
    50                  55                  60

Arg Ile Ile Leu Glu Asp Tyr His Asp His Gly Leu Leu Arg Val Arg
65                  70                  75                  80

Met Val Asn Leu Gln Val Glu Asp Ser Gly Leu Tyr Gln Cys Val Ile
                85                  90                  95

Tyr Gln Pro Pro Lys Glu Pro His Met Leu Phe Asp Arg Ile Arg Leu
            100                 105                 110

Ala Val Thr Lys Gly
        115
```

<210> SEQ ID NO 229
<211> LENGTH: 117
<212> TYPE: PRT
<213> ORGANISM: Artificial Sequence
<220> FEATURE:
<223> OTHER INFORMATION: Human TREM1 mutant 63_37_39_40

<400> SEQUENCE: 229

```
Ala Ala Thr Lys Leu Thr Glu Glu Lys Tyr Glu Leu Lys Glu Gly Gln
1               5                   10                  15

Thr Leu Asp Val Lys Cys Asp Tyr Thr Leu Glu Lys Phe Ala Ser Ser
            20                  25                  30

Gln Lys Ala Trp Gln Ala Ile Ala Ala Gly Glu Met Pro Lys Thr Leu
        35                  40                  45

Ala Cys Thr Glu Arg Pro Ser Lys Asn Ser His Pro Val Gln Val Gly
    50                  55                  60

Arg Ile Ile Leu Glu Asp Tyr His Asp His Gly Leu Leu Arg Val Arg
65                  70                  75                  80

Met Val Asn Leu Gln Val Glu Asp Ser Gly Leu Tyr Gln Cys Val Ile
                85                  90                  95

Tyr Gln Pro Pro Lys Glu Pro His Met Leu Phe Asp Arg Ile Arg Leu
            100                 105                 110

Val Val Thr Lys Gly
        115
```

<210> SEQ ID NO 230
<211> LENGTH: 117
<212> TYPE: PRT
<213> ORGANISM: Artificial Sequence
<220> FEATURE:
<223> OTHER INFORMATION: Human TREM1 mutant 64_40

<400> SEQUENCE: 230

```
Ala Ala Thr Lys Leu Thr Glu Glu Lys Tyr Glu Leu Lys Glu Gly Gln
1               5                   10                  15
```

```
Thr Leu Asp Val Lys Cys Asp Tyr Thr Leu Glu Lys Phe Ala Ser Ser
            20                  25                  30

Gln Lys Ala Trp Gln Ile Ile Arg Ala Gly Glu Met Pro Lys Thr Leu
        35                  40                  45

Ala Cys Thr Glu Arg Pro Ser Lys Asn Ser His Pro Val Gln Val Gly
    50                  55                  60

Arg Ile Ile Leu Glu Asp Tyr His Asp His Gly Leu Leu Arg Val Arg
65                  70                  75                  80

Met Val Asn Leu Gln Val Glu Asp Ser Gly Leu Tyr Gln Cys Val Ile
                85                  90                  95

Tyr Gln Pro Pro Lys Glu Pro His Met Leu Phe Asp Arg Ile Arg Leu
            100                 105                 110

Val Val Thr Lys Gly
        115


<210> SEQ ID NO 231
<211> LENGTH: 117
<212> TYPE: PRT
<213> ORGANISM: Artificial Sequence
<220> FEATURE:
<223> OTHER INFORMATION: Human TREM1 mutant  65_112

<400> SEQUENCE: 231

Ala Ala Thr Lys Leu Thr Glu Glu Lys Tyr Glu Leu Lys Glu Gly Gln
1               5                   10                  15

Thr Leu Asp Val Lys Cys Asp Tyr Thr Leu Glu Lys Phe Ala Ser Ser
            20                  25                  30

Gln Lys Ala Trp Gln Ile Ile Arg Asp Gly Glu Met Pro Lys Thr Leu
        35                  40                  45

Ala Cys Thr Glu Arg Pro Ser Lys Asn Ser His Pro Val Gln Val Gly
    50                  55                  60

Arg Ile Ile Leu Glu Asp Tyr His Asp His Gly Leu Leu Arg Val Arg
65                  70                  75                  80

Met Val Asn Leu Gln Val Glu Asp Ser Gly Leu Tyr Gln Cys Val Ile
                85                  90                  95

Tyr Gln Pro Pro Lys Glu Pro His Met Leu Phe Asp Arg Ile Arg Leu
            100                 105                 110

Ala Val Thr Lys Gly
        115


<210> SEQ ID NO 232
<211> LENGTH: 116
<212> TYPE: PRT
<213> ORGANISM: Artificial Sequence
<220> FEATURE:
<223> OTHER INFORMATION: Human TREM1 WT 01_WT_1A

<400> SEQUENCE: 232

Ala Thr Lys Leu Thr Glu Glu Lys Tyr Glu Leu Lys Glu Gly Gln Thr
1               5                   10                  15

Leu Asp Val Lys Cys Asp Tyr Thr Leu Glu Lys Phe Ala Ser Ser Gln
            20                  25                  30

Lys Ala Trp Gln Ile Ile Arg Asp Gly Glu Met Pro Lys Thr Leu Ala
        35                  40                  45

Cys Thr Glu Arg Pro Ser Lys Asn Ser His Pro Val Gln Val Gly Arg
    50                  55                  60

Ile Ile Leu Glu Asp Tyr His Asp His Gly Leu Leu Arg Val Arg Met
```

```
65                  70                  75                  80

Val Asn Leu Gln Val Glu Asp Ser Gly Leu Tyr Gln Cys Val Ile Tyr
                85                  90                  95

Gln Pro Pro Lys Glu Pro His Met Leu Phe Asp Arg Ile Arg Leu Val
            100                 105                 110

Val Thr Leu Glu
        115


<210> SEQ ID NO 233
<211> LENGTH: 116
<212> TYPE: PRT
<213> ORGANISM: Artificial Sequence
<220> FEATURE:
<223> OTHER INFORMATION: Human TREM1 mutant  02_1

<400> SEQUENCE: 233

Ala Ala Lys Leu Thr Glu Glu Lys Tyr Glu Leu Lys Glu Gly Gln Thr
1               5                   10                  15

Leu Asp Val Lys Cys Asp Tyr Thr Leu Glu Lys Phe Ala Ser Ser Gln
            20                  25                  30

Lys Ala Trp Gln Ile Ile Arg Asp Gly Glu Met Pro Lys Thr Leu Ala
        35                  40                  45

Cys Thr Glu Arg Pro Ser Lys Asn Ser His Pro Val Gln Val Gly Arg
    50                  55                  60

Ile Ile Leu Glu Asp Tyr His Asp His Gly Leu Leu Arg Val Arg Met
65                  70                  75                  80

Val Asn Leu Gln Val Glu Asp Ser Gly Leu Tyr Gln Cys Val Ile Tyr
                85                  90                  95

Gln Pro Pro Lys Glu Pro His Met Leu Phe Asp Arg Ile Arg Leu Val
            100                 105                 110

Val Thr Leu Glu
        115


<210> SEQ ID NO 234
<211> LENGTH: 116
<212> TYPE: PRT
<213> ORGANISM: Artificial Sequence
<220> FEATURE:
<223> OTHER INFORMATION: Human TREM1 mutant  03_2

<400> SEQUENCE: 234

Ala Thr Ala Leu Thr Glu Glu Lys Tyr Glu Leu Lys Glu Gly Gln Thr
1               5                   10                  15

Leu Asp Val Lys Cys Asp Tyr Thr Leu Glu Lys Phe Ala Ser Ser Gln
            20                  25                  30

Lys Ala Trp Gln Ile Ile Arg Asp Gly Glu Met Pro Lys Thr Leu Ala
        35                  40                  45

Cys Thr Glu Arg Pro Ser Lys Asn Ser His Pro Val Gln Val Gly Arg
    50                  55                  60

Ile Ile Leu Glu Asp Tyr His Asp His Gly Leu Leu Arg Val Arg Met
65                  70                  75                  80

Val Asn Leu Gln Val Glu Asp Ser Gly Leu Tyr Gln Cys Val Ile Tyr
                85                  90                  95

Gln Pro Pro Lys Glu Pro His Met Leu Phe Asp Arg Ile Arg Leu Val
            100                 105                 110

Val Thr Leu Glu
        115
```

<210> SEQ ID NO 235
<211> LENGTH: 116
<212> TYPE: PRT
<213> ORGANISM: Artificial Sequence
<220> FEATURE:
<223> OTHER INFORMATION: Human TREM1 mutant 04_4

<400> SEQUENCE: 235

```
Ala Thr Lys Leu Ala Glu Glu Lys Tyr Glu Leu Lys Glu Gly Gln Thr
1               5                   10                  15

Leu Asp Val Lys Cys Asp Tyr Thr Leu Glu Lys Phe Ala Ser Ser Gln
            20                  25                  30

Lys Ala Trp Gln Ile Ile Arg Asp Gly Glu Met Pro Lys Thr Leu Ala
        35                  40                  45

Cys Thr Glu Arg Pro Ser Lys Asn Ser His Pro Val Gln Val Gly Arg
    50                  55                  60

Ile Ile Leu Glu Asp Tyr His Asp His Gly Leu Leu Arg Val Arg Met
65                  70                  75                  80

Val Asn Leu Gln Val Glu Asp Ser Gly Leu Tyr Gln Cys Val Ile Tyr
                85                  90                  95

Gln Pro Pro Lys Glu Pro His Met Leu Phe Asp Arg Ile Arg Leu Val
            100                 105                 110

Val Thr Leu Glu
        115
```

<210> SEQ ID NO 236
<211> LENGTH: 116
<212> TYPE: PRT
<213> ORGANISM: Artificial Sequence
<220> FEATURE:
<223> OTHER INFORMATION: Human TREM1 mutant 05_5

<400> SEQUENCE: 236

```
Ala Thr Lys Leu Thr Ala Glu Lys Tyr Glu Leu Lys Glu Gly Gln Thr
1               5                   10                  15

Leu Asp Val Lys Cys Asp Tyr Thr Leu Glu Lys Phe Ala Ser Ser Gln
            20                  25                  30

Lys Ala Trp Gln Ile Ile Arg Asp Gly Glu Met Pro Lys Thr Leu Ala
        35                  40                  45

Cys Thr Glu Arg Pro Ser Lys Asn Ser His Pro Val Gln Val Gly Arg
    50                  55                  60

Ile Ile Leu Glu Asp Tyr His Asp His Gly Leu Leu Arg Val Arg Met
65                  70                  75                  80

Val Asn Leu Gln Val Glu Asp Ser Gly Leu Tyr Gln Cys Val Ile Tyr
                85                  90                  95

Gln Pro Pro Lys Glu Pro His Met Leu Phe Asp Arg Ile Arg Leu Val
            100                 105                 110

Val Thr Leu Glu
        115
```

<210> SEQ ID NO 237
<211> LENGTH: 116
<212> TYPE: PRT
<213> ORGANISM: Artificial Sequence
<220> FEATURE:
<223> OTHER INFORMATION: Human TREM1 mutant 06_6

<400> SEQUENCE: 237

```
Ala Thr Lys Leu Thr Glu Ala Lys Tyr Glu Leu Lys Glu Gly Gln Thr
```

```
1               5                   10                  15

Leu Asp Val Lys Cys Asp Tyr Thr Leu Glu Lys Phe Ala Ser Ser Gln
            20                  25                  30

Lys Ala Trp Gln Ile Ile Arg Asp Gly Glu Met Pro Lys Thr Leu Ala
        35                  40                  45

Cys Thr Glu Arg Pro Ser Lys Asn Ser His Pro Val Gln Val Gly Arg
    50                  55                  60

Ile Ile Leu Glu Asp Tyr His Asp His Gly Leu Leu Arg Val Arg Met
65                  70                  75                  80

Val Asn Leu Gln Val Glu Asp Ser Gly Leu Tyr Gln Cys Val Ile Tyr
                85                  90                  95

Gln Pro Pro Lys Glu Pro His Met Leu Phe Asp Arg Ile Arg Leu Val
            100                 105                 110

Val Thr Leu Glu
        115


<210> SEQ ID NO 238
<211> LENGTH: 116
<212> TYPE: PRT
<213> ORGANISM: Artificial Sequence
<220> FEATURE:
<223> OTHER INFORMATION: Human TREM1 mutant  07_7

<400> SEQUENCE: 238

Ala Thr Lys Leu Thr Glu Glu Ala Tyr Glu Leu Lys Glu Gly Gln Thr
1               5                   10                  15

Leu Asp Val Lys Cys Asp Tyr Thr Leu Glu Lys Phe Ala Ser Ser Gln
            20                  25                  30

Lys Ala Trp Gln Ile Ile Arg Asp Gly Glu Met Pro Lys Thr Leu Ala
        35                  40                  45

Cys Thr Glu Arg Pro Ser Lys Asn Ser His Pro Val Gln Val Gly Arg
    50                  55                  60

Ile Ile Leu Glu Asp Tyr His Asp His Gly Leu Leu Arg Val Arg Met
65                  70                  75                  80

Val Asn Leu Gln Val Glu Asp Ser Gly Leu Tyr Gln Cys Val Ile Tyr
                85                  90                  95

Gln Pro Pro Lys Glu Pro His Met Leu Phe Asp Arg Ile Arg Leu Val
            100                 105                 110

Val Thr Leu Glu
        115


<210> SEQ ID NO 239
<211> LENGTH: 116
<212> TYPE: PRT
<213> ORGANISM: Artificial Sequence
<220> FEATURE:
<223> OTHER INFORMATION: Human TREM1 mutant  08_8

<400> SEQUENCE: 239

Ala Thr Lys Leu Thr Glu Glu Lys Ala Glu Leu Lys Glu Gly Gln Thr
1               5                   10                  15

Leu Asp Val Lys Cys Asp Tyr Thr Leu Glu Lys Phe Ala Ser Ser Gln
            20                  25                  30

Lys Ala Trp Gln Ile Ile Arg Asp Gly Glu Met Pro Lys Thr Leu Ala
        35                  40                  45

Cys Thr Glu Arg Pro Ser Lys Asn Ser His Pro Val Gln Val Gly Arg
    50                  55                  60
```

```
Ile Ile Leu Glu Asp Tyr His Asp His Gly Leu Leu Arg Val Arg Met
65                  70                  75                  80

Val Asn Leu Gln Val Glu Asp Ser Gly Leu Tyr Gln Cys Val Ile Tyr
                85                  90                  95

Gln Pro Pro Lys Glu Pro His Met Leu Phe Asp Arg Ile Arg Leu Val
            100                 105                 110

Val Thr Leu Glu
        115


<210> SEQ ID NO 240
<211> LENGTH: 116
<212> TYPE: PRT
<213> ORGANISM: Artificial Sequence
<220> FEATURE:
<223> OTHER INFORMATION: Human TREM1 mutant  09_9

<400> SEQUENCE: 240

Ala Thr Lys Leu Thr Glu Glu Lys Tyr Ala Leu Lys Glu Gly Gln Thr
1               5                   10                  15

Leu Asp Val Lys Cys Asp Tyr Thr Leu Glu Lys Phe Ala Ser Ser Gln
            20                  25                  30

Lys Ala Trp Gln Ile Ile Arg Asp Gly Glu Met Pro Lys Thr Leu Ala
        35                  40                  45

Cys Thr Glu Arg Pro Ser Lys Asn Ser His Pro Val Gln Val Gly Arg
    50                  55                  60

Ile Ile Leu Glu Asp Tyr His Asp His Gly Leu Leu Arg Val Arg Met
65                  70                  75                  80

Val Asn Leu Gln Val Glu Asp Ser Gly Leu Tyr Gln Cys Val Ile Tyr
                85                  90                  95

Gln Pro Pro Lys Glu Pro His Met Leu Phe Asp Arg Ile Arg Leu Val
            100                 105                 110

Val Thr Leu Glu
        115


<210> SEQ ID NO 241
<211> LENGTH: 116
<212> TYPE: PRT
<213> ORGANISM: Artificial Sequence
<220> FEATURE:
<223> OTHER INFORMATION: Human TREM1 mutant  10_11

<400> SEQUENCE: 241

Ala Thr Lys Leu Thr Glu Glu Lys Tyr Glu Leu Ala Glu Gly Gln Thr
1               5                   10                  15

Leu Asp Val Lys Cys Asp Tyr Thr Leu Glu Lys Phe Ala Ser Ser Gln
            20                  25                  30

Lys Ala Trp Gln Ile Ile Arg Asp Gly Glu Met Pro Lys Thr Leu Ala
        35                  40                  45

Cys Thr Glu Arg Pro Ser Lys Asn Ser His Pro Val Gln Val Gly Arg
    50                  55                  60

Ile Ile Leu Glu Asp Tyr His Asp His Gly Leu Leu Arg Val Arg Met
65                  70                  75                  80

Val Asn Leu Gln Val Glu Asp Ser Gly Leu Tyr Gln Cys Val Ile Tyr
                85                  90                  95

Gln Pro Pro Lys Glu Pro His Met Leu Phe Asp Arg Ile Arg Leu Val
            100                 105                 110

Val Thr Leu Glu
        115
```

<210> SEQ ID NO 242
<211> LENGTH: 116
<212> TYPE: PRT
<213> ORGANISM: Artificial Sequence
<220> FEATURE:
<223> OTHER INFORMATION: Human TREM1 mutant 11_14

<400> SEQUENCE: 242

```
Ala Thr Lys Leu Thr Glu Glu Lys Tyr Glu Leu Lys Glu Gly Ala Thr
1               5                   10                  15

Leu Asp Val Lys Cys Asp Tyr Thr Leu Glu Lys Phe Ala Ser Ser Gln
            20                  25                  30

Lys Ala Trp Gln Ile Ile Arg Asp Gly Glu Met Pro Lys Thr Leu Ala
        35                  40                  45

Cys Thr Glu Arg Pro Ser Lys Asn Ser His Pro Val Gln Val Gly Arg
    50                  55                  60

Ile Ile Leu Glu Asp Tyr His Asp His Gly Leu Leu Arg Val Arg Met
65                  70                  75                  80

Val Asn Leu Gln Val Glu Asp Ser Gly Leu Tyr Gln Cys Val Ile Tyr
                85                  90                  95

Gln Pro Pro Lys Glu Pro His Met Leu Phe Asp Arg Ile Arg Leu Val
            100                 105                 110

Val Thr Leu Glu
        115
```

<210> SEQ ID NO 243
<211> LENGTH: 116
<212> TYPE: PRT
<213> ORGANISM: Artificial Sequence
<220> FEATURE:
<223> OTHER INFORMATION: Human TREM1 mutant 12_17

<400> SEQUENCE: 243

```
Ala Thr Lys Leu Thr Glu Glu Lys Tyr Glu Leu Lys Glu Gly Gln Thr
1               5                   10                  15

Leu Ala Val Lys Cys Asp Tyr Thr Leu Glu Lys Phe Ala Ser Ser Gln
            20                  25                  30

Lys Ala Trp Gln Ile Ile Arg Asp Gly Glu Met Pro Lys Thr Leu Ala
        35                  40                  45

Cys Thr Glu Arg Pro Ser Lys Asn Ser His Pro Val Gln Val Gly Arg
    50                  55                  60

Ile Ile Leu Glu Asp Tyr His Asp His Gly Leu Leu Arg Val Arg Met
65                  70                  75                  80

Val Asn Leu Gln Val Glu Asp Ser Gly Leu Tyr Gln Cys Val Ile Tyr
                85                  90                  95

Gln Pro Pro Lys Glu Pro His Met Leu Phe Asp Arg Ile Arg Leu Val
            100                 105                 110

Val Thr Leu Glu
        115
```

<210> SEQ ID NO 244
<211> LENGTH: 116
<212> TYPE: PRT
<213> ORGANISM: Artificial Sequence
<220> FEATURE:
<223> OTHER INFORMATION: Human TREM1 mutant 13_19

<400> SEQUENCE: 244

```
Ala Thr Lys Leu Thr Glu Glu Lys Tyr Glu Leu Lys Glu Gly Gln Thr
1               5                   10                  15

Leu Asp Val Ala Cys Asp Tyr Thr Leu Glu Lys Phe Ala Ser Ser Gln
            20                  25                  30

Lys Ala Trp Gln Ile Ile Arg Asp Gly Glu Met Pro Lys Thr Leu Ala
        35                  40                  45

Cys Thr Glu Arg Pro Ser Lys Asn Ser His Pro Val Gln Val Gly Arg
    50                  55                  60

Ile Ile Leu Glu Asp Tyr His Asp His Gly Leu Leu Arg Val Arg Met
65                  70                  75                  80

Val Asn Leu Gln Val Glu Asp Ser Gly Leu Tyr Gln Cys Val Ile Tyr
                85                  90                  95

Gln Pro Pro Lys Glu Pro His Met Leu Phe Asp Arg Ile Arg Leu Val
            100                 105                 110

Val Thr Leu Glu
        115


<210> SEQ ID NO 245
<211> LENGTH: 116
<212> TYPE: PRT
<213> ORGANISM: Artificial Sequence
<220> FEATURE:
<223> OTHER INFORMATION: Human TREM1 mutant  14_21

<400> SEQUENCE: 245

Ala Thr Lys Leu Thr Glu Glu Lys Tyr Glu Leu Lys Glu Gly Gln Thr
1               5                   10                  15

Leu Asp Val Lys Cys Ala Tyr Thr Leu Glu Lys Phe Ala Ser Ser Gln
            20                  25                  30

Lys Ala Trp Gln Ile Ile Arg Asp Gly Glu Met Pro Lys Thr Leu Ala
        35                  40                  45

Cys Thr Glu Arg Pro Ser Lys Asn Ser His Pro Val Gln Val Gly Arg
    50                  55                  60

Ile Ile Leu Glu Asp Tyr His Asp His Gly Leu Leu Arg Val Arg Met
65                  70                  75                  80

Val Asn Leu Gln Val Glu Asp Ser Gly Leu Tyr Gln Cys Val Ile Tyr
                85                  90                  95

Gln Pro Pro Lys Glu Pro His Met Leu Phe Asp Arg Ile Arg Leu Val
            100                 105                 110

Val Thr Leu Glu
        115


<210> SEQ ID NO 246
<211> LENGTH: 116
<212> TYPE: PRT
<213> ORGANISM: Artificial Sequence
<220> FEATURE:
<223> OTHER INFORMATION: Human TREM1 mutant  15_23

<400> SEQUENCE: 246

Ala Thr Lys Leu Thr Glu Glu Lys Tyr Glu Leu Lys Glu Gly Gln Thr
1               5                   10                  15

Leu Asp Val Lys Cys Asp Tyr Ala Leu Glu Lys Phe Ala Ser Ser Gln
            20                  25                  30

Lys Ala Trp Gln Ile Ile Arg Asp Gly Glu Met Pro Lys Thr Leu Ala
        35                  40                  45

Cys Thr Glu Arg Pro Ser Lys Asn Ser His Pro Val Gln Val Gly Arg
    50                  55                  60
```

```
Ile Ile Leu Glu Asp Tyr His Asp His Gly Leu Leu Arg Val Arg Met
65                  70                  75                  80

Val Asn Leu Gln Val Glu Asp Ser Gly Leu Tyr Gln Cys Val Ile Tyr
                85                  90                  95

Gln Pro Pro Lys Glu Pro His Met Leu Phe Asp Arg Ile Arg Leu Val
            100                 105                 110

Val Thr Leu Glu
        115
```

<210> SEQ ID NO 247
<211> LENGTH: 116
<212> TYPE: PRT
<213> ORGANISM: Artificial Sequence
<220> FEATURE:
<223> OTHER INFORMATION: Human TREM1 mutant 16_24

<400> SEQUENCE: 247

```
Ala Thr Lys Leu Thr Glu Glu Lys Tyr Glu Leu Lys Glu Gly Gln Thr
1               5                   10                  15

Leu Asp Val Lys Cys Asp Tyr Thr Ala Glu Lys Phe Ala Ser Ser Gln
            20                  25                  30

Lys Ala Trp Gln Ile Ile Arg Asp Gly Glu Met Pro Lys Thr Leu Ala
        35                  40                  45

Cys Thr Glu Arg Pro Ser Lys Asn Ser His Pro Val Gln Val Gly Arg
    50                  55                  60

Ile Ile Leu Glu Asp Tyr His Asp His Gly Leu Leu Arg Val Arg Met
65                  70                  75                  80

Val Asn Leu Gln Val Glu Asp Ser Gly Leu Tyr Gln Cys Val Ile Tyr
                85                  90                  95

Gln Pro Pro Lys Glu Pro His Met Leu Phe Asp Arg Ile Arg Leu Val
            100                 105                 110

Val Thr Leu Glu
        115
```

<210> SEQ ID NO 248
<211> LENGTH: 116
<212> TYPE: PRT
<213> ORGANISM: Artificial Sequence
<220> FEATURE:
<223> OTHER INFORMATION: Human TREM1 mutant 17_25

<400> SEQUENCE: 248

```
Ala Thr Lys Leu Thr Glu Glu Lys Tyr Glu Leu Lys Glu Gly Gln Thr
1               5                   10                  15

Leu Asp Val Lys Cys Asp Tyr Thr Leu Ala Lys Phe Ala Ser Ser Gln
            20                  25                  30

Lys Ala Trp Gln Ile Ile Arg Asp Gly Glu Met Pro Lys Thr Leu Ala
        35                  40                  45

Cys Thr Glu Arg Pro Ser Lys Asn Ser His Pro Val Gln Val Gly Arg
    50                  55                  60

Ile Ile Leu Glu Asp Tyr His Asp His Gly Leu Leu Arg Val Arg Met
65                  70                  75                  80

Val Asn Leu Gln Val Glu Asp Ser Gly Leu Tyr Gln Cys Val Ile Tyr
                85                  90                  95

Gln Pro Pro Lys Glu Pro His Met Leu Phe Asp Arg Ile Arg Leu Val
            100                 105                 110

Val Thr Leu Glu
```

115

<210> SEQ ID NO 249
<211> LENGTH: 116
<212> TYPE: PRT
<213> ORGANISM: Artificial Sequence
<220> FEATURE:
<223> OTHER INFORMATION: Human TREM1 mutant 18_26

<400> SEQUENCE: 249

```
Ala Thr Lys Leu Thr Glu Glu Lys Tyr Glu Leu Lys Glu Gly Gln Thr
1               5                   10                  15

Leu Asp Val Lys Cys Asp Tyr Thr Leu Glu Ala Phe Ala Ser Ser Gln
            20                  25                  30

Lys Ala Trp Gln Ile Ile Arg Asp Gly Glu Met Pro Lys Thr Leu Ala
        35                  40                  45

Cys Thr Glu Arg Pro Ser Lys Asn Ser His Pro Val Gln Val Gly Arg
    50                  55                  60

Ile Ile Leu Glu Asp Tyr His Asp His Gly Leu Leu Arg Val Arg Met
65                  70                  75                  80

Val Asn Leu Gln Val Glu Asp Ser Gly Leu Tyr Gln Cys Val Ile Tyr
                85                  90                  95

Gln Pro Pro Lys Glu Pro His Met Leu Phe Asp Arg Ile Arg Leu Val
            100                 105                 110

Val Thr Leu Glu
        115
```

<210> SEQ ID NO 250
<211> LENGTH: 116
<212> TYPE: PRT
<213> ORGANISM: Artificial Sequence
<220> FEATURE:
<223> OTHER INFORMATION: Human TREM1 mutant 19_29

<400> SEQUENCE: 250

```
Ala Thr Lys Leu Thr Glu Glu Lys Tyr Glu Leu Lys Glu Gly Gln Thr
1               5                   10                  15

Leu Asp Val Lys Cys Asp Tyr Thr Leu Glu Lys Phe Ala Ala Ser Gln
            20                  25                  30

Lys Ala Trp Gln Ile Ile Arg Asp Gly Glu Met Pro Lys Thr Leu Ala
        35                  40                  45

Cys Thr Glu Arg Pro Ser Lys Asn Ser His Pro Val Gln Val Gly Arg
    50                  55                  60

Ile Ile Leu Glu Asp Tyr His Asp His Gly Leu Leu Arg Val Arg Met
65                  70                  75                  80

Val Asn Leu Gln Val Glu Asp Ser Gly Leu Tyr Gln Cys Val Ile Tyr
                85                  90                  95

Gln Pro Pro Lys Glu Pro His Met Leu Phe Asp Arg Ile Arg Leu Val
            100                 105                 110

Val Thr Leu Glu
        115
```

<210> SEQ ID NO 251
<211> LENGTH: 116
<212> TYPE: PRT
<213> ORGANISM: Artificial Sequence
<220> FEATURE:
<223> OTHER INFORMATION: Human TREM1 mutant 20_30

<400> SEQUENCE: 251

```
Ala Thr Lys Leu Thr Glu Glu Lys Tyr Glu Leu Lys Glu Gly Gln Thr
1               5                   10                  15

Leu Asp Val Lys Cys Asp Tyr Thr Leu Glu Lys Phe Ala Ser Ala Gln
            20                  25                  30

Lys Ala Trp Gln Ile Ile Arg Asp Gly Glu Met Pro Lys Thr Leu Ala
        35                  40                  45

Cys Thr Glu Arg Pro Ser Lys Asn Ser His Pro Val Gln Val Gly Arg
    50                  55                  60

Ile Ile Leu Glu Asp Tyr His Asp His Gly Leu Leu Arg Val Arg Met
65                  70                  75                  80

Val Asn Leu Gln Val Glu Asp Ser Gly Leu Tyr Gln Cys Val Ile Tyr
                85                  90                  95

Gln Pro Pro Lys Glu Pro His Met Leu Phe Asp Arg Ile Arg Leu Val
            100                 105                 110

Val Thr Leu Glu
        115
```

<210> SEQ ID NO 252
<211> LENGTH: 116
<212> TYPE: PRT
<213> ORGANISM: Artificial Sequence
<220> FEATURE:
<223> OTHER INFORMATION: Human TREM1 mutant 21_38

<400> SEQUENCE: 252

```
Ala Thr Lys Leu Thr Glu Glu Lys Tyr Glu Leu Lys Glu Gly Gln Thr
1               5                   10                  15

Leu Asp Val Lys Cys Asp Tyr Thr Leu Glu Lys Phe Ala Ser Ser Gln
            20                  25                  30

Lys Ala Trp Gln Ile Ile Ala Asp Gly Glu Met Pro Lys Thr Leu Ala
        35                  40                  45

Cys Thr Glu Arg Pro Ser Lys Asn Ser His Pro Val Gln Val Gly Arg
    50                  55                  60

Ile Ile Leu Glu Asp Tyr His Asp His Gly Leu Leu Arg Val Arg Met
65                  70                  75                  80

Val Asn Leu Gln Val Glu Asp Ser Gly Leu Tyr Gln Cys Val Ile Tyr
                85                  90                  95

Gln Pro Pro Lys Glu Pro His Met Leu Phe Asp Arg Ile Arg Leu Val
            100                 105                 110

Val Thr Leu Glu
        115
```

<210> SEQ ID NO 253
<211> LENGTH: 116
<212> TYPE: PRT
<213> ORGANISM: Artificial Sequence
<220> FEATURE:
<223> OTHER INFORMATION: Human TREM1 mutant 22_39

<400> SEQUENCE: 253

```
Ala Thr Lys Leu Thr Glu Glu Lys Tyr Glu Leu Lys Glu Gly Gln Thr
1               5                   10                  15

Leu Asp Val Lys Cys Asp Tyr Thr Leu Glu Lys Phe Ala Ser Ser Gln
            20                  25                  30

Lys Ala Trp Gln Ile Ile Arg Ala Gly Glu Met Pro Lys Thr Leu Ala
        35                  40                  45

Cys Thr Glu Arg Pro Ser Lys Asn Ser His Pro Val Gln Val Gly Arg
```

```
    50                  55                  60

Ile Ile Leu Glu Asp Tyr His Asp His Gly Leu Leu Arg Val Arg Met
65                  70                  75                  80

Val Asn Leu Gln Val Glu Asp Ser Gly Leu Tyr Gln Cys Val Ile Tyr
                85                  90                  95

Gln Pro Pro Lys Glu Pro His Met Leu Phe Asp Arg Ile Arg Leu Val
            100                 105                 110

Val Thr Leu Glu
        115


<210> SEQ ID NO 254
<211> LENGTH: 116
<212> TYPE: PRT
<213> ORGANISM: Artificial Sequence
<220> FEATURE:
<223> OTHER INFORMATION: Human TREM1 mutant  23_41

<400> SEQUENCE: 254

Ala Thr Lys Leu Thr Glu Glu Lys Tyr Glu Leu Lys Glu Gly Gln Thr
1               5                   10                  15

Leu Asp Val Lys Cys Asp Tyr Thr Leu Glu Lys Phe Ala Ser Ser Gln
            20                  25                  30

Lys Ala Trp Gln Ile Ile Arg Asp Gly Ala Met Pro Lys Thr Leu Ala
        35                  40                  45

Cys Thr Glu Arg Pro Ser Lys Asn Ser His Pro Val Gln Val Gly Arg
    50                  55                  60

Ile Ile Leu Glu Asp Tyr His Asp His Gly Leu Leu Arg Val Arg Met
65                  70                  75                  80

Val Asn Leu Gln Val Glu Asp Ser Gly Leu Tyr Gln Cys Val Ile Tyr
                85                  90                  95

Gln Pro Pro Lys Glu Pro His Met Leu Phe Asp Arg Ile Arg Leu Val
            100                 105                 110

Val Thr Leu Glu
        115


<210> SEQ ID NO 255
<211> LENGTH: 116
<212> TYPE: PRT
<213> ORGANISM: Artificial Sequence
<220> FEATURE:
<223> OTHER INFORMATION: Human TREM1 mutant  24_42

<400> SEQUENCE: 255

Ala Thr Lys Leu Thr Glu Glu Lys Tyr Glu Leu Lys Glu Gly Gln Thr
1               5                   10                  15

Leu Asp Val Lys Cys Asp Tyr Thr Leu Glu Lys Phe Ala Ser Ser Gln
            20                  25                  30

Lys Ala Trp Gln Ile Ile Arg Asp Gly Glu Ala Pro Lys Thr Leu Ala
        35                  40                  45

Cys Thr Glu Arg Pro Ser Lys Asn Ser His Pro Val Gln Val Gly Arg
    50                  55                  60

Ile Ile Leu Glu Asp Tyr His Asp His Gly Leu Leu Arg Val Arg Met
65                  70                  75                  80

Val Asn Leu Gln Val Glu Asp Ser Gly Leu Tyr Gln Cys Val Ile Tyr
                85                  90                  95

Gln Pro Pro Lys Glu Pro His Met Leu Phe Asp Arg Ile Arg Leu Val
            100                 105                 110
```

```
Val Thr Leu Glu
        115


<210> SEQ ID NO 256
<211> LENGTH: 116
<212> TYPE: PRT
<213> ORGANISM: Artificial Sequence
<220> FEATURE:
<223> OTHER INFORMATION: Human TREM1 mutant  25_44

<400> SEQUENCE: 256

Ala Thr Lys Leu Thr Glu Glu Lys Tyr Glu Leu Lys Glu Gly Gln Thr
1               5                   10                  15

Leu Asp Val Lys Cys Asp Tyr Thr Leu Glu Lys Phe Ala Ser Ser Gln
            20                  25                  30

Lys Ala Trp Gln Ile Ile Arg Asp Gly Glu Met Pro Ala Thr Leu Ala
        35                  40                  45

Cys Thr Glu Arg Pro Ser Lys Asn Ser His Pro Val Gln Val Gly Arg
    50                  55                  60

Ile Ile Leu Glu Asp Tyr His Asp His Gly Leu Leu Arg Val Arg Met
65                  70                  75                  80

Val Asn Leu Gln Val Glu Asp Ser Gly Leu Tyr Gln Cys Val Ile Tyr
                85                  90                  95

Gln Pro Pro Lys Glu Pro His Met Leu Phe Asp Arg Ile Arg Leu Val
            100                 105                 110

Val Thr Leu Glu
        115


<210> SEQ ID NO 257
<211> LENGTH: 116
<212> TYPE: PRT
<213> ORGANISM: Artificial Sequence
<220> FEATURE:
<223> OTHER INFORMATION: Human TREM1 mutant  26_45

<400> SEQUENCE: 257

Ala Thr Lys Leu Thr Glu Glu Lys Tyr Glu Leu Lys Glu Gly Gln Thr
1               5                   10                  15

Leu Asp Val Lys Cys Asp Tyr Thr Leu Glu Lys Phe Ala Ser Ser Gln
            20                  25                  30

Lys Ala Trp Gln Ile Ile Arg Asp Gly Glu Met Pro Lys Ala Leu Ala
        35                  40                  45

Cys Thr Glu Arg Pro Ser Lys Asn Ser His Pro Val Gln Val Gly Arg
    50                  55                  60

Ile Ile Leu Glu Asp Tyr His Asp His Gly Leu Leu Arg Val Arg Met
65                  70                  75                  80

Val Asn Leu Gln Val Glu Asp Ser Gly Leu Tyr Gln Cys Val Ile Tyr
                85                  90                  95

Gln Pro Pro Lys Glu Pro His Met Leu Phe Asp Arg Ile Arg Leu Val
            100                 105                 110

Val Thr Leu Glu
        115


<210> SEQ ID NO 258
<211> LENGTH: 116
<212> TYPE: PRT
<213> ORGANISM: Artificial Sequence
<220> FEATURE:
<223> OTHER INFORMATION: Human TREM1 mutant  27_50
```

<400> SEQUENCE: 258

Ala Thr Lys Leu Thr Glu Glu Lys Tyr Glu Leu Lys Glu Gly Gln Thr
1 5 10 15

Leu Asp Val Lys Cys Asp Tyr Thr Leu Glu Lys Phe Ala Ser Ser Gln
20 25 30

Lys Ala Trp Gln Ile Ile Arg Asp Gly Glu Met Pro Lys Thr Leu Ala
35 40 45

Cys Thr Ala Arg Pro Ser Lys Asn Ser His Pro Val Gln Val Gly Arg
50 55 60

Ile Ile Leu Glu Asp Tyr His Asp His Gly Leu Leu Arg Val Arg Met
65 70 75 80

Val Asn Leu Gln Val Glu Asp Ser Gly Leu Tyr Gln Cys Val Ile Tyr
85 90 95

Gln Pro Pro Lys Glu Pro His Met Leu Phe Asp Arg Ile Arg Leu Val
100 105 110

Val Thr Leu Glu
115

<210> SEQ ID NO 259
<211> LENGTH: 116
<212> TYPE: PRT
<213> ORGANISM: Artificial Sequence
<220> FEATURE:
<223> OTHER INFORMATION: Human TREM1 mutant 28_51

<400> SEQUENCE: 259

Ala Thr Lys Leu Thr Glu Glu Lys Tyr Glu Leu Lys Glu Gly Gln Thr
1 5 10 15

Leu Asp Val Lys Cys Asp Tyr Thr Leu Glu Lys Phe Ala Ser Ser Gln
20 25 30

Lys Ala Trp Gln Ile Ile Arg Asp Gly Glu Met Pro Lys Thr Leu Ala
35 40 45

Cys Thr Glu Ala Pro Ser Lys Asn Ser His Pro Val Gln Val Gly Arg
50 55 60

Ile Ile Leu Glu Asp Tyr His Asp His Gly Leu Leu Arg Val Arg Met
65 70 75 80

Val Asn Leu Gln Val Glu Asp Ser Gly Leu Tyr Gln Cys Val Ile Tyr
85 90 95

Gln Pro Pro Lys Glu Pro His Met Leu Phe Asp Arg Ile Arg Leu Val
100 105 110

Val Thr Leu Glu
115

<210> SEQ ID NO 260
<211> LENGTH: 116
<212> TYPE: PRT
<213> ORGANISM: Artificial Sequence
<220> FEATURE:
<223> OTHER INFORMATION: Human TREM1 mutant 29_52

<400> SEQUENCE: 260

Ala Thr Lys Leu Thr Glu Glu Lys Tyr Glu Leu Lys Glu Gly Gln Thr
1 5 10 15

Leu Asp Val Lys Cys Asp Tyr Thr Leu Glu Lys Phe Ala Ser Ser Gln
20 25 30

Lys Ala Trp Gln Ile Ile Arg Asp Gly Glu Met Pro Lys Thr Leu Ala
35 40 45

```
Cys Thr Glu Arg Ala Ser Lys Asn Ser His Pro Val Gln Val Gly Arg
    50                  55                  60

Ile Ile Leu Glu Asp Tyr His Asp His Gly Leu Leu Arg Val Arg Met
65                  70                  75                  80

Val Asn Leu Gln Val Glu Asp Ser Gly Leu Tyr Gln Cys Val Ile Tyr
                85                  90                  95

Gln Pro Pro Lys Glu Pro His Met Leu Phe Asp Arg Ile Arg Leu Val
            100                 105                 110

Val Thr Leu Glu
        115


<210> SEQ ID NO 261
<211> LENGTH: 116
<212> TYPE: PRT
<213> ORGANISM: Artificial Sequence
<220> FEATURE:
<223> OTHER INFORMATION: Human TREM1 mutant  30_54

<400> SEQUENCE: 261

Ala Thr Lys Leu Thr Glu Glu Lys Tyr Glu Leu Lys Glu Gly Gln Thr
1               5                   10                  15

Leu Asp Val Lys Cys Asp Tyr Thr Leu Glu Lys Phe Ala Ser Ser Gln
            20                  25                  30

Lys Ala Trp Gln Ile Ile Arg Asp Gly Glu Met Pro Lys Thr Leu Ala
        35                  40                  45

Cys Thr Glu Arg Pro Ser Ala Asn Ser His Pro Val Gln Val Gly Arg
    50                  55                  60

Ile Ile Leu Glu Asp Tyr His Asp His Gly Leu Leu Arg Val Arg Met
65                  70                  75                  80

Val Asn Leu Gln Val Glu Asp Ser Gly Leu Tyr Gln Cys Val Ile Tyr
                85                  90                  95

Gln Pro Pro Lys Glu Pro His Met Leu Phe Asp Arg Ile Arg Leu Val
            100                 105                 110

Val Thr Leu Glu
        115


<210> SEQ ID NO 262
<211> LENGTH: 116
<212> TYPE: PRT
<213> ORGANISM: Artificial Sequence
<220> FEATURE:
<223> OTHER INFORMATION: Human TREM1 mutant  31_55

<400> SEQUENCE: 262

Ala Thr Lys Leu Thr Glu Glu Lys Tyr Glu Leu Lys Glu Gly Gln Thr
1               5                   10                  15

Leu Asp Val Lys Cys Asp Tyr Thr Leu Glu Lys Phe Ala Ser Ser Gln
            20                  25                  30

Lys Ala Trp Gln Ile Ile Arg Asp Gly Glu Met Pro Lys Thr Leu Ala
        35                  40                  45

Cys Thr Glu Arg Pro Ser Lys Ala Ser His Pro Val Gln Val Gly Arg
    50                  55                  60

Ile Ile Leu Glu Asp Tyr His Asp His Gly Leu Leu Arg Val Arg Met
65                  70                  75                  80

Val Asn Leu Gln Val Glu Asp Ser Gly Leu Tyr Gln Cys Val Ile Tyr
                85                  90                  95

Gln Pro Pro Lys Glu Pro His Met Leu Phe Asp Arg Ile Arg Leu Val
            100                 105                 110
```

```
Val Thr Leu Glu
        115


<210> SEQ ID NO 263
<211> LENGTH: 116
<212> TYPE: PRT
<213> ORGANISM: Artificial Sequence
<220> FEATURE:
<223> OTHER INFORMATION: Human TREM1 mutant  32_56

<400> SEQUENCE: 263

Ala Thr Lys Leu Thr Glu Glu Lys Tyr Glu Leu Lys Glu Gly Gln Thr
1               5                   10                  15

Leu Asp Val Lys Cys Asp Tyr Thr Leu Glu Lys Phe Ala Ser Ser Gln
            20                  25                  30

Lys Ala Trp Gln Ile Ile Arg Asp Gly Glu Met Pro Lys Thr Leu Ala
        35                  40                  45

Cys Thr Glu Arg Pro Ser Lys Asn Ala His Pro Val Gln Val Gly Arg
    50                  55                  60

Ile Ile Leu Glu Asp Tyr His Asp His Gly Leu Leu Arg Val Arg Met
65                  70                  75                  80

Val Asn Leu Gln Val Glu Asp Ser Gly Leu Tyr Gln Cys Val Ile Tyr
                85                  90                  95

Gln Pro Pro Lys Glu Pro His Met Leu Phe Asp Arg Ile Arg Leu Val
            100                 105                 110

Val Thr Leu Glu
        115


<210> SEQ ID NO 264
<211> LENGTH: 116
<212> TYPE: PRT
<213> ORGANISM: Artificial Sequence
<220> FEATURE:
<223> OTHER INFORMATION: Human TREM1 mutant  33_57

<400> SEQUENCE: 264

Ala Thr Lys Leu Thr Glu Glu Lys Tyr Glu Leu Lys Glu Gly Gln Thr
1               5                   10                  15

Leu Asp Val Lys Cys Asp Tyr Thr Leu Glu Lys Phe Ala Ser Ser Gln
            20                  25                  30

Lys Ala Trp Gln Ile Ile Arg Asp Gly Glu Met Pro Lys Thr Leu Ala
        35                  40                  45

Cys Thr Glu Arg Pro Ser Lys Asn Ser Ala Pro Val Gln Val Gly Arg
    50                  55                  60

Ile Ile Leu Glu Asp Tyr His Asp His Gly Leu Leu Arg Val Arg Met
65                  70                  75                  80

Val Asn Leu Gln Val Glu Asp Ser Gly Leu Tyr Gln Cys Val Ile Tyr
                85                  90                  95

Gln Pro Pro Lys Glu Pro His Met Leu Phe Asp Arg Ile Arg Leu Val
            100                 105                 110

Val Thr Leu Glu
        115


<210> SEQ ID NO 265
<211> LENGTH: 116
<212> TYPE: PRT
<213> ORGANISM: Artificial Sequence
<220> FEATURE:
<223> OTHER INFORMATION: Human TREM1 mutant  34_58
```

<400> SEQUENCE: 265

Ala Thr Lys Leu Thr Glu Glu Lys Tyr Glu Leu Lys Glu Gly Gln Thr
1               5                   10                  15

Leu Asp Val Lys Cys Asp Tyr Thr Leu Glu Lys Phe Ala Ser Ser Gln
            20                  25                  30

Lys Ala Trp Gln Ile Ile Arg Asp Gly Glu Met Pro Lys Thr Leu Ala
        35                  40                  45

Cys Thr Glu Arg Pro Ser Lys Asn Ser His Ala Val Gln Val Gly Arg
    50                  55                  60

Ile Ile Leu Glu Asp Tyr His Asp His Gly Leu Leu Arg Val Arg Met
65                  70                  75                  80

Val Asn Leu Gln Val Glu Asp Ser Gly Leu Tyr Gln Cys Val Ile Tyr
                85                  90                  95

Gln Pro Pro Lys Glu Pro His Met Leu Phe Asp Arg Ile Arg Leu Val
            100                 105                 110

Val Thr Leu Glu
        115

<210> SEQ ID NO 266
<211> LENGTH: 116
<212> TYPE: PRT
<213> ORGANISM: Artificial Sequence
<220> FEATURE:
<223> OTHER INFORMATION: Human TREM1 mutant 35_59

<400> SEQUENCE: 266

Ala Thr Lys Leu Thr Glu Glu Lys Tyr Glu Leu Lys Glu Gly Gln Thr
1               5                   10                  15

Leu Asp Val Lys Cys Asp Tyr Thr Leu Glu Lys Phe Ala Ser Ser Gln
            20                  25                  30

Lys Ala Trp Gln Ile Ile Arg Asp Gly Glu Met Pro Lys Thr Leu Ala
        35                  40                  45

Cys Thr Glu Arg Pro Ser Lys Asn Ser His Pro Ala Gln Val Gly Arg
    50                  55                  60

Ile Ile Leu Glu Asp Tyr His Asp His Gly Leu Leu Arg Val Arg Met
65                  70                  75                  80

Val Asn Leu Gln Val Glu Asp Ser Gly Leu Tyr Gln Cys Val Ile Tyr
                85                  90                  95

Gln Pro Pro Lys Glu Pro His Met Leu Phe Asp Arg Ile Arg Leu Val
            100                 105                 110

Val Thr Leu Glu
        115

<210> SEQ ID NO 267
<211> LENGTH: 116
<212> TYPE: PRT
<213> ORGANISM: Artificial Sequence
<220> FEATURE:
<223> OTHER INFORMATION: Human TREM1 mutant 36_60

<400> SEQUENCE: 267

Ala Thr Lys Leu Thr Glu Glu Lys Tyr Glu Leu Lys Glu Gly Gln Thr
1               5                   10                  15

Leu Asp Val Lys Cys Asp Tyr Thr Leu Glu Lys Phe Ala Ser Ser Gln
            20                  25                  30

Lys Ala Trp Gln Ile Ile Arg Asp Gly Glu Met Pro Lys Thr Leu Ala
        35                  40                  45

```
Cys Thr Glu Arg Pro Ser Lys Asn Ser His Pro Val Ala Val Gly Arg
    50                  55                  60

Ile Ile Leu Glu Asp Tyr His Asp His Gly Leu Leu Arg Val Arg Met
65                  70                  75                  80

Val Asn Leu Gln Val Glu Asp Ser Gly Leu Tyr Gln Cys Val Ile Tyr
                85                  90                  95

Gln Pro Pro Lys Glu Pro His Met Leu Phe Asp Arg Ile Arg Leu Val
            100                 105                 110

Val Thr Leu Glu
        115


<210> SEQ ID NO 268
<211> LENGTH: 116
<212> TYPE: PRT
<213> ORGANISM: Artificial Sequence
<220> FEATURE:
<223> OTHER INFORMATION: Human TREM1 mutant  37_61

<400> SEQUENCE: 268

Ala Thr Lys Leu Thr Glu Glu Lys Tyr Glu Leu Lys Glu Gly Gln Thr
1               5                   10                  15

Leu Asp Val Lys Cys Asp Tyr Thr Leu Glu Lys Phe Ala Ser Ser Gln
            20                  25                  30

Lys Ala Trp Gln Ile Ile Arg Asp Gly Glu Met Pro Lys Thr Leu Ala
        35                  40                  45

Cys Thr Glu Arg Pro Ser Lys Asn Ser His Pro Val Gln Ala Gly Arg
    50                  55                  60

Ile Ile Leu Glu Asp Tyr His Asp His Gly Leu Leu Arg Val Arg Met
65                  70                  75                  80

Val Asn Leu Gln Val Glu Asp Ser Gly Leu Tyr Gln Cys Val Ile Tyr
                85                  90                  95

Gln Pro Pro Lys Glu Pro His Met Leu Phe Asp Arg Ile Arg Leu Val
            100                 105                 110

Val Thr Leu Glu
        115


<210> SEQ ID NO 269
<211> LENGTH: 116
<212> TYPE: PRT
<213> ORGANISM: Artificial Sequence
<220> FEATURE:
<223> OTHER INFORMATION: Human TREM1 mutant  38_63

<400> SEQUENCE: 269

Ala Thr Lys Leu Thr Glu Glu Lys Tyr Glu Leu Lys Glu Gly Gln Thr
1               5                   10                  15

Leu Asp Val Lys Cys Asp Tyr Thr Leu Glu Lys Phe Ala Ser Ser Gln
            20                  25                  30

Lys Ala Trp Gln Ile Ile Arg Asp Gly Glu Met Pro Lys Thr Leu Ala
        35                  40                  45

Cys Thr Glu Arg Pro Ser Lys Asn Ser His Pro Val Gln Val Gly Ala
    50                  55                  60

Ile Ile Leu Glu Asp Tyr His Asp His Gly Leu Leu Arg Val Arg Met
65                  70                  75                  80

Val Asn Leu Gln Val Glu Asp Ser Gly Leu Tyr Gln Cys Val Ile Tyr
                85                  90                  95

Gln Pro Pro Lys Glu Pro His Met Leu Phe Asp Arg Ile Arg Leu Val
```

```
            100                 105                 110

Val Thr Leu Glu
        115


<210> SEQ ID NO 270
<211> LENGTH: 116
<212> TYPE: PRT
<213> ORGANISM: Artificial Sequence
<220> FEATURE:
<223> OTHER INFORMATION: Human TREM1 mutant  39_65

<400> SEQUENCE: 270

Ala Thr Lys Leu Thr Glu Glu Lys Tyr Glu Leu Lys Glu Gly Gln Thr
1               5                   10                  15

Leu Asp Val Lys Cys Asp Tyr Thr Leu Glu Lys Phe Ala Ser Ser Gln
            20                  25                  30

Lys Ala Trp Gln Ile Ile Arg Asp Gly Glu Met Pro Lys Thr Leu Ala
        35                  40                  45

Cys Thr Glu Arg Pro Ser Lys Asn Ser His Pro Val Gln Val Gly Arg
    50                  55                  60

Ile Ala Leu Glu Asp Tyr His Asp His Gly Leu Leu Arg Val Arg Met
65                  70                  75                  80

Val Asn Leu Gln Val Glu Asp Ser Gly Leu Tyr Gln Cys Val Ile Tyr
                85                  90                  95

Gln Pro Pro Lys Glu Pro His Met Leu Phe Asp Arg Ile Arg Leu Val
            100                 105                 110

Val Thr Leu Glu
        115


<210> SEQ ID NO 271
<211> LENGTH: 116
<212> TYPE: PRT
<213> ORGANISM: Artificial Sequence
<220> FEATURE:
<223> OTHER INFORMATION: Human TREM1 mutant  40_71

<400> SEQUENCE: 271

Ala Thr Lys Leu Thr Glu Glu Lys Tyr Glu Leu Lys Glu Gly Gln Thr
1               5                   10                  15

Leu Asp Val Lys Cys Asp Tyr Thr Leu Glu Lys Phe Ala Ser Ser Gln
            20                  25                  30

Lys Ala Trp Gln Ile Ile Arg Asp Gly Glu Met Pro Lys Thr Leu Ala
        35                  40                  45

Cys Thr Glu Arg Pro Ser Lys Asn Ser His Pro Val Gln Val Gly Arg
    50                  55                  60

Ile Ile Leu Glu Asp Tyr His Ala His Gly Leu Leu Arg Val Arg Met
65                  70                  75                  80

Val Asn Leu Gln Val Glu Asp Ser Gly Leu Tyr Gln Cys Val Ile Tyr
                85                  90                  95

Gln Pro Pro Lys Glu Pro His Met Leu Phe Asp Arg Ile Arg Leu Val
            100                 105                 110

Val Thr Leu Glu
        115


<210> SEQ ID NO 272
<211> LENGTH: 116
<212> TYPE: PRT
<213> ORGANISM: Artificial Sequence
<220> FEATURE:
```

<223> OTHER INFORMATION: Human TREM1 mutant 41_72

<400> SEQUENCE: 272

Ala Thr Lys Leu Thr Glu Glu Lys Tyr Glu Leu Lys Glu Gly Gln Thr
1 5 10 15

Leu Asp Val Lys Cys Asp Tyr Thr Leu Glu Lys Phe Ala Ser Ser Gln
20 25 30

Lys Ala Trp Gln Ile Ile Arg Asp Gly Glu Met Pro Lys Thr Leu Ala
35 40 45

Cys Thr Glu Arg Pro Ser Lys Asn Ser His Pro Val Gln Val Gly Arg
50 55 60

Ile Ile Leu Glu Asp Tyr His Asp Ala Gly Leu Leu Arg Val Arg Met
65 70 75 80

Val Asn Leu Gln Val Glu Asp Ser Gly Leu Tyr Gln Cys Val Ile Tyr
85 90 95

Gln Pro Pro Lys Glu Pro His Met Leu Phe Asp Arg Ile Arg Leu Val
100 105 110

Val Thr Leu Glu
115

<210> SEQ ID NO 273
<211> LENGTH: 116
<212> TYPE: PRT
<213> ORGANISM: Artificial Sequence
<220> FEATURE:
<223> OTHER INFORMATION: Human TREM1 mutant 42_78

<400> SEQUENCE: 273

Ala Thr Lys Leu Thr Glu Glu Lys Tyr Glu Leu Lys Glu Gly Gln Thr
1 5 10 15

Leu Asp Val Lys Cys Asp Tyr Thr Leu Glu Lys Phe Ala Ser Ser Gln
20 25 30

Lys Ala Trp Gln Ile Ile Arg Asp Gly Glu Met Pro Lys Thr Leu Ala
35 40 45

Cys Thr Glu Arg Pro Ser Lys Asn Ser His Pro Val Gln Val Gly Arg
50 55 60

Ile Ile Leu Glu Asp Tyr His Asp His Gly Leu Leu Arg Val Ala Met
65 70 75 80

Val Asn Leu Gln Val Glu Asp Ser Gly Leu Tyr Gln Cys Val Ile Tyr
85 90 95

Gln Pro Pro Lys Glu Pro His Met Leu Phe Asp Arg Ile Arg Leu Val
100 105 110

Val Thr Leu Glu
115

<210> SEQ ID NO 274
<211> LENGTH: 116
<212> TYPE: PRT
<213> ORGANISM: Artificial Sequence
<220> FEATURE:
<223> OTHER INFORMATION: Human TREM1 mutant 43_80

<400> SEQUENCE: 274

Ala Thr Lys Leu Thr Glu Glu Lys Tyr Glu Leu Lys Glu Gly Gln Thr
1 5 10 15

Leu Asp Val Lys Cys Asp Tyr Thr Leu Glu Lys Phe Ala Ser Ser Gln
20 25 30

Lys Ala Trp Gln Ile Ile Arg Asp Gly Glu Met Pro Lys Thr Leu Ala

```
        35                  40                  45

Cys Thr Glu Arg Pro Ser Lys Asn Ser His Pro Val Gln Val Gly Arg
    50                  55                  60

Ile Ile Leu Glu Asp Tyr His Asp His Gly Leu Leu Arg Val Arg Met
65                  70                  75                  80

Ala Asn Leu Gln Val Glu Asp Ser Gly Leu Tyr Gln Cys Val Ile Tyr
                85                  90                  95

Gln Pro Pro Lys Glu Pro His Met Leu Phe Asp Arg Ile Arg Leu Val
            100                 105                 110

Val Thr Leu Glu
        115


<210> SEQ ID NO 275
<211> LENGTH: 116
<212> TYPE: PRT
<213> ORGANISM: Artificial Sequence
<220> FEATURE:
<223> OTHER INFORMATION: Human TREM1 mutant  44_81

<400> SEQUENCE: 275

Ala Thr Lys Leu Thr Glu Glu Lys Tyr Glu Leu Lys Glu Gly Gln Thr
1               5                   10                  15

Leu Asp Val Lys Cys Asp Tyr Thr Leu Glu Lys Phe Ala Ser Ser Gln
            20                  25                  30

Lys Ala Trp Gln Ile Ile Arg Asp Gly Glu Met Pro Lys Thr Leu Ala
        35                  40                  45

Cys Thr Glu Arg Pro Ser Lys Asn Ser His Pro Val Gln Val Gly Arg
    50                  55                  60

Ile Ile Leu Glu Asp Tyr His Asp His Gly Leu Leu Arg Val Arg Met
65                  70                  75                  80

Val Ala Leu Gln Val Glu Asp Ser Gly Leu Tyr Gln Cys Val Ile Tyr
                85                  90                  95

Gln Pro Pro Lys Glu Pro His Met Leu Phe Asp Arg Ile Arg Leu Val
            100                 105                 110

Val Thr Leu Glu
        115


<210> SEQ ID NO 276
<211> LENGTH: 116
<212> TYPE: PRT
<213> ORGANISM: Artificial Sequence
<220> FEATURE:
<223> OTHER INFORMATION: Human TREM1 mutant  45_83

<400> SEQUENCE: 276

Ala Thr Lys Leu Thr Glu Glu Lys Tyr Glu Leu Lys Glu Gly Gln Thr
1               5                   10                  15

Leu Asp Val Lys Cys Asp Tyr Thr Leu Glu Lys Phe Ala Ser Ser Gln
            20                  25                  30

Lys Ala Trp Gln Ile Ile Arg Asp Gly Glu Met Pro Lys Thr Leu Ala
        35                  40                  45

Cys Thr Glu Arg Pro Ser Lys Asn Ser His Pro Val Gln Val Gly Arg
    50                  55                  60

Ile Ile Leu Glu Asp Tyr His Asp His Gly Leu Leu Arg Val Arg Met
65                  70                  75                  80

Val Asn Leu Ala Val Glu Asp Ser Gly Leu Tyr Gln Cys Val Ile Tyr
                85                  90                  95
```

```
Gln Pro Pro Lys Glu Pro His Met Leu Phe Asp Arg Ile Arg Leu Val
            100                 105                 110

Val Thr Leu Glu
        115


<210> SEQ ID NO 277
<211> LENGTH: 116
<212> TYPE: PRT
<213> ORGANISM: Artificial Sequence
<220> FEATURE:
<223> OTHER INFORMATION: Human TREM1 mutant  46_84

<400> SEQUENCE: 277

Ala Thr Lys Leu Thr Glu Glu Lys Tyr Glu Leu Lys Glu Gly Gln Thr
1               5                   10                  15

Leu Asp Val Lys Cys Asp Tyr Thr Leu Glu Lys Phe Ala Ser Ser Gln
            20                  25                  30

Lys Ala Trp Gln Ile Ile Arg Asp Gly Glu Met Pro Lys Thr Leu Ala
        35                  40                  45

Cys Thr Glu Arg Pro Ser Lys Asn Ser His Pro Val Gln Val Gly Arg
    50                  55                  60

Ile Ile Leu Glu Asp Tyr His Asp His Gly Leu Leu Arg Val Arg Met
65                  70                  75                  80

Val Asn Leu Gln Ala Glu Asp Ser Gly Leu Tyr Gln Cys Val Ile Tyr
                85                  90                  95

Gln Pro Pro Lys Glu Pro His Met Leu Phe Asp Arg Ile Arg Leu Val
            100                 105                 110

Val Thr Leu Glu
        115


<210> SEQ ID NO 278
<211> LENGTH: 116
<212> TYPE: PRT
<213> ORGANISM: Artificial Sequence
<220> FEATURE:
<223> OTHER INFORMATION: Human TREM1 mutant  47_85

<400> SEQUENCE: 278

Ala Thr Lys Leu Thr Glu Glu Lys Tyr Glu Leu Lys Glu Gly Gln Thr
1               5                   10                  15

Leu Asp Val Lys Cys Asp Tyr Thr Leu Glu Lys Phe Ala Ser Ser Gln
            20                  25                  30

Lys Ala Trp Gln Ile Ile Arg Asp Gly Glu Met Pro Lys Thr Leu Ala
        35                  40                  45

Cys Thr Glu Arg Pro Ser Lys Asn Ser His Pro Val Gln Val Gly Arg
    50                  55                  60

Ile Ile Leu Glu Asp Tyr His Asp His Gly Leu Leu Arg Val Arg Met
65                  70                  75                  80

Val Asn Leu Gln Val Ala Asp Ser Gly Leu Tyr Gln Cys Val Ile Tyr
                85                  90                  95

Gln Pro Pro Lys Glu Pro His Met Leu Phe Asp Arg Ile Arg Leu Val
            100                 105                 110

Val Thr Leu Glu
        115


<210> SEQ ID NO 279
<211> LENGTH: 116
<212> TYPE: PRT
<213> ORGANISM: Artificial Sequence
```

<220> FEATURE:
<223> OTHER INFORMATION: Human TREM1 mutant 48_87

<400> SEQUENCE: 279

```
Ala Thr Lys Leu Thr Glu Glu Lys Tyr Glu Leu Lys Glu Gly Gln Thr
1               5                   10                  15

Leu Asp Val Lys Cys Asp Tyr Thr Leu Glu Lys Phe Ala Ser Ser Gln
            20                  25                  30

Lys Ala Trp Gln Ile Ile Arg Asp Gly Glu Met Pro Lys Thr Leu Ala
        35                  40                  45

Cys Thr Glu Arg Pro Ser Lys Asn Ser His Pro Val Gln Val Gly Arg
    50                  55                  60

Ile Ile Leu Glu Asp Tyr His Asp His Gly Leu Leu Arg Val Arg Met
65                  70                  75                  80

Val Asn Leu Gln Val Glu Asp Ala Gly Leu Tyr Gln Cys Val Ile Tyr
                85                  90                  95

Gln Pro Pro Lys Glu Pro His Met Leu Phe Asp Arg Ile Arg Leu Val
            100                 105                 110

Val Thr Leu Glu
        115
```

<210> SEQ ID NO 280
<211> LENGTH: 116
<212> TYPE: PRT
<213> ORGANISM: Artificial Sequence
<220> FEATURE:
<223> OTHER INFORMATION: Human TREM1 mutant 49_95

<400> SEQUENCE: 280

```
Ala Thr Lys Leu Thr Glu Glu Lys Tyr Glu Leu Lys Glu Gly Gln Thr
1               5                   10                  15

Leu Asp Val Lys Cys Asp Tyr Thr Leu Glu Lys Phe Ala Ser Ser Gln
            20                  25                  30

Lys Ala Trp Gln Ile Ile Arg Asp Gly Glu Met Pro Lys Thr Leu Ala
        35                  40                  45

Cys Thr Glu Arg Pro Ser Lys Asn Ser His Pro Val Gln Val Gly Arg
    50                  55                  60

Ile Ile Leu Glu Asp Tyr His Asp His Gly Leu Leu Arg Val Arg Met
65                  70                  75                  80

Val Asn Leu Gln Val Glu Asp Ser Gly Leu Tyr Gln Cys Val Ile Ala
                85                  90                  95

Gln Pro Pro Lys Glu Pro His Met Leu Phe Asp Arg Ile Arg Leu Val
            100                 105                 110

Val Thr Leu Glu
        115
```

<210> SEQ ID NO 281
<211> LENGTH: 116
<212> TYPE: PRT
<213> ORGANISM: Artificial Sequence
<220> FEATURE:
<223> OTHER INFORMATION: Human TREM1 mutant 50_97

<400> SEQUENCE: 281

```
Ala Thr Lys Leu Thr Glu Glu Lys Tyr Glu Leu Lys Glu Gly Gln Thr
1               5                   10                  15

Leu Asp Val Lys Cys Asp Tyr Thr Leu Glu Lys Phe Ala Ser Ser Gln
            20                  25                  30
```

```
Lys Ala Trp Gln Ile Ile Arg Asp Gly Glu Met Pro Lys Thr Leu Ala
        35                  40                  45

Cys Thr Glu Arg Pro Ser Lys Asn Ser His Pro Val Gln Val Gly Arg
    50                  55                  60

Ile Ile Leu Glu Asp Tyr His Asp His Gly Leu Leu Arg Val Arg Met
65                  70                  75                  80

Val Asn Leu Gln Val Glu Asp Ser Gly Leu Tyr Gln Cys Val Ile Tyr
                85                  90                  95

Gln Ala Pro Lys Glu Pro His Met Leu Phe Asp Arg Ile Arg Leu Val
            100                 105                 110

Val Thr Leu Glu
        115


<210> SEQ ID NO 282
<211> LENGTH: 116
<212> TYPE: PRT
<213> ORGANISM: Artificial Sequence
<220> FEATURE:
<223> OTHER INFORMATION: Human TREM1 mutant  51_98

<400> SEQUENCE: 282

Ala Thr Lys Leu Thr Glu Glu Lys Tyr Glu Leu Lys Glu Gly Gln Thr
1               5                   10                  15

Leu Asp Val Lys Cys Asp Tyr Thr Leu Glu Lys Phe Ala Ser Ser Gln
            20                  25                  30

Lys Ala Trp Gln Ile Ile Arg Asp Gly Glu Met Pro Lys Thr Leu Ala
        35                  40                  45

Cys Thr Glu Arg Pro Ser Lys Asn Ser His Pro Val Gln Val Gly Arg
    50                  55                  60

Ile Ile Leu Glu Asp Tyr His Asp His Gly Leu Leu Arg Val Arg Met
65                  70                  75                  80

Val Asn Leu Gln Val Glu Asp Ser Gly Leu Tyr Gln Cys Val Ile Tyr
                85                  90                  95

Gln Pro Ala Lys Glu Pro His Met Leu Phe Asp Arg Ile Arg Leu Val
            100                 105                 110

Val Thr Leu Glu
        115


<210> SEQ ID NO 283
<211> LENGTH: 116
<212> TYPE: PRT
<213> ORGANISM: Artificial Sequence
<220> FEATURE:
<223> OTHER INFORMATION: Human TREM1 mutant  52_99

<400> SEQUENCE: 283

Ala Thr Lys Leu Thr Glu Glu Lys Tyr Glu Leu Lys Glu Gly Gln Thr
1               5                   10                  15

Leu Asp Val Lys Cys Asp Tyr Thr Leu Glu Lys Phe Ala Ser Ser Gln
            20                  25                  30

Lys Ala Trp Gln Ile Ile Arg Asp Gly Glu Met Pro Lys Thr Leu Ala
        35                  40                  45

Cys Thr Glu Arg Pro Ser Lys Asn Ser His Pro Val Gln Val Gly Arg
    50                  55                  60

Ile Ile Leu Glu Asp Tyr His Asp His Gly Leu Leu Arg Val Arg Met
65                  70                  75                  80

Val Asn Leu Gln Val Glu Asp Ser Gly Leu Tyr Gln Cys Val Ile Tyr
                85                  90                  95
```

Gln Pro Pro Ala Glu Pro His Met Leu Phe Asp Arg Ile Arg Leu Val
100 105 110

Val Thr Leu Glu
115

<210> SEQ ID NO 284
<211> LENGTH: 116
<212> TYPE: PRT
<213> ORGANISM: Artificial Sequence
<220> FEATURE:
<223> OTHER INFORMATION: Human TREM1 mutant 53_100

<400> SEQUENCE: 284

Ala Thr Lys Leu Thr Glu Glu Lys Tyr Glu Leu Lys Glu Gly Gln Thr
1 5 10 15

Leu Asp Val Lys Cys Asp Tyr Thr Leu Glu Lys Phe Ala Ser Ser Gln
20 25 30

Lys Ala Trp Gln Ile Ile Arg Asp Gly Glu Met Pro Lys Thr Leu Ala
35 40 45

Cys Thr Glu Arg Pro Ser Lys Asn Ser His Pro Val Gln Val Gly Arg
50 55 60

Ile Ile Leu Glu Asp Tyr His Asp His Gly Leu Leu Arg Val Arg Met
65 70 75 80

Val Asn Leu Gln Val Glu Asp Ser Gly Leu Tyr Gln Cys Val Ile Tyr
85 90 95

Gln Pro Pro Lys Ala Pro His Met Leu Phe Asp Arg Ile Arg Leu Val
100 105 110

Val Thr Leu Glu
115

<210> SEQ ID NO 285
<211> LENGTH: 116
<212> TYPE: PRT
<213> ORGANISM: Artificial Sequence
<220> FEATURE:
<223> OTHER INFORMATION: Human TREM1 mutant 54_101

<400> SEQUENCE: 285

Ala Thr Lys Leu Thr Glu Glu Lys Tyr Glu Leu Lys Glu Gly Gln Thr
1 5 10 15

Leu Asp Val Lys Cys Asp Tyr Thr Leu Glu Lys Phe Ala Ser Ser Gln
20 25 30

Lys Ala Trp Gln Ile Ile Arg Asp Gly Glu Met Pro Lys Thr Leu Ala
35 40 45

Cys Thr Glu Arg Pro Ser Lys Asn Ser His Pro Val Gln Val Gly Arg
50 55 60

Ile Ile Leu Glu Asp Tyr His Asp His Gly Leu Leu Arg Val Arg Met
65 70 75 80

Val Asn Leu Gln Val Glu Asp Ser Gly Leu Tyr Gln Cys Val Ile Tyr
85 90 95

Gln Pro Pro Lys Glu Ala His Met Leu Phe Asp Arg Ile Arg Leu Val
100 105 110

Val Thr Leu Glu
115

<210> SEQ ID NO 286
<211> LENGTH: 116
<212> TYPE: PRT

<213> ORGANISM: Artificial Sequence
<220> FEATURE:
<223> OTHER INFORMATION: Human TREM1 mutant 55_102

<400> SEQUENCE: 286

Ala Thr Lys Leu Thr Glu Glu Lys Tyr Glu Leu Lys Glu Gly Gln Thr
1 5 10 15

Leu Asp Val Lys Cys Asp Tyr Thr Leu Glu Lys Phe Ala Ser Ser Gln
20 25 30

Lys Ala Trp Gln Ile Ile Arg Asp Gly Glu Met Pro Lys Thr Leu Ala
35 40 45

Cys Thr Glu Arg Pro Ser Lys Asn Ser His Pro Val Gln Val Gly Arg
50 55 60

Ile Ile Leu Glu Asp Tyr His Asp His Gly Leu Leu Arg Val Arg Met
65 70 75 80

Val Asn Leu Gln Val Glu Asp Ser Gly Leu Tyr Gln Cys Val Ile Tyr
85 90 95

Gln Pro Pro Lys Glu Pro Ala Met Leu Phe Asp Arg Ile Arg Leu Val
100 105 110

Val Thr Leu Glu
115

<210> SEQ ID NO 287
<211> LENGTH: 116
<212> TYPE: PRT
<213> ORGANISM: Artificial Sequence
<220> FEATURE:
<223> OTHER INFORMATION: Human TREM1 mutant 56_103

<400> SEQUENCE: 287

Ala Thr Lys Leu Thr Glu Glu Lys Tyr Glu Leu Lys Glu Gly Gln Thr
1 5 10 15

Leu Asp Val Lys Cys Asp Tyr Thr Leu Glu Lys Phe Ala Ser Ser Gln
20 25 30

Lys Ala Trp Gln Ile Ile Arg Asp Gly Glu Met Pro Lys Thr Leu Ala
35 40 45

Cys Thr Glu Arg Pro Ser Lys Asn Ser His Pro Val Gln Val Gly Arg
50 55 60

Ile Ile Leu Glu Asp Tyr His Asp His Gly Leu Leu Arg Val Arg Met
65 70 75 80

Val Asn Leu Gln Val Glu Asp Ser Gly Leu Tyr Gln Cys Val Ile Tyr
85 90 95

Gln Pro Pro Lys Glu Pro His Ala Leu Phe Asp Arg Ile Arg Leu Val
100 105 110

Val Thr Leu Glu
115

<210> SEQ ID NO 288
<211> LENGTH: 116
<212> TYPE: PRT
<213> ORGANISM: Artificial Sequence
<220> FEATURE:
<223> OTHER INFORMATION: Human TREM1 mutant 57_104

<400> SEQUENCE: 288

Ala Thr Lys Leu Thr Glu Glu Lys Tyr Glu Leu Lys Glu Gly Gln Thr
1 5 10 15

Leu Asp Val Lys Cys Asp Tyr Thr Leu Glu Lys Phe Ala Ser Ser Gln
20 25 30

```
Lys Ala Trp Gln Ile Ile Arg Asp Gly Glu Met Pro Lys Thr Leu Ala
        35                  40                  45

Cys Thr Glu Arg Pro Ser Lys Asn Ser His Pro Val Gln Val Gly Arg
    50                  55                  60

Ile Ile Leu Glu Asp Tyr His Asp His Gly Leu Leu Arg Val Arg Met
65                  70                  75                  80

Val Asn Leu Gln Val Glu Asp Ser Gly Leu Tyr Gln Cys Val Ile Tyr
                85                  90                  95

Gln Pro Pro Lys Glu Pro His Met Ala Phe Asp Arg Ile Arg Leu Val
            100                 105                 110

Val Thr Leu Glu
        115


<210> SEQ ID NO 289
<211> LENGTH: 116
<212> TYPE: PRT
<213> ORGANISM: Artificial Sequence
<220> FEATURE:
<223> OTHER INFORMATION: Human TREM1 mutant  58_106

<400> SEQUENCE: 289

Ala Thr Lys Leu Thr Glu Glu Lys Tyr Glu Leu Lys Glu Gly Gln Thr
1               5                   10                  15

Leu Asp Val Lys Cys Asp Tyr Thr Leu Glu Lys Phe Ala Ser Ser Gln
            20                  25                  30

Lys Ala Trp Gln Ile Ile Arg Asp Gly Glu Met Pro Lys Thr Leu Ala
        35                  40                  45

Cys Thr Glu Arg Pro Ser Lys Asn Ser His Pro Val Gln Val Gly Arg
    50                  55                  60

Ile Ile Leu Glu Asp Tyr His Asp His Gly Leu Leu Arg Val Arg Met
65                  70                  75                  80

Val Asn Leu Gln Val Glu Asp Ser Gly Leu Tyr Gln Cys Val Ile Tyr
                85                  90                  95

Gln Pro Pro Lys Glu Pro His Met Leu Phe Ala Arg Ile Arg Leu Val
            100                 105                 110

Val Thr Leu Glu
        115


<210> SEQ ID NO 290
<211> LENGTH: 116
<212> TYPE: PRT
<213> ORGANISM: Artificial Sequence
<220> FEATURE:
<223> OTHER INFORMATION: Human TREM1 mutant  59_109

<400> SEQUENCE: 290

Ala Thr Lys Leu Thr Glu Glu Lys Tyr Glu Leu Lys Glu Gly Gln Thr
1               5                   10                  15

Leu Asp Val Lys Cys Asp Tyr Thr Leu Glu Lys Phe Ala Ser Ser Gln
            20                  25                  30

Lys Ala Trp Gln Ile Ile Arg Asp Gly Glu Met Pro Lys Thr Leu Ala
        35                  40                  45

Cys Thr Glu Arg Pro Ser Lys Asn Ser His Pro Val Gln Val Gly Arg
    50                  55                  60

Ile Ile Leu Glu Asp Tyr His Asp His Gly Leu Leu Arg Val Arg Met
65                  70                  75                  80

Val Asn Leu Gln Val Glu Asp Ser Gly Leu Tyr Gln Cys Val Ile Tyr
```

```
                85                  90                  95

Gln Pro Pro Lys Glu Pro His Met Leu Phe Asp Arg Ile Ala Leu Val
            100                 105                 110

Val Thr Leu Glu
        115


<210> SEQ ID NO 291
<211> LENGTH: 116
<212> TYPE: PRT
<213> ORGANISM: Artificial Sequence
<220> FEATURE:
<223> OTHER INFORMATION: Human TREM1 mutant  60_111

<400> SEQUENCE: 291

Ala Thr Lys Leu Thr Glu Glu Lys Tyr Glu Leu Lys Glu Gly Gln Thr
1               5                   10                  15

Leu Asp Val Lys Cys Asp Tyr Thr Leu Glu Lys Phe Ala Ser Ser Gln
            20                  25                  30

Lys Ala Trp Gln Ile Ile Arg Asp Gly Glu Met Pro Lys Thr Leu Ala
        35                  40                  45

Cys Thr Glu Arg Pro Ser Lys Asn Ser His Pro Val Gln Val Gly Arg
    50                  55                  60

Ile Ile Leu Glu Asp Tyr His Asp His Gly Leu Leu Arg Val Arg Met
65                  70                  75                  80

Val Asn Leu Gln Val Glu Asp Ser Gly Leu Tyr Gln Cys Val Ile Tyr
                85                  90                  95

Gln Pro Pro Lys Glu Pro His Met Leu Phe Asp Arg Ile Arg Leu Ala
            100                 105                 110

Val Thr Leu Glu
        115


<210> SEQ ID NO 292
<211> LENGTH: 116
<212> TYPE: PRT
<213> ORGANISM: Artificial Sequence
<220> FEATURE:
<223> OTHER INFORMATION: Human TREM1 mutant  61_113

<400> SEQUENCE: 292

Ala Thr Lys Leu Thr Glu Glu Lys Tyr Glu Leu Lys Glu Gly Gln Thr
1               5                   10                  15

Leu Asp Val Lys Cys Asp Tyr Thr Leu Glu Lys Phe Ala Ser Ser Gln
            20                  25                  30

Lys Ala Trp Gln Ile Ile Arg Asp Gly Glu Met Pro Lys Thr Leu Ala
        35                  40                  45

Cys Thr Glu Arg Pro Ser Lys Asn Ser His Pro Val Gln Val Gly Arg
    50                  55                  60

Ile Ile Leu Glu Asp Tyr His Asp His Gly Leu Leu Arg Val Arg Met
65                  70                  75                  80

Val Asn Leu Gln Val Glu Asp Ser Gly Leu Tyr Gln Cys Val Ile Tyr
                85                  90                  95

Gln Pro Pro Lys Glu Pro His Met Leu Phe Asp Arg Ile Arg Leu Val
            100                 105                 110

Val Ala Leu Glu
        115


<210> SEQ ID NO 293
<211> LENGTH: 116
```

-continued

```
<212> TYPE: PRT
<213> ORGANISM: Artificial Sequence
<220> FEATURE:
<223> OTHER INFORMATION: Human TREM1 mutant  62_114

<400> SEQUENCE: 293

Ala Thr Lys Leu Thr Glu Glu Lys Tyr Glu Leu Lys Glu Gly Gln Thr
1               5                   10                  15

Leu Asp Val Lys Cys Asp Tyr Thr Leu Glu Lys Phe Ala Ser Ser Gln
            20                  25                  30

Lys Ala Trp Gln Ile Ile Arg Asp Gly Glu Met Pro Lys Thr Leu Ala
        35                  40                  45

Cys Thr Glu Arg Pro Ser Lys Asn Ser His Pro Val Gln Val Gly Arg
    50                  55                  60

Ile Ile Leu Glu Asp Tyr His Asp His Gly Leu Leu Arg Val Arg Met
65                  70                  75                  80

Val Asn Leu Gln Val Glu Asp Ser Gly Leu Tyr Gln Cys Val Ile Tyr
                85                  90                  95

Gln Pro Pro Lys Glu Pro His Met Leu Phe Asp Arg Ile Arg Leu Val
            100                 105                 110

Val Thr Ala Glu
        115


<210> SEQ ID NO 294
<211> LENGTH: 116
<212> TYPE: PRT
<213> ORGANISM: Artificial Sequence
<220> FEATURE:
<223> OTHER INFORMATION: Human TREM1 mutant  63_115

<400> SEQUENCE: 294

Ala Thr Lys Leu Thr Glu Glu Lys Tyr Glu Leu Lys Glu Gly Gln Thr
1               5                   10                  15

Leu Asp Val Lys Cys Asp Tyr Thr Leu Glu Lys Phe Ala Ser Ser Gln
            20                  25                  30

Lys Ala Trp Gln Ile Ile Arg Asp Gly Glu Met Pro Lys Thr Leu Ala
        35                  40                  45

Cys Thr Glu Arg Pro Ser Lys Asn Ser His Pro Val Gln Val Gly Arg
    50                  55                  60

Ile Ile Leu Glu Asp Tyr His Asp His Gly Leu Leu Arg Val Arg Met
65                  70                  75                  80

Val Asn Leu Gln Val Glu Asp Ser Gly Leu Tyr Gln Cys Val Ile Tyr
                85                  90                  95

Gln Pro Pro Lys Glu Pro His Met Leu Phe Asp Arg Ile Arg Leu Val
            100                 105                 110

Val Thr Leu Ala
        115
```

ANTIBODIES

FIELD OF THE INVENTION

The present invention relates to anti-TREM1 antibodies and their use in the treatment of neurological disorders, and more particularly, for the treatment of amyotrophic lateral sclerosis (ALS) and Alzheimer's disease

BACKGROUND

Triggering receptors expressed on myeloid cells (TREM) are receptors including immune-activating and -inhibitory isoforms encoded by an MHC gene cluster mapping to human chromosome 6p21 and mouse chromosome 17. TREMs are members of the immunoglobulin (Ig) superfamily, primarily expressed in cells of the myeloid lineage including monocytes, neutrophils, and dendritic cells in the periphery and microglia in the central nervous system (CNS). Triggering receptor expressed on myeloid cells-1 (TREM1), otherwise known as cluster of differentiation 354 is the first member of the TREM family to be identified and it has limited homology with other receptors of the Ig superfamily. TREM1 is a transmembrane glycoprotein with a single Ig-like domain, a transmembrane region with a (+) charged lysine residue interacting with a negatively charged aspartic acid on its signaling partner DAP12 and a short cytoplasmic tail that lacks any signaling domains.

TREM1 activation through interactions with its proposed ligand peptidoglycan recognition protein 1 (PGLYRP1), high mobility group B1 (HMGB1), soluble CD177, heat shock protein 70 (HSP70), extracellular cold-inducible RNA-binding protein (eCIRP) has been proposed to induce formation of an "head-to-tail" homodimer. Dimer crosslinking triggers the phosphorylation of the immune receptor tyrosine-based activating motif (ITAM) on the recruited DAP12, which enables signaling and function by providing a docking site for spleen tyrosine kinase (SYK) and its downstream signaling partners including zeta-chain-associated protein kinase 70 (ZAP70), casitas b-lineage lymphoma (Cbl), son of sevenless (SOS) and growth factor receptor binding protein 2 (GRB2). These interactions trigger downstream signal transduction through phosphatidylinositol 3-kinase (PI3K), phospholipase-C-γ2 (PLC-γ2) and the ERK pathways. These events are followed by calcium mobilization, activation of transcription factors including ETS-containing protein (ELK1), nuclear factor of activated T-cells (NFAT), AP1, c-fos, c-Jun and NF-κB. This pathway is shared with another member of the TREM family TREM2.

Unlike TREM1 which is clearly an immune activator TREM2 can act as both pro- and anti-inflammatory when binding to high and low affinity ligands respectively. Under homeostatic conditions TREM2 interaction with low affinity ligands keeps the pathway in check maintaining homeostasis (Konishi H., et al. Frontiers Cellular Neuroscience 2018).

In neuroinflammatory neurodegenerative conditions intracellular factors (among others TREM1 ligands) otherwise known as Damage Associated Molecular Patterns (DAMPs) are spilled from dying neurons and activate surveilling microglia through TREM1 and other pattern recognition receptors. TREM1-DAMPs interaction overrides TREM2 activity resulting in microglia/innate immune activation, direct neurotoxicity and destruction of synaptic architecture through aberrant phagocytosis. Beyond its "Yin and Yang" dynamic with TREM2 in pathway regulation TREM1 carries unique and distinct functions as a potentiator of other key regulators of innate immune response including Toll-like (TLRs) and NOD-like receptor families. Amplification of these receptors occurs either through TREM1-induced overexpression of TLRs, their downstream nodes such as MYD88 and IKk or through direct cross-linking through TREM1 ligand complex formed between a TLR agonist and a TREM1 ligand as is the case with PGN (a TLR2/TLR4 stimulator) and PGLYRP1 (TREM1 ligand).

The consequence of TREM1 multi-pathway activation results in amplified innate immune/microglial pro-inflammatory responses including cytokine and chemokine release, upregulation of costimulatory molecules/antigen presentation and aberrant phagocytic activity. downstream (Buchon et al, 2000). These processes are a common denominator to the pathobiology in various neurodegenerative, neurodevelopmental and autoimmune central nervous system disorders. Human genetics including Genome Wide Association studies (GWAS) have implicated TREM2, several nodes downstream of TREM1/TREM2 pathway such as DAP12, Syk, PLCγ2 and TLRs as risk genes in various neurodegenerative disease.

U.S. Pat. No. 9,000,127 provides anti-TREM1 antibodies that disrupt the interaction of TREM1 with its ligand. The disclosed antibodies are provided for the treatment of individuals with an inflammatory disease, such as rheumatoid arthritis and inflammatory bowel disease.

WO 2017/152102 discloses antibodies that bind to a TREM1 protein and modulate or enhance one or more TREM1 activities.

SUMMARY OF THE INVENTION

The present invention addresses the need for new treatments of neurological disorders by providing anti-TREM1 antibodies with the functional and structural properties as described herein.

In particular, the present invention provides an antibody that binds to human TREM1, comprising:

- a light chain variable region comprising:
  - a CDR-L1 comprising SEQ ID NO:11,
  - a CDR-L2 comprising SEQ ID NO:12, and
  - a CDR-L3 comprising SEQ ID NO:13;
- and a heavy chain variable region comprising:
  - a CDR-H1 comprising SEQ ID NO:14,
  - a CDR-H2 comprising SEQ ID NO:15, and
  - a CDR-H3 comprising SEQ ID NO:16.

BRIEF DESCRIPTION OF THE DRAWINGS

The present invention is described below by reference to the following drawings, in which:

FIG. 1 shows humanization of antibody 12172 light chain. Different variants generated for that chain are also shown. The CDR sequences are underlined.

FIG. 2 shows humanization of antibody 12172 heavy chain. Different variants generated for that chain are also shown. The CDR sequences are underlined.

FIG. 8 shows efficacy of 12172 gL2gH11 hIgG4P on TNF-α and IL-6 release from healthy control and Alzheimer Disease (AD) PBMCs.

FIG. 10 shows efficacy of 12172 gL2gH11 hIgG4P on pro-inflammatory cytokine and chemokine release from ALS and AD PBMCs.

FIGS. 11A-11C show volcano plots showing Differentially Expressed Genes (DEGs) (considering an FDR of 0.05) following treatment of human monocytes with 12172 antibody variants (11A and 11B) or 0318-IgG1.3f (11C) and stimulation with TREM1 ligand complex (compared to isotype control).

FIGS. 12A-12C show volcano plots showing DEGs (considering an FDR of 0.05) following treatment of human monocytes with 12172 antibody variants (12A and 12B) or 0318-IgG1.3f (12C) and stimulation with apoptotic human iPSC-derived motor neurons (compared to isotype control).

DETAILED DESCRIPTION OF THE INVENTION

Abbreviations

TABLE 1

Figure 3B:
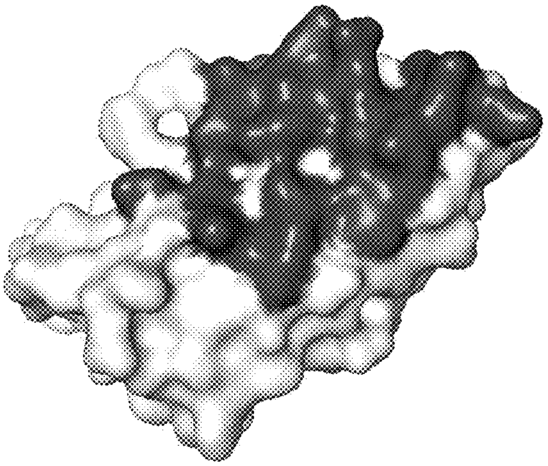
FIGS. 3A and 3B show crystal structure of human TREM1 bound to PGLYRP1 and 12172 rabbit Fab. (3A) Crystal structure of human TREM1 bound to PGLYRP1. TREM1 residues with atoms within 4 Angstroms of any atom belonging to PGLYRP1 are highlighted in black. (3B) Crystal structure of human TREM1 bound to 12172 Rabbit Fab. TREM1 residues with atoms within 4 Angstroms of any atom belonging to 12172 are highlighted in black.

| Abbreviations used throughout the specification | |
|---|---|
| ADCC | antibody-dependent cellular cytotoxicity |
| CDC | complement dependent cytotoxicity |
| CDR | complementarity-determining region |
| CH1, CH2, CH3 | constant heavy domains 1, 2, 3 |
| CL | constant light domain |
| dsscFv | disulphide stabilised scFv |
| Fab | fragment antigen-binding |
| Fc | fragment crystallizable |
| FR1, FR2, FR3, FR4 | framework regions 1, 2, 3, 4 |
| Fv | variable domain fragment |
| HVR | hyper-variable region |
| KD | constant of dissociation |
| mAb | monoclonal antibody |
| scFv | single chain variable-fragment |
| VH | Heavy chain variable region |
| VHH | single domain antibody (or a camelid) |

TABLE 1-continued

| Abbreviations used throughout the specification | |
|---|---|
| VL | variable light region |
| VNAR | variable domain of IgNAR |

TABLE 2

| Amino acids abbreviations | | |
|---|---|---|
| Abbreviation | 1 letter abbreviation | Amino acid name |
| Ala | A | Alanine |
| Arg | R | Arginine |
| Asn | N | Asparagine |
| Asp | D | Aspartic acid |
| Cys | C | Cysteine |
| Gln | Q | Glutamine |
| Glu | E | Glutamic acid |
| Gly | G | Glycine |
| His | H | Histidine |
| Ile | I | Isoleucine |
| Leu | L | Leucine |
| Lys | K | Lysine |
| Met | M | Methionine |
| Phe | F | Phenylalanine |
| Pro | P | Proline |
| Pyl | O | Pyrrolysine |
| Ser | S | Serine |
| Sec | U | Selenocysteine |
| Thr | T | Threonine |
| Trp | W | Tryptophan |
| Tyr | Y | Tyrosine |
| Val | V | Valine |

Definitions

The following terms are used throughout the specification.

The term "acceptor human framework" is used herein is a framework comprising the amino acid sequence of a light chain variable domain (VL) framework or a heavy chain variable domain (VH) framework derived from a human immunoglobulin framework or a human consensus framework. An acceptor human framework derived from a human immunoglobulin framework or a human consensus framework may comprise the same amino acid sequence thereof, or it may contain amino acid sequence changes.

The term "affinity" refers to the strength of all noncovalent interactions between an antibody thereof and the target protein. Unless indicated otherwise, as used herein, the term "binding affinity" refers to intrinsic binding affinity which reflects a 1:1 interaction between members of a binding pair (e.g., antibody and antigen). The affinity of a molecule for its binding partner can be generally represented by the dissociation constant (KD). Affinity can be measured by common methods known in the art, including those described herein.

The term "affinity matured" in the context of antibody refers to an antibody with one or more alterations in the hypervariable regions, compared to a parent antibody which does not possess such alterations, where such alterations resulting in an improvement in the affinity of the antibody for antigen.

The term "antibody" herein is used in the broadest sense and encompasses various antibody structures, including but not limited to monoclonal antibodies, polyclonal antibodies, and multi-specific antibodies as long as they exhibit the desired antigen-binding activity. The term antibody as used herein relates to whole (full-length) antibodies (i.e. comprising the elements of two heavy chains and two light chains) and functionally active fragments thereof (i.e., molecules that contain an antigen binding domain that specifically binds an antigen, also termed antibody fragments or antigen-binding fragments). Features described herein with respect to antibodies also apply to antibody fragments unless context dictates otherwise. The term "antibody" encompasses monovalent, i.e., antibodies comprising only one antigen binding domain (e.g. one-armed antibodies comprising a full-length heavy chain and a full-length light chain interconnected, also termed "half-antibody"), and multivalent antibodies, i. e. antibodies comprising more than one antigen binding domain, e.g bivalent.

The term "antibody binding to the same epitope as a reference antibody" refers to an antibody that blocks binding of the reference antibody to its antigen in a competition assay by 50% or more, and conversely, the reference antibody blocks binding of the antibody to its antigen in a competition assay by 50% or more.

The term "Antibody-dependent cellular cytotoxicity" or "ADCC" is a mechanism for inducing cell death that depends upon the interaction of antibody-coated target cells with effector cells possessing lytic activity, such as natural killer cells, monocytes, macrophages and neutrophils via Fc gamma receptors (FcγR) expressed on effector cells.

The term "antigen-binding fragment" as employed herein refers to functionally active antibody binding fragments including but not limited to Fab, modified Fab, Fab', modified Fab', F(ab')2, Fv, single domain antibodies, scFv, Fv, bi, tri or tetra-valent antibodies, Bis-scFv, diabodies, triabodies, tetrabodies and epitope-binding fragments of any of the above (see for example Holliger and Hudson, 2005, Nature Biotech. 23(9): 1126-1136; Adair and Lawson, 2005, Drug Design Reviews—Online 2(3), 209-217). A "binding fragment" as employed herein refers to a fragment capable of binding a target peptide or antigen with sufficient affinity to characterize the fragment as specific for the peptide or antigen.

The term "antibody variant" refers to a polypeptide, for example, an antibody possessing the desired characteristics described herein and comprising a VH and/or a VL that has at least about 80% amino acid sequence identity with a VH and/or a VL of the reference antibody. Such antibody variants include, for instance, antibodies wherein one or more amino acid residues are added to or deleted from the VH and/or a VL domain. Ordinarily, an antibody variant will have at least about 80% amino acid sequence identity, alternatively at least about 85%, 90%, 95%, 96%, 97%, 98%, or 99% amino acid sequence identity, to an antibody described herein. Optionally, variant antibodies will have no more than one conservative amino acid substitution as compared to an antibody sequence provided herein, alternatively no more than about any of 2, 3, 4, 5, 6, 7, 8, 9, or 10 conservative amino acid substitutions as compared to an antibody sequence provided herein. In embodiments, an "antibody variant" refers to an antibody or antigen-binding fragment thereof comprising a VH and/or a VL wherein the non-CDR regions of the antibody or antigen-binding fragment thereof has at least about 85%, 90%, 95%, 96%, 97%, 98%, or 99% amino acid sequence identity, to an antibody described herein.

The term "antigen-binding domain" as employed herein refers to a portion of the antibody, which comprises a part or the whole of one or more variable domains, for example a part or the whole of a pair of variable domains VH and VL, that interact specifically with the target antigen. A binding domain may comprise a single domain antibody. Each binding domain may be monovalent. Each binding domain may comprise no more than one VH and one VL.

The term "bispecific" or "bispecific antibody" as employed herein refers to an antibody with two antigen specificities.

The term "complementarity determining regions" or "CDRs" refers to generally, antibodies comprise six CDRs: three in the VH (H1, H2, H3), and three in the VL (L1, L2, L3). The CDRs of the heavy chain variable domain are located at residues 31-35 (CDR-H1), residues 50-65 (CDR-H2) and residues 95-102 (CDR-H3) according to the Kabat numbering system. However, according to Chothia (Chothia, C. and Lesk, A. M. J. Mol. Biol., 196, 901-917 (1987)), the loop equivalent to CDR-H1 extends from residue 26 to residue 32. Thus, unless indicated otherwise "CDR-H1" as employed herein is intended to refer to residues 26 to 35, as described by a combination of the Kabat numbering system and Chothia's topological loop definition. The CDRs of the light chain variable domain are located at residues 24-34 (CDR-L1), residues 50-56 (CDR-L2) and residues 89-97 (CDR-L3) according to the Kabat numbering system. Unless indicated otherwise, CDR residues and other residues in the variable domain (e.g., FR residues) are numbered herein according to Kabat.

The term "chimeric" antibody refers to an antibody in which the variable domain (or at least a portion thereof) of the heavy and/or light chain is derived from a particular source or species, while the remainder of the heavy and/or light chain (i.e. the constant domains) is derived from a different source or species. (Morrison; PNAS 81, 6851 (1984)). Chimeric antibodies can for instance comprise non-human variable domains and human constant domains. Chimeric antibodies are typically produced using recombinant DNA methods. A subcategory of "chimeric antibodies" is "humanized antibodies".

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG1, IgG2, IgG3, IgG4, IgA1, and IgA2. The heavy chain constant domains that correspond to the different classes of immunoglobulins are called α, δ, ε, γ, and, respectively.

The term "complement-dependent cytotoxicity", or "CDC" refers to a mechanism for inducing cell death in which an Fc effector domain of a target-bound antibody binds and activates complement component C1q which in turn activates the complement cascade leading to target cell death.

The terms "constant domain(s)" or "constant region", as used herein are used interchangeably to refer to the domain(s) of an antibody which is outside the variable regions. The constant domains are identical in all antibodies of the same isotype but are different from one isotype to another. Typically, the constant region of a heavy chain is formed, from N to C terminal, by CH1-hinge —CH2-CH3-optionally CH4, comprising three or four constant domains.

The term "competing antibody" or "cross-competing antibody" shall be interpreted as meaning that the claimed antibody binds to either (i) the same position on the antigen to which the reference antibody binds, or (ii) a position on the antigen where the antibody sterically hinders the binding of the reference antibody to the antigen.

The term "Derivatives" as used herein is intended to include reactive derivatives, for example thiol-selective reactive groups such as maleimides and the like. The reactive group may be linked directly or through a linker segment to the polymer. It will be appreciated that the residue of such a group will in some instances form part of the product as the linking group between the antibody fragment and the polymer.

The term "derived from" in the context of generating variable sequences refers to the fact that the sequence employed or a sequence highly similar to the sequence employed was obtained from the original genetic material, such as the light or heavy chain of an antibody.

The term "diabody" as employed herein refers to two Fv pairs, a first VH/VL pair and a further VH/VL pair which have two inter-Fv linkers, such that the VH of a first Fv is linked to the VL of the second Fv and the VL of the first Fv is linked to the VH of the second Fv.

The term "DiFab" as employed herein refers to two Fab molecules linked via their C-terminus of the heavy chains.

The term "DiFab'" as employed herein refers to two Fab' molecules linked via one or more disulfide bonds in the hinge region thereof.

The term "dsscFv" or "disulphide-stabilised single chain variable fragment" as employed herein refer to a single chain variable fragment which is stabilised by a peptide linker between the VH and VL variable domain and also includes an inter-domain disulphide bond between VH and VL. (see for example, Weatherill et al., Protein Engineering, Design & Selection, 25 (321-329), 2012, WO2007109254.

The term "DVD-Ig" (also known as dual V domain IgG) refers to a full-length antibody with 4 additional variable domains, one on the N-terminus of each heavy and each light chain.

The term "effector functions" refer to those biological activities attributable to the Fc region of an antibody, which vary with the antibody isotype. Examples of antibody effector functions include: Clq binding and complement dependent cytotoxicity (CDC), Fc receptor binding, antibody-dependent cell-mediated cytotoxicity (ADCC), phagocytosis, down regulation of cell surface receptors (e.g. B cell receptor), and B cell activation.

The term "effector molecule" as used herein includes, for example, antineoplastic agents, drugs, toxins, biologically active proteins, for example enzymes, other antibody or antibody fragments, synthetic or naturally occurring polymers, nucleic acids and fragments thereof e.g. DNA, RNA and fragments thereof, radionuclides, particularly radioiodide, radioisotopes, chelated metals, nanoparticles and reporter groups such as fluorescent compounds or compounds which may be detected by NMR or ESR spectroscopy.

The term "epitope" or "binding site" in the context of antibodies refer to a site (or a part) on an antigen to which the paratope of an antibody binds or recognizes. Epitopes can be formed both from contiguous amino acids (also often called "linear epitopes") or noncontiguous amino acids formed by tertiary folding of a protein (often called "conformational epitopes"). Epitopes formed from contiguous amino acids are typically retained on exposure to denaturing solvents whereas epitopes formed by folding are typically lost on treatment with denaturing solvents. An epitope typically includes at least 3, and more usually, at least 5-10 amino acids in a unique spatial conformation. Epitopes usually consist of chemically active surface groups of molecules such as amino acids, sugar side chains and usually have specific 3D structural and charge characteristics.

The "EU index" or "EU index as in Kabat" or "EU numbering scheme" refers to the numbering of the EU antibody (Edelman et al., 1969, Proc Natl Acad Sci USA 63:78-85). Such is generally used when referring to a residue in an antibody heavy chain constant region (e.g., as reported in Kabat et al). Unless stated otherwise, the EU numbering scheme is used to refer to residues in antibody heavy chain constant regions described herein.

The term "Fab" refers to as used herein refers to an antibody fragment comprising a light chain fragment comprising a VL (variable light) domain and a constant domain of a light chain (CL), and a VH (variable heavy) domain and a first constant domain (CH1) of a heavy chain. Dimers of a Fab' according to the present disclosure create a F(ab')2 where, for example, dimerization may be through the hinge.

The term "Fab'-Fv" as employed herein is similar to FabFv, wherein the Fab portion is replaced by a Fab'. The format may be provided as a PEGylated version thereof.

The term "Fab'-scFv" as employed herein is a Fab' molecule with a scFv appended on the C-terminal of the light or heavy chain.

The term "Fab-dsFv" as employed herein refers to a FabFv wherein an intra-Fv disulfide bond stabilises the appended C-terminal variable regions. The format may be provided as a PEGylated version thereof.

The term "Fab-Fv" as employed herein refers to a Fab fragment with a variable region appended to the C-terminal of each of the following, the CH1 of the heavy chain and CL of the light chain. The format may be provided as a PEGylated version thereof.

The term "Fab-scFv" as employed herein is a Fab molecule with a scFv appended on the C-terminal of the light or heavy chain.

The term "Fc", "Fc fragment", and "Fc region" are used interchangeably to refer to the C-terminal region of an antibody comprising the constant region of an antibody excluding the first constant region immunoglobulin domain. Thus, Fc refers to the last two constant domains, CH2 and CH3, of IgA, IgD, and IgG, or the last three constant domains of IgE and IgM, and the flexible hinge N-terminal to these domains. The human IgG1 heavy chain Fc region is defined herein to comprise residues C226 to its carboxyl-terminus, wherein the numbering is according to the EU index. In the context of human IgG1, the lower hinge refers to positions 226-236, the CH2 domain refers to positions 237-340 and the CH3 domain refers to positions 341-447 according to the EU index. The corresponding Fc region of other immunoglobulins can be identified by sequence alignments.

The term "Framework" or "FR" refers to variable domain residues other than hypervariable region residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The term "full length antibody" used herein to refer to an antibody having a structure substantially similar to a native antibody structure or having heavy chains that contain an Fc region as defined herein. Each light chain is comprised of a light chain variable region (abbreviated herein as VL) and a light chain constant region (CL). Each heavy chain is comprised of a heavy variable region (abbreviated herein as VH) and a heavy chain constant region (CH) constituted of three constant domains CH1, CH2 and CH3, or four constant domains CH1, CH2, CH3 and CH4, depending on the Ig class. The constant regions of the antibodies may mediate the binding of the immunoglobulin to host tissues or factors, including various cells of the immune system (e.g., effector cells) and the first component (Clq) of the classical complement system.

The term "Fv" refers to two variable domains of full length antibodies, for example co-operative variable domains, such as a cognate pair or affinity matured variable domains, i.e. a VH and VL pair.

The term "highly similar" as employed in the context of amino-acid sequences is intended to refer to an amino acid sequence which over its full length is 95% similar or more, such as 96, 97, 98 or 99% similar.

The term "human antibody" refers to an antibody which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

The term "human consensus framework" refers to a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., Sequences of Proteins of Immunological Interest, Fifth Edition, NIH Publication 91-3242, Bethesda MD (1991), vols. 1-3. In some embodiments, for the VL, the subgroup is subgroup kappa I as in Kabat et al., supra. In some embodiments, for the VH, the subgroup is subgroup III as in Kabat et al. In some embodiments, for the VH, the subgroup is subgroup IV as in Kabat et al.

The term "humanized" antibody refers to an antibody comprising amino acid residues from non-human HVRs and amino acid residues from human FRs. Typically the heavy and/or light chain contains one or more CDRs (including, if desired, one or more modified CDRs) from a donor antibody (e.g. a non-human antibody such as a murine or rabbit monoclonal antibody) and is grafted into a heavy and/or light chain variable region framework of an acceptor antibody (a human antibody) (see e.g. Vaughan et al, Nature Biotechnology, 16, 535-539, 1998). The advantage of such humanized antibodies is to reduce immunogenicity to humans, while retaining the specificity and affinity of the parental non-human antibody. Rather than the entire CDR being transferred, only one or more of the specificity determining residues from any one of the CDRs described herein above can be transferred to the human antibody framework (see e.g., Kashmiri et al., 2005, Methods, 36, 25-34). A "humanized" antibody refers to a chimeric antibody comprising amino acid residues from non-human HVRs and amino acid residues from human FRs. A "humanized form" of an antibody, e.g., a non-human antibody, refers to an antibody that has undergone humanization.

The term "hypervariable region" or "HVR" as used herein refers to each of the regions of an antibody variable domain which are hypervariable in sequence ("complementarity determining regions" or "CDRs") and/or form structurally defined loops ("hypervariable loops") and/or contain the antigen-contacting residues ("antigen contacts").

The term "IC50" as used herein refers to the half maximal inhibitory concentration which is a measure of the effectiveness of a substance, such as an antibody, in inhibiting a specific biological or biochemical function. The IC50 is a quantitative measure which indicates how much of a particular substance is needed to inhibit a given biological process by 50%.

The "identity" between amino acids in the sequence indicates that at any particular position in the aligned sequences, the amino acid residue is identical between the sequences.

The term "IgG-scFv" as employed herein is a full-length antibody with a scFv on the C-terminal of each of the heavy chains or each of the light chains.

The term "IgG-V" as employed herein is a full-length antibody with a variable domain on the C-terminal of each of the heavy chains or each of the light chains.

The term "IgG1 LALA" or "hIgG1 LALA" refers mutant of the wild-type human IgG1 isoform in which amino acid substitutions L234A/L235A in the constant region of an IgG1 have been introduced.

The term "IgG4P" or "hIgG4P" refers to a mutant of the wild-type human IgG4 isoform in which amino acid 228 (according to EU numbering) is replaced by proline, as described for example in Angal et al., Molecular Immunology, 1993, 30 (1), 105-108.

The term "isolated" means, throughout this specification, that the antibody, or polynucleotide, as the case may be, exists in a physical milieu distinct from that in which it may occur in nature. The term "isolated" nucleic acid refers to a nucleic acid molecule that has been isolated from its natural environment or that has been synthetically created. An isolated nucleic acid may comprise synthetic DNA, for instance produced by chemical processing, cDNA, genomic DNA or any combination thereof.

The term "Kabat residue designations" or "Kabat" refer to the residue numbering scheme commonly used for antibodies. Such do not always correspond directly with the linear numbering of the amino acid residues. The actual linear amino acid sequence may contain fewer or additional amino acids than in the strict Kabat numbering corresponding to a shortening of, or insertion into, a structural component, whether framework or complementarity determining region (CDR), of the basic variable domain structure. The correct Kabat numbering of residues may be determined for a given antibody by alignment of residues of homology in the sequence of the antibody with a "standard" Kabat numbered sequence. For details see Kabat et al., Sequences of Proteins of Immunological Interest, 5th Ed. Public Health Service, National Institutes of Health, Bethesda, MD (1991). Unless indicated otherwise, Kabat numbering is used throughout the specification The term "KD" as used herein refers to the constant of dissociation which is obtained from the ratio of Kd to Ka (i.e. Kd/Ka) and is expressed as a molar concentration (M). Kd and Ka refers to the dissociation rate and association rate, respectively, of a particular antigen-antibody interaction. KD values for antibodies can be determined using methods well established in the art.

The term "monoclonal antibody" (or "mAb") refers to an antibody obtained from a population of substantially homogeneous antibodies, i.e. each individual of a monoclonal antibody preparation are identical except for possible mutations (e.g., naturally occurring mutations), that may be present in minor amounts. Certain differences in the protein sequences linked to post-translational modifications (for example, cleavage of the heavy chain C-terminal lysine, deamidation of asparagine residues and/or isomerisation of aspartate residues) may nevertheless exist between the various different antibody molecules present in the composition. Contrary to polyclonal antibody preparations, each monoclonal antibody of a monoclonal antibody preparation is directed against a single determinant on an antigen.

The term "multi-paratopic antibody" as employed herein refers to an antibody as described herein which comprises two or more distinct paratopes, which interact with different epitopes either from the same antigen or from two different antigens. Multi-paratopic antibodies described herein may be biparatopic, triparatopic, tetraparatopic.

The term "multispecific" or "multi-specific antibody" as employed herein refers to an antibody as described herein which has at least two binding domains, i.e. two or more binding domains, for example two or three binding domains, wherein the at least two binding domains independently bind two different antigens or two different epitopes on the same antigen. Multi-specific antibodies are generally monovalent for each specificity (antigen). Multi-specific antibodies described herein encompass monovalent and multivalent, e.g. bivalent, trivalent, tetravalent multi-specific antibodies. For example, an antibody may comprise a Fab linked to two scFvs or dsscFvs, each scFv or dsscFv binding the same or a different target (e.g., one scFv or dsscFv binding a therapeutic target and one scFv or dsscFv that increases half-life by binding, for instance, albumin). Such antibodies are described in WO2015/197772.

The term "neutralizing" (or "neutralize") in the context of antibodies describes an antibody that is capable of inhibiting or attenuating the biological signaling activity of its target (target protein).

The term "paratope" refers to a region of an antibody which recognizes and binds to an antigen.

The term "percent (%) sequence identity (or similarity)" with respect to the polypeptide and antibody sequences is defined as the percentage of amino acid residues in a candidate sequence that are identical (or similar) to the amino acid residues in the polypeptide being compared, after aligning the sequences and introducing gaps, if necessary, to achieve the maximum percent sequence identity, and not considering any conservative substitutions as part of the sequence identity A "pharmaceutically acceptable carrier" refers to an ingredient in a pharmaceutical formulation, other than an active ingredient, which is nontoxic to a subject. Pharmaceutically acceptable carriers include, but are not limited to, a buffer, excipient, stabilizer, or preservative.

The term "polyclonal antibody" refers to a mixture of different antibody molecules which bind to (or otherwise interact with) more than one epitope of an antigen The term "prevent" in the context of antibodies is used herein interchangeably with the term "inhibit" and indicates the effect the antibodies according to the present invention have with respect to a particular biological process or molecular interaction.

The term "scDiabody" refers to a diabody comprising an intra-Fv linker, such that the molecule comprises three linkers and forms a normal scFv whose VH and VL terminals are each linked to a one of the variable regions of a further Fv pair.

The term "Scdiabody-CH3" as employed herein refers to two scdiabody molecules each linked, for example via a hinge to a CH3 domain.

The term "ScDiabody-Fc" as employed herein is two scdiabodies, wherein each one is appended to the N-terminus of a CH2 domain, for example via a hinge, of constant region fragment —CH2CH3.

The term "single chain variable fragment" or "scFv" as employed herein refers to a single chain variable fragment which is stabilised by a peptide linker between the VH and VL variable domains.

The term "ScFv-Fc-scFv" as employed herein refers to four scFvs, wherein one of each is appended to the N-terminus and the C-terminus of both the heavy chains of a CH2CH3 fragment.

The term "scFv-IgG" as employed herein is a full-length antibody with a scFv on the N-terminal of each of the heavy chains or each of the light chains.

The term "similarity", as used herein, indicates that, at any particular position in the aligned sequences, the amino acid residue is of a similar type between the sequences. For example, leucine may be substituted for isoleucine or valine. Other amino acids which can often be substituted for one another include but are not limited to:

- phenylalanine, tyrosine and tryptophan (amino acids having aromatic side chains);
- lysine, arginine and histidine (amino acids having basic side chains);
- aspartate and glutamate (amino acids having acidic side chains);
- asparagine and glutamine (amino acids having amide side chains); and
- cysteine and methionine (amino acids having sulphur-containing side chains).

The term "single domain antibody" as used herein refers to an antibody fragment consisting of a single monomeric variable domain. Examples of single domain antibodies include VH or VL or VHH or V-NAR.

The term "specific" as employed herein in the context of antibodies is intended to refer to an antibody that only recognizes the antigen to which it is specific or an antibody that has significantly higher binding affinity to the antigen to which it is specific compared to binding to antigens to which it is non-specific, for example at least 5, 6, 7, 8, 9, 10 times higher binding affinity.

The term "sterically blocking" or "sterically preventing" as employed herein is intended to refer to the means of blocking an interaction between first and second proteins by a third protein's binding to the first protein. The binding between the first and the third proteins prevents the second protein from binding to the first protein due to unfavorable van der Waals or electrostatic interactions between the second and third proteins.

The terms "subject" or "individual" in the context of the treatments and diagnosis generally refer to a mammal. Mammals include, but are not limited to, domesticated animals (e.g., cows, sheep, cats, dogs, and horses), primates (e.g., humans and non-human primates such as monkeys), rabbits, and rodents (e.g., mice and rats). More specifically, the individual or subject is a human The term "Tandem scFv" as employed herein refers to at least two scFvs linked via a single linker such that there is a single inter-Fv linker.

The term "Tandem scFv-Fc" as employed herein refers to at least two tandem scFvs, wherein each one is appended to the N-terminus of a CH2 domain, for example via a hinge, of constant region fragment —CH2CH3.

The term "target" or "antibody target" as used herein refers to target antigen to which the antibody binds.

The term "Tetrabody" as employed herein refers to a format similar to the diabody comprising fours Fvs and four inter-Fv linkers.

The term "therapeutically effective amount" refers to the amount of an antibody thereof that, when administered to a subject for treating a disease, is sufficient to produce such treatment for the disease. The therapeutically effective amount will vary depending on the antibody, the disease and its severity and the age, weight, etc., of the subject to be treated.

The term "tribody" (also referred to a $Fab(scFv)_2$) as employed herein refers to a Fab fragment with a first scFv appended to the C-terminal of the light chain and a second scFv appended to the C-terminal of the heavy the chain.

The term "trispecific or trispecific antibody" as employed herein refers to an antibody with three antigen binding specificities. For example, the antibody is an antibody with three antigen binding domains (trivalent), which independently bind three different antigens or three different epitopes on the same antigen, i.e. each binding domain is monovalent for each antigen. One of the examples of a trispecific antibody format is TrYbe.

The terms "prevent", or "preventing" and the like, refer to obtaining a prophylactic effect in terms of completely or partially preventing a disease or symptom thereof. Preventing thus encompasses stopping the disease from occurring in a subject who may be predisposed to the disease but has not yet been diagnosed as having the disease.

The terms "treatment", "treating" and the like, refer to obtaining a desired pharmacologic and/or physiologic effect. The effect may be therapeutic in terms of a partial or complete cure for a disease and/or adverse effect attributable to the disease. Treatment thus encompasses (a) inhibiting the disease, i.e., arresting its development; and (b) relieving the disease, i.e., causing regression of the disease.

The term "TrYbe" as employed herein refers to a tribody comprising two dsscFvs. dsFab as employed herein refers to a Fab with an intra-variable region disulfide bond.

The term "variable region" or "variable domain" refers to the domain of an antibody heavy or light chain that is involved in binding the antibody to antigen. The variable domains of the heavy chain (VH) and light chain (VL) of a full length antibody generally have similar structures, with each domain comprising four conserved framework regions (FRs) and three CDRs. (See, e.g., Kindt et al. Kuby Immunology, 6th ed., W. H. Freeman and Co., page 91 (2007).) A single VH or VL domain may be sufficient to confer antigen-binding specificity. Each VH and VL is composed of three CDRs and four FRs, arranged from amino-terminus to carboxy-terminus in the following order: FR1, CDR1, FR2, CDR2, FR3, CDR3, FR4. The CDRs and the FR together form a variable region. By convention, the CDRs in the heavy chain variable region of an antibody are referred as CDR-H1, CDR-H2 and CDR-H3 and in the light chain variable regions as CDR-L1, CDR-L2 and CDR-L3. They are numbered sequentially in the direction from the N-terminus to the C-terminus of each chain. CDRs are conventionally numbered according to a system devised by Kabat.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors." The term "vector" includes "expression vectors".

The term "VH" refers to the variable domain (or the sequence) of the heavy chain.

The term "V-IgG" as employed herein is a full-length antibody with a variable domain on the N-terminal of each of the heavy chains or each of the light chains.

The term "VL" refers to the variable domain (or the sequence) of the light chain.

TREM1

The term "TREM1" refers to "triggering receptor expressed on myeloid cells 1" (also known as TREM-1, and CD354) refers to a receptor that is expressed on monocytes, macrophages, neutrophils and other types of cells. Primary ligand for TREM1 include peptidoglycan-recognition-protein 1 (PGLYRP1), which belongs to a family of peptidoglycan (PGN) binding proteins (PGRPs). The term "TREM1" includes any variants or isoforms of TREM1 which are naturally expressed by cells.

Three isoforms of human TREM1 have been identified. Isoform 1 (Accession No. NP 061113.1; SEQ ID NO: 1) consists of 234 amino acids and represents the canonical sequence. Isoform 2 (Accession No. NP 001229518.1; SEQ ID NO: 2) consists of 225 amino acids and differ from the canonical sequence at amino acid residues 201-234. The amino acid residues encode part of the transmembrane domain and the cytoplasmic domain. Isoform 3 (Accession No. NP 001229519; SEQ ID NO: 3) consists of 150 amino acids, and is soluble. It lacks amino acid residues 151-234, which encode the transmembrane domain, the cytoplasmic domain, and part of the extracellular domain. The amino acid residues 138-150 also differ from the canonical sequence described above.

Method of Identifying Anti-TREM1 Antibodies

In order to identify antibodies that would interact with different amino-acid residues on TREM1 than PGLYRP1 ligand and neutralize one or more of TREM1 activities, a special screening and testing strategy had to be developed, that involves measurement of binding to TREM1 and functional properties of the test antibodies, as well high-throughput measurement of the structural aspects of the binding (the target epitope residues). By establishing TREM1 residues involved in the interaction with PGLYRP1, this method allows to perform rapid testing and select antibodies for further development that would bind to a different site on TREM1 than PGLYRP1. Such antibodies could provide additional benefits of preventing binding of other potential ligands interacting with a different site of TREM1.

Hence, a method of identifying an antibody that interacts with different amino-acid residues on TREM1 than PGLYRP1 and neutralizes activity of human TREM1 is provided herein, said method comprising:

a) immunizing an animal with cells transiently expressing human TREM1;
b) recovering B cells from said animal;
c) selecting the antibodies produced by said B cells based on their ability to:
    i. bind to human TREM1 with affinity of at least 1 nM; and
    ii. block PGLYRP1-mediated signaling in the THP1 monocyte TREM1/DAP12 NF-κB Luciferase reporter cell assay; and
    iii. bind to a different site on human TREM1 than PGLYRP1.

In order to identify antibodies that bind to a different site than PGLYRP1, a method using arrays of mutant TREM1 proteins has been developed that allows rapid testing of the binding sites (residues of TREM1 involved in interaction with a test antibody) on TREM1 protein. The same method is used to determine the binding site of PGLYRP1 ligand. Such method of identifying amino-acid residues on TREM1 that form a binding site of a test antibody (or PGLYRP1), comprises:

a) obtaining 3D structure information for TREM1;
b) identifying, using obtained 3D structural data, the amino-acid residues which are within the accessible surface area;

c) for each of the identified amino-acids selecting 1 or 2 amino-acids which are within a predetermined distance from the identified amino-acid and are within the accessible surface area, whereby such combination of amino-acid residues forms a patch of 2 or 3 amino acids (patch);
d) selecting, from the large number of generated possible patches, a set of representative patches that cover the majority of TREM1's accessible surface area, while minimizing the number of patches likely to cause TREM1 protein to misfold;
e) producing a set of mutant proteins, wherein each of the mutant proteins comprises a mutated sequence of the target protein, wherein each of the mutated sequences comprises a single mutated patch of amino acids identified in step (c), and wherein each of the amino acids of the patch is substituted by another amino-acid;
f) measuring binding properties of each of the mutant proteins; and
g) identifying the patches that demonstrate decreased binding properties of the antibody to corresponding mutant TREM1 protein comprising such patch, wherein the residues in such patches are identified as being a part of a binding site of the antibody.

In a preferred embodiment, an antibody is selected if it interacts with the residues E26, E27, K28, Y29, E30, L31, K32 and Q35 of human TREM1 (where the numbering is according to SEQ ID NO: 1).

In order to identify the amino-acid residues for producing mutant versions of TREM1, 3D structure data needs to be obtained for TREM1. Such data is available in the form of a PDB structure (PDB code: 1SMO, chain A). Alternatively, such structural data can be obtained using the techniques known to the skilled person. Such techniques include X-ray analysis or NMR data. Preferably, such 3D data is a of sufficient spatial resolution to allow identification of the target residues.

In particular, the pre-determined distance between the residues of each patch is 4, 5, 6, or 7 Å. Preferably, such distance is 6 Å. Preferably, alanines and glycines are not selected for substitution. Depending on the relevance of Cys residues in the 3D structure such can be either substituted or not selected for substitution. Cys is often involved into formation of S—S bonds in proteins and is important for tertiary structure. Gly is a very flexible amino acid and substituting such with a larger amino acid such as Ala may also have a structural effect. Optionally, Pro residues can also be left out of the analysis as such are often involved in secondary structure formation.

More specifically the amino-acids within the accessible surface area are selected based on the calculated solvent-accessible surface area of side chains. Standard methods to calculate solvent accessibility can be applied. In a typical example a probe of 1.4 Å is used for calculations (a simplified version of $H_2O$ molecule wherein such probe has a size similar to an $H_2O$ molecule). In such calculations atoms of the amino-acid residues that touch the probe are classified as surface accessible atoms. Surface accessibility of each amino-acid is calculated in $Å^2$. Subsequently a ratio between the actual surface exposed area (in $Å^2$) and theoretical probable surface exposure (in $Å^2$) is calculated. Different cut-offs can be selected depending on the desired accuracy and the size of the protein. Such cut off can be selected from 0.5, 0.2, preferably such cut-off is between 0.05-0.1, more preferably such cut-off is 0.07. Such filtering step is useful to eliminate potentially misfolding proteins.

Further steps to reduce the amount of misfolded TREM1 proteins in the final array can be performed. For example, residues that cause breakage of more than one hydrogen bond between any of the original residues of each mutated patch (2 or 3 residues) and the rest of the protein are preferably avoided. Similarly any breakage in the salt-bridges should also be preferably avoided. Additionally, mutating residues that expose large hydrophobic areas of the protein is also avoided. In another embodiment, residues that cause breakage of more than two hydrogen bonds within the protein are also avoided. Similarly, any breakage in the salt-bridges should also be preferably avoided.

Hence, in a preferred embodiment of the method, the method excludes or filters out 1) patches that result in the breakage of hydrogen bonds (preferably maximum of 2 broken bonds allowed) and 2) salt bridges (preferably maximum 1 broken bond allowed), as well as 3) the exposure of large hydrophobic patches (preferably maximum 15 Å 2 of exposed hydrophobic surface allowed). The distance threshold to define a patch could be set between 6 and 6.5 Å and the minimal sidechain surface exposure could be set to 7%.

Optionally, further granularity can be achieved by performing a molecular dynamics simulation with any widely used simulations package (e.g. AMBER, GROMACS, DESMOND, etc.) with a subsequent analysis of interaction persistence. Hydrogen bonds and salt bridges that are present in a large fraction of the simulation trajectory can be considered "essential" and should not be broken by an Ala mutation, whereas bonds that are only observed in a small fraction of the simulation are likely to have little impact on the protein's stability.

Additionally, after all the patches of residues have been identified any redundancy in such is eliminated by eliminating the patches that generate redundancy. This step is optional as it could be beneficial to have some redundancy in the coverage of the accessible surface area, however having such redundancy might provide technical difficulty in generating mutant clones subsequently. Hence, such redundancy should be considered in the context of the protein size, complexity and technical limitations in designing the corresponding mutant proteins.

Ideally, the steps above are performed for the whole protein surface to make sure that maximum surface-accessible area is covered by the identified patches. It would be preferable to avoid having some parts of the surface-accessible area not covered by such patches. The purpose is to cover the solvent accessible surface while minimizing the number of generated misfolded proteins.

If, for example, using patches of 2 substitutions would not cover the whole surface-accessible area, additional patches consisting of 3 substitutions can be designed. Larger patches of more than 3 substitutions can also be used, however going beyond 3 substitutions may lead to misfolding of a mutant TREM1 protein. Hence, preferably patches containing 2 or 3 Ala substitutions are used. If desired additional single Ala substitution could also be selected. However, such may not provide the desired sensitivity compared to 2 or 3 substitutions.

The arrays of mutant TREM1 proteins having 2 or 3 Ala patches following this strategy are provided in the Examples.

The generated sequences of mutated TREM1 protein are subsequently produced for experimental testing. A typical way to produce such is by cloning the sequences into a suitable expression vector. As a control, the wild type sequence of the target protein of interest is also cloned.

An array of mutant TREM1 proteins can be produced using techniques known to the skilled person. Any suitable expression system for expressing proteins in target cells can be used. Preferably a mammalian cell system is used for expression of the cloned mutant peptides. Mammalian cells would allow for the mutant polypeptides to be secreted out of such cells and make testing such peptides easier. Any mammalian cell or cell line could be used as long as such allows for sufficient expression of each of the mutant peptides. In such a mammalian system a suitable expression vector can be used. Many mammalian expression vectors are commercially available. Typically such a vector will comprise a constitutive promoter, such as cytomegalovirus (CMV) promoter.

Each of the mutant TREM1 proteins could be fused to an Fc region, preferably human Fc domain. Use of Fc domain in such fusion proteins offers practical advantages, such as higher robustness in detection and ease of capturing such fusion proteins on a surface. Optionally one or more linker sequences can be introduced into the fusion protein sequence between the Fc domain and the target mutant protein if necessary, such as triple Ala linker.

Preferably, such fusion proteins comprising human Fc domain are expressed in mammalian Expi293 cells, or any other cells that can generate sufficient concentration of the protein.

Optionally, TREM1 proteins that might potentially misfold could be removed from the array by pre-screening the array using polyclonal antibodies (targeting multiple epitopes) against TREM1 or any commercial monoclonal antibodies of known epitopes which are suitable for ELISA assays (as such antibodies would recognize a structural epitope).

Finally, binding properties of an antibody to each of the mutant target proteins on the array are measured. Such measurements can be performed using any suitable method available. Preferably, such measurements are performed using a high-throughput method.

The affinity of a molecule of interest, as well as the extent to which such molecule inhibits binding to the target protein, can be determined by one of ordinary skill in the art using conventional techniques, for example those described by Scatchard et al. (Ann. KY. Acad. Sci. 51:660-672 (1949)) or by surface plasmon resonance (SPR) using systems such as BIAcore. For surface plasmon resonance, mutant proteins are immobilized on a solid phase and exposed to ligands and/or the molecule of interest in a mobile phase running along a flow cell. If ligand binding to the immobilized target occurs, the local refractive index changes, leading to a change in SPR angle, which can be monitored in real time by detecting changes in the intensity of the reflected light. The rates of change of the SPR signal can be analyzed to yield apparent rate constants for the association and dissociation phases of the binding reaction. The ratio of these values gives the apparent equilibrium constant (affinity) (see, e.g., Wolff et al, Cancer Res. 53:2560-65 (1993)).

Alternative platforms using techniques similar to SPR are provides by Cartera (carterra-bio.com) such as Carterra LSA Platform. It is a high throughput antibody characterization platform that combines flow printing microfluidics with high throughput surface plasmon resonance (SPR) detection technology.

Other types of platforms include techniques utilizing cell surface-expression arrays. An example of such platform is LigandTracer (ligandtracer.com) which is particularly suited to follow protein binding to cell-surface receptors and allows to measure on- and off-rates as well as affinities.

In order to simplify the measurements, each of the mutant proteins of the array could be fused to a molecule or a protein to allow to capture such on a surface for easier detection of binding properties.

Preferably the binding to each of the mutant proteins is determined using Bio-Layer Interferometry (BLI) is a label-free technology. It is an optical analytical technique that analyzes the interference pattern of white light reflected from two surfaces: a layer of immobilized protein on the biosensor tip, and an internal reference layer. Any change in the number of molecules bound to the biosensor tip causes a shift in the interference pattern that can be measured in real-time (REF).

Typically arrays of 30, 60 cloned mutant proteins are used. However the size of such arrays depends on the size of the target protein and the desired coverage of the solvent-accessible area. Preferably the mutant proteins are provided on a 96 well plate or 384-well plate. Generally a BLI instrument can handle 96- or 384-well plates for measurements.

When using BLI technology typically each sensor is exposed to a solution containing the molecule of interest (such as an antibody or a ligand) for which the binding site is being determined. The advantage of BLI technology is that is almost as sensitive as a normal BIACore, it is high throughput (96 clones can be tested at the same time) and uses disposable sensor tips so there is no need to regenerate the surface and reuse a chip as you would typically do with BIACore.

Different measurements of binding of a test antibody to the mutant TREM1 proteins can be used to determine which of the mutant proteins demonstrate reduced binding. Typically, dissociation constants or binding constants are measured. Typically, complete loss of binding or how quickly the molecule of interest is coming off the mutant protein can be measured. Appropriate controls are generally used when measuring the binding properties of the antibody. Commonly the binding properties are compared to parental sequence of the target protein (wild type, WT). Typically the majority of mutant proteins will show the same $K_d$ as the WT. The mutant proteins showing a difference in binding should be considered. Typically, any dissociation constant difference of at least 2, 3, 4, 5, 6, 7, 8, 9, or 10 or more fold compared to wild-type TREM1 is considered. Preferably any difference of at least 3-fold is considered significant. The mutant TREM1 proteins that produce the results with low noise to signal resolutions are ignored or re-measured.

If desired mutant proteins comprising patches of different size, such as patches of 2 or 3 substitutions can be used on an array. Mutant proteins comprising single substitutions can also additionally be tested for binding properties if a higher precision is required, provided such offer sufficient sensitivity to obtain a measurable effect.

Antibodies Binding to TREM1

The present invention provides anti-TREM1 antibodies that bind to human TREM1 (target polypeptide) and have functional and structural properties as described further herein.

The antibodies in the context of the present invention include whole antibodies and functionally active antibody fragments (i.e., molecules that contain an antigen binding domain that specifically binds an antigen, also termed antigen-binding fragments). Features described herein also apply to antibody fragments unless context dictates otherwise. The antibody may be (or derived from) polyclonal, monoclonal, multi-valent, multi-specific, bispecific, fully human, humanized or chimeric.

The antibodies described further in are specific antibody types and do not limit the scope of invention.

An antibody used according to the invention may be a monoclonal antibody or a polyclonal antibody, and is preferably a monoclonal antibody. An antibody used according to the invention may be a chimeric antibody, a CDR-grafted antibody (e.g., any appropriate acceptor variable region framework sequence may be used having regard to the class/type of the donor antibody from which the CDRs are derived, including mouse, primate and human framework regions), a nanobody, a human or humanized antibody. For the production of both monoclonal and polyclonal antibodies, the animal used to raise such antibodies is typically a non-human mammal such as a goat, rabbit, rat or mouse but the antibody may also be raised in other species.

Polyclonal antibodies may be produced by routine methods such as immunization of a suitable animal with an antigen of interest. Blood may be subsequently removed from such animal and the produced antibodies purified.

Monoclonal antibodies may be made by a variety of techniques, including but not limited to, the hybridoma method, recombinant DNA methods, phage-display methods, and methods utilizing transgenic animals containing all or a part of the human immunoglobulin loci. Some exemplary methods for making monoclonal antibodies are described herein.

For example, monoclonal antibodies may be prepared using the hybridoma technique (Kohler & Milstein, 1975, Nature, 256:495-497), the trioma technique, the human B-cell hybridoma technique (Kozbor et al., 1983, Immunology Today, 4:72) and the EBV-hybridoma technique (Cole et al., Monoclonal Antibodies and Cancer Therapy, pp 77-96, Alan R Liss, Inc., 1985).

Antibodies may also be generated using single lymphocyte antibody methods by cloning and expressing immunoglobulin variable region cDNAs generated from single lymphocytes selected for the production of specific antibodies by for example the methods described in WO9202551, WO2004051268 and WO2004106377.

Antibodies generated against the target polypeptide may be obtained, where immunization of an animal is necessary, by administering the polypeptide to an animal, preferably a non-human animal, using well-known and routine protocols, see for example Handbook of Experimental Immunology, D. M. Weir (ed.), Vol 4, Blackwell Scientific Publishers, Oxford, England, 1986). Many animals, such as rabbits, mice, rats, sheep, cows, camels or pigs may be immunized. However, mice, rabbits, pigs and rats are generally used.

Monoclonal antibodies can also be generated using various phage display methods known in the art and include those disclosed by Brinkman et al. (in J. Immunol. Methods, 1995, 182: 41-50), Ames et al. (J. Immunol. Methods, 1995, 184:177-186), Kettleborough et al. (Eur. J. Immunol. 1994, 24:952-958), Persic et al. (Gene, 1997 187 9-18), Burton et al. (Advances in Immunology, 1994, 57:191-280). In certain phage display methods, repertoires of VH and VL genes are separately cloned by polymerase chain reaction (PCR) and recombined randomly in phage libraries, which can then be screened for antigen-binding phage as described in Winter et al., Ann. Rev. Immunol, 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., EMBO J 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, J. Mol. Biol, 227: 381-388 (1992). Patent publications describing human antibody phage libraries include, for example: U.S. Pat. No. 5,750,373, and US 2005/0079574, US2005/0119455, US2005/0266000, US2007/0117126, US2007/0160598, US2007/0237764, US2007/0292936, and US2009/0002360.

Screening for antibodies can be performed using assays to measure binding to the target polypeptide and/or assays to measure the ability of the antibody to block a particular interaction. An example of a binding assay is an ELISA, for example, using a fusion protein of the target polypeptide, which is immobilized on plates, and employing a conjugated secondary antibody to detect the antibody bound to the target. An example of a blocking assay is a flow cytometry based assay measuring the blocking of a ligand protein binding to the target polypeptide. A fluorescently labelled secondary antibody is used to detect the amount of such ligand protein binding to the target polypeptide.

Antibodies may be isolated by screening combinatorial libraries for antibodies with the desired activity or activities. For example, a variety of methods are known in the art for generating phage display libraries and screening such libraries for antibodies possessing the desired binding characteristics.

Antibodies or antibody fragments isolated from human antibody libraries are considered human antibodies or human antibody fragments.

The antibody may be a full-length antibody. More particularly the antibody may be of the IgG isotype. More particularly the antibody may be an IgG1 or IgG4.

The constant region domains of the antibody, if present, may be selected having regard to the proposed function of the antibody molecule, and in particular the effector functions which may be required. For example, the constant region domains may be human IgA, IgD, IgE, IgG or IgM domains. In particular, human IgG constant region domains may be used, especially of the IgG1 and IgG3 isotypes when the antibody molecule is intended for therapeutic uses and antibody effector functions are required. Alternatively, IgG2 and IgG4 isotypes may be used when the antibody molecule is intended for therapeutic purposes and antibody effector functions are not required. It will be appreciated that sequence variants of these constant region domains may also be used. It will also be known to the person skilled in the art that antibodies may undergo a variety of posttranslational modifications. The type and extent of these modifications often depends on the host cell line used to express the antibody as well as the cell culture conditions. Such modifications may include variations in glycosylation, methionine oxidation, diketopiperazine formation, aspartate isomerization and asparagine deamidation. A frequent modification is the loss of a carboxy-terminal basic residue (such as lysine or arginine) due to the action of carboxypeptidases (as described in Harris, R J. Journal of Chromatography 705:129-134, 1995). Accordingly, the C-terminal lysine of the antibody heavy chain may be absent.

Alternatively, the antibody is an antigen-binding fragment.

For a review of certain antigen-binding fragments, see Hudson et al. Nat. Med. 9: 129-134 (2003). For a review of scFv fragments, see, e.g., Plückthun, in The Pharmacology of Monoclonal Antibodies, vol. 113, Rosenburg and Moore eds., (Springer Verlag, New York), pp. 269-315 (1994); see also WO 93/16185; and U.S. Pat. Nos. 5,571,894 and 5,587,458. Fab and $F(ab')_2$ fragments comprising salvage receptor binding epitope residues and having increased in vivo half-life are disclosed in U.S. Pat. No. 5,869,046.

Antigen-binding fragments and methods of producing them are well known in the art, see for example Verma et al., 1998, Journal of Immunological Methods, 216, 165-181; Adair and Lawson, 2005. Therapeutic antibodies. Drug Design Reviews—Online 2(3):209-217. The Fab-Fv format was first disclosed in WO2009/040562 and the disulphide stabilized version thereof, the Fab-dsFv, was first disclosed in WO2010/035012, and TrYbe format is disclosed in WO2015/197772.

Various techniques have been developed for the production of antibody fragments. Such fragments might be derived via proteolytic digestion of intact antibodies (see, e.g., Morimoto et al., Journal of Biochemical and Biophysical Methods 24: 107-117 (1992) and Brennan et al, Science 229:81 (1985)). However, antibody fragments can also be produced directly by recombinant host cells. For example, antibody fragments can be isolated from the antibody phage libraries discussed above. Alternatively, Fab'-SH fragments can be directly recovered from *E. coli* and chemically coupled to form $F(ab')_2$ fragments (Carter et al., Bio/Technology 10: 163-167 (1992)).

$F(ab')_2$ fragments can be isolated directly from recombinant host cell culture. The antibody may be a single chain Fv fragment (scFv). Such are described in WO 93/16185; U.S. Pat. Nos. 5,571,894; and 5,587,458. The antibody fragment may also be a "linear antibody," e.g., as described in U.S. Pat. No. 5,641,870. Such linear antibody fragments may be monospecific or bispecific.

The antibody may be a Fab, Fab', $F(ab')_2$, Fv, dsFv, scFv, or dsscFv. The antibody may be a single domain antibody or a nanobody, for example VH or VL or VHH or VNAR. The antibody may be Fab or Fab' fragment described in WO2011/117648, WO2005/003169, WO2005/003170 and WO2005/003171.

The antibody may be a disulfide-stabilized single chain variable fragment (dsscFv).

The disulfide bond between the variable domains VH and VL may be between two of the residues listed below:

- $V_H37+V_L95$ see for example Protein Science 6, 781-788 Zhu et al (1997);
- $V_H44+V_L100$ see for example Weatherill et al., Protein Engineering, Design & Selection, 25 (321-329), 2012;
- $V_H44+V_L105$ see for example J Biochem. 118, 825-831 Luo et al (1995);
- $V_H45+V_L87$ see for example Protein Science 6, 781-788 Zhu et al (1997);
- $V_H55+V_L101$ see for example FEBS Letters 377 135-139 Young et al (1995);
- $V_H100+V_L50$ see for example Biochemistry 29 1362-1367 Glockshuber et al (1990);
- $V_H100b+V_L49$; see for example Biochemistry 29 1362-1367 Glockshuber et al (1990);
- $V_H98+V_L46$ see for example Protein Science 6, 781-788 Zhu et al (1997);
- $V_H101+V_L46$; see for example Protein Science 6, 781-788 Zhu et al (1997);
- $V_H105+V_L43$ see for example; Proc. Natl. Acad. Sci. USA Vol. 90 pp. 7538-7542 Brinkmann et al (1993); or Proteins 19, 35-47 Jung et al (1994),
- $V_H106+V_L57$ see for example FEBS Letters 377 135-139 Young et al (1995) and a position or positions corresponding thereto in a variable region pair located in the molecule.

The disulphide bond may be formed between positions VH44 and VL100.

It will be appreciated by the skilled person that antigen-binding fragments described herein may also be characterized as monoclonal, chimeric, humanized, fully human, multispecific, bispecific etc., and that discussion of these terms also relate to such fragments.

Multi-Specific Antibodies

The antibodies of the present invention may be multi-specific antibodies.

Examples of multi-specific antibodies or antigen-binding fragments thereof, which also are contemplated for use in the context of the disclosure, include bi, tri or tetra-valent antibodies, Bis-scFv, diabodies, triabodies, tetrabodies, bibodies and tribodies (see for example Holliger and Hudson, 2005, Nature Biotech 23(9): 1126-1136; Schoonjans et al. 2001, Biomolecular Engineering, 17(6), 193-202).

A variety of multi-specific antibody formats have been generated. Different classifications have been proposed, but multispecific IgG antibody formats generally include bispecific IgG, appended IgG, multispecific (e.g. bispecific) antibody fragments, multispecific (e.g. bispecific) fusion proteins, and multispecific (e.g. bispecific) antibody conjugates, as described for example in Spiess et al., Alternative molecular formats and therapeutic applications for bispecific antibodies. Mol Immunol. 67(2015):95-106.

The antibody may be a bi-specific antibody. In one embodiment, the antibody comprises two antigen binding domains wherein one binding domain binds TREM1 and the other binding domain binds another antigen, i.e. each binding domain is monovalent for each antigen. In one embodiment, the antibody is a tetravalent bispecific antibody, i.e. the antibody comprises four antigen binding domains, wherein for example two binding domains bind TREM1 and the other two binding domains bind to another antigen. In one embodiment, the antibody is a trivalent bispecific antibody.

Techniques for making bispecific antibodies include, but are not limited to, CrossMab technology (Klein et al. Engineering therapeutic bispecific antibodies using CrossMab technology, Methods 154 (2019) 21-31), Knobs-in-holes engineering (e.g. WO1996027011, WO1998050431), DuoBody technology (e.g. WO2011131746), Azymetric technology (e.g. WO2012058768). Further technologies for making bispecific antibodies have been described for example in Godar et al., 2018, Therapeutic bispecific antibody formats: a patent applications review (1994-2017), Expert Opinion on Therapeutic Patents, 28:3, 251-276. Bispecific antibodies include in particular CrossMab antibodies, DAF (two-in-one), DAF (four-in-one), DutaMab, DT-IgG, Knobs-in-holes common LC, Knobs-in-holes assembly, Charge pair, Fab-arm exchange, SEEDbody, Triomab, LUZ-Y, Fcab, κλ-body and orthogonal Fab.

The antibody construct may be a tri-specific antibody.

The antibody may be a multi-paratopic antibody.

In one embodiment, each binding domain is monovalent. Preferably each binding domain comprises no more than one VH and one VL.

Appended IgG classically comprise full-length IgG engineered by appending additional antigen-binding domain or antigen-binding fragment to the N- and/or C-terminus of the heavy and/or light chain of the IgG. Examples of such additional antigen-binding fragments include sdAb antibodies (e.g. VH or VL), Fv, scFv, dsscFv, Fab, scFab Appended IgG antibody formats include in particular DVD-IgG, IgG (H)-scFv, scFv-(H)lgG, IgG(L)-scFv, scFv-(L)IgG, lgG(L, H)-Fv, IgG(H)-V, V(H)-IgG, IgC(L)-V, V(L)-IgG, KIH IgG-scFab, 2scFv-IgG, lgG-2scFv, scFv4-Tg, Zybody and DVI-IgG (four-in-one), for example as described in Spiess et al., Alternative molecular formats and therapeutic applications for bispecific antibodies. Mol Immunol. 67(2015):95-106.

Multispecific antibody fragments include nanobody, nanobody-HSA, BiTEs, diabody, DART, TandAb, scDiabody, sc-Diabody-CH3, Diabody-CH3, Triple Body, Miniantibody; Minibody, Tri Bi minibody, scFv-CH3 KIH, Fab-scFv, scFv-CH-CL-scFv, $F(ab')_2$, $F(ab')_2$-$scFv_2$, scFv-KIH, Fab-scFv-Fc, Tetravalent HCAb, scDiabody-Fc, Diabody-Fc, Tandem scFv-Fc; and intrabody, as described, for example, Spiess et al., Alternative molecular formats and therapeutic applications for bispecific antibodies. Mol Immunol. 67(2015):95-106.

Multispecific fusion proteins include Dock and Lock, ImmTAC, HSAbody, scDiabody-HSA, and Tandem scFv-Toxin.

Multispecific antibody conjugates include IgG-IgG; Cov-X-Body; and scFv1-PEG-$scFv_2$.

Additional multispecific antibody formats have been described for example in Brinkmann et al, The making of bispecific antibodies, mAbs, 9:2, 182-212 (2017), in particular in FIG. 2, for example tandem scFv, triplebody, Fab-VHH, taFv-Fc, scFv4-Ig, scFv2-Fcab, scFv4-IgG. Bibodies, tribodies and methods for producing such are disclosed, for example, in WO99/37791.

The antibody for use in the present invention may be a Fab linked to two scFvs or dsscFvs, each scFv or dsscFv binding the same or a different target (e.g., one scFv or dsscFv binding a therapeutic target and one scFv or dsscFv that increases half-life by binding, for instance, albumin). Such antibody fragments are described in WO2015/197772. Another preferred antibody for use in the present invention fragment comprises a Fab linked to only one scFv or dsscFv, as described for example in WO2013/068571, and Dave et al., Mabs, 8(7) 1319-1335 (2016).

Another antibody for use in the present invention is a Knobs-into-holes antibody ("KiH"). It is a multi-specific antibody format consisting of heavy chain homodimers for heterodimerization (e.g., for the efficient production of bispecific antibodies, multi-specific antibodies, or one-armed antibodies). Generally, such technology involves introducing a protuberance ("knob") at the interface of a first polypeptide (such as a first CH3 domain in a first antibody heavy chain) and a corresponding cavity ("hole") in the interface of a second polypeptide (such as a second CH3 domain in a second antibody heavy chain), such that the protuberance can be positioned in the cavity so as to promote heterodimer formation and hinder homodimer formation. Protuberances are constructed by replacing small amino acid side chains from the interface of the first polypeptide (such as a first CH3 domain in a first antibody heavy chain) with larger side chains (e.g. arginine, phenylalanine, tyrosine or tryptophan). Compensatory cavities of identical or similar size to the protuberances are created in the interface of the second polypeptide (such as a second CH3 domain in a second antibody heavy chain) by replacing large amino acid side chains with smaller ones (e.g. alanine, serine, valine, or threonine). The protuberance and cavity can be made by altering the nucleic acid encoding the polypeptides, e.g. by site-specific mutagenesis, or by peptide synthesis. Further details regarding "knobs-into-holes" technology is described in, e.g., U.S. Pat. Nos. 5,731,168; 7,695,936; WO 2009/089004; US 2009/0182127; Marvin md Z u, Acta Pharmacologica Sincia (2005) 26(6):649-658; Kontermann Acta Pharmacologica Sincia (2005) 26: 1-9; Ridgway et al, Prot Eng 9, 617-621 (1996); and Carter, J Immunol Meth 248, 7-15 (2001).

Humanized, Human, and Chimeric Antibodies and Methods of Producing Such

The antibodies of the present invention may be, but are not limited to, humanized, fully human or chimeric antibodies.

In one embodiment the antibody is humanized. More particularly the antibody is a chimeric, human, or humanized antibody.

In certain embodiments, an antibody provided herein is a chimeric antibody. Examples of chimeric antibodies are described, e.g., in U.S. Pat. No. 4,816,567; and Morrison et al., Proc. Natl. Acad. Sci. USA, 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In one embodiment, the antibody is a humanized antibody.

Humanized antibodies may optionally further comprise one or more framework residues derived from the non-human species from which the CDRs were derived. It will be appreciated that it may only be necessary to transfer the specificity determining residues of the CDRs rather than the entire CDR (see for example, Kashmiri et al., 2005, Methods, 36, 25-34).

Suitably, the humanized antibody according to the present invention has a variable domain comprising human acceptor framework regions as well as one or more of the CDRs and optionally further including one or more donor framework residues.

Thus, provided in one embodiment is a humanized antibody wherein the variable domain comprises human acceptor framework regions and non-human donor CDRs.

When the CDRs or specificity determining residues are grafted, any appropriate acceptor variable region framework sequence may be used having regard to the class/type of the donor antibody from which the CDRs are derived, including mouse, primate and human framework regions.

Examples of human frameworks which can be used in the present invention are KOL, NEWM, REI, EU, TUR, TEI, LAY and POM (Kabat et al). For example, KOL and NEWM can be used for the heavy chain, REI can be used for the light chain and EU, LAY and POM can be used for both the heavy chain and the light chain. Alternatively, human germline sequences may be used; these are available at: www.imgt.org. In embodiments, the acceptor framework is IGKV1-9 human germline, and/or IGHV3-66 human germline. In embodiments, the human framework contains 1-5, 1-4, 1-3 or 1-2 donor antibody amino acid residues.

In a humanized antibody of the present invention, the acceptor heavy and light chains do not necessarily need to be derived from the same antibody and may, if desired, comprise composite chains having framework regions derived from different chains.

In certain embodiments, an antibody provided herein is a human antibody. Human antibodies can be produced using various techniques known in the art.

Human antibodies comprise heavy or light chain variable regions or full length heavy or light chains that are "the product of" or "derived from" a particular germline sequence if the variable regions or full-length chains of the antibody are obtained from a system that uses human germline immunoglobulin genes. Such systems include immunizing a transgenic mouse carrying human immunoglobulin genes with the antigen of interest or screening a human immunoglobulin gene library displayed on phage with the antigen of interest. A human antibody or fragment thereof that is "the product of" or "derived from" a human germline immunoglobulin sequence can be identified as such by comparing the amino acid sequence of the human antibody to the amino acid sequences of human germline immunoglobulins and selecting the human germline immunoglobulin sequence that is closest in sequence (i.e., greatest % identity) to the sequence of the human antibody. A human antibody that is "the product of" or "derived from" a particular human germline immunoglobulin sequence may contain amino acid differences as compared to the germline sequence, due to, for example, naturally occurring somatic mutations or intentional introduction of site-directed mutation. However, a selected human antibody typically is at least 90% identical in amino acid sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least 60%, 70%, 80%, 90%, or at least 95%, or even at least 96%, 97%, 98%, or 99% identical in amino acid sequence to the amino acid sequence encoded by the germline immunoglobulin gene. Typically, a human antibody derived from a particular human germline sequence will display no more than 10 amino acid differences from the amino acid sequence encoded by the human germline immunoglobulin gene. In certain cases, the human antibody may display no more than 5, or even no more than 4, 3, 2, or 1 amino acid difference from the amino acid sequence encoded by the germline immunoglobulin gene.

Structural Features of the Antibodies

The antibody of the invention comprises a binding domain. A binding domain will generally comprise 6 CDRs, three from a heavy chain and three from a light chain. In one embodiment the CDRs are in a framework and together form a variable region. Thus, the antibody has a binding domain specific for antigen, said binding domain comprising a light chain variable region and a heavy chain variable region.

In one embodiment, the antibody comprises a heavy chain and a light chain wherein the heavy chain comprises a CH1 domain and the light chain comprises a CL domain, either kappa or lambda.

As demonstrated by the Examples of the present invention, different variants of variable regions of heavy and light chains had been produced and tested for their binding affinity. Those variants comprise same set of CDR sequences and demonstrate similar range of binding affinity. An overview of different structural elements of selected antibody variants is presented in Table 3.

TABLE 3

Amino-acid sequences of the anti-TREM1 antibodies

| Feature | 12172 gL2gH11 SEQ ID NO | 12172 gL6gH6 SEQ ID NO |
|---|---|---|
| CDR-L1 | 11 | 11 |
| CDR-L2 | 12 | 12 |
| CDR-L3 | 13 | 13 |
| CDR-H1 | 14 | 14 |
| CDR-H2 | 15 | 15 |
| CDR-H3 | 16 | 16 |
| Light chain V region | 29 | 33 |
| Heavy chain V region | 79 | 57 |
| Light chain | 31 | 35 |
| Heavy chain IgG1 | 85 | 63 |
| Heavy chain IgG1 LALA | 87 | 65 |
| Heavy chain IgG4P | 81 | 59 |
| Heavy chain IgG4P FALA | 83 | 61 |

In one embodiment the present invention provides an antibody that binds to human TREM1, comprising a light chain variable domain which comprises at least one of:

a CDR-L1 comprising SEQ ID NO:11, a CDR-L2 comprising SEQ ID NO:12, and a CDR-L3 comprising SEQ ID NO:13.

In one embodiment the present invention provides an antibody that binds to human TREM1, comprising a light chain variable domain which comprises a CDR-L1 comprising SEQ ID NO:11, a CDR-L2 comprising SEQ ID NO:12, and a CDR-L3 comprising SEQ ID NO:13.

In one embodiment the present invention provides an antibody that binds to human TREM1, comprising a heavy chain variable domain which comprises at least one of:

a CDR-H1 comprising SEQ ID NO:14, a CDR-H2 comprising SEQ ID NO:15, and a CDR-H3 comprising SEQ ID NO:16.

In one embodiment the present invention provides an antibody that binds to human TREM1, comprising a heavy chain variable domain which comprises a CDR-H1 comprising SEQ ID NO:14, a CDR-H2 comprising SEQ ID NO:15, and a CDR-H3 comprising SEQ ID NO:16.

The antibody molecules of the present invention may comprise a complementary light chain or a complementary heavy chain, respectively.

Hence, in one embodiment the present invention provides an antibody that binds to human TREM1, comprising:

a light chain variable region comprising:

a CDR-L1 comprising SEQ ID NO:11, a CDR-L2 comprising SEQ ID NO:12, and a CDR-L3 comprising SEQ ID NO:13;

and a heavy chain variable region comprising:

a CDR-H1 comprising SEQ ID NO:14, a CDR-H2 comprising SEQ ID NO:15, and a CDR-H3 comprising SEQ ID NO:16.

In one embodiment, an antibody of the present invention comprises a light chain variable region comprising the sequence given in SEQ ID NO:29 or SEQ ID NO:33.

In one embodiment, an antibody of the present invention comprises a heavy chain variable region comprising the sequence given in SEQ ID NO:57 or SEQ ID NO:79.

In one embodiment, an antibody of the present invention comprises alight chain variable region comprising the sequence given in SEQ ID NO:33 and a heavy chain variable region comprising the sequence given in SEQ ID NO:57.

In an alternative embodiment, an antibody of the present invention comprises a light chain variable region comprising the sequence given in SEQ ID NO:29 and a heavy chain variable region comprising the sequence given in SEQ ID NO:79.

In one embodiment, an antibody of the present invention is a full-length antibody comprising a light chain variable region comprising:
a CDR-L1 comprising SEQ ID NO:11,
a CDR-L2 comprising SEQ ID NO:12, and
a CDR-L3 comprising SEQ ID NO:13;
and a heavy chain variable region comprising:
a CDR-H1 comprising SEQ ID NO:14,
a CDR-H2 comprising SEQ ID NO:15, and
a CDR-H3 comprising SEQ ID NO:16.

In one embodiment, an antibody of the present invention is a IgG1 LALA comprising a light chain variable region comprising:
a CDR-L1 comprising SEQ ID NO:11,
a CDR-L2 comprising SEQ ID NO:12, and
a CDR-L3 comprising SEQ ID NO:13;
and a heavy chain variable region comprising:
a CDR-H1 comprising SEQ ID NO:14,
a CDR-H2 comprising SEQ ID NO:15, and
a CDR-H3 comprising SEQ ID NO:16.

In another embodiment, the antibody of the present invention is an IgG1 LALA comprising a light chain comprising the sequence given in SEQ ID NO: 35 and a heavy chain comprising the sequence given in SEQ ID NO: 65.

In another embodiment, the antibody of the present invention is an IgG1 LALA comprising a light chain comprising the sequence given in SEQ ID NO: 31 and a heavy chain comprising the sequence given in SEQ ID NO: 87.

In another embodiment an IgG4P is preferred. Several variants of the 12172 antibody described herein were tested in multiple assays to determine their physical-chemical properties, they all demonstrated very similar developability profiles with IgG4P variant having less preferable properties than the other variants. However, the IgG4P variant demonstrated surprising biological properties not observed with other variants and, hence, is a preferred variant for applications where such properties are beneficial. For example, in the treatment of a condition where such properties provide a therapeutic effect.

IgG4P contains the Ser-228-Pro mutation in the hinge region where numbering is according to EU numbering (Ser-241-Pro according to Kabat numbering) to improve hinge stability (Angal S et al, (1993), Mol Immunol, 30(1), 105-108).

Hence, in one embodiment, an antibody of the present invention is an IgG4P comprising a light chain variable region comprising:
a CDR-L1 comprising SEQ ID NO:11,
a CDR-L2 comprising SEQ ID NO:12, and
a CDR-L3 comprising SEQ ID NO:13;
and a heavy chain variable region comprising:
a CDR-H1 comprising SEQ ID NO:14,
a CDR-H2 comprising SEQ ID NO:15, and
a CDR-H3 comprising SEQ ID NO:16.

In yet another embodiment, the antibody of the present invention is an IgG4P comprising a light chain comprising the sequence given in SEQ ID NO: 35 and a heavy chain comprising the sequence given in SEQ ID NO: 59.

In a more specific embodiment, the antibody of the present invention is an IgG4P comprising a light chain comprising the sequence given in SEQ ID NO: 31 and a heavy chain comprising the sequence given in SEQ ID NO: 81.

Functional Properties of the Anti-TREM1 Antibodies

In one embodiment, the antibody of the present invention is a neutralizing antibody. Preferably the antibody according to the present invention is neutralizing one or more TREM1 activities.

The antibodies of the present invention specifically bind human TREM1, and more specifically, a particular region within the extracellular domain of human TREM1. In some embodiments, the antibodies specifically bind to a different or minimally overlapping site on TREM1 to which a TREM1 ligand (e.g., PGLYRP1) binds. In some embodiments, the antibodies are antagonist antibodies, i.e., they inhibit or suppress the activity of TREM1 on cells. Such cells might be monocytes, macrophages, and/or neutrophils. In some embodiments, the antibodies may specifically bind to TREM1 allosterically, rather than orthosterically to a single ligand, and, hence, provide more effective inhibition of binding of other ligands which bind at a different site on TREM1 than PGLYRP1.

As demonstrated by the Examples, PGLYRP1 binds to an epitope on TREM1, said epitope comprising residues selected from the list consisting of E27, D42-E46, A49, Y90-L95, and F126 of human TREM1 (SEQ ID NO: 1) as determined at less than 4 Å contact distance.

In one particular embodiment, the present invention provides an antibody that binds to a region on TREM1 that is different from the binding site of PGLYRP1 such that the binding still prevents the interaction between TREM1 and PGLYRP1.

In some embodiments, the anti-TREM1 antibodies show very weak binding to cynomolgus TREM1. In some embodiments, the anti-TREM1 antibodies show no detectable binding to mouse, rat, pig or dog TREM1.

In some embodiments, the anti-TREM1 antibodies decrease the release of multiple cytokines and chemokines, such as, CCL-3, CCL-20, CXCL-9, GM-CSF, IFN-γ, IL-1α, IL-1β, IL-6, IL-10, IL-12p40, IL-15, IL-18, IL-27, TNF-α, and TNF-β from activated human monocytes.

In some embodiments, the anti-TREM1 antibody is an IgG4P and significantly increases the release of IL-1R antagonist (IL-1RA), an anti-inflammatory negative regulator of the IL-1 pathway, from primary human monocytes.

An antibody according to the present invention is specific for human TREM1.

In some embodiments, the antibody binds to human TREM1 with sufficient affinity and specificity. In certain embodiments, the antibody binds human TREM1 with a KD of about any one of 1 μM, 100 nM, 50 nM, 40 nM, 30 nM, 20 nM, 10 nM, 5 nM, 1 nM, 0.5 nM, including any range in between these values. In one embodiment, the antibody according to the present invention binds human TREM1 with a KD of less than 600 pM. In more specific embodiment, the antibody according to the present invention binds human TREM1 with a KD of 300-1200 pM, more preferably between 300-600 pM.

The affinity of an antibody, as well as the extent to which an antibody inhibits binding, can be determined by the skilled person using conventional techniques, for example those described by Scatchard et al. (Ann. K Y. Acad. Sci. 51:660-672 (1949) or by surface plasmon resonance (SPR) using systems such as BIAcore. For surface plasmon resonance, target molecules are immobilized on a solid phase and exposed to ligands in a mobile phase running along a flow cell. If ligand binding to the immobilized target occurs, the local refractive index changes, leading to a change in SPR angle, which can be monitored in real time by detecting changes in the intensity of the reflected light. The rates of change of the SPR signal can be analyzed to yield apparent rate constants for the association and dissociation phases of the binding reaction. The ratio of these values gives the apparent equilibrium constant (affinity) (see, e.g., Wolff et al, Cancer Res. 53:2560-65 (1993)).

Preferably the antibody according to the present invention is specific for human TREM1.

Disclosure herein relating to antibodies, particularly with respect to binding affinity and specificity, and activity, also is applicable to antigen-binding fragments and antibody-like molecules.

Antibodies Binding to the Same Epitope

Antibodies may compete for binding to TREM1 with, or bind to the same epitope as, those defined above in terms of light-chain, heavy-chain, light chain variable region (LCVR), heavy chain variable region (HCVR) or CDR sequences.

In particular, the present invention provides an antibody that competes for binding to TREM1 with, or bind to the same epitope as, an antibody which comprises a CDR-L1/CDR-L2/CDR-L3/CDR-H1/CDR-H2/CDR-H3 sequence combination of SEQ ID NOs: 11/12/13/14/15/16. An antibody may compete for binding to TREM1 with, or bind to the same epitope as, an antibody which comprises a LCVR and HCVR sequence pair of SEQ ID NOs: 29/79. An antibody may compete for binding to TREM1 with or bind to the same epitope as an IgG4P comprising a CDR-L1/CDR-L2/CDR-L3/CDR-H1/CDR-H2/CDR-H3 sequence combination of SEQ ID NOs: 11/12/13/14/15/16.

In some embodiments, the anti-TREM1 antibody binds to an epitope on human TREM1, said epitope comprising residues E26, E27, K28, Y29, E30, L31, K32 and Q35 (where the numbering is according to SEQ ID NO: 1). Such epitope can be determined using the method disclosed herein, which involved designing an array of mutant TREM1 proteins and measuring the binding of said antibody to the mutant TREM1 proteins comprising 2 or 3 of said residues being mutated into a smaller amino acid, such as Ala.

In one embodiment, the present invention provides an IgG4P antibody that binds to an epitope of human TREM1, the epitope comprising residues E26, E27, K28, Y29, E30, L31, K32 and Q35 of human TREM1 (SEQ ID NO: 1).

In one embodiment, the present invention provides an anti-TREM1 antibody which binds to an epitope on TREM1, said epitope comprising at least 3, at least 4, at least 5, at least 6, at least 7, at least 8, at least 9, at least 10, or all of residues selected from the list consisting of E26, E27, K28, Y29, E30, L31, K32, Q35, T36, D38, K40, D42, R97, D127, T134 and G136 of human TREM1 (SEQ ID NO: 1) as determined at less than 4 Å contact distance.

In one embodiment, the present invention provides an IgG4P antibody that binds to an epitope of human TREM1, said epitope comprising at least 3, at least 4, at least 5, at least 6, at least 7, at least 8, at least 9, at least 10, or all of residues selected from the list consisting of E26, E27, K28, Y29, E30, L31, K32, Q35, T36, D38, K40, D42, R97, D127, T134 and G136 of human TREM1 (SEQ ID NO: 1) as determined at less than 4 Å contact distance.

In some embodiments, the present invention provides an anti-TREM1 antibody which binds to a different epitope than PGLYRP1. In some embodiments, the present invention provides an anti-TREM1 antibody which binds to an epitope on TREM1, said epitope comprising not more that 1 or 2 residues selected from the list consisting of E27, D42-E46, A49, Y90-L95, and F126 of human TREM1 (SEQ ID NO: 1) as determined at less than 4 Å contact distance.

The epitope can be identified by any suitable binding site mapping method known in the art in combination with any one of the antibodies provided by the present invention. A specific method is provided by the present disclosure that is relying on arrays of mutant TREM1 proteins to establish which of the mutant residues are important for binding for a particular antibody. Using such method it is possible to identify antibodies that bind to essentially the same amino acid residues as the antibodies provided by the present invention. Other examples of epitope mapping methods include screening peptides of varying lengths derived from full length target protein for binding to the antibody or fragment thereof of the present invention and identify a fragment that can specifically bind to the antibody containing the sequence of the epitope recognized by the antibody. Target peptides may be produced synthetically. Peptides that bind the antibody can be identified by, for example, mass spectrometric analysis. In another example, NMR spectroscopy or X-ray crystallography can be used to identify the epitope bound by an antibody of the present invention. Typically, when the epitope determination is performed by X-ray crystallography, amino acid residues of the antigen within 4 Å from CDRs are considered to be amino acid residues part of the epitope. Once identified, the epitope may serve for preparing fragments which bind an antibody of the present invention and, if required, used as an immunogen to obtain additional antibodies which bind the same epitope.

In one embodiment the epitope of the antibody is determined by X-ray crystallography.

One can easily determine whether an antibody binds to the same epitope as, or competes for binding with, a reference antibody by using routine methods known in the art. For example, to determine if a test antibody binds to the same epitope as a reference antibody of the invention, the reference antibody is allowed to bind to a protein or peptide under saturating conditions. Next, the ability of a test antibody to bind to the protein or peptide is assessed. If the test antibody is able to bind to the protein or peptide following saturation binding with the reference antibody, it can be concluded that the test antibody binds to a different epitope than the reference antibody. On the other hand, if the test antibody is not able to bind to protein or peptide following saturation binding with the reference antibody, then the test antibody may bind to the same epitope as the epitope bound by the reference antibody of the invention or the reference antibody causes a conformation change in the antigen and hence preventing the binding of the test antibody.

To determine if an antibody competes for binding with a reference antibody, the above-described binding methodology is performed in two different experimental setups. In a first setup, the reference antibody is allowed to bind to the antigen under saturating conditions followed by assessment of binding of the test antibody to the antigen. In a second setup, the test antibody is allowed to bind to the antigen under saturating conditions followed by assessment of binding of the reference antibody to the protein/peptide. If, in both experimental setups, only the first (saturating) antibody is capable of binding to the protein/peptide, then it is concluded that the test antibody and the reference antibody compete for binding to the antigen. As will be appreciated by the skilled person, an antibody that competes for binding with a reference antibody may not necessarily bind to the identical epitope as the reference antibody, but may sterically block binding of the reference antibody by binding an overlapping or adjacent epitope or cause a conformational change leading to the lack of binding.

Two antibodies bind to the same or overlapping epitope if each competitively inhibits (blocks) binding of the other to the antigen. Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Additional routine experimentation (e.g., peptide mutation and binding analyses) can then be carried out to confirm whether the observed lack of binding of the test antibody is in fact due to binding to the same part of the antigen as the reference antibody or if steric blocking (or another phenomenon) is responsible for the lack of observed binding. Experiments of this sort can be performed using ELISA, RIA, surface plasmon resonance, flow cytometry or any other quantitative or qualitative antibody-binding assay available in the art.

Antibody Variants

In certain embodiments, antibody variants having one or more amino acid substitutions, insertions, and/or deletions are provided. Sites of interest for substitutional mutagenesis include the CDRs and FRs. Amino acid substitutions may be introduced into an antibody of interest and the products screened for a desired activity, e.g., retained/improved antigen binding, decreased immunogenicity, or improved ADCC or CDC.

In certain embodiments, amino acid sequence variants of the antibodies described herein are contemplated. For example, it may be desirable to improve the binding affinity and/or other biological properties of the antibody. Amino acid sequence variants of the anti-TREM1 antibody may be prepared by introducing appropriate modifications into the nucleotide sequence encoding the protein, or by peptide synthesis. Such modifications include, for example, deletions from, and/or insertions into and/or substitutions of residues within the amino acid sequences (such as in one or more CDRs and/or framework sequences or in a VH and/or a VL domain) of the anti-TREM1 antibody. Any combination of deletion, insertion, and substitution can be made to arrive at the final construct, provided that the final construct possesses the desired characteristics.

In certain embodiments of the variant VH and VL sequences provided herein, each HVR either is unaltered, or contains no more than one, two or three amino acid substitutions.

It will be appreciated that one or more amino acid substitutions, additions and/or deletions may be made to the CDRs provided by the present invention without significantly altering the ability of the antibody to bind to TREM1 and to neutralize TREM1 activity. The effect of any amino acid substitutions, additions and/or deletions can be readily tested by one skilled in the art, for example by using the methods described herein, particularly those illustrated in the Examples, to determine TREM1 binding and inhibition of the TREM1 interactions with its natural ligands.

Consequently, in certain embodiments of the variant VH and VL sequences, each CDR either contains no more than one, two or three amino acid substitutions, wherein such amino-acid substitutions are conservative, and wherein the antibody retains its binding properties to TREM1.

Accordingly, the present invention provides an anti-TREM1 antibody comprising one or more CDRs selected from CDR-L1 (comprising SEQ ID NO:11), CDR-L2 (comprising SEQ ID NO:12), CDR-L3 (comprising SEQ ID NO:13), CDR-H1 (comprising SEQ ID NO:14), CDR-H2 (comprising SEQ ID NO:15) and CDR-H3 (comprising SEQ ID NO:16) in which one or more amino acids in one or more of the CDRs has been substituted with another amino acid, for example a similar amino acid as defined herein below.

In one embodiment, the present invention provides an anti-TREM1 antibody comprising CDR-L1 (comprising SEQ ID NO:11), CDR-L2 (comprising SEQ ID NO:12), CDR-L3 (comprising SEQ ID NO:13), CDR-H1 (comprising SEQ ID NO:14), CDR-H2 (comprising SEQ ID NO:15) and CDR-H3 (comprising SEQ ID NO:16), for example in which one or more amino acids in one or more of the CDRs has been substituted with another amino acid, such as a similar amino acid as defined herein below.

In one embodiment, the present invention provides an anti-TREM1 antibody CDR-L2 (comprising SEQ ID NO:12) wherein the first amino acid of SEQ ID NO:12 has been substituted by another amino acid. More particularly the K is substituted by S.

In one embodiment, an anti-TREM1 antibody of the present invention comprises a light chain variable domain which comprises three CDRs wherein the sequence of CDR-L1 comprises a sequence that has at least 70%, 80%, 90%, 91%, 92%, 93%, 94%, 95%, 96%, 97%, 98%, or 99% identity or similarity to the sequence given in SEQ ID NO:11, CDR-L2 comprises a sequence that has at least 70%, 80%, 90%, 95% or 98% identity or similarity to the sequence given in SEQ ID NO:12 and/or CDR-L3 comprises a sequence that has at least 70%, 80%, 90%, 91%, 92%, 93%, 94%, 95%, 96%, 97%, 98%, or 99% identity or similarity to the sequence given in SEQ ID NO:13.

In one embodiment, an anti-TREM1 antibody of the present invention comprises a heavy chain variable domain which comprises three CDRs wherein the sequence of CDR-H1 comprises a sequence that has at least 70%, 80%, 90%, 91%, 92%, 93%, 94%, 95%, 96%, 97%, 98%, or 99% identity or similarity to the sequence given in SEQ ID NO:14, CDR-H2 comprises a sequence that has at least 70%, 80%, 90%, 91%, 92%, 93%, 94%, 95%, 96%, 97%, 98%, or 99% identity or similarity to the sequence given in SEQ ID NO:15 and/or CDR-H3 comprises a sequence that has at least 70%, 80%, 90%, 91%, 92%, 93%, 94%, 95%, 96%, 97%, 98%, or 99% identity or similarity to the sequence given in SEQ ID NO:16.

In one embodiment, an anti-TREM1 antibody of the present invention comprises alight chain variable region comprising a sequence having at least 70%, 80%, 90%, 91%, 92%, 93%, 94%, 95%, 96%, 97%, 98%, or 99% identity or similarity to the sequence given in SEQ ID NO:29.

In one embodiment, an antibody of the present invention comprises a heavy chain variable region comprising a sequence having at least 70%, 80%, 90%, 91%, 92%, 93%, 94%, 95%, 96%, 97%, 98%, or 99% identity or similarity to the sequence given in SEQ ID NO:79.

In one embodiment, an anti-TREM1 antibody of the present invention comprises alight chain variable region and a heavy chain variable region, wherein the light chain variable region comprises a sequence having at least 70%, 80%, 90%, 91%, 92%, 93%, 94%, 95%, 96%, 97%, 98%, or 99% identity or similarity to given in SEQ ID NO:29 and/or the heavy chain variable region comprises a sequence having at least 70%, 80%, 90%, 91%, 92%, 93%, 94%, 95%, 96%, 97%, 98%, or 99% identity or similarity to given in SEQ ID NO:79.

In one embodiment, an anti-TREM1 antibody of the present invention comprises CDR-L1/CDR-L2/CDR-L3/CDR-H1/CDR-H2/CDR-H3 sequences comprising SEQ ID NOs:11/12/13/14/15/16 respectively, and the remainder of the light chain and heavy chain variable regions have at least 70%, 80%, 90%, 91%, 92%, 93%, 94%, 95%, 96%, 97%, 98%, or 99% identity or similarity to SEQ ID NO:29 and 79 respectively.

In one embodiment the anti-TREM1 antibody of the present invention is a IgG4P comprising a light chain comprising sequence having at least 70%, 80%, 90%, 91%, 92%, 93%, 94%, 95%, 96%, 97%, 98%, or 99% identity or similarity to the sequence given in SEQ ID NO:31 and a heavy chain comprising sequence having at least 70%, 80%, 90%, 91%, 92%, 93%, 94%, 95%, 96%, 97%, 98%, or 99% identity or similarity to the sequence given in SEQ ID NO:81.

In one embodiment, an anti-TREM1 antibody of the present invention is a IgG4P comprising CDR-L1/CDR-L2/CDR-L3/CDR-H1/CDR-H2/CDR-H3 sequences given in SEQ ID NOs:11/12/13/14/15/16 respectively, and the remainder of the of the light chain and heavy chain has at least 70%, 80%, 90%, 91%, 92%, 93%, 94%, 95%, 96%, 97%, 98%, or 99% identity or similarity to SEQ ID Nos: 31 and 81 respectively.

In one embodiment, an antibody of the present invention comprises a light chain variable region and a heavy chain variable region, wherein the light chain variable region comprises the sequence given in SEQ ID NO:29, wherein one or more residues at the positions 1, 2, 3, 18 and 50 have been substituted by another amino-acid; and the heavy chain variable region comprises the sequence given in SEQ ID NO:79, wherein one or more residues at the positions 23, 48, 49, 71, 73, 75 and 78 have been substituted by another amino-acid.

Sequence Identity and Similarity

Degrees of identity and similarity between sequences can be readily calculated. The "% sequence identity" (or "% sequence similarity") is calculated by: (1) comparing two optimally aligned sequences over a window of comparison (e.g., the length of the longer sequence, the length of the shorter sequence, a specified window, etc.), (2) determining the number of positions containing identical (or similar) amino-acids (e.g., identical amino acids occurs in both sequences, similar amino acid occurs in both sequences) to yield the number of matched positions, (3) dividing the number of matched positions by the total number of positions in the comparison window (e.g., the length of the longer sequence, the length of the shorter sequence, a specified window), and (4) multiplying the result by 100 to obtain the % sequence identity or percent sequence similarity.

Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

Preferred examples of algorithms that are suitable for determining percent sequence identity and sequence similarity include the BLAST and BLAST 2.0 algorithms, which are described in Altschul et al., Nuc. Acids Res. 25:3389-3402 (1977) and Altschul et al., J. Mol. Biol. 215:403-410 (1990). Polypeptide sequences also can be compared using FASTA using default or recommended parameters. FASTA (e.g., FASTA2 and FASTA3) provides alignments and percent sequence identity of the regions of the best overlap between the query and search sequences.

In certain embodiments, substitutions, insertions, or deletions may occur within one or more CDR so long as such alterations do not substantially reduce the ability of the antibody to bind the target.

For example, conservative alterations that do not substantially reduce binding affinity may be made in CDRs. Such alterations may be made outside of antigen contacting residues in the CDRs.

Conservative substitutions are shown in Table 4 together with more substantial "exemplary substitutions".

TABLE 4

Examples of amino-acid substitutions

| Original Residue | Exemplary Substitutions | Conservative Substitution |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys(C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe | Leu |
| Leu (L) | Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; | Leu |

Substantial modifications in the biological properties of an antibody variant can be accomplished by selecting substitutions that differ significantly in their effect on maintaining the structure of the polypeptide backbone in the area of the substitution, the charge or hydrophobicity of the molecule at the target site, or the bulk of the side chain. Amino acids may be grouped according to similarities in the properties of their side chains (in A. L. Lehninger, Biochemistry second ed., pp. 73-75, Worth Publishers, New York (1975))

One type of substitutional variant involves substituting one or more CDR region residues of a parent antibody (humanized or human antibody). Generally, the resulting variant(s) selected for further study will have changes in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques. Briefly, one or more CDR residues are mutated and the variant antibodies displayed on phage and screened for a particular biological activity (e.g. binding affinity).

Alterations (e.g., substitutions) may be made in CDRs, e.g., to improve antibody affinity. Such alterations may be made in HVR "hotspots," i.e., residues encoded by codons that undergo mutation at high frequency during the somatic maturation process (see, e.g., Chowdhury, Methods Mol. Biol. 207: 179-196 (2008)), and/or residues that contact antigen, with the resulting variant VH or VL being tested for binding affinity. Affinity maturation by constructing and reselecting from secondary libraries has been described, e.g., in Hoogenboom et al. Methods in Molecular Biology 178: 1-37 (O'Brien et al., ed., Human Press, Totowa, NJ, (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity.

One of the methods that can be used for identification of residues or regions of an antibody that may be targeted for mutagenesis is alanine scanning mutagenesis (Cunningham and Wells (1989) Science, 244: 1081-1085). In this method, a residue or a number of target residues are identified and replaced by alanine to determine whether the interaction of the antibody with antigen is affected. Alternatively, or additionally, an X-ray structure of an antigen-antibody complex can be used to identify contact points between the antibody and its antigen. Variants may be screened to determine whether they contain the desired properties.

Constant Region Variants

In some embodiments, one or more amino acid modifications may be introduced into the Fc region of an antibody provided herein, thereby generating an Fc region variant. The Fc region variant may comprise a human Fc region sequence (e.g., a human IgGl, IgG2, IgG3 or IgG4 Fc region) comprising an amino acid modification (e.g. a substitution) at one or more amino acid positions.

Certain antibody variants with improved or diminished binding to FcRs are described. (See, e.g., U.S. Pat. No. 6,737,056; WO 2004/056312, and Shields et al., J. Biol. Chem. 9(2): 6591-6604 (2001).)

Antibodies with increased half-lives and improved binding to the neonatal Fc receptor (FcRn) are described in US2005/0014934A1. Those antibodies comprise an Fc region with one or more substitutions therein which improve binding of the Fc region to FcRn.

In certain embodiments, an antibody variant comprises an Fc region with one or more amino acid substitutions which improve ADCC, e.g., substitutions at positions 298, 333, and/or 334 of the Fc region (EU numbering of residues).

Antibodies with reduced effector function include those with substitution of one or more of Fc region residues 234, 235, 237, 238, 265, 269, 270, 297, 327 and 329 (see, e.g., U.S. Pat. No. 6,737,056). Such Fc mutants include Fc mutants with substitutions at two or more of amino acid positions 265, 269, 270, 297 and 327 wherein the amino acid residue is numbered according to the EU numbering system.

In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcRI, FcγRII and FcγRIII. FcR expression on hematopoietic cells is summarized in Ravetch and Kinet, Annu. Rev. Immunol. 9:457-492 (1991). Non-limiting examples of in vitro assays to assess ADCC activity of a molecule of interest is described in U.S. Pat. Nos. 5,500,362; 5,821,337. Alternatively, or additionally, ADCC activity of the molecule of interest may be assessed in vivo, e.g., in an animal model such as that disclosed in Clynes et. al. Proc. Natl Acad. Sci. USA 95:652-656 (1998). Clq binding assays may also be carried out to confirm that the antibody is unable to bind Clq and hence lacks CDC activity. See, e.g., Clq and C3c binding ELISA in WO 2006/029879 and WO 2005/100402. To assess complement activation, a CDC assay may be performed (see, for example, Gazzano-Santoro et al, J. Immunol. Methods 202: 163 (1996); Cragg, M. S. et al, Blood 101:1045-1052 (2003); and Cragg, M. S. and M. I Glennie, Blood 103:2738-2743 (2004)). FcRn binding and in vivo clearance/half-life determinations can also be performed using methods known in the art (see, e.g., Petkova, S. B. et al, Intl. Immunol. 18(12): 1759-1769 (2006)).

The constant region domains of the antibody molecule of the present invention, if present, may be selected having regard to the proposed function of the antibody molecule, and in particular the effector functions which may be required. For example, the constant region domains may be human IgA, IgD, IgE, IgG or IgM domains. In particular, human IgG constant region domains may be used, especially of the IgG1 and IgG3 isotypes when the antibody molecule is intended for therapeutic uses and antibody effector functions are required. Alternatively, IgG2 and IgG4 isotypes may be used when the antibody molecule is intended for therapeutic purposes and antibody effector functions are not required. It will be appreciated that sequence variants of these constant region domains may also be used.

In some embodiments, the antibody is an IgG1 LALA, a mutant of the wild-type human IgG1 isoform in which amino acid substitutions L234A/L235A (according to EU numbering) in the constant region of IgG1 have been introduced.

In some embodiments, the antibody is an IgG4P, a mutant of the wild-type human IgG4 isoform in which amino acid 228 (according to EU numbering) is replaced by proline, as described for example in Angal et al., Molecular Immunology, 1993, 30 (1), 105-108.

Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Humanized, Human, and Chimeric Antibodies

The antibodies of the present invention may be, but are not limited to, humanized, fully human or chimeric antibodies.

In one embodiment, the antibody is humanized. More particular the anti-TREM1 antibody is a chimeric, human, or humanized antibody.

In certain embodiments, an antibody provided herein is a chimeric antibody. Examples of chimeric antibodies are described, e.g., in U.S. Pat. No. 4,816,567; and Morrison et al., Proc. Natl. Acad. Sci. USA, 81:6851-6855 (1984)). In one example, a chimeric antibody comprises a non-human variable region (e.g., a variable region derived from a mouse, rat, hamster, rabbit, or non-human primate, such as a monkey) and a human constant region. In another example, a chimeric antibody is a "class switched" antibody in which the class or subclass has been changed from that of the parent antibody.

Chimeric antibodies are composed of elements derived from two different species such that the element retains the characteristics of the species from which it is derived. Generally a chimeric antibody will comprise a variable region from one species, for example a mouse, rat, rabbit or similar and constant region from another species such as a human.

In certain embodiments, a chimeric antibody is a humanized antibody.

It will be appreciated that it may only be necessary to transfer the specificity determining residues of the CDRs rather than the entire CDR (see for example, Kashmiri et al., 2005, Methods, 36, 25-34). Humanized antibodies may optionally further comprise one or more framework residues derived from the non-human species from which the CDRs were derived.

Suitably, the humanized antibody according to the present invention has a variable domain comprising human acceptor framework regions as well as one or more of the CDRs and optionally further including one or more donor framework residues.

In one embodiment the antibody is a humanized antibody, wherein the variable domain comprises human acceptor framework regions and non-human donor CDRs.

When the CDRs are grafted, any appropriate acceptor variable region framework sequence may be used having regard to the class/type of the donor antibody from which the CDRs are derived, including mouse, primate and human framework regions.

Examples of human frameworks which can be used in the present invention are KOL, NEWM, REI, EU, TUR, TEI, LAY and POM (Kabat et al). For example, KOL and NEWM can be used for the heavy chain, REI can be used for the light chain and EU, LAY and POM can be used for both the heavy chain and the light chain. Alternatively, human germline sequences may be used; these are available at: www.imgt.org. In embodiments, the acceptor framework is IGKV1-9 human germline and/or IGHV3-66 human germline. In embodiments, the human framework contains 1-5, 1-4, 1-3 or 1-2 donor antibody amino acid residues.

In a humanized antibody of the present invention, the acceptor heavy and light chains do not necessarily need to be derived from the same antibody and may, if desired, comprise composite chains having framework regions derived from different chains.

In some embodiments, the antibody is a human antibody. Human antibodies can be produced using various techniques known in the art. More particular the anti-TREM1 antibody comprises a human antibody heavy chain constant region and a human light chain constant region.

Human antibodies comprise heavy or light chain variable regions or full length heavy or light chains that are derived from a particular germline sequence if the variable regions or full-length chains of the antibody are obtained from a system that uses human germline immunoglobulin genes. Such systems include immunizing a transgenic mouse carrying human immunoglobulin genes with the antigen of interest or screening a human immunoglobulin gene library displayed on phage with the antigen of interest. A human antibody that is derived from a human germline immunoglobulin sequence can be identified as such by comparing the amino acid sequence of the human antibody to the amino acid sequences of human germline immunoglobulins and selecting the human germline immunoglobulin sequence that is closest in sequence (i.e., greatest % identity) to the sequence of the human antibody. A human antibody that is derived from a particular human germline immunoglobulin sequence may contain amino acid differences as compared to the germline sequence, due to, for example, naturally occurring somatic mutations or intentional introduction of site-directed mutation. However, a selected human antibody typically is at least 90% identical in amino acid sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least 60%, 70%, 80%, 90%, or at least 95%, or even at least 96%, 97%, 98%, or 99% identical in amino acid sequence to the amino acid sequence encoded by the germline immunoglobulin gene. Typically, a human antibody derived from a particular human germline sequence will display no more than 10 amino acid differences from the amino acid sequence encoded by the human germline immunoglobulin gene. In certain cases, the human antibody may display no more than 5, or even no more than 4, 3, 2, or 1 amino acid difference from the amino acid sequence encoded by the germline immunoglobulin gene.

Human antibodies may be produced by a number of methods known to those of skill in the art. Human antibodies can be made by the hybridoma method using human myeloma or mouse human heteromyeloma cells lines (Kozbor, J Immunol; (1984) 133:3001; Brodeur, Monoclonal Isolated Antibody Production Techniques and Applications, pp 51-63, Marcel Dekker Inc, 1987). Alternative methods include the use of phage libraries or transgenic mice both of which utilize human variable region repertories (Winter G; (1994) Annu Rev Immunol 12:433-455, Green L L, (1999) J Immunol Methods 231:11-23). Human antibodies may be produced, for example, by mice in which the murine immunoglobulin variable and optionally the constant region genes have been replaced by their human counterparts as described, for example, in U.S. Pat. Nos. 5,545,806, 5,569,825, 5,625,126, 5,633,425, 5,661,016, and 5,770,429.

Effector Molecules

If desired an antibody according to the present invention may be conjugated to one or more effector molecule(s). In one embodiment the antibody is not attached an effector molecule.

It will be appreciated that the effector molecule may comprise a single effector molecule or two or more such molecules so linked as to form a single moiety that can be attached to the antibodies of the present invention. Where it is desired to obtain an antibody fragment linked to an effector molecule, this may be prepared by standard chemical or recombinant DNA procedures in which the antibody fragment is linked either directly or via a coupling agent to the effector molecule. Techniques for conjugating such effector molecules to antibodies are well known in the art (see, Hellstrom et al., Controlled Drug Delivery, 2nd Ed., Robinson et al., eds., 1987, pp. 623-53; Thorpe et al., 1982, Immunol. Rev., 62:119-58 and Dubowchik et al., 1999, Pharmacology and Therapeutics, 83, 67-123). Particular chemical procedures include, for example, those described in WO 93/06231, WO 92/22583, WO 89/00195, WO 89/01476 and WO 03/031581. Alternatively, where the effector molecule is a protein or polypeptide the linkage may be achieved using recombinant DNA procedures, for example as described in WO 86/01533 and EP0392745.

Examples of effector molecules may include cytotoxins or cytotoxic agents including any agent that is detrimental to (e.g. kills) cells. Examples include combrestatins, dolastatins, epothilones, staurosporin, maytansinoids, spongistatins, rhizoxin, halichondrins, roridins, hemiasterlins, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

Effector molecules also include, but are not limited to, antimetabolites (e.g. methotrexate, 6-mercaptopurine, 6-thioguanine, cytarabine, 5-fluorouracil decarbazine), alkylating agents (e.g. mechlorethamine, thiotepa chlorambucil, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines (e.g. daunorubicin (formerly daunomycin) and doxorubicin), antibiotics (e.g. dactinomycin (formerly actinomycin), bleomycin, mithramycin, anthramycin (AMC), calicheamicins or duocarmycins), and anti-mitotic agents (e.g. vincristine and vinblastine).

Other effector molecules may include chelated radionuclides such as 111In and 90Y, Lu177, Bismuth213, Californium252, Iridium192 and Tungsten188/Rhenium188; or drugs such as but not limited to, alkylphosphocholines, topoisomerase I inhibitors, taxoids and suramin.

Other effector molecules include proteins, peptides and enzymes. Enzymes of interest include, but are not limited to, proteolytic enzymes, hydrolases, lyases, isomerases, transferases. Proteins, polypeptides and peptides of interest include, but are not limited to, immunoglobulins, toxins such as abrin, ricin A, *Pseudomonas* exotoxin, or diphtheria toxin, a protein such as insulin, tumour necrosis factor, α-interferon, β-interferon, nerve growth factor, platelet derived growth factor or tissue plasminogen activator, a thrombotic agent or an anti-angiogenic agent, e.g. angiostatin or endostatin, or, a biological response modifier such as a lymphokine, interleukin-1 (IL-1), interleukin-2 (IL-2), granulocyte macrophage colony stimulating factor (GM-CSF), granulocyte colony stimulating factor (G-CSF), nerve growth factor (NGF) or other growth factor and immunoglobulins.

Other effector molecules may include detectable substances useful for example in diagnosis. Examples of detectable substances include various enzymes, prosthetic groups, fluorescent materials, luminescent materials, bioluminescent materials, radioactive nuclides, positron emitting metals (for use in positron emission tomography), and nonradioactive paramagnetic metal ions. See generally U.S. Pat. No. 4,741,900 for metal ions which can be conjugated to antibodies for use as diagnostics. Suitable enzymes include horseradish peroxidase, alkaline phosphatase, beta galactosidase, or acetylcholinesterase; suitable prosthetic groups include streptavidin, avidin and biotin; suitable fluorescent materials include umbelliferone, fluorescein, fluorescein isothiocyanate, rhodamine, dichlorotriazinylamine fluorescein, dansyl chloride and phycoerythrin; suitable luminescent materials include luminol; suitable bioluminescent materials include luciferase, luciferin, and aequorin; and suitable radioactive nuclides include 125I, 131I, 111In and 99Tc.

In another example the effector molecule may increase the half-life of the antibody in vivo, and/or reduce immunogenicity of the antibody and/or enhance the delivery of an antibody across an epithelial barrier to the immune system. Examples of suitable effector molecules of this type include polymers, albumin, albumin binding proteins or albumin binding compounds such as those described in WO2005/117984.

Where the effector molecule is a polymer it may, in general, be a synthetic or a naturally occurring polymer, for example an optionally substituted straight or branched chain polyalkylene, polyalkenylene or polyoxyalkylene polymer or a branched or unbranched polysaccharide, e.g. a homo- or hetero polysaccharide.

Specific optional substituents which may be present on the above-mentioned synthetic polymers include one or more hydroxy, methyl or methoxy groups.

Specific examples of synthetic polymers include optionally substituted straight or branched chain poly(ethyleneglycol), poly(propyleneglycol) poly(vinylalcohol) or derivatives thereof, especially optionally substituted poly(ethyleneglycol) such as methoxypoly(ethyleneglycol) or derivatives thereof.

Specific naturally occurring polymers include lactose, amylose, dextran, glycogen or derivatives thereof.

In one embodiment, the polymer is albumin or a fragment thereof, such as human serum albumin or a fragment thereof.

The size of the polymer may be varied as desired, but will generally be in an average molecular weight range from 500 Da to 50000 Da, for example from 5000 to 40000 Da such as from 20000 to 40000 Da. The polymer size may in particular be selected on the basis of the intended use of the product for example ability to localize to certain tissues such as tumors or extend circulating half-life (for review see Chapman, 2002, Advanced Drug Delivery Reviews, 54, 531-545). Thus, for example, where the product is intended to leave the circulation and penetrate tissue, for example for use in the treatment of a tumor, it may be advantageous to use a small molecular weight polymer, for example with a molecular weight of around 5000 Da. For applications where the product remains in the circulation, it may be advantageous to use a higher molecular weight polymer, for example having a molecular weight in the range from 20000 Da to 40000 Da.

Suitable polymers include a polyalkylene polymer, such as a poly(ethyleneglycol) or, especially, a methoxypoly(ethyleneglycol) or a derivative thereof, and especially with a molecular weight in the range from about 15000 Da to about 40000 Da.

In one example, the antibody according to the present invention are attached to poly(ethyleneglycol) (PEG) moieties. In one particular embodiment, the antigen-binding fragment according to the present invention and the PEG molecules may be attached through any available amino acid side-chain or terminal amino acid functional group located in the antibody fragment, for example any free amino, imino, thiol, hydroxyl or carboxyl group. Such amino acids may occur naturally in the antibody fragment or may be engineered into the fragment using recombinant DNA methods (see for example U.S. Pat. Nos. 5,219,996; 5,667,425; WO98/25971, WO2008/038024). In one example the antibody molecule of the present invention is a modified Fab fragment wherein the modification is the addition to the C-terminal end of its heavy chain one or more amino acids to allow the attachment of an effector molecule. Suitably, the additional amino acids form a modified hinge region containing one or more cysteine residues to which the effector molecule may be attached. Multiple sites can be used to attach two or more PEG molecules.

Suitably PEG molecules are covalently linked through a thiol group of at least one cysteine residue located in the antibody fragment. Each polymer molecule attached to the modified antibody fragment may be covalently linked to the sulphur atom of a cysteine residue located in the fragment. The covalent linkage will generally be a disulphide bond or, in particular, a sulphur-carbon bond. Where a thiol group is used as the point of attachment appropriately activated effector molecules, for example thiol selective derivatives such as maleimides and cysteine derivatives may be used. An activated polymer may be used as the starting material in the preparation of polymer-modified antibody fragments as described above. The activated polymer may be any polymer containing a thiol reactive group such as an α-halocarboxylic acid or ester, e.g. iodoacetamide, an imide, e.g. maleimide, a vinyl sulphone or a disulphide. Such starting materials may be obtained commercially (for example from Nektar, formerly Shearwater Polymers Inc., Huntsville, AL, USA) or may be prepared from commercially available starting materials using conventional chemical procedures. Particular PEG molecules include 20K methoxy-PEG-amine (obtainable from Nektar, formerly Shearwater; Rapp Polymere; and SunBio) and M-PEG-SPA (obtainable from Nektar, formerly Shearwater).

In one embodiment, the antibody is a modified Fab fragment, Fab' fragment or diFab which is PEGylated, i.e. has PEG (poly(ethyleneglycol)) covalently attached thereto, e.g. according to the method disclosed in EP0948544 or EP1090037 [see also "Poly(ethyleneglycol) Chemistry, Biotechnical and Biomedical Applications", 1992, J. Milton Harris (ed), Plenum Press, New York, "Poly(ethyleneglycol) Chemistry and Biological Applications", 1997, J. Milton Harris and S. Zalipsky (eds), American Chemical Society, Washington DC and "Bioconjugation Protein Coupling Techniques for the Biomedical Sciences", 1998, M. Aslam and A. Dent, Grove Publishers, New York; Chapman, A. 2002, Advanced Drug Delivery Reviews 2002, 54:531-545]. In one example PEG is attached to a cysteine in the hinge region. In one example, a PEG modified Fab fragment has a maleimide group covalently linked to a single thiol group in a modified hinge region. A lysine residue may be covalently linked to the maleimide group and to each of the amine groups on the lysine residue may be attached a methoxypoly(ethyleneglycol) polymer having a molecular weight of approximately 20,000 Da. The total molecular weight of the PEG attached to the Fab fragment may therefore be approximately 40,000 Da.

In one embodiment, the antibody is a modified Fab' fragment having at the C-terminal end of its heavy chain a modified hinge region containing at least one cysteine residue to which an effector molecule is attached. Suitably the effector molecule is PEG and is attached using the methods described in (WO 98/25971 and WO 2004072116 or in WO 2007/003898. Effector molecules may be attached to antibody fragments using the methods described in International patent applications WO 2005/003169, WO 2005/003170 and WO 2005/003171.

In one embodiment the antibody is not attached an effector molecule.

Polynucleotides and Vectors

The present invention also provides an isolated polynucleotide encoding the antibody or a part thereof according to the present invention (such as Amino-acid SEQ IDs listed in Table 5). The isolated polynucleotide according to the present invention may comprise synthetic DNA, for instance produced by chemical processing, cDNA, genomic DNA or any combination thereof.

TABLE 5

Amino-acid sequences of the anti-TREM1 antibodies and their corresponding nucleic acid sequences.

| Antibody sequence | Amino-acid SEQ ID NO | Nucleic acid SEQ ID NO |
|---|---|---|
| 12172 gL6gH6 light chain V region | 33 | 34 |
| 12172 gL6gH6 heavy chain V region | 57 | 58 |
| 12172 gL6gH6 light chain | 35 | 36 |
| 12172 gL6gH6 heavy chain IgG1 | 63 | 64 |
| 12172 gL6gH6 heavy chain IgG1 LALA | 65 | 66 |
| 12172 gL6gH6 heavy chain IgG4P | 59 | 60 |
| 12172 gL6gH6 heavy chain IgG4P FALA | 61 | 62 |
| 12172 gL2gH11 light chain V region | 29 | 30 |
| 12172 gL2gH11 heavy chain V region | 79 | 80 |
| 12172 gL2gH11 light chain | 31 | 32 |
| 12172 gL2gH11 heavy chain IgG1 | 85 | 86 |
| 12172 gL2gH11 heavy chain IgG1 LALA | 87 | 88 |
| 12172 gL2gH11 heavy chain IgG4P | 81 | 82 |
| 12172 gL2gH11 heavy chain IgG4P FALA | 83 | 84 |

Examples of suitable sequences are provided herein. Thus in one embodiment the present invention provides an isolated polynucleotide encoding an antibody, comprising a sequence given in SEQ ID NOs 34, 58, 36, 64, 66, 60, 62, 30, 80, 32, 86, 88, 82, or 84.

In one embodiment, the present invention provides an isolated polynucleotide encoding the heavy chain of an IgG1 LALA or IgG4P antibody of the present invention which comprises the sequence given in SEQ ID NO: 88 or 82 respectively.

Also provided is an isolated polynucleotide encoding the light chain of an IgG1 LALA or IgG4P antibody of the present invention which comprises the sequence given in SEQ ID NO: 32.

In another embodiment, the present invention provides an isolated polynucleotide encoding the heavy chain and the light chain of an IgG4P antibody of the present invention in which the polynucleotide encoding the heavy chain comprises the sequence given in SEQ ID NO: 82 and the polynucleotide encoding the light chain comprises the sequence given in SEQ ID NO: 32.

The present invention also provides for a cloning or expression vector comprising one or more polynucleotides described herein. In one example, the cloning or expression vector according to the present invention comprises one or more isolated polynucleotides comprising a sequence selected from SEQ ID NO: 34, 58, 36, 64, 66, 60, 62, 30, 80, 32, 86, 88, 82, or 84.

Standard techniques of molecular biology may be used to prepare DNA sequences coding for the antibody or antigen-binding fragment thereof of the present invention. Desired DNA sequences may be synthesized completely or in part using oligonucleotide synthesis techniques. Site-directed mutagenesis and polymerase chain reaction (PCR) techniques may be used as appropriate.

General methods by which the vectors may be constructed, transfection methods and culture methods are well known to those skilled in the art. In this respect, reference is made to "Current Protocols in Molecular Biology", 1999, F. M. Ausubel (ed), Wiley Interscience, New York and the Maniatis Manual produced by Cold Spring Harbor Publishing.

Host Cells for Production of the Antibodies and Antigen-Binding Fragments Thereof Also provided is a host cell comprising one or more isolated polynucleotide sequences according to the invention or one or more cloning or expression vectors comprising one or more isolated polynucleotide sequences encoding an antibody of the present invention. Any suitable host cell/vector system may be used for expression of the polynucleotide sequences encoding the antibody or antigen-binding fragment thereof of the present invention. Bacterial, for example *E. coli*, and other microbial systems may be used or eukaryotic, for example mammalian, host cell expression systems may also be used. Suitable mammalian host cells include CHO, myeloma or hybridoma cells.

In a further embodiment, a host cell comprising such nucleic acid(s) or vector(s) is provided. In one such embodiment, a host cell comprises (e.g., has been transformed with): (1) a vector comprising a nucleic acid that encodes an amino acid sequence comprising the VL of the anti-TREM1 antibody and an amino acid sequence comprising the VH of the anti-TREM1 antibody, or (2) a first vector comprising a nucleic acid that encodes an amino acid sequence comprising the VL of the anti-TREM1 antibody and a second vector comprising a nucleic acid that encodes an amino acid sequence comprising the VH of the anti-TREM1 antibody. In one embodiment, the host cell is eukaryotic, e.g. a Chinese Hamster Ovary (CHO) cell or lymphoid cell (e.g., Y0, NS0, Sp20 cell). In one embodiment, the host cell is prokaryotic, e.g. an *E. coli* cell. In one embodiment, a method of making an anti-TREM1 antibody is provided, wherein the method comprises culturing a host cell comprising a nucleic acid encoding the antibody, as provided above, under conditions suitable for expression of the antibody, and optionally recovering the antibody from the host cell (or host cell culture medium).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, Methods in Molecular Biology, Vol. 248 (B. K. C. Lo, ed., Humana Press, Totowa, NJ, 2003), pp. 245-254, describing expression of antibody fragments in *E. coli*). After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, Nat. Biotech. 22: 1409-1414 (2004), and Li et al., Nat. Biotech. 24:210-215 (2006).

Suitable types of Chinese Hamster Ovary (CHO cells) for use in the present invention may include CHO and CHO-K1 cells including dhfr− CHO cells, such as CHO-DG44 cells and CHO-DXB11 cells and which may be used with a DHFR selectable marker or CHOK1-SV cells which may be used with a glutamine synthetase selectable marker. Other cell types of use in expressing antibodies include lymphocytic cell lines, e.g., NS0 myeloma cells and SP2 cells, COS cells. The host cell may be stably transformed or transfected with the isolated polynucleotide sequences or the expression vectors according to the present invention.

Process for the Production of the Antibodies

The present invention also provides a process for the production of an antibody according to the present invention comprising culturing a host cell according to the present invention under conditions suitable for producing the antibody according to the invention and isolating the antibody.

The antibody may comprise only a heavy or light chain polypeptide, in which case only a heavy chain or light chain polypeptide coding sequence needs to be used to transfect the host cells. For production of antibodies or antigen-binding fragments thereof comprising both heavy and light chains, the cell line may be transfected with two vectors, a first vector encoding a light chain polypeptide and a second vector encoding a heavy chain polypeptide. Alternatively, a single vector may be used, the vector including sequences encoding light chain and heavy chain polypeptides.

Thus, there is provided a process for culturing a host cell and expressing an antibody, isolating the antibody and optionally purifying the antibody to provide an isolated antibody. In one embodiment, the process further comprises the step of conjugating an effector molecule to the isolated antibody.

The present invention also provides a process for the production of an antibody according to the present invention comprising culturing a host cell containing a vector of the present invention under conditions suitable for leading to expression of protein from DNA encoding the antibody molecule of the present invention and isolating the antibody molecule.

The antibody molecule may comprise only a heavy or light chain polypeptide, in which case only a heavy chain or light chain polypeptide coding sequence needs to be used to transfect the host cells. For production of products comprising both heavy and light chains, the cell line may be transfected with two vectors, a first vector encoding a light chain polypeptide and a second vector encoding a heavy chain polypeptide. Alternatively, a single vector may be used, the vector including sequences encoding light chain and heavy chain polypeptides.

The antibodies according to the present invention are expressed at good levels from host cells. Thus the properties of the antibodies appear to be optimized for commercial processing.

Purified Antibody

In one embodiment there is provided a purified antibody, for example a humanized antibody, in particular an antibody according to the invention, in substantially purified form, in particular free or substantially free of endotoxin and/or host cell protein or DNA.

Substantially free of endotoxin is generally intended to refer to an endotoxin content of 1 EU per mg antibody product or less such as 0.5 or 0.1 EU per mg product.

Substantially free of host cell protein or DNA is generally intended to refer to host cell protein and/or DNA content 400 μg per mg of antibody product or less such as 100 μg per mg or less, in particular 20 μg per mg, as appropriate.

Therapeutic Use of the Antibodies

The antibodies of the invention, formulations, or pharmaceutical compositions thereof may be administered for prophylactic and/or therapeutic treatments.

The present invention provides an anti-TREM1 antibody of the invention or pharmaceutical composition thereof for use as a medicament.

In prophylactic applications, antibodies, formulations, or compositions are administered to a subject at risk of a disorder or condition as described herein, in an amount sufficient to prevent or reduce the subsequent effects of the condition or one or more of its symptoms.

In therapeutic applications, the antibodies are administered to a subject already suffering from a disorder or condition as described herein, in an amount sufficient to cure, alleviate or partially arrest the condition or one or more of its symptoms. Such therapeutic treatment may result in a decrease in severity of disease symptoms, or an increase in frequency or duration of symptom-free periods.

The subjects to be treated can be animals. Preferably, the pharmaceutical compositions according to the present invention are adapted for administration to human subjects.

The present invention provides a method of treating a disorder or condition as described herein in a subject in need thereof, the method comprising administering to the subject an antibody according to the present invention. Such antibody is administered in a therapeutically effective amount.

The present invention also provides an antibody of the invention for use in the treatment of a disorder or condition as described herein.

Therapeutic Indications

Antibodies of the present invention may be used in treating, preventing or ameliorating any condition that is associated with TREM1 activity; for example, any condition which results in whole or in part from signaling through TREM1.

TREM1 and its multiple pathways have been implicated in a number of neurological, neurodevelopmental, psychiatric, systemic and autoimmune inflammatory conditions. Some examples of the conditions that can treated using the antibodies and the compositions of the present invention include amyotrophic lateral sclerosis, Alzheimer's disease (AD), Parkinson's disease (PD), tauopathy disease, dementia, frontotemporal dementia, vascular dementia, mixed dementia, multiple system atrophy, epilepsy including Tuberous Sclerosis Complex and Focal Cortical Dysplasia, Huntington's disease, spinal cord injury, traumatic brain injury, chronic traumatic encephalopathy, ischemic stroke, multiple sclerosis, autoimmune neuritis, schizophrenia, autism spectrum disorders, major depressive disorders, bipolar disorder, hereditary conditions, or any combination thereof.

The antibodies and compositions of the present invention can be used to treat neurological disorders. More specifically said neurological disorder is amyotrophic lateral sclerosis (ALS) or Alzheimer's disease.

Diagnostic Use of the Antibodies and Antigen-Binding Fragments Thereof

The present invention also provides the use of the antibodies of the present invention as diagnostically active agents or in diagnostic assays, for example, for diagnosing a disease or its severity.

The diagnosis may preferably be performed on biological samples. A "biological sample" encompasses a variety of sample types obtained from an individual and can be used in a diagnostic or monitoring assay. The definition encompasses cerebrospinal fluid, blood such as plasma and serum, and other liquid samples of biological origin such as urine and saliva, solid tissue samples such as a biopsy specimen or tissue cultures or cells derived therefrom and the progeny thereof. The definition also includes samples that have been manipulated in any way after their procurement, such as by treatment with reagents, solubilization, or enrichment for certain components, such as polynucleotides.

Diagnostic testing may preferably be performed on biological samples which are not in contact with the human or animal body. Such diagnostic testing is also referred to as in vitro testing. In vitro diagnostic testing may rely on an in vitro method of detecting of TREM1 in a biological sample, which has been obtained from a subject.

Pharmaceutical and Diagnostic Compositions

An antibody of the invention may be provided in a pharmaceutical composition. The pharmaceutical composition will normally be sterile and may additionally comprise a pharmaceutically acceptable adjuvant and/or carrier.

As the antibodies of the present invention are useful in the treatment, diagnosis and/or prophylaxis of a disorder or condition as described herein, the present invention also provides for a pharmaceutical or diagnostic composition comprising an antibody or antigen-binding fragment thereof according to the present invention in combination with one or more of a pharmaceutically acceptable carrier, excipient or diluent.

In particular the antibody or antigen-binding fragment thereof is provided as a pharmaceutical composition comprising one or more of a pharmaceutically acceptable excipient, diluent or carrier.

These compositions may comprise, in addition to the therapeutically active ingredient(s), a pharmaceutically acceptable excipient, carrier, diluent, buffer, stabilizer or other materials well known to those skilled in the art. Such materials should be non-toxic and should not interfere with the efficacy of the active ingredient.

Also provided are compositions, including pharmaceutical formulations, comprising an anti-TREM1 antibody of the invention, or polynucleotides comprising sequences encoding an antibody of the invention. In certain embodiments, compositions comprise one or more antibodies of the invention, or one or more polynucleotides comprising sequences encoding one or more antibodies of the invention. These compositions may further comprise suitable carriers, such as pharmaceutically acceptable excipients and/or adjuvants including buffers, which are well known in the art.

Pharmaceutical compositions of an antibody of the present invention are prepared by mixing such antibody having the desired degree of purity with one or more optional pharmaceutically acceptable carriers in the form of lyophilized formulations or aqueous solutions.

Examples of the techniques and protocols mentioned above can be found in Remington's Pharmaceutical Sciences, 20th Edition, 2000, pub. Lippincott, Williams & Wilkins.

Pharmaceutically acceptable carriers are generally non-toxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include interstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US 2005/0260186 and 2006/0104968. In one aspect, a sHASEGP is combined with one or more additional glycosaminoglycanases such as chondroitinases.

Active ingredients may be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations may be also prepared. Suitable examples of sustained-release preparations include semipermeable matrices of solid hydrophobic polymers containing the antibody, which matrices are in the form of shaped articles, e.g. films, or microcapsules.

The formulations to be used for in vivo administration are generally sterile. Sterility may be readily accomplished, e.g., by filtration through sterile filtration membranes.

The pharmaceutical compositions of the invention may include one or more pharmaceutically acceptable salts.

Pharmaceutically acceptable carriers comprise aqueous carriers or diluents. Examples of suitable aqueous carriers that may be employed in the pharmaceutical compositions of the invention include water, buffered water and saline. Examples of other carriers include ethanol, polyols (such as glycerol, propylene glycol, polyethylene glycol, and the like), and suitable mixtures thereof, vegetable oils, such as olive oil, and injectable organic esters, such as ethyl oleate. In many cases, it will be desirable to include isotonic agents, for example, sugars, polyalcohols such as mannitol, sorbitol, or sodium chloride in the composition.

Pharmaceutical compositions typically must be sterile and stable under the conditions of manufacture and storage. The composition can be formulated as a solution, microemulsion, liposome, or other ordered structure suitable to high drug concentration.

In one embodiment, the antibody of the present invention is the sole active ingredient. In another embodiment, an antibody of the present invention is in combination with one or more additional active ingredients. Alternatively, the pharmaceutical compositions comprise the antibody of the present invention which is the sole active ingredient and it may be administered individually to a patient in combination (e.g. simultaneously, sequentially or separately) with other agents, drugs or hormones.

The precise nature of the carrier or other material may depend on the route of administration, e.g. oral, intravenous, cutaneous or subcutaneous, nasal, intramuscular and intraperitoneal routes. For example, solid oral forms may contain, together with the active substance, diluents, e.g. lactose, dextrose, saccharose, cellulose, corn starch or potato starch; lubricants, e.g. silica, talc, stearic acid, magnesium or calcium stearate, and/or polyethylene glycols; binding agents; e.g. starches, gum arabic, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulphates; and, in general, non-toxic and pharmacologically inactive substances used in pharmaceutical formulations. Such pharmaceutical preparations may be manufactured in known manner, for example, by means of mixing, granulating, tabletting, sugar-coating, or film-coating processes.

Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and contain 10% to 95% of active ingredient, preferably 25% to 70%. Where the pharmaceutical composition is lyophilised, the lyophilised material may be reconstituted prior to administration, e.g. a suspension. Reconstitution is preferably effected in buffer.

Solutions for intravenous administration or infusion may contain as carrier, for example, sterile water or preferably they may be in the form of sterile, aqueous, isotonic saline solutions.

Preferably, the pharmaceutical or diagnostic composition comprises a humanized antibody according to the present invention.

Therapeutically Effective Amount and Dosage Determination

The antibodies and pharmaceutical compositions according to the present invention may be administered suitably to a patient to identify the therapeutically effective amount required. For any antibody, the therapeutically effective amount can be estimated initially either in cell culture assays or in animal models, usually in rodents, rabbits, dogs, pigs or primates. The animal model may also be used to determine the appropriate concentration range and route of administration. Such information can then be used to determine useful doses and routes for administration in humans.

The precise therapeutically effective amount for a human subject will depend upon the severity of the disease state, the general health of the subject, the age, weight and gender of the subject, diet, time and frequency of administration, drug combination(s), reaction sensitivities and tolerance/response to therapy. Compositions may be conveniently presented in unit dose forms containing a predetermined amount of an active agent of the disclosure per dose. Dose ranges and regimens for any of the embodiments described herein include, but are not limited to, dosages ranging from 1 mg-1000 mg unit doses.

A suitable dosage of an antibody or pharmaceutical composition of the invention may be determined by a skilled medical practitioner. Actual dosage levels of the active ingredients in the pharmaceutical compositions of the present invention may be varied so as to obtain an amount of the active ingredient that is effective to achieve the desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A suitable dose may be, for example, in the range of from about 0.01 μg/kg to about 1000 mg/kg body weight, typically from about 0.1 μg/kg to about 100 mg/kg body weight, of the patient to be treated.

Dosage regimens may be adjusted to provide the optimum desired response (e.g., a therapeutic response). For example, a single dose may be administered, several divided doses may be administered over time or the dose may be proportionally reduced or increased as indicated by the exigencies of the therapeutic situation. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

Administration of Pharmaceutical Compositions or Formulations

The antibodies described herein or formulations or compositions thereof may be administered for prophylactic and/or therapeutic treatments.

An antibody or pharmaceutical composition of the invention may be administered via one or more routes of administration using one or more of a variety of methods known in the art. As will be appreciated by the skilled person, the route and/or mode of administration will vary depending upon the desired results. Examples of routes of administration for the antibodies or pharmaceutical compositions of the invention include intravenous, intramuscular, intradermal, intraocular, intraperitoneal, subcutaneous, spinal or other parenteral routes of administration, for example by injection or infusion. Alternatively, the antibody or pharmaceutical composition of the invention may be administered via a non-parenteral route, such as a topical, epidermal or mucosal route of administration. The antibody or pharmaceutical composition of the invention may be for oral administration.

Suitable forms for administration include forms suitable for parenteral administration, e.g. by injection or infusion, for example by bolus injection or continuous infusion, in intravenous, inhalable or sub-cutaneous form. Where the product is for injection or infusion, it may take the form of a suspension, solution or emulsion in an oily or aqueous vehicle and it may contain additional agents, such as suspending, preservative, stabilizing and/or dispersing agents. Alternatively, the antibody or antigen-binding fragment thereof according to the invention may be in dry form, for reconstitution before use with an appropriate sterile liquid. Solid forms suitable for solution in, or suspension in, liquid vehicles prior to injection may also be prepared.

Once formulated, the pharmaceutical compositions of the invention can be administered directly to the subject. Accordingly, provided herein is the use of an antibody or an antigen-binding fragment thereof according to the invention for the manufacture of a medicament.

Articles of Manufacture and Kits

The present disclosure also provides kits comprising the anti-TREM1 antibodies of the present invention and instructions for use. The kit may further contain one or more additional reagents, such as an additional therapeutic or prophylactic agent as discussed above.

The present invention provides use of an antibody according to the invention or pharmaceutical composition thereof for the manufacture of a medicament.

The present invention also provides use of an antibody of the present invention for the manufacture of a medicament for the treatment of a disorder or condition as described herein.

In certain embodiments, the article of manufacture or kit comprises a container containing one or more of the antibodies of the invention, or the compositions described herein. In certain embodiments, the article of manufacture or kit comprises a container containing nucleic acids(s) encoding one (or more) of the antibodies or the compositions described herein. In some embodiments, the kit includes a cell or cell line that produces an antibody as described herein.

In certain embodiments, the article of manufacture or kit comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treatment, prevention and/or diagnosis and may have a sterile access port. At least one agent in the composition is an antibody of the present invention. The label or package insert indicates that the composition is used for the treatment of a disorder or condition as described herein.

It should be noted that the above-mentioned embodiments illustrate rather than limit the invention, and that those skilled in the art will be able to design many alternative embodiments without departing from the scope of the claims. In the claims, any reference signs placed between parentheses shall not be construed as limiting the claim.

The sequences included in the present invention are shown in Tables 6 and 7:

TABLE 6

Sequences of TREM1

| Name | Sequence | SEQ ID NO |
|---|---|---|
| Human TREM1 isoform 1 (Accession No. NP_061113.1) SwissProt: Q9NP99 | MRKTRLWGLLWMLFVSELRAATKLTEEKYELKEGQTLDVKCDYTLEKFASSQKAWQIIRDGEMPKTLACTERPSKNSHPVQVGRIILEDYHDHGLLRVRMVNLQVEDSGLYQCVIYQPPKEPHMLFDRIRLVVTKGFSGTPGSNENSTQNVYKIPPTTTKALCPLYTSPRTVTQAPPKSTADVSTPDSEINLTNVTDIIRVPVFNIVILLAGGFLSKSLVFSVLFAVTLRSFVP | 1 |
| Human TREM1 isoform 1 (21-234) Without signal peptide | ATKLTEEKYELKEGQTLDVKCDYTLEKFASSQKAWQIIRDGEMPKTLACTERPSKNSHPVQVGRIILEDYHDHGLLRVRMVNLQVEDSGLYQCVIYQPPKEPHMLFDRIRLVVTKGFSGTPGSNENSTQNVYKIPPTTTKALCPLYTSPRTVTQAPPKSTADVSTPDSEINLTNVTDIIRVPVFNIVILLAGGFLSKSLVFSVLFAVTLRSFVP | 2 |
| Human TREM1 isoform 2 (Accession No. NP_001229518.1) | MRKTRLWGLLWMLFVSELRAATKLTEEKYELKEGQTLDVKCDYTLEKFASSQKAWQIIRDGEMPKTLACTERPSKNSHPVQVGRIILEDYHDHGLLRVRMVNLQVEDSGLYQCVIYQPPKEPHMLFDRIRLVVTKGFSGTPGSNENSTQNVYKIPPTTTKALCPLYTSPRTVTQAPPKSTADVSTPDSEINLTNVTDIIRYSFQVPGPLVWTLSPLFPSLCAERM | 3 |

TABLE 6-continued

Sequences of TREM1

| Name | Sequence | SEQ ID NO |
|---|---|---|
| Human TREM1 isoform 3 (Accession No. NP_001229519) | MRKTRLWGLLWMLFVSELRAATKLTEEKYELKEGQTLDVKCDYTLEKF ASSQKAWQIIRDGEMPKTLACTERPSKNSHPVQVGRIILEDYHDHGLL RVRMVNLQVEDSGLYQCVIYQPPKEPHMLFDRIRLVVTKGFRCSTLSF SWLVDS | 4 |
| Cynomolgus TREM1 protein (XP_001082517) | MRKTRLWGLLWMLFVSELRATTELTEEKYEYKEGQTLEVKCDYALEKY ANSRKAWQKMEGKMPKILAKTERPSENSHPVQVGRITLEDYPDHGLLQ VQMTNLQVEDSGLYQCVIYQHPKESHVLFNPICLVVTKGSSGTPGSSE NSTQNVYRTPSTTAKALGPRYTSPRTVTQAPPESTVVVSTPGSEINLT NVTDIIRVPVFNIVIIVAGGFLSKSLVFSVLFAVTLRSFGP | 5 |
| PGLYRP1 (NP_005082.1) | MSRRSMLLAWALPSLLRLGAAQETEDPACCSPIVPRNEWKALASECAQ HLSLPLRYVVVSHTAGSSCNTPASCQQQARNVQHYHMKTLGWCDVGYN FLIGEDGLVYEGRGWNFTGAHSGHLWNPMSIGISFMGNYMDRVPTPQA IRAAQGLLACGVAQGALRSNYVLKGHRDVQRTLSPGNQLYHLIQNWPH YRSP | 6 |
| CID101904 hTREM1_1-200-Avi-Tev-HKH | MRKTRLWGLLWMLFVSELRAATKLTEEKYELKEGQTLDVKCDYTLEKF ASSQKAWQIIRDGEMPKTLACTERPSKNSHPVQVGRIILEDYHDHGLL RVRMVNLQVEDSGLYQCVIYQPPKEPHMLFDRIRLVVTKGFSGTPGSN ENSTQNVYKIPPTTTKALCPLYTSPRTVTQAPPKSTADVSTPDSEINL TNVTDIIRLEGGGSGGSGGLNDIFEAQKIEWHENLYFQGGSHHHHHHK AKGSKGKGSKKAGHHHHHHHHHH | 7 |
| CID101953 CTREM1_1-201-Avi-Tev-HKH | MRKTRLWGLLWMLFVSELRATTELTEEKYEYKEGQTLEVKCDYALEKY ANSRKAWQKMEGKMPKILAKTERPSENSHPVQVGRITLEDYPDHGLLQ VRMTNLQVEDSGLYQCVIYQHPKESHVLFNPICLVVTKGSSGTPGSSE NSTQNVYRTPSTTAKALGPRYTSPRTVTQAPPESTVVVSTPGSEINLT NVTDIIRVPLEGGGSGGSGGLNDIFEAQKIEWHENLYFQGGSHHHHHH KAKGSKGKGSKKAGHHHHHHHHHH | 8 |
| CID101907 hTREM1 IgV (His-Smt-TREM1_21-139) | MGHHHHHHSGEVKPEVKPETHINLKVSDGSSEIFFKIKKTTPLRRLME AFAKRQGKEMDSLRFLYDGIRIQADQTPEDLDMEDNDIIEAHREQIGG ATKLTEEKYELKEGQTLDVKCDYTLEKFASSQKAWQIIRDGEMPKTLA CTERPSKNSHPVQVGRIILEDYHDHGLLRVRMVNLQVEDSGLYQCVIY QPPKEPHMLFDRIRLVVTKGFSG | 9 |
| CID101951 hPGLYRP1_1-196-His | MSRRSMLLAWALPSLLRLGAAQETEDPACCSPIVPRNEWKALASECAQ HLSLPLRYVVVSHTAGSSCNTPASCQQQARNVQHYHMKTLGWCDVGYN FLIGEDGLVYEGRGWNFTGAHSGHLWNPMSIGISFMGNYMDRVPTPQA IRAAQGLLACGVAQGALRSNYVLKGHRDVQRTLSPGNQLYHLIQNWPH YRSPHHHHHH | 10 |

TABLE 7

Sequences of the 12172 antibody and related variants

| Name | Sequence | SEQ ID NO |
|---|---|---|
| CDRL1 | QASQNIGSDLA | 11 |
| CDRL2 | KAATLAS | 12 |
| CDRL3 | QQYYYGSAGADTDT | 13 |
| CDRH1 | GFSLSSYAMT | 14 |
| CDRH2 | IIYAGGSPSYASWAKG | 15 |
| CDRH3 | GTGDTVYTYFNI | 16 |
| Rabbit Ab 12172 VL region | AVVLTQTASPVSAPVGGTVTIKCQASQNIGSDLAWYQQEPGQPPKLLI YKAATLASGVPSRFKGSGSGTEFTLTISGVQCEDGATYYCQQYYYGSA GADTDTFGGGTEVVVK | 17 |
| Rabbit Ab 12172 VL region | gccgtcgtgctgacccagactgcatcccccgtgtctgcacctgtggga ggcacagtcaccatcaagtgccaggccagtcagaacattggtagcgac ttagcctggtatcagcaggaaccagggcagccacccaagctcctgatc | 18 |

TABLE 7-continued

Sequences of the 12172 antibody and related variants

| Name | Sequence | SEQ ID NO |
| --- | --- | --- |
| | tacaaggcagccactctggcatctggggtcccatcgcggttcaaaggc<br>agtggatctgggacagagttcactctcaccatcagtggcgtgcagtgt<br>gaagatggtgccacttactactgtcaacagtattattatggtagtgct<br>ggtgctgatacggatactttcggcggagggaccgaggtggtggtcaaa | |
| CID102770: Rabbit Ab 12172 light chain (Fab) | AVVLTQTASPVSAPVGGTVTIKCQASQNIGSDLAWYQQEPGQPPKLLI<br>YKAATLASGVPSRFKGSGSGTEFTLTISGVQCEDGATYYCQQYYYGSA<br>GADTDTFGGGTEVVVKRTPVAPTVLIFPPAADQVATGTVTIVCVANKY<br>FPDVTVTWEVDGTTQTTGIENSKTPQNSADCTYNLSSTLTLTSTQYNS<br>HKEYTCKVTQGTTSVVQSFNRGDC | 19 |
| Rabbit Ab 12172 light chain | gccgtcgtgctgacccagactgcatccccgtgtctgcacctgtggga<br>ggcacagtcaccatcaagtgccaggccagtcagaacattggtagcgac<br>ttagcctggtatcagcaggaaccagggcagccacccaagctcctgatc<br>tacaaggcagccactctggcatctggggtcccatcgcggttcaaaggc<br>agtggatctgggacagagttcactctcaccatcagtggcgtgcagtgt<br>gaagatggtgccacttactactgtcaacagtattattatggtagtgct<br>ggtgctgatacggatactttcggcggagggaccgaggtggtggtcaaa<br>cgtacgccagttgcacctactgtcctcatcttcccaccagctgctgat<br>caggtggcaactggaacagtcaccatcgtgtgtgtggcgaataaatac<br>tttcccgatgtcaccgtcacctgggaggtggatggcaccacccaaaca<br>actggcatcgagaacagtaaaacaccgcagaattctgcagattgtacc<br>tacaacctcagcagcactctgacactgaccagcacacagtacaacagc<br>cacaaagagtacacctgcaaggtgacccagggcacgacctcagtcgtc<br>cagagcttcaataggggtgactgt | 20 |
| Rabbit Ab 12172 VH region | QSLEESGGRLVTPGTPLTLTCTASGFSLSSYAMTWVRQAPGKGLEWIG<br>IIYAGGSPSYASWAKGRFTISKTSTTVDLKMTSPTTEDTATYFCARGT<br>GDTVYTYFNIWGPGTLVTVSS | 21 |
| Rabbit Ab 12172 VH region | cagtcgctggaggagtccgggggtcgcctggtcacgcctgggacaccc<br>ctgacactcacctgcacagcctctggattctccctcagtagctatgca<br>atgacctgggtccgccaggctccagggaaggggctggaatggatcgga<br>atcatttatgctggtggtagcccatcctacgcgagctgggcgaaaggc<br>cgattcaccatctccaaaacctcgaccacggtggatctgaaaatgacc<br>agtccgacaaccgaggacacggccacctatttctgtgccagagggact<br>ggtgatactgtttatacctactttaatatttggggcccaggcaccctg<br>gtcaccgtctcgagt | 22 |
| CID120769: Rabbit Ab 12172 heavy chain (Fab) | QSLEESGGRLVTPGTPLTLTCTASGFSLSSYAMTWVRQAPGKGLEWIG<br>IIYAGGSPSYASWAKGRFTISKTSTTVDLKMTSPTTEDTATYFCARGT<br>GDTVYTYFNIWGPGTLVTVSSGQPKAPSVFPLAPCCGDTPSSTVTLGC<br>LVKGYLPEPVTVTWNSGTLTNGVRTFPSVRQSSGLYSLSSVVSVTSSS<br>QPVTCNVAHPATNTKVDKTVAPSTCSKP | 23 |
| Rabbit Ab 12172 heavy chain (Fab) | cagtcgctggaggagtccgggggtcgcctggtcacgcctgggacaccc<br>ctgacactcacctgcacagcctctggattctccctcagtagctatgca<br>atgacctgggtccgccaggctccagggaaggggctggaatggatcgga<br>atcatttatgctggtggtagcccatcctacgcgagctgggcgaaaggc<br>cgattcaccatctccaaaacctcgaccacggtggatctgaaaatgacc<br>agtccgacaaccgaggacacggccacctatttctgtgccagagggact<br>ggtgatactgtttatacctactttaatatttggggcccaggcaccctg<br>gtcaccgtctcgagtgggcaacctaaggctccatcagtcttcccactg<br>gccccctgctgcggggacacacccagctccacggtgaccctgggctgc<br>ctggtcaaaggctacctcccggagccagtgaccgtgacctggaactcg<br>ggcaccctcaccaatggggtacgcaccttcccgtccgtccggcagtcc<br>tcaggcctctactcgctgagcagcgtggtgagcgtgacctcaagcagc<br>cagcccgtcacctgcaacgtggcccacccagccaccaacaccaaagtg<br>gacaagaccgttgcgccctcgacatgcagcaagccc | 24 |
| 12172gL1 V-region | AVVLTQSPSFLSASVGDRVTITCQASQNIGSDLAWYQQKPGKAPKLLI<br>YKAATLASGVPSRFSGSGSGTEFTLTISSLQPEDFATYYCQQYYYGSA<br>GADTDTFGGGTKVEIK | 25 |
| 12172gL1 V-region | gccgtggtgctgactcagtccccctccttcctgagcgcctcagtggga<br>gatcgcgtgaccatcacctgtcaagccagccagaacattgggtccgac<br>ttggcctggtatcagcagaagcctggcaaagcgccgaagctgctgatc<br>tacaaggccgctactctcgcgtcgggagtgccatcccggttttccggt<br>tcgggaagcgggaccgagttcaccccttaccatttcctcgctccaaccg<br>gaggacttcgccacgtactactgccagcagtactactacggttcagcc<br>ggagcagacactgataccttcggcggaggcaccaaggtcgaaatcaag | 26 |

TABLE 7-continued

Sequences of the 12172 antibody and related variants

| Name | Sequence | SEQ ID NO |
|---|---|---|
| 12172gL1 light chain | AVVLTQSPSFLSASVGDRVTITCQASQNIGSDLAWYQQKPGKAPKLLI YKAATLASGVPSRFSGSGSGTEFTLTISSLQPEDFATYYCQQYYYGSA GADTDTFGGGTKVEIKRTVAAPSVFIFPPSDEQLKSGTASVVCLLNNE YPREAKVQWKVDNALQSGNSQESVTEQDSKDSTYSLSSTLTLSKADYE KHKVYACEVTHQGLSSPVTKSFNRGEC | 27 |
| 12172gL1 light chain | gccgtggtgctgactcagtccccctccttcctgagcgcctcagtggga gatcgcgtgaccatcacctgtcaagccagccagaacattgggtccgac ttggcctggtatcagcagaagcctggcaaagcgccgaagctgctgatc tacaaggccgctactctcgcgtcgggagtgccatcccggttttccggt tcgggaagcgggaccgagttcacccttaccatttcctcgctccaaccg gaggacttcgccacgtactactgccagcagtactactacggttcagcc ggagcagacactgataccttcggcggaggcaccaaggtcgaaatcaag cgtacggtagcggccccatctgtcttcatcttcccgccatctgatgag cagttgaaatctggaactgcctctgttgtgtgcctgctgaataacttc tatcccagagaggccaaagtacagtggaaggtggataacgccctccaa tcgggtaactcccaggagagtgtcacagagcaggacagcaaggacagc acctacagcctcagcagcaccctgacgctgagcaaagcagactacgag aaacacaaagtctacgcctgcgaagtcacccatcagggcctgagctcg cccgtcacaaagagcttcaacaggggagagtgt | 28 |
| 12172gL2 V-region | DIQLTQSPSFLSASVGDRVTITCQASQNIGSDLAWYQQKPGKAPKLLI YKAATLASGVPSRFSGSGSGTEFTLTISSLQPEDFATYYCQQYYYGSA GADTDTFGGGTKVEIK | 29 |
| 12172gL2 V-region | gacatccagctgactcagtccccctccttcctgagcgcctcagtggga gatcgcgtgaccatcacctgtcaagccagccagaacattgggtccgac ttggcctggtatcagcagaagcctggcaaagcgccgaagctgctgatc tacaaggccgctactctcgcgtcgggagtgccatcccggttttccggt tcgggaagcgggaccgagttcacccttaccatttcctcgctccaaccg gaggacttcgccacgtactactgccagcagtactactacggttcagcc ggagcagacactgataccttcggcggaggcaccaaggtcgaaatcaag | 30 |
| 12172gL2 light chain | DIQLTQSPSFLSASVGDRVTITCQASQNIGSDLAWYQQKPGKAPKLLI YKAATLASGVPSRFSGSGSGTEFTLTISSLQPEDFATYYCQQYYYGSA GADTDTFGGGTKVEIKRTVAAPSVFIFPPSDEQLKSGTASVVCLLNNE YPREAKVQWKVDNALQSGNSQESVTEQDSKDSTYSLSSTLTLSKADYE KHKVYACEVTHQGLSSPVTKSFNRGEC | 31 |
| 12172gL2 light chain | gacatccagctgactcagtccccctccttcctgagcgcctcagtggga gatcgcgtgaccatcacctgtcaagccagccagaacattgggtccgac ttggcctggtatcagcagaagcctggcaaagcgccgaagctgctgatc tacaaggccgctactctcgcgtcgggagtgccatcccggttttccggt tcgggaagcgggaccgagttcacccttaccatttcctcgctccaaccg gaggacttcgccacgtactactgccagcagtactactacggttcagcc ggagcagacactgataccttcggcggaggcaccaaggtcgaaatcaag cgtacggtggccgctccctccgtgttcatcttcccaccctccgacgag cagctgaagtccggcaccgcctccgtcgtgtgcctgctgaacaacttc taccccgcgaggccaaggtgcagtggaaggtggacaacgccctgcag tccggcaactcccaggaatccgtcaccgagcaggactccaaggacagc acctactccctgtcctccaccctgaccctgtccaaggccgactacgag aagcacaaggtgtacgcctgcgaagtgacccaccagggcctgtccagc cccgtgaccaagtccttcaaccggggcgagtgc | 32 |
| 12172gL6 V-region | DIVLTQSPSFLSASVGDRVTITCQASQNIGSDLAWYQQKPGKAPKLLI YKAATLASGVPSRFSGSGSGTEFTLTISSLQPEDFATYYCQQYYYGSA GADTDTFGGGTKVEIK | 33 |
| 12172gL6 V-region | gacatcgtgctgactcagtccccctccttcctgagcgcctcagtggga gatcgcgtgaccatcacctgtcaagccagccagaacattgggtccgac ttggcctggtatcagcagaagcctggcaaagcgccgaagctgctgatc tacaaggccgctactctcgcgtcgggagtgccatcccggttttccggt tcgggaagcgggaccgagttcacccttaccatttcctcgctccaaccg gaggacttcgccacgtactactgccagcagtactactacggttcagcc ggagcagacactgataccttcggcggaggcaccaaggtcgaaatcaag | 34 |
| 12172gL6 light chain | DIVLTQSPSFLSASVGDRVTITCQASQNIGSDLAWYQQKPGKAPKLLI YKAATLASGVPSRFSGSGSGTEFTLTISSLQPEDFATYYCQQYYYGSA GADTDTFGGGTKVEIKRTVAAPSVFIFPPSDEQLKSGTASVVCLLNNE YPREAKVQWKVDNALQSGNSQESVTEQDSKDSTYSLSSTLTLSKADYE KHKVYACEVTHQGLSSPVTKSFNRGEC | 35 |

TABLE 7-continued

| Sequences of the 12172 antibody and related variants | | |
|---|---|---|
| Name | Sequence | SEQ ID NO |
| 12172gL6 light chain | gacatcgtgctgactcagtcccccctccttcctgagcgcctcagtgggagatcgcgtgaccatcacctgtcaagccagccagaacattgggtccgacttggcctggtatcagcagaagcctggcaaagcgccgaagctgctgatctacaaggccgctactctcgcgtcgggagtgccatcccggttttccggttcgggaagcgggaccgagttcacccttaccatttcctcgctccaaccggaggacttcgccacgtactactgccagcagtactactacggttcagccggagcagacactgataccttcggcggaggcaccaaggtcgaaatcaagcgtacggtggccgctccctccgtgttcatcttcccaccctccgacgagcagctgaagtccggcaccgcctccgtcgtgtgcctgctgaacaacttctacccccgcgaggccaaggtgcagtggaaggtggacaacgccctgcagtccggcaactcccaggaatccgtcaccgagcaggactccaaggacagcacctactccctgtcctccaccctgaccctgtccaaggccgactacgagaagcacaaggtgtacgcctgcgaagtgacccaccagggcctgtccagccccgtgaccaagtccttcaaccggggcgagtgc | 36 |
| 12172gL9 V-region | DIQLTQSPSFLSASVGDSVTITCQASQNIGSDLAWYQQKPGKAPKLLIYKAATLASGVPSRFSGSGSGTEFTLTISSLQPEDFATYYCQQYYYGSAGADTDTFGGGTKVEIK | 37 |
| 12172gL9 V-region | gacatccagctgactcagtcccccctccttcctgagcgcctcagtgggagatagcgtgaccatcacctgtcaagccagccagaacattgggtccgacttggcctggtatcagcagaagcctggcaaagcgccgaagctgctgatctacaaggccgctactctcgcgtcgggagtgccatcccggttttccggttcgggaagcgggaccgagttcacccttaccatttcctcgctccaaccggaggacttcgccacgtactactgccagcagtactactacggttcagccggagcagacactgataccttcggcggaggcaccaaggtcgaaatcaag | 38 |
| 12172gL9 light chain | DIQLTQSPSFLSASVGDSVTITCQASQNIGSDLAWYQQKPGKAPKLLIYKAATLASGVPSRFSGSGSGTEFTLTISSLQPEDFATYYCQQYYYGSAGADTDTFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 39 |
| 12172gL9 light chain | gacatccagctgactcagtcccccctccttcctgagcgcctcagtgggagatagcgtgaccatcacctgtcaagccagccagaacattgggtccgacttggcctggtatcagcagaagcctggcaaagcgccgaagctgctgatctacaaggccgctactctcgcgtcgggagtgccatcccggttttccggttcgggaagcgggaccgagttcacccttaccatttcctcgctccaaccggaggacttcgccacgtactactgccagcagtactactacggttcagccggagcagacactgataccttcggcggaggcaccaaggtcgaaatcaagcgtacggtagcggccccatctgtcttcatcttcccgccatctgatgagcagttgaaatctggaactgcctctgttgtgtgcctgctgaataacttctatcccagagaggccaaagtacagtggaaggtggataacgccctccaatcgggtaactcccaggagagtgtcacagagcaggacagcaaggacagcacctacagcctcagcagcaccctgacgctgagcaaagcagactacgagaaacacaaagtctacgcctgcgaagtcacccatcagggcctgagctcgcccgtcacaaagagcttcaacaggggagagtgt | 40 |
| 12172gL11 V-region | DIQLTQSPSFLSASVGDRVTITCQASQNIGSDLAWYQQKPGKAPKLLIYSAATLASGVPSRFSGSGSGTEFTLTISSLQPEDFATYYCQQYYYGSAGADTDTFGGGTKVEIK | 41 |
| 12172gL11 V-region | gacatccagctgactcagtcccccctccttcctgagcgcctcagtgggagatcgcgtgaccatcacctgtcaagccagccagaacattgggtccgacttggcctggtatcagcagaagcctggcaaagcgccgaagctgctgatctacagcgccgctactctcgcgtcgggagtgccatcccggttttccggttcgggaagcgggaccgagttcacccttaccatttcctcgctccaaccggaggacttcgccacgtactactgccagcagtactactacggttcagccggagcagacactgataccttcggcggaggcaccaaggtcgaaatcaag | 42 |
| 12172gL11 light chain | DIQLTQSPSFLSASVGDRVTITCQASQNIGSDLAWYQQKPGKAPKLLIYSAATLASGVPSRFSGSGSGTEFTLTISSLQPEDFATYYCQQYYYGSAGADTDTFGGGTKVEIKRTVAAPSVFIFPPSDEQLKSGTASVVCLLNNEYPREAKVQWKVDNALQSGNSQESVTEQDSKDSTYSLSSTLTLSKADYEKHKVYACEVTHQGLSSPVTKSFNRGEC | 43 |
| 12172gL11 light chain | gacatccagctgactcagtcccccctccttcctgagcgcctcagtgggagatcgcgtgaccatcacctgtcaagccagccagaacattgggtccgacttggcctggtatcagcagaagcctggcaaagcgccgaagctgctgatctacagcgccgctactctcgcgtcgggagtgccatcccggttttccggttcgggaagcgggaccgagttcacccttaccatttcctcgctccaaccggaggacttcgccacgtactactgccagcagtactactacggttcagccggagcagacactgataccttcggcggaggcaccaaggtcgaaatcaag | 44 |

TABLE 7-continued

Sequences of the 12172 antibody and related variants

| Name | Sequence | SEQ ID NO |
|---|---|---|
| | cgtacggtagcggccccatctgtcttcatcttcccgccatctgatgag cagttgaaatctggaactgcctctgttgtgtgcctgctgaataacttc tatcccagagaggccaaagtacagtggaaggtggataacgccctccaa tcgggtaactcccaggagagtgtcacagagcaggacagcaaggacagc acctacagcctcagcagcaccctgacgctgagcaaagcagactacgag aaacacaaagtctacgcctgcgaagtcacccatcagggcctgagctcg cccgtcacaaagagcttcaacaggggagagtgt | |
| 12172gH1 V-region | EVQLVESGGGLVQPGGSLRLSCTASGFSLSSYAMTWVRQAPGKGLEWI GIIYAGGSPSYASWAKGRFTISKDSSKNTVYLQMNSLRAEDTAVYYCA RGTGDTVYTYFNIWGQGTLVTVSS | 45 |
| 12172gH1 V-region | gaagtgcagctcgtggagtcgggcggaggtctggtgcagcccggagga agcctgcgcctgtcatgcaccgccagcgggttctcgctttcctcctac gccatgacctgggtcagacaggcaccgggaaagggcctcgaatggatt ggcattatctatgcgggtggcagcccttcctacgcctcctgggctaaa gggggttcaccatctcgaaggactcctccaagaacacggtgtacttg caaatgaactcactgagggccgaggacactgcggtgtactactgtgcc cggggaactggagataccgtgtacacctactttaacatctggggccag ggaaccctggtcactgtctcgagc | 46 |
| 12172gH1 heavy chain (IgG4P) | EVQLVESGGGLVQPGGSLRLSCTASGFSLSSYAMTWVRQAPGKGLEWI GIIYAGGSPSYASWAKGRFTISKDSSKNTVYLQMNSLRAEDTAVYYCA RGTGDTVYTYFNIWGQGTLVTVSSASTKGPSVFPLAPCSRSTSESTAA LGCLVKDYFPEPVTVSWNSGALTSGVHTFPAVLQSSGLYSLSSVVTVP SSSLGTKTYTCNVDHKPSNTKVDKRVESKYGPPCPPCPAPEFLGGPSV FLFPPKPKDTLMISRTPEVTCVVVDVSQEDPEVQFNWYVDGVEVHNAK TKPREEQFNSTYRVVSVLTVLHQDWLNGKEYKCKVSNKGLPSSIEKTI SKAKGQPREPQVYTLPPSQEEMTKNQVSLTCLVKGFYPSDIAVEWESN GQPENNYKTTPPVLDSDGSFFLYSRLTVDKSRWQEGNVFSCSVMHEAL HNHYTQKSLSLSLGK | 47 |
| 12172gH1 heavy chain (IgG4P) | gaagtgcagctcgtggagtcgggcggaggtctggtgcagcccggagga agcctgcgcctgtcatgcaccgccagcgggttctcgctttcctcctac gccatgacctgggtcagacaggcaccgggaaagggcctcgaatggatt ggcattatctatgcgggtggcagcccttcctacgcctcctgggctaaa gggcggttcaccatctcgaaggactcctccaagaacacggtgtacttg caaatgaactcactgagggccgaggacactgcggtgtactactgtgcc cggggaactggagataccgtgtacacctactttaacatctggggccag ggaaccctggtcactgtctcgagcgcttctacaaagggcccatccgtc ttcccctggcgccctgctccaggagcacctccgagagcacagccgcc ctgggctgcctggtcaaggactacttccccgaaccggtgacggtgtcg tggaactcaggcgccctgaccagcggcgtgcacaccttcccggctgtc ctacagtcctcaggactctactccctcagcagcgtggtgaccgtgccc tccagcagcttgggcacgaagacctacacctgcaacgtagatcacaag cccagcaacaccaaggtggacaagagagttgagtccaaatatggtccc ccatgcccaccatgcccagcacctgagttcctggggggaccatcagtc ttcctgttccccccaaaacccaaggacactctcatgatctcccggacc cctgaggtcacgtgcgtggtggtggacgtgagccaggaagaccccgag gtccagttcaactggtacgtggatggcgtggaggtgcataatgccaag acaaagccgcgggaggagcagttcaacagcacgtaccgtgtggtcagc gtcctcaccgtcctgcaccaggactggctgaacggcaaggagtacaag tgcaaggtctccaacaaaggcctcccgtcctccatcgagaaaaccatc tccaaagccaaagggcagccccgagagccacaggtgtacaccctgccc ccatcccaggaggagatgaccaagaaccaggtcagcctgacctgcctg gtcaaaggcttctaccccagcgacatcgccgtggagtgggagagcaat gggcagccggagaacaactacaagaccacgcctcccgtgctggactcc gacggctccttcttcctctacagcaggctaaccgtggacaagagcagg tggcaggaggggaatgtcttctcatgctccgtgatgcatgaggctctg cacaaccactacacacagaagagcctctccctgtctctgggtaaa | 48 |
| 12172gH2 V-region | EVQLVESGGGLVQPGGSLRLSCAASGFSLSSYAMTWVRQAPGKGLEWV GIIYAGGSPSYASWAKGRFTISKDSSKNTVYLQMNSLRAEDTAVYYCA RGTGDTVYTYFNIWGQGTLVTVSS | 49 |
| 12172gH2 V-region | gaagtgcagctcgtggagtcgggcggaggtctggtgcagcccggagga agcctgcgcctgtcatgcgctgccagcgggttctcgctttcctcctac gccatgacctgggtcagacaggcaccgggaaagggcctcgaatgggtc ggcattatctatgcgggtggcagcccttcctacgcctcctgggctaaa gggcggttcaccatctcgaaggactcctccaagaacacggtgtacttg caaatgaactcactgagggccgaggacactgcggtgtactactgtgcc cggggaactggagataccgtgtacacctactttaacatctggggccag ggaaccctggtcactgtctcgagc | 50 |

TABLE 7-continued

Sequences of the 12172 antibody and related variants

| Name | Sequence | SEQ ID NO |
|---|---|---|
| 12172gH2 heavy chain (IgG4P) | EVQLVESGGGLVQPGGSLRLSCAASGFSLSSYAMTWVRQAPGKGLEWV GIIYAGGSPSYASWAKGRFTISKDSSKNTVYLQMNSLRAEDTAVYYCA RGTGDTVYTYFNIWGQGTLVTVSSASTKGPSVFPLAPCSRSTSESTAA LGCLVKDYFPEPVTVSWNSGALTSGVHTFPAVLQSSGLYSLSSVVTVP SSSLGTKTYTCNVDHKPSNTKVDKRVESKYGPPCPPCPAPEFLGGPSV FLFPPKPKDTLMISRTPEVTCVVVDVSQEDPEVQFNWYVDGVEVHNAK TKPREEQFNSTYRVVSVLTVLHQDWLNGKEYKCKVSNKGLPSSIEKTI SKAKGQPREPQVYTLPPSQEEMTKNQVSLTCLVKGFYPSDIAVEWESN GQPENNYKTTPPVLDSDGSFFLYSRLTVDKSRWQEGNVFSCSVMHEAL HNHYTQKSLSLSLGK | 51 |
| 12172gH2 heavy chain (IgG4P) | gaagtgcagctcgtggagtcgggcggaggtctggtgcagcccggagga agcctgcgcctgtcatgcgctgccagcgggttctcgctttcctcctac gccatgacctgggtcagacaggcaccgggaaagggcctcgaatgggtc ggcattatctatgcgggtggcagcccttcctacgcctcctgggctaaa gggcggttcaccatctcgaaggactcctccaagaacacggtgtacttg caaatgaactcactgagggccgaggacactgcggtgtactactgtgcc cggggaactggagataccgtgtacacctactttaacatctggggccag ggaaccctggtcactgtctcgagcgcttctacaaagggcccatccgtc ttcccccctggcgccctgctccaggagcacctccgagagcacagccgcc ctgggctgcctggtcaaggactacttccccgaaccggtgacggtgtcg tggaactcaggcgccctgaccagcggcgtgcacaccttcccggctgtc ctacagtcctcaggactctactccctcagcagcgtggtgaccgtgccc tccagcagcttgggcacgaagacctacacctgcaacgtagatcacaag cccagcaacaccaaggtggacaagagagttgagtccaaatatggtccc ccatgcccaccatgcccagcacctgagttcctggggggaccatcagtc ttcctgttccccccaaaacccaaggacactctcatgatctcccggacc cctgaggtcacgtgcgtggtggtggacgtgagccaggaagaccccgag gtccagttcaactggtacgtggatggcgtggaggtgcataatgccaag acaaagccgcgggaggagcagttcaacagcacgtaccgtgtggtcagc gtcctcaccgtcctgcaccaggactggctgaacggcaaggagtacaag tgcaaggtctccaacaaaggcctcccgtcctccatcgagaaaaccatc tccaaagccaaagggcagccccgagagccacaggtgtacaccctgccc ccatcccaggaggagatgaccaagaaccaggtcagcctgacctgcctg gtcaaaggcttctaccccagcgacatcgccgtggagtgggagagcaat gggcagccggagaacaactacaagaccacgcctcccgtgctggactcc gacggctccttcttcctctacagcaggctaaccgtggacaagagcagg tggcaggaggggaatgtcttctcatgctccgtgatgcatgaggctctg cacaaccactacacacagaagagcctctccctgtctctgggtaaa | 52 |
| 12172gH4 V-region | EVQLVESGGGLVQPGGSLRLSCTASGFSLSSYAMTWVRQAPGKGLEWI GIIYAGGSPSYASWAKGRFTISRDSSKNTVYLQMNSLRAEDTAVYYCA RGTGDTVYTYFNIWGQGTLVTVSS | 53 |
| 12172gH4 V-region | gaagtgcagctcgtggagtcgggcggaggtctggtgcagcccggagga agcctgcgcctgtcatgcaccgccagcgggttctcgctttcctcctac gccatgacctgggtcagacaggcaccgggaaagggcctcgaatggatt ggcattatctatgcgggtggcagcccttcctacgcctcctgggctaaa gggcggttcaccatctcgcgcgactcctccaagaacacggtgtacttg caaatgaactcactgagggccgaggacactgcggtgtactactgtgcc cggggaactggagataccgtgtacacctactttaacatctggggccag ggaaccctggtcactgtctcgagc | 54 |
| 12172gH4 heavy chain (IgG4P) | EVQLVESGGGLVQPGGSLRLSCTASGFSLSSYAMTWVRQAPGKGLEWI GIIYAGGSPSYASWAKGRFTISRDSSKNTVYLQMNSLRAEDTAVYYCA RGTGDTVYTYFNIWGQGTLVTVSSASTKGPSVFPLAPCSRSTSESTAA LGCLVKDYFPEPVTVSWNSGALTSGVHTFPAVLQSSGLYSLSSVVTVP SSSLGTKTYTCNVDHKPSNTKVDKRVESKYGPPCPPCPAPEFLGGPSV FLFPPKPKDTLMISRTPEVTCVVVDVSQEDPEVQFNWYVDGVEVHNAK TKPREEQFNSTYRVVSVLTVLHQDWLNGKEYKCKVSNKGLPSSIEKTI SKAKGQPREPQVYTLPPSQEEMTKNQVSLTCLVKGFYPSDIAVEWESN GQPENNYKTTPPVLDSDGSFFLYSRLTVDKSRWQEGNVFSCSVMHEAL HNHYTQKSLSLSLGK | 55 |
| 12172gH4 heavy chain (IgG4P) | gaagtgcagctcgtggagtcgggcggaggtctggtgcagcccggagga agcctgcgcctgtcatgcaccgccagcgggttctcgctttcctcctac gccatgacctgggtcagacaggcaccgggaaagggcctcgaatggatt ggcattatctatgcgggtggcagcccttcctacgcctcctgggctaaa gggcggttcaccatctcgcgcgactcctccaagaacacggtgtacttg caaatgaactcactgagggccgaggacactgcggtgtactactgtgcc cggggaactggagataccgtgtacacctactttaacatctggggccag ggaaccctggtcactgtctcgagcgcttctacaaagggcccatccgtc ttcccccctggcgccctgctccaggagcacctccgagagcacagccgcc ctgggctgcctggtcaaggactacttccccgaaccggtgacggtgtcg | 56 |

TABLE 7-continued

| Sequences of the 12172 antibody and related variants | | |
|---|---|---|
| Name | Sequence | SEQ ID NO |
| | tggaactcaggcgccctgaccagcggcgtgcacaccttcccggctgtc ctacagtcctcaggactctactccctcagcagcgtggtgaccgtgccc tccagcagcttgggcacgaagacctacacctgcaacgtagatcacaag cccagcaacaccaaggtggacaagagagttgagtccaaatatggtccc ccatgcccaccatgcccagcacctgagttcctggggggaccatcagtc ttcctgttccccccaaaacccaaggacactctcatgatctcccggacc cctgaggtcacgtgcgtggtggtggacgtgagccaggaagaccccgag gtccagttcaactggtacgtggatggcgtggaggtgcataatgccaag acaaagccgcgggaggagcagttcaacagcacgtaccgtgtggtcagc gtcctcaccgtcctgcaccaggactggctgaacggcaaggagtacaag tgcaaggtctccaacaaaggcctcccgtcctccatcgagaaaaccatc tccaaagccaaagggcagccccgagagccacaggtgtacaccctgccc ccatcccaggaggagatgaccaagaaccaggtcagcctgacctgcctg gtcaaaggcttctaccccagcgacatcgccgtggagtgggagagcaat gggcagccggagaacaactacaagaccacgcctcccgtgctggactcc gacggctccttcttcctctacagcaggctaaccgtggacaagagcagg tggcaggaggggaatgtcttctcatgctccgtgatgcatgaggctctg cacaaccactacacacagaagagcctctccctgtctctgggtaaa | |
| 12172gH6 V-region | EVQLVESGGGLVQPGGSLRLSCTASGFSLSSYAMTWVRQAPGKGLEWI GIIYAGGSPSYASWAKGRFTISKDSSKNTLYLQMNSLRAEDTAVYYCA RGTGDTVYTYFNIWGQGTLVTVSS | 57 |
| 12172gH6 V-region | gaagtgcagctcgtggagtcgggcggaggtctggtgcagcccggagga agcctgcgcctgtcatgcaccgccagcgggttctcgctttcctcctac gccatgacctgggtcagacaggcaccgggaaagggcctcgaatggatt ggcattatctatgcgggtggcagcccttcctacgcctcctgggctaaa gggcggttcaccatctcgaaggactcctccaagaacacgctgtacttg caaatgaactcactgagggccgaggacactgcggtgtactactgtgcc cggggaactggagataccgtgtacacctactttaacatctggggccag ggaaccctggtcactgtctcgagc | 58 |
| 12172gH6 heavy chain (IgG4P) | EVQLVESGGGLVQPGGSLRLSCTASGFSLSSYAMTWVRQAPGKGLEWI GIIYAGGSPSYASWAKGRFTISKDSSKNTLYLQMNSLRAEDTAVYYCA RGTGDTVYTYFNIWGQGTLVTVSSASTKGPSVFPLAPCSRSTSESTAA LGCLVKDYFPEPVTVSWNSGALTSGVHTFPAVLQSSGLYSLSSVVTVP SSSLGTKTYTCNVDHKPSNTKVDKRVESKYGPPCPPCPAPEFLGGPSV FLFPPKPKDTLMISRTPEVTCVVVDVSQEDPEVQFNWYVDGVEVHNAK TKPREEQFNSTYRVVSVLTVLHQDWLNGKEYKCKVSNKGLPSSIEKTI SKAKGQPREPQVYTLPPSQEEMTKNQVSLTCLVKGFYPSDIAVEWESN GQPENNYKTTPPVLDSDGSFFLYSRLTVDKSRWQEGNVFSCSVMHEAL HNHYTQKSLSLSLGK | 59 |
| 12172gH6 heavy chain (IgG4P) | gaagtgcagctcgtggagtcgggcggaggtctggtgcagcccggagga agcctgcgcctgtcatgcaccgccagcgggttctcgctttcctcctac gccatgacctgggtcagacaggcaccgggaaagggcctcgaatggatt ggcattatctatgcgggtggcagcccttcctacgcctcctgggctaaa gggcggttcaccatctcgaaggactcctccaagaacacgctgtacttg caaatgaactcactgagggccgaggacactgcggtgtactactgtgcc cggggaactggagataccgtgtacacctactttaacatctggggccag ggaaccctggtcactgtctcgagcgcttctacaaagggcccatccgtc ttccccctggcgccctgctccaggagcacctccgagagcacagccgcc ctgggctgcctggtcaaggactacttccccgaaccggtgacggtgtcg tggaactcaggcgccctgaccagcggcgtgcacaccttcccggctgtc ctacagtcctcaggactctactccctcagcagcgtggtgaccgtgccc tccagcagcttgggcacgaagacctacacctgcaacgtagatcacaag cccagcaacaccaaggtggacaagagagttgagtccaaatatggtccc ccatgcccaccatgcccagcacctgagttcctggggggaccatcagtc ttcctgttccccccaaaacccaaggacactctcatgatctcccggacc cctgaggtcacgtgcgtggtggtggacgtgagccaggaagaccccgag gtccagttcaactggtacgtggatggcgtggaggtgcataatgccaag acaaagccgcgggaggagcagttcaacagcacgtaccgtgtggtcagc gtcctcaccgtcctgcaccaggactggctgaacggcaaggagtacaag tgcaaggtctccaacaaaggcctcccgtcctccatcgagaaaaccatc tccaaagccaaagggcagccccgagagccacaggtgtacaccctgccc ccatcccaggaggagatgaccaagaaccaggtcagcctgacctgcctg gtcaaaggcttctaccccagcgacatcgccgtggagtgggagagcaat gggcagccggagaacaactacaagaccacgcctcccgtgctggactcc gacggctccttcttcctctacagcaggctaaccgtggacaagagcagg tggcaggaggggaatgtcttctcatgctccgtgatgcatgaggctctg cacaaccactacacacagaagagcctctccctgtctctgggtaaa | 60 |

TABLE 7-continued

Sequences of the 12172 antibody and related variants

| Name | Sequence | SEQ ID NO |
|---|---|---|
| 12172gH6 heavy chain (IgG4P F234A L235A) | EVQLVESGGGLVQPGGSLRLSCTASGFSLSSYAMTWVRQAPGKGLEWI<br>GIIYAGGSPSYASWAKGRFTISKDSSKNTLYLQMNSLRAEDTAVYYCA<br>RGTGDTVYTYFNIWGQGTLVTVSSASTKGPSVFPLAPCSRSTSESTAA<br>LGCLVKDYFPEPVTVSWNSGALTSGVHTFPAVLQSSGLYSLSSVVTVP<br>SSSLGTKTYTCNVDHKPSNTKVDKRVESKYGPPCPPCPAPEAAGGPSV<br>FLFPPKPKDTLMISRTPEVTCVVVDVSQEDPEVQFNWYVDGVEVHNAK<br>TKPREEQFNSTYRVVSVLTVLHQDWLNGKEYKCKVSNKGLPSSIEKTI<br>SKAKGQPREPQVYTLPPSQEEMTKNQVSLTCLVKGFYPSDIAVEWESN<br>GQPENNYKTTPPVLDSDGSFFLYSRLTVDKSRWQEGNVFSCSVMHEAL<br>HNHYTQKSLSLSLGK | 61 |
| 12172gH6 heavy chain (IgG4P F234A L235A) | gaagtgcagctcgtggagtcgggcggaggtctggtgcagcccggagga<br>agcctgcgcctgtcatgcaccgccagcgggttctcgctttcctcctac<br>gccatgacctgggtcagacaggcaccgggaaagggcctcgaatggatt<br>ggcattatctatgcgggtggcagcccttcctacgcctcctgggctaaa<br>gggcggttcaccatctcgaaggactcctccaagaacacgctgtacttg<br>caaatgaactcactgagggccgaggacactgcggtgtactactgtgcc<br>cggggaactggagataccgtgtacacctactttaacatctggggccag<br>ggaaccctggtcactgtctcgagcgcttctacaaagggcccatccgtc<br>ttccccctggcgccctgctccaggagcacctccgagagcacagccgcc<br>ctgggctgcctggtcaaggactacttccccgaaccggtgacggtgtcg<br>tggaactcaggcgccctgaccagcggcgtgcacaccttcccggctgtc<br>ctacagtcctcaggactctactccctcagcagcgtggtgaccgtgccc<br>tccagcagcttgggcacgaagacctacacctgcaacgtagatcacaag<br>cccagcaacaccaaggtggacaagagagttgagtccaaatatggtccc<br>ccatgcccaccatgcccagcacctgaagccgcggggggaccgtcagtc<br>ttcctgttccccccaaaacccaaggacactctcatgatctcccggacc<br>cctgaggtcacgtgcgtggtggtggacgtgagccaggaagaccccgag<br>gtccagttcaactggtacgtggatggcgtggaggtgcataatgccaag<br>acaaagccgcgggaggagcagttcaacagcacgtaccgtgtggtcagc<br>gtcctcaccgtcctgcaccaggactggctgaacggcaaggagtacaag<br>tgcaaggtctccaacaaaggcctcccgtcctccatcgagaaaaccatc<br>tccaaagccaaagggcagccccgagagccacaggtgtacaccctgccc<br>ccatcccaggaggagatgaccaagaaccaggtcagcctgacctgcctg<br>gtcaaaggcttctaccccagcgacatcgccgtggagtgggagagcaat<br>gggcagccggagaacaactacaagaccacgcctcccgtgctggactcc<br>gacggctccttcttcctctacagcaggctaaccgtggacaagagcagg<br>tggcaggaggggaatgtcttctcatgctccgtgatgcatgaggctctg<br>cacaaccactacacacagaagagcctctccctgtctctgggtaaa | 62 |
| 12172gH6 heavy chain (IgG1) | EVQLVESGGGLVQPGGSLRLSCTASGFSLSSYAMTWVRQAPGKGLEWI<br>GIIYAGGSPSYASWAKGRFTISKDSSKNTLYLQMNSLRAEDTAVYYCA<br>RGTGDTVYTYFNIWGQGTLVTVSSASTKGPSVFPLAPSSKSTSGGTAA<br>LGCLVKDYFPEPVTVSWNSGALTSGVHTFPAVLQSSGLYSLSSVVTVP<br>SSSLGTQTYICNVNHKPSNTKVDKKVEPKSCDKTHTCPPCPAPELLGG<br>PSVFLFPPKPKDTLMISRTPEVTCVVVDVSHEDPEVKFNWYVDGVEVH<br>NAKTKPREEQYNSTYRVVSVLTVLHQDWLNGKEYKCKVSNKALPAPIE<br>KTISKAKGQPREPQVYTLPPSRDELTKNQVSLTCLVKGFYPSDIAVEW<br>ESNGQPENNYKTTPPVLDSDGSFFLYSKLTVDKSRWQQGNVFSCSVMH<br>EALHNHYTQKSLSLSPGK | 63 |
| 12172gH6 heavy chain (IgG1) | gaagtgcagctcgtggagtcgggcggaggtctggtgcagcccggagga<br>agcctgcgcctgtcatgcaccgccagcgggttctcgctttcctcctac<br>gccatgacctgggtcagacaggcaccgggaaagggcctcgaatggatt<br>ggcattatctatgcgggtggcagcccttcctacgcctcctgggctaaa<br>gggcggttcaccatctcgaaggactcctccaagaacacgctgtacttg<br>caaatgaactcactgagggccgaggacactgcggtgtactactgtgcc<br>cggggaactggagataccgtgtacacctactttaacatctggggccag<br>ggaaccctggtcactgtctcgagcgcttctacaaagggcccatcggtc<br>ttccccctggcaccctcctccaagagcacctctgggggcacagcggcc<br>ctgggctgcctggtcaaggactacttccccgaaccggtgacggtgtcg<br>tggaactcaggcgccctgaccagcggcgtgcacaccttcccggctgtc<br>ctacagtcctcaggactctactccctcagcagcgtggtgaccgtgccc<br>tccagcagcttgggcacccagacctacatctgcaacgtgaatcacaag<br>cccagcaacaccaaggtggacaagaaagttgagcccaaatcttgtgac<br>aaaactcacacatgcccaccgtgcccagcacctgaactcctgggggga<br>ccgtcagtcttcctcttccccccaaaacccaaggacaccctcatgatc<br>tcccggacccctgaggtcacatgcgtggtggtggacgtgagccacgaa<br>gaccctgaggtcaagttcaactggtacgtggacggcgtggaggtgcat<br>aatgccaagacaaagccgcgggaggagcagtacaacagcacgtaccgt<br>gtggtcagcgtcctcaccgtcctgcaccaggactggctgaatggcaag<br>gagtacaagtgcaaggtctccaacaaagccctcccagcccccatcgag<br>aaaaccatctccaaagccaaagggcagccccgagaaccacaggtgtac | 64 |

TABLE 7-continued

Sequences of the 12172 antibody and related variants

| Name | Sequence | SEQ ID NO |
|---|---|---|
| | accctgcccccatcccgggatgagctgaccaagaaccaggtcagcctg acctgcctggtcaaaggcttctatcccagcgacatcgccgtggagtgg gagagcaatgggcagccggagaacaactacaagaccacgcctcccgtg ctggactccgacggctccttcttcctctacagcaagctcaccgtggac aagagcaggtggcagcaggggaacgtcttctcatgctccgtgatgcat gaggctctgcacaaccactacacgcagaagagcctctccctgtctccg ggtaaa | |
| 12172gH6 heavy chain (IgG1 L234A L235A) | EVQLVESGGGLVQPGGSLRLSCTASGFSLSSYAMTWVRQAPGKGLEWI GIIYAGGSPSYASWAKGRFTISKDSSKNTLYLQMNSLRAEDTAVYYCA RGTGDTVYTYFNIWGQGTLVTVSSASTKGPSVFPLAPSSKSTSGGTAA LGCLVKDYFPEPVTVSWNSGALTSGVHTFPAVLQSSGLYSLSSVVTVP SSSLGTQTYICNVNHKPSNTKVDKKVEPKSCDKTHTCPPCPAPEAAGG PSVFLFPPKPKDTLMISRTPEVTCVVVDVSHEDPEVKFNWYVDGVEVH NAKTKPREEQYNSTYRVVSVLTVLHQDWLNGKEYKCKVSNKALPAPIE KTISKAKGQPREPQVYTLPPSRDELTKNQVSLTCLVKGFYPSDIAVEW ESNGQPENNYKTTPPVLDSDGSFFLYSKLTVDKSRWQQGNVFSCSVMH EALHNHYTQKSLSLSPGK | 65 |
| 12172gH6 heavy chain (IgG1 L234A L235A) | gaagtgcagctcgtggagtcgggcggaggtctggtgcagcccggagga agcctgcgcctgtcatgcaccgccagcgggttctcgctttcctcctac gccatgacctgggtcagacaggcaccgggaaagggcctcgaatggatt ggcattatctatgcgggggcagcccttcctacgcctcctgggctaaa gggcggttcaccatctcgaaggactcctccaagaacacgctgtacttg caaatgaactcactgagggccgaggacactgcggtgtactactgtgcc cggggaactggagataccgtgtacacctactttaacatctggggccag ggaaccctggtcactgtctcgagcgcttctacaaagggcccctccgtg ttcccgctcgctccatcatcgaagtctaccagcggaggcactgcggct ctcggttgcctcgtgaaggactacttcccggagccggtgaccgtgtcg tggaacagcggagccctgaccagcggggtgcacacctttccggccgtc ttgcagtcaagcggcctttactccctgtcatcagtggtgactgtcccg tccagctcattgggaacccaaacctacatctgcaatgtgaatcacaaa cctagcaacaccaaggttgacaagaaagtcgagcccaaatcgtgtgac aagactcacacttgtccgccgtgcccggcacccgaagccgcaggaggt cccagcgtctttctgttccctccaaagccgaaagacacgctgatgatc tcccgcaccccggaggtcacttgcgtggtcgtggacgtgtcacatgag gacccagaggtgaagttcaattggtacgtggatggcgtcgaagtccac aatgccaaaactaagcccagagaagaacagtacaattcgacctaccgc gtcgtgtccgtgctcacggtgttgcatcaggattggctgaacgggaag gaatacaagtgcaaagtgtccaacaaggcgctgccggcaccgatcgag aaaactatctccaaagcgaagggacagcctagggaacctcaagtctac acgctgccaccatcacgggatgaactgactaagaatcaagtctcactg acttgtctggtgaaggggttttaccctagcgacattgccgtggagtgg gaatccaacggccagccagagaacaactacaagactacccctccagtg ctcgactcggatggatcgttcttcctttactcgaagctcaccgtggat aagtcccggtggcagcagggaaacgtgttctcctgctcggtgatgcat gaagccctccataaccactatacccaaaagtcgctgtccctgtcgccg ggaaag | 66 |
| 12172gH8 V-region | EVQLVESGGGLVQPGGSLRLSCAASGFSLSSYAMTWVRQAPGKGLEWI GIIYAGGSPSYASWAKGRFTISKDSSKNTVYLQMNSLRAEDTAVYYCA RGTGDTVYTYFNIWGQGTLVTVSS | 67 |
| 12172gH8 V-region | gaagtgcagctcgtggagtcgggcggaggtctggtgcagcccggagga agcctgcgcctgtcatgcgctgccagcgggttctcgctttcctcctac gccatgacctgggtcagacaggcaccgggaaagggcctcgaatggatt ggcattatctatgcgggtggcagcccttcctacgcctcctgggctaaa gggcggttcaccatctcgaaggactcctccaagaacacggtgtacttg caaatgaactcactgagggccgaggacactgcggtgtactactgtgcc cggggaactggagataccgtgtacacctactttaacatctggggccag ggaaccctggtcactgtctcgagc | 68 |
| 12172gH8 heavy chain (IgG4P) | EVQLVESGGGLVQPGGSLRLSCAASGFSLSSYAMTWVRQAPGKGLEWI GIIYAGGSPSYASWAKGRFTISKDSSKNTVYLQMNSLRAEDTAVYYCA RGTGDTVYTYFNIWGQGTLVTVSSASTKGPSVFPLAPCSRSTSESTAA LGCLVKDYFPEPVTVSWNSGALTSGVHTFPAVLQSSGLYSLSSVVTVP SSSLGTKTYTCNVDHKPSNTKVDKRVESKYGPPCPPCPAPEFLGGPSV FLFPPKPKDTLMISRTPEVTCVVVDVSQEDPEVQFNWYVDGVEVHNAK TKPREEQFNSTYRVVSVLTVLHQDWLNGKEYKCKVSNKGLPSSIEKTI SKAKGQPREPQVYTLPPSQEEMTKNQVSLTCLVKGFYPSDIAVEWESN GQPENNYKTTPPVLDSDGSFFLYSRLTVDKSRWQEGNVFSCSVMHEAL HNHYTQKSLSLSLGK | 69 |

TABLE 7-continued

Sequences of the 12172 antibody and related variants

| Name | Sequence | SEQ ID NO |
|---|---|---|
| 12172gH8 heavy chain (IgG4P) | gaagtgcagctcgtggagtcgggcggaggtctggtgcagcccggagga agcctgcgcctgtcatgcgctgccagcgggttctcgctttcctcctac gccatgacctgggtcagacaggcaccgggaaagggcctcgaatggatt ggcattatctatgcgggtggcagcccttcctacgcctcctgggctaaa gggcggttcaccatctcgaaggactcctccaagaacacggtgtacttg caaatgaactcactgagggccgaggacactgcggtgtactactgtgcc cggggaactggagataccgtgtacacctactttaacatctggggccag ggaaccctggtcactgtctcgagcgcttctacaaagggcccatccgtc ttccccctggcgccctgctccaggagcacctccgagagcacagccgcc ctgggctgcctggtcaaggactacttccccgaaccggtgacggtgtcg tggaactcaggcgccctgaccagcggcgtgcacaccttcccggctgtc ctacagtcctcaggactctactccctcagcagcgtggtgaccgtgccc tccagcagcttgggcacgaagacctacacctgcaacgtagatcacaag cccagcaacaccaaggtggacaagagagttgagtccaaatatggtccc ccatgcccaccatgcccagcacctgagttcctggggggaccatcagtc ttcctgttccccccaaaacccaaggacactctcatgatctcccggacc cctgaggtcacgtgcgtggtggtggacgtgagccaggaagaccccgag gtccagttcaactggtacgtggatggcgtggaggtgcataatgccaag acaaagccgcgggaggagcagttcaacagcacgtaccgtgtggtcagc gtcctcaccgtcctgcaccaggactggctgaacggcaaggagtacaag tgcaaggtctccaacaaaggcctcccgtcctccatcgagaaaaccatc tccaaagccaaagggcagccccgagagccacaggtgtacaccctgccc ccatcccaggaggagatgaccaagaaccaggtcagcctgacctgcctg gtcaaaggcttctaccccagcgacatcgccgtggagtgggagagcaat gggcagccggagaacaactacaagaccacgcctcccgtgctggactcc gacggctccttcttcctctacagcaggctaaccgtggacaagagcagg tggcaggaggggaatgtcttctcatgctccgtgatgcatgaggctctg cacaaccactacacacagaagagcctctccctgtctctgggtaaa | 70 |
| 12172gH9 V-region | EVQLVESGGGLVQPGGSLRLSCAASGFSLSSYAMTWVRQAPGKGLEWI GIIYAGGSPSYASWAKGRFTISRDNSKNTVYLQMNSLRAEDTAVYYCA RGTGDTVYTYFNIWGQGTLVTVSS | 71 |
| 12172gH9 V-region | gaagtgcagctcgtggagtcgggcggaggtctggtgcagcccggagga agcctgcgcctgtcatgcgctgccagcgggttctcgctttcctcctac gccatgacctgggtcagacaggcaccgggaaagggcctcgaatggatt ggcattatctatgcgggtggcagcccttcctacgcctcctgggctaaa gggcggttcaccatctcgcgcgacaattccaagaacacggtgtacttg caaatgaactcactgagggccgaggacactgcggtgtactactgtgcc cggggaactggagataccgtgtacacctactttaacatctggggccag ggaaccctggtcactgtctcgagc | 72 |
| 12172gH9 heavy chain (IgG4P) | EVQLVESGGGLVQPGGSLRLSCAASGFSLSSYAMTWVRQAPGKGLEWI GIIYAGGSPSYASWAKGRFTISRDNSKNTVYLQMNSLRAEDTAVYYCA RGTGDTVYTYFNIWGQGTLVTVSSASTKGPSVFPLAPCSRSTSESTAA LGCLVKDYFPEPVTVSWNSGALTSGVHTFPAVLQSSGLYSLSSVVTVP SSSLGTKTYTCNVDHKPSNTKVDKRVESKYGPPCPPCPAPEFLGGPSV FLFPPKPKDTLMISRTPEVTCVVVDVSQEDPEVQFNWYVDGVEVHNAK TKPREEQFNSTYRVVSVLTVLHQDWLNGKEYKCKVSNKGLPSSIEKTI SKAKGQPREPQVYTLPPSQEEMTKNQVSLTCLVKGFYPSDIAVEWESN GQPENNYKTTPPVLDSDGSFFLYSRLTVDKSRWQEGNVFSCSVMHEAL HNHYTQKSLSLSLGK | 73 |
| 12172gH9 heavy chain (IgG4P) | gaagtgcagctcgtggagtcgggcggaggtctggtgcagcccggagga agcctgcgcctgtcatgcgctgccagcgggttctcgctttcctcctac gccatgacctgggtcagacaggcaccgggaaagggcctcgaatggatt ggcattatctatgcgggtggcagcccttcctacgcctcctgggctaaa gggcggttcaccatctcgcgcgacaattccaagaacacggtgtacttg caaatgaactcactgagggccgaggacactgcggtgtactactgtgcc cggggaactggagataccgtgtacacctactttaacatctggggccag ggaaccctggtcactgtctcgagcgcttctacaaagggcccatccgtc ttccccctggcgccctgctccaggagcacctccgagagcacagccgcc ctgggctgcctggtcaaggactacttccccgaaccggtgacggtgtcg tggaactcaggcgccctgaccagcggcgtgcacaccttcccggctgtc ctacagtcctcaggactctactccctcagcagcgtggtgaccgtgccc tccagcagcttgggcacgaagacctacacctgcaacgtagatcacaag cccagcaacaccaaggtggacaagagagttgagtccaaatatggtccc ccatgcccaccatgcccagcacctgagttcctggggggaccatcagtc ttcctgttccccccaaaacccaaggacactctcatgatctcccggacc cctgaggtcacgtgcgtggtggtggacgtgagccaggaagaccccgag gtccagttcaactggtacgtggatggcgtggaggtgcataatgccaag acaaagccgcgggaggagcagttcaacagcacgtaccgtgtggtcagc gtcctcaccgtcctgcaccaggactggctgaacggcaaggagtacaag | 74 |

TABLE 7-continued

| Sequences of the 12172 antibody and related variants | | |
|---|---|---|
| Name | Sequence | SEQ ID NO |
| | tgcaaggtctccaacaaaggcctcccgtcctccatcgagaaaaccatc tccaaagccaaagggcagccccgagagccacaggtgtacaccctgccc ccatcccaggaggagatgaccaagaaccaggtcagcctgacctgcctg gtcaaaggcttctaccccagcgacatcgccgtggagtgggagagcaat gggcagccggagaacaactacaagaccacgcctcccgtgctggactcc gacggctccttcttcctctacagcaggctaaccgtggacaagagcagg tggcaggaggggaatgtcttctcatgctccgtgatgcatgaggctctg cacaaccactacacacagaagagcctctccctgtctctgggtaaa | |
| 12172gH10 V-region | EVQLVESGGGLVQPGGSLRLSCAASGFSLSSYAMTWVRQAPGKGLEWI GIIYAGGSPSYASWAKGRFTISRDSSKNTLYLQMNSLRAEDTAVYYCA RGTGDTVYTYFNIWGQGTLVTVSS | 75 |
| 12172gH10 V-region | gaagtgcagctcgtggagtcgggcggaggtctggtgcagcccggagga agcctgcgcctgtcatgcgctgccagcgggttctcgctttcctcctac gccatgacctgggtcagacaggcaccgggaaagggcctcgaatggatt ggcattatctatgcgggtggcagcccttcctacgcctcctgggctaaa gggggttcaccatctcgcgcgactcctccaagaacacgctgtacttg caaatgaactcactgagggccgaggacactgcggtgtactactgtgcc cggggaactggagataccgtgtacacctactttaacatctggggccag ggaaccctggtcactgtctcgagc | 76 |
| 12172gH10 heavy chain (IgG4P) | EVQLVESGGGLVQPGGSLRLSCAASGFSLSSYAMTWVRQAPGKGLEWI GIIYAGGSPSYASWAKGRFTISRDSSKNTLYLQMNSLRAEDTAVYYCA RGTGDTVYTYFNIWGQGTLVTVSSASTKGPSVFPLAPCSRSTSESTAA LGCLVKDYFPEPVTVSWNSGALTSGVHTFPAVLQSSGLYSLSSVVTVP SSSLGTKTYTCNVDHKPSNTKVDKRVESKYGPPCPPCPAPEFLGGPSV FLFPPKPKDTLMISRTPEVTCVVVDVSQEDPEVQFNWYVDGVEVHNAK TKPREEQFNSTYRVVSVLTVLHQDWLNGKEYKCKVSNKGLPSSIEKTI SKAKGQPREPQVYTLPPSQEEMTKNQVSLTCLVKGFYPSDIAVEWESN GQPENNYKTTPPVLDSDGSFFLYSRLTVDKSRWQEGNVFSCSVMHEAL HNHYTQKSLSLSLGK | 77 |
| 12172gH10 heavy chain (IgG4P) | gaagtgcagctcgtggagtcgggcggaggtctggtgcagcccggagga agcctgcgcctgtcatgcgctgccagcgggttctcgctttcctcctac gccatgacctgggtcagacaggcaccgggaaagggcctcgaatggatt ggcattatctatgcgggtggcagcccttcctacgcctcctgggctaaa gggcggttcaccatctcgcgcgactcctccaagaacacgctgtacttg caaatgaactcactgagggccgaggacactgcggtgtactactgtgcc cggggaactggagataccgtgtacacctactttaacatctggggccag ggaaccctggtcactgtctcgagcgcttctacaaagggcccatccgtc ttccccctggcgccctgctccaggagcacctccgagagcacagccgcc ctgggctgcctggtcaaggactacttccccgaaccggtgacggtgtcg tggaactcaggcgccctgaccagcggcgtgcacaccttcccggctgtc ctacagtcctcaggactctactccctcagcagcgtggtgaccgtgccc tccagcagcttgggcacgaagacctacacctgcaacgtagatcacaag cccagcaacaccaaggtggacaagagagttgagtccaaatatggtccc ccatgcccaccatgcccagcacctgagttcctggggggaccatcagtc ttcctgttccccccaaaacccaaggacactctcatgatctcccggacc cctgaggtcacgtgcgtggtggtggacgtgagccaggaagaccccgag gtccagttcaactggtacgtggatggcgtggaggtgcataatgccaag acaaagccgcgggaggagcagttcaacagcacgtaccgtgtggtcagc gtcctcaccgtcctgcaccaggactggctgaacggcaaggagtacaag tgcaaggtctccaacaaaggcctcccgtcctccatcgagaaaaccatc tccaaagccaaagggcagccccgagagccacaggtgtacaccctgccc ccatcccaggaggagatgaccaagaaccaggtcagcctgacctgcctg gtcaaaggcttctaccccagcgacatcgccgtggagtgggagagcaat gggcagccggagaacaactacaagaccacgcctcccgtgctggactcc gacggctccttcttcctctacagcaggctaaccgtggacaagagcagg tggcaggaggggaatgtcttctcatgctccgtgatgcatgaggctctg cacaaccactacacacagaagagcctctccctgtctctgggtaaa | 78 |
| 12172gH11 V-region | EVQLVESGGGLVQPGGSLRLSCAASGFSLSSYAMTWVRQAPGKGLEWI GIIYAGGSPSYASWAKGRFTISKDNSKNTLYLQMNSLRAEDTAVYYCA RGTGDTVYTYFNIWGQGTLVTVSS | 79 |
| 12172gH11 V-region | gaagtgcagctcgtggagtcgggcggaggtctggtgcagcccggagga agcctgcgcctgtcatgcgctgccagcgggttctcgctttcctcctac gccatgacctgggtcagacaggcaccgggaaagggcctcgaatggatt ggcattatctatgcgggtggcagcccttcctacgcctcctgggctaaa gggcggttcaccatctcgaaggacaattccaagaacacgctgtacttg caaatgaactcactgagggccgaggacactgcggtgtactactgtgcc cggggaactggagataccgtgtacacctactttaacatctggggccag ggaaccctggtcactgtctcgagc | 80 |

TABLE 7-continued

Sequences of the 12172 antibody and related variants

| Name | Sequence | SEQ ID NO |
|---|---|---|
| 12172gH11 heavy chain (IgG4P) | EVQLVESGGGLVQPGGSLRLSCAASGFSLSSYAMTWVRQAPGKGLEWI<br>GIIYAGGSPSYASWAKGRFTISKDNSKNTLYLQMNSLRAEDTAVYYCA<br>RGTGDTVYTYFNIWGQGTLVTVSSASTKGPSVFPLAPCSRSTSESTAA<br>LGCLVKDYFPEPVTVSWNSGALTSGVHTFPAVLQSSGLYSLSSVVTVP<br>SSSLGTKTYTCNVDHKPSNTKVDKRVESKYGPPCPPCPAPEFLGGPSV<br>FLFPPKPKDTLMISRTPEVTCVVVDVSQEDPEVQFNWYVDGVEVHNAK<br>TKPREEQFNSTYRVVSVLTVLHQDWLNGKEYKCKVSNKGLPSSIEKTI<br>SKAKGQPREPQVYTLPPSQEEMTKNQVSLTCLVKGFYPSDIAVEWESN<br>GQPENNYKTTPPVLDSDGSFFLYSRLTVDKSRWQEGNVFSCSVMHEAL<br>HNHYTQKSLSLSLGK | 81 |
| 12172gH11 heavy chain (IgG4P) | gaagtgcagctcgtggagtcgggcggaggtctggtgcagcccggagga<br>agcctgcgcctgtcatgcgctgccagcgggttctcgctttcctcctac<br>gccatgacctgggtcagacaggcaccgggaaagggcctcgaatggatt<br>ggcattatctatgcgggtggcagcccttcctacgcctcctgggctaaa<br>gggcggttcaccatctcgaaggacaattccaagaacacgctgtacttg<br>caaatgaactcactgagggccgaggacactgcggtgtactactgtgcc<br>cggggaactggagataccgtgtacacctactttaacatctggggccag<br>ggaaccctggtcactgtctcgagcgcttctacaaagggcccctccgtg<br>ttccctctggccccttgctcccggtccacctccgagtctaccgccgct<br>ctgggctgcctggtcaaggactacttccccgagcccgtgacagtgtcc<br>tggaactctggcgccctgacctccggcgtgcacaccttccctgccgtg<br>ctgcagtcctccggcctgtactccctgtcctccgtcgtgaccgtgccc<br>tcctccagcctgggcaccaagacctacacctgtaacgtggaccacaag<br>ccctccaacaccaaggtggacaagcgggtggaatctaagtacggccct<br>ccctgccccccctgccctgcccctgaatttctgggcggaccttccgtg<br>ttcctgttccccccaaagcccaaggacaccctgatgatctcccggacc<br>cccgaagtgacctgcgtggtggtggacgtgtcccaggaagatcccgag<br>gtccagttcaattggtacgtggacggcgtggaagtgcacaatgccaag<br>accaagcccagagaggaacagttcaactccacctaccgggtggtgtcc<br>gtgctgaccgtgctgcaccaggactggctgaacggcaaagagtacaag<br>tgcaaggtgtccaacaagggcctgccctccagcatcgaaaagaccatc<br>tccaaggccaagggccagccccgcgagccccaggtgtacaccctgccc<br>cctagccaggaagagatgaccaagaaccaggtgtccctgacctgtctg<br>gtcaagggcttctaccccctccgacattgccgtggaatgggagtccaac<br>ggccagcccgagaacaactacaagaccacccccccctgtgctggacagc<br>gacggctccttcttcctgtactctcggctgaccgtggacaagtcccgg<br>tggcaggaaggcaacgtcttctcctgctccgtgatgcacgaggccctg<br>cacaaccactacacccagaagtccctgtccctgagcctgggcaag | 82 |
| 12172gH11 heavy chain (IgG4P F234A L235A) | EVQLVESGGGLVQPGGSLRLSCAASGFSLSSYAMTWVRQAPGKGLEWI<br>GIIYAGGSPSYASWAKGRFTISKDNSKNTLYLQMNSLRAEDTAVYYCA<br>RGTGDTVYTYFNIWGQGTLVTVSSASTKGPSVFPLAPCSRSTSESTAA<br>LGCLVKDYFPEPVTVSWNSGALTSGVHTFPAVLQSSGLYSLSSVVTVP<br>SSSLGTKTYTCNVDHKPSNTKVDKRVESKYGPPCPPCPAPEAAGGPSV<br>FLFPPKPKDTLMISRTPEVTCVVVDVSQEDPEVQFNWYVDGVEVHNAK<br>TKPREEQFNSTYRVVSVLTVLHQDWLNGKEYKCKVSNKGLPSSIEKTI<br>SKAKGQPREPQVYTLPPSQEEMTKNQVSLTCLVKGFYPSDIAVEWESN<br>GQPENNYKTTPPVLDSDGSFFLYSRLTVDKSRWQEGNVFSCSVMHEAL<br>HNHYTQKSLSLSLGK | 83 |
| 12172gH11 heavy chain (IgG4P F234A L235A) | gaagtgcagctcgtggagtcgggcggaggtctggtgcagcccggagga<br>agcctgcgcctgtcatgcgctgccagcgggttctcgctttcctcctac<br>gccatgacctgggtcagacaggcaccgggaaagggcctcgaatggatt<br>ggcattatctatgcgggtggcagcccttcctacgcctcctgggctaaa<br>gggcggttcaccatctcgaaggacaattccaagaacacgctgtacttg<br>caaatgaactcactgagggccgaggacactgcggtgtactactgtgcc<br>cggggaactggagataccgtgtacacctactttaacatctggggccag<br>ggaaccctggtcactgtctcgagcgcttctacaaagggcccatccgtc<br>ttccccctggcgccctgctccaggagcacctccgagagcacagccgcc<br>ctgggctgcctggtcaaggactacttccccgaaccggtgacggtgtcg<br>tggaactcaggcgccctgaccagcggcgtgcacaccttcccggctgtc<br>ctacagtcctcaggactctactccctcagcagcgtggtgaccgtgccc<br>tccagcagcttgggcacgaagacctacacctgcaacgtagatcacaag<br>cccagcaacaccaaggtggacaagagagttgagtccaaatatggtccc<br>ccatgcccaccatgcccagcacctgaagccgcggggggaccgtcagtc<br>ttcctgttccccccaaaacccaaggacactctcatgatctcccggacc<br>cctgaggtcacgtgcgtggtggtggacgtgagccaggaagaccccgag<br>gtccagttcaactggtacgtggatggcgtggaggtgcataatgccaag<br>acaaagccgcgggaggagcagttcaacagcacgtaccgtgtggtcagc<br>gtcctcaccgtcctgcaccaggactggctgaacggcaaggagtacaag<br>tgcaaggtctccaacaaaggcctcccgtcctccatcgagaaaaccatc<br>tccaaagccaaagggcagccccgagagccacaggtgtacaccctgccc | 84 |

TABLE 7-continued

Sequences of the 12172 antibody and related variants

| Name | Sequence | SEQ ID NO |
|---|---|---|
| | ccatcccaggaggagatgaccaagaaccaggtcagcctgacctgcctg<br>gtcaaaggcttctaccccagcgacatcgccgtggagtgggagagcaat<br>gggcagccggagaacaactacaagaccacgcctcccgtgctggactcc<br>gacggctccttcttcctctacagcaggctaaccgtggacaagagcagg<br>tggcaggaggggaatgtcttctcatgctccgtgatgcatgaggctctg<br>cacaaccactacacacagaagagcctctccctgtctctgggtaaa | |
| 12172gH11 heavy chain (IgG1) | EVQLVESGGGLVQPGGSLRLSCAASGFSLSSYAMTWVRQAPGKGLEWI<br>GIIYAGGSPSYASWAKGRFTISKDNSKNTLYLQMNSLRAEDTAVYYCA<br>RGTGDTVYTYFNIWGQGTLVTVSSASTKGPSVFPLAPSSKSTSGGTAA<br>LGCLVKDYFPEPVTVSWNSGALTSGVHTFPAVLQSSGLYSLSSVVTVP<br>SSSLGTQTYICNVNHKPSNTKVDKKVEPKSCDKTHTCPPCPAPELLGG<br>PSVFLFPPKPKDTLMISRTPEVTCVVVDVSHEDPEVKFNWYVDGVEVH<br>NAKTKPREEQYNSTYRVVSVLTVLHQDWLNGKEYKCKVSNKALPAPIE<br>KTISKAKGQPREPQVYTLPPSRDELTKNQVSLTCLVKGFYPSDIAVEW<br>ESNGQPENNYKTTPPVLDSDGSFFLYSKLTVDKSRWQQGNVFSCSVMH<br>EALHNHYTQKSLSLSPGK | 85 |
| 12172gH11 heavy chain (IgG1) | gaagtgcagctcgtggagtcgggcggaggtctggtgcagcccggagga<br>agcctgcgcctgtcatgcgctgccagcgggttctcgctttcctcctac<br>gccatgacctgggtcagacaggcaccgggaaagggcctcgaatggatt<br>ggcattatctatgcgggggcagcccttcctacgcctcctgggctaaa<br>gggcggttcaccatctcgaaggacaattccaagaacacgctgtacttg<br>caaatgaactcactgagggccgaggacactgcggtgtactactgtgcc<br>cggggaactggagataccgtgtacacctactttaacatctggggccag<br>ggaaccctggtcactgtctcgagcgcttctacaaagggcccatcggtc<br>ttccccctggcaccctcctccaagagcacctctgggggcacagcggcc<br>ctgggctgcctggtcaaggactacttccccgaaccggtgacggtgtcg<br>tggaactcaggcgccctgaccagcggcgtgcacaccttcccggctgtc<br>ctacagtcctcaggactctactccctcagcagcgtggtgaccgtgccc<br>tccagcagcttgggcacccagacctacatctgcaacgtgaatcacaag<br>cccagcaacaccaaggggacaagaaagttgagcccaaatcttgtgac<br>aaaactcacacatgcccaccgtgcccagcacctgaactcctgggggga<br>ccgtcagtcttcctcttccccccaaaacccaaggacaccctcatgatc<br>tcccggacccctgaggtcacatgcgtggtggtggacgtgagccacgaa<br>gaccctgaggtcaagttcaactggtacgtggacggcgtggaggtgcat<br>aatgccaagacaaagccgcgggaggagcagtacaacagcacgtaccgt<br>gtggtcagcgtcctcaccgtcctgcaccaggactggctgaatggcaag<br>gagtacaagtgcaaggtctccaacaaagccctcccagcccccatcgag<br>aaaaccatctccaaagccaaagggcagccccgagaaccacaggtgtac<br>accctgcccccatcccgggatgagctgaccaagaaccaggtcagcctg<br>acctgcctggtcaaaggcttctatcccagcgacatcgccgtggagtgg<br>gagagcaatgggcagccggagaacaactacaagaccacgcctcccgtg<br>ctggactccgacggctccttcttcctctacagcaagctcaccgtggac<br>aagagcaggtggcagcaggggaacgtcttctcatgctccgtgatgcat<br>gaggctctgcacaaccactacacgcagaagagcctctccctgtctccg<br>ggtaaa | 86 |
| 12172gH11 heavy chain (IgG1 L234A L235A) | EVQLVESGGGLVQPGGSLRLSCAASGFSLSSYAMTWVRQAPGKGLEWI<br>GIIYAGGSPSYASWAKGRFTISKDNSKNTLYLQMNSLRAEDTAVYYCA<br>RGTGDTVYTYFNIWGQGTLVTVSSASTKGPSVFPLAPSSKSTSGGTAA<br>LGCLVKDYFPEPVTVSWNSGALTSGVHTFPAVLQSSGLYSLSSVVTVP<br>SSSLGTQTYICNVNHKPSNTKVDKKVEPKSCDKTHTCPPCPAPEAAGG<br>PSVFLFPPKPKDTLMISRTPEVTCVVVDVSHEDPEVKFNWYVDGVEVH<br>NAKTKPREEQYNSTYRVVSVLTVLHQDWLNGKEYKCKVSNKALPAPIE<br>KTISKAKGQPREPQVYTLPPSRDELTKNQVSLTCLVKGFYPSDIAVEW<br>ESNGQPENNYKTTPPVLDSDGSFFLYSKLTVDKSRWQQGNVFSCSVMH<br>EALHNHYTQKSLSLSPGK | 87 |
| 12172gH11 heavy chain (IgG1 L234A L235A) | gaagtgcagctcgtggagtcgggcggaggtctggtgcagcccggagga<br>agcctgcgcctgtcatgcgctgccagcgggttctcgctttcctcctac<br>gccatgacctgggtcagacaggcaccgggaaagggcctcgaatggatt<br>ggcattatctatgcgggtggcagcccttcctacgcctcctgggctaaa<br>gggcggttcaccatctcgaaggacaattccaagaacacgctgtacttg<br>caaatgaactcactgagggccgaggacactgcggtgtactactgtgcc<br>cggggaactggagataccgtgtacacctactttaacatctggggccag<br>ggaaccctggtcactgtctcgagcgcttctacaaagggcccctccgtg<br>ttcccgctcgctccatcatcgaagtctaccagcggaggcactgcggct<br>ctcggttgcctcgtgaaggactacttcccggagccggtgaccgtgtcg<br>tggaacagcggagccctgaccagcggggtgcacacctttccggccgtc<br>ttgcagtcaagcggcctttactccctgtcatcagtggtgactgtcccg<br>tccagctcattgggaacccaaacctacatctgcaatgtgaatcacaaa<br>cctagcaacaccaaggttgacaagaaagtcgagcccaaatcgtgtgac<br>aagactcacacttgtccgccgtgcccggcacccgaagccgcaggaggt | 88 |

TABLE 7-continued

| Sequences of the 12172 antibody and related variants | | |
|---|---|---|
| Name | Sequence | SEQ ID NO |
| | cccagcgtctttctgttccctccaaagccgaaagacacgctgatgatc tcccgcaccccggaggtcacttgcgtggtcgtggacgtgtcacatgag gacccagaggtgaagttcaattggtacgtggatggcgtcgaagtccac aatgccaaaactaagcccagagaagaacagtacaattcgacctaccgc gtcgtgtccgtgctcacggtgttgcatcaggattggctgaacgggaag gaatacaagtgcaaagtgtccaacaaggcgctgccggcaccgatcgag aaaactatctccaaagcgaagggacagcctagggaacctcaagtctac acgctgccaccatcacgggatgaactgactaagaatcaagtctcactg acttgtctggtgaaggggttttaccctagcgacattgccgtggagtgg gaatccaacggccagccagagaacaactacaagactacccctccagtg ctcgactcggatggatcgttcttcctttactcgaagctcaccgtggat aagtcccggtggcagcagggaaacgtgttctcctgctcggtgatgcat gaagccctccataaccactatacccaaaagtcgctgtccctgtcgccg ggaaag | |
| 12172gH12 V-region | EVQLVESGGGLVQPGGSLRLSCAASGFSLSSYAMTWVRQAPGKGLEWI GIIYAGGSPSYASWAKGRFTISRDNSKNTLYLQMNSLRAEDTAVYYCA RGTGDTVYTYFNIWGQGTLVTVSS | 89 |
| 12172gH12 V-region | gaagtgcagctcgtggagtcgggcggaggtctggtgcagcccggagga agcctgcgcctgtcatgcgctgccagcgggttctcgctttcctcctac gccatgacctgggtcagacaggcaccgggaaagggcctcgaatggatt ggcattatctatgcgggtggcagcccttcctacgcctcctgggctaaa gggcggttcaccatctcgcgcgacaattccaagaacacgctgtacttg caaatgaactcactgagggccgaggacactgcggtgtactactgtgcc cggggaactggagataccgtgtacacctactttaacatctggggccag ggaaccctggtcactgtctcgagc | 90 |
| 12172gH12 heavy chain (IgG4P) | EVQLVESGGGLVQPGGSLRLSCAASGFSLSSYAMTWVRQAPGKGLEWI GIIYAGGSPSYASWAKGRFTISRDNSKNTLYLQMNSLRAEDTAVYYCA RGTGDTVYTYFNIWGQGTLVTVSSASTKGPSVFPLAPCSRSTSESTAA LGCLVKDYFPEPVTVSWNSGALTSGVHTFPAVLQSSGLYSLSSVVTVP SSSLGTKTYTCNVDHKPSNTKVDKRVESKYGPPCPPCPAPEFLGGPSV FLFPPKPKDTLMISRTPEVTCVVVDVSQEDPEVQFNWYVDGVEVHNAK TKPREEQFNSTYRVVSVLTVLHQDWLNGKEYKCKVSNKGLPSSIEKTI SKAKGQPREPQVYTLPPSQEEMTKNQVSLTCLVKGFYPSDIAVEWESN GQPENNYKTTPPVLDSDGSFFLYSRLTVDKSRWQEGNVFSCSVMHEAL HNHYTQKSLSLSLGK | 91 |
| 12172gH12 heavy chain (IgG4P) | gaagtgcagctcgtggagtcgggcggaggtctggtgcagcccggagga agcctgcgcctgtcatgcgctgccagcgggttctcgctttcctcctac gccatgacctgggtcagacaggcaccgggaaagggcctcgaatggatt ggcattatctatgcgggtggcagcccttcctacgcctcctgggctaaa gggcggttcaccatctcgcgcgacaattccaagaacacgctgtacttg caaatgaactcactgagggccgaggacactgcggtgtactactgtgcc cggggaactggagataccgtgtacacctactttaacatctggggccag ggaaccctggtcactgtctcgagcgcttctacaaagggcccatccgtc ttccccctggcgccctgctccaggagcacctccgagagcacagccgcc ctgggctgcctggtcaaggactacttccccgaaccggtgacggtgtcg tggaactcaggcgccctgaccagcggcgtgcacaccttcccggctgtc ctacagtcctcaggactctactccctcagcagcgtggtgaccgtgccc tccagcagcttgggcacgaagacctacacctgcaacgtagatcacaag cccagcaacaccaaggtggacaagagagttgagtccaaatatggtccc ccatgcccaccatgcccagcacctgagttcctggggggaccatcagtc ttcctgttccccccaaaacccaaggacactctcatgatctcccggacc cctgaggtcacgtgcgtggtggtggacgtgagccaggaagaccccgag gtccagttcaactggtacgtggatggcgtggaggtgcataatgccaag acaaagccgcgggaggagcagttcaacagcacgtaccgtgtggtcagc gtcctcaccgtcctgcaccaggactggctgaacggcaaggagtacaag tgcaaggtctccaacaaaggcctcccgtcctccatcgagaaaaccatc tccaaagccaaagggcagccccgagagccacaggtgtacaccctgccc ccatcccaggaggagatgaccaagaaccaggtcagcctgacctgcctg gtcaaaggcttctaccccagcgacatcgccgtggagtgggagagcaat gggcagccggagaacaactacaagaccacgcctcccgtgctggactcc gacggctccttcttcctctacagcaggctaaccgtggacaagagcagg tggcaggaggggaatgtcttctcatgctccgtgatgcatgaggctctg cacaaccactacacacagaagagcctctccctgtctctgggtaaa | 92 |
| 12172gH26 V-region | EVQLVESGGGLVQPGGSLRLSCAASGFSLSSYAMTWVRQAPGKGLEWI GIIYAGGSPSYASWAKGRFTISKDNSSNTLYLQMNSLRAEDTAVYYCA RGTGDTVYTYFNIWGQGTLVTVSS | 93 |

TABLE 7-continued

Sequences of the 12172 antibody and related variants

| Name | Sequence | SEQ ID NO |
|---|---|---|
| 12172gH26 V-region | gaagtgcagctcgtggagtcgggcggaggtctggtgcagcccggagga agcctgcgcctgtcatgcgctgccagcgggttctcgctttcctcctac gccatgacctgggtcagacaggcaccgggaaagggcctcgaatggatt ggcattatctatgcgggtggcagcccttcctacgcctcctgggctaaa gggcggttcaccatctcgaaggacaattccagcaacacgctgtacttg caaatgaactcactgagggccgaggacactgcggtgtactactgtgcc cggggaactggagataccgtgtacacctactttaacatctggggccag ggaaccctggtcactgtctcgagc | 94 |
| 12172gH26 heavy chain (hIgG4P) | EVQLVESGGGLVQPGGSLRLSCAASGFSLSSYAMTWVRQAPGKGLEWI GIIYAGGSPSYASWAKGRFTISKDNSSNTLYLQMNSLRAEDTAVYYCA RGTGDTVYTYFNIWGQGTLVTVSSASTKGPSVFPLAPCSRSTSESTAA LGCLVKDYFPEPVTVSWNSGALTSGVHTFPAVLQSSGLYSLSSVVTVP SSSLGTKTYTCNVDHKPSNTKVDKRVESKYGPPCPPCPAPEFLGGPSV FLFPPKPKDTLMISRTPEVTCVVVDVSQEDPEVQFNWYVDGVEVHNAK TKPREEQFNSTYRVVSVLTVLHQDWLNGKEYKCKVSNKGLPSSIEKTI SKAKGQPREPQVYTLPPSQEEMTKNQVSLTCLVKGFYPSDIAVEWESN GQPENNYKTTPPVLDSDGSFFLYSRLTVDKSRWQEGNVFSCSVMHEAL HNHYTQKSLSLSLGK | 95 |
| 12172gH26 heavy chain (hIgG4P) | gaagtgcagctcgtggagtcgggcggaggtctggtgcagcccggagga agcctgcgcctgtcatgcgctgccagcgggttctcgctttcctcctac gccatgacctgggtcagacaggcaccgggaaagggcctcgaatggatt ggcattatctatgcgggggcagcccttcctacgcctcctgggctaaa gggcggttcaccatctcgaaggacaattccagcaacacgctgtacttg caaatgaactcactgagggccgaggacactgcggtgtactactgtgcc cggggaactggagataccgtgtacacctactttaacatctggggccag ggaaccctggtcactgtctcgagcgcttctacaaagggcccatccgtc ttccccctggcgccctgctccaggagcacctccgagagcacagccgcc ctgggctgcctggtcaaggactacttccccgaaccggtgacggtgtcg tggaactcaggcgccctgaccagcggcgtgcacaccttcccggctgtc ctacagtcctcaggactctactccctcagcagcgtggtgaccgtgccc tccagcagcttgggcacgaagacctacacctgcaacgtagatcacaag cccagcaacaccaaggtggacaagagagttgagtccaaatatggtccc ccatgcccaccatgcccagcacctgagttcctggggggaccatcagtc ttcctgttccccccaaaacccaaggacactctcatgatctcccggacc cctgaggtcacgtgcgtggtggtggacgtgagccaggaagaccccgag gtccagttcaactggtacgtggatggcgtggaggtgcataatgccaag acaaagccgcgggaggagcagttcaacagcacgtaccgtgtggtcagc gtcctcaccgtcctgcaccaggactggctgaacggcaaggagtacaag tgcaaggtctccaacaaaggcctcccgtcctccatcgagaaaaccatc tccaaagccaaagggcagccccgagagccacaggtgtacaccctgccc ccatcccaggaggagatgaccaagaaccaggtcagcctgacctgcctg gtcaaaggcttctaccccagcgacatcgccgtggagtgggagagcaat gggcagccggagaacaactacaagaccacgcctcccgtgctggactcc gacggctccttcttcctctacagcaggctaaccgtggacaagagcagg tggcaggaggggaatgtcttctcatgctccgtgatgcatgaggctctg cacaaccactacacacagaagagcctctccctgtctctgggtaaa | 96 |
| 12172gH48 V-region | EVQLVESGGGLVQPGGSLRLSCAASGFSLSSYAMTWVRQAPGKGLEWI GIIYAGGSPSYASWAKGRFTISKDNSQNTLYLQMNSLRAEDTAVYYCA RGTGDTVYTYFNIWGQGTLVTVSS | 97 |
| 12172gH48 V-region | gaagtgcagctcgtggagtcgggcggaggtctggtgcagcccggagga agcctgcgcctgtcatgcgctgccagcgggttctcgctttcctcctac gccatgacctgggtcagacaggcaccgggaaagggcctcgaatggatt ggcattatctatgcgggggcagcccttcctacgcctcctgggctaaa gggcggttcaccatctcgaaggacaattcccagaacacgctgtacttg caaatgaactcactgagggccgaggacactgcggtgtactactgtgcc cggggaactggagataccgtgtacacctactttaacatctggggccag ggaaccctggtcactgtctcgagc | 98 |
| 12172gH48 heavy chain (hIgG4P) | EVQLVESGGGLVQPGGSLRLSCAASGFSLSSYAMTWVRQAPGKGLEWI GIIYAGGSPSYASWAKGRFTISKDNSQNTLYLQMNSLRAEDTAVYYCA RGTGDTVYTYFNIWGQGTLVTVSSASTKGPSVFPLAPCSRSTSESTAA LGCLVKDYFPEPVTVSWNSGALTSGVHTFPAVLQSSGLYSLSSVVTVP SSSLGTKTYTCNVDHKPSNTKVDKRVESKYGPPCPPCPAPEFLGGPSV FLFPPKPKDTLMISRTPEVTCVVVDVSQEDPEVQFNWYVDGVEVHNAK TKPREEQFNSTYRVVSVLTVLHQDWLNGKEYKCKVSNKGLPSSIEKTI SKAKGQPREPQVYTLPPSQEEMTKNQVSLTCLVKGFYPSDIAVEWESN GQPENNYKTTPPVLDSDGSFFLYSRLTVDKSRWQEGNVFSCSVMHEAL HNHYTQKSLSLSLGK | 99 |

TABLE 7-continued

Sequences of the 12172 antibody and related variants

| Name | Sequence | SEQ ID NO |
|---|---|---|
| 12172gH48 heavy chain (hIgG4P) | gaagtgcagctcgtggagtcgggcggaggtctggtgcagcccggagga agcctgcgcctgtcatgcgctgccagcgggttctcgctttcctcctac gccatgacctgggtcagacaggcaccgggaaagggcctcgaatggatt ggcattatctatgcgggtggcagcccttcctacgcctcctgggctaaa gggcggttcaccatctcgaaggacaattcccagaacacgctgtacttg caaatgaactcactgagggccgaggacactgcggtgtactactgtgcc cggggaactggagataccgtgtacacctactttaacatctggggccag ggaaccctggtcactgtctcgagcgcttctacaaagggcccatccgtc ttccccctggcgccctgctccaggagcacctccgagagcacagccgcc ctgggctgcctggtcaaggactacttccccgaaccggtgacggtgtcg tggaactcaggcgccctgaccagcggcgtgcacaccttcccggctgtc ctacagtcctcaggactctactccctcagcagcgtggtgaccgtgccc tccagcagcttgggcacgaagacctacacctgcaacgtagatcacaag cccagcaacaccaaggtggacaagagagttgagtccaaatatggtccc ccatgcccaccatgcccagcacctgagttcctggggggaccatcagtc ttcctgttccccccaaaacccaaggacactctcatgatctcccggacc cctgaggtcacgtgcgtggtggtggacgtgagccaggaagaccccgag gtccagttcaactggtacgtggatggcgtggaggtgcataatgccaag acaaagccgcgggaggagcagttcaacagcacgtaccgtgtggtcagc gtcctcaccgtcctgcaccaggactggctgaacggcaaggagtacaag tgcaaggtctccaacaaaggcctcccgtcctccatcgagaaaaccatc tccaaagccaaagggcagccccgagagccacaggtgtacaccctgccc ccatcccaggaggagatgaccaagaaccaggtcagcctgacctgcctg gtcaaaggcttctaccccagcgacatcgccgtggagtgggagagcaat gggcagccggagaacaactacaagaccacgcctcccgtgctggactcc gacggctccttcttcctctacagcaggctaaccgtggacaagagcagg tggcaggaggggaatgtcttctcatgctccgtgatgcatgaggctctg cacaaccactacacacagaagagcctctccctgtctctgggtaaa | 100 |
| 12172gH49 V-region | EVQLVESGGGLVQPGGSLRLSCAASGFSLSSYAMTWVRQAPGKGLEWI GIIYAGGSPSYASWAKGRFTISKDNSENTLYLQMNSLRAEDTAVYYCA RGTGDTVYTYFNIWGQGTLVTVSS | 101 |
| 12172gH49 V-region | gaagtgcagctcgtggagtcgggcggaggtctggtgcagcccggagga agcctgcgcctgtcatgcgctgccagcgggttctcgctttcctcctac gccatgacctgggtcagacaggcaccgggaaagggcctcgaatggatt ggcattatctatgcgggtggcagcccttcctacgcctcctgggctaaa gggcggttcaccatctcgaaggacaattccgagaacacgctgtacttg caaatgaactcactgagggccgaggacactgcggtgtactactgtgcc cggggaactggagataccgtgtacacctactttaacatctggggccag ggaaccctggtcactgtctcgagc | 102 |
| 12172gH49 heavy chain (hIgG4P) | EVQLVESGGGLVQPGGSLRLSCAASGFSLSSYAMTWVRQAPGKGLEWI GIIYAGGSPSYASWAKGRFTISKDNSENTLYLQMNSLRAEDTAVYYCA RGTGDTVYTYFNIWGQGTLVTVSSASTKGPSVFPLAPCSRSTSESTAA LGCLVKDYFPEPVTVSWNSGALTSGVHTFPAVLQSSGLYSLSSVVTVP SSSLGTKTYTCNVDHKPSNTKVDKRVESKYGPPCPPCPAPEFLGGPSV FLFPPKPKDTLMISRTPEVTCVVVDVSQEDPEVQFNWYVDGVEVHNAK TKPREEQFNSTYRVVSVLTVLHQDWLNGKEYKCKVSNKGLPSSIEKTI SKAKGQPREPQVYTLPPSQEEMTKNQVSLTCLVKGFYPSDIAVEWESN GQPENNYKTTPPVLDSDGSFFLYSRLTVDKSRWQEGNVFSCSVMHEAL HNHYTQKSLSLSLGK | 103 |
| 12172gH49 heavy chain (hIgG4P) | gaagtgcagctcgtggagtcgggcggaggtctggtgcagcccggagga agcctgcgcctgtcatgcgctgccagcgggttctcgctttcctcctac gccatgacctgggtcagacaggcaccgggaaagggcctcgaatggatt ggcattatctatgcgggtggcagcccttcctacgcctcctgggctaaa gggcggttcaccatctcgaaggacaattccgagaacacgctgtacttg caaatgaactcactgagggccgaggacactgcggtgtactactgtgcc cggggaactggagataccgtgtacacctactttaacatctggggccag ggaaccctggtcactgtctcgagcgcttctacaaagggcccatccgtc ttccccctggcgccctgctccaggagcacctccgagagcacagccgcc ctgggctgcctggtcaaggactacttccccgaaccggtgacggtgtcg tggaactcaggcgccctgaccagcggcgtgcacaccttcccggctgtc ctacagtcctcaggactctactccctcagcagcgtggtgaccgtgccc tccagcagcttgggcacgaagacctacacctgcaacgtagatcacaag cccagcaacaccaaggtggacaagagagttgagtccaaatatggtccc ccatgcccaccatgcccagcacctgagttcctggggggaccatcagtc ttcctgttccccccaaaacccaaggacactctcatgatctcccggacc cctgaggtcacgtgcgtggtggtggacgtgagccaggaagaccccgag gtccagttcaactggtacgtggatggcgtggaggtgcataatgccaag acaaagccgcgggaggagcagttcaacagcacgtaccgtgtggtcagc gtcctcaccgtcctgcaccaggactggctgaacggcaaggagtacaag tgcaaggtctccaacaaaggcctcccgtcctccatcgagaaaaccatc | 104 |

TABLE 7-continued

Sequences of the 12172 antibody and related variants

| Name | Sequence | SEQ ID NO |
|---|---|---|
| | tccaaagccaaagggcagccccgagagccacaggtgtacaccctgccc<br>ccatcccaggaggagatgaccaagaaccaggtcagcctgacctgcctg<br>gtcaaaggcttctaccccagcgacatcgccgtggagtgggagagcaat<br>gggcagccggagaacaactacaagaccacgcctcccgtgctggactcc<br>gacggctccttcttcctctacagcaggctaaccgtggacaagagcagg<br>tggcaggaggggaatgtcttctcatgctccgtgatgcatgaggctctg<br>cacaaccactacacacagaagagcctctccctgtctctgggtaaa | |
| Human IGKV1-9 IGKJ4 acceptor framework | DIQLTQSPSFLSASVGDRVTITCRASQGISSYLAWYQQKPGKAPKLLI<br>YAASTLQSGVPSRFSGSGSGTEFTLTISSLQPEDFATYYCQQLNSYPL<br>TFGGGTKVEIK | 105 |
| Human IGKV1-9 IGKJ4 acceptor framework | gacatccagttgacccagtctccatccttcctgtctgcatctgtagga<br>gacagagtcaccatcacttgccgggccagtcagggcattagcagttat<br>ttagcctggtatcagcaaaaaccagggaaagcccctaagctcctgatc<br>tatgctgcatccactttgcaaagtggggtcccatcaaggttcagcggc<br>agtggatctgggacagaattcactctcacaatcagcagcctgcagcct<br>gaagattttgcaacttattactgtcaacagcttaatagttaccctctc<br>actttcggcggagggaccaaggtggagatcaaa | 106 |
| Human IGHV3-66 IGHJ4 acceptor framework | EVQLVESGGGLVQPGGSLRLSCAASGFTVSSNYMSWVRQAPGKGLEWV<br>SVIYSGGSTYYADSVKGRFTISRDNSKNTLYLQMNSLRAEDTAVYYCA<br>RYFDYWGQGTLVTVSS | 107 |
| Human IGHV3-66 IGHJ4 acceptor framework | gaggtgcagctggtggagtctgggggaggcttggtccagcctgggggg<br>tccctgagactctcctgtgcagcctctggattcaccgtcagtagcaac<br>tacatgagctgggtccgccaggctccagggaaggggctggagtgggtc<br>tcagttatttatagcggtggtagcacatactacgcagactccgtgaag<br>ggcagattcaccatctccagagacaattccaagaacacgctgtatctt<br>caaatgaacagcctgagagccgaggacacggctgtgtattactgtgcg<br>agatactttgactactggggccaaggaaccctggtcaccgtctcctca | 108 |

EXAMPLES

Example 1: Generation of TREM1 Proteins

Human TREM1 IgV-like domain fused with an N-terminal hexahistidine SUMO (small ubiquitin-related modifier) solubility tag (CID101907) was expressed in *Escherichia coli* BL21 (DE3). Bacteria were harvested by centrifugation, resuspended in 100 mM Tris pH 8, 300 mM NaCl, 250 U Benzonase, 1 PI tab and lysed by sonication. The lysate was clarified by centrifugation at 42,000 RPM (Ti45), 4° C., 45 minutes and applied to a 5 ml HiTrap Ni Chelating Column. The column was washed with 100 mM Tris, pH 8, 300 mM NaCl for 5CV. The bound TREM1 proteins were eluted with a linear gradient 2-60% 100 mM Tris, pH 8, 300 mM NaCl, 500 mM Imidazole buffer for 15 CV, then 100% buffer B for 4CV. Fractions containing TREM1 were pooled, dialyzed (10 kDa MWCO) into 100 mM Tris pH 8, 300 mM NaCl, and digested with ULP-1 overnight at 4° C. The cleaved protein was applied to a 5 ml HiTrap Ni Chelating Column and the flow-through fractions were collected and concentrated in a Vivaspin PES Turbo, 10 kDa MWCO concentrator. A superdex s75 column (GE Healthcare) was then used to polish and buffer exchange the cleaved IgV protein into 100 mM Tris pH 8.0, 300 mM NaCl, 0.5 mM EDTA. The final protein concentration was determined by measuring 280 nm absorbance with a Nanodrop UV spectrometer. Protein purity was assessed by sodium dodecyl sulfate polyacrylamide gel electrophoresis (SDS-PAGE)

Both human (CID101904) and cyno (CID101953) TREM1 extracellular domain (ECD) containing the native N-terminal signal sequence and a C-terminal avidin affinity tag (AVI), TEV protease cleavage site, and a HKH affinity tag were expressed in mammalian HEK cells. The media was passed through tangential flow filtration (TFF) and applied to a HiTrap Ni Chelating 5 mL column and washed with 100 mM HEPES pH 7.0, 300 mM NaCl. The bound TREM1 proteins were eluted, respectively with 2-60% then 100% 100 mM HEPES pH 7.0, 300 mM NaCl, 500 mM Imidazole linear gradient over 4 CV. Fractions containing TREM1 were pooled and concentrated in a Vivaspin PES Turbo, 10 kDa MWCO concentrator. A sephacryl s300 column was then used to polish and buffer exchange the proteins into 50 mM HEPES pH 7.0, 250 mM NaCl. The final protein concentration and purity was assessed as previously described.

Human PGLYRP1 containing the native N-terminal signal sequence and a non-cleavable C-terminal his tag (CID101951) was expressed in mammalian HEK cells. The media was applied to a HiTrap Ni Excel 2×5 mL column and washed with 100 mM HEPES pH 7.0, 300 mM NaCl. The bound PGLYRP1 proteins were eluted, respectively with 0-60% then 100% 100 mM HEPES pH 7.0, 300 mM NaCl, 500 mM Imidazole linear gradient over 4 CV. Fractions containing PGLYRP1 were pooled and concentrated in a Vivaspin PES Turbo, 10 kDa MWCO concentrator. A superdex S200 column was then used to polish and buffer exchange the proteins into PBS pH 7.0. The final protein concentration and purity was assessed as previously described.

Example 2. Generation and Selection of Therapeutic Anti-TREM1 Antibody 12172

One female New Zealand White rabbit was immunized sub-cutaneously with $3\times10^7$ rabbit fibroblast cells transiently expressing human TREM1 on the cell surface. Cells were transfected via electroporation and expression of TREM1 was verified by flow cytometry using anti-TREM1 antibody (R&D FAB1278P). An equal volume of complete Freunds adjuvant was injected sub-cutaneous into the rabbit at a separate site at the same time as immunization with cells.

The rabbit was given two booster injections at 14 day intervals with the rabbit fibroblast cells transiently expressing human TREM1 on the cell surface. Heparinised bleeds (200 μl) were taken from the ear vein prior to each immunization. Sera was collected from the bleeds after spinning 10,000 rpm for 5 minutes in a bench top centrifuge and frozen down at −20° C. Termination occurred 14 days after the final boost with single cell suspensions of spleen, lymph node, bone marrow and peripheral blood mononuclear cells prepared and frozen in 10% DMSO/FCS at −80° C. until required for B cell discovery purposes. A bleed was also taken at termination and sera prepared as previously described.

Memory B cell cultures were set up using the method described by Tickle et al. (2015) in J Biomol Screen 20(4): 492-7 and supernatants were first screened for their ability to bind human and cynomolgus TREM1 in a cell-based assay on the TTP Labtech Mirrorball system. Cell-based assays were a homogeneous multiplex assay using HEK 293 cells transiently transfected with either human TREM1 or cynomolgus TREM1 DNA, and counter screened against HEK 293 cells transiently transfected with irrelevant DNA. Cells were stained with either Vybrant™ DIO or DIL labelling (ThermoFisher) and a goat anti-rabbit Fc-AF647 conjugate as a reveal agent.

Approx. 7000 TREM1-specific positive hits were identified in the primary Mirrorball screens from a total of 20×200-plate B-cell culture experiments. Positive supernatants from this assay were then progressed for further characterization by profiling in BIAcore to estimate off-rate.

Wells with off-rates resulting in less than a 25% loss of binding during interrogation of a 300 s disassociation step were progressed for V region gene recovery using the fluorescent foci method and single cell reverse transcription (RT) and PCR (RT-PCR).

Following reverse transcription (RT) and PCR of the picked cells, 'transcriptionally active PCR' (TAP) products encoding the antibodies' V regions were generated and used to transiently transfect HEK-293 cells. The resultant TAP supernatants, containing recombinant antibody, were tested for their ability to: bind human (CID101904; SEQ ID NO: 7) and cynomolgus (CID101953; SEQ ID NO: 8) TREM1 extracellular domain (generated as described in Example 1) by ELISA, bind to human sTREM1 in the BIAcore with affinity of at least 1000 pM, and block PGLYRP1-mediated signaling in the THP1 monocyte TREM1/DAP12 NF-κB Luciferase reporter cell assay.

Functionality was assessed by the ability of antibodies to inhibit PGLYRP1/PGN mediated NF-κB signaling activation through human TREM1. To do this, THP1 monocyte TREM1/DAP12 NF-κB Luciferase reporter cells were used (generated at UCB). These cells stably express human TREM1, human DAP12 and a NF-κB luciferase reporter gene. PGLYRP1 complexed with soluble peptidoglycan from *E. coli* (PGN) was used as the TREM1 ligand, which induces NF-κB activation by binding to TREM1. PGN which does not bind to TREM1 also induces NF-κB activation, but to a lesser extent and through an alternative signaling pathway. Inhibition of luciferase activity demonstrates the functional blocking activity of antibodies in this system.

THP1 monocyte TREM1/DAP12 NF-κB Luciferase reporter cells were cultured in complete media containing selection antibiotics (RPMI+10% FBS+50 μM 2-mercaptoethanol+10 μg/ml blasticidin+1 μg/ml puromycin+200 μg/ml geneticin) using standard tissue culture techniques. Three days before assay set up, the cells were seeded at $10\times10^6$ cells in 50 ml complete media (200,000 cells/ml) in a T175 flask, placed flat in the incubator. On the day of the assay, the cells were removed from the flask and transferred to a 50 ml falcon and centrifuged at 300×g for five minutes. Media was removed and the cells were resuspended in 5-10 ml of complete media and counted. Cells were then resuspended at $1\times10^6$ cells/ml by adding cell suspension to complete media, and 10 μl/well was added to an assay plate (Corning #3570). Antibodies were serially diluted in complete media in a 384-well dilution plate (Greiner #781281). The serial dilution of antibodies was then transferred to the assay plate (10 μl/well) and the assay plate was incubated at 37° C./5% $CO_2$ for 1 hour. Recombinant human PGLYRP1 (R&D Systems #2590-PGB) was complexed with PGN (Invivogen #tlrl-ksspgn) for one hour at room temperature in sterile DPBS. After one hour, the solution was diluted in complete media, then transferred to the assay plate (10 μl/well) to a final assay concentration of 2.5 μg/ml PGLYRP1 and 10 μg/ml PGN. The plate controls (no antibody added) included PGLYRP1/PGN complex and PGN alone, as assay maximum and minimum values, respectively. The assay plate was then incubated at 37° C./5% $CO_2$ for 16 hours±2 hours. Following the incubation, luciferase activity was measured using the SteadyGlo Luciferase assay system (Promega #E2520). The SteadyGlo reagent was prepared according to the manufacturer's instructions and 30 μl/well was added to the assay plate. The plate was then centrifuged at 200×g for three minutes and then incubated at room temperature for a further two minutes so that the total incubation time with the SteadyGlo reagent was five minutes. Luminescence was then measured using a Synergy Neo 2 plate reader and the raw luminescence values were used to determine the relative percentage inhibition as compared to the control wells. 4 PL curve fitting and the calculation of $IC_{50}$ values was performed using ActivityBase v9.4.

Heavy and light chain variable region gene pairs from interesting TAP products were then cloned as rabbit IgG antibodies and re-expressed in a HEK-293 transient expression system. In total 144 V regions were cloned. Recombinant cloned antibodies were then retested for their ability to bind human and cynomolgus TREM1 by ELISA, binding in the BIAcore and inhibition of PGLYRP1+PGN-mediated signaling in the NF-κB luciferase reporter cell assay. Following characterization of the ligand binding site of known TREM1 ligand PGLYRP1 using a human TREM1 Alanine mutant array (the same approach as described further below for the TREM1-inhibiting antibodies), it was postulated that antibodies that bind to the same binding site regulate TREM1 function through direct ligand blocking. To identify alternative antibody binding sites on TREM1 which confer function, antibodies proven to inhibit TREM1 activity in the NF-κB luciferase reporter cell assay were assessed for epitope location using a human TREM1 Alanine mutant array.

Arrays of human TREM1 IgV domain mutant clones were produced. They consisted of either 58 clones each with three surface residues, in close proximity, mutated to alanine; 65 clones each with two surface residues, in close proximity, mutated to alanine; or 63 clones each with a single surface residue mutated to alanine. All arrays included the wild type human TREM1 clone. Sequences of the mutant human TREM1 array clones including the wild type are shown in Tables 8, 9, and 10.

TABLE 8

List of TREM1 protein sequences used to design the three-alanine mutant array

| ID | SEQ ID NO | TREM1 polypeptide sequence |
|---|---|---|
| 01_WT | 109 | MELRAATKLTEEKYELKEGQTLDVKCDYTLEKFASSQKAWQIIRDGEMPKTLACTERPSKNSHPV QVGRIILEDYHDHGLLRVRMVNLQVEDSGLYQCVIYQPPKEPHMLFDRIRLVVTLE |
| 02_6 | 110 | MELRAAAKLTEEKYELKEGQTLDVKCDYTLEKFASSQKAWQIIRDGEMPKTLACTERPSKNSHPV QVGRIILEDYHDHGLLRVRMVNLQVEDSGLYQCVIYQPPKEPHMLFDRIRLVVTLE |
| 03_6_7 | 111 | MELRAAAALTEEKYELKEGQTLDVKCDYTLEKFASSQKAWQIIRDGEMPKTLACTERPSKNSHPV QVGRIILEDYHDHGLLRVRMVNLQVEDSGLYQCVIYQPPKEPHMLFDRIRLVVTLE |
| 04_6_7_9 | 112 | MELRAAAALAEEKYELKEGQTLDVKCDYTLEKFASSQKAWQIIRDGEMPKTLACTERPSKNSHPV QVGRIILEDYHDHGLLRVRMVNLQVEDSGLYQCVIYQPPKEPHMLFDRIRLVVTLE |
| 05_7_8_9 | 113 | MELRAATAAAEEKYELKEGQTLDVKCDYTLEKFASSQKAWQIIRDGEMPKTLACTERPSKNSHPV QVGRIILEDYHDHGLLRVRMVNLQVEDSGLYQCVIYQPPKEPHMLFDRIRLVVTLE |
| 06_9_10_ 111 | 114 | MELRAATKLAAEKYELKEGQTLDVKCDYTLEKFASSQKAWQIIRDGEMPKTLACTERPSKNSHPV QVGRIILEDYHDHGLLRVRMVNLQVEDSGLYQCVIYQPPKEPHMLFARIRLVVTLE |
| 07_9_10_ 11 | 115 | MELRAATKLAAAKYELKEGQTLDVKCDYTLEKFASSQKAWQIIRDGEMPKTLACTERPSKNSHPV QVGRIILEDYHDHGLLRVRMVNLQVEDSGLYQCVIYQPPKEPHMLFDRIRLVVTLE |
| 08_10_11_ 12 | 116 | MELRAATKLTAAAYELKEGQTLDVKCDYTLEKFASSQKAWQIIRDGEMPKTLACTERPSKNSHPV QVGRIILEDYHDHGLLRVRMVNLQVEDSGLYQCVIYQPPKEPHMLFDRIRLVVTLE |
| 09_11_12_ 13 | 117 | MELRAATKLTEAAAELKEGQTLDVKCDYTLEKFASSQKAWQIIRDGEMPKTLACTERPSKNSHPV QVGRIILEDYHDHGLLRVRMVNLQVEDSGLYQCVIYQPPKEPHMLFDRIRLVVTLE |
| 10_16_118_ 119 | 118 | MELRAATKLTEEKYELAEGQTLDVKCDYTLEKFASSQKAWQIIRDGEMPKTLACTERPSKNSHPV QVGRIILEDYHDHGLLRVRMVNLQVEDSGLYQCVIYQPPKEPHMLFDRIRLVVAAE |
| 11_19_20_ 85 | 119 | MELRAATKLTEEKYELKEGAALDVKCDYTLEKFASSQKAWQIIRDGEMPKTLACTERPSKNSHPV QVGRIILEDYHDHGLLRVRMANLQVEDSGLYQCVIYQPPKEPHMLFDRIRLVVTLE |
| 12_22_24_ 26 | 120 | MELRAATKLTEEKYELKEGQTLAVACAYTLEKFASSQKAWQIIRDGEMPKTLACTERPSKNSHPV QVGRIILEDYHDHGLLRVRMVNLQVEDSGLYQCVIYQPPKEPHMLFDRIRLVVTLE |
| 13_24_26_ 28 | 121 | MELRAATKLTEEKYELKEGQTLDVACAYALEKFASSQKAWQIIRDGEMPKTLACTERPSKNSHPV QVGRIILEDYHDHGLLRVRMVNLQVEDSGLYQCVIYQPPKEPHMLFDRIRLVVTLE |
| 14_26_28_ 29 | 122 | MELRAATKLTEEKYELKEGQTLDVKCAYAAEKFASSQKAWQIIRDGEMPKTLACTERPSKNSHPV QVGRIILEDYHDHGLLRVRMVNLQVEDSGLYQCVIYQPPKEPHMLFDRIRLVVTLE |
| 15_28_29_ 30 | 123 | MELRAATKLTEEKYELKEGQTLDVKCDYAAAKFASSQKAWQIIRDGEMPKTLACTERPSKNSHPV QVGRIILEDYHDHGLLRVRMVNLQVEDSGLYQCVIYQPPKEPHMLFDRIRLVVTLE |
| 16_29_30_ 31 | 124 | MELRAATKLTEEKYELKEGQTLDVKCDYTAAAFASSQKAWQIIRDGEMPKTLACTERPSKNSHPV QVGRIILEDYHDHGLLRVRMVNLQVEDSGLYQCVIYQPPKEPHMLFDRIRLVVTLE |
| 17_31_32_ 35 | 125 | MELRAATKLTEEKYELKEGQTLDVKCDYTLEAAASAQKAWQIIRDGEMPKTLACTERPSKNSHPV QVGRIILEDYHDHGLLRVRMVNLQVEDSGLYQCVIYQPPKEPHMLFDRIRLVVTLE |
| 18_30_34_ | 126 | MELRAATKLTEEKYELKEGQTLDVKCDYTLAKFAASQKAWQIIRDGEMPKTLACTERPSKNSHPV QVGRIILEDYHDHGLLRVRMVNLQVEDSGLYQCVIYQPPKEPHMLFDRIRLVVTLE |
| 19_34_35_ 57 | 127 | MELRAATKLTEEKYELKEGQTLDVKCDYTLEKFAAAQKAWQIIRDGEMPKTLACTERASKNSHPV QVGRIILEDYHDHGLLRVRMVNLQVEDSGLYQCVIYQPPKEPHMLFDRIRLVVTLE |
| 20_35_36_ 56 | 128 | MELRAATKLTEEKYELKEGQTLDVKCDYTLEKFASAAKAWQIIRDGEMPKTLACTEAPSKNSHPV QVGRIILEDYHDHGLLRVRMVNLQVEDSGLYQCVIYQPPKEPHMLFDRIRLVVTLE |
| 21_40_49_ 50 | 129 | MELRAATKLTEEKYELKEGQTLDVKCDYTLEKFASSQKAWAIIRDGEMPAALACTERPSKNSHPV QVGRIILEDYHDHGLLRVRMVNLQVEDSGLYQCVIYQPPKEPHMLFDRIRLVVTLE |
| 22_43_44_ 47 | 130 | MELRAATKLTEEKYELKEGQTLDVKCDYTLEKFASSQKAWQIIAAGEAPKTLACTERPSKNSHPV QVGRIILEDYHDHGLLRVRMVNLQVEDSGLYQCVIYQPPKEPHMLFDRIRLVVTLE |
| 23_43_44_ 45 | 131 | MELRAATKLTEEKYELKEGQTLDVKCDYTLEKFASSQKAWQIIAAAEMPKTLACTERPSKNSHPV QVGRIILEDYHDHGLLRVRMVNLQVEDSGLYQCVIYQPPKEPHMLFDRIRLVVTLE |

TABLE 8-continued

List of TREM1 protein sequences used to design the three-alanine mutant array

| ID | SEQ ID NO | TREM1 polypeptide sequence |
|---|---|---|
| 24_44_45_46 | 132 | MELRAATKLTEEKYELKEGQTLDVKCDYTLEKFASSQKAWQIIRAAAMPKTLACTERPSKNSHPV QVGRIILEDYHDHGLLRVRMVNLQVEDSGLYQCVIYQPPKEPHMLFDRIRLVVTLE |
| 25_45_46_47 | 133 | MELRAATKLTEEKYELKEGQTLDVKCDYTLEKFASSQKAWQIIRDAAAPKTLACTERPSKNSHPV QVGRIILEDYHDHGLLRVRMVNLQVEDSGLYQCVIYQPPKEPHMLFDRIRLVVTLE |
| 26_43_46_47 | 134 | MELRAATKLTEEKYELKEGQTLDVKCDYTLEKFASSQKAWQIIADGAAPKTLACTERPSKNSHPV QVGRIILEDYHDHGLLRVRMVNLQVEDSGLYQCVIYQPPKEPHMLFDRIRLVVTLE |
| 27_47_48_49 | 135 | MELRAATKLTEEKYELKEGQTLDVKCDYTLEKFASSQKAWQIIRDGEAAATLACTERPSKNSHPV QVGRIILEDYHDHGLLRVRMVNLQVEDSGLYQCVIYQPPKEPHMLFDRIRLVVTLE |
| 28_47_49_50 | 136 | MELRAATKLTEEKYELKEGQTLDVKCDYTLEKFASSQKAWQIIRDGEAPAALACTERPSKNSHPV QVGRIILEDYHDHGLLRVRMVNLQVEDSGLYQCVIYQPPKEPHMLFDRIRLVVTLE |
| 29_49_50_53 | 137 | MELRAATKLTEEKYELKEGQTLDVKCDYTLEKFASSQKAWQIIRDGEMPAALAATERPSKNSHPV QVGRIILEDYHDHGLLRVRMVNLQVEDSGLYQCVIYQPPKEPHMLFDRIRLVVTLE |
| 30_50_53_55 | 138 | MELRAATKLTEEKYELKEGQTLDVKCDYTLEKFASSQKAWQIIRDGEMPKALAATARPSKNSHPV QVGRIILEDYHDHGLLRVRMVNLQVEDSGLYQCVIYQPPKEPHMLFDRIRLVVTLE |
| 31_55_56_57 | 139 | MELRAATKLTEEKYELKEGQTLDVKCDYTLEKFASSQKAWQIIRDGEMPKTLACTAAASKNSHPV QVGRIILEDYHDHGLLRVRMVNLQVEDSGLYQCVIYQPPKEPHMLFDRIRLVVTLE |
| 32_34_56_57 | 140 | MELRAATKLTEEKYELKEGQTLDVKCDYTLEKFAASQKAWQIIRDGEMPKTLACTEAASKNSHPV QVGRIILEDYHDHGLLRVRMVNLQVEDSGLYQCVIYQPPKEPHMLFDRIRLVVTLE |
| 33_57_59_60 | 141 | MELRAATKLTEEKYELKEGQTLDVKCDYTLEKFASSQKAWQIIRDGEMPKTLACTERASAASHPV QVGRIILEDYHDHGLLRVRMVNLQVEDSGLYQCVIYQPPKEPHMLFDRIRLVVTLE |
| 34_59_60_61 | 142 | MELRAATKLTEEKYELKEGQTLDVKCDYTLEKFASSQKAWQIIRDGEMPKTLACTERPSAAAHPV QVGRIILEDYHDHGLLRVRMVNLQVEDSGLYQCVIYQPPKEPHMLFDRIRLVVTLE |
| 35_60_61_62 | 143 | MELRAATKLTEEKYELKEGQTLDVKCDYTLEKFASSQKAWQIIRDGEMPKTLACTERPSKAAAPV QVGRIILEDYHDHGLLRVRMVNLQVEDSGLYQCVIYQPPKEPHMLFDRIRLVVTLE |
| 36_61_62_63 | 144 | MELRAATKLTEEKYELKEGQTLDVKCDYTLEKFASSQKAWQIIRDGEMPKTLACTERPSKNAAAV QVGRIILEDYHDHGLLRVRMVNLQVEDSGLYQCVIYQPPKEPHMLFDRIRLVVTLE |
| 37_62_63_64 | 145 | MELRAATKLTEEKYELKEGQTLDVKCDYTLEKFASSQKAWQIIRDGEMPKTLACTERPSKNSAAA QVGRIILEDYHDHGLLRVRMVNLQVEDSGLYQCVIYQPPKEPHMLFDRIRLVVTLE |
| 38_63_64_65 | 146 | MELRAATKLTEEKYELKEGQTLDVKCDYTLEKFASSQKAWQIIRDGEMPKTLACTERPSKNSHAA AVGRIILEDYHDHGLLRVRMVNLQVEDSGLYQCVIYQPPKEPHMLFDRIRLVVTLE |
| 39_64_65_66 | 147 | MELRAATKLTEEKYELKEGQTLDVKCDYTLEKFASSQKAWQIIRDGEMPKTLACTERPSKNSHPA AAGRIILEDYHDHGLLRVRMVNLQVEDSGLYQCVIYQPPKEPHMLFDRIRLVVTLE |
| 40_60_74_76 | 148 | MELRAATKLTEEKYELKEGQTLDVKCDYTLEKFASSQKAWQIIRDGEMPKTLACTERPSKASHPV QVGRIILEDAHAHGLLRVRMVNLQVEDSGLYQCVIYQPPKEPHMLFDRIRLVVTLE |
| 41_60_75_76 | 149 | MELRAATKLTEEKYELKEGQTLDVKCDYTLEKFASSQKAWQIIRDGEMPKTLACTERPSKASHPV QVGRIILEDYAAHGLLRVRMVNLQVEDSGLYQCVIYQPPKEPHMLFDRIRLVVTLE |
| 42_60_76_77 | 150 | MELRAATKLTEEKYELKEGQTLDVKCDYTLEKFASSQKAWQIIRDGEMPKTLACTERPSKASHPV QVGRIILEDYHAAGLLRVRMVNLQVEDSGLYQCVIYQPPKEPHMLFDRIRLVVTLE |
| 43_28_76_77 | 151 | MELRAATKLTEEKYELKEGQTLDVKCDYALEKFASSQKAWQIIRDGEMPKTLACTERPSKNSHPV QVGRIILEDYHAAGLLRVRMVNLQVEDSGLYQCVIYQPPKEPHMLFDRIRLVVTLE |
| 44_28_77_78 | 152 | MELRAATKLTEEKYELKEGQTLDVKCDYALEKFASSQKAWQIIRDGEMPKTLACTERPSKNSHPV QVGRIILEDYHDAALLRVRMVNLQVEDSGLYQCVIYQPPKEPHMLFDRIRLVVTLE |
| 45_96_109_111 | 153 | MELRAATKLTEEKYELKEGQTLDVKCDYTLEKFASSQKAWQIIRDGEMPKTLACTERPSKNSHPV QVGRIILEDYHDHGLLRVRMVNLQVEDSGLYACVIYQPPKEPHMAFARIRLVVTLE |
| 46_98_100_109 | 154 | MELRAATKLTEEKYELKEGQTLDVKCDYTLEKFASSQKAWQIIRDGEMPKTLACTERPSKNSHPV QVGRIILEDYHDHGLLRVRMVNLQVEDSGLYQCAIAQPPKEPHMAFDRIRLVVTLE |
| 47_35_100_102 | 155 | MELRAATKLTEEKYELKEGQTLDVKCDYTLEKFASAQKAWQIIRDGEMPKTLACTERPSKNSHPV QVGRIILEDYHDHGLLRVRMVNLQVEDSGLYQCVIAQAPKEPHMLFDRIRLVVTLE |
| 48_102_103_104 | 156 | MELRAATKLTEEKYELKEGQTLDVKCDYTLEKFASSQKAWQIIRDGEMPKTLACTERPSKNSHPV QVGRIILEDYHDHGLLRVRMVNLQVEDSGLYQCVIYQAAAEPHMLFDRIRLVVTLE |

TABLE 8-continued

List of TREM1 protein sequences used to design the three-alanine mutant array

| ID | SEQ ID NO | TREM1 polypeptide sequence |
|---|---|---|
| 49_103_104_105 | 157 | MELRAATKLTEEKYELKEGQTLDVKCDYTLEKFASSQKAWQIIRDGEMPKTLACTERPSKNSHPV QVGRIILEDYHDHGLLRVRMVNLQVEDSGLYQCVIYQPAAAPHMLFDRIRLVVTLE |
| 50_104_105_106 | 158 | MELRAATKLTEEKYELKEGQTLDVKCDYTLEKFASSQKAWQIIRDGEMPKTLACTERPSKNSHPV QVGRIILEDYHDHGLLRVRMVNLQVEDSGLYQCVIYQPPAAAHMLFDRIRLVVTLE |
| 51_105_106_107 | 159 | MELRAATKLTEEKYELKEGQTLDVKCDYTLEKFASSQKAWQIIRDGEMPKTLACTERPSKNSHPV QVGRIILEDYHDHGLLRVRMVNLQVEDSGLYQCVIYQPPKAAAMLFDRIRLVVTLE |
| 52_106_107_108 | 160 | MELRAATKLTEEKYELKEGQTLDVKCDYTLEKFASSQKAWQIIRDGEMPKTLACTERPSKNSHPV QVGRIILEDYHDHGLLRVRMVNLQVEDSGLYQCVIYQPPKEAAALFDRIRLVVTLE |
| 53_107_108_109 | 161 | MELRAATKLTEEKYELKEGQTLDVKCDYTLEKFASSQKAWQIIRDGEMPKTLACTERPSKNSHPV QVGRIILEDYHDHGLLRVRMVNLQVEDSGLYQCVIYQPPKEPAAAFDRIRLVVTLE |
| 54_109_110_111 | 162 | MELRAATKLTEEKYELKEGQTLDVKCDYTLEKFASSQKAWQIIRDGEMPKTLACTERPSKNSHPV QVGRIILEDYHDHGLLRVRMVNLQVEDSGLYQCVIYQPPKEPHMAAARIRLVVTLE |
| 55_11_113_114 | 163 | MELRAATKLTEAKYELKEGQTLDVKCDYTLEKFASSQKAWQIIRDGEMPKTLACTERPSKNSHPV QVGRIILEDYHDHGLLRVRMVNLQVEDSGLYQCVIYQPPKEPHMLFDRAALVVTLE |
| 56_10_12_114 | 164 | MELRAATKLTAEAYELKEGQTLDVKCDYTLEKFASSQKAWQIIRDGEMPKTLACTERPSKNSHPV QVGRIILEDYHDHGLLRVRMVNLQVEDSGLYQCVIYQPPKEPHMLFDRIALVVTLE |
| 57_118_119_120 | 165 | MELRAATKLTEEKYELKEGQTLDVKCDYTLEKFASSQKAWQIIRDGEMPKTLACTERPSKNSHPV QVGRIILEDYHDHGLLRVRMVNLQVEDSGLYQCVIYQPPKEPHMLFDRIRLVVAAA |
| 58_16_119_120 | 166 | MELRAATKLTEEKYELAEGQTLDVKCDYTLEKFASSQKAWQIIRDGEMPKTLACTERPSKNSHPV QVGRIILEDYHDHGLLRVRMVNLQVEDSGLYQCVIYQPPKEPHMLFDRIRLVVTAA |

TABLE 9

List of TREM1 protein sequences used to design the two-alanine mutant array

| ID | SEQ ID NO | TREM1 polypeptide sequence |
|---|---|---|
| 01_WT | 167 | AATKLTEEKYELKEGQTLDVKCDYTLEKFASSQKAWQIIRDGEMPKTLACTERPSKNSHPVQVGRI ILEDYHDHGLLRVRMVNLQVEDSGLYQCVIYQPPKEPHMLFDRIRLVVTKG |
| 02_2_3 | 168 | AAAALTEEKYELKEGQTLDVKCDYTLEKFASSQKAWQIIRDGEMPKTLACTERPSKNSHPVQVGRI ILEDYHDHGLLRVRMVNLQVEDSGLYQCVIYQPPKEPHMLFDRIRLVVTKG |
| 03_3_4 | 169 | AATAATEEKYELKEGQTLDVKCDYTLEKFASSQKAWQIIRDGEMPKTLACTERPSKNSHPVQVGRI ILEDYHDHGLLRVRMVNLQVEDSGLYQCVIYQPPKEPHMLFDRIRLVVTKG |
| 04_4_5 | 170 | AATKAAEEKYELKEGQTLDVKCDYTLEKFASSQKAWQIIRDGEMPKTLACTERPSKNSHPVQVGRI ILEDYHDHGLLRVRMVNLQVEDSGLYQCVIYQPPKEPHMLFDRIRLVVTKG |
| 05_5_104 | 171 | AATKLAEEKYELKEGQTLDVKCDYTLEKFASSQKAWQIIRDGEMPKTLACTERPSKNSHPVQVGRI ILEDYHDHGLLRVRMVNLQVEDSGLYQCVIYQPPKEPHALFDRIRLVVTKG |
| 06_5_106 | 172 | AATKLAEEKYELKEGQTLDVKCDYTLEKFASSQKAWQIIRDGEMPKTLACTERPSKNSHPVQVGRI ILEDYHDHGLLRVRMVNLQVEDSGLYQCVIYQPPKEPHMLADRIRLVVTKG |
| 07_5_107 | 173 | AATKLAEEKYELKEGQTLDVKCDYTLEKFASSQKAWQIIRDGEMPKTLACTERPSKNSHPVQVGRI ILEDYHDHGLLRVRMVNLQVEDSGLYQCVIYQPPKEPHMLFARIRLVVTKG |
| 08_7_9 | 174 | AATKLTEAKAELKEGQTLDVKCDYTLEKFASSQKAWQIIRDGEMPKTLACTERPSKNSHPVQVGRI ILEDYHDHGLLRVRMVNLQVEDSGLYQCVIYQPPKEPHMLFDRIRLVVTKG |
| 09_7_107 | 175 | AATKLTEAKYELKEGQTLDVKCDYTLEKFASSQKAWQIIRDGEMPKTLACTERPSKNSHPVQVGRI ILEDYHDHGLLRVRMVNLQVEDSGLYQCVIYQPPKEPHMLFARIRLVVTKG |
| 10_8_10 | 176 | AATKLTEEAYALKEGQTLDVKCDYTLEKFASSQKAWQIIRDGEMPKTLACTERPSKNSHPVQVGRI ILEDYHDHGLLRVRMVNLQVEDSGLYQCVIYQPPKEPHMLFDRIRLVVTKG |
| 11_11_12 | 177 | AATKLTEEKYEAAEGQTLDVKCDYTLEKFASSQKAWQIIRDGEMPKTLACTERPSKNSHPVQVGRI ILEDYHDHGLLRVRMVNLQVEDSGLYQCVIYQPPKEPHMLFDRIRLVVTKG |

TABLE 9-continued

List of TREM1 protein sequences used to design the two-alanine mutant array

| ID | SEQ ID NO | TREM1 polypeptide sequence |
|---|---|---|
| 12_12_13 | 178 | AATKLTEEKYELAAGQTLDVKCDYTLEKFASSQKAWQIIRDGEMPKTLACTERPSKNSHPVQVGRI ILEDYHDHGLLRVRMVNLQVEDSGLYQCVIYQPPKEPHMLFDRIRLVVTKG |
| 13_12_15 | 179 | AATKLTEEKYELAEGATLDVKCDYTLEKFASSQKAWQIIRDGEMPKTLACTERPSKNSHPVQVGRI ILEDYHDHGLLRVRMVNLQVEDSGLYQCVIYQPPKEPHMLFDRIRLVVTKG |
| 14_13_85 | 180 | AATKLTEEKYELKAGQTLDVKCDYTLEKFASSQKAWQIIRDGEMPKTLACTERPSKNSHPVQVGRI ILEDYHDHGLLRVRMVNLQAEDSGLYQCVIYQPPKEPHMLFDRIRLVVTKG |
| 15_16_81 | 181 | AATKLTEEKYELKEGQALDVKCDYTLEKFASSQKAWQIIRDGEMPKTLACTERPSKNSHPVQVGRI ILEDYHDHGLLRVRMANLQVEDSGLYQCVIYQPPKEPHMLFDRIRLVVTKG |
| 16_20_75 | 182 | AATKLTEEKYELKEGQTLDVACDYTLEKFASSQKAWQIIRDGEMPKTLACTERPSKNSHPVQVGRI ILEDYHDHGALRVRMVNLQVEDSGLYQCVIYQPPKEPHMLFDRIRLVVTKG |
| 17_24_25 | 183 | AATKLTEEKYELKEGQTLDVKCDYAAEKFASSQKAWQIIRDGEMPKTLACTERPSKNSHPVQVGRI ILEDYHDHGLLRVRMVNLQVEDSGLYQCVIYQPPKEPHMLFDRIRLVVTKG |
| 18_24_26 | 184 | AATKLTEEKYELKEGQTLDVKCDYALAKFASSQKAWQIIRDGEMPKTLACTERPSKNSHPVQVGRI ILEDYHDHGLLRVRMVNLQVEDSGLYQCVIYQPPKEPHMLFDRIRLVVTKG |
| 19_24_27 | 185 | AATKLTEEKYELKEGQTLDVKCDYALEAFASSQKAWQIIRDGEMPKTLACTERPSKNSHPVQVGRI ILEDYHDHGLLRVRMVNLQVEDSGLYQCVIYQPPKEPHMLFDRIRLVVTKG |
| 20_25_26 | 186 | AATKLTEEKYELKEGQTLDVKCDYTAAKFASSQKAWQIIRDGEMPKTLACTERPSKNSHPVQVGRI ILEDYHDHGLLRVRMVNLQVEDSGLYQCVIYQPPKEPHMLFDRIRLVVTKG |
| 21_26_27 | 187 | AATKLTEEKYELKEGQTLDVKCDYTLAAFASSQKAWQIIRDGEMPKTLACTERPSKNSHPVQVGRI ILEDYHDHGLLRVRMVNLQVEDSGLYQCVIYQPPKEPHMLFDRIRLVVTKG |
| 22_30_31 | 188 | AATKLTEEKYELKEGQTLDVKCDYTLEKFAAAQKAWQIIRDGEMPKTLACTERPSKNSHPVQVGRI ILEDYHDHGLLRVRMVNLQVEDSGLYQCVIYQPPKEPHMLFDRIRLVVTKG |
| 23_30_53 | 189 | AATKLTEEKYELKEGQTLDVKCDYTLEKFAASQKAWQIIRDGEMPKTLACTERASKNSHPVQVGRI ILEDYHDHGLLRVRMVNLQVEDSGLYQCVIYQPPKEPHMLFDRIRLVVTKG |
| 24_37_38 | 190 | AATKLTEEKYELKEGQTLDVKCDYTLEKFASSQKAWQAARDGEMPKTLACTERPSKNSHPVQVGRI ILEDYHDHGLLRVRMVNLQVEDSGLYQCVIYQPPKEPHMLFDRIRLVVTKG |
| 25_37_39 | 191 | AATKLTEEKYELKEGQTLDVKCDYTLEKFASSQKAWQAIADGEMPKTLACTERPSKNSHPVQVGRI ILEDYHDHGLLRVRMVNLQVEDSGLYQCVIYQPPKEPHMLFDRIRLVVTKG |
| 26_37_45 | 192 | AATKLTEEKYELKEGQTLDVKCDYTLEKFASSQKAWQAIRDGEMPATLACTERPSKNSHPVQVGRI ILEDYHDHGLLRVRMVNLQVEDSGLYQCVIYQPPKEPHMLFDRIRLVVTKG |
| 27_37_47 | 193 | AATKLTEEKYELKEGQTLDVKCDYTLEKFASSQKAWQAIRDGEMPKTAACTERPSKNSHPVQVGRI ILEDYHDHGLLRVRMVNLQVEDSGLYQCVIYQPPKEPHMLFDRIRLVVTKG |
| 28_38_44 | 194 | AATKLTEEKYELKEGQTLDVKCDYTLEKFASSQKAWQIARDGEMAKTLACTERPSKNSHPVQVGRI ILEDYHDHGLLRVRMVNLQVEDSGLYQCVIYQPPKEPHMLFDRIRLVVTKG |
| 29_38_90 | 195 | AATKLTEEKYELKEGQTLDVKCDYTLEKFASSQKAWQIARDGEMPKTLACTERPSKNSHPVQVGRI ILEDYHDHGLLRVRMVNLQVEDSGAYQCVIYQPPKEPHMLFDRIRLVVTKG |
| 30_42_43 | 196 | AATKLTEEKYELKEGQTLDVKCDYTLEKFASSQKAWQIIRDGAAPKTLACTERPSKNSHPVQVGRI ILEDYHDHGLLRVRMVNLQVEDSGLYQCVIYQPPKEPHMLFDRIRLVVTKG |
| 31_42_45 | 197 | AATKLTEEKYELKEGQTLDVKCDYTLEKFASSQKAWQIIRDGAMPATLACTERPSKNSHPVQVGRI ILEDYHDHGLLRVRMVNLQVEDSGLYQCVIYQPPKEPHMLFDRIRLVVTKG |
| 32_43_44 | 198 | AATKLTEEKYELKEGQTLDVKCDYTLEKFASSQKAWQIIRDGEAAKTLACTERPSKNSHPVQVGRI ILEDYHDHGLLRVRMVNLQVEDSGLYQCVIYQPPKEPHMLFDRIRLVVTKG |
| 33_43_10 | 199 | AATKLTEEKYELKEGQTLDVKCDYTLEKFASSQKAWQIIRDGEAPKTLACTERPSKNSHPVQVGRI ILEDYHDHGLLRVRMVNLQVEDSGLYQCVIYQPPKAPHMLFDRIRLVVTKG |
| 34_44_45 | 200 | AATKLTEEKYELKEGQTLDVKCDYTLEKFASSQKAWQIIRDGEMAATLACTERPSKNSHPVQVGRI ILEDYHDHGLLRVRMVNLQVEDSGLYQCVIYQPPKEPHMLFDRIRLVVTKG |
| 35_45_47 | 201 | AATKLTEEKYELKEGQTLDVKCDYTLEKFASSQKAWQIIRDGEMPATAACTERPSKNSHPVQVGRI ILEDYHDHGLLRVRMVNLQVEDSGLYQCVIYQPPKEPHMLFDRIRLVVTKG |

TABLE 9-continued

List of TREM1 protein sequences used to design the two-alanine mutant array

| ID | SEQ ID NO | TREM1 polypeptide sequence |
| --- | --- | --- |
| 36_47_65 | 202 | AATKLTEEKYELKEGQTLDVKCDYTLEKFASSQKAWQIIRDGEMPKTAACTERPSKNSHPVQVGRA ILEDYHDHGLLRVRMVNLQVEDSGLYQCVIYQPPKEPHMLFDRIRLVVTKG |
| 37_51_55 | 203 | AATKLTEEKYELKEGQTLDVKCDYTLEKFASSQKAWQIIRDGEMPKTLACTARPSANSHPVQVGRI ILEDYHDHGLLRVRMVNLQVEDSGLYQCVIYQPPKEPHMLFDRIRLVVTKG |
| 38_56_57 | 204 | AATKLTEEKYELKEGQTLDVKCDYTLEKFASSQKAWQIIRDGEMPKTLACTERPSKAAHPVQVGRI ILEDYHDHGLLRVRMVNLQVEDSGLYQCVIYQPPKEPHMLFDRIRLVVTKG |
| 39_58_59 | 205 | AATKLTEEKYELKEGQTLDVKCDYTLEKFASSQKAWQIIRDGEMPKTLACTERPSKNSAAVQVGRI ILEDYHDHGLLRVRMVNLQVEDSGLYQCVIYQPPKEPHMLFDRIRLVVTKG |
| 40_59_60 | 206 | AATKLTEEKYELKEGQTLDVKCDYTLEKFASSQKAWQIIRDGEMPKTLACTERPSKNSHAAQVGRI ILEDYHDHGLLRVRMVNLQVEDSGLYQCVIYQPPKEPHMLFDRIRLVVTKG |
| 41_59_61 | 207 | AATKLTEEKYELKEGQTLDVKCDYTLEKFASSQKAWQIIRDGEMPKTLACTERPSKNSHAVAVGRI ILEDYHDHGLLRVRMVNLQVEDSGLYQCVIYQPPKEPHMLFDRIRLVVTKG |
| 42_59_66 | 208 | AATKLTEEKYELKEGQTLDVKCDYTLEKFASSQKAWQIIRDGEMPKTLACTERPSKNSHAVQVGRI ALEDYHDHGLLRVRMVNLQVEDSGLYQCVIYQPPKEPHMLFDRIRLVVTKG |
| 43_60_61 | 209 | AATKLTEEKYELKEGQTLDVKCDYTLEKFASSQKAWQIIRDGEMPKTLACTERPSKNSHPAAVGRI ILEDYHDHGLLRVRMVNLQVEDSGLYQCVIYQPPKEPHMLFDRIRLVVTKG |
| 44_60_62 | 210 | AATKLTEEKYELKEGQTLDVKCDYTLEKFASSQKAWQIIRDGEMPKTLACTERPSKNSHPAQAGRI ILEDYHDHGLLRVRMVNLQVEDSGLYQCVIYQPPKEPHMLFDRIRLVVTKG |
| 45_61_62 | 211 | AATKLTEEKYELKEGQTLDVKCDYTLEKFASSQKAWQIIRDGEMPKTLACTERPSKNSHPVAAGRI ILEDYHDHGLLRVRMVNLQVEDSGLYQCVIYQPPKEPHMLFDRIRLVVTKG |
| 46_61_66 | 212 | AATKLTEEKYELKEGQTLDVKCDYTLEKFASSQKAWQIIRDGEMPKTLACTERPSKNSHPVAVGRI ALEDYHDHGLLRVRMVNLQVEDSGLYQCVIYQPPKEPHMLFDRIRLVVTKG |
| 47_62_65 | 213 | AATKLTEEKYELKEGQTLDVKCDYTLEKFASSQKAWQIIRDGEMPKTLACTERPSKNSHPVQAGRA ILEDYHDHGLLRVRMVNLQVEDSGLYQCVIYQPPKEPHMLFDRIRLVVTKG |
| 48_65_66 | 214 | AATKLTEEKYELKEGQTLDVKCDYTLEKFASSQKAWQIIRDGEMPKTLACTERPSKNSHPVQVGRA ALEDYHDHGLLRVRMVNLQVEDSGLYQCVIYQPPKEPHMLFDRIRLVVTKG |
| 49_66_81 | 215 | AATKLTEEKYELKEGQTLDVKCDYTLEKFASSQKAWQIIRDGEMPKTLACTERPSKNSHPVQVGRI ALEDYHDHGLLRVRMANLQVEDSGLYQCVIYQPPKEPHMLFDRIRLVVTKG |
| 50_72_73 | 216 | AATKLTEEKYELKEGQTLDVKCDYTLEKFASSQKAWQIIRDGEMPKTLACTERPSKNSHPVQVGRI ILEDYHAAGLLRVRMVNLQVEDSGLYQCVIYQPPKEPHMLFDRIRLVVTKG |
| 51_73_75 | 217 | AATKLTEEKYELKEGQTLDVKCDYTLEKFASSQKAWQIIRDGEMPKTLACTERPSKNSHPVQVGRI ILEDYHDAGALRVRMVNLQVEDSGLYQCVIYQPPKEPHMLFDRIRLVVTKG |
| 52_81_82 | 218 | AATKLTEEKYELKEGQTLDVKCDYTLEKFASSQKAWQIIRDGEMPKTLACTERPSKNSHPVQVGRI ILEDYHDHGLLRVRMAALQVEDSGLYQCVIYQPPKEPHMLFDRIRLVVTKG |
| 53_85_86 | 219 | AATKLTEEKYELKEGQTLDVKCDYTLEKFASSQKAWQIIRDGEMPKTLACTERPSKNSHPVQVGRI ILEDYHDHGLLRVRMVNLQAADSGLYQCVIYQPPKEPHMLFDRIRLVVTKG |
| 54_98_99 | 220 | AATKLTEEKYELKEGQTLDVKCDYTLEKFASSQKAWQIIRDGEMPKTLACTERPSKNSHPVQVGRI ILEDYHDHGLLRVRMVNLQVEDSGLYQCVIYQAAKEPHMLFDRIRLVVTKG |
| 55_99_100 | 221 | AATKLTEEKYELKEGQTLDVKCDYTLEKFASSQKAWQIIRDGEMPKTLACTERPSKNSHPVQVGRI ILEDYHDHGLLRVRMVNLQVEDSGLYQCVIYQPAAEPHMLFDRIRLVVTKG |
| 56_100_101 | 222 | AATKLTEEKYELKEGQTLDVKCDYTLEKFASSQKAWQIIRDGEMPKTLACTERPSKNSHPVQVGRI ILEDYHDHGLLRVRMVNLQVEDSGLYQCVIYQPPAAPHMLFDRIRLVVTKG |
| 57_101_102 | 223 | AATKLTEEKYELKEGQTLDVKCDYTLEKFASSQKAWQIIRDGEMPKTLACTERPSKNSHPVQVGRI ILEDYHDHGLLRVRMVNLQVEDSGLYQCVIYQPPKAAHMLFDRIRLVVTKG |
| 58_102_103 | 224 | AATKLTEEKYELKEGQTLDVKCDYTLEKFASSQKAWQIIRDGEMPKTLACTERPSKNSHPVQVGRI ILEDYHDHGLLRVRMVNLQVEDSGLYQCVIYQPPKEAAMLFDRIRLVVTKG |
| 59_103_104 | 225 | AATKLTEEKYELKEGQTLDVKCDYTLEKFASSQKAWQIIRDGEMPKTLACTERPSKNSHPVQVGRI ILEDYHDHGLLRVRMVNLQVEDSGLYQCVIYQPPKEPAALFDRIRLVVTKG |

TABLE 9-continued

List of TREM1 protein sequences used to design the two-alanine mutant array

| ID | SEQ ID NO | TREM1 polypeptide sequence |
|---|---|---|
| 60_104_106 | 226 | AATKLTEEKYELKEGQTLDVKCDYTLEKFASSQKAWQIIRDGEMPKTLACTERPSKNSHPVQVGRI ILEDYHDHGLLRVRMVNLQVEDSGLYQCVIYQPPKEPHALADRIRLVVTKG |
| 61_106_107 | 227 | AATKLTEEKYELKEGQTLDVKCDYTLEKFASSQKAWQIIRDGEMPKTLACTERPSKNSHPVQVGRI ILEDYHDHGLLRVRMVNLQVEDSGLYQCVIYQPPKEPHMLAARIRLVVTKG |
| 62_8_10_112 | 228 | AATKLTEEAYALKEGQTLDVKCDYTLEKFASSQKAWQIIRDGEMPKTLACTERPSKNSHPVQVGRI ILEDYHDHGLLRVRMVNLQVEDSGLYQCVIYQPPKEPHMLFDRIRLAVTKG |
| 63_37_39_40 | 229 | AATKLTEEKYELKEGQTLDVKCDYTLEKFASSQKAWQAIAAGEMPKTLACTERPSKNSHPVQVGRI ILEDYHDHGLLRVRMVNLQVEDSGLYQCVIYQPPKEPHMLFDRIRLVVTKG |
| 64_40 | 230 | AATKLTEEKYELKEGQTLDVKCDYTLEKFASSQKAWQIIRAGEMPKTLACTERPSKNSHPVQVGRI ILEDYHDHGLLRVRMVNLQVEDSGLYQCVIYQPPKEPHMLFDRIRLVVTKG |
| 112 | 231 | AATKLTEEKYELKEGQTLDVKCDYTLEKFASSQKAWQIIRDGEMPKTLACTERPSKNSHPVQVGRI ILEDYHDHGLLRVRMVNLQVEDSGLYQCVIYQPPKEPHMLFDRIRLAVTKG |

TABLE 10

List of TREM1 protein sequences used to design the single-alanine mutant array

| ID | SEQ ID NO | TREM1 polypeptide sequence |
|---|---|---|
| 01_WT | 232 | ATKLTEEKYELKEGQTLDVKCDYTLEKFASSQKAWQIIRDGEMPKTLACTERPSKNSHPVQVGRII LEDYHDHGLLRVRMVNLQVEDSGLYQCVIYQPPKEPHMLFDRIRLVVTLE |
| 02_1 | 233 | AAKLTEEKYELKEGQTLDVKCDYTLEKFASSQKAWQIIRDGEMPKTLACTERPSKNSHPVQVGRII LEDYHDHGLLRVRMVNLQVEDSGLYQCVIYQPPKEPHMLFDRIRLVVTLE |
| 03_2 | 234 | ATALTEEKYELKEGQTLDVKCDYTLEKFASSQKAWQIIRDGEMPKTLACTERPSKNSHPVQVGRII LEDYHDHGLLRVRMVNLQVEDSGLYQCVIYQPPKEPHMLFDRIRLVVTLE |
| 04_4 | 235 | ATKLAEEKYELKEGQTLDVKCDYTLEKFASSQKAWQIIRDGEMPKTLACTERPSKNSHPVQVGRII LEDYHDHGLLRVRMVNLQVEDSGLYQCVIYQPPKEPHMLFDRIRLVVTLE |
| 05_5 | 236 | ATKLTAEKYELKEGQTLDVKCDYTLEKFASSQKAWQIIRDGEMPKTLACTERPSKNSHPVQVGRII LEDYHDHGLLRVRMVNLQVEDSGLYQCVIYQPPKEPHMLFDRIRLVVTLE |
| 06_6 | 237 | ATKLTEAKYELKEGQTLDVKCDYTLEKFASSQKAWQIIRDGEMPKTLACTERPSKNSHPVQVGRII LEDYHDHGLLRVRMVNLQVEDSGLYQCVIYQPPKEPHMLFDRIRLVVTLE |
| 07_7 | 238 | ATKLTEEAYELKEGQTLDVKCDYTLEKFASSQKAWQIIRDGEMPKTLACTERPSKNSHPVQVGRII LEDYHDHGLLRVRMVNLQVEDSGLYQCVIYQPPKEPHMLFDRIRLVVTLE |
| 08_8 | 239 | ATKLTEEKAELKEGQTLDVKCDYTLEKFASSQKAWQIIRDGEMPKTLACTERPSKNSHPVQVGRII LEDYHDHGLLRVRMVNLQVEDSGLYQCVIYQPPKEPHMLFDRIRLVVTLE |
| 09_9 | 240 | ATKLTEEKYALKEGQTLDVKCDYTLEKFASSQKAWQIIRDGEMPKTLACTERPSKNSHPVQVGRII LEDYHDHGLLRVRMVNLQVEDSGLYQCVIYQPPKEPHMLFDRIRLVVTLE |
| 10_11 | 241 | ATKLTEEKYELAEGQTLDVKCDYTLEKFASSQKAWQIIRDGEMPKTLACTERPSKNSHPVQVGRII LEDYHDHGLLRVRMVNLQVEDSGLYQCVIYQPPKEPHMLFDRIRLVVTLE |
| 11_14 | 242 | ATKLTEEKYELKEGATLDVKCDYTLEKFASSQKAWQIIRDGEMPKTLACTERPSKNSHPVQVGRII LEDYHDHGLLRVRMVNLQVEDSGLYQCVIYQPPKEPHMLFDRIRLVVTLE |
| 12_17 | 243 | ATKLTEEKYELKEGQTLAVKCDYTLEKFASSQKAWQIIRDGEMPKTLACTERPSKNSHPVQVGRII LEDYHDHGLLRVRMVNLQVEDSGLYQCVIYQPPKEPHMLFDRIRLVVTLE |
| 13_19 | 244 | ATKLTEEKYELKEGQTLDVACDYTLEKFASSQKAWQIIRDGEMPKTLACTERPSKNSHPVQVGRII LEDYHDHGLLRVRMVNLQVEDSGLYQCVIYQPPKEPHMLFDRIRLVVTLE |
| 14_21 | 245 | ATKLTEEKYELKEGQTLDVKCAYTLEKFASSQKAWQIIRDGEMPKTLACTERPSKNSHPVQVGRII LEDYHDHGLLRVRMVNLQVEDSGLYQCVIYQPPKEPHMLFDRIRLVVTLE |
| 15_23 | 246 | ATKLTEEKYELKEGQTLDVKCDYALEKFASSQKAWQIIRDGEMPKTLACTERPSKNSHPVQVGRII LEDYHDHGLLRVRMVNLQVEDSGLYQCVIYQPPKEPHMLFDRIRLVVTLE |

TABLE 10-continued

List of TREM1 protein sequences used to design the single-alanine mutant array

| ID | SEQ ID NO | TREM1 polypeptide sequence |
|---|---|---|
| 16_24 | 247 | ATKLTEEKYELKEGQTLDVKCDYTAEKFASSQKAWQIIRDGEMPKTLACTERPSKNSHPVQVGRII LEDYHDHGLLRVRMVNLQVEDSGLYQCVIYQPPKEPHMLFDRIRLVVTLE |
| 17_25 | 248 | ATKLTEEKYELKEGQTLDVKCDYTLAKFASSQKAWQIIRDGEMPKTLACTERPSKNSHPVQVGRII LEDYHDHGLLRVRMVNLQVEDSGLYQCVIYQPPKEPHMLFDRIRLVVTLE |
| 18_26 | 249 | ATKLTEEKYELKEGQTLDVKCDYTLEAFASSQKAWQIIRDGEMPKTLACTERPSKNSHPVQVGRII LEDYHDHGLLRVRMVNLQVEDSGLYQCVIYQPPKEPHMLFDRIRLVVTLE |
| 19_29 | 250 | ATKLTEEKYELKEGQTLDVKCDYTLEKFAASQKAWQIIRDGEMPKTLACTERPSKNSHPVQVGRII LEDYHDHGLLRVRMVNLQVEDSGLYQCVIYQPPKEPHMLFDRIRLVVTLE |
| 20_30 | 251 | ATKLTEEKYELKEGQTLDVKCDYTLEKFASAQKAWQIIRDGEMPKTLACTERPSKNSHPVQVGRII LEDYHDHGLLRVRMVNLQVEDSGLYQCVIYQPPKEPHMLFDRIRLVVTLE |
| 21_38 | 252 | ATKLTEEKYELKEGQTLDVKCDYTLEKFASSQKAWQIIADGEMPKTLACTERPSKNSHPVQVGRII LEDYHDHGLLRVRMVNLQVEDSGLYQCVIYQPPKEPHMLFDRIRLVVTLE |
| 22_39 | 253 | ATKLTEEKYELKEGQTLDVKCDYTLEKFASSQKAWQIIRAGEMPKTLACTERPSKNSHPVQVGRII LEDYHDHGLLRVRMVNLQVEDSGLYQCVIYQPPKEPHMLFDRIRLVVTLE |
| 23_41 | 254 | ATKLTEEKYELKEGQTLDVKCDYTLEKFASSQKAWQIIRDGAMPKTLACTERPSKNSHPVQVGRII LEDYHDHGLLRVRMVNLQVEDSGLYQCVIYQPPKEPHMLFDRIRLVVTLE |
| 24_42 | 255 | ATKLTEEKYELKEGQTLDVKCDYTLEKFASSQKAWQIIRDGEAPKTLACTERPSKNSHPVQVGRII LEDYHDHGLLRVRMVNLQVEDSGLYQCVIYQPPKEPHMLFDRIRLVVTLE |
| 25_44 | 256 | ATKLTEEKYELKEGQTLDVKCDYTLEKFASSQKAWQIIRDGEMPATLACTERPSKNSHPVQVGRII LEDYHDHGLLRVRMVNLQVEDSGLYQCVIYQPPKEPHMLFDRIRLVVTLE |
| 26_45 | 257 | ATKLTEEKYELKEGQTLDVKCDYTLEKFASSQKAWQIIRDGEMPKALACTERPSKNSHPVQVGRII LEDYHDHGLLRVRMVNLQVEDSGLYQCVIYQPPKEPHMLFDRIRLVVTLE |
| 27_50 | 258 | ATKLTEEKYELKEGQTLDVKCDYTLEKFASSQKAWQIIRDGEMPKTLACTARPSKNSHPVQVGRII LEDYHDHGLLRVRMVNLQVEDSGLYQCVIYQPPKEPHMLFDRIRLVVTLE |
| 28_51 | 259 | ATKLTEEKYELKEGQTLDVKCDYTLEKFASSQKAWQIIRDGEMPKTLACTEAPSKNSHPVQVGRII LEDYHDHGLLRVRMVNLQVEDSGLYQCVIYQPPKEPHMLFDRIRLVVTLE |
| 29_52 | 260 | ATKLTEEKYELKEGQTLDVKCDYTLEKFASSQKAWQIIRDGEMPKTLACTERASKNSHPVQVGRII LEDYHDHGLLRVRMVNLQVEDSGLYQCVIYQPPKEPHMLFDRIRLVVTLE |
| 30_54 | 261 | ATKLTEEKYELKEGQTLDVKCDYTLEKFASSQKAWQIIRDGEMPKTLACTERPSANSHPVQVGRII LEDYHDHGLLRVRMVNLQVEDSGLYQCVIYQPPKEPHMLFDRIRLVVTLE |
| 31_55 | 262 | ATKLTEEKYELKEGQTLDVKCDYTLEKFASSQKAWQIIRDGEMPKTLACTERPSKASHPVQVGRII LEDYHDHGLLRVRMVNLQVEDSGLYQCVIYQPPKEPHMLFDRIRLVVTLE |
| 32_56 | 263 | ATKLTEEKYELKEGQTLDVKCDYTLEKFASSQKAWQIIRDGEMPKTLACTERPSKNAHPVQVGRII LEDYHDHGLLRVRMVNLQVEDSGLYQCVIYQPPKEPHMLFDRIRLVVTLE |
| 33_57 | 264 | ATKLTEEKYELKEGQTLDVKCDYTLEKFASSQKAWQIIRDGEMPKTLACTERPSKNSAPVQVGRII LEDYHDHGLLRVRMVNLQVEDSGLYQCVIYQPPKEPHMLFDRIRLVVTLE |
| 34_58 | 265 | ATKLTEEKYELKEGQTLDVKCDYTLEKFASSQKAWQIIRDGEMPKTLACTERPSKNSHAVQVGRII LEDYHDHGLLRVRMVNLQVEDSGLYQCVIYQPPKEPHMLFDRIRLVVTLE |
| 35_59 | 266 | ATKLTEEKYELKEGQTLDVKCDYTLEKFASSQKAWQIIRDGEMPKTLACTERPSKNSHPAQVGRII LEDYHDHGLLRVRMVNLQVEDSGLYQCVIYQPPKEPHMLFDRIRLVVTLE |
| 36_60 | 267 | ATKLTEEKYELKEGQTLDVKCDYTLEKFASSQKAWQIIRDGEMPKTLACTERPSKNSHPVAVGRII LEDYHDHGLLRVRMVNLQVEDSGLYQCVIYQPPKEPHMLFDRIRLVVTLE |
| 37_61 | 268 | ATKLTEEKYELKEGQTLDVKCDYTLEKFASSQKAWQIIRDGEMPKTLACTERPSKNSHPVQAGRII LEDYHDHGLLRVRMVNLQVEDSGLYQCVIYQPPKEPHMLFDRIRLVVTLE |
| 38_63 | 269 | ATKLTEEKYELKEGQTLDVKCDYTLEKFASSQKAWQIIRDGEMPKTLACTERPSKNSHPVQVGAII LEDYHDHGLLRVRMVNLQVEDSGLYQCVIYQPPKEPHMLFDRIRLVVTLE |
| 39_65 | 270 | ATKLTEEKYELKEGQTLDVKCDYTLEKFASSQKAWQIIRDGEMPKTLACTERPSKNSHPVQVGRIA LEDYHDHGLLRVRMVNLQVEDSGLYQCVIYQPPKEPHMLFDRIRLVVTLE |
| 40_71 | 271 | ATKLTEEKYELKEGQTLDVKCDYTLEKFASSQKAWQIIRDGEMPKTLACTERPSKNSHPVQVGRII LEDYHAHGLLRVRMVNLQVEDSGLYQCVIYQPPKEPHMLFDRIRLVVTLE |

TABLE 10-continued

List of TREM1 protein sequences used to design the single-alanine mutant array

| ID | SEQ ID NO | TREM1 polypeptide sequence |
|---|---|---|
| 41_72 | 272 | ATKLTEEKYELKEGQTLDVKCDYTLEKFASSQKAWQIIRDGEMPKTLACTERPSKNSHPVQVGRII LEDYHDAGLLRVRMVNLQVEDSGLYQCVIYQPPKEPHMLFDRIRLVVTLE |
| 42_78 | 273 | ATKLTEEKYELKEGQTLDVKCDYTLEKFASSQKAWQIIRDGEMPKTLACTERPSKNSHPVQVGRII LEDYHDHGLLRVAMVNLQVEDSGLYQCVIYQPPKEPHMLFDRIRLVVTLE |
| 43_80 | 274 | ATKLTEEKYELKEGQTLDVKCDYTLEKFASSQKAWQIIRDGEMPKTLACTERPSKNSHPVQVGRII LEDYHDHGLLRVRMANLQVEDSGLYQCVIYQPPKEPHMLFDRIRLVVTLE |
| 44_81 | 275 | ATKLTEEKYELKEGQTLDVKCDYTLEKFASSQKAWQIIRDGEMPKTLACTERPSKNSHPVQVGRII LEDYHDHGLLRVRMVALQVEDSGLYQCVIYQPPKEPHMLFDRIRLVVTLE |
| 45_83 | 276 | ATKLTEEKYELKEGQTLDVKCDYTLEKFASSQKAWQIIRDGEMPKTLACTERPSKNSHPVQVGRII LEDYHDHGLLRVRMVNLAVEDSGLYQCVIYQPPKEPHMLFDRIRLVVTLE |
| 46_84 | 277 | ATKLTEEKYELKEGQTLDVKCDYTLEKFASSQKAWQIIRDGEMPKTLACTERPSKNSHPVQVGRII LEDYHDHGLLRVRMVNLQAEDSGLYQCVIYQPPKEPHMLFDRIRLVVTLE |
| 47_85 | 278 | ATKLTEEKYELKEGQTLDVKCDYTLEKFASSQKAWQIIRDGEMPKTLACTERPSKNSHPVQVGRII LEDYHDHGLLRVRMVNLQVADSGLYQCVIYQPPKEPHMLFDRIRLVVTLE |
| 48_87 | 279 | ATKLTEEKYELKEGQTLDVKCDYTLEKFASSQKAWQIIRDGEMPKTLACTERPSKNSHPVQVGRII LEDYHDHGLLRVRMVNLQVEDAGLYQCVIYQPPKEPHMLFDRIRLVVTLE |
| 49_95 | 280 | ATKLTEEKYELKEGQTLDVKCDYTLEKFASSQKAWQIIRDGEMPKTLACTERPSKNSHPVQVGRII LEDYHDHGLLRVRMVNLQVEDSGLYQCVIAQPPKEPHMLFDRIRLVVTLE |
| 50_97 | 281 | ATKLTEEKYELKEGQTLDVKCDYTLEKFASSQKAWQIIRDGEMPKTLACTERPSKNSHPVQVGRII LEDYHDHGLLRVRMVNLQVEDSGLYQCVIYQAPKEPHMLFDRIRLVVTLE |
| 51_98 | 282 | ATKLTEEKYELKEGQTLDVKCDYTLEKFASSQKAWQIIRDGEMPKTLACTERPSKNSHPVQVGRII LEDYHDHGLLRVRMVNLQVEDSGLYQCVIYQPAKEPHMLFDRIRLVVTLE |
| 52_99 | 283 | ATKLTEEKYELKEGQTLDVKCDYTLEKFASSQKAWQIIRDGEMPKTLACTERPSKNSHPVQVGRII LEDYHDHGLLRVRMVNLQVEDSGLYQCVIYQPPAEPHMLFDRIRLVVTLE |
| 53_100 | 284 | ATKLTEEKYELKEGQTLDVKCDYTLEKFASSQKAWQIIRDGEMPKTLACTERPSKNSHPVQVGRII LEDYHDHGLLRVRMVNLQVEDSGLYQCVIYQPPKAPHMLFDRIRLVVTLE |
| 54_101 | 285 | ATKLTEEKYELKEGQTLDVKCDYTLEKFASSQKAWQIIRDGEMPKTLACTERPSKNSHPVQVGRII LEDYHDHGLLRVRMVNLQVEDSGLYQCVIYQPPKEAHMLFDRIRLVVTLE |
| 55_102 | 286 | ATKLTEEKYELKEGQTLDVKCDYTLEKFASSQKAWQIIRDGEMPKTLACTERPSKNSHPVQVGRII LEDYHDHGLLRVRMVNLQVEDSGLYQCVIYQPPKEPAMLFDRIRLVVTLE |
| 56_103 | 287 | ATKLTEEKYELKEGQTLDVKCDYTLEKFASSQKAWQIIRDGEMPKTLACTERPSKNSHPVQVGRII LEDYHDHGLLRVRMVNLQVEDSGLYQCVIYQPPKEPHALFDRIRLVVTLE |
| 57_104 | 288 | ATKLTEEKYELKEGQTLDVKCDYTLEKFASSQKAWQIIRDGEMPKTLACTERPSKNSHPVQVGRII LEDYHDHGLLRVRMVNLQVEDSGLYQCVIYQPPKEPHMAFDRIRLVVTLE |
| 58_106 | 289 | ATKLTEEKYELKEGQTLDVKCDYTLEKFASSQKAWQIIRDGEMPKTLACTERPSKNSHPVQVGRII LEDYHDHGLLRVRMVNLQVEDSGLYQCVIYQPPKEPHMLFARIRLVVTLE |
| 59_109 | 290 | ATKLTEEKYELKEGQTLDVKCDYTLEKFASSQKAWQIIRDGEMPKTLACTERPSKNSHPVQVGRII LEDYHDHGLLRVRMVNLQVEDSGLYQCVIYQPPKEPHMLFDRIALVVTLE |
| 60_111 | 291 | ATKLTEEKYELKEGQTLDVKCDYTLEKFASSQKAWQIIRDGEMPKTLACTERPSKNSHPVQVGRII LEDYHDHGLLRVRMVNLQVEDSGLYQCVIYQPPKEPHMLFDRIRLAVTLE |
| 61_113 | 292 | ATKLTEEKYELKEGQTLDVKCDYTLEKFASSQKAWQIIRDGEMPKTLACTERPSKNSHPVQVGRII LEDYHDHGLLRVRMVNLQVEDSGLYQCVIYQPPKEPHMLFDRIRLVVALE |
| 62_114 | 293 | ATKLTEEKYELKEGQTLDVKCDYTLEKFASSQKAWQIIRDGEMPKTLACTERPSKNSHPVQVGRII LEDYHDHGLLRVRMVNLQVEDSGLYQCVIYQPPKEPHMLFDRIRLVVTAE |
| 63_115 | 294 | ATKLTEEKYELKEGQTLDVKCDYTLEKFASSQKAWQIIRDGEMPKTLACTERPSKNSHPVQVGRII LEDYHDHGLLRVRMVNLQVEDSGLYQCVIYQPPKEPHMLFDRIRLVVTLA |

Each of the above clones were expressed as fusion proteins consisting of the TREM1 IgV domain followed by a triple alanine linker fused to a human Fc domain. Each clone was captured onto a sensor coated with an anti-human Fc antibody. The sensors were subsequently dipped into a solution containing an antibody of interest. Binding kinetics were monitored using a Bio-Layer Interferometry (BLI) instrument (Octet RED384 or Octet HTX, ForteBio).

By monitoring the binding kinetics of the antibody to each mutant TREM1 clone and comparing them to the kinetics against the wild type protein, the epitope could be deduced. An increase in the antibody dissociation rate constant or loss of antibody binding to the protein indicated that the mutated residues in that clone were important for antibody binding, and hence part of its epitope.

12172 antibody was selected as a potent inhibitor of TREM1 activity. Interestingly, the alanine scanning approach demonstrated that this molecule possessed an epitope distant to the identified PGLYRP1 ligand binding site. This was subsequently selected as the lead molecule.

Using the above method, and taking into consideration all three arrays, the key epitope residues of 12172 antibody were determined to be residues E26, E27, K28, Y29, E30, L31, K32 and Q35 (where the numbering is according to SEQ ID NO: 1).

Example 3: Antibody Humanization

Antibody 12172 was humanized by grafting the CDRs from the rabbit V-region onto human germline antibody V-region frameworks. In order to recover the activity of the antibody, a number of framework residues from the rabbit V-region were also retained in the humanized sequence. These residues were selected using the protocol outlined by Adair et al. (1991) (WO91/09967). Alignments of the rabbit antibody (donor) V-region sequences with the human germline (acceptor) V-region sequences are shown in FIGS. 1 and 2, together with the designed humanized sequences. The CDRs grafted from the donor to the acceptor sequence are as defined by Kabat (Kabat et al., 1987), with the exception of CDR-H1 where the combined Chothia/Kabat definition is used (see Adair et al., WO91/09967).

Human V-region IGKV1-9 plus IGKJ4 J-region (IMGT, http://www.imgt.org/) was chosen as the acceptor for antibody 12172 light chain CDRs. The light chain framework residues in the humanized graft variants are all from the human germline gene, with the exception of none, one, two or three residues from the group comprising residues 1, 2 and 3 (with reference to SEQ ID NO:25), where the donor residues Alanine (A1), Valine (V2) and Valine (V3) were retained, respectively (FIG. 1 and Table 11).

Human V-region IGHV3-66 plus IGHJ4 J-region (IMGT, http://www.imgt.org/) was chosen as the acceptor for the heavy chain CDRs of antibody 12172. In common with many rabbit antibodies, the VH gene of antibody 12172 is shorter than the selected human acceptor. When aligned with the human acceptor sequence, framework 1 of the VH region of antibody 12172 lacks the N-terminal residue, which is retained in the humanized antibody (FIG. 2). Framework 3 of the 12172 rabbit VH region also lacks two residues (75 and 76, with reference to SEQ ID NO:45) in the loop between beta sheet strands D and E: in the humanized graft variants the gap is filled with the corresponding residues (Lysine 75, K75; Asparagine 76, N76) from the selected human acceptor sequence (FIG. 2). The heavy chain framework residues in the humanized graft variants are all from the human germline gene, with the exception of one or more residues from the group comprising residues 23, 48, 49, 71, 73 and 78 (with reference to SEQ ID NO: 45), where the donor residues Threonine (T23), Isoleucine (I48), Glycine (G49), Lysine (K71), Serine (S73) and Valine (V78) were retained, respectively.

Genes encoding a number of variant heavy and light chain V-region sequences were designed and constructed by an automated synthesis approach by ATUM (CA, USA). Further variants of heavy and light chain V-regions were created by modifying the VH and VK genes by oligonucleotide-directed mutagenesis. For transient expression in mammalian cells, the humanized light chain V-region genes were cloned into the UCB light chain expression vector pMhCK, which contains DNA encoding the human Kappa chain constant region (Km3 allotype). The humanized heavy chain V-region genes were cloned into the UCB human gamma-4 heavy chain expression vector pMhγ4PFL, which contains DNA encoding the human gamma-4 heavy chain constant region with the hinge stabilising mutation S228P (Angal S., King D. J., Bodmer M. W., Turner A., Lawson A. D. G., Roberts G., Pedley B. and Adair J. R. A single amino acid substitution abolishes the heterogeneity of chimeric mouse/human (IgG4) antibody. Mol. Immunol. 1993, 30 (1):105-8), or into the UCB gamma-1 LALA heavy chain expression vector pMhγ1 L234A L235A, which contains DNA encoding the human gamma-1 heavy chain constant region with mutations L234A and L235A to reduce binding to Fc gamma receptors (FcγR) (Canfield S. M. and Morrison S. L. The Binding affinity of Human IgG for its High Affinity Fc Receptor Is Determined by Multiple Amino Acids in the CH2 Domain and Is Modulated by the Hinge Region. J. Exp. Med. 1991, 173:1483-1491). Co-transfection of the resulting heavy and light chain vectors into Expi293 ™ suspension cells was achieved using ExpiFectamine™ 293 transfection reagent (A14525, ThermoFisher Scientific), and gave expression of the humanized, recombinant IgG4P and IgG1 LALA antibodies.

The variant humanized antibody chains, and combinations thereof, were expressed and assessed for their binding affinity for human TREM1 relative to the parent antibody, their thermal stability by fluorescence based thermal shift assay (as described in Example 13) and propensity to self-interact by AC-SINS (Affinity Capture Self-Interaction Nanoparticle Spectroscopy, as described in Example 17). Retention of VH framework donor residues 148, G49 and K71 in graft gH11 was essential for the highest affinity binding to human TREM1, as measured by surface plasmon resonance (Table 11). The light chain framework residues in graft gL2 were all from the human germline gene. Retention of VL donor residue V3 in graft gL6 reduced the propensity for self-interaction as measured by AC-SINS assay (Table 22).

Resistance to thermal unfolding (denaturation) is an indicator of conformational stability and long-term storage stability. The humanized IgG4P antibodies have good thermal stability, with the midpoint of unfolding (Tm) for the Fab domains in the range of 73.5-74.6° C. (Table 11).

Molecular self-interaction can lead to native state aggregation and poor solubility, particularly at high protein concentrations used for the sub-cutaneous administration of therapeutic mAbs. The net charge of an antibody Fv domain has been shown to influence native state aggregation of human IgGs at pH 7.4 and pH 5.0 in an isotype specific manner (Heads J T, Lamb R, Kelm S, Adams R, Elliott P, Tyson K, Topia S, West S, Nan R, Turner A, Lawson A D G. Electrostatic interactions modulate the differential aggregation propensities of IgG1 and IgG4P antibodies and inform charged residue substitutions for improved developability. Protein Eng Des Sel. 2019 Dec. 31; 32(6):277-288. doi: 10.1093/protein/gzz046. PMID: 31868219; PMCID: PMC7036597). In order to reduce the propensity for self-interaction of humanized 12172 hIgG4P antibodies, as indicated by a high Δλmax value measured by AC-SINS assay (Table 12 in this Example and Table 22 in Example 17), the net positive charge of the Fv domain was decreased by the mutation of positively charged residues to either neutral or negatively charged residues. These residues were selected using the rationale outlined by Heads et al (2019) (WO2019/234094). Residues 18 and 50 of the humanized light chain graft 12712gL2 (SEQ ID NO: 29) were mutated from Arginine (R18) to Serine (S18) and Lysine (K50) to Serine (S50) in grafts gL9 and gL11, respectively. Residue 75 in the humanized heavy chain graft 12172gH11 (SEQ ID NO: 79) was mutated from Lysine (K75) to either Serine (S75), Glutamine (Q75) or Glutamic acid (E75) in grafts gH26, gH48 and gH49, respectively. The modified heavy and light chain genes were transiently expressed in Expi293™ suspension cells in combination, and the recombinant IgG4P antibodies assessed for their binding affinity to human TREM1, thermal stability and propensity to self-interact (Table 12). The humanized 12172 charge mutants retained affinity to human TREM1, and demonstrated a decreased propensity for self-interaction as indicated by a decrease in the Δλmax measured by AC-SINS assay.

Biophysical characterization of humanized 12172 gL2gH11 and 12172 gL6gH6, (both hIgG4P and hIgG1 LALA formats) was performed using different stress conditions to assess developability as described in examples 12-20. Additionally, all molecules were analysed by liquid chromatography mass spectrometry (LC-MS) to confirm that the predicted sequence molecular weight (MW) was consistent with experimental data.

The humanized 12172gL2gH11 IgG4P antibody showed similar inhibition of NF-κB in the THP1 monocyte TREM1/DAP12 NF-κB Luciferase reporter cell assay (described in Example 2) to the rabbit parental 12172 antibody (see Table 13).

TABLE 11

Affinity and Tm of various 12172 antibody variants.

| Antibody 12172 variant | Light chain Donor residues | Heavy chain Donor residues | Affinity (KD) pM | Tm (deg. C.) |
|---|---|---|---|---|
| 12172 | — | — | 519/461 | |
| 12172gL1gH1 | A1, V2, V3 | T23, I48, G49, K71, S73, V78 | 437 | 73.5 |
| 12172gL2gH1 | — | T23, I48, G49, K71, S73, V78 | 442 | 74.1 |
| 12172gL2gH4 | — | T23, I48, G49, S73, V78 | 693 | 74.3 |
| 12172gL2gH6 | — | T23, I48, G49, K71, S73 | 581 | 73.9 |
| 12172gL2gH8 | — | I48, G49, K71, S73, V78 | 476 | 74.2 |
| 12172gL6gH4 | V3 | T23, I48, G49, S73, V78 | 619 | 74.1 |
| 12172gL6gH6 | V3 | T23, I48, G49, K71, S73 | 463 | 74.5 |
| 12172gL6gH11 | V3 | I48, G49, K71 | 336 | 74.5 |
| 12172gL2gH2 | — | G49, K71, S73, V78 | 989 | 73.6 |
| 12172gL2gH9 | — | I48, G49, V78 | 362 | 74.6 |
| 12172gL2gH10 | — | I48, G49, S73 | 1970 | 74.1 |
| 12172gL2gH11 | — | I48, G49, K71 | 453 | 74.4 |
| 12172gL2gH12 | — | I48, G49 | 718 | 74.1 |

TABLE 12

Affinity, Tm and AC-SINS of various 12172 antibody variants (replicate values are provided for some of the variants)

| Antibody 12172 variant | Light chain Donor residues | Light chain Mutation | Heavy chain Donor residues | Heavy chain Mutation | Affinity (KD) pM | Fab Tm | AC-SINS |
|---|---|---|---|---|---|---|---|
| 12172 | — | — | — | — | 570 | | |
| 12172gL2gH11 | — | — | I48, G49, K71 | — | 445 | 74.4 | 10.2 |
| 12172gL2gH26 | — | — | I48, G49, K71 | K75S | 624/672 | 74.1 | 1.98/1.17 |
| 12172gL9gH11 | — | R18S | I48, G49, K71 | — | 550 | ND | 9.38 |
| 12172gL11gH11 | — | K50S | I48, G49, K71 | — | 550 | 73.8 | 7.02/10.56 |
| 12172gL9gH26 | — | R18S | I48, G49, K71 | K75S | 559/616 | 73.8 | 1.73/0.68 |
| 12172gL10gH26 | — | K42Q | I48, G49, K71 | K75S | 578/659 | 73.8 | 2.06/1.33 |
| 12172gL11gH26 | — | K50S | I48, G49, K71 | K75S | 532/633 | 74 | 2.03/1.36 |
| 12172gL9gH48 | — | R18S | I48, G49, K71 | K75Q | 370 | 73.6 | 10.46 |
| 12172gL9gH49 | — | R18S | I48, G49, K71 | K75E | 394 | 73.6 | 6.45 |

TABLE 13

Summary of potency, efficacy and hill slope values for 12172gL2gH11 IgG4P and 12172 Rabbit IgG1

| Antibody | Geomean IC50 (pM) ± SD | Average Emax (%) ± SD | Average Slope ± SD | N* |
|---|---|---|---|---|
| 12172gL2gH11 IgG4P | 64 ± 36 | 72 ± 4 | 2.1 ± 0.9 | 3 |
| 12172 Rabbit IgG1 | 84 ± 40 | 89 ± 6 | 2.7 ± 1.2 | 3 |

*Values for each molecule were calculated from three independent experiments.

Example 4. Expression and Purification of Rabbit 12172 Fab

Co-transfection of heavy and light chain vectors CID102769 and CID102770 into Exp1293™ suspension cells was achieved using ExpiFectamine™ 293 transfection reagent (A 14525, ThermoFisher Scientific), and gave expression of the rabbit recombinant 12172 Fab. The media was filtered through a PALL 0.4/0.2 µm capsule filter and applied to Protein G GammaBind Plus resin (7 mL) settled in XK16/60 column and washed with 10CV 1×PBS pH 7.4. The bound Fab complex proteins were eluted, with 50 mL 100 mM glycine, pH 2.7 and immediately neutralized with 10% 1M Tris, pH 8. Fractions containing 12172 Fab complex were pooled and concentrated in a Vivaspin PES 20, 10 kDa MWCO concentrator. A superdex s200 16/60 column (GE Healthcare) was then used to polish and buffer exchange into 1×PBS pH 7.4. The final protein concentration and purity was assessed as previously described in Example 1.

Example 5. Expression and Purification of 12172 gL2gH11/gL6gH6 hIgG4P and hIgG1 LALA Transient Mammalian Expression, CHOSXE Cultivation Suspension CHOSXE cells were pre-adapted to CDCHO serum-free media (Invitrogen) supplemented with 2 mM (100×) Glutamax.

Cells were maintained in their logarithmic growth phase, agitated at 190 rpm in a shaking incubator (Kuhner A G, Birsfelden, Switzerland) and cultured at 37° C. supplemented with 8% $CO_2$.

Electroporation Transfection

Prior to transfection, cell numbers and viability were determined using a Vi-Cell™ XR Cell Viability Analyser (Beckman Coulter) and the required number of cells ($2.3\times10^8$ cells/ml) at 99% viability were transferred into centrifuge conical tubes and spun at 1500 rpm for 15 minutes. The pelleted cells were washed in Hyclone™ MaxCyte® buffer (Thermo Scientific) and centrifuged for a further 15 minutes. Pellets were resuspended at $2.3\times10^8$ cells/ml in fresh buffer.

Plasmid DNA, purified using a Qiagen Plasmid Plus Giga Kit®, was added at 400 μg/ml. Following electroporation using a MaxCyte STx® flow electroporation instrument, the cells were transferred to ProCHO™ 5 Protein-free CHO medium (Lonza) containing 2 mM Glutamax, 0.75 mM Sodium Butyrate (n-Butyric Acid Sodium Salt, Sigma B-5887), antibiotic antimitotic 100× solutions (1 in 500) and a bolus feed added at day 0.

Transfected cells were then transferred directly into vented flasks and cultured in a Kuhner Shaker Incubator set at 37° C., 8% $CO_2$ and 190 rpm shaking. Temperature was dropped to 32° C. 24 hrs post transfection and cells were cultured for a further 11-13 days.

On day 12-14, cultures were transferred to centrifuge tubes and supernatant separated from cells after spinning for 30 minutes at 4000 rpm. Retained supernatants were further clarified by filtering through a 0.22 μm Sartobran® P Millipore cartridge, followed by 0.22 μm Millipak® Gamma Gold filters. Final expression titres were determined by Protein G Quantification HPLC assay using A33 hIgG1 at 1 mg/ml as the standard, a 0.8 ml POROS™ G 20 μm column and an Agilent 1100 Series HPLC System. The clarified cell culture harvest was stored at 4° C. prior to purification.

Antibody Purification and Analysis

Clarified cell culture harvest was allowed to warm to room temperature before loading onto a 215 ml MabSelect™ SuRe™ column (Cytiva) pre-equilibrated into Hyclone™ Phosphate Buffered Saline (PBS) pH7.4, using an ÅKTA Pure 25 L chromatography system (Cytiva). After washing in PBS pH7.4, bound material was eluted by reducing the pH to 3.4 (0.1M Sodium Citrate buffer) for human IgG1 isotypes or pH3.7 (30 mM Sodium Acetate) followed by pH3.6 (0.1M Sodium Citrate buffer) for human IgG4P isotypes. Post elution, the column was stripped with 0.1M Citric Acid pH2.0 to remove any strongly bound aggregates. Affinity capture elution peak fractions were pooled and neutralized to pH5.5-7.5 by the addition of 2M Tris-HCl pH8.5. Protein concentration was determined by reading absorbance at 280 nm using a nanodrop and purity was determined by analytical size exclusion HPLC (method below).

Affinity pools were concentrated, using centrifugal filtration devices (Centricon® Plus-70 or Amicon® Ultra-15) or pressurized stirred cell chambers (Amicon®) with a 10 KDa or 30 KDa MWCO membrane depending on volume, for loading onto a HiLoad Superdex 200 26/60 (Cytiva) or 50/60 prep. grade column (custom packed by Cytiva). The HiLoad Superdex 200 26/60 or 50/60 column was equilibrated into 50 mM Sodium Acetate, 125 mM Sodium Chloride buffer pH5.0 prior to sample loading using an ÅKTA chromatography system (Cytiva). An isocratic elution was run, and fractions were collected after 0.3 CV's. Fractions containing monomer were identified by running fractions or mock pools on analytical size exclusion HPLC. Fractions were pooled to obtain >98% monomer content. Pools were concentrated to 10-15 mg/ml, using centrifugal filtration devices (Centricon® Plus-70 or Amicon® Ultra-15) or pressurized stirred cell chambers (Amicon®) with a 10 KDa or 30 KDa MWCO membrane depending on volume, then recovered and 0.22 μm sterile filtered using Stericup® filtration units or Millex GV syringe filters.

Final protein concentration was determined by reading absorbance at 280 nm using a nanodrop. Monomer content was determined by analytical size exclusion HPLC. Correct banding pattern was determined by SDS-PAGE using the Invitrogen Novex™ WedgeWell™ 4-20% Tris-Glycine and XCell SureLock™ Mini-Cell Electrophoresis system and Coomassie stain. Endotoxin level was determined using the Charles River Endosafe® LAL Reagent Cartridge Technology and Endosafe® nexgen-PTS reader, with a level of <1 EU/mg being of acceptable quality. Samples were analyzed by intact mass spectrometry to confirm heavy and light chain masses, expected modifications and identity.

Analytical Size Exclusion HPLC

TSKgel G3000SWXL HPLC column (Tosoh) was equilibrated into Hyclone Phosphate Buffered Saline (PBS) pH7.4 using an Agilent 1100 or 1200 series HPLC. 20-50 μg of sample was injected and run in isocratic elution conditions (PBS pH7.4) at 1 ml/min for 16 minutes. Data was compared to BioRad Molecular Weight marker standards. Retention times and percentages were reported for monomer and high and low molecular weight product related impurities.

Example 6. Binding Kinetics of 12172gL2gH11 hIgG4P to Human and Cynomolgus TREM1

The kinetics of 12172gL2gH11 hIgG4P binding to human and cynomolgus TREM1 were measured at 25° C. by surface plasmon resonance on a Biacore T200 instrument and a Biacore 8k instrument.

A goat anti human IgG, Fc fragment specific antibody (F(ab')2 fragment, Jackson ImmunoResearch 109-006-098) was immobilized on a CM5 Sensor Chip via amine coupling chemistry to a level of approximately 5000 RU. A reference cell was treated in the same manner. After amine coupling was complete, all subsequent solutions were flowed over the reference cell and the sample cell in series, except for the capture solution, and the response of the reference cell was subtracted from the sample cell throughout the run.

Each analysis cycle consisted of capture of approximately 250 RU of 12172gL2gH11 hIgG4P to the anti Fc surface, injection of analyte for 180 s (at 25° C. at a flow rate of 30 μl per minute), dissociation of analyte for 600 s, followed by surface regeneration (with a 60 s injection of 50 mM HCl, a 30 s injection of 5 mM NaOH, and a further 60 s injection of 50 mM HCl). Human TREM1 ECD analyte (in house, His tagged) was injected at 3-fold serial dilutions in HBS-EP+ running buffer (GE Healthcare) at concentrations of 200 nM to 2.5 nM on the T200, and concentrations of 500 nM to 2 nM on the 8k. Cyno TREM1 ECD analyte (in house, His tagged) was injected at 3-fold serial dilutions in HBS-EP+ running buffer (GE Healthcare) at concentrations of 4100 nM to 17 nM—this was run on the T200 only. Buffer blank injections were included to subtract instrument noise and drift.

Kinetic parameters were determined using a 1:1 binding model using Biacore T200 Evaluation software (version 3.0) or Biacore Insight Evaluation software (version 3.0), as appropriate. 12172gL2gH11 hIgG4P was shown to have an affinity of 0.52 nM for human TREM1 and 870 nM for cyno TREM1. The kinetic parameters are summarized in Table 14.

TABLE 14

Kinetic parameters of 12172gL2gH11 hIgG4P binding to human and cynomolgus TREM1

| Species | $k_a$ (1/Ms) | $k_d$ (1/s) | $K_D$ (nM) | n= |
|---|---|---|---|---|
| Human | 1.8E+05 | 9.2E−05 | 0.52 | 2 |
| Cynomolgus | 1.2E+05 | 1.0E−01 | 870 | 1 |

Each analysis cycle consisted of capture of approximately 250 RU of 12172gL2gH11 hIgG4P to the anti Fc surface, injection of analyte for 180 s (at 25° C. at a flow rate of 30 µl per minute), dissociation of analyte for 600 s, followed by surface regeneration (with a 60 s injection of 50 mM HCl, a 30 s injection of 5 mM NaOH, and a further 60 s injection of 50 mM HCl). TREM1 ECD analyte (in house, His tagged) was injected at 3-fold serial dilutions in HBS-EP+ running buffer (GE Healthcare), top concentrations are shown in Table 15, and three-fold serial dilutions were performed to a bottom concentration of 2 nM. Buffer blank injections were included to subtract instrument noise and drift.

Kinetic parameters were determined using a 1:1 binding model using Biacore Insight Evaluation software (version 3.0). 12172 gL2gH11 hIgG4P was shown to have an affinity of 0.54 nM for human TREM1 in this experiment (kinetic parameters summarised in Table 15). A minimal binding response was observed for cynomolgus and rhesus monkey, though insufficient to determine binding kinetics. No binding of 12172gL2gH11 hIgG4P to TREM1 of any other species was detected (as summarised in Table 16).

TABLE 15

Kinetic parameters of 12172gL2gH11 hIgG4P binding to human TREM1

| Species | $k_a$ (1/Ms) | $k_d$ (1/s) | $K_D$ (nM) | n= |
|---|---|---|---|---|
| Human | 1.7E+05 | 9.1E−05 | 0.54 | 1 |

TABLE 16

Report point data showing binding of TREM1 species to 12172gL2gH11 hIgG4P. BL denotes binding late: the average signal 7.5-12.5 s before the end of the TREM1 injection, subtracted from the average signal 7.5-12.5 s before the start of this injection. SE denotes stability early: the average signal 7.5-12.5 s after the end of the TREM1 injection is subtracted from the average signal 7.5-12.5 s before the start of this injection. The theoretical Rmax is the signal that would be produced if all captured antibodies (150 kDa) were fully bound to 2 molecules of TREM1. SR_BL is BL divided by the theoretical Rmax, SR_SE is SE divided by the theoretical Rmax.

| Species | Concentration (nM) | BL (RU) | SE (RU) | Capture level (RU) | TREM1 MW (kDa) | Theoretical Rmax (RU) | SR_BL | SR_SE |
|---|---|---|---|---|---|---|---|---|
| human | 490 | 78 | 78 | 223 | 21 | 62 | 1.3 | 1.3 |
| cynomolgus | 460 | 26 | 16 | 231 | 21 | 65 | 0.4 | 0.3 |
| rhesus | 450 | 12 | 5 | 229 | 21 | 64 | 0.2 | 0.1 |
| marmoset | 510 | 0 | 0 | 224 | 22 | 66 | 0.0 | 0.0 |
| mouse | 520 | 0 | 0 | 228 | 21 | 64 | 0.0 | 0.0 |
| rat | 470 | 0 | 0 | 233 | 21 | 65 | 0.0 | 0.0 |
| pig | 490 | 0 | 0 | 233 | 22 | 68 | 0.0 | 0.0 |
| dog | 460 | 0 | 0 | 226 | 22 | 66 | 0.0 | 0.0 |

Example 7. Binding of 12172gL2gH11 hIgG4P to Different Species of TREM1

The kinetics of 12172gL2gH11 hIgG4P binding to various species of TREM1 were measured at 25° C. by surface plasmon resonance on a Biacore T200 instrument. The species tested were human, cynomolgus, rhesus, marmoset, rat, mouse, dog and pig.

A goat anti human IgG, Fc fragment specific antibody (F(ab')2 fragment, Jackson ImmunoResearch 109-006-098) was immobilized on a CM5 Sensor Chip via amine coupling chemistry to a level of approximately 5000 RU. A reference cell was treated in the same manner. After amine coupling was complete, all subsequent solutions were flowed over the reference cell and the sample cell in series, excepting the capture solution, and the response of the reference cell was subtracted from the sample cell throughout the run.

Example 8. Blocking of the TREM1/PGLYRP1 Interaction by 12172gL2gH11 hIgG4P

12172gL2gH11 hIgG4P was demonstrated to block the interaction between human TREM1 and human PGLYRP1 at 25° C. by surface plasmon resonance on a Biacore T200 instrument.

A goat anti human IgG, Fc fragment specific antibody F(ab')$_2$ fragment, Jackson ImmunoResearch 109-006-098) was immobilized on all four flow cells of an HC30M Sensor Chip (XanTec Bioanalytics) via amine coupling chemistry to a level of approximately 4000 RU. The response of flow cell 1 was subtracted from the response of flow cell 2 throughout the run, similarly the response of flow cell 3 was subtracted from the response of flow cell 4 throughout.

Each analysis cycle consisted of capture of approximately 100 RU of TREM1-Fc (R&D 1278-TR Lot GZF0220071) to the surface of flow cell 2, capture of approximately 150 RU 12172gL2gH11 hIgG4P to the surface of flow cell 4, and TREM1 ECD analyte (in house, His tagged) was flowed over the surface of flow cells 3 and 4 for 180 s. A mixture of PGLYRP1 (R&D 2590-PGB, NLC1520031) and PGN (Invivogen tlrl-ksspgn lot KSS-41-01) was flowed over all surfaces for 180 s and the binding monitored, followed by a 300 s dissociation period. The surfaces were then regenerated (with a 60 s injection of 50 mM HCl, a 30 s injection of 5 mM NaOH, and a further 60 s injection of 50 mM HCl).

12172gL2gH11 hIgG4P blocked the interaction of PGLYRP1 and TREM1 in the presence and absence of PGN (see Table 17).

TABLE 17

Relative response at the binding late report point. This is calculated during the injection of PGLYRP1 and PGN: the average signal 7.5-12.5 s before the end of the injection is subtracted from the average signal 7.5-12.5 s before the start of this injection. This value is then subtracted from the value in an equivalent cycle with no captured ligand. This shows that TREM1-Fc binds 5 RU of PGLYRP1 alone, and it binds 12 RU of a mixture of PGLYPR1 and PGN, however PGLYRP1 does not bind TREM1 which has been captured to a surface coated in 12172gL2gH11 hIgG4P.

| All flow cells | | Flow cell 2 | | Flow cell 4 | | |
|---|---|---|---|---|---|---|
| Concentration PGLYRP1 (nM) | Concentration PGN (μg/ml) | Ligand | Binding late (RU) | Ligand | Concentration of TREM1 (nM) | Binding late (RU) |
| 0 | 0 | TREM1-Fc | 0 | 12172 gL2gH11 hIgG4P | 552 | −1.8 |
| 30 | 0 | TREM1-Fc | 4.5 | 12172 gL2gH11 hIgG4P | 552 | −1.8 |
| 0 | 0.55 | TREM1-Fc | −0.5 | 12172 gL2gH11 hIgG4P | 552 | −1.9 |
| 30 | 0.55 | TREM1-Fc | 11.8 | 12172 gL2gH11 hIgG4P | 552 | −1.7 |

Example 9: Determination of the Binding Interface of Human PGLYRP1 with Human TREM1 by Crystallography Crystallography The human TREM1 IgV domain was complexed with full-length human PGLYRP1 (1:1 molar ratio) in PBS, pH 7.0 at 15 mg/ml and incubated for an hour at 4° C. The proteins were co-crystallized in a hanging drop, vapor diffusion consisting of 0.2 ul protein and 0.2 ul reservoir Molecular Dimensions ProPlex screen D7 (15% (w/V) PEG 6000, 100 mM sodium citrate tribasic/sodium hydroxide pH 5.5). 20% ethylene glycol was used for cryo protection.

X-Ray Diffraction, Data Collection, Structure Determination and Refinement

The cryogenic (100K) X-ray diffraction data were collected remotely at APS 21-ID-F. Raw data frames were indexed, integrated, and scaled using XDS. The Space Group of the crystal was P21, with unit cell parameters, a=58.68 Å, b=98.73 Å, c=60.43 Å, $\alpha$=90°, $\beta$=109.145°, $\gamma$=90° to a resolution of 2.55 Å. The quality parameters of the structure were good with overall R-factor of the structure=17.9% and the free R-Factor=22.9%. The protein complex structure was modelled in COOT and refined using PHENIX, including TLS protocol. Water molecules were added and checked by COOT.

Figure 3A:
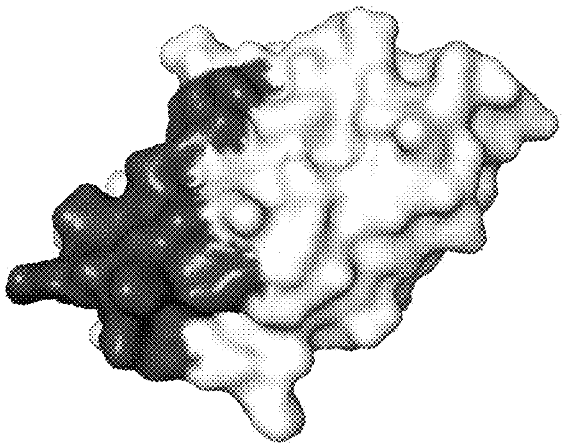

Human TREM1 IgV domain (positions 21-139) (SEQ ID NO: 9) complexed with full-length PGLYRP1 (SEQ ID NO: 10)). The stoichiometry of the crystal complex is 1:2, with a single hTREM1 molecule bound to a PGLYRP1 molecule that is dimerized, despite equimolar mixing. The analysis of intermolecular distances of less than or equal to 4 Å between the IgV-like domain of human TREM1 and hPGLYRP1 was carried out using the program NCONT in the CCP4 program suite. The epitope has been determined crystallographically as follows: residues E27, D42-E46, A49, Y90-L95, and F126 (the positions correspond to SEQ ID NO:1). FIG. 3A shows structural mapping of the PGLYRP1 ligand binding site on hTREM1:PDBPDB 1SMO.

Example 10: Determination of the 12172 Rabbit Parental Fab Human TREM1 Epitope by X-Ray Crystallography Crystallography To identify the precise epitope of the 12172 antibody, X-ray crystallography was used. The human TREM1 IgV domain (SEQ ID NO: 9) was complexed with rabbit parental Fab (1:1 molar ratio) in PBS, pH 7.4 and applied to size exclusion. Chaperone Fab 11994 was mixed with the hTREM1:Fab complex at 15 mg/ml and incubated for an hour at 4° C. The proteins were co-crystallized in a hanging drop, vapor diffusion consisting of 0.2 ul protein and 0.1 ul reservoir Molecular Dimensions ProPlex screen A6 (25% (w/V) PEG 1000, 200 mM Sodium chloride, 100 m potassium phosphate dibasic/sodium phosphate monobasic pH 6.5). 20% ethylene glycol was used for cryo protection.

X-Ray Diffraction, Data Collection, Structure Determination and Refinement

The cryogenic (100K) X-ray diffraction data were collected remotely at APS 21-ID-F. Raw data frames were indexed, integrated, and scaled using XDS. The Space Group of the crystal was I222, with unit cell parameters, a=91.98 Å, b=139.10 Å, c=224.81 Å, $\alpha$=90°, $\beta$=90°, $\gamma$=90° to a resolution of 2.60 Å. The quality parameters of the structure were good with overall R-factor of the structure=19.3% and the free R-Factor=22.6% The protein complex structure was modelled in COOT and refined using PHENIX, including TLS protocol. Water molecules were added and checked by COOT.

Human TREM1 IgV domain (positions 21-139) (SEQ ID NO: 9) complexed with rabbit parental Fab (12172) (SEQ ID NO: 19 and 23) was obtained in the presence of a chaperone Fab molecule (11994). Using Hydrogen Deuterium Exchange Mass Spectrometry (HDX-MS), it has been confirmed that the 11994 Fab chaperone used for crystallography of 12172 rabbit parental Fab does not influence 12172 binding to TREM1. The stoichiometry of the crystal complex is 1:1:1, with the Fab epitopes binding to opposite sides on the hTREM1 molecule. The analysis of intermolecular distances of less than or equal to 4 Å between the IgV-like domain of human TREM1 and Fab 12172 was carried out using the program NCONT in the CCP4 program suite. The epitope was determined crystallographically as follows: residues E26-K32, Q35, T36, D38, K40, D42, R97, D127, T134 and G136 (the positions correspond to SEQ ID NO: 1). FIG. 3B shows structural mapping of the Fab 12172 epitope on hTREM1:PDBPDB 1SMO. The epitope was confirmed to be different from the epitope of PGLYRP1 (see Example 9).

Example 11. Full Length Antibody 12172gL2gH11 hIgG4P—Mammalian Cell Line Development To demonstrate stable expression of 12172gL2gH11 hIgG4P, a stably expressing mammalian cell line was created. A CHO cell line was transfected with the plasmid vector 12172_gL2_ckappa_gH11_IgG4(p). The cell lines were cloned and evaluated for fit to a suitable manufacturing process. To assess the quality and quantity of the protein of interest and to ensure the optimal cell line was selected, the cell line was evaluated in a small-scale model of a manufacturing fed-batch bioreactor. Clonal CHO cell lines were selected that express 12172gL2gH11 hIgG4P at acceptable levels and containing more than 95% of monomer.

Example 12. Characterization of Antibody Molecules by Liquid Chromatography-Mass Spectrometry (LC-MS)

The molecular weight (MW) of produced 12172 gL2gH11 (hIgG4P and hIGI LALA) and 12172 gL6gH6 (hIgG4P and hIgG1 LALA) antibody molecules was measured both on the intact molecules (non-reduced) and the separate heavy and light chains (reduced) by LC-MS using a Waters ACQUITY UPLC System with a Xevo G2 Q-ToF mass spectrometer. Samples (~5 μg) were reduced with 5 mM tris(2-carboxyethyl) phosphine (TCEP) in 150 mM ammonium acetate at 37° C. for 40 minutes. For non-reduced (intact) measurement, the samples were diluted with PBS pH 7.4 to the same concentration and incubated as above prior to analysis The LC column was a Waters BioResolve™ RP mAb Polyphenyl, 450 Å, 2.7 μm held at 80° C., equilibrated with 95% solvent A (water/0.02% trifluoroacetic acid (TFA)/0.08% formic acid) and 5% Solvent B (95% acetonitrile/5% water/0.02% TFA/0.08% formic acid) at a flow rate of 0.6 mL/minute. Proteins were eluted with a gradient from 5% to 50% solvent B over 8.8 minutes followed by a 95% solvent B wash and re-equilibration. UV data were acquired at 280 nm. MS conditions were as follows: Ion mode: ESI positive ion, resolution mode, mass range: 400-5000 m/z and external calibration with NaI.

Data were analyzed using Waters MassLynx™ and MaxEnt Software.

As shown in Tables 18 and 19 the predicted MW from the sequences of 12172 gL2gH11 (hIgG4P and hIgG1 LALA) and 12172 gL6gH6 (hIgG4P and hIgG1 LALA) antibody molecules were consistent with the measured MW for the intact molecules and the heavy and light chains by LC-MS.

TABLE 18

Intact (non-reduced) LC-MS data of 12172 gL2gH11 and 12172 gL6gH6 (hIgG4P and hIgG1 LALA) antibody molecules.

| | | Intact Antibody MW (Da) | | |
|---|---|---|---|---|
| Graft | Format | Expected | Observed | Δm |
| 12172 | hIgG4P | 147482.6 | 147485.0 | 2.4 |
| gL2gH11 | hIgG1 LALA | 147624.9 | 147628.0 | 3.1 |
| 12172 | hIgG4P | 147430.6 | 147433.0 | 2.4 |
| gL6gH6 | hIgG1 LALA | 147572.9 | 147578.5 | 5.6 |

TABLE 19

Reduced LC-MS data of 12172 gL2gH11 and 12172 gL6gH6 (hIgG4P and hIgG1 LALA) antibody molecules.

| | | Light Chain MW (Da) | | | Heavy Chain MW (Da) | | |
|---|---|---|---|---|---|---|---|
| Graft | Format | Expected | Observed | Δm | Expected | Observed | Δm |
| 12172 | hIgG4P | 23651.2 | 23650.8 | −0.4 | 50094.1 | 50095.4 | 1.3 |
| gL2gH11 | hIgG1 LALA | 23651.2 | 23650.6 | −0.6 | 50165.3 | 50166.4 | 1.1 |
| 12172 | hIgG4P | 23622.2 | 23621.6 | −0.6 | 50097.1 | 50098.2 | 1.1 |
| gL6gH6 | hIgG1 LALA | 23622.21 | 23621.8 | −0.4 | 50168.3 | 50169.4 | 1.1 |

Example 13. Thermal Stability (Tm) Measurements

The melting temperature (Tm) or temperature at the midpoint of unfolding was determined using the (i) thermal shift assay or (ii) Differential Scanning Calorimetry (DSC) to assess the conformational stability of the molecules and hence robustness to manufacture and long term stability.

Thermal Shift Assay

The thermal shift assay was performed on early graft screening and selection, see Example 3.

The fluorescent dye SYPRO® orange was used to monitor the protein unfolding process by binding to hydrophobic regions that become exposed as the temperature increases. The reaction mix contained 5 μL of 30×SYPRO® Orange Protein Gel Stain (Thermofisher scientific, S6651), diluted from 5000× concentrate with test buffer. 45 μL of sample at 0.2 mg/mL, in a common pre-formulation storage buffer, pH 7.4, was added to the dye and mixed. 10 μL of this solution was dispensed in quadruplicate into a 384 PCR optical well plate and was run on a QuantStudio 7 Real-Time PCR System (Thermofisher™). The PCR system heating device was set at 20° C. and increased to 99° C. at a rate of 1.1° C./min. A charge-coupled device monitored fluorescence changes in the wells. Fluorescence intensity increases were plotted, the inflection point of the slope(s) was used to generate apparent midpoint temperatures (Tm). The data is shown in Table 11 and 12 (see Example 3).

Differential Scanning Calorimetry (DSC)

Figure 4:
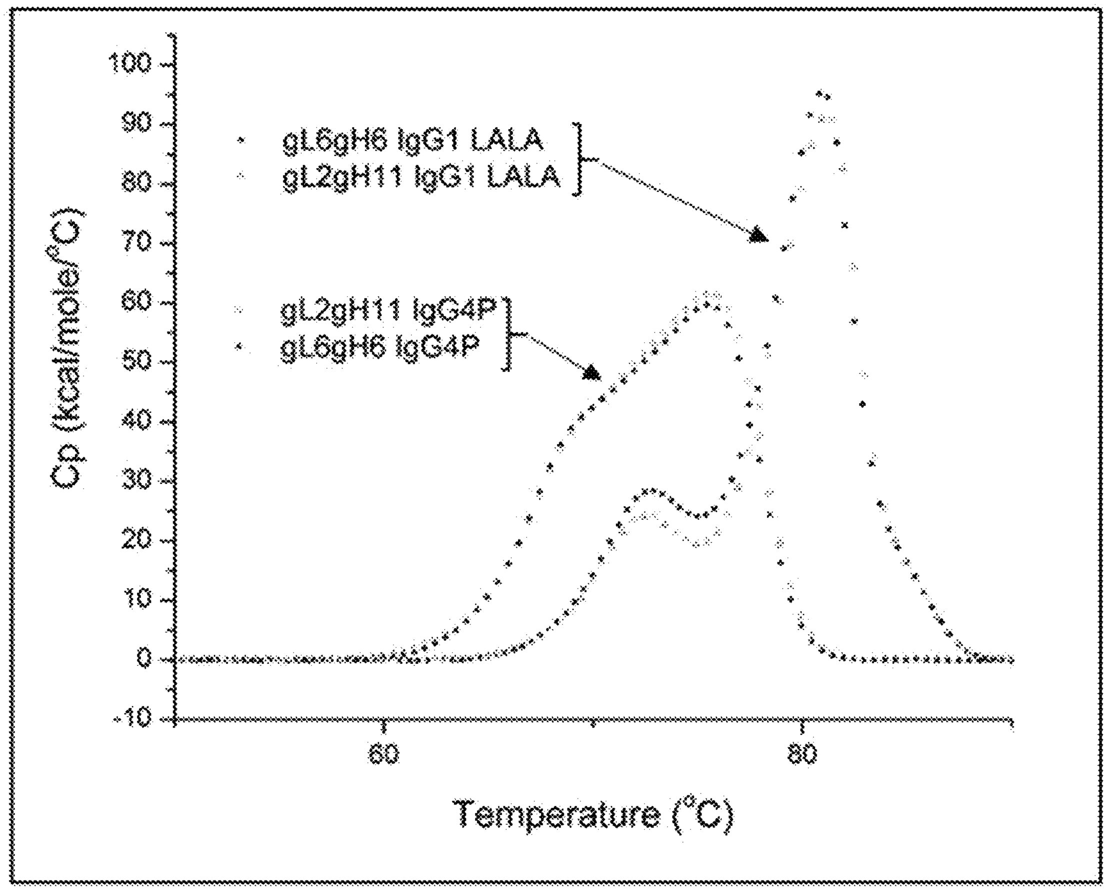
FIG. 4 shows thermal stability of different variants of 12172 antibody. Thermograms for 12172 gL2gH11 and 12172 gL6gH6 (hIgG4P and hIgG1 LALA) measured in a common pre-formulation storage buffer pH7.4.

Differential Scanning calorimetry was used to assess thermal stability. All samples were diluted to 10 μM in a common pre-formulation storage buffer, pH7.4 or pH5.0 in a total volume of 400 μL, added to a 96-well plate and centrifuged at 4,000×g for 5 min to remove air bubbles. The plate was run on an automated MicroCal VP DSC (Malvern Panalytical), from 10-100° C., at a rate of 1° C./min, with a pre-scan thermostat of 15 min, filtering period of 8 s and in passive feedback mode. Data was buffer subtracted, with manual baseline correction and data fitted to a non-2-state model in Origin 7.0. Transition midpoints (Tm) and onset of unfolding are shown below Table 20 and FIG. 4.

The IgG4P isotypes were fitted to three transitions whilst the IgG1 LALA's were fitted to two transitions, where the Fab and CH3 unfolding were unable to be differentiated. Thermal stability was within the expected ranges for each isotype.

TABLE 20

Summary of Thermal Stability data for 12172 gL2gH11 and 12172 gL6gH6 (hIgG4P and hIgG1 LALA) in a common pre-formulation storage buffer pH 7.4. Tm1 = CH2 unfolding, Tm2 = Fab unfolding, Tm3 = CH3 unfolding

| | | Thermal Stability PH 7.4 (° C.) | | | |
|---|---|---|---|---|---|
| Graft | Format | Tm1 | Tm2 | Tm3 | onset |
| gL2gH11 | hIgG4P | 69.94 | 74.30 | 76.84 | 60.93 |
| | hIgG1 LALA | 72.86 | 80.81 | | 65.76 |
| gL6gH6 | hIgG4P | 69.72 | 74.08 | 76.67 | 61.20 |
| | hIgG1 LALA | 73.12 | 80.65 | | 66.05 |

Example 14. Experimental Isoelectric Point (pI) Measurement

The experimental pI was found to be similar for the 12172 gL2gH11 and 12172 gL6gH6 as hIgG4P formats. This was also observed for the hIgG1 LALA molecules. The pI was in a range that was expected to be good for manufacturing steps and formulation buffers. The presence of different charged species was consistent with observations of other therapeutic molecules and attributed to common post-translation modifications, such as C terminal heavy chain removal of lysine.

Example 15. Hydrophobic Interaction Chromatography (HIC)

Hydrophobic Interaction chromatography (HIC) was used to measure hydrophobicity of 12172 gL2gH11 and 12172 gL6gH6 as hIgG4P formats. HIC separates molecules in order of increasing hydrophobicity. Molecules bind to the hydrophobic stationary phase in the presence of high concentrations of polar salts and desorb into the mobile phase as the concentration of salt decreases. A longer retention time equates to a greater hydrophobicity.

All molecules showed low apparent hydrophobicity (less than 15 minutes retention time). There was no meaningful difference between 12172 gL2gH11 and 12172 gL6gH6 hIgG4P molecules. Similarly, there was no meaningful difference in hydrophobic retention times for the hIgG1 LALA samples. The hIgG4P molecules showed slightly later retention times compared with the corresponding hIgG1 LALA molecules.

Example 16. Solubility Measurement Using Polyethylene Glycol (PEG) Aggregation Assay The PEG aggregation assay was used as a mimic of high concentration solubility. PEG is a nonadsorbing, nondenaturing polymer and due to its inert nature, has been used to promote protein precipitation primarily via an excluded volume effect. Samples were exposed to increasing concentrations of PEG 3350; the amount of sample remaining in solution was determined by plotting absorbance at A280 nm. The determination of % PEG concentration at which half the sample had precipitated generated a PEG midpoint (PEGmdpnt) score. This score permitted test molecules to be ranked on apparent native state aggregation propensity, a low PEGmdpnt score (for example ≤10) indicates a greater propensity for native state aggregation.

Stock 40% PEG 3350 (Merck, 202444) solutions (w/v) were prepared in common pre-formulation storage buffers pH 7.4 and 5.0 and a common pre-formulation buffer pH 5.5). A serial titration was performed by an ASSIST PLUS liquid handling robot (INTEGRA 4505), resulting in a range of 40% to 15.4% PEG 3350. To minimize non-equilibrium precipitation, sample preparation consisted of mixing antibody and PEG solutions at a 1:1 volume ratio. 35 μL of the PEG 3350 stock solutions was added to a 96 well v bottom PCR plate (A1 to H1) by a liquid handling robot. 35 μL of a 2 mg/mL sample solution was added to the PEG stock solutions resulting in a 1 mg/mL test concentration and a final PEG 3350 concentration of 20% to 7.7%. This solution was mixed by automated slow repeat pipetting and incubated at 37° C. for 0.5 h to re-dissolve any non-equilibrium aggregates. Samples were then incubated at 20° C. for 24 h. The sample plate was subsequently centrifuged at 4000×g for 1 h at 20° C. 50 μL of supernatant was dispensed into a UV-Star®, half area, 96 well, μClear®, microplate (Greiner, 675801). Protein concentrations were determined by UV spectrophotometry at 280 nm using a FLUOstar® Omega multi-detection microplate reader (BMG LABTECH). The resulting values were plotted using Graphpad prism (version 7.04); the PEG midpoint ($PEG_{mdpnt}$) score was derived from the midpoint of the sigmoidal dose-response (variable slope) fit.

The data is shown in Table 21 where the higher PEG mid-point (%) equates to greater solubility.

Buffer dependent solubility was observed for the molecules tested. In a common pre-formulation storage buffer pH 7.4, both isotypes (hIgG4P and hIgG1 LALA) of 12172 gL2gH11 and 12172 gL6gH6 exhibited low PEG midpoints scores, indicating low solubility at high concentration. Increased PEG midpoint scores were observed in the common pre-formulation storage buffer pH 5 buffer. Notably all the samples showed substantially improved PEG midpoint scores when formulated in the common pre-formulation buffer pH 5.5. The hIgG1 LALA samples did not precipitate at the highest test concentration of PEG 3350 in this buffer.

TABLE 21

PEG aggregation assay data for 12172 gL2gH11 and 12172 gL6gH6 (hIgG4P and hIgG1 LALA) in the common pre-formulation storage buffers pH 7.4 and 5.5, and the common pre-formulation buffer pH 5.5. Higher PEG % midpoint = greater high concentration solubility. NB *samples showed signs of aggregation at the lowest test concentration of PEG 3350 (7.7%) therefore accurate PEG midpoints could not be generated.

| | | % midpoint | | |
|---|---|---|---|---|
| Graft | Format | common pre-formulation storage buffer pH7.4 | common pre-formulation buffer pH 5.5 | common pre-formulation storage buffer pH 5 |
| gL2gH11 | hIgG4P | *<7.7 | 13.0 | 10.0 |
| | hIgG1 LALA | *<7.7 | >20 | 12.2 |
| gL6gH6 | hIgG4P | *<7.7 | 14.4 | 10.7 |
| | hIgG1 LALA | *<7.7 | >20 | 12.9 |

Example 17. Assessment of Protein-Protein Self-Interaction Using AC-SINS (Affinity Capture Self-Interaction Nanoparticle Spectroscopy)

The AC-SINS assay was used to screen the developability of humanized molecules including 12172 gL2gH11 and 12172 gL6gH6 (as hIgG4P and hIgG1 LALA; also see Example 3) by determining protein-protein self-interaction propensity, hence informing on potential aggregation stability. This was performed in a common pre-formulation storage buffer pH 7.4.

Goat anti human-Fcγ specific capture antibody (Jackson ImmunoResearch) was buffer exchanged into 20 mM sodium acetate, pH4.3, diluted to 0.4 mg/mL and 50 μL added to 450 μL citrate-stabilized 20 nm gold nanoparticles (TedPella, USA) and left overnight at room temperature. The conjugated nanoparticles were blocked with 55 μL PEG methyl ether thiol (average Mn=2,000 (Sigma #729140) for 1 hour, centrifuged at 21,000×g for 6 min, the supernatant removed and resuspended in 20 mM sodium acetate, pH4.3 to a final volume of 150 μL.

The antibody samples were diluted to 22 pg/mL in a common pre-formulation storage buffer, pH7.4 (180 μL) and added to 20 μL of mock supernatant and 200 μL non-specific whole IgG at 222 μg/mL (Jackson ImmunoResearch), vortexed briefly and 72 μL added to a 96-well plate. 8 μL of nanoparticles were added to each well (n=4). Absorbance were read on a BMG plate reader from 500-600 nm, fitted to Lorenzian curves (RShiny) and a common pre-formulation storage buffer-only subtracted from the samples to give Δλmax.

The data is summarized in Table 22 where the higher Δλ max (nm) value equates to a higher protein-protein self-interaction propensity. The hIgG1 LALA molecules for both 12172 gL2gH11 and 12172 gL6gH6 were found to show less self-interaction than the corresponding hIgG4P molecules as shown by a lower Δλ max (nm). Additionally, 12172 gL6gH6 (hIgG4P and hIgG1 LALA) molecules showed slightly lower Δλ max (nm) values than the 12172 gL2gH11 (hIgG4P and hIgG1 LALA) molecules.

TABLE 22

Self-interaction measurement (AC SINS) for 12172 gL2gH11 and 12172 gL6gH6 (hIgG4P and hIgG1). Low value = less protein-protein self-interaction.

| Graft | Format | λΔ max (nm) |
|---|---|---|
| gL2gH11 | hIgG4P | 13.15 |
| | hIgG1 LALA | 5.970 |
| gL6gH6 | hIgG4P | 8.58 |
| | hIgG1 LALA | 3.93 |

Example 18. kD Interaction Parameter Measurement (Colloidal Stability)

The kD interaction parameter was used to assess colloidal stability, where positive and negative values relate to repulsive and attractive intermolecular forces respectively.

Dynamic light scattering (DLS) was performed on a DynaPro III plate reader (Wyatt Technology Corp, Santa Barbara, CA, USA). Samples were diluted in a common pre-formulation storage buffer, pH7.4 or buffer exchanged into a common pre-formulation storage buffer, pH5.0 and diluted from 7 mg/mL to 1 mg/mL in increments of 1 mg/mL. Wells containing buffer were selected as solvent offsets and the measurements performed at 25° C., with the laser power set to 20% and auto-attenuation enabled. Each measurement was the average of five, 5 s scans in triplicate (5×3). The Diffusion co-efficient was measured (Dm) and the interaction parameter (kD) calculated according to the equation below, where $D_0$ represents the diffusion coefficient at infinite dilution.

$$Dm = D_0(1 + K_D C)$$

Equation: $D_0$ given by Debye plot at Y-intercept. The slope=kD*$D_0$.

The Diffusion coefficient was measured as a function of protein concentration and the kD used to assess colloidal stability, where positive and negative values suggest repulsive and attractive intermolecular forces respectively. For samples that show attractive forces/self-association, the diffusion coefficient gets larger as a function of protein concentration and this is reflected in a negative kD value. The data is shown in Table 23.

The kD interaction parameter was shown to be less negative (more colloidally stable) for both the hIgG4P and hIgG1 LALA molecules in the common pre-formulation storage buffer pH 5 compared with the data obtained in the common pre-formulation storage buffer pH 7.4. The hIgG1 LALA molecules were shown to be more stable than the corresponding hIgG4P molecules. Additionally, 12172 gL6gH6 (hIgG4P and hIgG1 LALA) molecules exhibited slightly greater colloidal stability than 12172 gL2gH11 (hIgG4P and hIgG1 LALA). This data confirmed the data generated from the AC-SINS assay (see Example 17).

TABLE 23 kD interaction parameter data for 12172 gL2gH11 and 12172 gH6gL6 (hIgG4P and hIgG1 LALA). The more negative value = greater attraction (higher protein-protein self-interaction).

| | | ml/g | |
|---|---|---|---|
| Graft | Format | PBS | Ac pH 5 |
| gL2gH11 | hIgG4P | −14.7 | −7.6 |
| | hIgG1 LALA | −10.8 | −5.1 |
| gL6gH6 | hIgG4P | −12.4 | −5.5 |
| | hIgG1 LALA | −9.8 | −4.1 |

Example 19. Effect of Mechanical Stress on Aggregation Stability (Aggregation Assay)

Proteins tend to unfold when exposed to an air-liquid interface, where hydrophobic surfaces are presented to the hydrophobic environment (air) and hydrophilic surfaces to the hydrophilic environment (water). Agitation of protein solutions achieves a large air-liquid interface that can drive aggregation. This assay serves to mimic stresses that the molecule would be subjected to during manufacture (for example ultra-filtration) and to provide stringent conditions in order to try to discriminate between different antibody molecules.

Samples in a common pre-formulation storage buffer pH 7.4 or pH 5 were stressed by vortexing using an Eppendorf Thermomixer Comfort™. Prior to vortexing the concentration was adjusted to 1 mg/mL using the appropriate extinction coefficients (1.42 and 1.43 Abs 280 nm, 1 mg/mL, 1 cm path length for hIgG1 LALA and hIgG4P respectively) and the absorbance at 595 nm obtained using a Varian Cary® 50-Bio spectrophotometer to establish the time zero reading. Each sample was sub-aliquoted into 1.5 mL conical Eppendorf®-style capped tubes (3×250 μL) and subjected to vortexing at 1400 rpm at 25° C. for 24 hours. Aggregation (turbidity) was monitored by measurement of the samples at 595 nm at 3 hours and 24 hours post vortexing using a Varian Cary® 50-Bio spectrophotometer. The data is summarized in Table 24.

Both 12172 gL2gH11 and 12172 gL6gH6 (hIgG4P and hIgG1 LALA) showed good aggregation stability in both buffers (a common pre-formulation storage buffer pH 7.4 and pH 5) at 3 hours post vortexing, that is, no turbidity was observed at 595 nm. At 24 hours it was possible to discriminate between the molecules where 12172 gL2gH11 and 12172 gL6gH6 (hIgG1 LALA) showed greater aggregation stability than the corresponding hIgG4P molecules in both buffers. For the hIgG4P molecules, greater aggregation stability was observed in a common pre-formulation storage buffer at pH 7.4 compared with pH 5. It would be envisaged that 12172 gL2gH11 and 12172 gL6gH6, (as hIgG4P and hIgG1 LALA) would be aggregation stable to shear stress conditions during manufacture, for example ultra-filtration.

TABLE 24

Effect of Stress at an air-liquid interface (turbidity at 595 nm) on 12172 gL2gH11 and 12172 gL6gH6 (hIgG4P and hIgG1) in a common pre-formulation storage buffer pH 7.4 and pH 5.

| | | OD 595 nm | | | |
|---|---|---|---|---|---|
| | | pH 7.4 | | pH 5 | |
| Graft | Format | 3 h | 24 h | 3 h | 24 h |
| gL2gH11 | hIgG4P | 0.06 | 0.87 | 0.21 | 1.48 |
| | hIgG1 LALA | 0.00 | 0.06 | 0.00 | 0.06 |
| gL6gH6 | hIgG4P | 0.01 | 0.67 | 0.20 | 1.68 |
| | hIgG1 LALA | 0.00 | 0.13 | 0.01 | 0.03 |

Example 20. Viscosity Assessment at Different Concentrations for 12172 gL2gH11 (hIgG4P and hIgG1 LALA)

Low viscosity at high antibody concentration is important for sub cutaneous administration of the therapeutic molecule, therefore viscosity at increasing concentrations in a common pre-formulation buffer, pH 5 was obtained to assess suitability for sub cutaneous administration. This was determined for 12172 gL2gH11 (hIgG4P and hIgG1 LALA).

The study was performed by (i) initial concentration of the samples and (ii) viscosity measurement as detailed below.

Concentration of 12172 gL2gH11 (hIgG4P and hIgG1 LALA).

12 mL of 12172 gL2gH11 hIgG4P (15.2 mg/mL) and 11 mL of 12172 gL2 gH11 IgG1 LALA (15.5 mg/mL) in a common pre-formulation storage buffer pH 5.0 were concentrated using Vivaspin 20 MWCO 30 kDa centrifugal filters (Z14637, Sigma-Aldrich) at 4000×g at 20° C. The samples were centrifuged until a volume of ~750 μL was obtained. The retentate solution was recovered and the resulting antibody concentrations were determined using UV absorbance measurements (NanoDrop™ 1000) at 280 nm. Extinction coefficients of 1.43 mL/(mg cm) for 12172gL2gH11 hIgG4P and 1.42 mL/(mg cm) for 12172 gL2gH11 IgG1 LALA were used.

The antibody samples were then diluted using a common pre-formulation storage buffer pH 5.0 to give a range of concentrations suitable for viscosity testing. The concentration of the diluted antibodies was confirmed by remeasurement of UV absorbance at 280 nm. Concentrations were found to be 158 mg/mL, 94 mg/mL and 52 mg/mL for 12172 gL2gH11 hIgG4P and 144 mg/mL 100 mg/mL, and 45 mg/mL for 12172 gL2gH11 hIgG1 LALA.

Viscosity Measurements of 12172 gL2gH11 (hIgG4P and hIgG1 LALA).

The viscosity at each concentration was measured using Discovery Hybrid Rheometer-1 (DHR-1, TA Instruments) with Peltier plate and liquid cooling system for temperature control, and 20 mm stainless steel parallel plate geometry for measurement. The sample (80 μL) was placed on the center of the Peltier plate, and the viscosity (in mPa·s, or cP) was measured with steady state flow sweep procedure setting at 20° C. with varying shear rates, from 2.87918 to 287.918 $s^{-1}$. The measured viscosity was averaged when the values at each shear rate points are constant (SD±5%). Both 12172 gL2gH11 hIgG4P and 12172 hIgG1 LALA molecules at different concentration were measured using the instrument, to observe the changes in viscosity regarding the sample concentration. The results are summarized in Table 25.

Both 12172 gL2gH11 hIgG4P and 12172 hIgG1 LALA molecules showed an increasing trend between the concentration and the viscosity coefficient. The viscosity increased from 1.2 to 4.1 cP with the concentration from 52 to 158 mg/ml for 12172 hIgG4P. Similarly, the viscosity for IgG1 LALA molecule increased from 1.4 to 5.4 cP with the concentration from 45 to 144 mg/ml. All these samples showed a constant viscosity coefficient (variability less than 5%) at different shear rates. This results showed that 12172 hIgG4P and 12172 hIgG1 LALA exhibited low viscosity levels at a higher concentrations and therefore could be envisaged to be suitable for subcutaneous administration.

TABLE 25

Average viscosity ((centipoise (cP)) at different concentrations of 12172 gL2gH11 (hIgG4P and hIgG1 LALA) at 20° C. in a common pre-formulation storage buffer pH 5.

| gL2gH11 IgG4P | | gL2gH11 IgG1 LALA | |
|---|---|---|---|
| Concentration (mg/mL) | Viscosity (cP) | Concentration (mg/mL) | Viscosity (cP) |
| 52 | 1.2 | 45 | 1.4 |
| 94 | 2.1 | 100 | 2.4 |
| 158 | 4.1 | 144 | 5.4 |

Example 21. Assessment of the Functional Activity of 12172 gL2gH11 hIgG4P Using a Human TREM1 THP1 NF-κB Reporter Cell Line The purpose of this study was to assess the ability of 12172 gL2gH11 hIgG4P to inhibit PGLYRP1/PGN mediated NF-κB signalling activation through human TREM1. To do this, THP1 monocyte TREM1/DAP12 NF-κB Luciferase reporter cells were used These cells stably express human TREM1, human DAP12 and a NF-κB luciferase reporter gene. PGLYRP1 complexed with soluble peptidoglycan from *E. coli* (PGN) was used as the TREM1 ligand, which induces NF-κB activation by binding to TREM1. PGN which does not bind to TREM1 also induces NF-κB activation, but to a lesser extent and through an alternative signalling pathway. Inhibition of luciferase activity demonstrates the functional blocking activity of 12172 gL2gH11 hIgG4P in this system.

THP1 monocyte TREM1/DAP12 NF-κB Luciferase reporter cells were cultured in complete media containing selection antibiotics (RPMI+10% FBS+50 μM 2-mercaptoethanol+10 μg/ml blasticidin+1 μg/ml puromycin+200 μg/ml geneticin) using standard tissue culture techniques. Three days before assay set up, the cells were seeded at $10\times10^6$ cells in 50 ml complete media (200,000 cells/ml) in a T175 flask, placed flat in the incubator. On the day of the assay, the cells were removed from the flask and transferred to a 50 ml falcon and centrifuged at 300×g for five minutes. Media was removed and the cells were resuspended in 5-10 ml of complete media and counted. Cells were then resuspended at $1\times10^6$ cells/ml by adding cell suspension to complete media, and 10 μl/well was added to an assay plate (Corning #3570). 12172 gL2gH11 hIgG4P was serially diluted in complete media in a 384-well dilution plate (Greiner #781281) to a final assay concentration range of 33.3 nM to 1.69 pM. The serial dilution of 12172 gL2gH11 hIgG4P was then transferred to the assay plate (10 μl/well) and the assay plate was incubated at 37° C./5% $CO_2$ for 1 hour. Recombinant human PGLYRP1 (R&D Systems #2590-PGB) was complexed with PGN (Invivogen #tlrl-ksspgn) for one hour at room temperature in sterile DPBS. After one hour, the solution was diluted in complete media, then transferred to the assay plate (10 μl/well) to a final assay concentration 2.5 μg/ml PGLYRP1 and 10 μg/ml PGN. The plate controls (no antibody added) included PGLYRP1/PGN complex and PGN alone, as assay maximum and minimum values, respectively. The assay plate was then incubated at 37° C. 5% $CO_2$ for 16±2 hours. Following the incubation, luciferase activity was measured using the SteadyGlo Luciferase assay system (Promega #E2520). The Steady-Glo reagent was prepared according to the manufacturer's instructions and 30 μl/well was added to the assay plate. The plate was then centrifuged at 200×g for three minutes and then incubated at room temperature for a further two minutes so that the total incubation time with the SteadyGlo reagent was five minutes. Luminescence was then measured using a Synergy Neo 2 plate reader and the raw luminescence values were used to determine the relative percentage inhibition as compared to the control wells. 4 PL curve fitting and the calculation of $IC_{50}$ values was performed using ActivityBase v9.4.

TABLE 26

Summary of potency, efficacy, and hill slope values for 12172 gL2gH11 hIgG4P

| Geomean $IC_{50}$ (pM) ± SD | Average Emax (%) ± SD | Average Slope ± SD | N* |
|---|---|---|---|
| 64 ± 36 | 72 ± 4 | 2.1 ± 0.9 | 3 |

*Values were calculated from three independent experiments.

Example 22. Efficacy and Potency of 12172 Antibodies in Blocking TREM1-Mediated Pro-Inflammatory Cytokine and Chemokine Release from Primary Human Monocytes To evaluate the ability of anti-TREM1 12172 variant antibodies to block TREM1 signaling, the release of pro-inflammatory cytokines and chemokines from activated primary human monocytes was measured following 12172 antibody treatment. Monocytes were isolated from cryopreserved peripheral blood mononuclear cells (PBMCs) of healthy human donors by negative selection (Miltenyi, 130-117-337). Monocyte viability and purity was assessed by flow cytometry and exceeded ≥90%. Monocytes were seeded at a density of $5\times10^4$ cells per well in 96-well plates (Falcon) and stimulated with pre-complexed peptidoglycan from *Bacillus subtilis* (PGN-BS; 3 μg/ml; Invivogen, tlrl-pgnb3) and recombinant human peptidoglycan recognition protein 1 (PGLYRP1; 1 μg/ml; R&D Systems, 2590-PGB) to activate TREM1. Cell supernatants were collected after 24 hours for measurement of pro-inflammatory cytokine release (TNF-α, IL-6, IL-1β) by homogeneous time resolved Fluorescence® technology (HTRF®; Cisbio).

Figure 5:
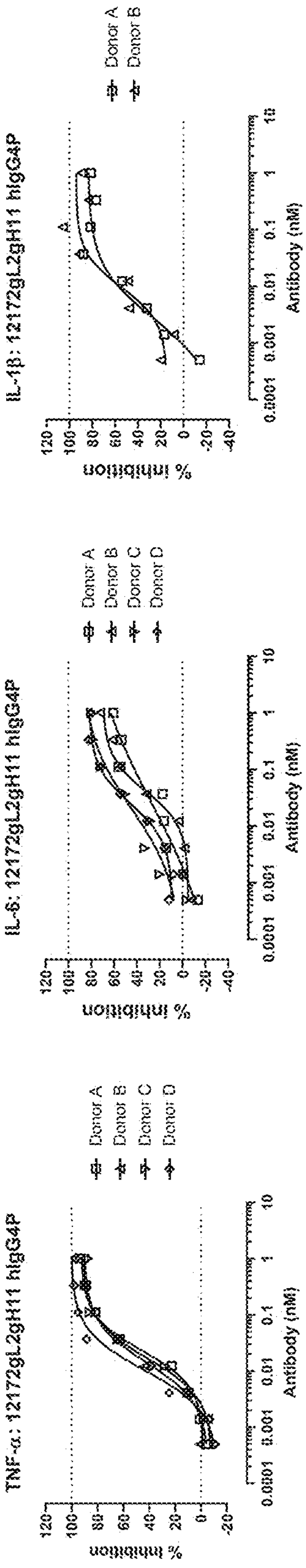
FIG. 5 shows inhibition of TREM1-mediated release of TNF-α, IL-6 and IL-1β by 12172 gL2gH11 hIgG4P from primary human monocytes.

As shown in Table 27, the 12172 gL2gH11 hIgG4P variant was the most potent in inhibiting TREM1-mediated release of TNF-α (Geomean $IC_{50}$=15 pM), IL-6 (Geomean $IC_{50}$=27 pM) and IL-1β (Geomean $IC_{50}$=5 pM) from primary human monocytes. As shown in FIG. 5, the potency of 12172 gL2gH11 hIgG4P in primary human monocytes was observed across donors.

To further evaluate the ability of anti-TREM1 12172 variant antibodies in blocking TREM1-mediated pro-inflammatory cytokine and chemokine release, supernatants from primary human monocytes treated with anti-TREM1 antibodies (1 nM) and activated with pre-complexed PGN-BS/PGLYRP1 were quantitatively analyzed using two multiplex immunoassays: the MILLIPLEX® Human Cytokine/Chemokine/Growth Factor Panel A (Merck Millipore, HCYTA-60K-PX48) and a custom LegendPlex panel (Biolegend).

Figure 6:
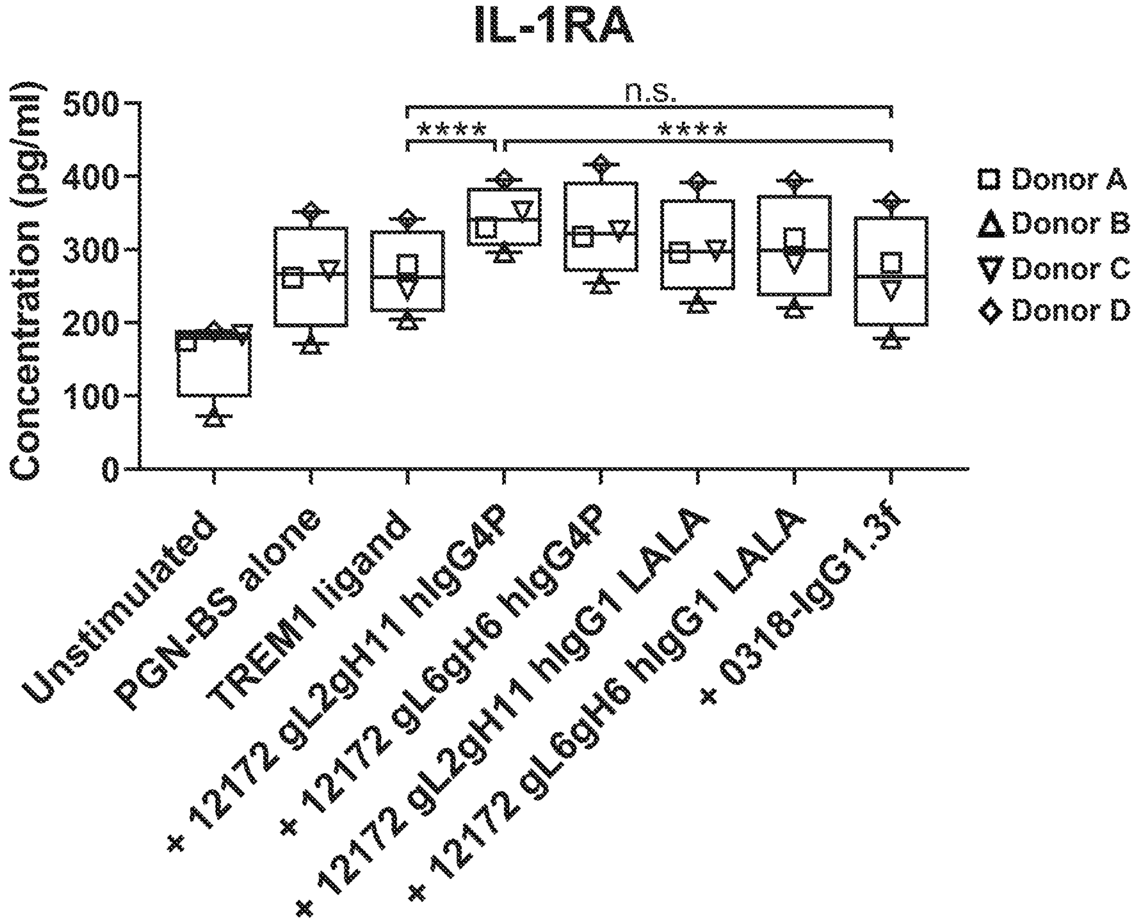
FIG. 6 shows increase of the release of IL-1R antagonist from primary human monocytes by various 12172 variants and a reference antibody.

As shown in Table 28, inhibition of TREM1 with different 12172 antibody variants strongly decreased the release of multiple cytokines and chemokines (CCL-3, CCL-20, CXCL-9, G-CSF, GM-CSF, IFN-γ, IL-1α, IL-1β, IL-6, IL-10, IL-12p40, IL-15, IL-18, IL-27, TNF-α, TNF-β) from activated primary human monocytes (n=4 donors). The 12172 gL2gH11 hIgG4P variant was the most efficacious 12172 variant with percent inhibition values ranging between 57-110%. As shown in FIG. 6, 12172 gL2gH11 hIgG4P significantly increased the release of IL-1R antagonist (IL-1RA), a negative regulator of the IL-1 pathway, from primary monocytes across donors. IL-1RA is monogenically (mutations causing low levels of IL-1RA) linked to severe systemic autoimmune disease. Single nucleotide polymorphisms in IL-1RN (encoding for IL-1RA) have been identified in ALS patients. Higher circulating IL-1RA levels are significantly associated with lower risk of ALS (Yuan et al. 2020 Eur J Neurol). IL-1RA levels are also significantly decreased in the cerebrospinal fluid of AD patients compared to healthy controls (Tarkowski et al. 2001 Dement Geriatr Cogn Disord). In contrast to 12172 gL2gH11 hIgG4P, a prior art ani-TREM2 antibody (0318-IgG1.3f) had no effect on IL-1RA release from primary monocytes.

TABLE 27

Potency of different 12172 variants on TNF-α, IL-6 and IL-1β release

| Description | TNF-α (n = 4) Geo IC50 (pM) | IL-6 (n = 4) Geo IC50 (pM) | IL-1β (n = 2) Geo IC50 (pM) |
|---|---|---|---|
| 12172 gL2gH11 hIgG4P | 15 | 27 | 5 |
| 12172 gL6gH6 hIgG4P | 26 | 36 | 28 |
| 12172 gL2gH11 hIgG1 LALA | 43 | 112 | 32 |
| 12172 gL6gH6 hIgG1 LALA | 54 | 178 | 25 |

TABLE 28

Efficacy (percentage inhibition) of different 12172 antibody variants on the release of cytokines and chemokines

| | 12172 gL2gH11 hIgG4P | 12172 gL6gH6 hIgG4P | 12172 gL2gH11 hIgG1 LALA | 12172 gL6gH6 hIgG1 LALA |
|---|---|---|---|---|
| CCL-3 | 57 | 38 | 48 | 26 |
| CCL-20 | 69 | 56 | 65 | 66 |
| CXCL-9 | 77 | 73 | 72 | 68 |
| G-CSF | 92 | 88 | 89 | 86 |
| GM-CSF | 91 | 89 | 91 | 89 |
| IFN-γ | 59 | 57 | 60 | 53 |
| IL-1α | 110 | 107 | 112 | 110 |
| IL-1β | 98 | 96 | 96 | 97 |
| IL-6 | 64 | 57 | 58 | 55 |
| IL-10 | 86 | 83 | 77 | 73 |
| IL-12p40 | 96 | 96 | 96 | 95 |
| IL-15 | 78 | 69 | 86 | 92 |
| IL-18 | 87 | 78 | 85 | 81 |
| IL-27 | 81 | 57 | 88 | 74 |

TABLE 28-continued

Efficacy (percentage inhibition) of different 12172 antibody variants on the release of cytokines and chemokines

| | 12172 gL2gH11 hIgG4P | 12172 gL6gH6 hIgG4P | 12172 gL2gH11 hIgG1 LALA | 12172 gL6gH6 hIgG1 LALA |
|---|---|---|---|---|
| TNF-α | 94 | 93 | 94 | 94 |
| TNF-β | 65 | 63 | 62 | 60 |

Example 23: Efficacy and Potency of 12172 gL2gH11 hIgG4P in Increasing IL-1RA Release from Unstimulated Primary Human Monocytes Having observed that 12172 gL2gH11 hIgG4P significantly increased the release of IL-1RA from TREM1 ligand-stimulated human monocytes, its effects on IL-1RA release from unstimulated human monocytes was also assessed. Human monocytes were isolated and seeded as described previously in Example 22 and antibodies added for 24 hours prior to collection of supernatants for IL-1RA measurement using the IL-1RA Quantikine ELISA kit (R&D Systems).

Figure 7:
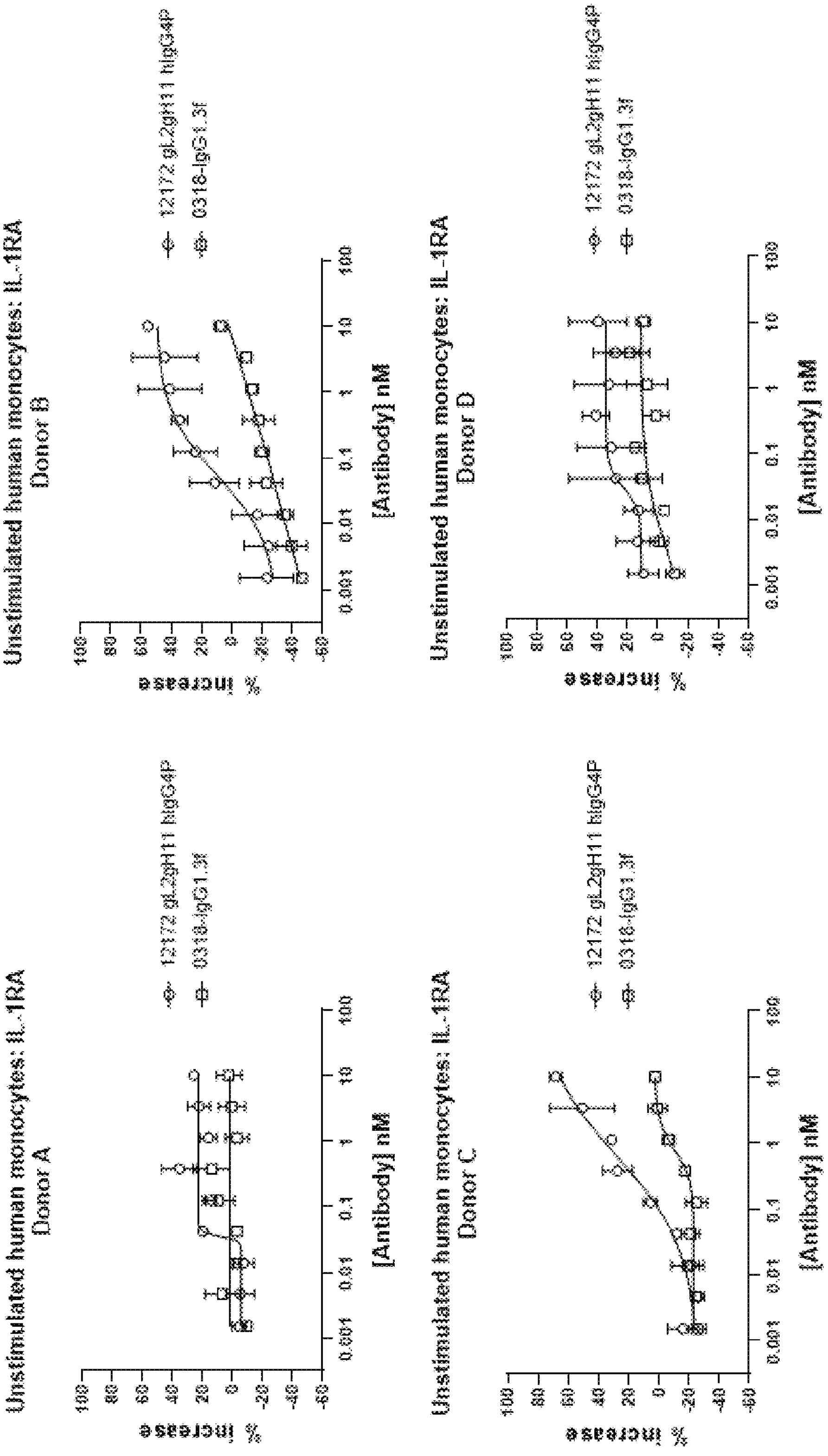
FIG. 7 shows the effects of 12172 gL2gH11 hIgG4P and 0318-IgG1.3f in increasing IL-1RA release from unstimulated primary human monocytes.

As shown in Table 29 and FIG. 7, 12172 gL2gH11 hIgG4P dose-dependently increased the release of IL-1RA in unstimulated primary human monocytes. In contrast to 12172 gL2gH11 hIgG4P, another prior art anti-TREM1 antibody (0318-IgG1.3f) had no effect on IL-1RA release from unstimulated primary human monocytes.

TABLE 29

Efficacy and potency of 12172 gL2gH11 hIgG4P and 0318-IgG1.3f in increasing IL-1RA release from unstimulated primary human monocytes.

| | 12172 gL2gH11 hIgG4P | | 0318-IgG1.3f | |
|---|---|---|---|---|
| | % increase | IC50 (pM) | % increase | IC50 (pM) |
| Donor A | n.d. | | n.d. | |
| Donor B | 50 | 54 | n.d. | |
| Donor C | 83 | 624 | n.d. | |
| Donor D | 35 | 30 | n.d. | |

* n.d. = non-detectable

Example 24. Efficacy of 12172 gL2gH11 hIgG4P in Blocking TREM1-Mediated Pro-Inflammatory Cytokine and Chemokine Release from PBMCs of Alzheimer's Disease (AD) and Amyotrophic Lateral Sclerosis (ALS) Patients Neurodegeneration and neural inflammation in AD and ALS is associated with elevated levels of multiple pro-inflammatory cytokines and chemokines in the CSF and blood of patients. For example, levels of TNF-α, IL-6 and IL-1β are significantly increased in the blood of ALS patients (Hu et al. 2017 Sci Rep) while CCL-3, G-CSF and TNF-α are elevated in the CSF of ALS patients (Chen et al. 2018 Front Immunol), all factors we observed to be decreased by TREM1 inhibition in human monocytes.

To evaluate the efficacy of anti-TREM1 12172 gL2gH11 hIgG4P to block TREM1 signaling in patient-derived cells, the release of pro-inflammatory cytokines and chemokines was measured in PBMCs from AD and ALS patients following TREM1 activation. PBMCs were isolated by density gradient centrifugation from whole blood of AD and ALS patients and corresponding matched healthy controls.

PBMCs were seeded at a density of $1\times10^5$ cells per well in 96-well plates (Falcon), pre-treated for 1 hour with 12172 gL2gH11 hIgG4P (1 nM) and stimulated with pre-complexed peptidoglycan from *Bacillus subtilis* (PGN-BS; 3 μg/ml; Invivogen, tlrl-pgnb3) and recombinant human peptidoglycan recognition protein 1 (PGLYRP1; 1 μg/ml; R&D Systems, 2590-PGB) to activate TREM1. Cell supernatants were collected after 24 hours for measurement of pro-inflammatory cytokine and chemokine release using homogeneous time resolved Fluorescence® technology (HTRF®; Cisbio) and the MILLIPLEX® Human Cytokine/Chemokine/Growth Factor Panel A (Merck Millipore, HCYTA-60K-PX48).

Figure 9:
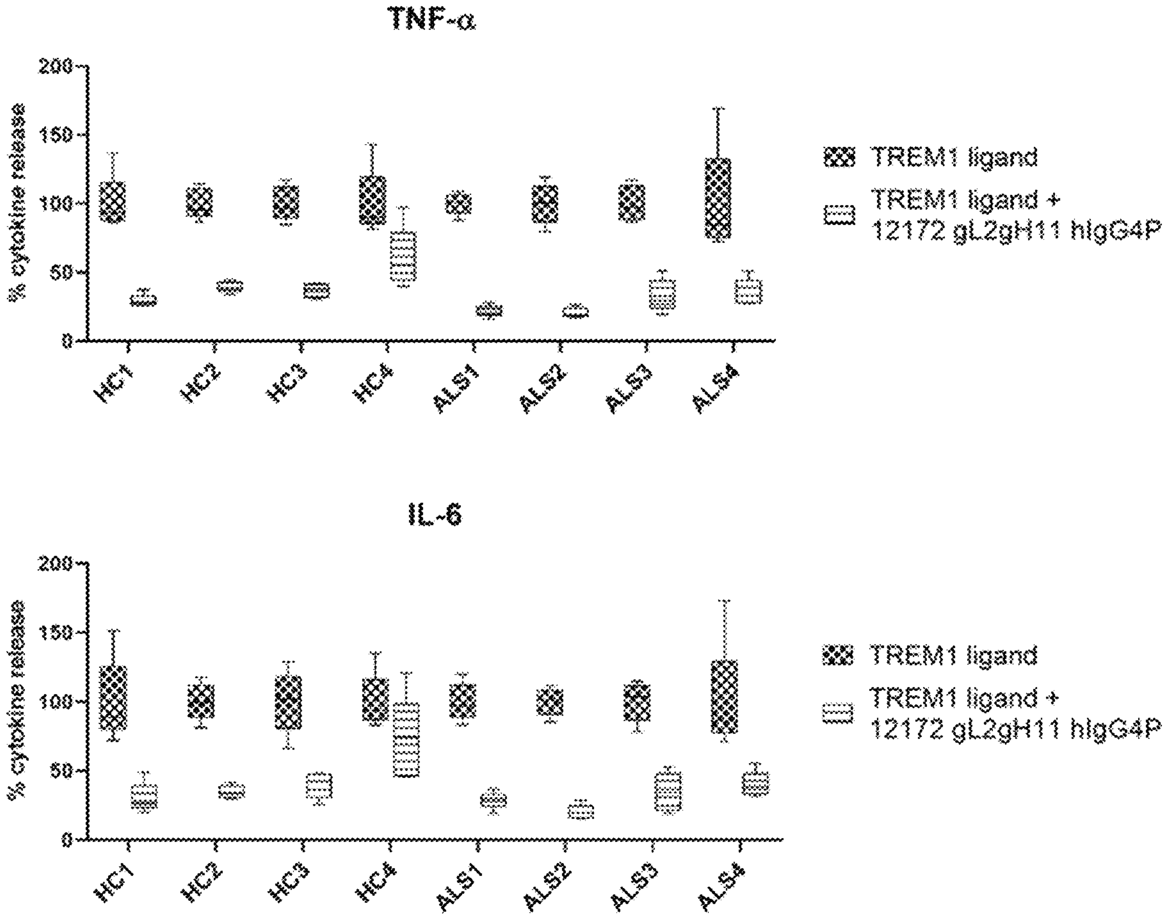
FIG. 9 shows efficacy of 12172 gL2gH11 hIgG4P on TNF-α and IL-6 release from healthy control and ALS PBMCs.

As shown in FIG. 8 and Table 30, 12172 gL2gH11 hIgG4P was efficacious in inhibiting TREM1-mediated TNF-α release (inhibition of 66%±15) and IL-6 release (70%±17) from PBMCs of AD patients. As shown in FIG. 9 and Table 31 12172 gL2gH11 hIgG4P was also efficacious in inhibiting TREM1-mediated TNF-α release (inhibition of 72%±7) and IL-6 release (69%±9) from PBMCs of ALS patients. As shown in FIG. 10, inhibition of TREM1 with 12172 gL2gH11 hIgG4P also strongly decreased the release of multiple cytokines and chemokines (CCL-3, CCL-4, CCL-20, CCL-22, CXCL-9, G-CSF, GM-CSF, GRO-α, IL-1α, IL-1β, IL-6, IL-10, IL-12p40, TNF-α) from ALS PBMCs (representative of n=4 donors) and AD PBMCs (representative of n=5 donors).

TABLE 30

Efficacy of 12172 gL2gH11 hIgG4P on TNF-α and IL-6 release from healthy control and AD PBMCs.

| | TNF-α | | IL-6 | |
|---|---|---|---|---|
| | % inhibition | S.D. | % inhibition | S.D. |
| Healthy control (HC) n = 8 | 79 | 16 | 85 | 18 |
| Alzheimer's disease (AD) n = 8 | 66 | 15 | 70 | 17 |

TABLE 31

Efficacy of 12172 gL2gH11 hIgG4P on TNF-α and IL-6 release from healthy control and ALS PBMCs.

| | TNF-α | | IL-6 | |
|---|---|---|---|---|
| | % inhibition | S.D. | % inhibition | S.D. |
| Healthy control (HC) n = 4 | 59 | 13 | 56 | 19 |
| Amyotrophic lateral sclerosis (ALS) n = 4 | 72 | 7 | 69 | 9 |

Example 25. Transcriptomic Profiles of Human Monocytes Following Stimulation with TREM1 Ligand Complex or Apoptotic iPSC-Derived Human Motor Neurons and Treatment with 12172 Antibody Variants To further characterize the cellular profiles of anti-TREM1 12172 antibody variants, transcriptomic analysis was performed on human monocytes stimulated with TREM1 ligand complex or apoptotic induced pluripotent stem cell (iPSC)-derived human motor neurons, an ALS disease-relevant ligand. Monocytes were isolated from cryopreserved peripheral blood mononuclear cells (PBMCs) of healthy human donors (n=8) by negative selection (Miltenyi, 130-117-337). Monocyte viability and purity was assessed by flow cytometry and exceeded ≥90%. Monocytes were seeded at a density of $2\times10^6$ cells per well in 6-well plates (Falcon) and pre-treated for 1 hour with 12172 antibody variants (1 nM). Monocytes were then stimulated for 4 hours with (i) pre-complexed peptidoglycan from *Bacillus subtilis* (PGN-BS; 3 μg/ml; Invivogen, tlrl-pgnb3) and recombinant human peptidoglycan recognition protein 1 (PGLYRP1; 1 μg/ml; R&D Systems, 2590-PGB) to activate TREM1 or (ii) ultraviolet light-induced apoptotic iPSC-derived human motor neurons. RNA was isolated using the RNeasy Plus Mini Kit (Qiagen) and RNA quality assessed using Experion™ RNA analysis kits (BioRad). Sequencing libraries were prepared using NEBNext Ultra II Directional RNA Library Prep Kit (New England BioLabs) and samples sequenced using Illumina NovaSeq6000.

Figure 11A:
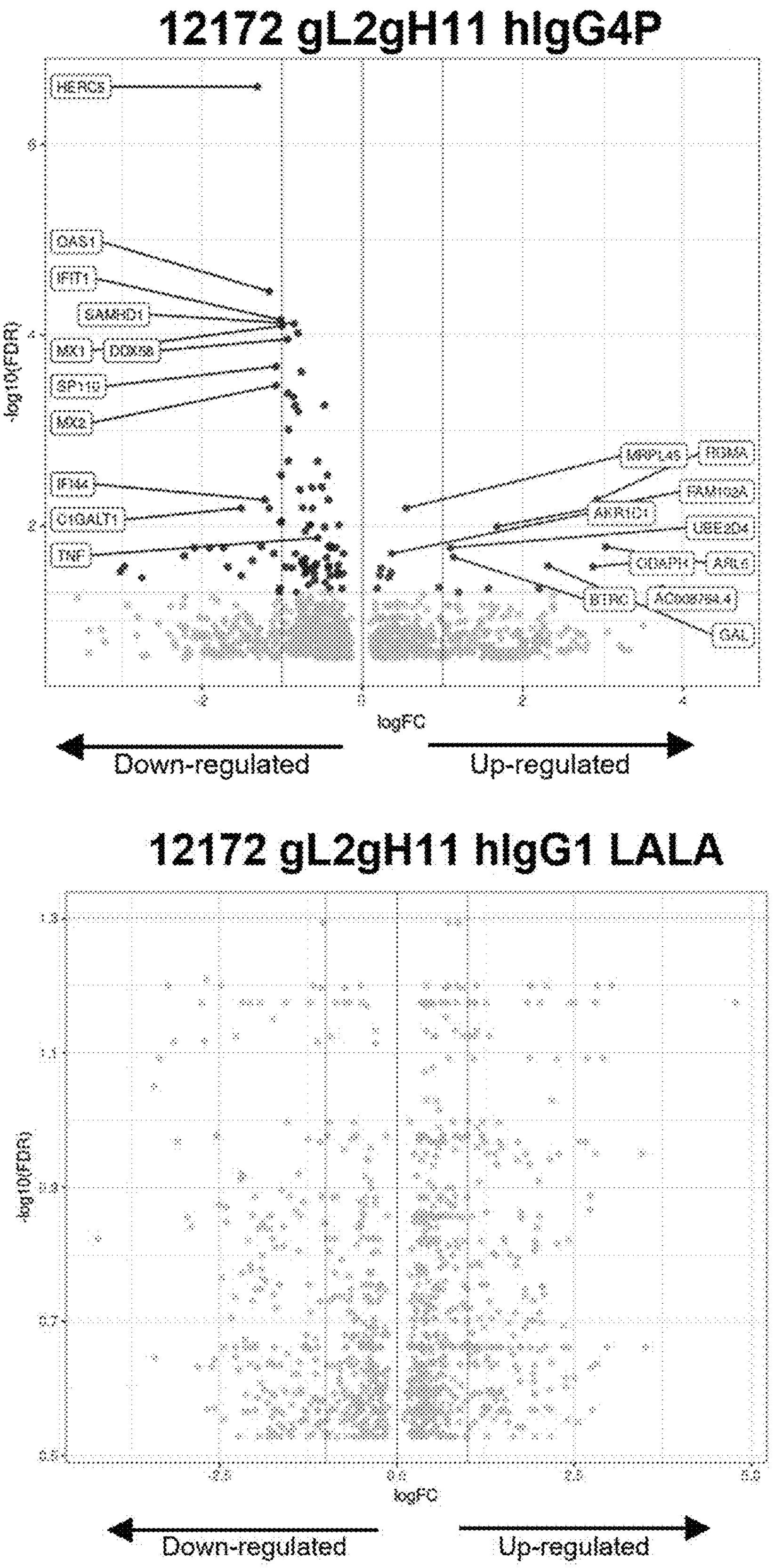
Figure 11C:
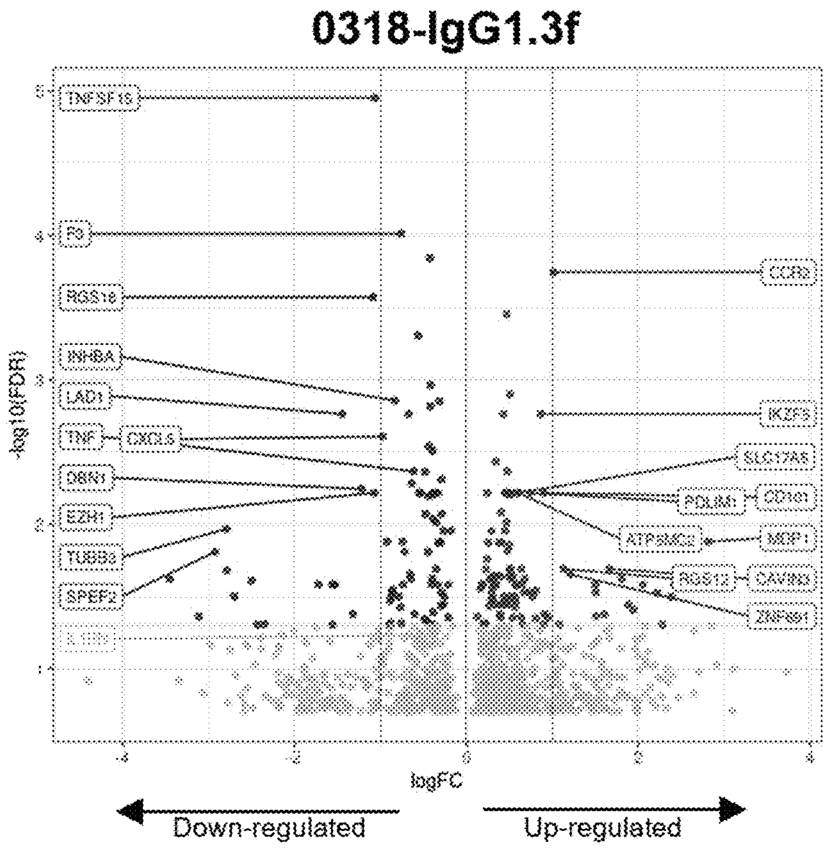

As shown in FIGS. 11 (A and B) and Table 32, following TREM1 ligand complex stimulation, the highest number of significant differentially expressed genes (DEGs) was observed with hIgG4P formats of 12172 gL2gH11 and 12172 gL6gH6. Among the top DEGs, the two 12172 hIgG4P antibodies also showed a similar transcriptome profile (e.g. down-regulation of HERC5, OAS1, DDX58, TNF-α). These profiles were in contrast to a prior art anti-TREM1 antibody (0318-IgG1.3f) (FIG. 11C). In addition, as shown in Table 33, there were 111 genes significantly up-regulated and 121 genes significantly down-regulated in 12172 gL2gH11 hIgG4P-treated monocytes when compared to 0318-IgG1.3f-treated monocytes.

TABLE 32

Number of differentially expressed genes (DEGs), considering a false discovery rate (FDR) of 0.05, following treatment of human monocytes with 12172 antibody variants and stimulation with TREM1 ligand complex (compared to ligand or isotype control).

| | | Up-regulated genes | | Down-regulated genes | |
|---|---|---|---|---|---|
| | | Ab/ligand | Ab/isotype | Ab/ligand | Ab/isotype |
| 12172 gL2gH11 | hIgG4P | 6 | 19 | 4 | 86 |
| | hIgG1 LALA | 0 | 0 | 0 | 0 |
| 12172 gL6gH6 | hIgG4P | 20 | 71 | 63 | 255 |
| | hIgG1 LALA | 9 | 10 | 47 | 9 |
| 0318-IgG1.3f | | 9 | 99 | 38 | 82 |

TABLE 33

Number of DEGs, considering a FDR of 0.05, between 12172 gL2gH11 hIgG4P and 0318-IgG1.3f following stimulation of human monocytes with TREM1 ligand complex.

| 12172 gL2gH11 hIgG4P:0318-IgG1.3f | |
|---|---|
| Up-regulated genes | Down-regulated genes |
| 111 | 121 |

Figure 12B:
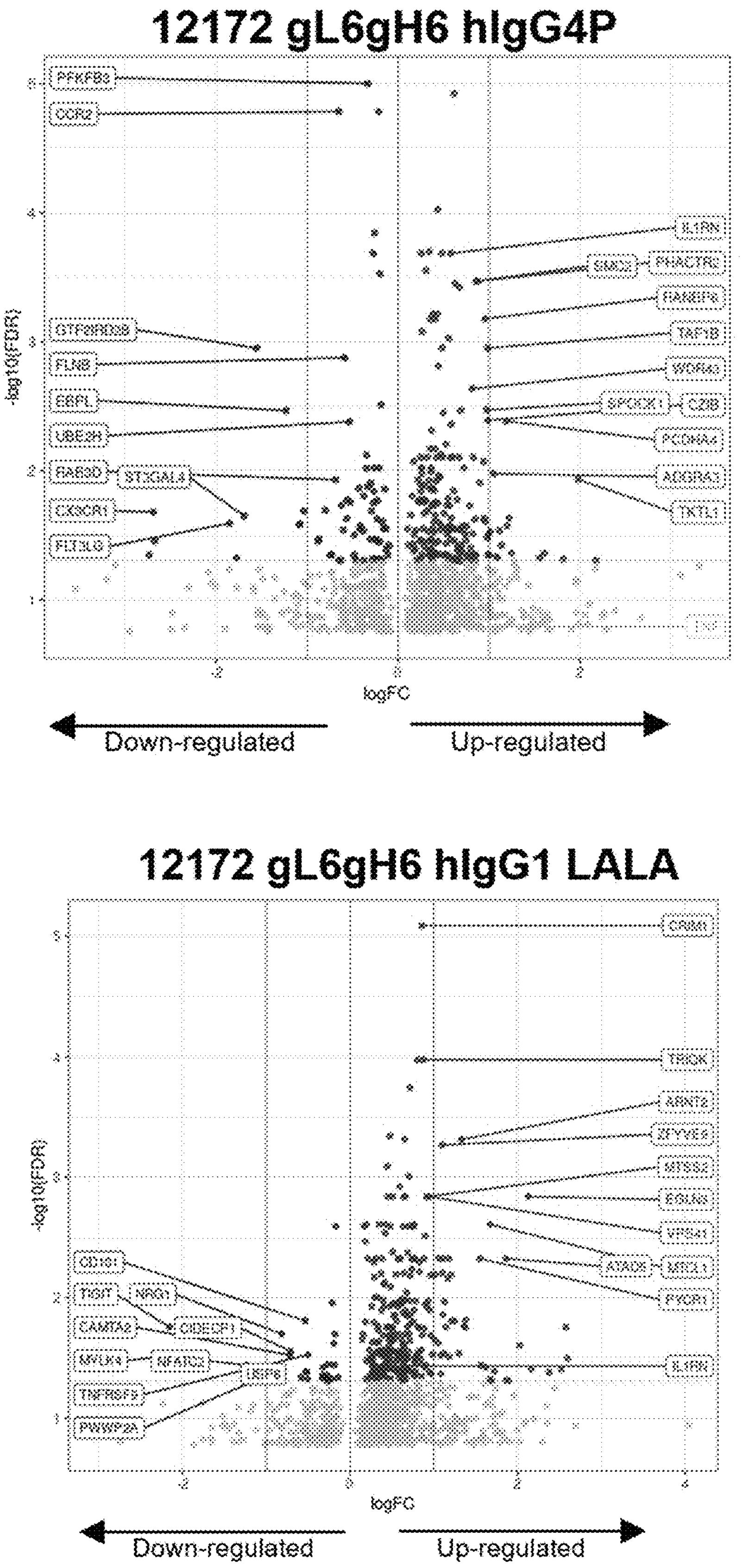
Figure 12C:
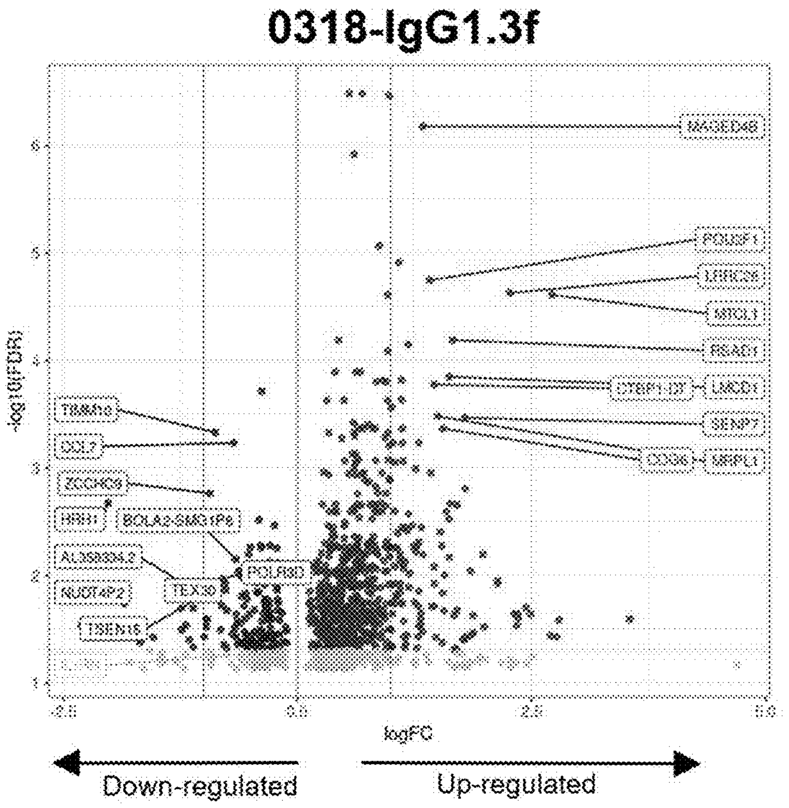

As shown in FIGS. 12 (A and B) and Table 34, there were a higher number of DEGs following stimulation with apoptotic iPSC-derived human motor neurons in comparison to TREM1 ligand complex stimulation. Among the top DEGs, the two 12172 hIgG4P antibodies showed some overlap including for example down-regulation of CCR2 and up-regulation of IL-1RN, the gene encoding IL-1RA. In contrast, the top DEGs were different with a prior art anti-TREM1 antibody (0318-IgG1.3f) (FIG. 12C) and no significant up-regulation of IL-1RN was observed with this antibody. In addition, as shown in Table 35, there were 598 genes significantly up-regulated and 808 genes significantly down-regulated in 12172 gL2gH11 hIgG4P-treated monocytes when compared to 0318-IgG1.3f-treated monocytes.

TABLE 34

Number of DEGs, considering an FDR of 0.05, following treatment of human monocytes with 12172 antibody variants and stimulation with apoptotic iPSC-derived human motor neurons (compared to ligand or isotype control).

| | | Up-regulated genes | | Down-regulated genes | |
|---|---|---|---|---|---|
| | | Ab/ligand | Ab/isotype | Ab/ligand | Ab/isotype |
| 12172 | hIgG4P | 420 | 221 | 453 | 151 |
| gL2gH11 | hIgG1 LALA | 563 | 64 | 728 | 19 |
| 12172 | hIgG4P | 484 | 183 | 253 | 69 |
| gL6gH6 | hIgG1 LALA | 836 | 280 | 725 | 29 |
| 0318-IgG1.3f | | 674 | 623 | 545 | 139 |

TABLE 35

Number of DEGs, considering a FDR of 0.05, between 12172 gL2gH11 hIgG4P and 0318-IgG1.3f following stimulation of human monocytes with apoptotic iPSC-derived human motor neurons.
12172 gL2gH11 hIgG4P:0318-IgG1.3f

| Up-regulated genes | Down-regulated genes |
|---|---|
| 598 | 808 |

Example 26. Efficacy of 12172 Antibody in Blocking TREM1-Mediated Phagocytosis and Production of Reactive Oxygen Species (ROS) by Primary Human Monocytes and Neutrophils To assess the impact of blocking TREM1 signaling on anti-microbial immune responses, both phagocytosis and ROS production from activated primary human monocytes and neutrophils in whole blood was evaluated by flow cytometry. To examine ROS production, dihydrorhodamine-123 (5 μg/ml) was added to blood (25 μl) from healthy human donors for 5 minutes prior to being preincubated with 12172 gL2gH11 hIgG4P or 0318-IgG1.3f antibodies (10 μg/ml) for an additional 30 minutes. Whole blood samples were then cultured with $1\times10^6$ mCherry expressing bacteria for 1 h. Samples were washed, stained with surface antibodies for CD45 and CD14 to discriminate neutrophils and monocytes by flow cytometry.

Figure 13:
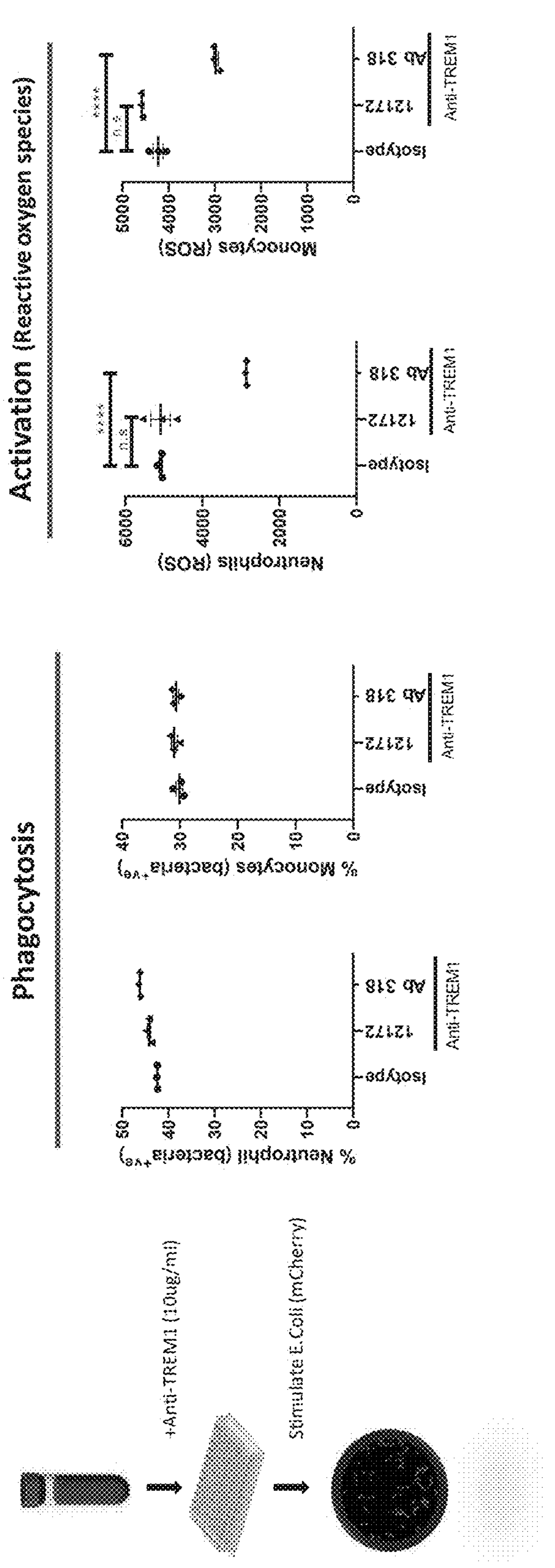
FIG. 13 shows that 12172 gL2gH11 hIgG4P does not impact *E. coli* clearance by human neutrophils and monocytes in vitro. The data is representative of 3 individual donors for 12172 gL2gH11 hIgG4P v Isotype and one donor including 0318-IgG1.3f(Ab 318) molecule for comparison. Statistical analysis, One-way ANOVA Dunnet post test was performed to compare anti-TREM1 antibodies against isotype control **** ($p<0.0001$)

As shown in FIG. 13, the 12172 gL2gH11 hIgG4P variant did not impair bacterial clearance by neutrophils or monocytes, nor impact their ability to produce reactive oxygen species. In contrast, analysis of the 0318-IgG1.3f revealed a significant reduction in *E. coli* induced ROS production by both neutrophils and monocytes. The phagocytic capacity of both immune cell types was not significantly influenced by 0318-IgG1.3f.

Example 27: Efficacy and Potency of 12172 Antibodies in Blocking TREM1-Mediated Activation of Spleen Tyrosine Kinase (SYK)

Association of TREM1 with its adaptor protein DAP-12 leads to phosphorylation of DAP-12 and subsequent recruitment and phosphorylation of spleen tyrosine kinase (SYK; Carrasco et al. 2018 Cell Mol Immunol). SYK has previously been implicated in driving TREM1-mediated neuroinflammatory injury (Xu et al. 2019 Cell Death Dis) and is known to be activated following amyloid-β deposition and formation of pathological tau species (Schweig et al. 2017 Acta Neuropathol Commun). To evaluate the ability of anti-TREM1 12172 variant antibodies to block TREM1-mediated SYK activation, phosphorylated SYK (pSYK) levels were measured in Flp-In™ 293 cells stably expressing human TREM1 and human DAP-12. Cells were seeded at a density of 25,000 cells per well in 384-well plates (Greiner), pre-treated for 1 hour with 12172 variant antibodies or isotype antibodies and stimulated with pre-complexed peptidoglycan from *Escherichia coli* (PGN-EC; 5 μg/ml; Invivogen, tlrl-pgnb3) and recombinant human peptidoglycan recognition protein 1 (PGLYRP1; 2.5 μg/ml; R&D Systems, 2590-PGB) to activate TREM1. Protein lysates were collected after 30 mins for measurement of pSYK levels using the AlphaLISA SureFire Ultra p-SYK (Tyr525/526) Assay Kit® (PerkinElmer).

Figure 14:
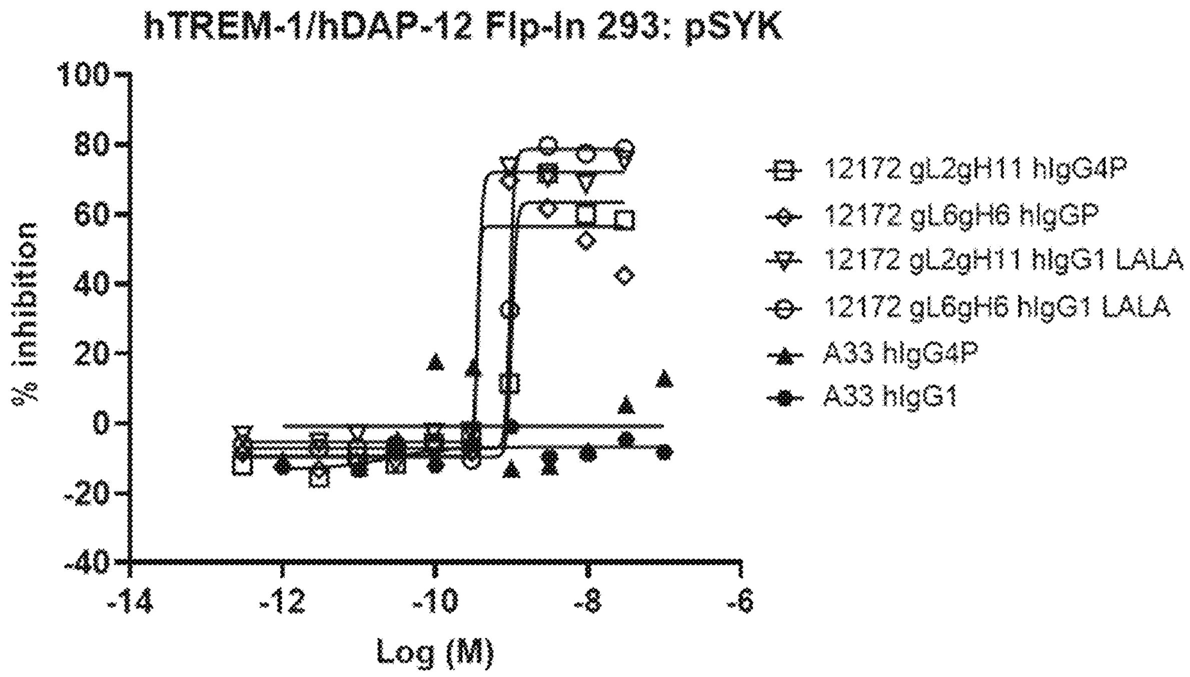
FIG. 14 shows efficacy and potency of 12172 antibody variants in blocking SYK activation in hTREM1/hDAP-12 Flp-In 293 cells.

As shown in Table 36 and FIG. 14, all four 12172 variant antibodies were efficient (Emax=57-72%) and potent (357-1015 pM) in blocking SYK activation following TREM1 activation whereas A33 isotype antibodies showed no activity.

TABLE 36

Efficacy and potency of 12172 variant anti-TREM1 antibodies in blocking SYK activation in hTREM1/hDAP-12 Flp-In 293 cells (ND—non-detectable)

| | hTREM1/hDAP-12 Flp-In 293: pSYK inhibition | |
|---|---|---|
| Description | Emax (%) | IC50 (pM) |
| 12172 gL2gH11 hIgG4P | 63 | 1015 |
| 12172 gL6gH6 hIgG4P | 57 | 357 |
| 12172 gL2gH11 hIgG1 LALA | 72 | 372 |
| 12172 gL6gH6 hIgG1 LALA | 79 | 960 |
| A33 hIgG1 | ND | ND |
| A33 hIgG4P | ND | ND |

Example 28: 12172 gL2gH11 hIgG4P Cell Surface TREM1 Affinity Measurement

The kinetics of 12172 gL2gH11 hIgG4P binding to human or cynomolgus TREM1 expressed on live cells was measured at 25° C. using LigandTracer. Two HEK293 polyclonal cell lines were developed in-house to express either human or cynomolgus TREM1, and the parental normal adherent HEK293 were used as control cells. All three cell types were maintained in growth medium DMEM (Gibco, 21969-035) supplemented with Foetal Calf Serum (Invitrogen, 10082), GlutaMAX (Gibco, 35050061), and to maintain selection in the TREM1 polyclonal cell lines, 0.5 mg/ml Geneticin (Gibco, 10131-027) was additionally included. The day before an experiment $1.4\times10^6$ cells were seeded into each quarter of a LigandTracer MultiDish 2×2 (Ridgeview, 1-04-204-5) previously coated according to manufacturer's instructions with poly-D-lysine (Gibco, A38904-01), and incubated overnight at 37° C./5% $CO_2$. TREM1 expressing cells were seeded in one quarter of each dish compartment, and negative expressing control cells in the other. The next morning, the medium was exchanged for exactly 1.8 ml fresh growth medium (without geneticin) in each dish compartment (half), and placed in the LigandTracer instrument. Rotation was started to record baseline readings for approximately 20 minutes or until stable. Rotation was halted and AlexaFluor647-labelled 12172 gL2gH11 hIgG4P (in house) was added at a concentration of 0.5 nM, a concentration close to the expected 12172 gL2gH11 hIgG4P $K_D$. Rotation was restarted, and fluorescent measurements representing the real-time binding of the antibody to the cells were recorded until curvature indicating a degree of equilibrium was observed (taking approximately 2 hrs). Two further additions of antibody were made in this manner at 1.5 nM and 5 nM, each ~3 times higher than the last. Finally, all medium containing the antibody was removed, and replaced with fresh medium. Rotation and measurements were continued until the dissociation signal had dropped by at least 10% or continued overnight if the dissociation was slow. Affinity measurements were analyzed and calculated within the LigandTracer "TraceDrawer" software (version 1.9.2). Raw data readings for binding of 12172 gL2gH11 hIgG4P to TREM1-expressing cells were first normalized by subtracting the equivalent reading from binding to the control cells. The subtracted traces were evaluated using the software's 1:1 binding model. Alternative models were considered if the 1:1 model was not appropriate for the data traces. 12172 gL2gH11 hIgG4P was shown to have an affinity of 16.5 pM for human TREM1 and a weaker affinity, around 300 times weaker, for cyno TREM1. The kinetic parameters are summarized in Table 37 and 38. 12172 gL2gH11 hIgG4P showed binding that was well represented by the 1:1 model. Slow dissociation rates are difficult for the LigandTracer instrument to measure, being towards the limit of the accurate range, but the five replicate experiments gave similar data. The binding of 12172 gL2gH11 hIgG4P to cynomolgus TREM1 was noticeably more complex and did not fit a 1:1 binding model. A 1:2 model, or 1:1-Two State model better represented the data and gave similar affinity values (not all data shown), although further experiments would be required to determine which of these alternative fits correctly describes the binding. However, in general the affinity of 12172 gL2gH11 hIgG4P for cynomolgus TREM1 compared to human TREM1 was clearly reduced, by approximately 300 times. In conclusion, 12172 gL2gH11 hIgG4P displayed stronger affinity to cell surface human TREM1 compared to the soluble human TREM1 ECD (Example 6) due to binding avidity on cells, with both methods (Biacore and LigandTracer) showing considerably weaker affinity of 12172 gL2gH11 hIgG4P to cynomolgus TREM1 compared to human TREM1.

TABLE 37

Kinetic parameters of 12172 gL2gH11 hIgG4P binding to human TREM1. U-values represent the quality of the fit model to the data. A low U-value of less than 10% is considered a good fit, values >20% are considered poor.

| 1:1 fit model | ka (1/(M*s)) | kd (1/s) | $K_D$ (pM) | U-value: kd (%) |
|---|---|---|---|---|
| N = 1 | 3.50E+05 | 6.80E−06 | 19.4 | 3.6 |
| N = 2 | 3.56E+05 | 8.89E−06 | 25.0 | 4.3 |
| N = 3 | 2.44E+05 | 3.71E−06 | 15.2 | 10.4 |
| N = 4 | 2.38E+05 | 2.97E−06 | 12.5 | 3.8 |
| N = 5 | 4.43E+05 | 5.88E−06 | 13.3 | 5.7 |
| Average | 3.26E+05 | 5.65E−06 | 17.1 | |
| SD | 8.61E+04 | 2.39E−06 | 5.2 | |
| Geometric mean | 3.17E+05 | 5.23E−06 | 16.5 | |

TABLE 38

Kinetic parameters of 12172 gL2gH11 hIgG4P binding to cyno TREM1. U-values represent the quality of the fit model to the data. A low U-value of less than 10% is considered a good fit, values >20% are considered poor. The 1:2 model generates two sets of affinity values, describing the two contributing binding events.

| 1:2 fit model | ka 1 (1/(M*s)) | kd 1 (1/s) | $K_D$ 1 (pM) | ka 2 (1/(M*s)) | kd 2 (1/s) | $K_D$ 2 (pM) | U-value: kd (%) |
|---|---|---|---|---|---|---|---|
| N = 1 | 8.87E+05 | 7.58E−03 | 8550 | 1.08E+05 | 8.69E−06 | 80.8 | 17.7 |
| N = 2 | 3.12E+05 | 1.84E−03 | 5910 | 7.27E+04 | 3.08E−05 | 423 | 4 |
| N = 3 | 4.69E+05 | 1.92E−03 | 4090 | 5.97E+04 | 3.13E−05 | 524 | 3.6 |
| N = 4 | 3.00E+05 | 1.78E−03 | 5940 | 5.97E+04 | 2.36E−06 | 39.5 | 11.8 |
| N = 5 | 7.06E+05 | 1.90E−03 | 2690 | 3.27E+04 | 4.03E−06 | 124 | 6.5 |
| Average | 6.78E+05 | 4.75E−03 | 5436 | 8.39E+04 | 2.00E−05 | 238 | |
| SD | 2.96E+05 | 4.00E−03 | 2210 | 3.42E+04 | 1.60E−05 | 220 | |
| Geometric mean | 6.45E+05 | 3.81E−03 | 5055 | 8.03E+04 | 1.65E−05 | 154 | |

All references cited herein, including patents, patent applications, papers, textbooks and the like, and the references cited therein, to the extent that they are not already, are hereby incorporated herein by reference in their entirety.

What is claimed is:

1. An antibody that binds to human triggering receptor expressed on myeloid cells 1 (TREM1), comprising:

a light chain variable region comprising:

a CDR-L1 comprising SEQ ID NO:11, a CDR-L2 comprising SEQ ID NO:12, and a CDR-L3 comprising SEQ ID NO:13;

and a heavy chain variable region comprising:

a CDR-H1 comprising SEQ ID NO:14, a CDR-H2 comprising SEQ ID NO:15, and a CDR-H3 comprising SEQ ID NO:16.

2. The antibody according to claim 1, wherein the antibody inhibits or attenuates TREM1 binding to one or more of its natural ligands.

3. The antibody according to claim 2, wherein the antibody inhibits or attenuates TREM1 binding to peptidoglycan recognition protein 1 (PGLYRP1).

4. The antibody according to claim 1, wherein the antibody has a dissociation equilibrium constant (KD) of less than 600 pM for human TREM1.

5. The antibody according to claim 1, wherein the antibody binds to a different site on TREM1 than PGLYRP1.

6. The antibody according to claim 1, wherein the antibody binds to an epitope of human TREM1, the epitope comprising residues E26, E27, K28, Y29, E30, L31, K32 of human TREM1 (SEQ ID NO: 1).

7. The antibody according to claim 1, wherein the antibody binds to an epitope of human TREM1, the epitope comprising five or more residues selected from E26, E27, K28, Y29, E30, L31, K32, Q35, T36, D38, K40, D42, R97, D127, T134 and G136 of human TREM1 (SEQ ID NO: 1) as determined at the distance of less than 4 Å contact distance between the antibody and TREM1.

8. The antibody according to claim 7, wherein the binding is determined using X-ray crystallography.

9. The antibody according to claim 1, wherein the light chain variable region comprises the amino acid sequence set forth in SEQ ID NO:29.

10. The antibody according to claim 1, wherein the heavy chain variable region comprises the amino acid sequence set forth in SEQ ID NO:79.

11. The antibody according to claim 1, wherein the light chain variable region comprises the amino acid sequence set forth in SEQ ID NO: 29, or a sequence which is at least 90% identical thereto; and the heavy chain variable region comprises the amino acid sequence set forth in SEQ ID NO: 79, or a sequence which is at least 90% identical thereto.

12. The antibody according to claim 1, wherein the antibody is an antibody fragment.

13. The antibody according to claim 12, wherein the antibody fragment is Fab, Fab', $F(ab')_2$, Fv, dsFv, scFv, or dsscFv.

14. The antibody according to claim 1, wherein the antibody is a full length antibody.

15. The antibody according to claim 14, wherein the antibody is an IgG1, IgG1 LALA, IgG4, IgG4P, or IgG4P FALA.

16. The antibody according to claim 14, wherein the antibody is an IgG4P comprising a light chain comprising the sequence given in SEQ ID NO: 31 and a heavy chain comprising the sequence given in SEQ ID NO: 81.

17. A pharmaceutical composition comprising the antibody of claim 1, and a pharmaceutically acceptable adjuvant or carrier.

* * * * *